United States Patent
Tanimoto et al.

(10) Patent No.: US 7,084,136 B2
(45) Date of Patent: Aug. 1, 2006

(54) DRUG COMPOSITION ANTAGONISTIC TO BOTH PGD$_2$/TXA$_2$ RECEPTORS

(75) Inventors: Norihiko Tanimoto, Osaka (JP); Akinori Arimura, Toyonaka (JP)

(73) Assignee: Shionogi & Co., Ltd., Osaka (JP)

( * ) Notice: Subject to any disclaimer, the term of this patent is extended or adjusted under 35 U.S.C. 154(b) by 326 days.

(21) Appl. No.: 10/297,065

(22) PCT Filed: May 28, 2001

(86) PCT No.: PCT/JP01/04430

§ 371 (c)(1),
(2), (4) Date: Dec. 2, 2002

(87) PCT Pub. No.: WO01/94309

PCT Pub. Date: Dec. 13, 2001

(65) Prior Publication Data

US 2004/0024019 A1 Feb. 5, 2004

(30) Foreign Application Priority Data

Jun. 2, 2000 (JP) .............................. 2000-166305

(51) Int. Cl.
*A61K 31/535* (2006.01)
*A61K 31/40* (2006.01)
*C07D 417/00* (2006.01)
*C07D 209/02* (2006.01)
*C07D 333/78* (2006.01)

(52) U.S. Cl. .................. 514/222.8; 514/414; 514/422; 514/438; 514/441; 514/443; 514/444; 514/445; 514/465; 544/60; 548/465; 548/562; 549/49; 549/51; 549/59; 549/60; 549/78; 549/80; 549/469

(58) Field of Classification Search ................ 514/381, 514/443, 530, 563, 222.8, 414, 422, 438, 514/441, 444, 445, 465; 548/254, 465, 562; 549/49, 51, 59, 60, 78, 80, 469; 560/48; 562/461; 544/60
See application file for complete search history.

(56) References Cited

U.S. PATENT DOCUMENTS 6,172,113 B1 * 1/2001 Ohtani et al. ............... 514/562
6,225,336 B1 5/2001 Honma ....................... 514/443

FOREIGN PATENT DOCUMENTS

DE 42 25 488 2/1994
WO 92/09573 6/1992
WO 97/00853 1/1997
WO 97/853 A 1/1997
WO 99/15502 4/1999

OTHER PUBLICATIONS

T. Tsuri et al., "Bicyclo[2.2.1.]heptane and 6,6-Dimethylbicyclo[3.1.1]heptane Derivatives: Orally Active, Potent, and Selective Prostaglandin D$_2$ Receptor Antagonists", Journal of Medicinal Chemistry, vol. 40, pp. 3504-3507, 1997.
W. Skuballa et al., "Synthesis of a New Chemically and Metabolically Stable Prostacyclin Analogue with High and Long-Lasting Oral Activity", Journal of Medicinal Chemistry, vol. 29, No. 3, pp. 313-315, 1986.
P. Deicke et al., "Synthesis of New Metabolically Stabilized TXA$_2$/PGH$_2$-Receptor Antagonists and Their Biological Properties", Bioorganic & Medicinal Chemistry Letters, vol. 2, No. 9, pp. 1069-1072, 1992.
S. Sturzebecher et al., "Pharmacological Profile of a Novel Carbacyclin Derivative with High Metabolic Stability and Oral Activity in the Rat", Prostaglandins, vol. 31, pp. 95-109, 1986.
M. Hildebrand et al., "Pharmacokinetics of Iloprost and Cicaprost in Mice", Prostaglandins, vol. 44, pp. 431-442, 1992.
U. Klar et al., "Novel Prostanoid Thromboxane A$_2$ Antagonists", Bioorganic & Medicinal Chemistry Letters, vol. 5, No. 12, pp. 1219-1224, 1995.

* cited by examiner

Primary Examiner—Paul A. Zucker
(74) Attorney, Agent, or Firm—Wenderoth, Lind & Ponack, L.L.P.

(57) ABSTRACT

A compound of the formula (I):

(I)

wherein A is alkylene optionally having an unsaturated bond; R is —C(=O)—R$^1$; R$^1$ is hydroxy or the like; m is 0 or 1; p is 0 or 1; X$^1$ and X$^3$ are each independently optionally substituted aryl or optionally substituted heteroaryl or the like; X$^2$ is a bond, —CH$_2$—, —S—, —SO$_2$—, —CH$_2$—O—, —O—CH$_2$—, —CH$_2$—S—, —S—CH$_2$—, or the like; X$^4$ is —CH$_2$—, —CH$_2$—CH$_2$—, —C(=O)—, or the like, having a dual antagonistic activity against both a thromboxane A$_2$ receptor and a prostaglandin D$_2$ receptor is found.

24 Claims, No Drawings

DRUG COMPOSITION ANTAGONISTIC TO BOTH PGD$_2$/TXA$_2$ RECEPTORS

This application is a U.S. national stage of International Application No. PCT/JP01/04430 filed May 28, 2001.

TECHNICAL FIELD

This invention relates to a pharmaceutical composition comprising a dual antagonist against thromboxane A$_2$ and prostagrandin D$_2$ receptors and in detail, a compound having a [2.2.1] or [3.1.1.] bicyclo skeleton.

BACKGROUND ART

As a pharmaceutical composition comprising a dual antagonist against PGD$_2$/TXA$_2$ receptors, a compound of the formula:

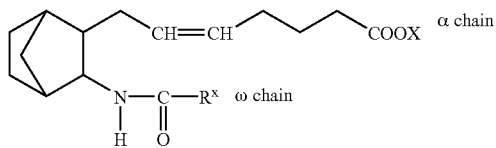

wherein R$^X$ is optionally substituted single ring or fused heterocyclyl; X is hydrogen or alkyl, was described in WO 99/15502. The above mentioned compound has a substituent of the formula: —CH$_2$—CH=CH—CH$_2$—CH$_2$—CH$_2$—COOX wherein X is hydrogen or alkyl, as an α chain and R on an ω chain is a single or fused heterocycl optionally substituted with amino, halogen, hydroxy and the like.

Further, the other compounds having a [2.2.1] bicyclo skeleton similar to the compounds of the present invention have been described in WO97/00853 and the like. In this publication, it is described that the compounds are useful as prostagrandin D$_2$ (PGD$_2$) antagonists.

However, in these publications, almost none of compound having other substituents than those represented by the formula:

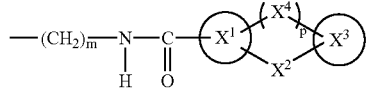

wherein X$^1$ and X$^3$ are each independently optionally substituted aryl, optionally substituted heteroaryl or optionally substituted non-aromatic heterocyclyl; X$^2$ is a bond, —CH$_2$—, —S—, —SO$_2$— and the like; X$^4$ is —CH$_2$— and the like; m is 0 or 1; p is 0 or 1 as the ω chain, and furthermore, the formula: —CH$^2$—CH=CH—CH$_2$—CH$_2$—CH$_2$—COOR$^2$ wherein R$^2$ is hydrogen or alkyl, as the α chain of bicyclic ring, has been described.

PGD$_2$ receptor antagonists have a quite different character from that of TXA$_2$ receptor antagonists in the site and mechanism of action and indications thereof.

On the other hand, a compound having a dual antagonistic activity against both a TXA$_2$ receptor and a PGD$_2$ receptor can be useful as therapeutic agents for various diseases caused by TXA$_2$ or PGD$_2$.

For example, in the case of bronchial asthma, it is known that TXA$_2$ cause potent tracheal contraction and respiratory anaphylaxis and PGD$_2$ effects infiltration of eosionophils. From these comprehension, TXA$_2$ and PGD$_2$ are thought to be one of causative substances of the pathopoiesis and advance of asthma, thus the dual antagonistic compounds are expected to be more potent agents for treating asthma than ever known antagonists.

Further, in the case of allergic rhinitis, it is recognized that TXA$_2$ and PGD$_2$ cause the swelling of nasal mucosa through the aggravation of vascular permeability, and PGD$_2$ induces the nasal blockage through the enlargement of vascular volume. Therefore, the dual antagonistic compounds are expected to be more potent agents for treating nasal blockage than ever known antagonists.

These diseases and condition thereof might be treated by administering both a TXA$_2$ receptor antagonist and a PGD$_2$ receptor antagonist at the same time, for example, in combination therapy or as a mixture thereof. But the administration of two or more agents often causes some problems due to the difference of their metabolic rate. For example, when the antagonists are different from each other in the time to reach a maximum blood concentration or the duration of action, they do not always efficiently exhibit each receptor antagonistic effect at the same time, failing to give a desired additive or synergic effect.

It has therefore been desired to develop medicines having a dual antagonistic activity against TXA$_2$/PGD$_2$ receptors, which exhibit new excellent therapeutic effects and can be used for many indications.

On the other hand, it was disclosed that 3-oxa-derivatives were prepared as metabolically stable TXA$_2$/PGH$_2$ receptor antagonists in Bioorganic & Medicinal Chemistry Letters, Vol.2, No.9, pp. 1069–1072, 1992. The active value of the compound was only described but the metabolic stability has not been described in the literature.

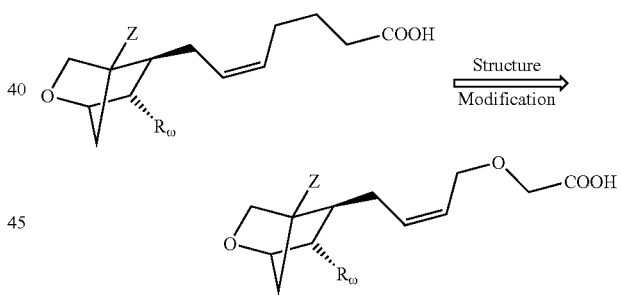

wherein, Z is p-fluorophenyl; Rω is benzenesulfonamino and the like.

Furthermore, it was reported in PROSTAGLANDINS, 1986, 31, 95 that ILOPROST, PGI$_2$ mimetics was stabilized metabolically by converting to the 3-oxa-derivative. But, remaining activity of each compound was only compared under a presence of the metabolic enzyme of a rat and the metabolic stability did not mentioned, since there was a possibility of a production of active metabolites

DISCLOSURE OF INVENTION

The present inventors have studied intensively to develop a pharmaceutical composition having a dual antagonistic activity against TXA$_2$/PGD$_2$ receptors and found out new compounds and pharmaceutical compositions comprising them.

The present invention provides:

(1) a compound of the formula (I):

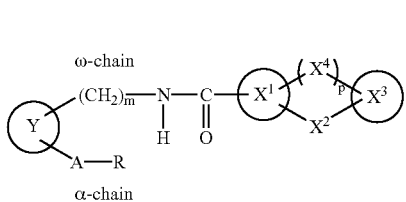

wherein

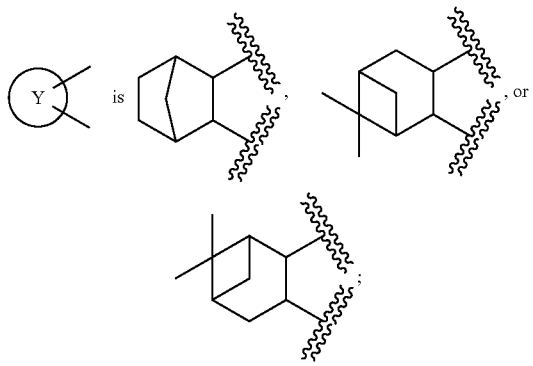

A is alkylene optionally intervened with a heteroatom, optionally having an oxo group, optionally substituted with halogen and/or optionally having an unsaturated bond;

R is —C(=O)—$R^1$, —$CH_2$—$R^1$, or tetrazolyl;

$R^1$ is hydroxy, alkyloxy, or optionally substituted amino;

m is 0 or 1;

provided that combinations wherein m is 1, A is —CH=CH—$CH_2$—$CH_2$—$CH_2$— and R is —C(=O)—$R^1$ ($R^1$ is hydroxy or alkyloxy) and wherein A is —$CH_2$—CH=CH—$CH_2$—$CH_2$—$CH_2$— and R is —C(=O)—$R^1$ wherein $R^1$ is hydroxy or alkyloxy are excluded, p is 0 or 1, provided when p=0, $X^1$ is not bonded to $X^3$ via $X^4$;

$X^1$ and $X^3$ are each independently optionally substituted aryl, optionally substituted heteroaryl or optionally substituted non-aromatic heterocyclyl;

$X^2$ is a bond, —$CH_2$—, —$CH_2$—$CH_2$—, —C(=O)—, —O—, —S—, —SO—, —$SO_2$—, —NH—, —N($CH_3$)—, —C(=N—O—$CH_3$)—, —N=N—, —CH=CH—, —(C=O)—NH—, —NH—(C=O)—, —$CH_2$—NH—, —NH—$CH_2$—, —$CH_2$—O—, —O—$CH_2$—, —$CH_2$—, —S—$CH_2$—, —$CH_2$—$SO_2$—, —$SO_2$—$CH_2$—, —$SO_2$—NH—, —NH—$SO_2$—, —C(=$CH_2$)—, —$SO_2$N(Me)—, —$CH_2NHSO_2$—, —$CH_2NH$—(C=O)—, —NH—C(=O)—NH or —NH—C(=O)—N(Me)—;

$X^4$ is —$CH_2$—, —$CH_2$—$CH_2$—, —C(=O)—, —SO—, —$SO_2$—, —(C=O)—NH—, —NH—(C=O)—, —$CH_2$—NH—, —NH—$CH_2$—, —$CH_2$—O—, —O—$CH_2$—, —$CH_2$—S—, —S—$CH_2$—, —$CH_2$—$SO_2$—, —$SO_2$—$CH_2$—, —$SO_2$—NH— or —NH—$SO_2$—, provided that a combination wherein

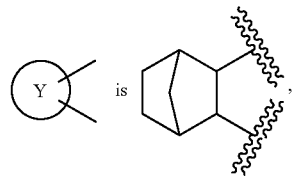

A is —CH=CH—$CH_2$—$CH_2$—$CH_2$—, R is —COOH, m is 1, p is 0, $X^1$ and $X^3$ are phenyl, and $X^2$ is —N=N—, is excluded and provided that when

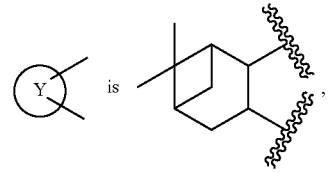

$X^1$ and $X^3$ are phenyl, $X^2$ is —CH=CH—, —O—, or —S—, m is 0, and p is 0, a compound wherein A is —CH=CH—$CH_2$—$CH_2$—$CH_2$—C($CH_3$)$_2$— and R is COOH, A is —$CH_2$—C(=O)—$CH_2$—$CH_2$—$CH_2$—$CH_2$— and R is COOH, A is —$CH_2$—$CH_2$—$CH_2$—$CH_2$—$CH_2$— and R is —COOH, or A is —CH=CH—$CH_2$—$CH_2$—$CH_2$— and R is —$CH_2$OH, is excluded, a prodrug, a pharmaceutically acceptable salt or a solvate thereof, (2) A compound as described in (1) wherein A is alkylene optionally intervened with a heteroatom, optionally having an oxo group, optionally substituted with halogen and/or optionally having a unsaturated bond;

R is —C(=O)—$R^1$, —$CH_2$—$R^1$, or tetrazolyl;

$R^1$ is hydroxy, alkyloxy, or optionally substituted amino;

provided compounds wherein A is —CH=CH—$CH_2$—$CH_2$—$CH_2$— and R is —C(=O)—$R^1$ ($R^1$ is hydroxy or alkyloxy), or A is —$CH_2$—CH=CH—$CH_2$—$CH_2$—$CH_2$— and R is —C(=O)—$R^1$ wherein $R^1$ is hydroxy or alkyloxy are excluded, a prodrug, a pharmaceutically acceptable salt or a solvate thereof, (3) A compound as described in (1) or (2), wherein A is alkylene intervened with a heteroatom, optionally having an oxo group, optionally substituted with halogen and/or optionally having an unsaturated bond, a prodrug, a pharmaceutically acceptable salt, or a solvate thereof, (4) A compound as described in (1) or (2), wherein A is C1 to C4 or C7 to C9 alkylene optionally intervened with a heteroatom, optionally having an oxo group, optionally substituted with halogen and/or optionally having an unsaturated bond, a prodrug, a pharmaceutically acceptable salt, or a solvate thereof, (5) A compound as described in (1) or (2), wherein A is —$CH_2$—$CH_2$—$CH_2$—, —$CH_2$—$CH_2$—CH(F)—, —$CH_2$CH=CH—, —$CH_2$—O—$CH_2$—, —$CH_2$CH=C(F)—, —$CH_2$—$CH_2$—$CH_2$—$CH_2$—, —$CH_2$CH=CH—

—CH₂—, —CH₂—CH₂—CH═CH—, —CH═CH—CH₂—CH₂—, —CH₂—CH₂—O—CH₂—, —CH₂—CH₂—S—CH₂—, —CH₂—CO—NH—CH₂—, —CH₂—CH₂—CH₂—CH₂—CH₂—, —CH₂CH═CH—CH₂—CH₂—, —CH₂ CH₂—CH₂—CH═CH—, —CH₂—CH₂—CH₂—O—CH₂—, —CH₂—CH₂—CH₂—S—CH₂—, —CH₂—CH₂—CO—NH—CH₂—, —CH₂—CH₂—CH₂—CH₂—CH₂—CH₂—, —CH₂—CH₂—CH₂—CH₂—CH(Me)—, —CH₂—CH₂—CH₂—CH₂—CH₂—C(Me)₂—, —CH₂—CH₂—CH₂—CH₂—CH₂—CH(F)—, —CH₂—CH═CH—CH₂—CH₂—CH(Me)—, —CH₂—CH═CH—CH₂—CH₂—C(Me)₂—, —CH₂—CH═CH—CH₂—CH₂—CH(F)—, —CH₂—CH₂—CH₂—CH₂—CH═CH—, —CH₂—CH₂—CH₂—CH₂—CH═C(Me)—, —CH₂—CH₂—CH₂—CH₂—C(Me)═CH—, —CH₂—CH₂—CH₂—CH₂—CH═C(F)—, —CH₂—CH₂—CH₂—CH₂—O—CH₂—, —CH₂—CH═CH—CH₂—O—CH₂—, —CH₂—CH═CH—CH₂—S—CH₂—, —CH₂—CH═C(F)—CH₂—O—CH₂—, —CH₂—CH₂—O—CH₂—CH═CH—, —CH₂—CH₂—CH₂—CH₂—S—CH₂—, —CH₂—CH₂—CH₂—CO—NH—CH₂—, —CH₂—CH₂CH═N—O—CH₂—, —CH₂—CH₂—S—CH₂—CH₂—CH₂—, —CH₂—CH₂—CH₂—CH₂—CH₂—CH₂—CH₂—, —CH₂—CH═CH—CH₂—CH₂—CH₂—CH₂—, —CH₂—CH₂—CH₂—CH₂—CH₂—O—CH₂—, —CH₂—CH₂—CH₂—CH₂—CH₂—CH₂—CH₂—, or —CH₂—CH═CH—CH₂—CH₂—CH₂—CH₂—CH₂—, a prodrug, a pharmaceutically acceptable salt, or a solvate thereof, (6) A compound as described in (5), wherein A is —CH₂—CH₂—CH₂—CH₂—, —CH₂—CH₂—CH₂—CH₂—CH═CH—, —CH₂—CH₂—CH₂—CH₂—O—CH₂—, —CH₂—CH═CH—CH₂—O—CH₂—, —CH₂—CH═CH—CH₂—S—CH₂—, or —CH₂—CH₂—CH₂—CH₂—S—CH₂—, a prodrug, a pharmaceutically acceptable salt, or a solvate thereof, (7) A compound as described in (6), wherein A is —CH₂—CH₂—CH₂—CH₂—O—CH₂—, a prodrug, a pharmaceutically acceptable salt, or a solvate thereof, (8) A compound as described in any one of (1) to (7), wherein $X^1$ and $X^3$ are each independently optionally substituted aryl or optionally substituted heteroaryl, a prodrug, a pharmaceutically acceptable salt, or a solvate thereof, (9) A compound as described in (8), wherein at least one of $X^1$ and $X^3$ is optionally substituted heteroaryl, a prodrug, a pharmaceutically acceptable salt, or a solvate thereof,

(10) A compound as described in (9), wherein $X^1$ and $X^3$ are each independently optionally substituted heteroaryl, a prodrug, a pharmaceutically acceptable salt, or a solvate thereof,

(11) A compound as described in (9), wherein at least one of $X^1$ and $X^3$ is optionally substituted thienyl or optionally substituted benzothienyl, a prodrug, a pharmaceutically acceptable salt, or a solvate thereof,

(12) A compound as described in any one of (1) to (11), wherein $X^2$ is a bond, —CH₂—, —S—, —SO₂—, —CH₂—O—, —O—CH₂—, —CH₂—S—, —S—CH₂—, or —NH—C(═O)—NH—, a prodrug, a pharmaceutically acceptable salt, or a solvate thereof,

(13) A compound as described in any one of (1) to (12), wherein m is 0 and p is 0, a prodrug, a pharmaceutically acceptable salt, or a solvate thereof,

(14) A compound as described in any one of (1) to (13), wherein R is —C(═O)—$R^1$ and $R^1$ is hydroxy, alkyloxy, or optionally substituted amino, a prodrug, a pharmaceutically acceptable salt, or a solvate thereof,

(15) A pharmaceutical composition containing a compound, a prodrug, a pharmaceutically acceptable salt, or a solvate thereof as described in any one of above (1) to (14),

(16) A pharmaceutical composition having a dual antagonistic activity against $PGD_2/TXA_2$ receptors as described in the above (15),

(17) A pharmaceutical composition as described in the above (15), which is used for treatment of asthma,

(18) A pharmaceutical composition as described in the above (15), which is used for the treatment of nasal blockage,

(19) A pharmaceutical composition as described in the above (15), which is used for the treatment of allergic conjunctivitis,

(20) A pharmaceutical composition as described in the above (15), which is used for the treatment of allergic rhinitis,

(21) Use of the compound as described in any one of (1) to (14) for the preparation of a pharmaceutical composition for treating asthma, nasal blockage, allergic conjunctivitis or allergic rhinitis,

(22) A method for treating nasal blockage, allergic conjunctivitis or allergic rhinitis, which comprises administrating a compound as described in any one of (1) to (14),

(23) A compound of formula: $X^3$—$X^2$—$X^1$—COOH wherein $X^3$ is pyrrolyl optionally substituted with alkyl, alkyloxy or halogen, indolyl optionally substituted with alkyl, alkyloxy or halogen, indolinyl optionally substituted with alkyl, alkyloxy or halogen, or 1,2,3,4-tetrahydroquinolyl optionally substituted with alkyl, alkyloxy or halogen; $X^2$ is —SO₂—, —S— or —CH₂—; $X^1$ is thienyl, or a salt thereof,

(24) A compound as described in (23), wherein a substituent of the formula: —$X^1$—$X^2$—$X^3$ is 5-(1-pyrrolylsulfonyl)thiophen-2-yl, 5-[(2-methyl-1-pyrrolyl)sulfonyl]thiophen-2-yl, or 5-[(2,5-dimethyl-1-pyrrolyl)sulfonyl]thiophen-2-yl, or a salt thereof.

BEST MODE FOR CARRYING OUT THE INVENTION

Special feature of a compound in the present invention is
(A) a bicyclic ring represented by the Y ring of the above formula (I) is [2.2.1] or [3.1.1] skeleton,
(B) an ω chain attached to the bicyclic ring, a group represented by the formula:

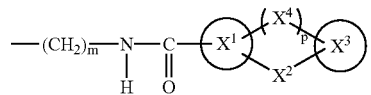

of the above formula (I), includes —NH—CO—, and $X^1$ and $X^3$ are each independently optionally substituted aryl, optionally substituted heteroaryl or optionally substituted non-aromatic heterocyclyl;

(C) $X^1$ bonds to $X^3$ via $X^2$, (D) an α chain is represented by the formula: —A—R, wherein A is alkylene optionally intervened with a heteroatom, optionally having an oxo group, optionally substituted with halogen and/or optionally having an unsaturated bond; R is —C(=O)—$R^1$, —$CH_2$—$R^1$, or tetrazolyl; $R^1$ is hydroxy, alkyloxy, or optionally substituted amino, and the like.

Provided that a compound wherein A is —$CH_2$—CH=CH—$CH_2$—$CH_2$—$CH_2$— and R is —C(=O)—$R^1$ ($R^1$ is hydroxy or alkyloxy), is not included in the present invention, since the compound is metabolically unstable coused by oxidizaton of an α-chain at β-position.

Therefore, a compound of the present invention has a special feature at A and R and has an improved metabolic property. Further, a compound of the present invention is a dual antagonistic activity against $PGD_2/TXA_2$ receptors having the above mentioned features (A) to (D).

A preferred embodiment is a compound of the formula (I) wherein
(1) $X^1$ and $X^3$ are each independently optionally substituted aryl or optionally substituted heteroaryl,
(2) at least one of $X^1$ and $X^3$ is optionally substituted heteroaryl,
(3) $X^1$ and $X^3$ are each independently optionally substituted heteroaryl,
(4) at least one of $X^1$ and $X^3$ is optionally substituted thienyl or optionally substituted benzothienyl,
(5) $X^2$ is a bond, —$CH_2$—, —S—, —$SO_2$—, —$CH_2$—O—, —O—$CH_2$—, —$CH_2$—S—, —S—$CH_2$— or —NH—C(=O)—NH—,
(6) m is 0 and p is 0,
(7) R is —C(=O)—$R^1$, wherein $R^1$ is hydroxy, alkyloxy or optionally substituted amino,
(8) in a case of a combination of any one of (1) to (4) with (5),
(9) in a case of a combination of any one of (1) to (4) with (6),
(10) in a case of a combination of any one of (1) to (4) with (7).

Each term used herein is defined to have meanings below in either case of a single or a joint use with other terms, unless otherwise noted.

"Alkylene" used herein means a straight chain and branched chain C1 to C9 and refers to methylene, methylmethylene, dimethylmethylene, ethylmethylmethylene, ethylene, trimethylene, tetramethylene, pentamethylene, hexamethylene, heptamethylene, octamethylene, nonamethylene, and the like. The above mentioned alkylene optionally contains a hetero atom (oxygen atom, sulfur, nitrogen atom or the like), optionally has an oxo group (=O), is optionally substituted with halogen (e.g. F, Cl, Br, I, preferable is F) and/or optionally contains one or more unsaturated bond (double bond or triple bond) on the chain at any position. Examples are —$CH_2$—$CH_2$—$CH_2$—, —$CH_2$—$CH_2$—CH(F)—, —$CH_2$—CH=CH—, —$CH_2$—O—$CH_2$—, —$CH_2$—CH=C(F)—, —$CH_2$—$CH_2$—$CH_2$—$CH_2$—, —$CH_2$—CH=CH—$CH_2$—, —$CH_2$—$CH_2$—CH=CH—, —CH=CH—$CH_2$—$CH_2$—, —$CH_2$—$CH_2$—$O_2$—$CH_2$—, —$CH_2$—$CH_2$—S—$CH_2$—, —$CH_2$—CO—NH—$CH_2$—, —$CH_2$—$CH_2$—$CH_2$—$CH_2$—$CH_2$—, —$CH_2$—CH=CH—$CH_2$—$CH_2$—, —$CH_2$—$CH_2$—CH=CH—$CH_2$—, —$CH_2$— $CH_2$—$CH_2$—O—$CH_2$—, —$CH_2$—$CH_2$—$CH_2$—S—$CH_2$—, —$CH_2$—$CH_2$—CO—NH—$CH_2$—, —$CH_2$—$CH_2$—$CH_2$—$CH_2$—$CH_2$—, —$CH_2$—$CH_2$—$CH_2$—$CH_2$—$CH_2$—, —$CH_2$—$CH_2$—CH(Me)—, —$CH_2$—$CH_2$—$CH_2$—$CH_2$—$CH_2$—C(Me)$_2$—, —$CH_2$—$CH_2$—$CH_2$—$CH_2$—$CH_2$—CH(F)—, —$CH_2$—CH=CH—$CH_2$—$CH_2$—$CH_2$—, —$CH_2$—CH=CH—$CH_2$—$CH_2$—CH(Me)—, —$CH_2$—CH=CH—$CH_2$—$CH_2$—C(Me)$_2$—, —$CH_2$—CH=CH—$CH_2$—$CH_2$—CH(F)—, —$CH_2$—$CH_2$—$CH_2$—$CH_2$—CH=CH—, —$CH_2$—$CH_2$—$CH_2$—$CH_2$—CH=C(Me)—, —$CH_2$—$CH_2$—$CH_2$—C(Me)=CH—, —$CH_2$—$CH_2$—$CH_2$—$CH_2$—CH=C(F)—, —$CH_2$—$CH_2$—$CH_2$—$CH_2$—O—$CH_2$—, —$CH_2$—CH=CH—$CH_2$—O—$CH_2$—, —$CH_2$—CH=CH—$CH_2$—S—$CH_2$—, —$CH_2$—CH=C(F)—$CH_2$—O—$CH_2$—, —$CH_2$—$CH_2$—O—$CH_2$—CH=CH—, —$CH_2$—$CH_2$—$CH_2$—$CH_2$—S—$CH_2$—, —$CH_2$—$CH_2$—$CH_2$—CO—NH—$CH_2$—, —$CH_2$—$CH_2$—CH=N—O—$CH_2$—, —$CH_2$—$CH_2$—S—$CH_2$—$CH_2$—$CH_2$—, —$CH_2$—$CH_2$—$CH_2$—$CH_2$—$CH_2$—$CH_2$—$CH_2$—, —$CH_2$—CH=CH—$CH_2$—$CH_2$—$CH_2$—$CH_2$—, —$CH_2$—$CH_2$—$CH_2$—$CH_2$—$CH_2$—O—$CH_2$—, and the like.

Especially, the following embodiment is preferred for the above mentioned "alkylene":

1) alkylene intervened with a heteroatom, optionally having an oxo group, optionally substituted halogen and/or optionally containing unsaturated bond(s), 2) C1 to C4 or C7 to C9 alkylene optionally intervened with a heteroatom, optionally having an oxo group, optionally substituted halogen and/or optionally containing unsaturated bond(s), 3) —$CH_2$—$CH_2$—$CH_2$—, —$CH_2$—$CH_2$—CH(F)—, —$CH_2$—CH=CH—, —$CH_2$—O—$CH_2$—, —$CH_2$—$CH_2$—CH(F)—, —$CH_2$—$CH_2$—$CH_2$—$CH_2$—, —$CH_2$—CH=CH—$CH_2$—, —$CH_2$—$CH_2$—CH=CH—, —CH=CH—$CH_2$—$CH_2$—, —$CH_2$—$CH_2$—$O_2$—$CH_2$—, —$CH_2$—$CH_2$—S—$CH_2$—, —$CH_2$—CO—NH—$CH_2$—, —$CH_2$—$CH_2$—$CH_2$—$CH_2$—$CH_2$—, —$CH_2$—CH=CH—$CH_2$—$CH_2$—, —$CH_2$—$CH_2$—$CH_2$—CH=CH—, —$CH_2$—$CH_2$—$CH_2$—O—$CH_2$—, —$CH_2$—$CH_2$—$CH_2$—S—$CH_2$—, —$CH_2$—$CH_2$—CO—NH—$CH_2$—, —$CH_2$—$CH_2$—$CH_2$—$CH_2$—$CH_2$—, —$CH_2$—$CH_2$—$CH_2$—$CH_2$—$CH_2$—, —$CH_2$—$CH_2$—CH(Me)—, —$CH_2$—$CH_2$—$CH_2$—$CH_2$—$CH_2$—C(Me)$_2$—, —$CH_2$—$CH_2$—$CH_2$—$CH_2$—$CH_2$—CH(F)—, —$CH_2$—CH=CH—$CH_2$—CH(Me)—, —$CH_2$—CH=CH—$CH_2$—$CH_2$—C(Me)$_2$—, —$CH_2$—CH=CH—$CH_2$—$CH_2$—CH(F)—, —$CH_2$—$CH_2$—$CH_2$—$CH_2$—CH=CH—, —$CH_2$—$CH_2$—$CH_2$—$CH_2$—CH=C(Me)—, —$CH_2$—$CH_2$—$CH_2$—$CH_2$—C(Me)=CH—, —$CH_2$—$CH_2$—$CH_2$—$CH_2$—CH=C(F)—, —$CH_2$—$CH_2$—$CH_2$—$CH_2$—O—$CH_2$—, —$CH_2$—CH=CH—$CH_2$—O—$CH_2$—, —$CH_2$—CH=CH—$CH_2$—S—$CH_2$—, —$CH_2$—CH=C(F)—$CH_2$—O—$CH_2$—, —$CH_2$—$CH_2$—O—$CH_2$—CH=CH—, —$CH_2$—$CH_2$—$CH_2$—S—$CH_2$—, —$CH_2$—$CH_2$—CO—NH—$CH_2$—, —$CH_2$—$CH_2$—CH=N—O—$CH_2$—, —$CH_2$—$CH_2$—S—$CH_2$—$CH_2$—$CH_2$—, —$CH_2$—$CH_2$—$CH_2$—$CH_2$—$CH_2$—$CH_2$—$CH_2$—, —$CH_2$—CH=CH—$CH_2$—$CH_2$—$CH_2$—$CH_2$—, —$CH_2$—$CH_2$—$CH_2$—$CH_2$—$CH_2$—O—$CH_2$—, —CH₂—CH₂—CH₂—CH₂—CH₂—CH₂—CH₂—CH₂—, or —CH₂CH=CH—CH₂—CH₂—CH₂—CH₂—CH₂—, 4) —CH₂—CH₂—CH₂—CH₂—, —CH₂—CH₂—CH₂—CH₂—CH=CH—, —CH₂—CH₂—CH₂—CH₂—O—CH₂—, —CH₂—CH=CH—CH₂—O—CH₂—, —CH₂—CH=CH—CH₂—O—CH₂—, or —CH₂—CH₂—CH₂—CH₂—S—CH₂—, and

5) —CH₂—CH₂—CH₂—CH₂—O—CH₂—.

The term "heteroaryl" includes a group which has a bond at any substitutable and which can be converted from a 5- to 7-membered aromatic heterocycle containing one or more oxygen atom, sulfur atom and/or nitrogen atom in the ring, or such an aromatic heterocycle as fused with one or more carbocycle or other aromatic heterocycle. Any one of aromatic heterocycle and aromatic carbocycle may have a bond. "Heteroaryl" may have a bond at a nitrogen atom as well as a carbon atom of aromatic heterocycle or aromatic carbocycle. Examples of "heteroaryl" include pyrrolyl (e.g., 1-pyrrolyl, 2-pyrrolyl, 3-pyrrolyl), pyridyl (e.g., 2-pyridyl, 3-pyridyl, 4-pyridyl), pyrazolyl (e.g., 1-pyrazolyl, 3-pyrazolyl, 4-pyrazolyl), imidazolyl (e.g., 1-imidazolyl, 2-imidazolyl, 4-imidazolyl), pyrimidinyl (e.g., 2-pyrimidinyl, 4-pyrimidinyl, 5-pyrimidinyl), pyrazinyl (e.g., 2-pyrazinyl), indolyl (e.g., 1-indolyl, 2-indolyl, 3-indolyl, 4-indolyl, 5-indolyl, 6-indolyl, 7-indolyl), carbazolyl (e.g., 1-carbazolyl, 2-carbazolyl, 3-carbazolyl, 4-carbazolyl, 9-carbazolyl), benzimidazolyl (e.g., 1-benzimidazolyl, 2-benzimidazolyl, 4-benzimidazolyl, 5-benzimidazolyl), indazolyl (e.g., 1-indazolyl, 2-indazolyl, 3-indazolyl, 4-indazolyl, 5-indazolyl, 6-indazolyl, 7-indazolyl), quinolyl (e.g., 2-quinolyl, 3-quinolyl, 4-quinolyl, 5-quinolyl, 6-quinolyl, 7-quinolyl, 8-quinolyl), isoquinolyl (e.g., 1-isoquinolyl, 3-isoquinolyl, 4-isoquinolyl, 5-isoquinolyl, 6-isoquinolyl, 7-isoquinolyl, 8-isoquinolyl), furyl (e.g., 2-furyl, 3-furyl), benzofuryl (e.g., 2-benzofuryl, 3-benzofuryl, 4-benzofuryl, 5-benzofuryl, 6-benzofuryl, 7-benzofuryl), thienyl (e.g., 2-thienyl, 3-thienyl), benzothienyl (e.g., benzo[b]thiophen-2-yl, benzo[b]thiophen-3-yl, benzo[b]thiophen-4-yl, benzo[b]thiophen-5-yl, benzo[b]thiophen-6-yl, benzo[b]thiophen-7-yl), dibenzothienyl (e.g., 2-dibenzothienyl, 3-dibenzothienyl), dibenzofuryl (e.g., 2-dibenzofuryl, 3-dibenzofuryl), naphthothienyl (e.g., naphtho[2,3-b]thiophen-2-yl, naphtho[2,3-b]thiophen-3-yl, naphtho[1.2-b]thiophen-2-yl, naphtho[1.2-b]thiophen-3-yl), oxazolyl (e.g., 2-oxazolyl, 4-oxazolyl, 5-oxazolyl), isoxazolyl (e.g., 3-isoxazolyl, 4-isoxazolyl, 5-isoxazolyl), thiazolyl (e.g., 2-thiazolyl, 4-thiazolyl, 5-thiazolyl), isothiazolyl (e.g., 3-isothiazolyl, 4-isothiazolyl, 5-isothiazolyl), imidazothiazolyl (e.g., imidazo[2.1-b]thiazol-2-yl, imidazo[2.1-b]thiazol-3-yl), benzoisoxazolyl (e.g., benzo[d]isoxazol-3-yl), benzothiazolyl (e.g., benzo[d]thiazol-2-yl), and the like.

The term of "aromatic carbocycle or other aromatic heterocycle" which may fuse the above "heteroaryl" includes 5- to 7-membered aromatic cycle which may contains one or more oxygen atom, sulfur atom and/or nitrogen atom in the ring, or such an aromatic ring as fused with one or more other aromatic rings.

The term of "aryl" includes mono aromatic carbocyclyl (e.g., phenyl) or fused aromatic carbocyclyl (e.g., 1-naphthyl, 2-naphthyl, 1-anthryl, 9-anthryl, 1-phenanthryl, 10-phenanthryl).

The term of "non-aromatic heterocyclyl" includes a group which has a bond at any substitutable and which can be converted from 3- to 7-membered non-aromatic heterocyclyl which contains one or more oxygen atom, sulfur atom and/or nitrogen atom in the ring, or non-aromatic heterocyclyl which is fused with a carbon ring (e.g. aromatic carbocycle) or other heterocyclyl (e.g. aromatic heterocycle). The substitutable bond may exist not only on the carbon atom but also on the nitrogen atom in the non-aromatic heterocyclyl. Examples are aziridinyl, piperidino, piperidinyl, morphorino, morphorinyl, pyrrolinyl, pyrrolidinyl, imidazolinyl, piperadino, piperadinyl, isooxazolinyl, thiolanyl, tetrahydrofuranyl, dioxanyl, oxathianyl, tetrahydropyranyl, and the like. Preferable is 5- or 6-membered non-aromatic heterocyclyl containing a nitrogen atom. The following groups are eexemplified as a group which has a bond at any substitutable and which can be converted from non-aromatic heterocyclyl fused with one or more carbon ring (e.g. aromatic carbocycle) or other heterocyclyl (e.g. aromatic heterocycle):

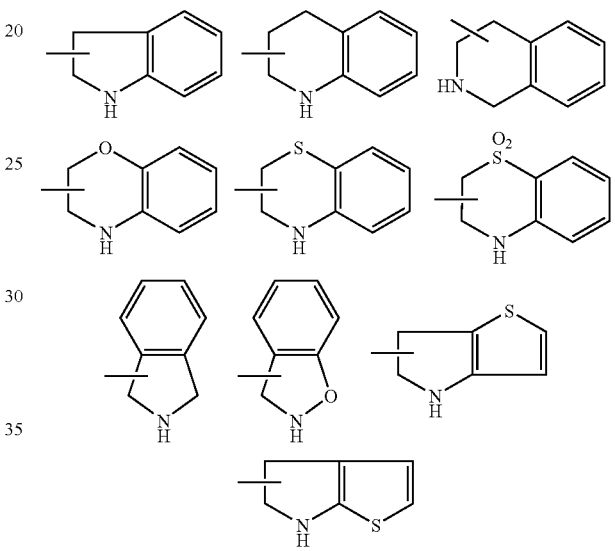

Furthermore, the substitutable bond may exist at any position of the carbon atom or the nitrogen atom.

"Aryl" or "heteroaryl" may be fused 4- to 7-membered cycloalkane or 4- to 7-membered non-aromatic heterocycle. Examples of cycloalkane include cyclobutane, cyclopentane, cyclohexane, and cycloheptane. Examples of non-aromatic heterocycle include pyrrolidine, piperazine, oxorane, 1,3-dioxorane, 1,4-dioxane, thiorane, or the like. The above "cycloalkane" and "non-aromatic heterocycle" may be fused with other aromatic carbocycle or aromatic heterocycle. Examples of aryl or heteroaryl fused with 4- to 7-membered cycloalkane or 4- to 7-membered non-aromatic heterocycle are illustrated below.

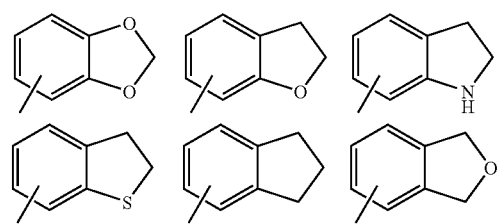

-continued

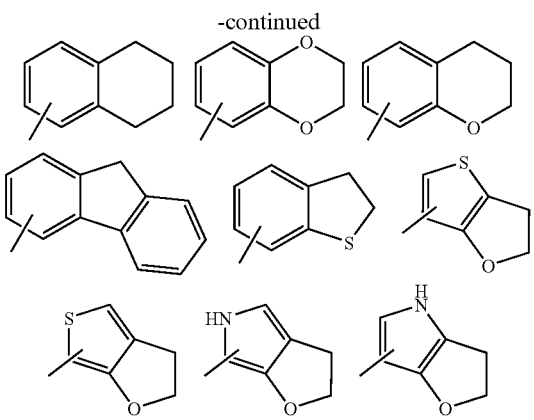

Examples of the substituent on "optionally substituted aryl", "optionally substituted heteroaryl" or "optionally substituted non-aromatic heterocyclyl" include a group of the formula: —$Z^1$—$Z^2$ wherein $Z^1$ is a bond, —O—, —S—, —NH—, —NH—C(=O)—, —NH—C(=O)—O—, —NH—$SO_2$—, —C(=O)—, —O—C(=O)—, —C(=O)—O—, or —$SO_2$—; and $Z^2$ is alkyl, haloalkyl, alkenyl, alkynyl, aryl optionally substituted with alkyl or halogen, heteroaryl optionally substituted with alkyl or halogen, arylalkyl optionally substituted with alkyl or halogen, heteroarylalkyl optionally substituted with alkyl or halogen, carboxy, halogen (F, Cl, Br, I), hydroxyalkyl, hydroxy, nitro, cyano, mercapto, thioformyl, thioacetyl, thiocarboxy, dithiocarboxy, thiocarbamoyl, sulfino, sulfo, sulfamoyl, sulfoamino, optionally substituted amino, optionally substituted aminoalkyl, hydroxyamino, carbamoyl, or hydorazino. One to three substituents may be at any suitable position on the above aryl, heteroaryl, or non-aromatic heterocyclyl.

"Alkyl" includes a straight or branched C1 to C8 alkyl group or a C3 to C8 cycloalkyl group. Examples are methyl, ethyl, n-propyl, isopropyl, n-butyl, isobutyl, tert-butyl, n-pentyl, isopentyl, n-hexyl, n-heptyl, n-octyl, cyclopropyl, cyclobutyl, cyclopentyl, cyclohexyl, cycloheptyl and the like.

"Haloalkyl" includes a straight or branched C1 to C8 alkyl or C3 to C8 cycloalkyl group substituted with one or more halogen, for example, chloromethyl, fluoromethyl, trifluoromethyl, 2,2,2-trifluoroethyl, 1,1-difluoroethyl, trichloromethyl, 2,2,2-trichloroethyl, 1,1-dichloroethyl or the like.

"Alkenyl" includes a straight or branched C2 to C8 alkenyl or C3 to C8 cycloalkenyl group having one or more double bond(s), for example, vinyl, 1-propenyl, 2-propenyl, isopropenyl, 2-cyclobuten-1-yl, 2-cyclopenten-1-yl, 3-cyclopenten-1-yl, 2-cyclohexen-1-yl or the like.

"Alkynyl" includes a straight or branched C2 to C8 alkynyl having one or more triple bond(s), for example, ethynyl, 1-propynyl, 2-propynyl, 1-butynyl, 2-butynyl, 3-butynyl or the like.

"Halogen" includes fluoro, chloro, bromo, and iodo.

"Alkyl" used in the term "arylalkyl" or "heteroarylalkyl" have the same meaning of the above "alkyl", "aryl" used in the term "arylalkyl" have the same meaning of the above "aryl" and "heteroaryl" used in the term "heteroarylalkyl" have the same meaning of the above "heteroaryl".

"Hydroxy alkyl" includes the above "alkyl" substituted with one or two hydroxy, for example, hydroxymethyl, 1-hydroxyethyl, 2-hydroxyethyl, 1,2-dihydroxyethyl, 1,2-dihydroxy-n-propyl or the like.

Examples of the substituent of "optionally substituted amino" or "optionally substituted amino alkyl" include the above "alkyl", the above "arylalkyl", the above "aryl", the above "heteroaryl", the above "heteroarylalkyl" hydroxy. Alkylsulfonyl, or the like. They may be mono- or di-substituted with these substituents. When the substituent is alkyl, alkyl may form a ring together with a nitrogen atom of an amino group.

Example of "optionally substituted amino" includes amino, N,N-dimethylamino, N-ethyl-N-methylamino, N,N-(diethylamino, pyrrolidino, piperidino, N-methyl-N-phenylamino, isopropylamino, diisopropylamino, hydroxyamino, alkylsulfonylamino (e.g., methanesulfonylamino, ethanesulfonylamino, etc.), arylsulfonyl (e.g., benzenesulfonylamino, toluenesulfonylamino, etc.), N-alkyl-N-alkylsulfonylamino (e.g., N-methyl-N-methanesulfonylamino, etc.), halogenated alkylsulfonylamino (e.g., trifluoromethanesulfonylamino, etc.), or the like.

Examples of "optionally substituted aminoalkyl" include N,N-dimethylaminomethyl, N-ethyl-N-methylaminomethyl, N,N-diethylaminomethyl, pyrrolidinomethyl, piperidinomethyl, N-methyl-N-phenylaminomethyl, isopropylaminomethyl, diisopropylaminomethyl or the like.

"A pharmaceutical composition having a dual antagonistic activity against $PGD_2$/$TXA_2$ receptors" means a pharmaceutical composition comprising at least one compound of the formula (I) having an antagonistic activity against both a $PGD_2$ receptor and a $TXA_2$ receptor. In addition to a compound of the formula (I), the other active agents (e.g. antiinflammatory agents, antiallergy agents and the like) and pharmaceutically acceptable admixtures (e.g., binding agent, filler and the like) may be included.

The compound of the present invention has an antagonistic activity against $PGD_2$ receptor and $TXA_2$ receptor and can exhibit antagonistic activities against $PGD_2$ receptor and $TXA_2$ receptor in vivo. For example, even if a compound has both antagonistic activities against receptors in vitro, the compound administered can not always exhibit both of the antagonistic activity in vivo, owing to the preferential binding to the receptor of stronger affinity. Therefore, as a compound of the present invention, preferable is that the compound has antagonistic activities against $PGD_2$ and $TXA_2$ receptors and is 100 times, preferably 50 time and more preferably ca. 10 times in a ratio between affinities against $PGD_2$ and $TXA_2$ receptors. The ratio between affinities against $PGD_2$ and $TXA_2$ receptors can be calculated by the use of $IC_{50}$ values and the like.

Furthermore, as a compound of the present invention, preferable is less than 0.1 μM in the binding activity against $TXA_2$ receptor using human platelet membrane ($IC_{50}$ value) and 0.1 μM in the antagonistic activity against $PGD_2$ receptor using human platelet ($IC_{50}$ value). In particular, the compound is preferable, in which both of the binding activity against $TXA_2$ receptor using human platelet membrane ($IC_{50}$ value) and the antagonistic activity against $PGD_2$ receptor using human platelet ($IC_{50}$ value) are less than 0.1 μM. Furthermore, the compound is preferable, in which their ratio is 100 times, preferably 50 time and more preferably ca. 10 times.

The present invention includes a method for treating asthma, nasal blockage, allergic conjunctivitis or allergic rhinitis which comprises administering a compound of the formula (I) and use of a compound of the formula (I) for manufacturing a medicine for asthma, nasal blockage allergic conjunctivitis or allergic rhinitis.

Furthermore, in a compound displayed in formula (I), "α chain" means a group represented by the formula: —A—R¹, and "ω chain" means a group represented by the formula:

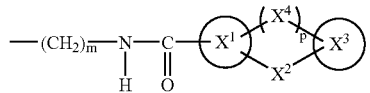

Preferable is following substituents as the α chain. Furthermore, E and Z mean E-form and Z-form in double bond of each formula, respectively. Each sign in 4A to 9B means an A part of the formula and means the same group in Table 1 to Table 15 in this description.

| | |
|---|---|
| 4A | —CH₂CH₂CH₂—R |
| 4B | —CH₂CH₂CH(F)—R |
| 4C | —CH₂CH=CH—R (E) |
| 4D | —CH₂CH=CH—R (Z) |
| 4E | —CH₂OCH₂—R |
| 5A | —CH₂CH₂CH₂CH₂—R |
| 5B | —CH₂CH=CHCH₂—R (Z) |
| 5C | —CH₂CH₂CH=CH—R (E) |
| 5D | —CH=CHCH₂CH₂—R (Z) |
| 5E | —CH₂CH₂OCH₂—R |
| 5F | —CH₂CH₂SCH₂—R |
| 5G | —CH₂CONHCH₂—R |
| 6A | —CH₂CH₂CH₂CH₂CH₂—R |
| 6B | —CH₂CH=CHCH₂CH₂—R (Z) |
| 6C | —CH₂CH₂CH₂CH=CH—R (E) |
| 6D | —CH=CHCH₂CH₂CH₂—R (Z) |
| 6E | —CH₂CH₂CH₂OCH₂—R |
| 6F | —CH₂CH₂CH₂SCH₂—R |
| 6G | —CH₂CH₂CONHCH₂—R |
| 7A | —CH₂CH₂CH₂CH₂CH₂CH₂—R |
| 7B | —CH₂CH₂CH₂CH₂CH₂CH(Me)—R |
| 7C | —CH₂CH₂CH₂CH₂CH₂C(Me)₂—R |
| 7D | —CH₂CH₂CH₂CH₂CH₂CH(F)—R |
| 7E | —CH₂CH=CHCH₂CH₂CH₂—R (Z) |
| 7F | —CH₂CH=CHCH₂CH₂CH(Me)—R (Z) |
| 7G | —CH₂CH=CHCH₂CH₂C(Me)—R (Z) |
| 7H | —CH₂CH=CHCH₂CH₂CH(F)—R (Z) |
| 7I | —CH₂CH₂CH₂CH₂CH=CH—R (E) |
| 7J | —CH₂CH₂CH₂CH₂CH=C(Me)—R (E) |
| 7K | —CH₂CH₂CH₂CH₂C(Me)=CH—R (E) |
| 7L | —CH₂CH₂CH₂CH₂CH=C(F)—R (E) |
| 7M | —CH₂CH₂CH₂CH₂OCH₂—R |
| 7N | —CH₂CH=CHCH₂OCH₂—R (Z) |
| 7O | —CH₂CH=CHCH₂OCH₂—R (E) |
| 7P | —CH₂CH=C(F)CH₂OCH₂—R (E) |
| 7Q | —CH₂CH₂OCH₂CH=CH—R (E) |
| 7R | —CH₂CH₂CH₂CH₂SCH₂—R |
| 7S | —CH₂CH₂CH₂CONHCH₂—R² |
| 7T | —CH₂CH₂CH=N—OCH₂—R² |
| 7U | —CH₂CH₂SCH₂CH₂CH₂—R² |
| 7V | —CH₂CH₂CH₂CH₂CH=C(F)—R² (Z) |
| 8A | —CH₂CH₂CH₂CH₂CH₂CH₂CH₂—R² |
| 8B | —CH₂CH=CHCH₂CH₂CH₂CH₂—R² (Z) |
| 8C | —CH₂CH₂CH₂CH₂CH₂OCH₂—R² |
| 9A | —CH₂CH₂CH₂CH₂CH₂CH₂CH₂CH₂—R² |
| 9B | —CH₂CH=CHCH₂CH₂CH₂CH₂CH₂—R² (Z) |

R is exemplified by —C(=O)—R¹, —CH₂—R¹, or tetrazolyl and preferable is —C(=O)—R¹, wherein, R¹ is hydroxy, alkyloxy, or optionally substituted amino. Examples of R are COOH, COOMe, CONH₂, CONHSO₂Me, CH₂OH, CH₂OMe, CONHMe, CON(Me)SO₂Me, 5-tetrazolyl, CONHSO₂Ph, CONHSO₂CF₃ and the like.

Furthermore, the combination of A and R includes all of the combination and preferable is a combination described in Table 1 to Table 15.

As an ω chain, the following embodiments are preferred in the formula:

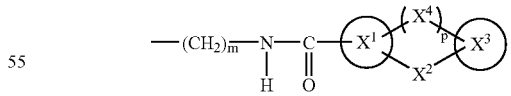

1) wherein m is 0 and p is 0,
2) wherein X¹ and X³ are each independently optionally substituted aryl or optionally substituted heteroaryl,
3) wherein at least one of X¹ and X³ is optionally substituted heteroaryl,
4) wherein X¹ and X³ are each independently optionally substituted heteroaryl,
5) wherein at least one of X¹ and X³ is optionally substituted thienyl or optionally substituted benzothienyl, 6) wherein $X^2$ is a bond, —$CH_2$—, —S—, —$SO_2$—, —$CH_2$—O—, —O—$CH_2$—, —$CH_2$—S—, —S—$CH_2$—, or NH—C(=O)—NH—.
Concretely, preferable is a combination described below for the formula: —$X^1$—$X^2$—$X^3$. Furthermore, each sign of 1 to 513 below means a group shown by the formula: —$X^1$—$X^2$—$X^3$ and the compound number both in Table 1 to Table 15 and in Examples of reference in the present invention means the same group.
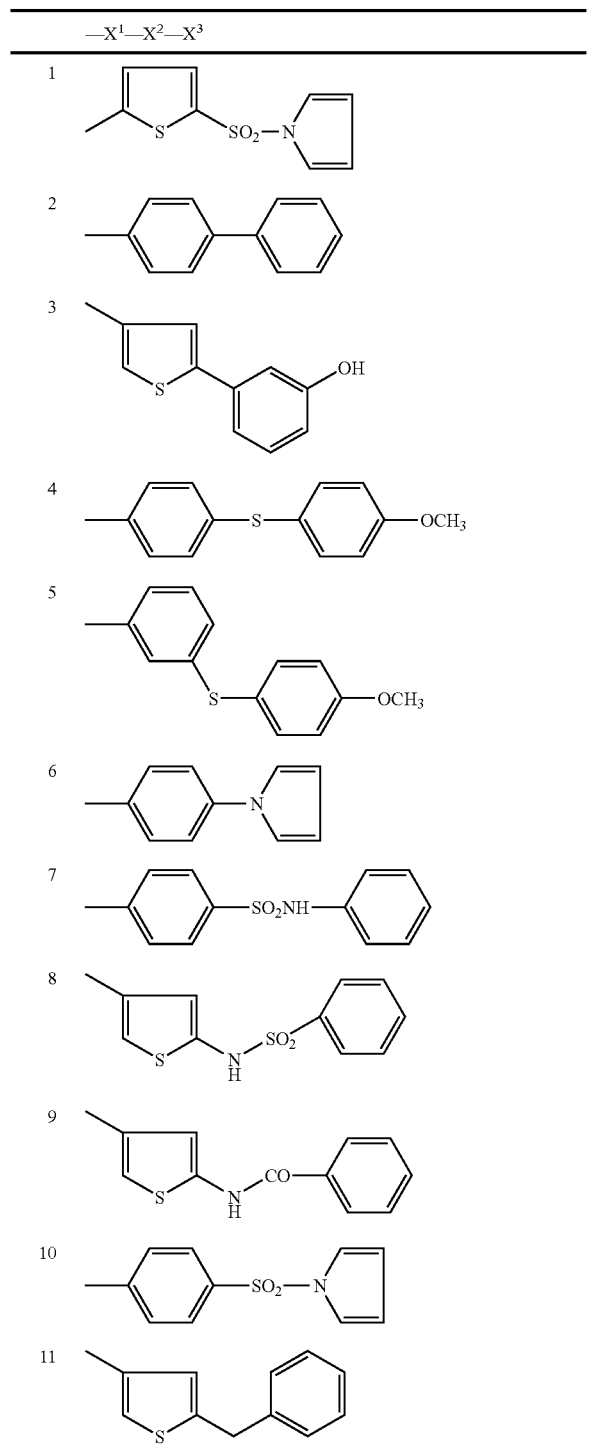
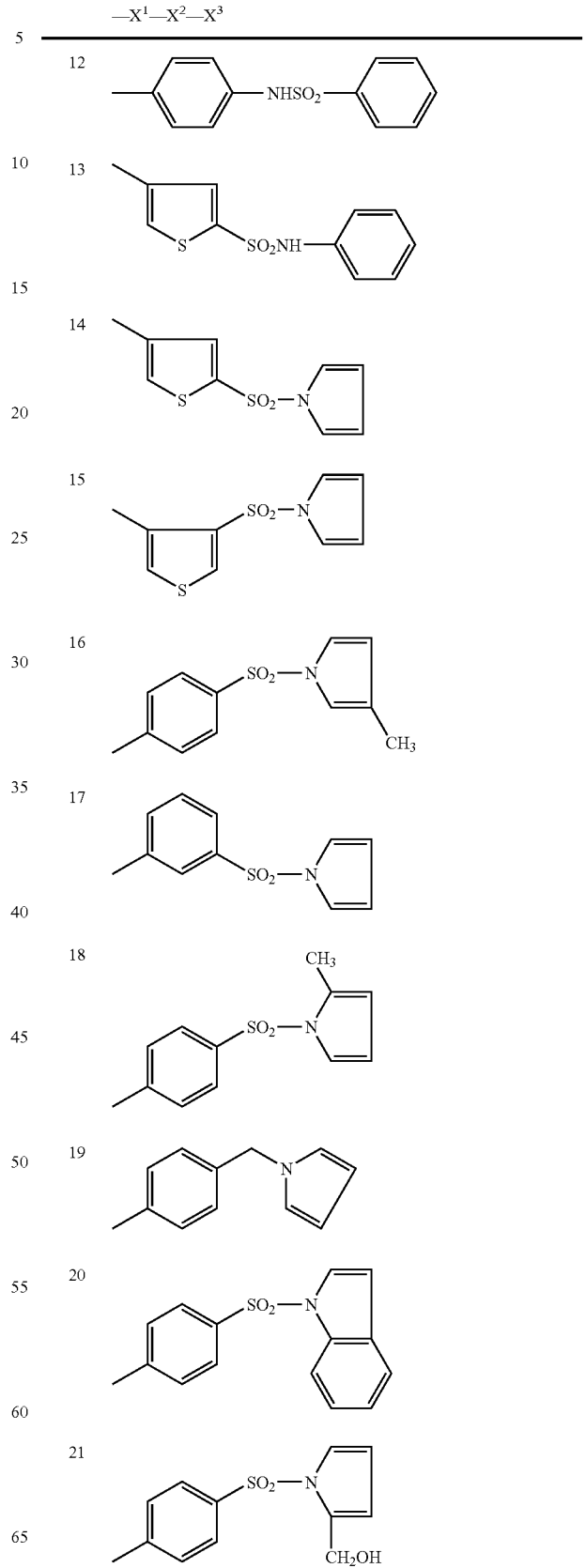

-continued
| —X¹—X²—X³ |
|---|
| 22 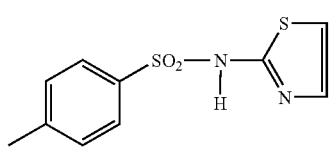 |
| 23 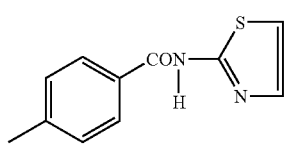 |
| 24 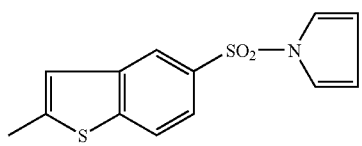 |
| 25 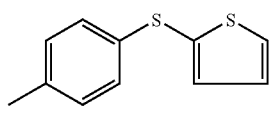 |
| 26 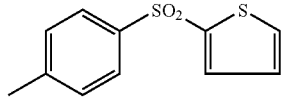 |
| 27 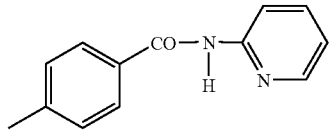 |
| 28 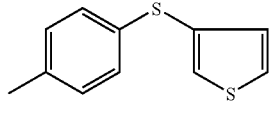 |
| 29 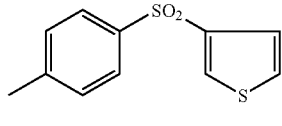 |
| 30 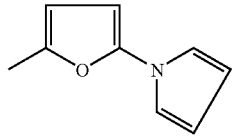 |
| 31 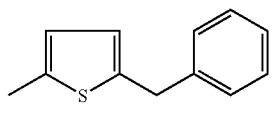 |
| 32 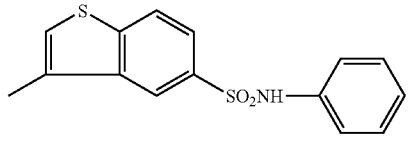 |
-continued
| —X¹—X²—X³ |
|---|
| 33 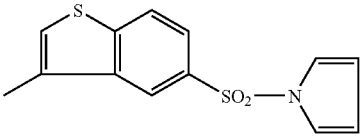 |
| 34 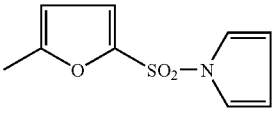 |
| 35 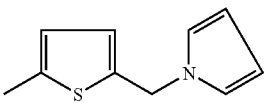 |
| 36 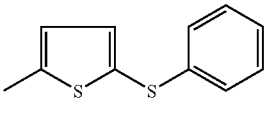 |
| 37 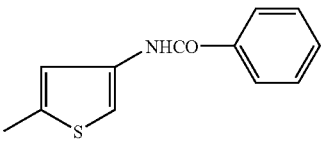 |
| 38 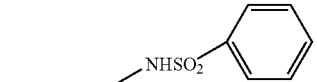 |
| 39  |
| 40 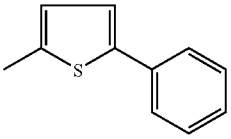 |
| 41 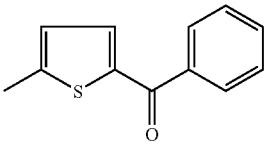 |
| 42 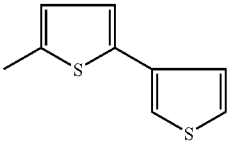 |
| 43 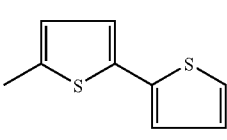 |

-continued
—X¹—X²—X³
| | |
|---|---|
| 44 | 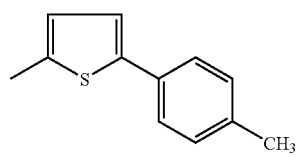 |
| 45 | 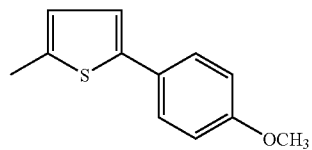 |
| 46 | 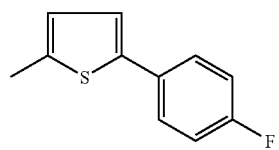 |
| 47 | 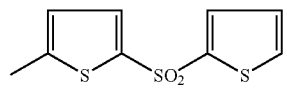 |
| 48 | 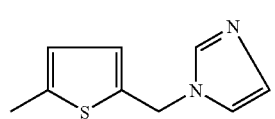 |
| 49 | 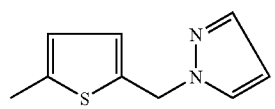 |
| 50 | 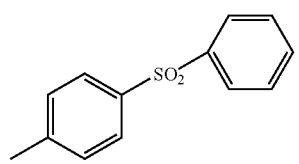 |
| 51 | 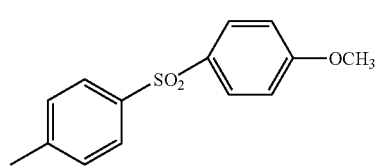 |
| 52 | 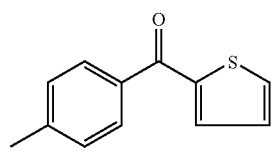 |
| 53 | 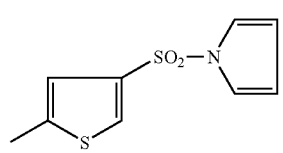 |
-continued
—X¹—X²—X³
| | |
|---|---|
| 54 | 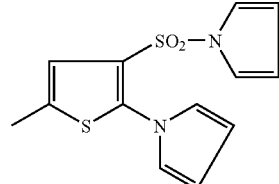 |
| 55 | 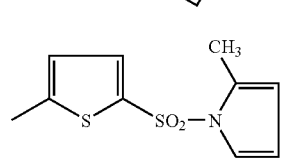 |
| 56 | 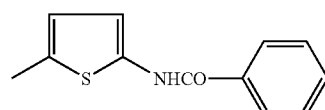 |
| 57 | 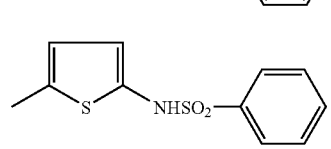 |
| 58 | 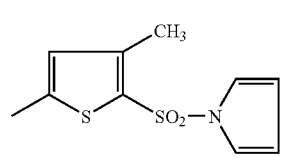 |
| 59 | 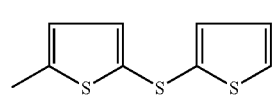 |
| 60 | 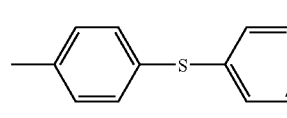 |
| 61 | 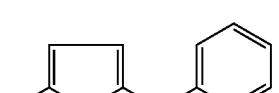 |
| 62 | 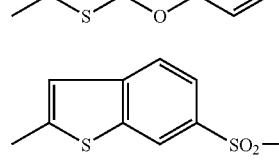 |
| 63 | 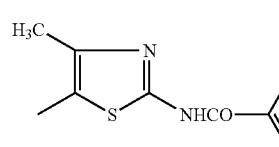 |
| 64 | 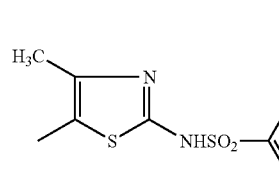 |

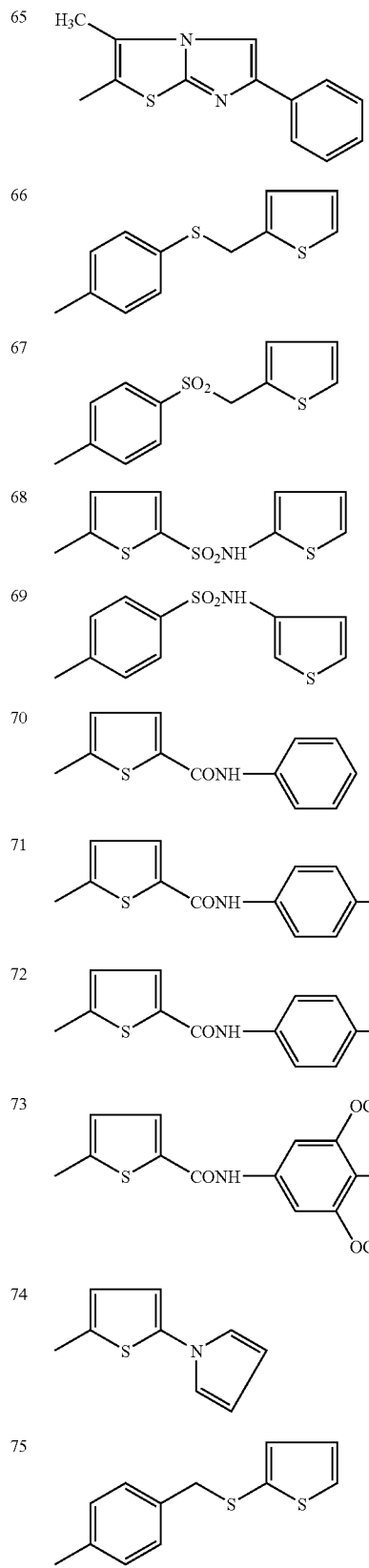
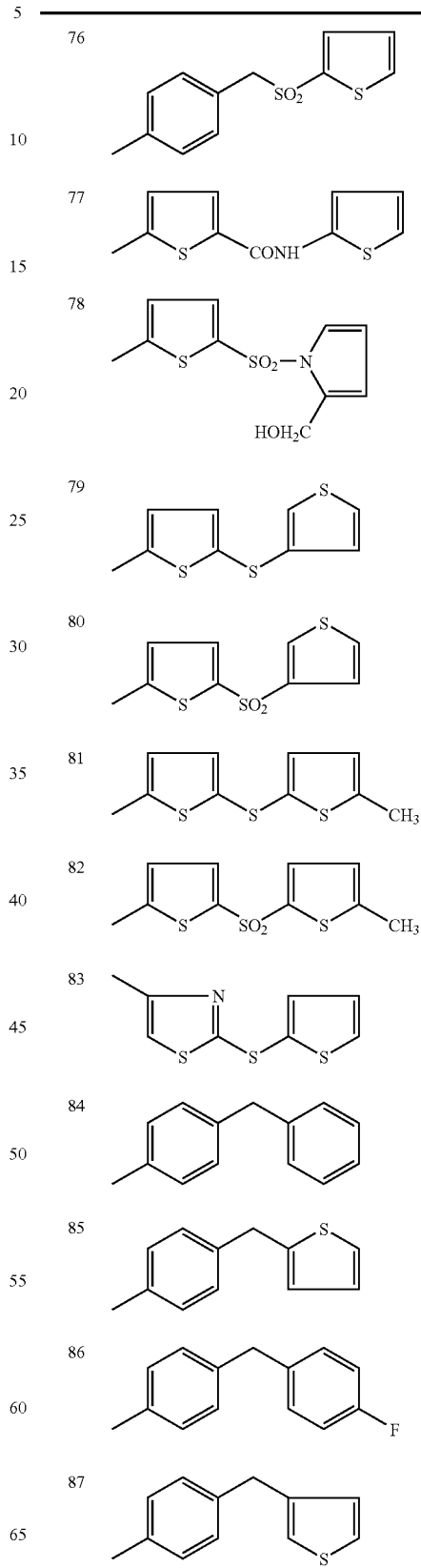

-continued
| | —X¹—X²—X³ |
|---|---|
| 88 | 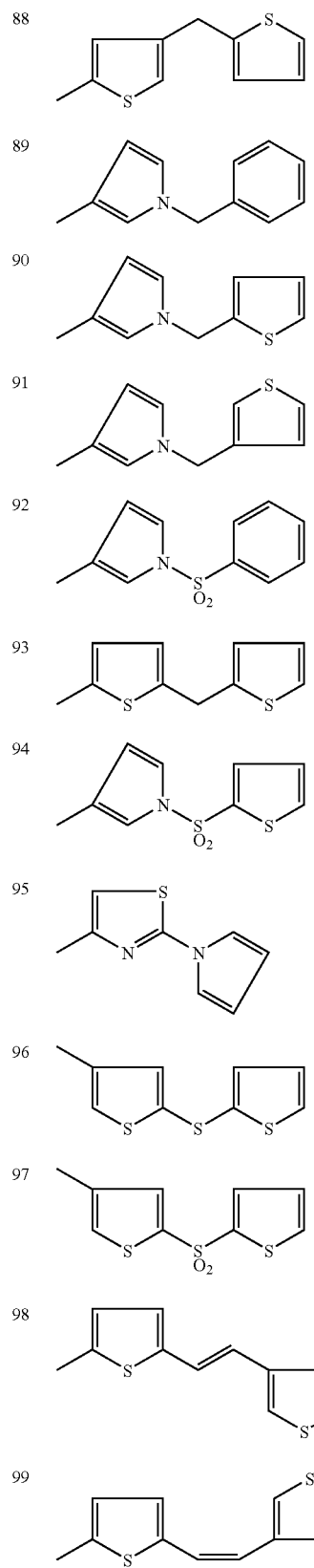 |
| 89 | |
| 90 | |
| 91 | |
| 92 | |
| 93 | |
| 94 | |
| 95 | |
| 96 | |
| 97 | |
| 98 | |
| 99 | |
-continued
| | —X¹—X²—X³ |
|---|---|
| 100 | 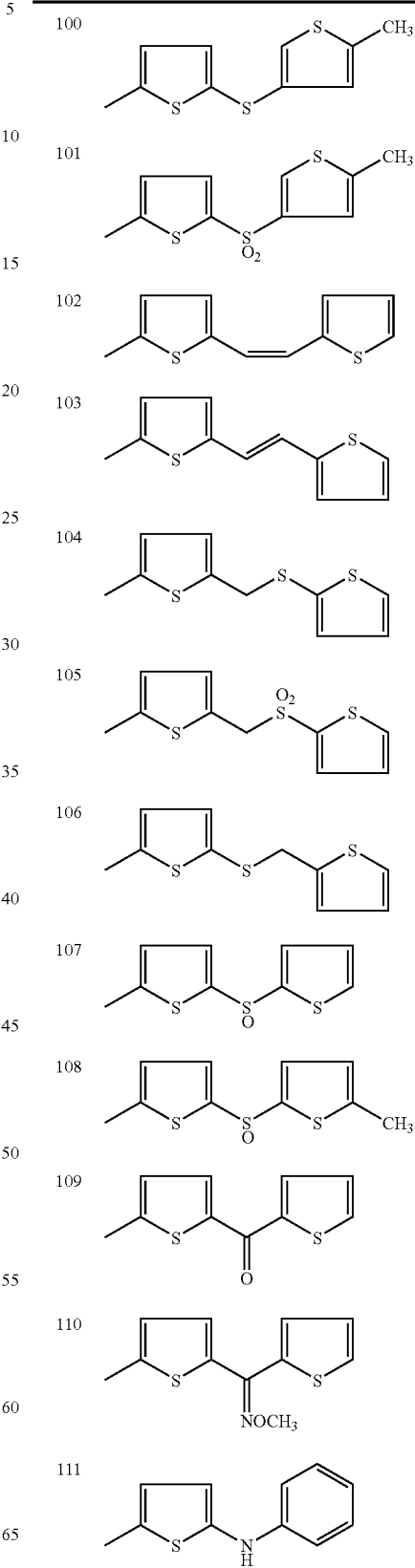 |
| 101 | |
| 102 | |
| 103 | |
| 104 | |
| 105 | |
| 106 | |
| 107 | |
| 108 | |
| 109 | |
| 110 | |
| 111 | |

| | —X¹—X²—X³ |
|---|---|
| 112 | 5-methylthiophen-2-yl-N(CH₃)-phenyl |
| 113 | 5-methylthiophen-2-yl-S-(3-methylphenyl) |
| 114 | 5-methylthiophen-2-yl-SO₂-(3-methylphenyl) |
| 115 | 5-methylthiophen-2-yl-S-(3-methoxyphenyl) |
| 116 | 5-methylthiophen-2-yl-SO₂-(3-methoxyphenyl) |
| 117 | 5-methylthiophen-2-yl-SO₂-(3-hydroxyphenyl) |
| 118 | 5-methylthiophen-2-yl-S-(3-hydroxyphenyl) |
| 119 | 5-methylthiophen-2-yl-CH₂-(3-methoxyphenyl) |
| 120 | 5-methylthiophen-2-yl-CH₂-(3-hydroxyphenyl) |
| 121 | 5-methylthiophen-2-yl-CH₂-(3-acetoxyphenyl) |
| 122 | 5-methylthiophen-2-yl-CH₂-S-phenyl |
| 123 | 5-methylthiophen-2-yl-CH₂-O-phenyl |
| 124 | 5-methylthiophen-2-yl-CH₂-NH-phenyl |
| 125 | 5-methylthiophen-2-yl-CH₂-(2-methylphenyl) |
| 126 | 5-methylthiophen-2-yl-CH₂-(2-methoxyphenyl) |
| 127 | 5-methylthiophen-2-yl-CH₂-(2-ethylphenyl) |
| 128 | 5-methylthiophen-2-yl-CH₂-(2,4-dimethylphenyl) |
| 129 | 5-methylthiophen-2-yl-CH₂-(5-methylthiophen-2-yl) |
| 130 | 5-methylthiophen-2-yl-CH₂-(4-methylphenyl) |
| 131 | 5-methylthiophen-2-yl-CH₂-(3-methylphenyl) |
| 132 | 5-methylthiophen-2-yl-CH₂-S-(3-methylphenyl) |
| 133 | 5-methylthiophen-2-yl-CH₂-(furan-2-yl) |
| 134 | 5-methylthiophen-2-yl-CH₂-(furan-3-yl) |

-continued
| —X¹—X²—X³ |
|---|
| 135 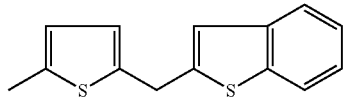 |
| 136 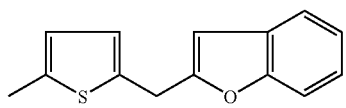 |
| 137 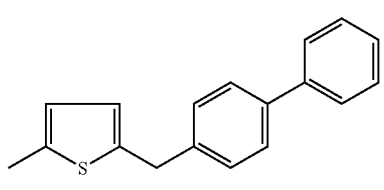 |
| 138 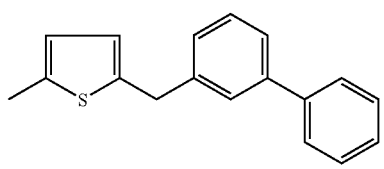 |
| 139 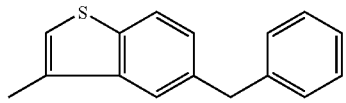 |
| 140 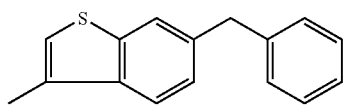 |
| 141 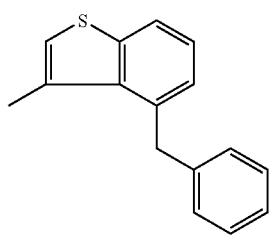 |
| 142 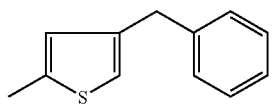 |
| 143 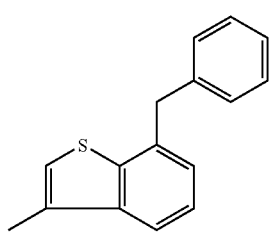 |
-continued
| —X¹—X²—X³ |
|---|
| 144 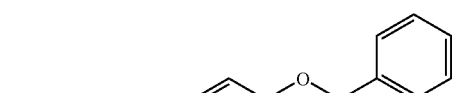 |
| 145 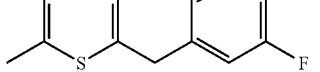 |
| 146 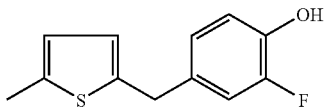 |
| 147 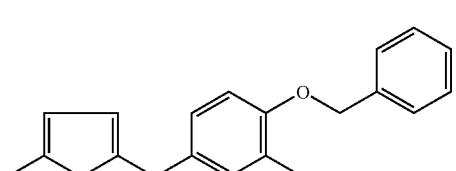 |
| 148 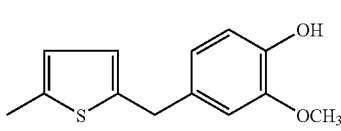 |
| 149 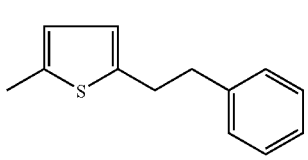 |
| 150 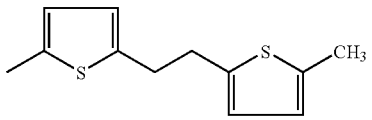 |
| 151 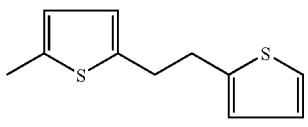 |
| 152 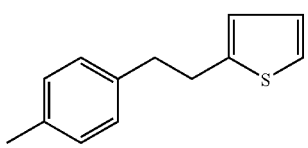 |
| 153 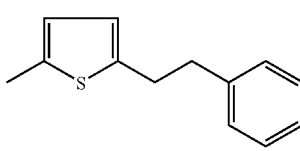 |

| | —X¹—X²—X³ |
|---|---|
| 154 | 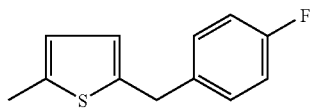 |
| 155 | 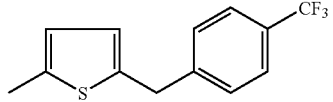 |
| 156 | 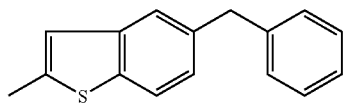 |
| 157 | 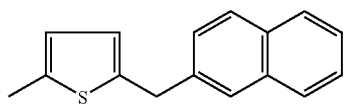 |
| 158 | 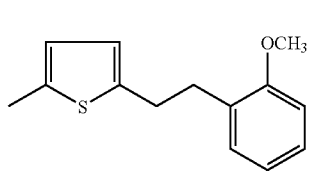 |
| 159 | 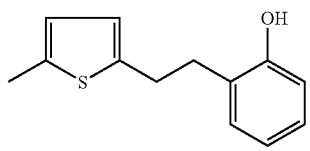 |
| 160 | 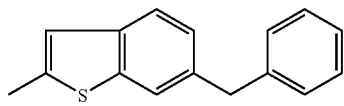 |
| 161 | 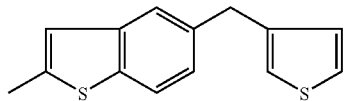 |
| 162 | 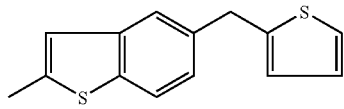 |
| 163 | 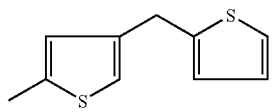 |
| 164 | 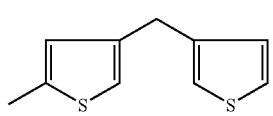 |
| 165 | 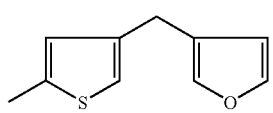 |
| | —X¹—X²—X³ |
|---|---|
| 166 | 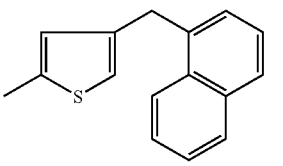 |
| 167 | 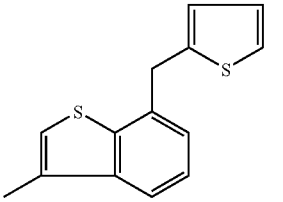 |
| 168 | 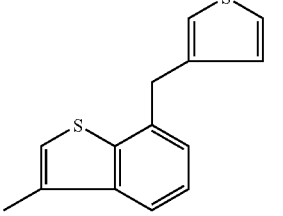 |
| 169 | 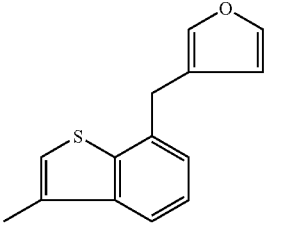 |
| 170 | 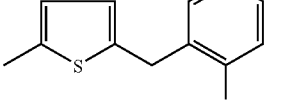 |
| 171 | 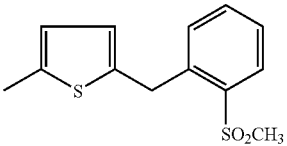 |
| 172 | 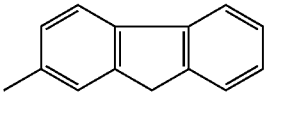 |
| 173 |  |

-continued
| | $-X^1-X^2-X^3$ |
|---|---|
| 174 | 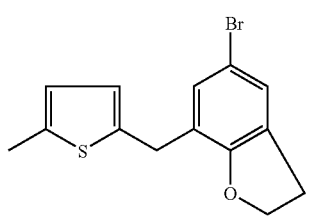 |
| 175 | 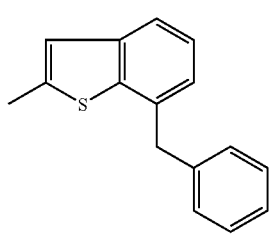 |
| 176 | 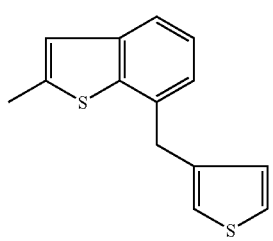 |
| 177 | 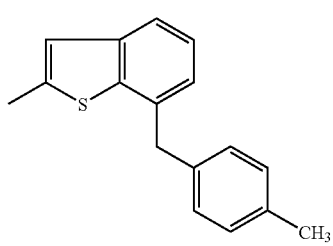 |
| 178 | 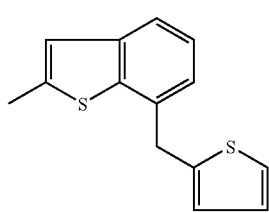 |
| 179 | 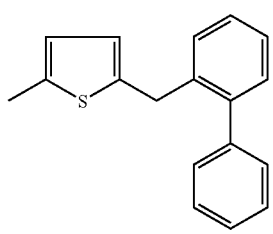 |
| 180 | 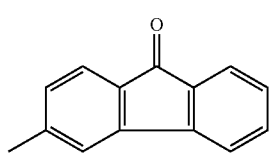 |
-continued
| | $-X^1-X^2-X^3$ |
|---|---|
| 181 | 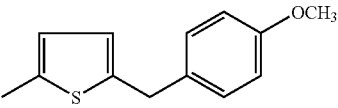 |
| 182 | 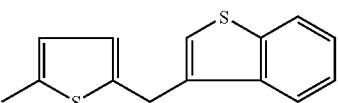 |
| 183 | 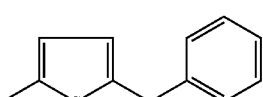 |
| 184 | 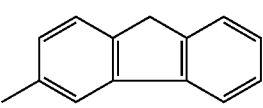 |
| 185 | 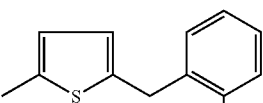 |
| 186 | 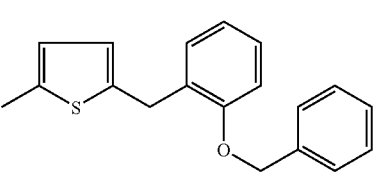 |
| 187 | 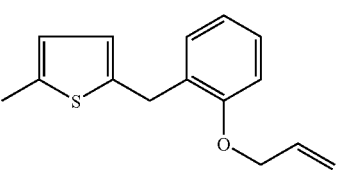 |
| 188 | 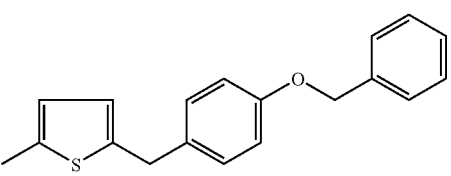 |
| 189 | 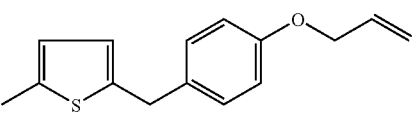 |
| 190 | 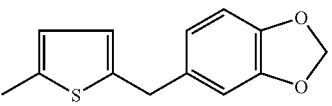 |
| 191 | 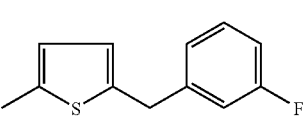 |

| —X¹—X²—X³ |
|---|
| 192 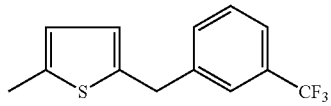 |
| 193 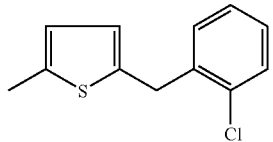 |
| 194 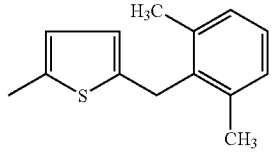 |
| 195 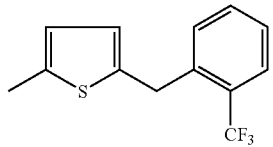 |
| 196 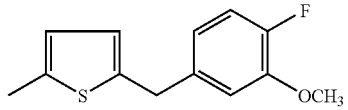 |
| 197 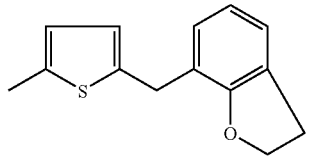 |
| 198 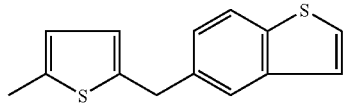 |
| 199 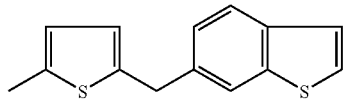 |
| 200 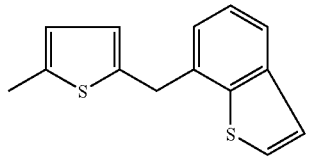 |
| 201 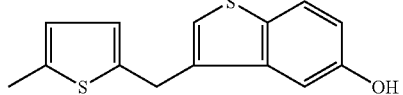 |
| —X¹—X²—X³ |
|---|
| 202 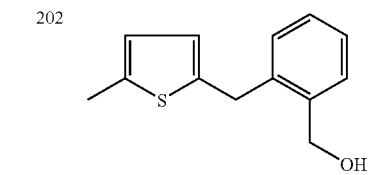 |
| 203  |
| 204  |
| 205 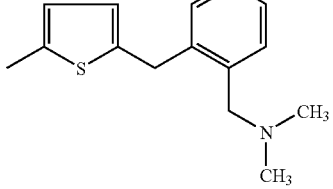 |
| 206 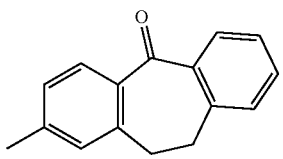 |
| 207 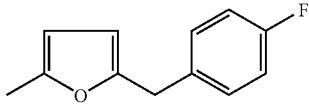 |
| 208 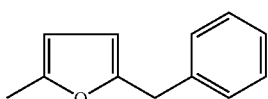 |
| 208 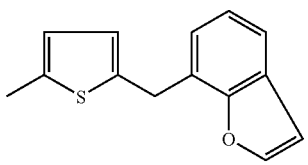 |
| 209 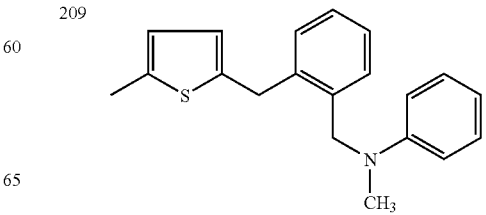 |

-continued
| —X¹—X²—X³ |
| 210 | 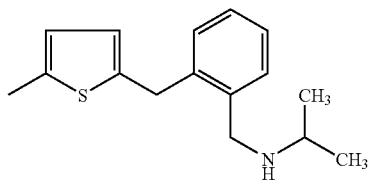 |
| 211 | 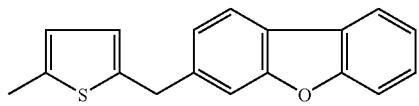 |
| 212 | 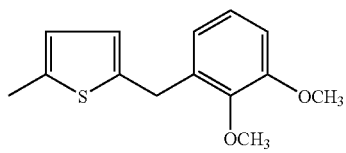 |
| 213 | 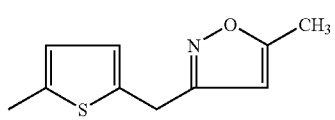 |
| 214 | 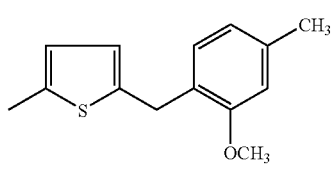 |
| 215 | 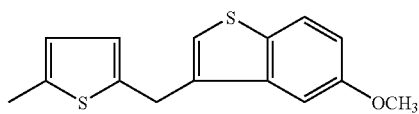 |
| 216 | 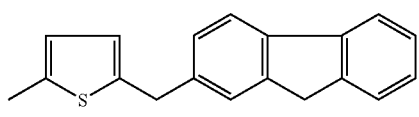 |
| 217 | 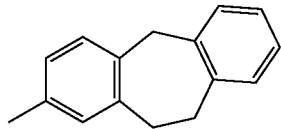 |
| 218 | 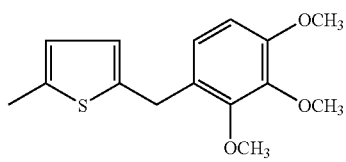 |
| 219 | 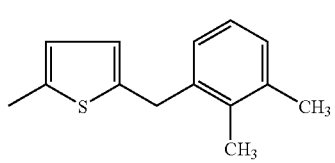 |
-continued
| —X¹—X²—X³ |
| 220 | 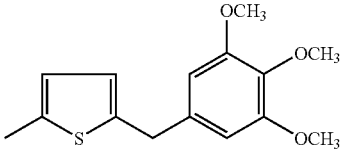 |
| 221 | 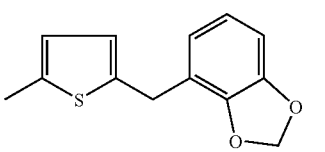 |
| 222 | 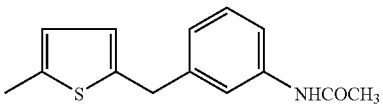 |
| 223 | 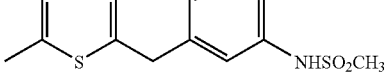 |
| 224 | 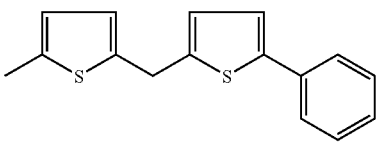 |
| 225 | 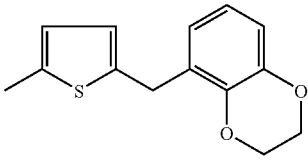 |
| 226 | 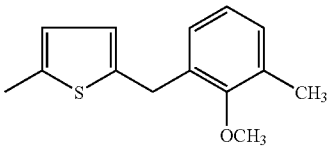 |
| 227 | 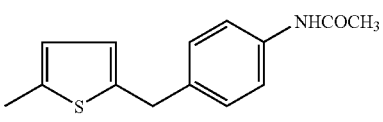 |
| 228 | 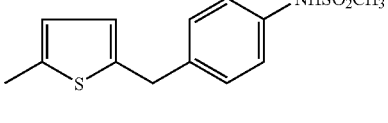 |
| 229 | 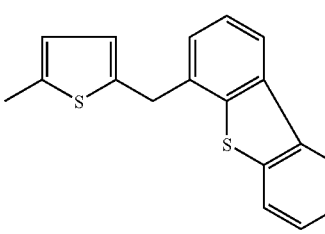 |

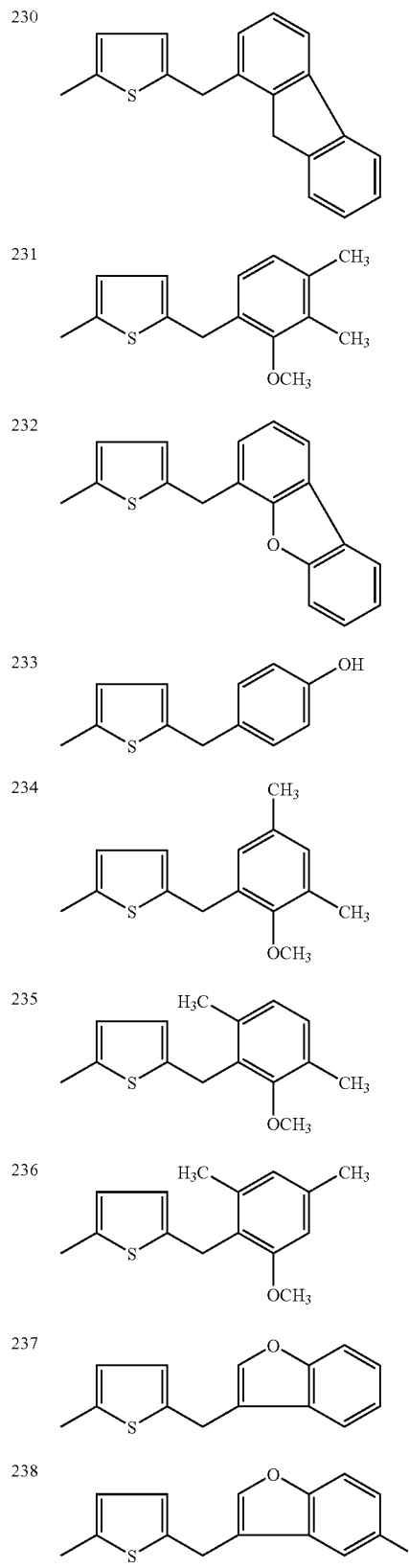
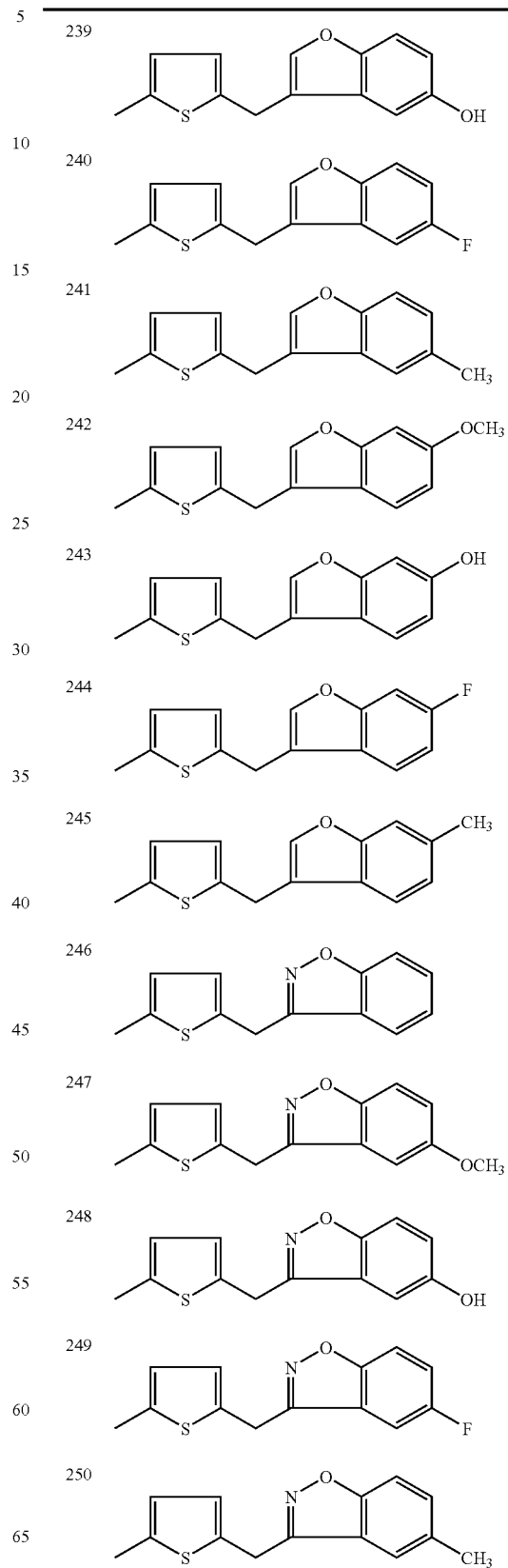

-continued
| | —X¹—X²—X³ |
|---|---|
| 251 | 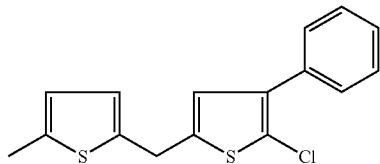 |
| 252 | 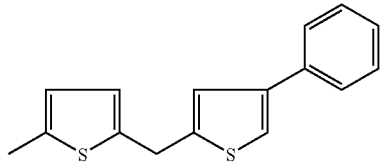 |
| 253 | 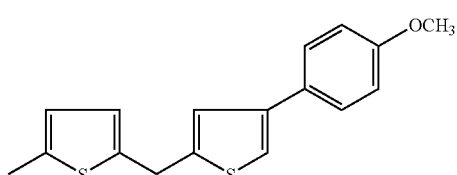 |
| 254 | 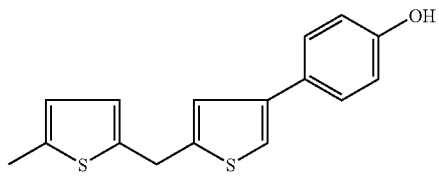 |
| 255 | 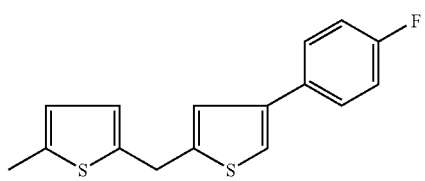 |
| 256 | 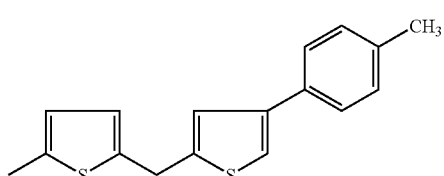 |
| 257 | 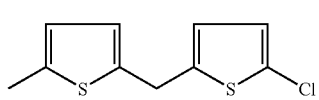 |
| 258 | 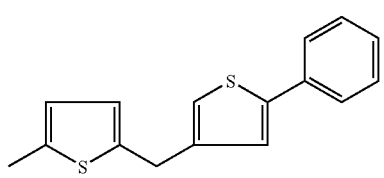 |
| 259 | 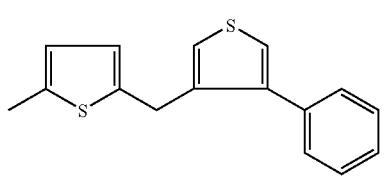 |
-continued
| | —X¹—X²—X³ |
|---|---|
| 260 | 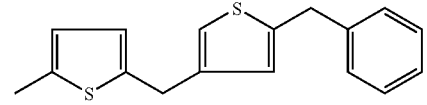 |
| 261 | 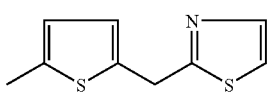 |
| 262 | 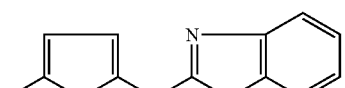 |
| 263 | 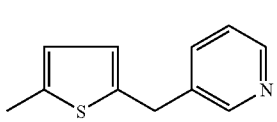 |
| 264 | 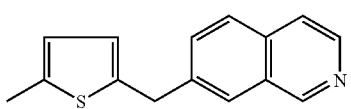 |
| 265 | 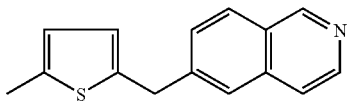 |
| 266 | 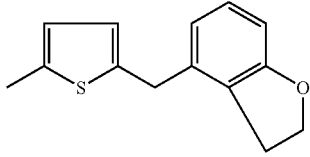 |
| 267 | 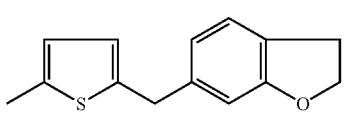 |
| 268 | 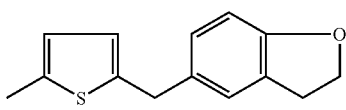 |
| 269 | 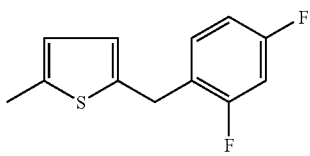 |
| 270 | 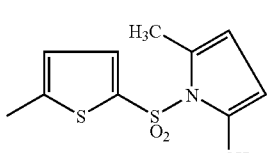 |
| 271 | 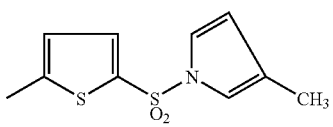 |

-continued
| —X¹—X²—X³ |
|---|
| 272 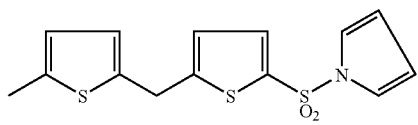 |
| 273 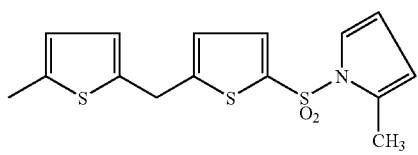 |
| 274 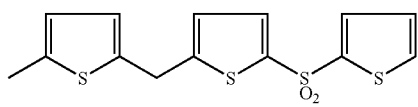 |
| 275 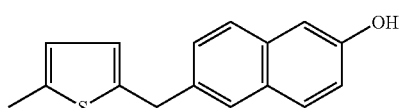 |
| 276 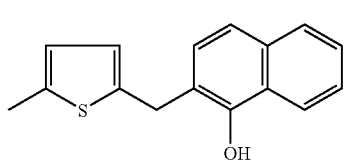 |
| 277 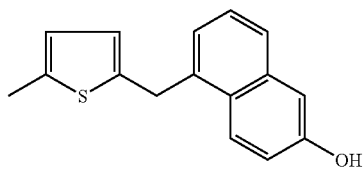 |
| 278 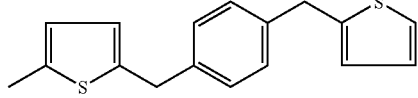 |
| 279 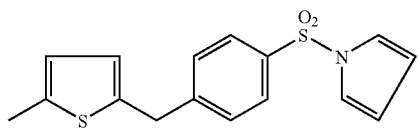 |
| 280 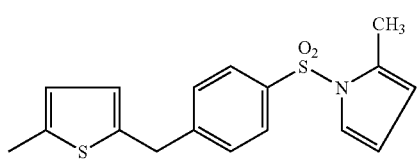 |
| 281 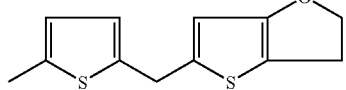 |
| 282 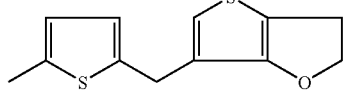 |
-continued
| —X¹—X²—X³ |
|---|
| 283 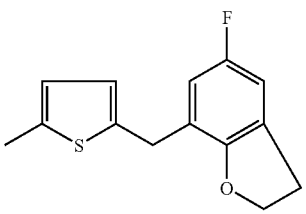 |
| 284 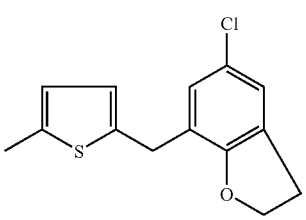 |
| 285 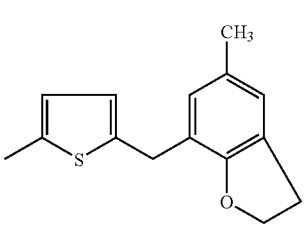 |
| 286 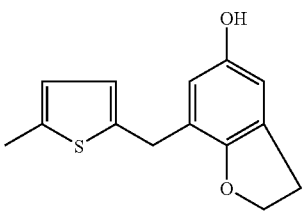 |
| 287 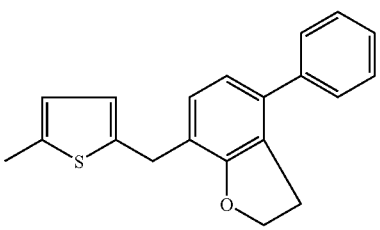 |
| 288 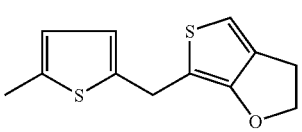 |
| 289 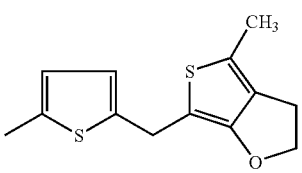 |

-continued
| $-X^1-X^2-X^3$ |
|---|
| 290 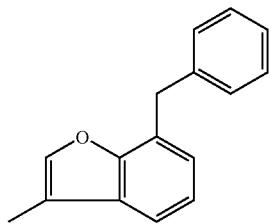 |
| 291 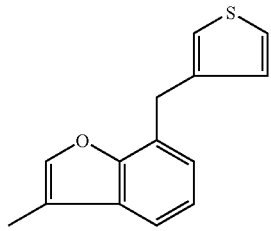 |
| 292 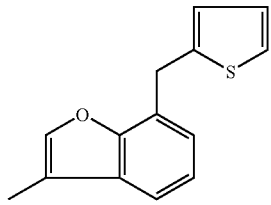 |
| 293 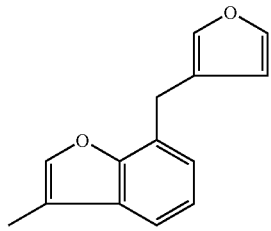 |
| 294 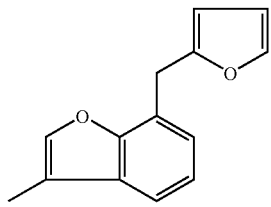 |
| 295 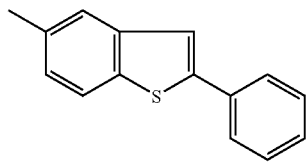 |
| 296 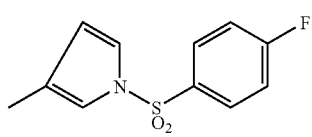 |
-continued
| $-X^1-X^2-X^3$ |
|---|
| 297 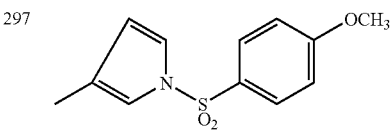 |
| 298 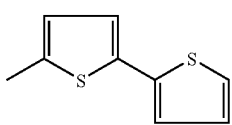 |
| 299 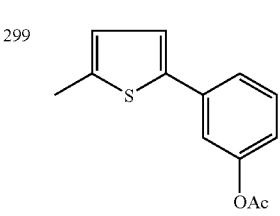 |
| 300 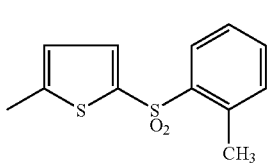 |
| 301 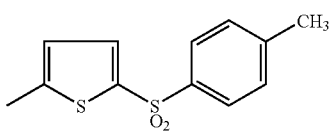 |
| 302 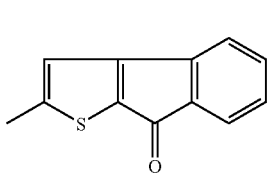 |
| 303 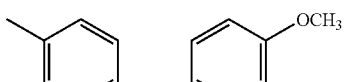 |
| 304 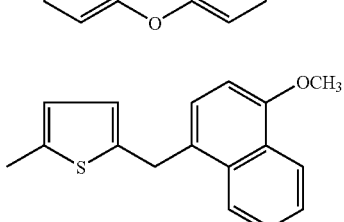 |
| 305 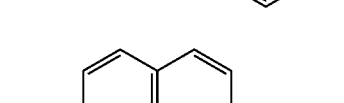 |

| —X¹—X²—X³ |
|---|
| 306 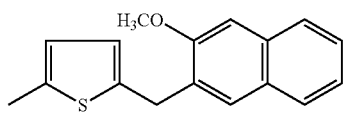 |
| 307 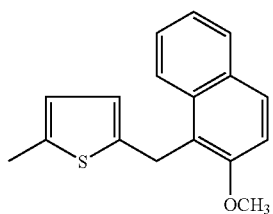 |
| 308 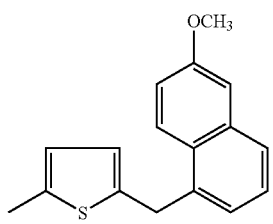 |
| 309 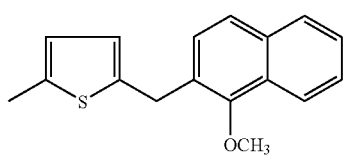 |
| 310 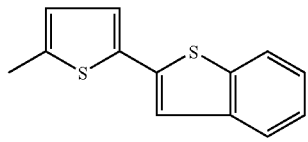 |
| 311 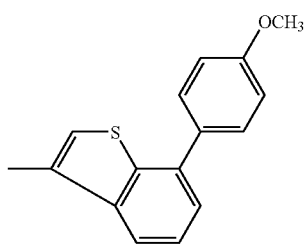 |
| 312 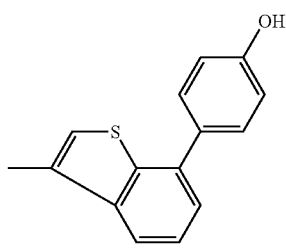 |
| —X¹—X²—X³ |
|---|
| 313 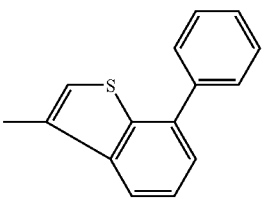 |
| 314 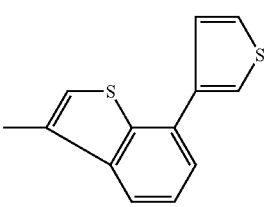 |
| 315 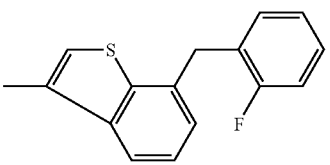 |
| 316 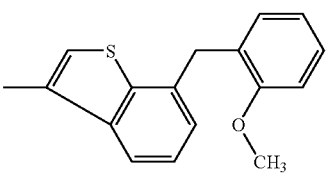 |
| 317 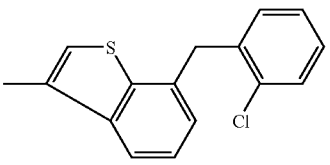 |
| 318 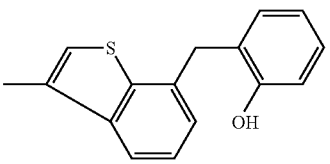 |
| 319 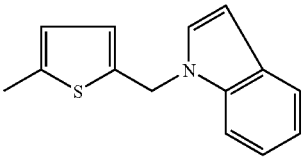 |
| 320 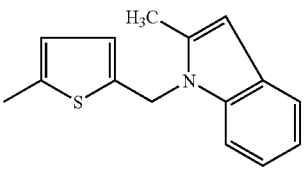 |

-continued
| —X¹—X²—X³ |
|---|
| 321 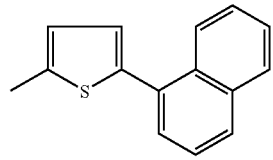 |
| 322 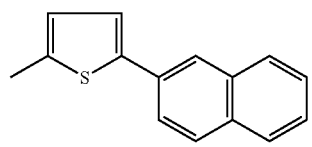 |
| 323 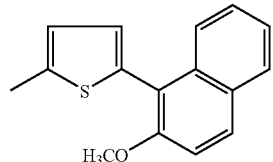 |
| 324 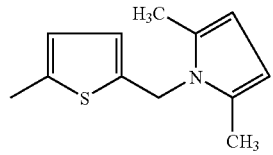 |
| 325 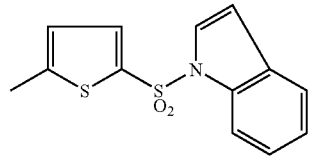 |
| 326 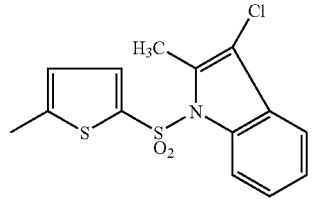 |
| 327 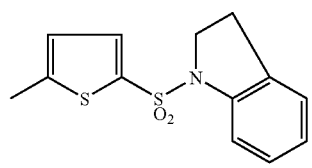 |
| 328 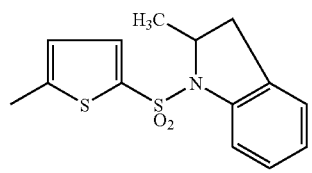 |
| 329 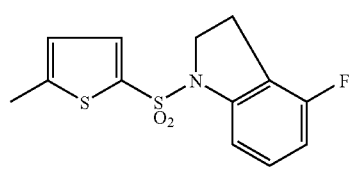 |
-continued
| —X¹—X²—X³ |
|---|
| 330 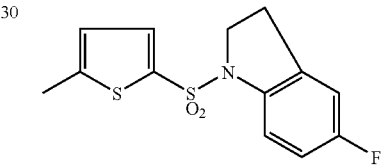 |
| 331 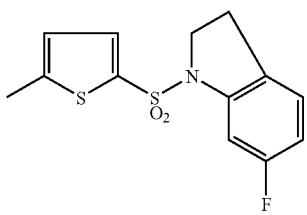 |
| 332 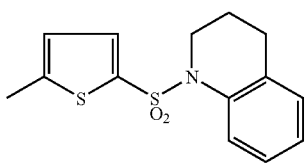 |
| 333 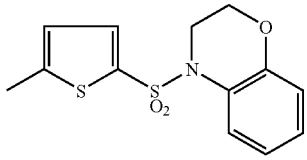 |
| 334 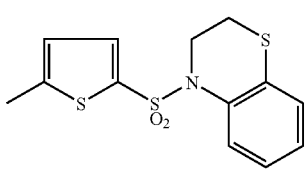 |
| 335 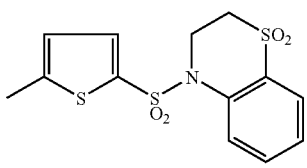 |
| 336 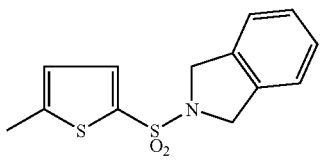 |
| 337 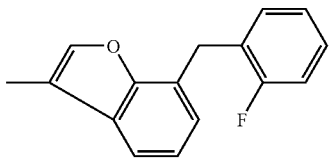 |

-continued
| $-X^1-X^2-X^3$ |
| --- |
338 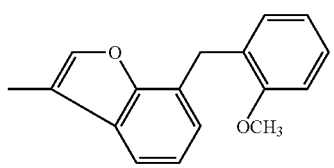
339 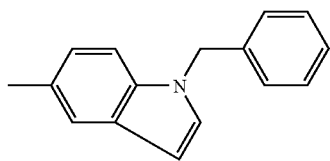
340 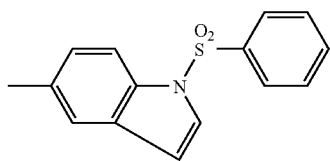
341 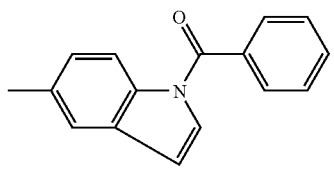
342 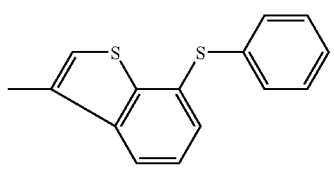
343 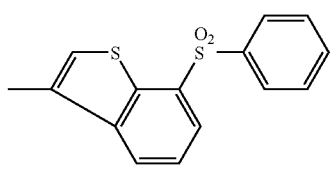
344 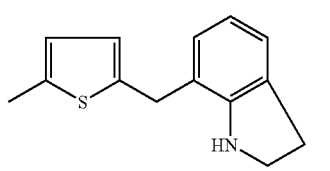
345 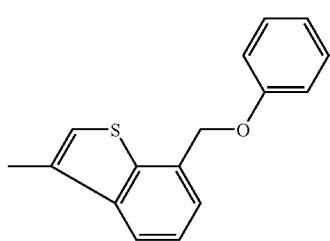
-continued
| $-X^1-X^2-X^3$ |
| --- |
346 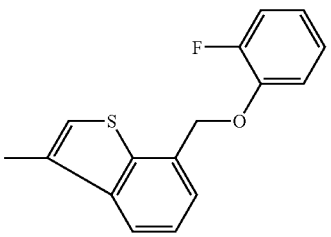
347 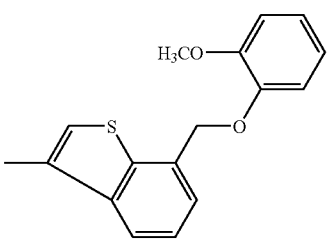
348 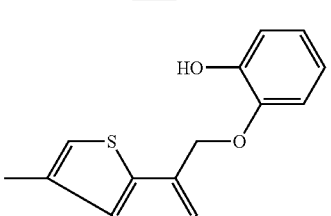
349 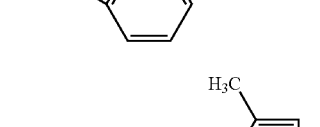
350 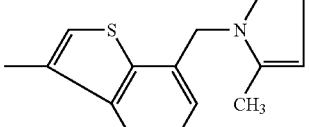
351 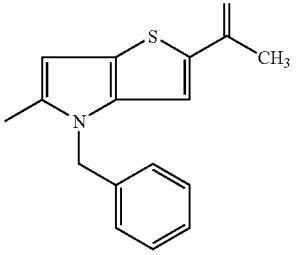
352 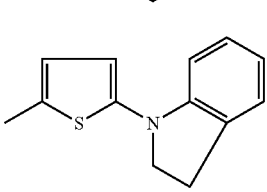

-continued
| | —X¹—X²—X³ |
|---|---|
| 353 | 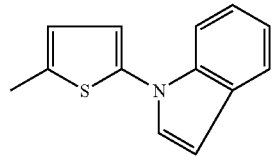 |
| 354 | 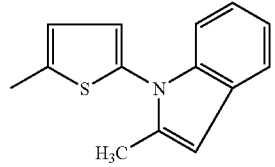 |
| 355 | 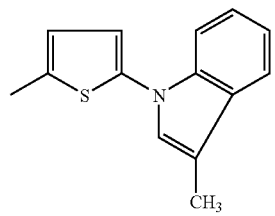 |
| 356 | 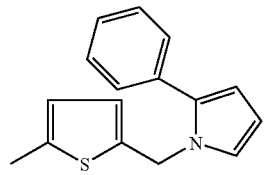 |
| 357 | 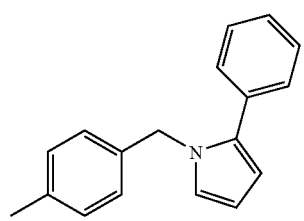 |
| 358 | 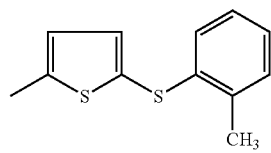 |
| 359 | 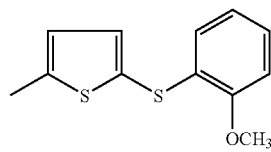 |
| 360 | 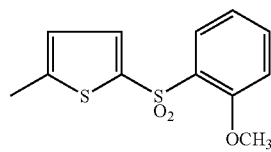 |
-continued
| | —X¹—X²—X³ |
|---|---|
| 361 | 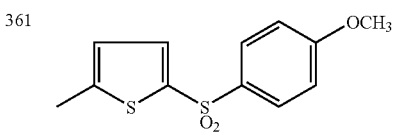 |
| 362 | 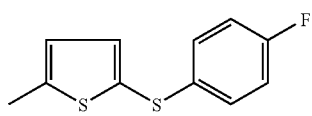 |
| 363 | 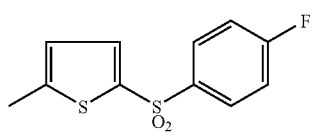 |
| 364 | 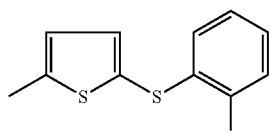 |
| 365 | 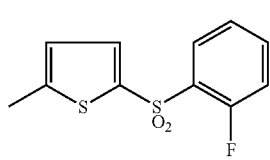 |
| 366 | 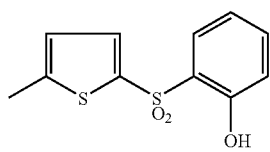 |
| 367 | 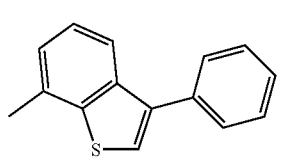 |
| 368 | 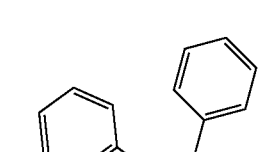 |
| 369 | 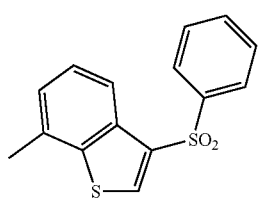 |

-continued
| —X¹—X²—X³ |
|---|
370 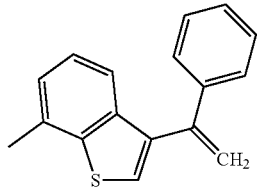
371 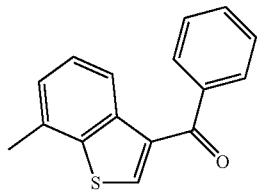
372 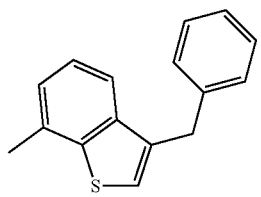
373 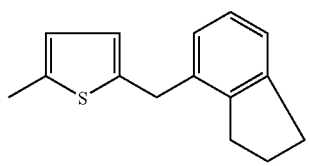
374 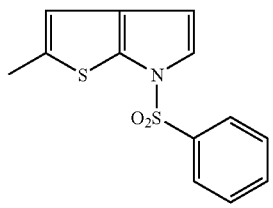
375 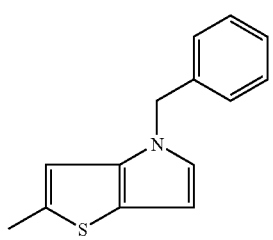
376 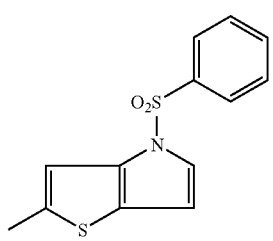
-continued
| —X¹—X²—X³ |
|---|
377 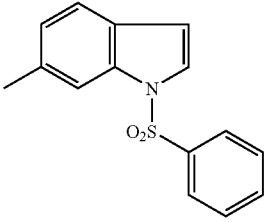
378 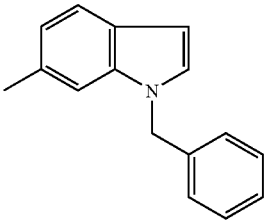
379 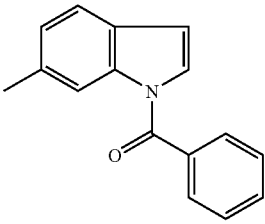
380 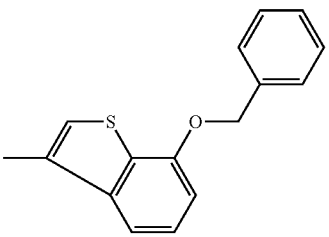
381 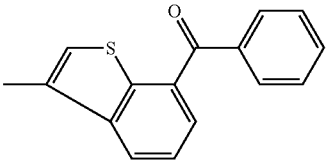
382 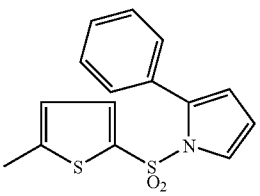
383 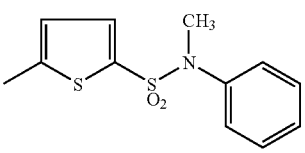

-continued
—X¹—X²—X³
| | |
|---|---|
| 384 | 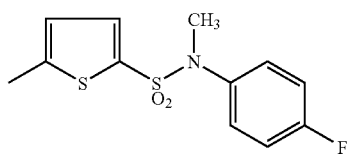 |
| 385 | 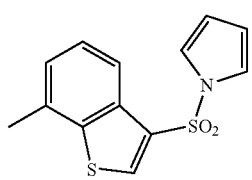 |
| 386 | 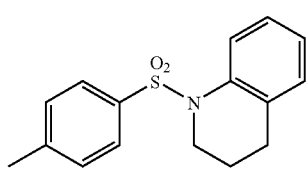 |
| 387 | 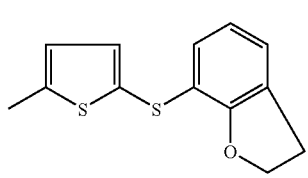 |
| 388 | 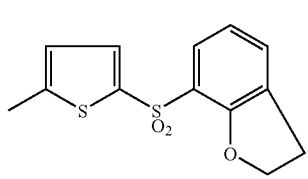 |
| 389 | 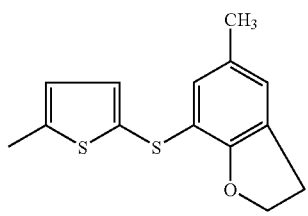 |
| 390 | 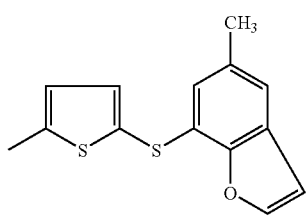 |
| 391 | 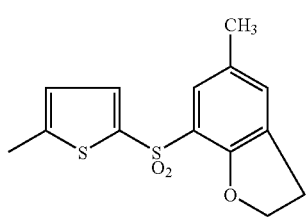 |
-continued
—X¹—X²—X³
| | |
|---|---|
| 392 | 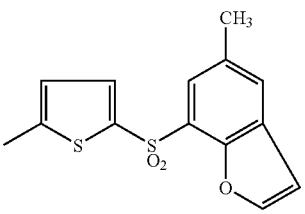 |
| 393 | 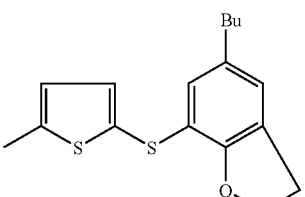 |
| 394 | 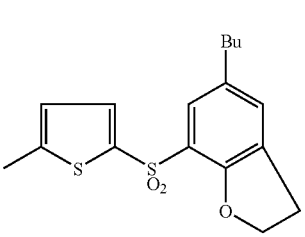 |
| 395 | 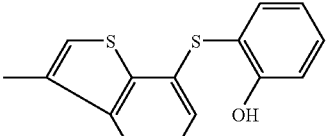 |
| 396 | 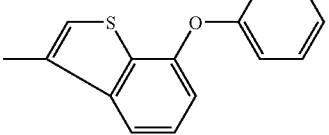 |
| 397 | 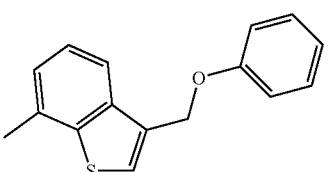 |
| 398 | 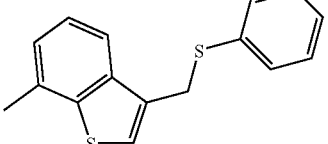 |
| 399 | 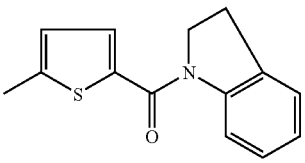 |

-continued
|   | —X¹—X²—X³ |
|---|---|
| 400 | 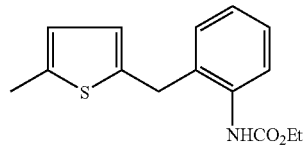 |
| 401 | 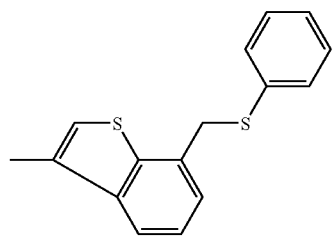 |
| 402 | 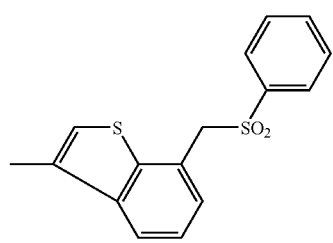 |
| 403 | 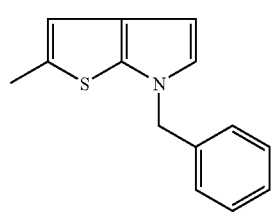 |
| 404 | 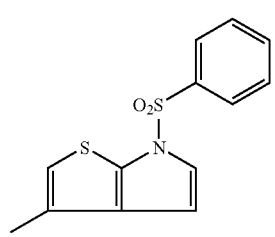 |
| 405 | 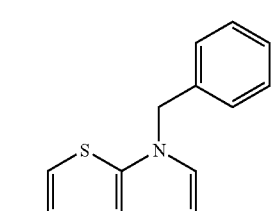 |
| 406 | 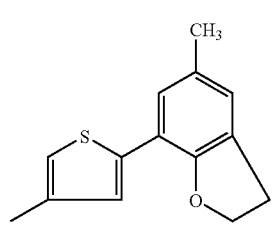 |
-continued
|   | —X¹—X²—X³ |
|---|---|
| 407 | 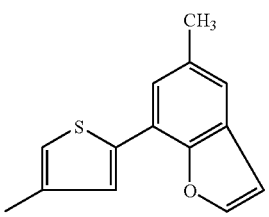 |
| 408 | 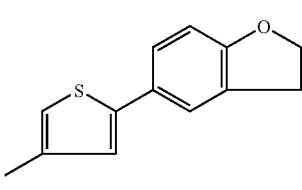 |
| 409 | 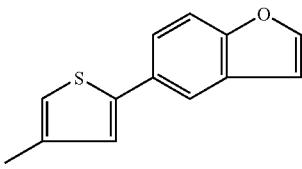 |
| 410 | 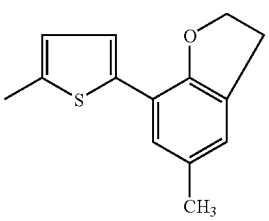 |
| 411 | 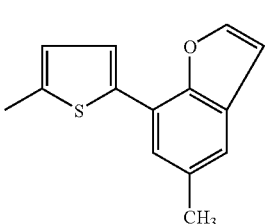 |
| 412 | 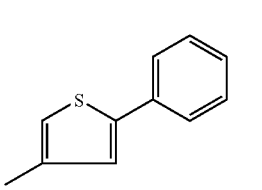 |
| 413 | 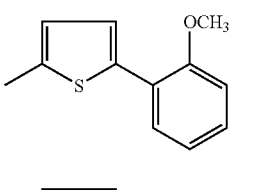 |
| 414 | 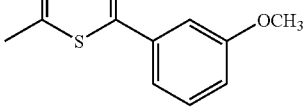 |

-continued
|   | $-X^1-X^2-X^3$ |
|---|---|
| 415 | 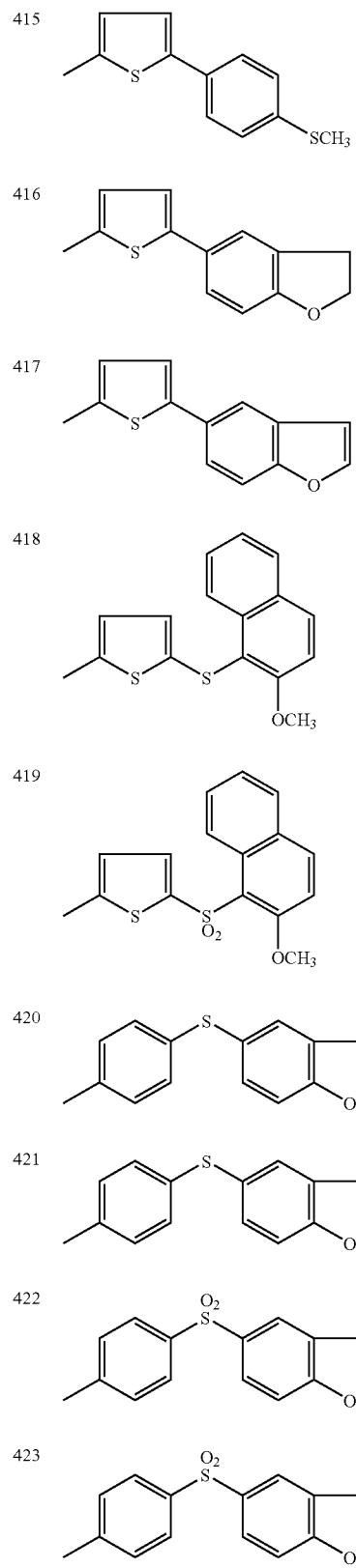 |
| 416 | |
| 417 | |
| 418 | |
| 419 | |
| 420 | |
| 421 | |
| 422 | |
| 423 | |
-continued
|   | $-X^1-X^2-X^3$ |
|---|---|
| 424 | 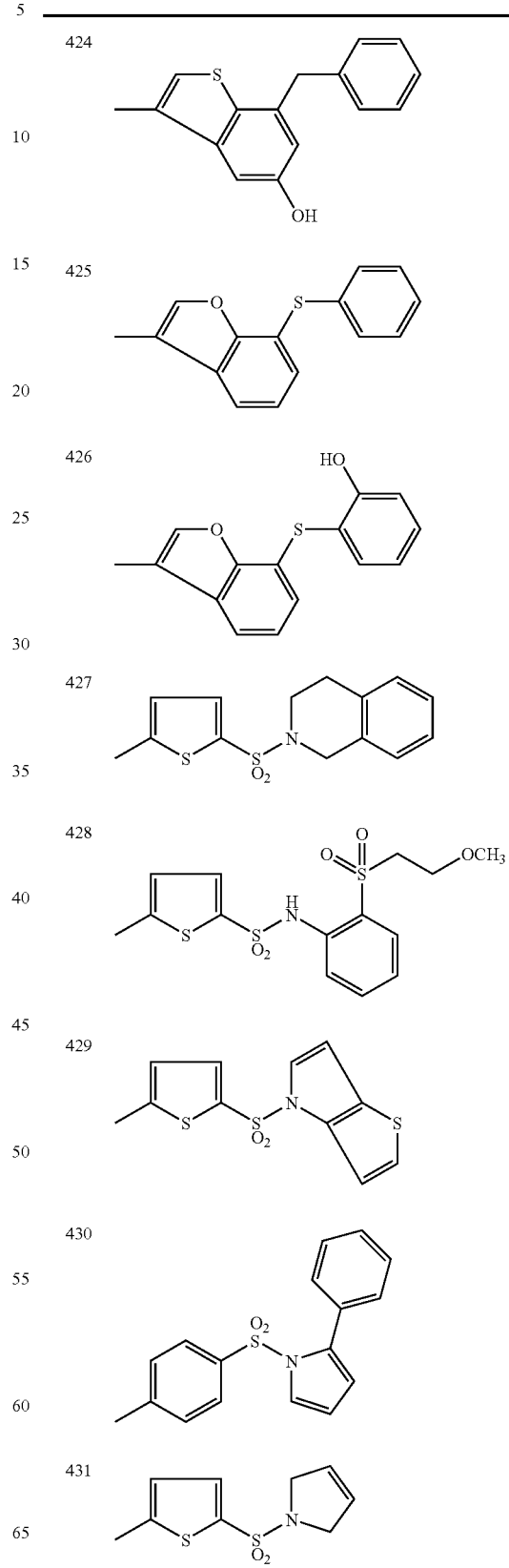 |
| 425 | |
| 426 | |
| 427 | |
| 428 | |
| 429 | |
| 430 | |
| 431 | |

-continued
—X¹—X²—X³
432 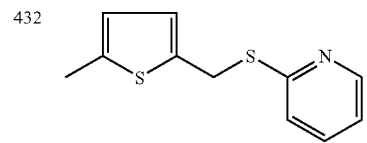
433 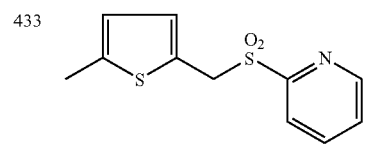
434 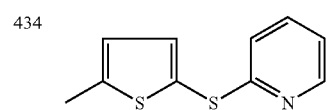
435 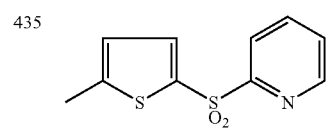
436 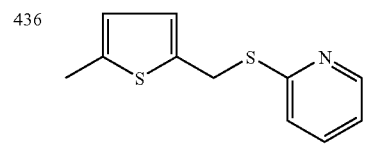
437 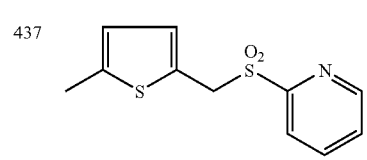
438 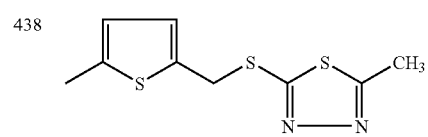
439 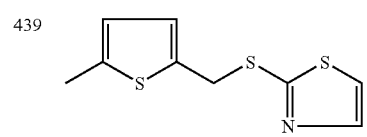
440 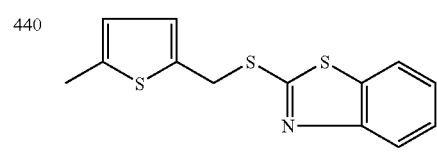
441 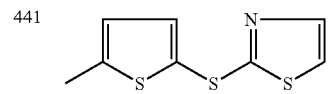
442 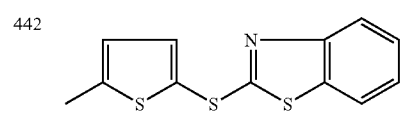
-continued
—X¹—X²—X³
443 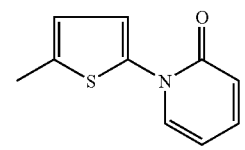
444 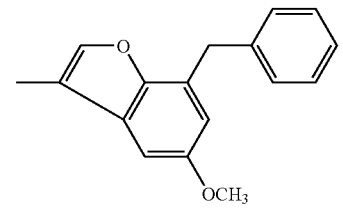
445 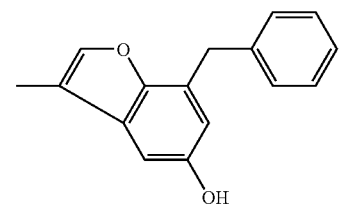
446 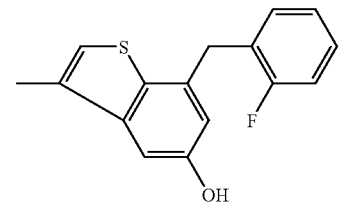
447 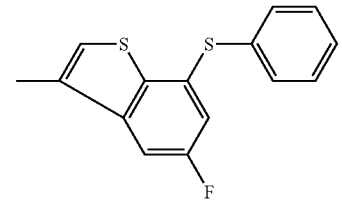
448 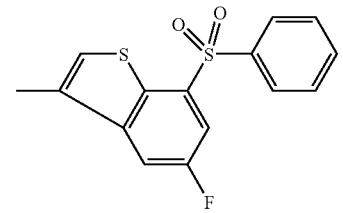
449 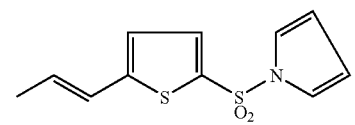

-continued
| —X¹—X²—X³ |
|---|
| 450 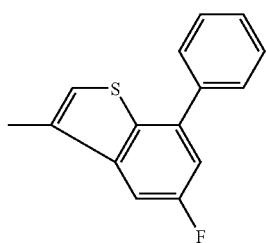 |
| 451 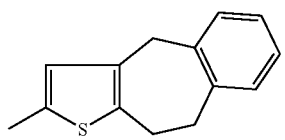 |
| 452 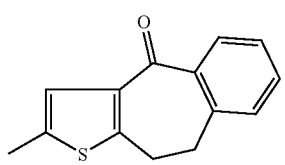 |
| 453 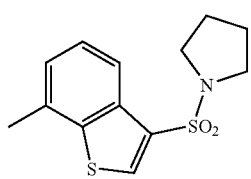 |
| 454 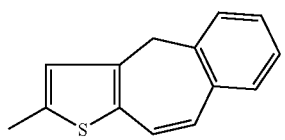 |
| 455 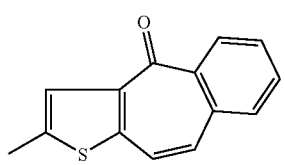 |
| 456 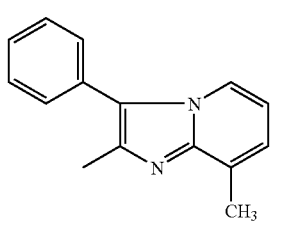 |
| 457 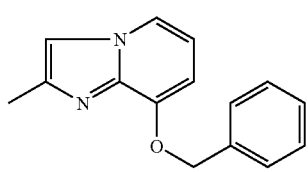 |
-continued
| —X¹—X²—X³ |
|---|
| 458 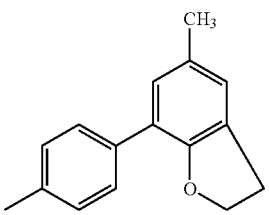 |
| 459 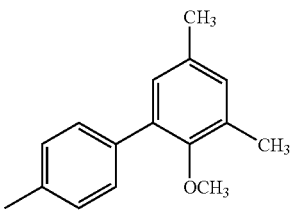 |
| 460 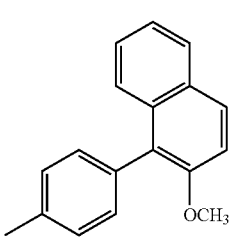 |
| 461 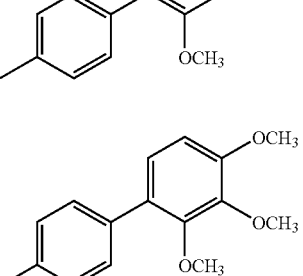 |
| 462 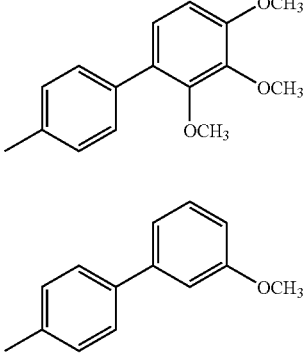 |
| 463 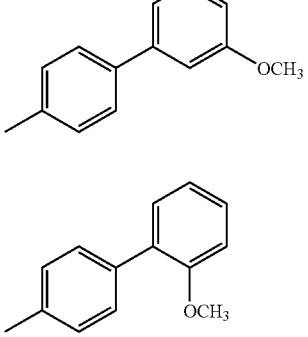 |
| 464 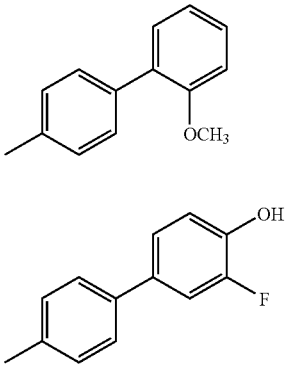 |

-continued
| —X¹—X²—X³ |
|---|
| 465 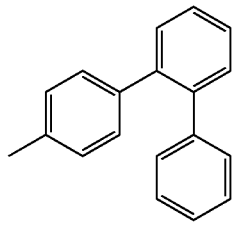 |
| 466 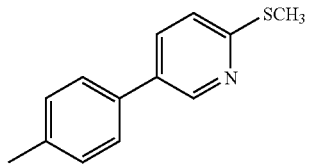 |
| 467 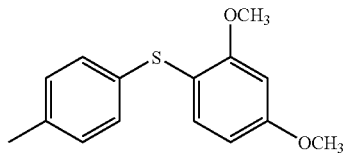 |
| 468 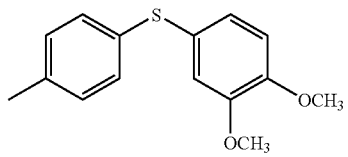 |
| 469 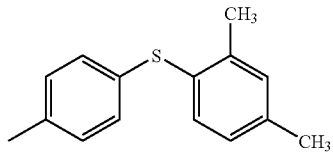 |
| 470 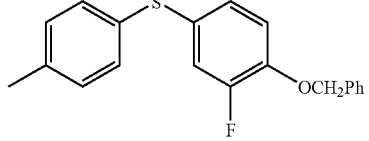 |
| 471 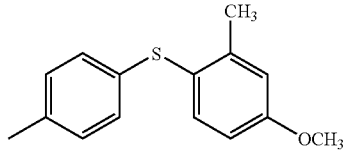 |
| 472 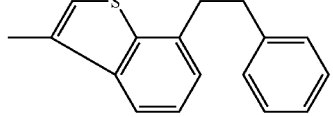 |
| 473 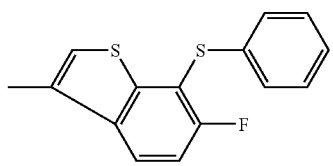 |
-continued
| —X¹—X²—X³ |
|---|
| 474 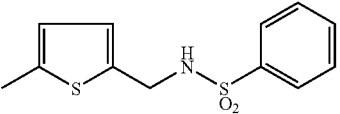 |
| 475 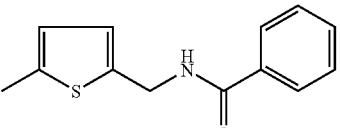 |
| 476 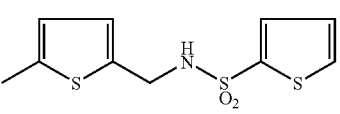 |
| 477 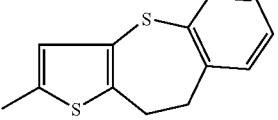 |
| 478 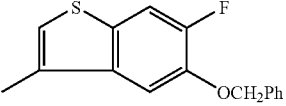 |
| 479 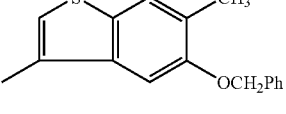 |
| 480 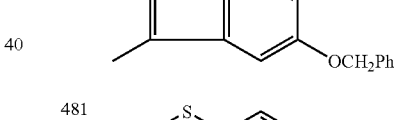 |
| 481 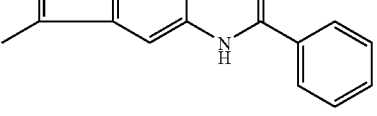 |
| 482 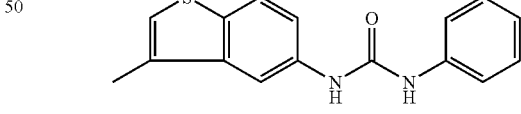 |
| 483 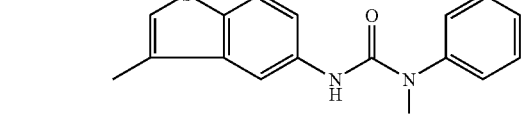 |
| 484 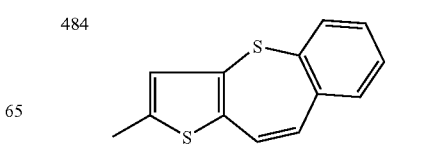 |

-continued
| —X¹—X²—X³ |
|---|
| 485 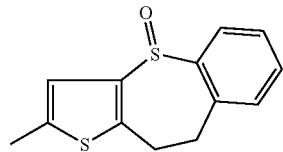 |
| 486 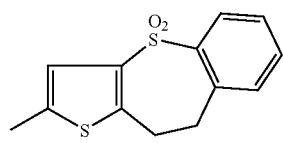 |
| 487 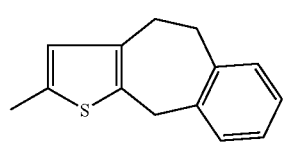 |
| 488 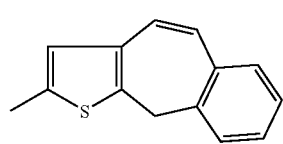 |
| 489 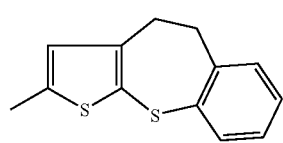 |
| 490 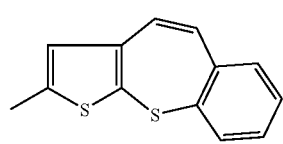 |
| 491 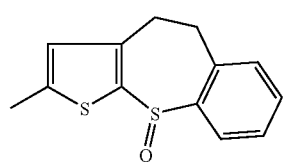 |
| 492 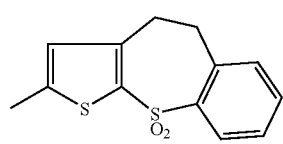 |
| 493 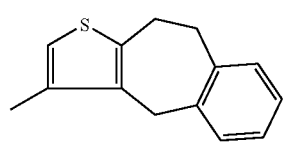 |
| 494 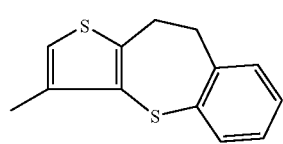 |
-continued
| —X¹—X²—X³ |
|---|
| 495 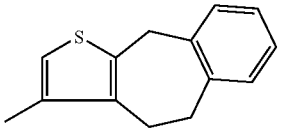 |
| 496 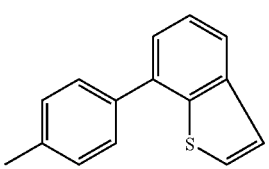 |
| 497 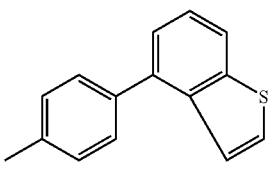 |
| 498 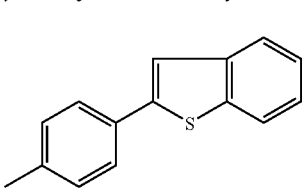 |
| 499 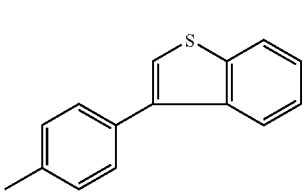 |
| 500 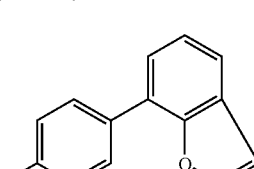 |
| 501 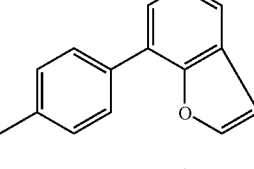 |
| 502 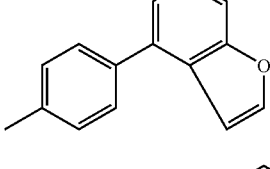 |
| 503 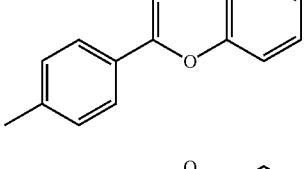 |

-continued
| —X$^1$—X$^2$—X$^3$ |
|---|
| 504 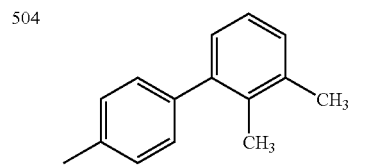 |
| 505 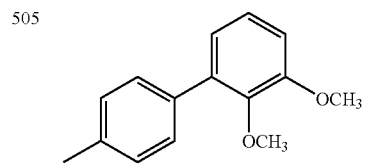 |
| 506 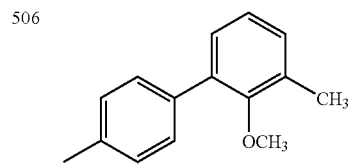 |
| 507 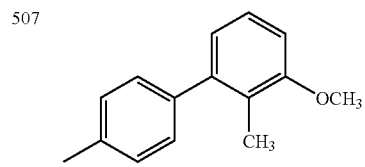 |
| 508 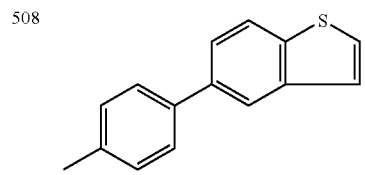 |
| 509 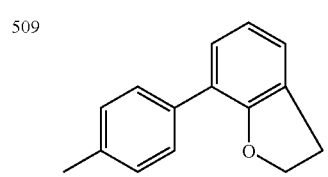 |
| 510 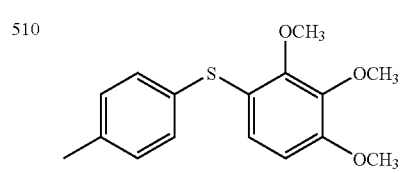 |
| 511 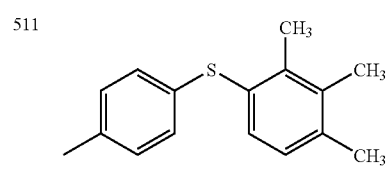 |
| 512 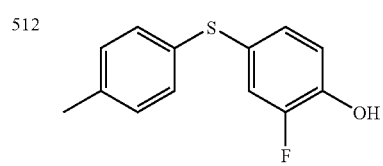 |
-continued
| —X$^1$—X$^2$—X$^3$ |
|---|
| 513 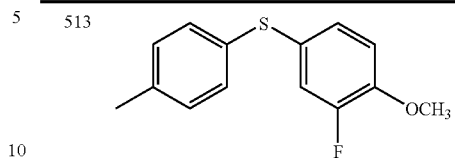 |
A compound of the present invention can be any of the following stereo isomers of [2.2.1] and [3.1.1] bicyclic skeleton.
In case of 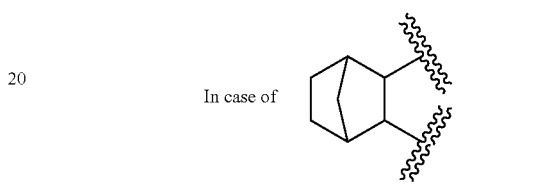
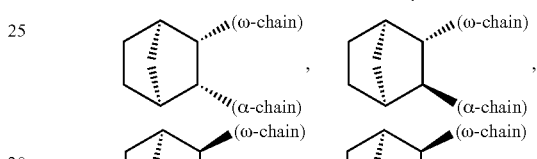
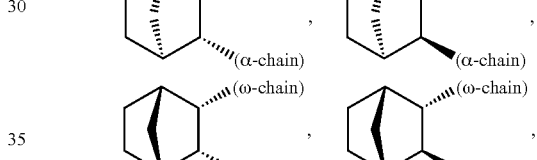
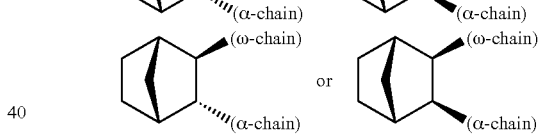
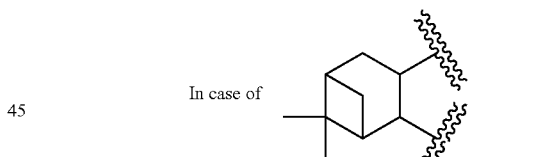
In case of 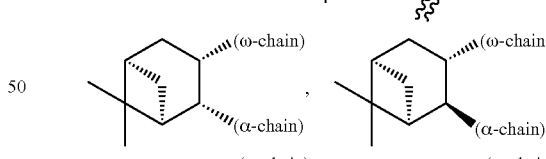
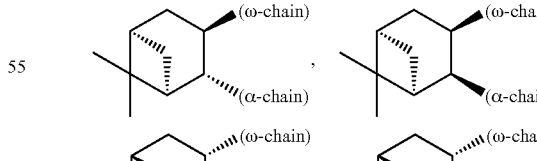
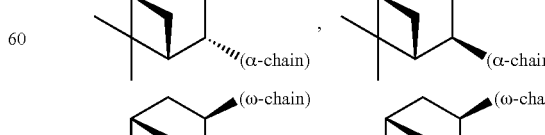
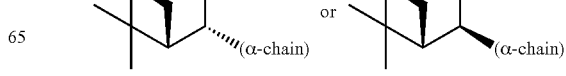

-continued

In case of

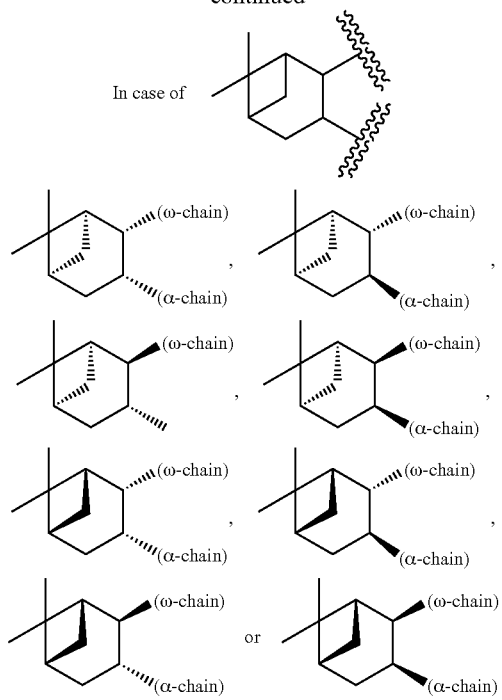

In these stereo isomers, preferable is a compound having the skeleton of the formula:

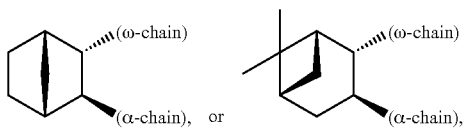

The present invention includes all stereo isomers of them and the optional mixtures thereof. Namely, the bond binding to the bicyclic ring is in R configuration or S configuration, and all of the stereo isomers (diastereomer, epimer, enantiomer and the like), racemates, and optional mixture thereof are included in the present invention.

Moreover, the α chain of the compound of the present invention can be in Z configuration or E configuration, thus a compound having any of the configurations and the mixture thereof are included in the present invention.

A prodrug of a compound of the formula (I) is a derivative of the compound of the present invention having a group which can be decomposed chemically or metabolically, and such prodrug is converted to a pharmaceutically active compound of the present invention by means of solvolysis or by placing the compound in vivo under a physiological condition. Method for the selection and process of an appropriate prodrug derivative are described in the literature such as Design of Prodrugs, Elsevier, Amsterdam 1985.

When the compound of the formula (I) has a carboxyl group, an ester derivative prepared by reacting a basal acid compound with a suitable alcohol or an amide derivative prepared by reacting a basal acid compound with a suitable amine is exemplified as a prodrug. A particularly preferred ester derivative as an prodrug is an optionally substituted alkyl ester derivative (e.g., methyl ester, ethyl ester, n-propyl ester, isopropyl ester, n-butyl ester, isobutyl ester, tert-butyl ester, morpholinoethyl ester), an arylalkyl ester derivative (e.g., benzyl ester, phenethyl ester, benzhydryl ester), or the like. A particularly preferred amide derivative as a prodrug is alkyl amide derivative (e.g., N-methyl amide, N-ethyl amide, N-(n-propyl)amide, N-isopropyl amide, N-(n-butyl) amide, N-isobutyl amide, N-(tert-butyl)amide), aryl alkyl amide (e.g., N-benzyl amide, N-phenethyl amide, benzhydryl amide), or the like.

When the compound of the formula (I) has a hydroxy group, an acyloxy derivative prepared by reacting with a suitable acyl halide (e.g., acid chloride, halogenated acid) or a suitable acid anhydride (e.g., mixed acid anhydride) is exemplified as a prodrug. A particularly preferred acyloxy derivative as a prodrug is a derivative substituted with optionally substituted alkylcarbonyloxy (e.g., —OCOC$_2$H$_5$, —OCO(tert-Bu), —OCOC$_{15}$H$_{31}$, —OCOCH$_2$CH$_2$COONa, —OCOCH(NH$_2$)CH$_3$, —OCOCH$_2$N(CH$_3$)$_2$—), optionally substituted arylcarbonyloxy (e.g., —OCO(m-COONa-Ph) or the like.

When the compound of the formula (I) has an amino group, an amide derivative prepared by reacting with a suitable acid halide or a suitable acid anhydride is exemplified as a prodrug. A particularly preferred amide derivative as a prodrug is a derivative substituted with optionally substituted alkylcarbonyl (e.g., —NHCO(CH$_2$)$_{20}$CH$_3$, —NHCOCH(NH$_2$)CH$_3$) or the like.

Examples of a salt of the compound of the formula (I) or its prodrug include alkali metal salts such as lithium salts, sodium salts or potassium salts, alkaline-earth metal salts such as calcium salts, salts with organic bases such as tromethamine, trimethylamine, triethylamine, 2-aminobutane, tert-butylamine, diisopropylethylamine, n-butylmethylamine, cyclohexylamine, dicyclohexylamine, N-isopropylcyclohexylamine, furfurylamine, benzylamine, methylbenzylamine, dibenzylamine, N,N-dimethylbenzylamine, 2-chlorobenzylamine, 4-methoxybenzylamine, 1-naphthylene methylamine, diphenylbenzylamine, triphenylamine, 1-naphthylamine, 1-aminoanthorathene, 2-aminoanthorathene, dehydroabiethylamine, N-methylmorpholine, pyridine), basic amino acid salts such as arginine salts or lysine salts.

A solvate means a solvate with an organic solvent, a hydrate and the like of the compound of the formula (I), its prodrug or its pharmaceutically acceptable salt, for example, monohydrate, dihydrate or the like.

General processes for the preparation of the compounds of the formula (I) are illustrated as follows.

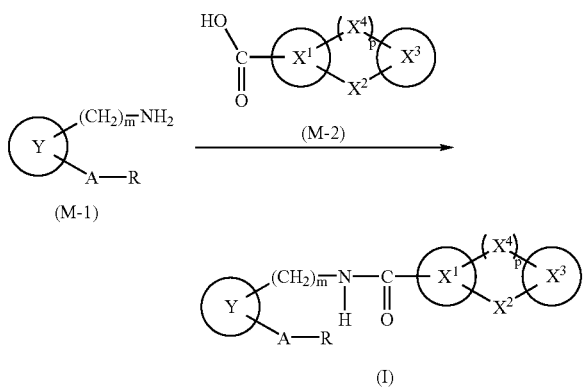

-continued

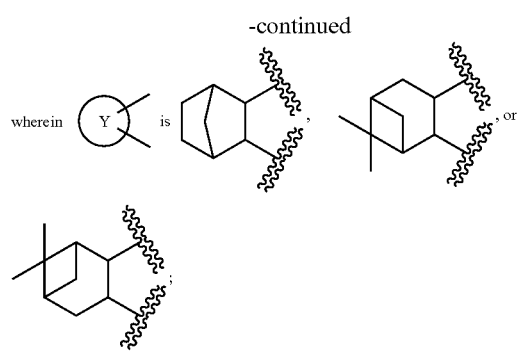

wherein Y is

A is alkylene optionally intervened with a heteroatom, optionally having an oxo group, optionally substituted with halogen and/or optionally having an unsaturated bond;

R is —C(=O)—$R^1$, —$CH_2$—$R^1$, or tetrazolyl;

$R^1$ is hydroxy, alkyloxy, or optionally substituted amino;

m is 0 or 1;

provided that when m is 1, A is —CH=CH—$CH_2$—$CH_2$—$CH_2$— and furthermore R is —C(=O)—$R^1$ wherein $R^1$ is hydroxy or alkyloxy, and provided that when A is —$CH_2$—CH=CH—$CH_2$—$CH_2$—$CH_2$— and R is —C(=O)—$R^1$ wherein $R^1$ is hydroxy or alkyloxy, a compound is excluded;

p is 0 or 1, provided that when p=0, $X^1$ is not bonded to $X^3$ via $X^4$;

$X^1$ and $X^3$ are each independently optionally substituted aryl, optionally substituted heteroaryl, or optionally substituted non-aromatic heterocyclyl;

$X^2$ is a bond, —$CH_2$—, —$CH_2$—$CH_2$—, —C(=O)—, —O—, —S—, —SO—, —$SO_2$—, —NH—, —N($CH_3$)—, —C(=N—O—$CH_3$)—, —N=N—, —CH=CH—, —(C=O)—NH—, —NH—(C=O)—, —$CH_2$—NH—, —NH—$CH_2$—, —$CH_2$—O—, —O—$CH_2$—, —$CH_2$—S—, —S—$CH_2$—, —$CH_2$—$SO_2$—, —$SO_2$—$CH_2$—, —$SO_2$—NH—, —NH—$SO_2$—, —C(=$CH_2$)—, —$SO_2$N(Me)—, —$CH_2$$NHSO_2$—, —$CH_2$NH—(C=O)—, —NH—C(=O)—NH, or —NH—C(=O)—N(Me)—;

$X^4$ is —$C_2$—, —$CH_2$—$CH_2$—, —C(=O)—, —SO—, —$SO_2$—, —(C=O)—NH—, —NH—(C=O)—, —$CH_2$—NH—, —NH—$CH_2$—, —$CH_2$—O—, —O—$CH_2$—, —$CH_2$—S—, —S—$CH_2$—, —$CH_2$$SO_2$—, —$SO_2$—$CH_2$—, —$SO_2$—NH— or —NH—$SO_2$—.

As shown in the above process, the compound of the formula (I) can be prepared by reacting a carboxylic acid of the formula (M-2) or its reactive derivative with an amino compound of the formula (M-1).

The reactive derivatives of carboxylic acid of the formula (M-2) mean the corresponding acid halides (e.g., chloride, bromide, iodide), anhydrides (e.g., mixed anhydride with formic acid or acetic acid), active esters (e.g., N-hydroxysuccinimide ester), and the like, and include acylating agents used for the usual acylation of amino group.

For example, an acid halide is obtained by reacting the compound (M-2) with a thionyl halide (e.g., thionyl chloride), phosphorous halide (e.g., phosphorous trichloride, phosphorous pentachloride), oxalyl halide (e.g., oxalyl chloride), and the like, in accordance with known methods as described in the literatures.

The reaction can be conducted under a condition generally used for the acylation of amino group. For example, in the case of condensation with the acid halide, the reaction is carried out in a solvent such as an ether solvent (e.g., diethyl ether, tetrahydrofuran, dioxane), benzene solvent (e.g., benzene, toluene, xylene), halogenated hydrocarbon solvent (e.g., dichloromethane, dichloroethane, chloroform) as well as ethyl acetate, dimethylformamide, dimethyl sulfoxide, acetonitrile, or the like, if necessary, in the presence of a base (e.g., organic base such as triethylamine, pyridine, N,N-dimethylaminopyridine, N-methylmorpholine; inorganic base such as sodium hydroxide, potassium hydroxide, potassium carbonate, or the like) under cooling, at room temperature, or under heating, preferably at a temperature ranging from –20° C. to ice-cooling temperature, or from room temperature to a refluxing temperature of the reaction system, during several min to several hr, preferably for 0.5 hr to 24 hr, more preferably for 1 hr to 12 hr.

Unless R of a compound represented by the formula (M-1) is a carboxyl group, a free form may be used without converting the carboxy group (M-2) into the reactive derivatives and the reaction may be conducted in the presence of a condensing agent (e.g., dicyclohexylcarbodiimide (DCC), 1-ethyl-3-(3-methylaminopropyl)carbodiimide, N,N'-carbonyldiimidazole, or the like) usually used in the condensation reaction of amine and carboxylic acid.

When "optionally substituted aryl", "optionally substituted heteroaryl" or "optionally substituted non-aromatic heterocyclyl" in $X^1$ or $X^3$ of the compound of the formula (M-2) is substituted with a hydroxy group or an amino group, such a compound can be used after protection by acetyl group or the like in accordance with the well known method.

In the reaction of the other reactive derivatives or free acid (M-2) with the amine (M-1), the reaction conditions are determined according to the property of each reactive derivative or free acid, in accordance with a known method. The reaction product can be purified in accordance with a conventional purification, such as the extraction with a solvent, chromatography, recrystallization, and the like.

In an object compound of the present invention, various derivatives in which R is —C(=O)—$R^1$, —$CH_2$—$R^1$ or tetrazolyl ($R^1$ is hydroxy, alkyloxy or optionally substituted amino) can be converted from a compound in which R is carboxylic acid. For instance, a derivative of the ester or the amide can be prepared by esterification or amidation, in accordance with the well known method. Furthermore, the ester derivative can be converted by reduction to an alcoholic derivative, which can be derived to an ether derivative by O-alkylation. A compound in which R is 5-tetrazolyl, can be prepared by converting an amide derivative having R; $CONH_2$ to R: CN by dehydration in accordance with the well known method, followed by a reaction with sodium azide (J. Am. Chem. Soc. 1958, 80, 3908) or trimethylsilylazide (J. Org. Chem. 1993, 58, 4139).

In this process, the starting compound (M-1) wherein $R^1$ is —$CH_2$—CH=CH—$CH_2$—$CH_2$—$CH_2$—COOMe, m is 0, Y is [2.2.1]bicyclic skeleton, 7-(3-amino-bicyclo[2.2.1]hept-2-yl)-5-heptenoic acid methyl ester is described in the Japanese Patent Publication (Kokoku) No. 79060/1993. The other starting compounds can be prepared from the aldehyde derivative (Q is a protecting group such as benzyloxycarbonyl, t-butoxycarbonyl and the like) represented by a general formula (M-1a) or (M-1b) by one or more reaction(s) of a ylide compound under a Wittig reaction condition (Org. Reaction, 1965, 14, 270) in combination with other reactions. In a starting compound, various derivatives wherein R is —C(=O)—R$^1$, —CH$_2$—R$^1$ or tetrazolyl (R$^1$ is hydroxy, alkyloxy or optionally substituted amino) can be converted from a compound wherein R is COOH.

ester, ether, or amide and the like in the presence of a base in accordance with known methods as described in the literatures.

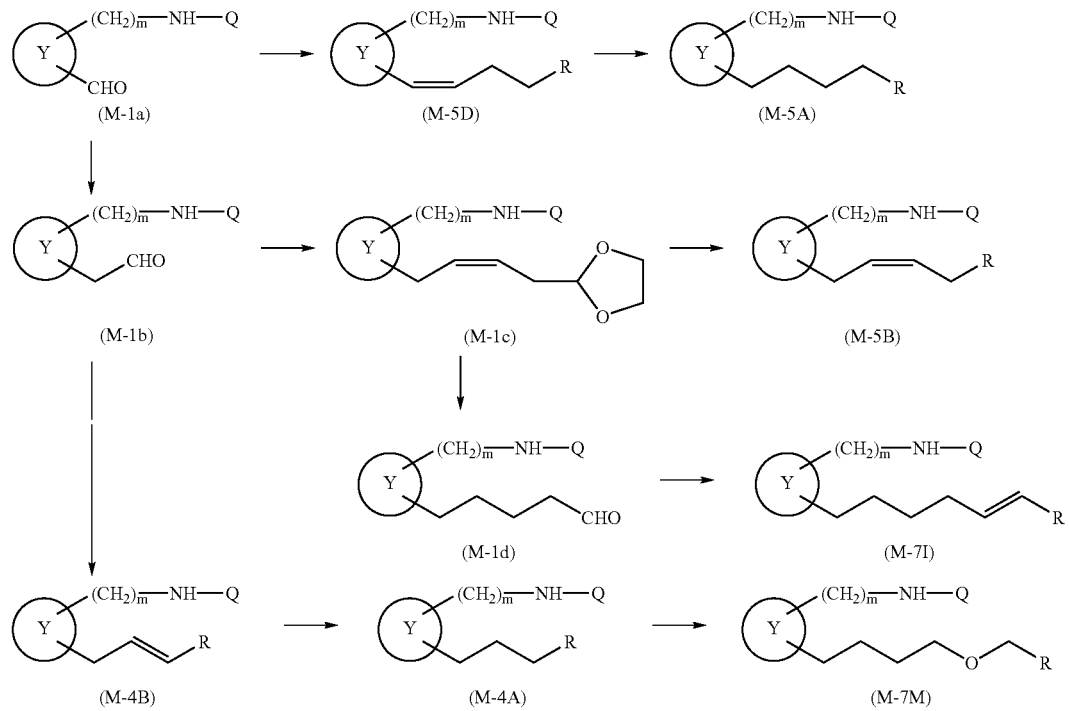

For example, the aldehyde (M-1a) is reacted with (3-carboxypropyl)triphenylphosphonium salt under a well known Wittig reaction condition to give a starting material (M-5D), wherein A is —CH$_2$=CH—CH$_2$—CH$_2$—. The compound M-5D is hydrogenated in the presence of palladium, platinum and the like to give a starting material (M-5A), wherein A is —CH$_2$—CH$_2$—CH$_2$—CH$_2$—. Furthermore, after a Wittig reaction using methoxymethyltriphenyl-phosphonium salt, followed by a hydrolysis with hydrochloric acid, formic acid, acetic acid and the like can furnish an aldehyde (M-1b) with one additional carbon atom and moreover a Wittig reaction with 2-(1,3-dioxoran-2-yl)ethyltriphenylphosphonium salt can give a compound represented by a general formula (M-1c). A Jones oxidation (J. Chem. Soc., 1946, 39) of the compound gives a starting material (M-5B) wherein A is —CH$_2$—CH=CHCH$_2$— in the formula (M-1). And by the above similar method, after an aldehyde (M-1d) was obtained by hydrogenation, followed by hydrolysis of the acetal with acid, either a Wittig reaction with a stable yield such as methyl (triphenylphophoranidene)acetate and the like or a Honer-Emmons reaction with methyl dimethylphosphonoacetate can convert to a starting material (M-7I), wherein A is —CH$_2$—CH$_2$—CH$_2$—CH$_2$—CH=CH—. When the above mentioned reaction is applied to an aldehyde (M-1b), a corresponding starting material (M-4B), wherein A is —CH$_2$CH=CH— is obtained and furthermore a corresponding starting material (M-4A) wherein A is —CH$_2$—CH$_2$—CH$_2$— is obtained by a hydrogenation of the double bond. When a starting material wherein A is —CH$_2$—CH$_2$—CH$_2$—CH$_2$—O—CH$_2$— is required, a compound of the formula (M-4A) wherein R is CH$_2$OH can be reacted with halogenated acetic acid or its Amidation with a starting carboxylic acid (M-2) can be accomplished after a deprotection of an amino protecting group Q in a way of conversion to α-chain, if necessary.

When p is 0, the carboxylic acid of the formula (M-2) can be prepared by reacting a carboxylic acid having X$^1$ or its reactive derivative with a compound having X$^3$. A person ordinary skilled in the art can carry out such a reaction by selecting the kinds of reactions and their conditions depending on the kind of X$^2$.

A compound represented by the formula: X$^3$—X$^2$—X$^1$—COOH wherein X$^3$ is pyrrolyl optionally substituted with alkyl, alkyloxy or halogen, indolyl optionally substituted with alkyl, alkyloxy or halogen, indolinyl optionally substituted with alkyl, alkyloxy or halogen or 1,2,3,4-tetrahydroquinolyl optionally substituted with alkyl, alkyloxy or halogen; X$^2$ is —SO$_2$—, —S— or —CH$_2$—; X$^1$ is thienyl, or the pharmaceutically acceptable salt, or especially a substituent represented by the formula: X$^1$—X$^2$—X$^3$ is 5-[(1-pyrrolyl)sulfonyl]thiophen-2-yl, 5-[(2-methyl-1-pyrrolyl)sulfonyl]thiophen-2-yl or 5-[(2,5-dimethyl-1-pyrrolyl)sulfonyl]thiophen-2-yl, or the pharmaceutically acceptable salt is important as an intermediate. Salt refers to lithium salt, sodium salt, potassium salt, calcium salt, triethylammonium salt, pyridinium salt or the like.

When p is 0, a group of the formula: —NHCO—X$^1$—X$^2$—X$^3$ of the compound (I) can be introduced by reacting a carboxylic acid of the formula: X$^3$—X$^2$—X$^1$—COOH (M-2) or its reactive derivative with amine (M-1), or by reacting a carboxylic acid having X$^1$ or its reactive derivatives with amine (M-1) and reacting the obtained compound with a compound having X$^3$.

In case of the introduction of a substituent(s) into the "optionally substituted aryl", "optionally substituted heteroaryl" or "optionally substituted non-aromatic heterocyclyl", the change of the functional group can be performed before or after reacting a carboxylic acid or its reactive derivative thereof (M-2) with the amine (M-1).

In an aromatic part such as aryl, heteroaryl and the like, usual methods of introduction or conversion of the functional group known for an aromatic ring can be applied. For example, the compound having an aromatic heterocycle substituted with a nitro group can be prepared through the nitration of the compound with a nitrating acid. Moreover, the compound having an aromatic heterocycle substituted with an amino group can be prepared through the reduction of the above-obtained compound with tin in the presence of hydrochloride. Moreover, the compound having an aromatic heterocycle substituted with hydroxy group can be prepared through the diazonization of the above-obtained compound and the hydrolysis with alkali. On the other hand, the compound having an aromatic heterocycle substituted with an alkoxy group can be prepared through the reaction of the diazonium derivative with alcohol. The compound having an aromatic heterocycle substituted with halogen can be prepared through Sandmeyer reaction, the reaction of the diazonium derivative with a copper salt (e.g., $CuCl_2$, $CuBr_2$). The compound having an aromatic heterocycle substituted with halogen can be also prepared through the direct reaction of the compound having an aromatic heterocycle with chlorine and the like. Using the above-mentioned methods appropriately, halogen can be introduced into a desired position(s). The group of alkyl, alkenyl or acyl group can be directly introduced into an aromatic heterocycle through Friedel Crafts reaction with alkylating agent, an alkenylating agent, or an acylating agent, respectively, in the presence of anhydrous aluminum chloride and the like.

The objective compound (I) of the present invention can be converted into a corresponding ester derivative, if desired. For example, the ester derivative can be prepared by esterification of a carboxylic acid in accordance with a known method.

When using the compound (I) of the present invention in treatment, it can be formulated into ordinary formulations for oral and parenteral administration. A pharmaceutical composition containing the compound (I) of the present invention can be in the form for oral and parenteral administration. Specifically, it can be formulated into formulations for oral administration such as tablets, capsules, granules, powders, syrup, and the like; or those for parenteral administration such as injectable solution or suspension for intravenous, intramuscular, or subcutaneous injection, inhalant, eye drops, nasal drops, suppositories, or percutaneous formulations such as ointment.

In preparing the formulations, carriers, excipients, solvents, and bases known to one having ordinary skill in the art may be used. In case of tablets, they are prepared by compressing or formulating an active ingredient together with auxiliary components. Examples of usable auxiliary components include pharmaceutically acceptable excipients such as binders (e.g., cornstarch), fillers (e.g., lactose, microcrystalline cellulose), disintegrants (e.g., starch sodium glycolate) or lubricants (e.g., magnesium stearate). Tablets may be coated appropriately. In case of liquid formulations such as syrups, solutions, or suspensions, they may contain suspending agents (e.g., methyl cellulose), emulsifiers (e.g., lecithin), preservatives, and the like. In case of injectable formulations, it may be in the form of solution, suspension, or oily or aqueous emulsion, which may contain suspension-stabilizing agents or dispersing agent, and the like. In case of an inhalant, it is formulated into a liquid formulation applicable to an inhaler. In case of eye drops, it is formulated into a solution or a suspension.

Especially, in case of a nasal drug for treating nasal blockage, it can be used as a solution or suspension prepared by a conventional formulating method, or administered as a powder formulated using a powdering agent (e.g., hydroxypropyl cellulose, carbopole) into the nasal cavity. Alternatively, it can be used as an aerosol filled into a special container together with a solvent of low boiling point.

In a case using as an eyewash drug for treating allergic conjunctivitis, it can be used as a solution or suspension of the compound or can be used by solving or suspending the compound before use. A stabilizing agent, solubilizing agent, suspending agent, emulsifier, buffer, preservatives and the like can be included. In a case using as an eyewash drug, aseptic treatment is preferable.

Pharmaceutical preparation of injection, oral agent, inhalation and the like is preferable for treating asthma.

Although an appropriate dosage of the compound (I) varies depending on the administration route, age, body weight, sex, or conditions of the patient, and the kind of drug(s) used together, if any, and should be determined by the physician in the end, in the case of oral administration, the daily dosage can generally be between 0.01–100 mg, preferably 0.01–10 mg, more preferably 0.01–1 mg, per kg body weight. In case of parenteral administration, the daily dosage can generally be between 0.001–100 mg, preferably 0.001–1 mg, more preferably 0.001–0.1 mg, per kg body weight. The daily dosage can be administered in 1–4 divisions.

EXAMPLE

The following examples are provided to further illustrate the present invention and are not to be construed as limiting the scope.

Example 1

Preparation of (I-5A-59a), (I-5A-59b)

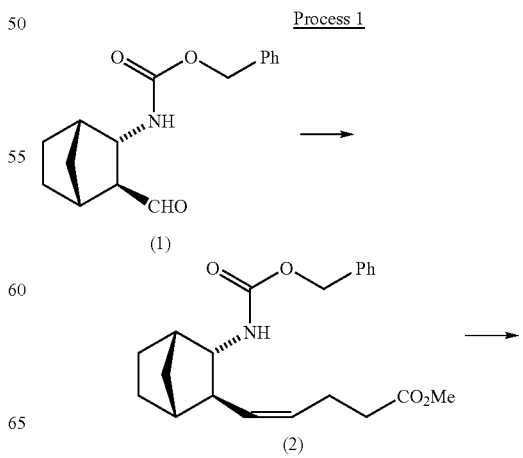

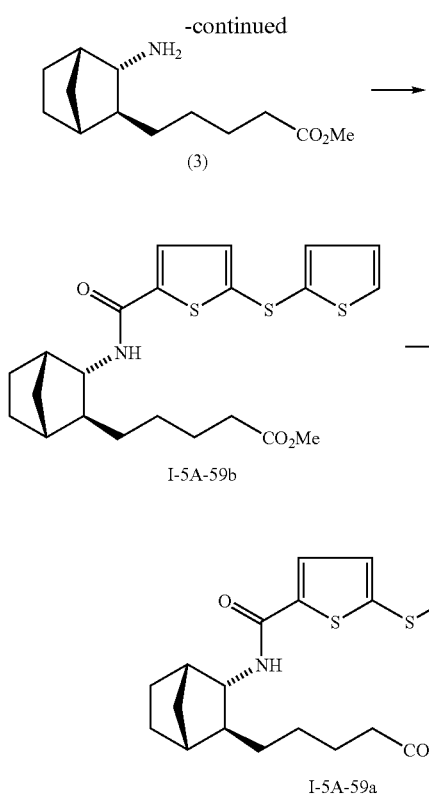

Potassium t-butoxide (4.32 g, 38.5 mmol) was added to a suspension of (3-carboxypropyl)triphenylphosphonium bromide (9.42 g, 22.0 mmol) in THF (45 ml) with cooling in ice. The mixture was stirred for 1 h and cooled to −10° C. A solution of compound (I) (3.0 g, 11.0 mmol) in THF (15 ml) was added dropwise over 15 min. The mixture was stirred at the temperature for 1 h, diluted with water, washed twice with toluene, acidified (pH=1) with hydrochloric acid and extracted with ethyl acetate. The extracts were washed with water and brine, dried and concentrated. An excess diazomethane solution in ether was added to a solution of the residue in ethyl acetate (20 ml) with cooling in ice. The mixture was concentrated and purified by silica gel chromatography (hexane-ethyl acetate, 85:15) to give a compound (2) (3.32 g; yield 85%).

Process 2

10% Palladium-carbon (0.32 g) was added to a solution of compound (2) (3.22 g, 9.0 mmol) in methanol (30 ml). The mixture was stirred under a hydrogen atmosphere for 17 h, filtered and concentrated to give a compound (3) (2.05 g; yield 100%)

Process 3

5-(2-Thienylthio)thiophene-2-carboxylic acid (233 mg, 0.96 mmol) and 1-hydroxybenzotriazole (10.8 mg, 0.08 mmol) were added to a solution of compound (3) (180 mg, 0.80 mmol) in THF (8 ml) and 1-ethyl-3-(3-dimethylaminopropyl)-carbodiimide (149 mg, 0.96 mmol) under cooling in ice. The mixture was stirred at room temperature for 14 h, diluted with ethyl acetate, washed with dilute hydrochloric acid, aq. sodium hydrogencarbonate successively, dried and concentrated. The residue was purified by silica gel chromatography (hexane-ethyl acetate, 5:1) to give a compound (I-5A-59b) (325 mg; yield 90%).

Process 4

1N aq. lithium hydroxide (1.8 ml, 1.8 mmol) was added to a solution of compound (I-5A-59b) (325 mg, 0.72 mmol) in THF (8 ml). The mixture was stirred at room temperature for 14 h, acidified and extracted with ethyl acetate. The extracts were washed with water and brine, successively, dried and concentrated to give a compound (I-5A-59a) (300 mg; yield 96%).

Example 2

Preparation of Compound (I-7M-1a), (I-7N-1a), (I-7N-1b)

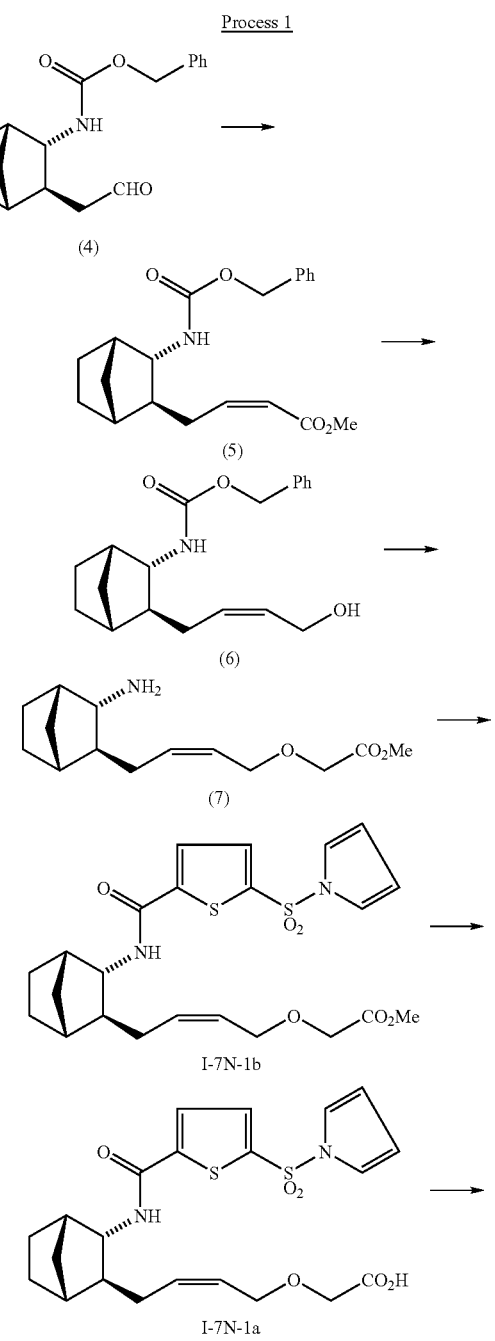

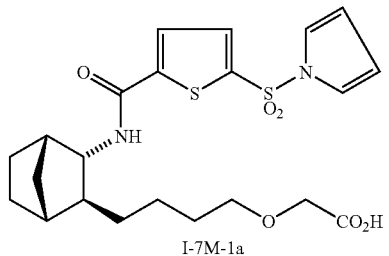

I-7M-1a

Methyl bis(2,2,2-trifluoroethyl)phosphonoacetate (2.94 ml, 13.92 mmol) and 18-crown-6 (5.52 g, 20.88 mmol) in THF (100 ml) were cooled at −60° C. A solution of potassium bis(trimethylsilyl)amide (0.5 M toluene solution, 27.8 ml, 13.9 mmol) was added. The mixture was stirred for 15 h. A solution of compound (4) (2.0 g, 6.96 mmol) in THF (20 ml) was added dropwise during 15 min. The mixture was stirred at the same temperature for 2 h. The temperature was raised to 0° C. and the mixture was diluted with water and extracted with ethyl acetate. The extracts were washed with water and brine, successively, dried, concentrated and purified by silica gel chromatography (hexane-ethyl acetaqte, 5:1) to give a compound (5) (2.10 g; yield 88%).

Process 2

Diisopropylaluminum hydride (1M toluene solution, 13.1 ml, 13.1 mmol) was added dropwise to a solution of compound (5) (1.80 g, 5.24 mmol) in dichloromethane (20 ml)-hexane (20 ml) at −78° C. The mixture was stirred at the temperature for 1 h. Methanol (1 ml) was added. The mixture was warmed to the room temperature. 2N Hydrochloric acid was added. The mixture was extracted with ethyl acetate. The extracts were washed with sodium hydrogencarbonate and brine successively, dried, concentrated and purified by silica gel chromatography (hexane-ethyl acetate, 7:3) to give a compound (6) (5.92 g; yield 96%).

Process 3

A mixture of compound (6) (1.58 g, 5.01 mmol), t-butyl bromoacetate (1.05 ml, 6.50 mmol), tetrabutylammonium hydrogensulfate (170 mg, 0.5 mmol) and 50% sodium hydroxide (4 ml) were vigorously stirred at room temperature for 18 h. The phase of toluene was separated, washed with water and brine successively, dried and concentrated. The residue obtained, trifluoroacetic acid (6.38 ml, 83 mmol) and anisole (3.37 ml. 31 mmol) were stirred at 60° C. for 15 h and concentrated under a reduced pressure. The residue was washed with hexane. Methanol (20 ml) and conc. sulfuric acid (0.44 ml) were added. The mixture was heated under reflux for 2 h. 2N sodium hydroxide was added to be alkaline. The mixture was extracted with ethyl acetate. The extracts were washed with water and brine successively, dried and concentrate to give a compound (7) (461 mg; yield 44%).

Process 4

5-(2-Methyl-1-pyrrolylsulfonyl)thiophene-2-carboxylic acid (21.8 mg, 0.85 mmol) and 1-hydroxybenzotriazole (13 mg, 0.09 mmol) were added to a solution of compound (7) (215 mg, 0.85 mmol) in THF (6 ml). 1-Ethyl-3-(3-dimethylaminopropyl)-carbodiimide (137 mg, 1.02 mmol) was further added under cooling in ice. The mixture was stirred at room temperature for 16 h, diluted with ethyl acetate, washed with dilute hydrochloric acid and sodium hydrogencarbonate successively, dried and concentrated. The residue was purified by silica gel chromatography (hexane-ethyl acetate 2:1) to give a compound (I-7N-1b) (328 mg; yield 78%).

Process 5

1 N Sodium hydroxide solution (1.57 ml, 1.57 mmol) was added to a solution of compound (I-7N-1b) (310 mg, 0.63 mmol) in THF (3.2 ml)-methanol (6.3 ml) and the mixture was stirred at room temperature 16 h. 2N Hydrochloric acid was added to acidify and the mixture was extracted with ethyl acetate. The extracts were washed with water and brine successively, dried and concentrated to give a compound (I-7N-1a) (399 mg; yield 73%).

Process 6

10% Palladium-carbon (170 mg, 0.36 mmol) was added to a solution of compound (1-7N-1a) (170 mg, 0.36 mmol) in methanol (5 ml). The mixture was stirred under a hydrogen atmosphere for 17 h and filtered. The filtrate was concentrated to give a compound (I-7M-1a) (162 mg; yield 95%).

Example 3

Preparation of Compounds (I-7I-55a), (II-7I-55b)

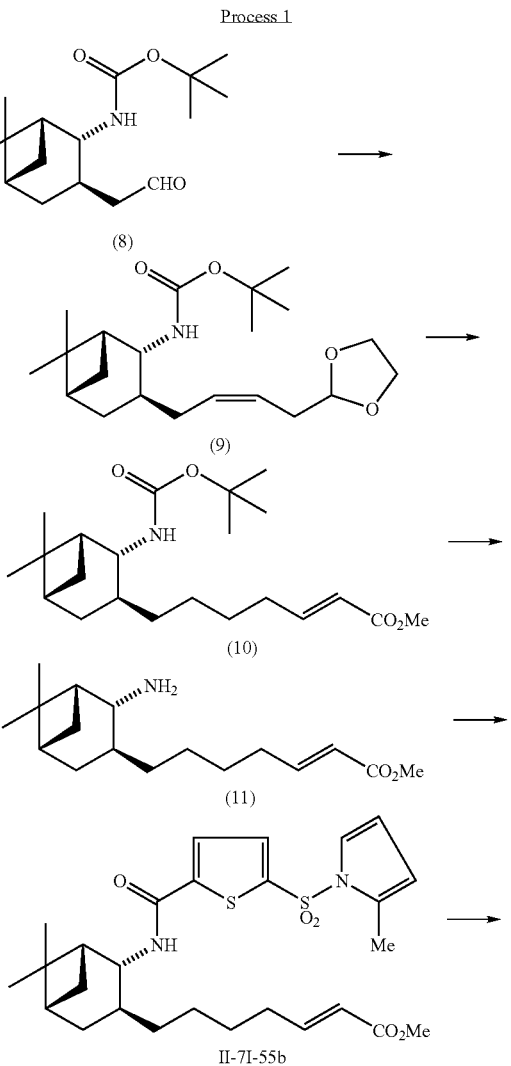

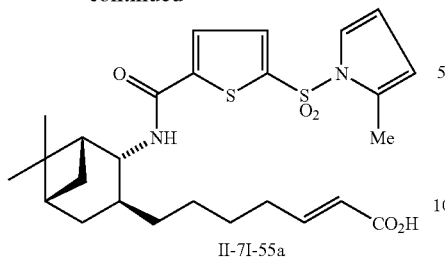

II-7I-55a

Potassium t-butoxide (6.73 g, 60.0 mmol) was added to a suspension of 2-(1,3-dioxolan-2-yl)ethyltriphenylphosphonium bromide (13.28 g, 30.0 mmol) in THF (60 ml) at −30° C. The mixture was stirred at −30° C. to 0° C. for 1 h. A solution of compound (8) (5.62 g, 20.0 mmol) in THF (40 ml) was added dropwise at −25° C. during 15 min. The mixture was warmed to 0° C., stirred for 1.5 h, diluted with water and extracted with ethyl acetate. The extracts were washed with water and brine, dried and concentrated. The residue was purified by silica gel chromatography (hexane-ethyl acetate 85:15) to give a compound (9) (6.27 g, yield 86%)

Process 2

10% Palladium-carbon (0.21 g) was added to a solution of compound (9) (4.10 g, 11.2 mmol) in methanol (41 ml). The mixture was stirred under a hydrogen atmosphere for 2 h and filtered. The filtrate was concentrated to give a residue. Pydidinium p-toluenesulfonate (503 mg, 2.0 mmol) was added to a solution of the residue in acetone-water (4:1, 50 ml). The mixture was heated under reflux for 16 h, diluted with water and extracted with ethyl acetate. The extracts were washed with water and brine, dried and concentrated. A mixture of the residue and methyl (triphenylphosphoraniliden)acetate (2.93 g, 8.76 mmol) in toluene (35 ml) was stirred at room temperature for 18 h, diluted with ethyl acetate, washed with water and brine and concentrated. The residue was purified by silica gel chromatography in (hexane-ethyl acetate 35:15) to give a compound (10) (2.71 g; yield 71%).

Process 3

Trifluoroacetic acid (3.82 ml, 49.5 mmol) was added to a solution of compound (10) (2.35 g, 6.19 mmol) in dicholoromethane (38 ml) and the mixture was stirred at room temperature for 3 h and concentrated under a reduced pressure. The residue was dissolved in toluene (50 ml) and water (10 ml). 2N Sodium hydroxide was added to be alkaline in the aq. layer. The toluene phase was separated, washed with water and brine, dried and concentrated to give a compound (11) (1.70 g; yield 98%).

Process 4

1-Ethyl-3-(3-dimethylaminopropyl)-carbodiimide (252 mg, 1.62 mmol) was added to a mixture of a compound (11) (433 mg, 1.55 mmol), 5-(2-methyl-1-pyrrolylsulfonyl) thiophen-2-carboxylic acid (400 mg, 1.47 mmol) and 1-hydroxybenzotriazole (20 mg, 0.15 mmol) in THF (6 ml) with cooling in ice. The mixture was stirred at room temperature for 16 h, diluted with ethyl acetate, washed with dilute hydrochloric acid and aq. sodium hydrogencarbonate successively, dried and concentrated. The residue was purified by silica gel chromatography (hexane-ethyl acetate, 4:1) to give a product (II-7I-55b) (585 mg; yield 74%).

Process 5

2N Lithium hydroxide (1.58 ml, 3.15 mmol) was added to a solution of compound (II-7I-55b) (560 mg, 1.05 mmol) in THF (8 ml). A mixture was stirred at room temperature for 48 h, acidified with 2N Hydrochloric acid and extracted with ethyl acetate. The extracts were washed with water and brine successively, dried and concentrated. The residue was purified by silica gel chromatography (hexane-ethyl acetate, 1:3) to give a compound (II-7I-55a) (399 mg; yield 73%).

Example 4

Preparation of Compounds (I-7A-1e), (I-7E-1e)

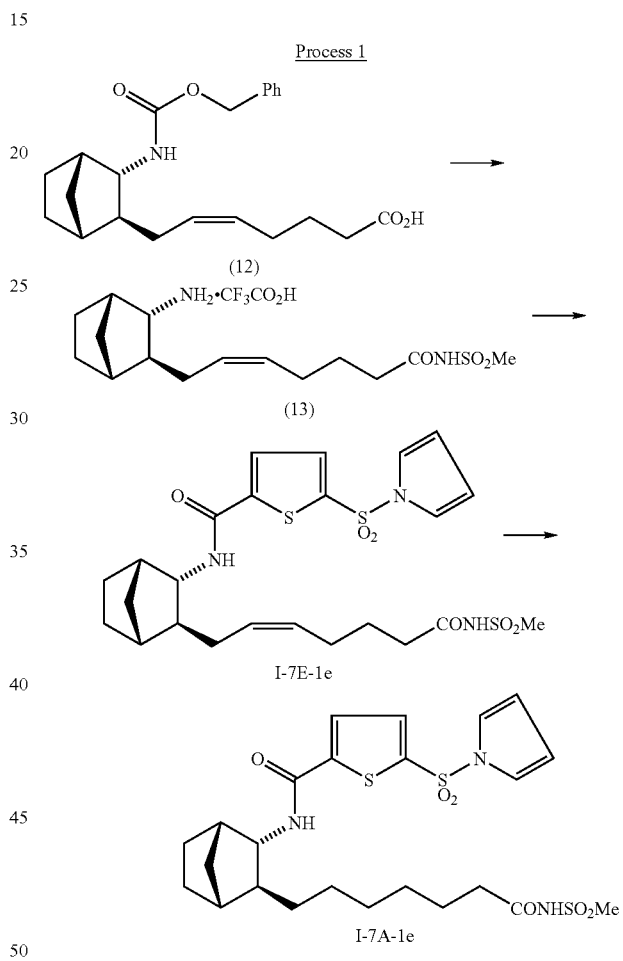

Oxalyl chloride (0.236 ml, 2.71 mmol) and N,N-dimethylformamide (a drop) were added to a solution compound (12) (840 mg, 2.26 mmol) in dichloromethane (20 ml) with cooling in ice. The mixture was stirred for 30 min and concentrated under a reduced pressure. The residue was dissolved in dichloromethane (20 ml). Methanesulfonamide (258 mg, 2.71 mmol) and 1,8-diazabicyclo[5.4.0]-7-undecene (0.744 ml, 4.97 mmol) were added. The mixture was stirred for 2.5 h, diluted with ethyl acetate, washed with dilute hydrochloric acid, aq. sodium hydrogencarbonate and brine successively, dried and concentrated. Trifluoroacetic acid (25 ml) and anisole (2 ml, 18.40 mmol) were added to the residue. The mixture was stirred at 50° C. for 13 h and concentrated under a reduced pressure. The oily residue was washed with hexane to give a compound (13) (0.776 g; yield 65%).

Process 2

Oxalyl chloride (0.081 ml, 0.929 mmol) and N,N-dimethylformamide (a drop) were added to a solution 5-(1-pyrrolylsulfonyl)thiophene-2-carboxylic acid (209 mg, 0.812 mmol) in dichloromethane (4 ml) with cooling in ice. The mixture was stirred for 20 min and at room temperature for 40 min and concentrated under a reduced pressure. The residue was dissolved in dichloromethane (4 ml). A solution of compound (13) (0.42, 0.774 mmol) in dichloromethane (4 ml)-THF (3 ml) and triethylamine (0.486 ml, 3.49 mmol) were added to the solution with cooling in ice. The mixture was stirred for 1.5 h and at room temperature for 19 h, diluted with ethyl acetate, washed with dilute hydrochloric acid, aq. sodium hydrogencarbonate and brine successively, dried and concentrated. The residue was purified by silica gel chromatography (hexane-ethyl acetate-acetic acid, 1:1:0.003) to give a compound (I-7E-1e) (157 mg; yield 37%).

Process 3

20% Palladium hydroxide-carbon (64 mg) was added to a solution of compound (I-7E-1e) (116 mg, 0.21 mmol) in methanol (3 ml). The mixture was stirred under a hydrogen atmosphere for 20 h and filtered. The filtrate was concentrated to give a compound (I-7A-1e) (109 mg; yield 94%).

Example 5

Preparation of Compound (Formula: $X^3$—$X^2$—$X^1$—COOH)

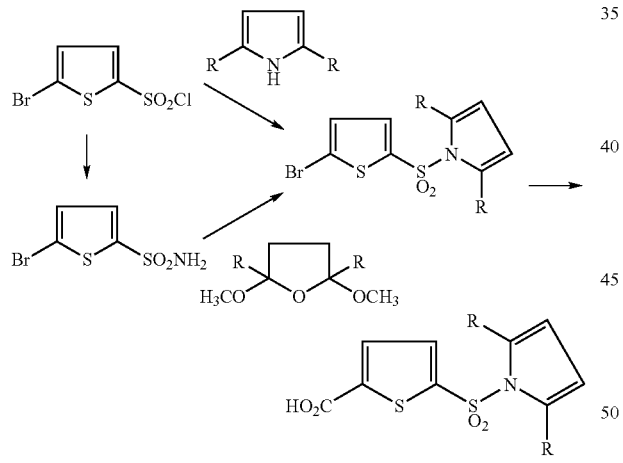

5-Bromothiophene-2-sulfonyl chloride was reacted directly with a pyrrole derivative or the acid chloride was converted to the sulfonamide followed by condensation with 2,5-dimethoxytetrahydro-derivative to give a sulfonylpyrrole derivative. Then, the product was converted to the organolithium or the organomagnesium compound by a halogen-metal exchange reaction, followed by reacting with carbon dioxide to give a desired compound.

5-(1-Pyrrolylsulfonyl)-2-thiophenecarboxylic acid mp 191–194° C.; $^1$H-NMR (CDCl$_3$) δ6.36 (2H, t, J=2.4 Hz), 7.18 (2H, t, J=2.4 Hz), 7.61 (1H, d, J=4.2 Hz), 7.74 (1H, d, J=4.2 Hz).

5-(2-Methyl-1-pyrrolylsulfonyl)-2-thiophenecarboxylic acid mp 159–160° C.; $^1$H-NMR (CDCl$_3$) δ2.40 (3H, d, J=0.9 Hz), 6.01 (1H, m), 6.23 (1H, t, J=3.0 Hz), 7.20 (1H, dd, J=1.8, 3.6 Hz), 7.58 (1H, d, J=4.2 Hz), 7.76 (1H, d, J=4.2 Hz).

5-(2,5-Dimethyl-1-pyrrolylsulfonyl)-2-thiophenecarboxylic acid mp 167–171° C.; $^1$H-NMR (CDCl$_3$) δ2.43 (6H, s), 5.90 (2H, s), 7.52 (1H, d, J=3.9 Hz), 7.75 (1H, d, J=3.9 Hz).

The structure and physical property of the compound prepared in accordance with the above examples are shown below. Each sign used for —$X^1$—$X^2$—$X^3$ and A in Tables means the sign represented before.

TABLE 1

| Compd. No.. | —$X^1$—$X^2$—$X^3$ | A | R |
|---|---|---|---|
| I-4A-1a | 1 | 4A | CO$_2$H |
| I-4B-1a | 1 | 4B | CO$_2$H |
| I-4C-1a | 1 | 4C | CO$_2$H |
| I-4D-1a | 1 | 4D | CO$_2$H |
| I-4E-1a | 1 | 4E | CO$_2$H |
| I-4F-1a | 1 | 4F | CO$_2$H |
| I-5A-1a | 1 | 5A | CO$_2$H |
| I-5A-1b | 1 | 5A | CO$_2$Me |
| I-5A-31a | 31 | 5A | CO$_2$H |
| I-5A-47a | 47 | 5A | CO$_2$H |
| I-5A-55a | 55 | 5A | CO$_2$H |
| I-5A-59a | 59 | 5A | CO$_2$H |
| I-5A-59b | 59 | 5A | CO$_2$Me |
| I-5A-80a | 80 | 5A | CO$_2$H |
| I-5A-88a | 88 | 5A | CO$_2$H |
| I-5A-88b | 88 | 5A | CO$_2$Me |
| I-5A-104a | 104 | 5A | CO$_2$H |
| I-5A-126a | 126 | 5A | CO$_2$H |
| I-5A-143a | 143 | 5A | CO$_2$H |
| I-5A-197a | 197 | 5A | CO$_2$H |
| I-5B-1a | 1 | 5B | CO$_2$H |
| I-5B-47a | 47 | 5B | CO$_2$H |
| I-5B-59a | 59 | 5B | CO$_2$H |
| I-5C-1a | 1 | 5C | CO$_2$H |
| I-5C-1b | 1 | 5C | CO$_2$Me |
| I-5C-55a | 55 | 5C | CO$_2$H |
| I-5C-31a | 31 | 5C | CO$_2$H |
| I-5C-47a | 47 | 5C | CO$_2$H |
| I-5C-88a | 88 | 5C | CO$_2$H |
| I-5D-1a | 1 | 5D | CO$_2$H |
| I-5E-1a | 1 | 5E | CO$_2$H |
| I-5E-55a | 55 | 5E | CO$_2$H |
| I-5F-1a | 1 | 5F | CO$_2$H |
| I-5F-47a | 47 | 5F | CO$_2$H |
| I-5G-47a | 47 | 5G | CO$_2$H |
| I-6A-1a | 1 | 6A | CO$_2$H |
| I-6A-31a | 31 | 6A | CO$_2$H |
| I-6A-55a | 55 | 6A | CO$_2$H |
| I-6A-88a | 88 | 6A | CO$_2$H |
| I-6B-1a | 1 | 6B | CO$_2$H |
| I-6B-31a | 31 | 6B | CO$_2$H |
| I-6B-88a | 88 | 6B | CO$_2$H |
| I-6C-1a | 1 | 6C | CO$_2$H |

TABLE 2

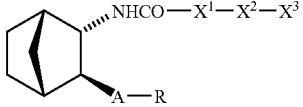

| Compd. No.. | —X¹—X²—X³ | A | R |
|---|---|---|---|
| I-6D-1a | 1 | 6D | $CO_2H$ |
| I-6E-1a | 1 | 6E | $CO_2H$ |
| I-6E-59a | 59 | 6E | $CO_2H$ |
| I-6F-1a | 1 | 6E | $CO_2H$ |
| I-6G-1a | 1 | 6G | $CO_2H$ |
| I-7A-1a | 1 | 7A | $CO_2H$ |
| I-7A-1b | 1 | 7A | $CO_2Me$ |
| I-7A-1c | 1 | 7A | $CONH_2$ |
| I-7A-1e | 1 | 7A | $CONHSO_2Me$ |
| I-7A-1h | 1 | 7A | $CH_2OH$ |
| I-7A-1i | 1 | 7A | $CH_2OMe$ |
| I-7A-31a | 31 | 7A | $CO_2H$ |
| I-7A-47a | 47 | 7A | $CO_2H$ |
| I-7A-47i | 47 | 7A | $CH_2OMe$ |
| I-7A-55a | 55 | 7A | $CO_2H$ |
| I-7A-59a | 59 | 7A | $CO_2H$ |
| I-7A-80a | 80 | 7A | $CO_2H$ |
| I-7A-88a | 88 | 7A | $CO_2H$ |
| I-7A-88e | 88 | 7A | $CONHSO_2Me$ |
| I-7A-88h | 88 | 7A | $CH_2OH$ |
| I-7A-88i | 88 | 7A | $CH_2OMe$ |
| I-7A-104a | 104 | 7A | $CO_2H$ |
| I-7A-143a | 143 | 7A | $CO_2H$ |
| I-7A-197a | 197 | 7A | $CO_2H$ |
| I-7A-315a | 315 | 7A | $CO_2H$ |
| I-7A-316a | 316 | 7A | $CO_2H$ |
| I-7B-1a | 1 | 7B | $CO_2H$ |
| I-7C-1a | 1 | 7C | $CO_2H$ |
| I-7D-1a | 1 | 7D | $CO_2H$ |
| I-7E-1c | 1 | 7E | $CONH_2$ |
| I-7I-1d | 1 | 7E | $CONHMe$ |
| I-7I-1e | 1 | 7E | $CONHSO_2Me$ |
| I-7I-1f | 1 | 7E | $CON(Me)SO_2Me$ |
| I-7E-1g | 1 | 7E | 5-tetrazolyl |
| I-7E-1h | 1 | 7E | $CH_2OH$ |
| I-7I-1i | 1 | 7E | $CH_2OMe$ |
| I-7I-47c | 47 | 7E | $CONH_2$ |
| I-7I-47i | 47 | 7E | $CH_2OMe$ |
| I-7E-88e | 88 | 7E | $CONHSO_2Me$ |
| I-7E-88h | 88 | 7E | $CH_2OH$ |
| I-7I-88i | 88 | 7I | $CH_2OMe$ |
| I-7F-1a | 1 | 7F | $CO_2H$ |

TABLE 3

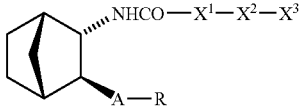

| Compd. No.. | —X¹—X²—X³ | A | R |
|---|---|---|---|
| I-7F-31a | 31 | 7F | $CO_2H$ |
| I-7F-47a | 47 | 7F | $CO_2H$ |
| I-7F-88a | 88 | 7F | $CO_2H$ |
| I-7F-143a | 143 | 7F | $CO_2H$ |
| I-7G-1a | 1 | 7G | $CO_2H$ |
| I-7G-88a | 88 | 7G | $CO_2H$ |
| I-7G-126a | 126 | 7G | $CO_2H$ |
| I-7I-1a | 1 | 7H | $CO_2H$ |
| I-7I-1a | 1 | 7I | $CO_2H$ |
| I-7I-1b | 1 | 7I | $CO_2Me$ |
| I-7I-1c | 1 | 7I | $CONH_2$ |
| I-7I-1e | 1 | 7I | $CONHSO_2Me$ |
| I-7I-31a | 31 | 7I | $CO_2H$ |
| I-7I-47a | 47 | 7I | $CO_2H$ |
| I-7I-55a | 55 | 7I | $CO_2H$ |

TABLE 3-continued

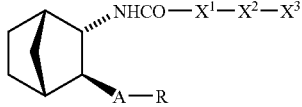

| Compd. No.. | —X¹—X²—X³ | A | R |
|---|---|---|---|
| I-7I-59a | 59 | 7I | $CO_2H$ |
| I-7I-80a | 80 | 7I | $CO_2H$ |
| I-7I-88a | 88 | 7I | $CO_2H$ |
| I-7I-93a | 93 | 7I | $CO_2H$ |
| I-7I-126a | 126 | 7I | $CO_2H$ |
| I-7I-143a | 143 | 7I | $CO_2H$ |
| I-7I-197a | 197 | 7I | $CO_2H$ |
| I-7I-270a | 270 | 7I | $CO_2H$ |
| I-7I-307a | 307 | 7I | $CO_2H$ |
| I-7I-327a | 327 | 7I | $CO_2H$ |
| I-7I-332a | 332 | 7I | $CO_2H$ |
| I-7I-343a | 343 | 7I | $CO_2H$ |
| I-7I-385a | 385 | 7I | $CO_2H$ |
| I-7I-389a | 389 | 7I | $CO_2H$ |
| I-7I-391a | 391 | 7I | $CO_2H$ |
| I-7J-1a | 1 | 7J | $CO_2H$ |
| I-7J-31a | 31 | 7J | $CO_2H$ |
| I-7K-1a | 1 | 7K | $CO_2H$ |
| I-7K-47a | 47 | 7K | $CO_2H$ |
| I-7K-59a | 59 | 7K | $CO_2H$ |
| I-7K-143a | 143 | 7K | $CO_2H$ |
| I-7L-1a | 1 | 7L | $CO_2H$ |
| I-7M-1a | 1 | 7M | $CO_2H$ |
| I-7M-1b | 1 | 7M | $CO_2Me$ |
| I-7M-1c | 1 | 7M | $CONH_2$ |
| I-7M-1e | 1 | 7M | $CONHSO_2Me$ |
| I-7M-31a | 31 | 7M | $CO_2H$ |
| I-7M-40a | 40 | 7M | $CO_2H$ |

TABLE 4

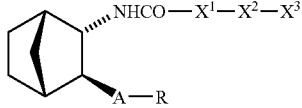

| Compd. No.. | —X¹—X²—X³ | A | R |
|---|---|---|---|
| I-7M-43a | 43 | 7M | $CO_2H$ |
| I-7M-47a | 47 | 7M | $CO_2H$ |
| I-7M-55a | 55 | 7M | $CO_2H$ |
| I-7M-59a | 59 | 7M | $CO_2H$ |
| I-7M-80a | 80 | 7M | $CO_2H$ |
| I-7M-88a | 88 | 7M | $CO_2H$ |
| I-7M-88e | 88 | 7M | $CONHSO_2Me$ |
| I-7M-88h | 88 | 7M | $CH_2OH$ |
| I-7M-88i | 88 | 7M | $CH_2OMe$ |
| I-7M-104a | 104 | 7M | $CO_2H$ |
| I-7M-126a | 126 | 7M | $CO_2H$ |
| I-7M-143a | 143 | 7M | $CO_2H$ |
| I-7M-197a | 197 | 7M | $CO_2H$ |
| I-7M-270a | 270 | 7M | $CO_2H$ |
| I-7M-307a | 307 | 7M | $CO_2H$ |
| I-7M-315a | 315 | 7M | $CO_2H$ |
| I-7M-316a | 316 | 7M | $CO_2H$ |
| I-7M-317a | 317 | 7M | $CO_2H$ |
| I-7M-318a | 318 | 7M | $CO_2H$ |
| I-7M-327a | 327 | 7M | $CO_2H$ |
| I-7M-329a | 329 | 7M | $CO_2H$ |
| I-7M-330a | 330 | 7M | $CO_2H$ |
| I-7M-331a | 331 | 7M | $CO_2H$ |
| I-7M-332a | 332 | 7M | $CO_2H$ |
| I-7M-333a | 333 | 7M | $CO_2H$ |
| I-7M-334a | 334 | 7M | $CO_2H$ |
| I-7M-336a | 336 | 7M | $CO_2H$ |
| I-7M-337a | 337 | 7M | $CO_2H$ |
| I-7M-342a | 342 | 7M | $CO_2H$ |

TABLE 4-continued

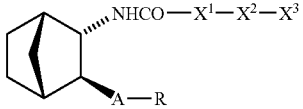

| Compd. No.. | —$X^1$—$X^2$—$X^3$ | A | R |
|---|---|---|---|
| I-7M-343a | 343 | 7M | $CO_2H$ |
| I-7M-385a | 385 | 7M | $CO_2H$ |
| I-7M-389a | 389 | 7M | $CO_2H$ |
| I-7M-390a | 390 | 7M | $CO_2H$ |
| I-7M-391a | 391 | 7M | $CO_2H$ |
| I-7M-392a | 392 | 7M | $CO_2H$ |
| I-7M-393a | 393 | 7M | $CO_2H$ |
| I-7M-396a | 396 | 7M | $CO_2H$ |
| I-7M-412a | 412 | 7M | $CO_2H$ |
| I-7M-424a | 424 | 7M | $CO_2H$ |
| I-7M-446a | 446 | 7M | $CO_2H$ |
| I-7M-447a | 447 | 7M | $CO_2H$ |
| I-7M-448a | 448 | 7M | $CO_2H$ |
| I-7N-1a | 1 | 7N | $CO_2H$ |

TABLE 5

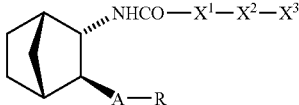

| Compd. No.. | —$X^1$—$X^2$—$X^3$ | A | R |
|---|---|---|---|
| I-7N-1b | 1 | 7N | $CO_2Me$ |
| I-7N-55a | 55 | 7N | $CO_2H$ |
| I-7N-88a | 88 | 7N | $CO_2H$ |
| I-7N-143a | 143 | 7N | $CO_2H$ |
| I-7O-1a | 1 | 7O | $CO_2H$ |
| I-7P-1a | 1 | 7P | $CO_2H$ |
| I-7P-1e | 1 | 7P | $CONHSO_2Me$ |
| I-7Q-1a | 1 | 7Q | $CO_2H$ |
| I-7R-1a | 1 | 7R | $CO_2H$ |
| I-7R-59a | 59 | 7R | $CO_2H$ |
| I-7R-88a | 88 | 7R | $CO_2H$ |
| I-7R-270a | 270 | 7R | $CO_2H$ |
| I-7R-307a | 307 | 7R | $CO_2H$ |
| I-7S-1a | 1 | 7S | $CO_2H$ |
| I-7T-1a | 1 | 7T | $CO_2H$ |
| I-8A-1a | 1 | 8A | $CO_2H$ |
| I-8A-47a | 47 | 8A | $CO_2H$ |
| I-8A-88a | 88 | 8A | $CO_2H$ |
| I-8B-1a | 1 | 8B | $CO_2H$ |
| I-8B-47a | 47 | 8B | $CO_2H$ |
| I-8B-88a | 88 | 8B | $CO_2H$ |
| I-8C-1a | 1 | 8C | $CO_2H$ |
| I-8C-88a | 88 | 8C | $CO_2H$ |
| I-9A-1a | 1 | 9A | $CO_2H$ |
| I-9A-47a | 47 | 9A | $CO_2H$ |
| I-9A-88a | 88 | 9A | $CO_2H$ |
| I-9B-1a | 1 | 9B | $CO_2H$ |
| I-9B-47a | 47 | 9B | $CO_2H$ |
| I-9B-88a | 88 | 9B | $CO_2H$ |

TABLE 6

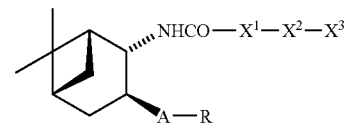

| Compd. No.. | —$X^1$—$X^2$—$X^3$ | A | R |
|---|---|---|---|
| II-4A-55a | 55 | 4A | $CO_2H$ |
| II-4B-55a | 55 | 4B | $CO_2H$ |
| II-4C-55a | 55 | 4C | $CO_2H$ |
| II-4D-55a | 55 | 4D | $CO_2H$ |
| II-4E-55a | 55 | 4E | $CO_2H$ |
| II-4F-55a | 55 | 4F | $CO_2H$ |
| II-5A-1a | 1 | 5A | $CO_2H$ |
| II-5A-1b | 1 | 5A | $CO_2Me$ |
| II-5A-31a | 31 | 5A | $CO_2H$ |
| II-5A-47a | 47 | 5A | $CO_2H$ |
| II-5A-55a | 55 | 5A | $CO_2H$ |
| II-5A-55c | 55 | 5A | $CONH_2$ |
| II-5A-55g | 55 | 5A | 5-tetrazolyl |
| II-5A-59a | 59 | 5A | $CO_2H$ |
| II-5A-80a | 80 | 5A | $CO_2H$ |
| II-5A-88a | 88 | 5A | $CO_2H$ |
| II-5A-88b | 88 | 5A | $CO_2Me$ |
| II-5A-104a | 104 | 5A | $CO_2H$ |
| II-5A-126a | 126 | 5A | $CO_2H$ |
| II-5A-143a | 143 | 5A | $CO_2H$ |
| II-5A-197a | 197 | 5A | $CO_2H$ |

TABLE 7

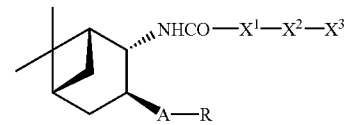

| Compd. No.. | —$X^1$—$X^2$—$X^3$ | A | R |
|---|---|---|---|
| II-5B-1a | 1 | 5B | $CO_2H$ |
| II-5B-47a | 47 | 5B | $CO_2H$ |
| II-5B-55a | 55 | 5B | $CO_2H$ |
| II-5C-1a | 1 | 5C | $CO_2H$ |
| II-5C-1b | 1 | 5C | $CO_2Me$ |
| II-5C-55a | 55 | 5C | $CO_2H$ |
| II-5C-88a | 88 | 5C | $CO_2H$ |
| II-5D-1a | 1 | 5D | $CO_2H$ |
| II-5E-1a | 1 | 5E | $CO_2H$ |
| II-5E-55a | 55 | 5E | $CO_2H$ |
| II-5F-31a | 31 | 5F | $CO_2H$ |
| II-5F-47a | 47 | 5F | $CO_2H$ |
| II-5F-55a | 55 | 5F | $CO_2H$ |
| II-5F-88a | 88 | 5F | $CO_2H$ |
| II-5G-47a | 47 | 5G | $CO_2H$ |
| II-6A-1a | 1 | 6A | $CO_2H$ |
| II-6A-31a | 31 | 6A | $CO_2H$ |
| II-6A-55a | 55 | 6A | $CO_2H$ |
| II-6A-88a | 88 | 6A | $CO_2H$ |
| II-6B-1a | 1 | 6B | $CO_2H$ |
| II-6B-31a | 31 | 6B | $CO_2H$ |
| II-6B-55a | 55 | 6B | $CO_2H$ |
| II-6B-88a | 88 | 6B | $CO_2H$ |

TABLE 8

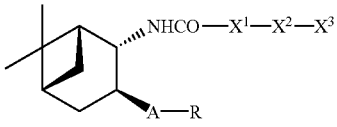

| Compd. No.. | —$X^1$—$X^2$—$X^3$ | A | R |
|---|---|---|---|
| II-6C-31a | 31 | 6C | $CO_2H$ |
| II-6D-1a | 1 | 6D | $CO_2H$ |
| II-6E-1a | 1 | 6E | $CO_2H$ |
| II-6E-59a | 59 | 6E | $CO_2H$ |
| II-6F-1a | 1 | 6F | $CO_2H$ |
| II-6G-1a | 1 | 6G | $CO_2H$ |
| II-7A-1a | 1 | 7A | $CO_2H$ |
| II-7A-1b | 1 | 7A | $CO_2Me$ |
| II-7A-1c | 1 | 7A | $CONH_2$ |
| II-7A-31a | 31 | 7A | $CO_2H$ |
| II-7A-47a | 47 | 7A | $CO_2H$ |
| II-7A-55a | 55 | 7A | $CO_2H$ |
| II-7A-55e | 55 | 7A | $CONHSO_2Me$ |
| II-7A-55g | 55 | 7A | 5-tetrazolyl |
| II-7A-59a | 59 | 7A | $CO_2H$ |
| II-7A-80a | 80 | 7A | $CO_2H$ |
| II-7A-88a | 88 | 7A | $CO_2H$ |
| II-7A-88e | 88 | 7A | $CONHSO_2Me$ |
| II-7A-88h | 88 | 7A | $CH_2OH$ |
| II-7A-88i | 88 | 7A | $CH_2OMe$ |
| II-7A-104a | 104 | 7A | $CO_2H$ |
| II-7A-143a | 143 | 7A | $CO_2H$ |
| II-7A-197a | 197 | 7A | $CO_2H$ |
| II-7A-315a | 315 | 7A | $CO_2H$ |
| II-7A-316a | 316 | 7A | $CO_2H$ |
| II-7B-55a | 55 | 7B | $CO_2H$ |
| II-7C-1a | 1 | 7C | $CO_2H$ |
| II-7D-1a | 1 | 7D | $CO_2H$ |
| II-7E-1c | 1 | 7E | $CONH_2$ |
| II-7E-1d | 1 | 7E | $CONHMe$ |
| II-7E-1e | 1 | 7E | $CONHSO_2Me$ |
| II-7E-1f | 1 | 7E | $CON(Me)SO_2Me$ |
| II-7E-1g | 1 | 7E | 5-tetrazolyl |
| II-7E-1h | 1 | 7E | $CH_2OH$ |
| II-7E-1i | 1 | 7E | $CH_2OMe$ |
| II-7E-47c | 47 | 7E | $CONH_2$ |
| II-7E-55c | 55 | 7E | $CONH_2$ |
| II-7E-55e | 55 | 7E | $CONHSO_2Me$ |
| II-7E-55g | 55 | 7E | 5-tetrazolyl |
| II-7E-88e | 88 | 7E | $CONHSO_2Me$ |
| II-7E-88h | 88 | 7E | $CH_2OH$ |
| II-7E-88i | 88 | 7E | $CH_2OMe$ |
| II-7F-1a | 1 | 7F | $CO_2H$ |

TABLE 9

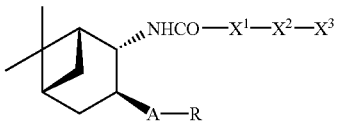

| Compd. No.. | —$X^1$—$X^2$—$X^3$ | A | R |
|---|---|---|---|
| II-7F-47a | 47 | 7F | $CO_2H$ |
| II-7F-55a | 55 | 7F | $CO_2H$ |
| II-7F-88a | 88 | 7F | $CO_2H$ |
| II-7F-143a | 143 | 7F | $CO_2H$ |
| II-7G-1a | 1 | 7G | $CO_2H$ |
| II-7H-1a | 1 | 7H | $CO_2H$ |
| II-7I-1a | 1 | 7I | $CO_2H$ |
| II-7I-1b | 1 | 7I | $CO_2Me$ |
| II-7I-1c | 1 | 7I | $CONH_2$ |
| II-7I-1e | 1 | 7I | $CONHSO_2Me$ |
| II-7I-31a | 31 | 7I | $CO_2H$ |
| II-7I-47a | 47 | 7I | $CO_2H$ |

TABLE 9-continued

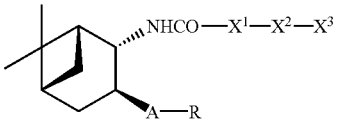

| Compd. No.. | —$X^1$—$X^2$—$X^3$ | A | R |
|---|---|---|---|
| II-7I-55a | 55 | 7I | $CO_2H$ |
| II-7I-55b | 55 | 7I | $CO_2Me$ |
| II-7I-59a | 59 | 7I | $CO_2H$ |
| II-7I-80a | 80 | 7I | $CO_2H$ |
| II-7I-88a | 88 | 7I | $CO_2H$ |
| II-7I-104a | 104 | 7I | $CO_2H$ |
| II-7I-126a | 126 | 7I | $CO_2H$ |
| II-7I-197a | 197 | 7I | $CO_2H$ |
| II-7I-239a | 239 | 7I | $CO_2H$ |
| II-7I-270a | 270 | 7I | $CO_2H$ |
| II-7I-327a | 327 | 7I | $CO_2H$ |
| II-7I-332a | 332 | 7I | $CO_2H$ |
| II-7I-343a | 343 | 7I | $CO_2H$ |
| II-7I-389a | 389 | 7I | $CO_2H$ |
| II-7I-391a | 391 | 7I | $CO_2H$ |
| II-7J-1a | 1 | 7I | $CO_2H$ |
| II-7J-55a | 55 | 7I | $CO_2H$ |
| II-7K-1a | 1 | 7K | $CO_2H$ |
| II-7K-47a | 47 | 7K | $CO_2H$ |
| II-7K-55a | 55 | 7K | $CO_2H$ |
| II-7K-59a | 59 | 7K | $CO_2H$ |
| II-7K-143a | 143 | 7K | $CO_2H$ |
| II-7L-1a | 1 | 7L | $CO_2H$ |
| II-7L-55a | 55 | 7L | $CO_2H$ |
| II-7M-1a | 1 | 7M | $CO_2H$ |
| II-7M-1b | 1 | 7M | $CO_2Me$ |
| II-7M-1c | 1 | 7M | $CONH_2$ |
| II-7M-1e | 1 | 7M | $CONHSO_2Me$ |
| II-7M-1k | 1 | 7M | $CONHSO_2Ph$ |
| II-7M-31a | 31 | 7M | $CO_2H$ |
| II-7M-40a | 40 | TM | $CO_2H$ |

TABLE 10

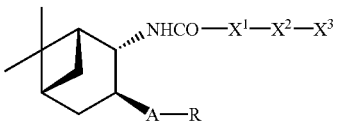

| Compd. No.. | —$X^1$—$X^2$—$X^3$ | A | R |
|---|---|---|---|
| II-7M-43a | 43 | 7M | $CO_2H$ |
| II-7M-47a | 47 | 7M | $CO_2H$ |
| II-7M-55a | 55 | 7M | $CO_2H$ |
| II-7M-59a | 59 | 7M | $CO_2H$ |
| II-7M-80a | 80 | 7M | $CO_2H$ |
| II-7M-88a | 88 | 7M | $CO_2H$ |
| II-7M-88e | 88 | 7M | $CONHSO_2Me$ |
| II-7M-88h | 88 | 7M | $CH_2OH$ |
| II-7M-88i | 88 | 7M | $CH_2OMe$ |
| II-7M-104a | 104 | 7M | $CO_2H$ |
| II-7M-126a | 126 | 7M | $CO_2H$ |
| II-7M-143a | 143 | 7M | $CO_2H$ |
| II-7M-197a | 197 | 7M | $CO_2H$ |
| II-7M-239a | 239 | 7M | $CO_2H$ |
| II-7M-270a | 270 | 7M | $CO_2H$ |
| II-7M-307a | 307 | 7M | $CO_2H$ |
| II-7M-327a | 327 | 7M | $CO_2H$ |
| II-7M-329a | 329 | 7M | $CO_2H$ |
| II-7M-330a | 330 | 7M | $CO_2H$ |
| II-7M-331a | 331 | 7M | $CO_2H$ |
| II-7M-332a | 332 | 7M | $CO_2H$ |
| II-7M-333a | 333 | 7M | $CO_2H$ |
| II-7M-334a | 334 | 7M | $CO_2H$ |
| II-7M-336a | 336 | 7M | $CO_2H$ |

TABLE 10-continued

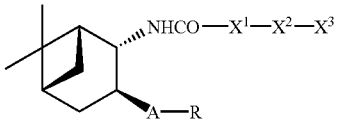

| Compd. No.. | —X¹—X²—X³ | A | R |
|---|---|---|---|
| II-7M-343a | 343 | 7M | $CO_2H$ |
| II-7M-385a | 385 | 7M | $CO_2H$ |
| II-7M-389a | 389 | 7M | $CO_2H$ |
| II-7M-390a | 390 | 7M | $CO_2H$ |
| II-7M-391a | 391 | 7M | $CO_2H$ |
| II-7M-392a | 392 | 7M | $CO_2H$ |
| II-7M-393a | 393 | 7M | $CO_2H$ |
| II-7N-1a | 1 | 7N | $CO_2Fl$ |
| II-7N-55a | 55 | 7N | $CO_2H$ |
| II-7N-88a | 88 | 7N | $CO_2H$ |
| II-7N-143a | 143 | 7N | $CO_2H$ |
| II-7O-55a | 55 | 7O | $CO_2H$ |
| II-7P-55a | 55 | 7P | $CO_2H$ |
| II-7P-55e | 55 | 7P | $CONHSO_2Me$ |
| II-7P-55j | 55 | 7P | $CONHSO_2CF_3$ |
| II-7Q-1a | 1 | 7Q | $CO_2H$ |
| II-7Q-55a | 55 | 7Q | $CO_2H$ |
| II-7R-55a | 55 | 7R | $CO_2H$ |
| II-7R-88a | 88 | 7R | $CO_2H$ |

TABLE 11

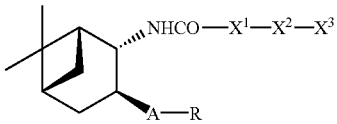

| Compd. No.. | —X¹—X²—X³ | A | R |
|---|---|---|---|
| II-7R-270a | 270 | 7R | $CO_2H$ |
| II-7S-1a | 1 | 7S | $CO_2H$ |
| II-7S-47a | 47 | 7S | $CO_2H$ |
| II-7S-55a | 55 | 7S | $CO_2H$ |
| II-7T-55a | 55 | 7T | $CO_2H$ |
| II-7U-31a | 31 | 7U | $CO_2H$ |
| II-7U-55a | 55 | 7U | $CO_2H$ |
| II-7U-88a | 88 | 7U | $CO_2H$ |
| II-7V-55a | 55 | 7V | $CO_2H$ |
| II-8A-1a | 1 | 8A | $CO_2H$ |
| II-8A-47a | 47 | 8A | $CO_2H$ |
| II-8A-88a | 88 | 8A | $CO_2H$ |
| II-8B-1a | 1 | 8B | $CO_2H$ |
| II-8B-47a | 47 | 8B | $CO_2H$ |
| II-8B-88a | 88 | 8B | $CO_2H$ |
| II-8C-55a | 55 | 8C | $CO_2H$ |
| II-8C-88a | 88 | 8C | $CO_2H$ |
| II-9A-1a | 1 | 9A | $CO_2H$ |
| II-9A-47a | 47 | 9A | $CO_2H$ |
| II-9A-88a | 88 | 9A | $CO_2H$ |
| II-9B-1a | 1 | 9B | $CO_2H$ |
| II-9B-47a | 47 | 9B | $CO_2H$ |
| II-9B-88a | 88 | 9B | $CO_2H$ |

TABLE 12

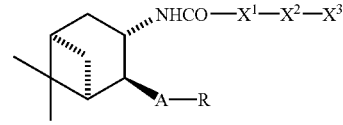

| Compd. No.. | —X¹—X²—X³ | A | R |
|---|---|---|---|
| III-5A-1a | 1 | 5A | $CO_2H$ |
| III-5A-47a | 47 | 5A | $CO_2H$ |
| III-5A-55a | 55 | 5A | $CO_2H$ |
| III-5A-80a | 80 | 5A | $CO_2H$ |
| III-7A-1a | 1 | 7A | $CO_2H$ |
| III-7A-47a | 47 | 7A | $CO_2H$ |
| III-7A-55a | 55 | 7A | $CO_2H$ |
| III-7A-80a | 80 | 7A | $CO_2H$ |

TABLE 13

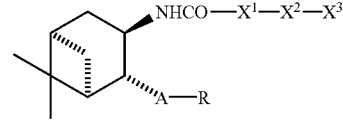

| Compd. No.. | —X¹—X²—X³ | A | R |
|---|---|---|---|
| IV-5A-1a | 1 | 5A | $CO_2H$ |
| IV-5A-47a | 47 | 5A | $CO_2H$ |
| IV-7A-1a | 1 | 7A | $CO_2H$ |
| IV-7A-47a | 47 | 7A | $CO_2H$ |

TABLE 14

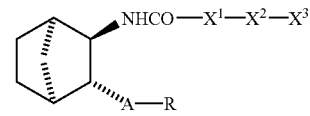

| Compd. No.. | —X¹—X²—X³ | A | R |
|---|---|---|---|
| V-5A-88a | 88 | 5A | $CO_2H$ |
| V-7A-88a | 88 | 7A | $CO_2H$ |

TABLE 15

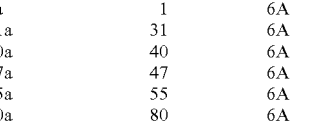

| Compd. No.. | —X¹—X²—X³ | A | R |
|---|---|---|---|
| VI-6A-1a | 1 | 6A | $CO_2H$ |
| VI-6A-31a | 31 | 6A | $CO_2H$ |
| VI-6A-40a | 40 | 6A | $CO_2H$ |
| VI-6A-47a | 47 | 6A | $CO_2H$ |
| VI-6A-55a | 55 | 6A | $CO_2H$ |
| VI-6A-80a | 80 | 6A | $CO_2H$ |
| VI-6A-88a | 88 | 6A | $CO_2H$ |
| VI-6A-104a | 104 | 6A | $CO_2H$ |
| VI-6A-122a | 122 | 6A | $CO_2H$ |
| VI-6A-123a | 123 | 6A | $CO_2H$ |
| VI-6A-124a | 124 | 6A | $CO_2H$ |
| VI-6A-133a | 133 | 6A | $CO_2H$ |

TABLE 16

[Structure: bicyclic norbornane with CH₂NHCO—X¹—X²—X³ and A—R substituents]

| Compd. No.. | —X¹—X²—X³ | A | R |
|---|---|---|---|
| VII-6A-1a | 1 | 6A | CO₂H |
| VII-6A-47a | 47 | 6A | CO₂H |
| VII-6A-88a | 88 | 6A | CO₂H |

TABLE 17

| Compd. No.. | Physical property |
|---|---|
| I-4B-1a | $^1$H-NMR(CD$_3$OD) δ 1.24–2.33(11H, m), 2.46(1H, m), 3.69–3.76(2H, m), 6.11(1H, dt, J=7.8and33.3Hz), 6.36(2H, m), 7.23(2H, m), 7.71(2H, m), 8.54(1H, br); IR(CHCl$_3$)3442, 2877, 1741, 1657, 1529, 1504, 1456, 1383, 1167, 1076, 1057, 1036cm$^{-1}$; $[α]_D^{25}$+37.7±0.7° (c=1.05, MeOH) |
| I-4E-1a | $^1$H-NMR(CDCl$_3$) δ 1.26–1.76(7H, m), 2.10(1H, m), 2.47 (1H, m), 3.35(1H, dd, J=8.4and9.0Hz), 3.58(1H, dd, J= 6.3and8.4Hz), 3.98(1H, d, J=16.2Hz), 4.08(1H, m), 4.13(1H, d, J=16.2Hz), 6.27(1H, d, J=8.1Hz), 6.34 (2H, d, J=4.8Hz), 7.15(2H, d, J=4.8Hz), 7.37(1H, d, J=4.2Hz), 7.58(1H, d, J=4.2Hz); IR(CHCl$_3$)3440, 2958, 2879, 1753, 1734, 1655, 1533, 1508, 1477, 1456, 1427, 1383, 1315, 1167, 1122, 1057, 1034cm$^{-1}$; $[α]_D^{24}$+ 41.7±0.8°(c=1.00, CHCl$_3$)Anal.(C$_{19}$H$_{22}$N$_2$O$_6$S$_2$·0.6H$_2$O) Calcd.(%): C, 50.79; H, 5.20; N, 6.23; S, 14.27Found(%): C, 50.76; H, 5.00; N, 6.26; S, 14.09 |
| I-4F-1a | mp126–128°C.; $^1$H-NMR(CD$_3$OD) δ 1.26–1.66(8H, m), 2.03(1H, m), 2.48(1H, m), 2.57(1H, m), 3.76(1H, m), 5.69(1H, dt, J=8.1and21.3Hz), 6.36(1H, m), 7.23 (2H, m), 7.72(2H, m), 8.53(1H, d, J=5.4Hz); IR (CHCl$_3$)3417, 3322, 2958, 2877, 1730, 1653, 1535, 1508, 1456, 1427, 1379, 1302, 1167, 1128, 1057, 1036cm$^{-1}$; $[α]_D^{25}$+68.3±1.0°(c=1.04, MeOH)Anal. (C$_{20}$H$_{21}$FN$_2$O$_5$S$_2$·0.9H$_2$O)Calcd.(%): C, 51.52; H, 4.90; N, 5.98; F, 4.05; S, 13.68Found(%): C, 51.46; H, 4.62; N, 5.72; F, 3.72; S, 12.93 |
| I-5A-1a | $^1$H-NMR(CDCl$_3$) δ 1.02(1H, m), 1.23–1.44(8H, m), 1.54–1.65(4H, m), 2.00(1H, m), 2.29–2.36(2H, m), 2.49 (1H, brs), 3.80(1H, m), 6.17(1H, d, J=7.5Hz), 6.33–6.34 (2H, m), 7.15–7.16(2H, m), 7.35(1H, d, J=3.9Hz), 7.55(1H, d, J=3.9Hz); IR(CHCl$_3$)3516, 3442, 1709, 1658, 1529, 1504, 1456, 1383, 1192, 1167, 1057, 1034cm$^{-1}$; $[α]_D^{27}$+48.7±0.9°(c=1.006, MeOH)Anal. (C$_{21}$H$_{26}$N$_2$O$_5$S$_2$)Calcd.(%): C, 55.98; H, 5.82; N, 6.22; S, 14.23Found(%): C, 56.10; H, 5.81; N, 6.08; S, 13.77 |
| I-5A-31a | $^1$H-NMR(CDCl$_3$) δ 0.95(1H, m), 1.16–1.70(12H, m), 1.97 (1H, m), 2.32(2H, t, J=7.2Hz), 2.48(1H, m), 3.81(1H, m), 4.14(2H, s), 5.83(1H, d, J=6.6Hz), 6.77(1H, d, J= 3.3Hz), 7.21–7.37(6H, m); IR(CHCl$_3$)3514, 3446, 3427, 1709, 1643, 1543, 1506, 1456cm$^{-1}$; $[α]_D^{24.0}$+46.9±0.9° (c=1.011, MeOH)Anal.(C$_{24}$H$_{29}$NO$_3$S·0.5H$_2$O)Calcd.(%): C, 68.54; H, 7.19; N, 3.33; S, 7.62Found(%): C, 68.62; H, 7.03; N, 3.47; S, 7.54 |

TABLE 18

| Compd. No.. | Physical property |
|---|---|
| I-5A-47a | $^1$H-NMR(CDCl$_3$) δ 1.03(1H, m), 1.18–1.70(12H, m), 1.98 (1H, m), 2.32(2H, dt, J=8.1, 2.1Hz), 2.50(1H, m), 3.81 (1H, dd, J=5.1, 3.9Hz), 6.19(1H, d, J=7.8Hz), 7.11 (1H, dd, J=5.1, 3.9Hz), 7.39(1H, d, J=3.9Hz), 7.61(1H, d, J=3.9Hz), 7.70(1H, dd, J=5.1, 1.2Hz), 7.75(1H, dd, J=3.9, 1.2Hz); IR(CHCl$_3$)3512, 3442, 3375, 2679, 1709, 1655, 1529, 1504, 1402, 1336, 1153, 1095, 1022cm$^{-1}$; $[α]_D^{24.0}$+ 48.6±0.9°(c=1.009, MeOH)Anal. (C$_{21}$H$_{25}$NO$_5$S$_3$·0.2H$_2$O)Calcd.(%): C, 53.53; H, 5.43; N, 2.97; S, 20.41Found(%): C, 53.56; H, 5.32; N, 2.92; S, 20.17 |
| I-5A-55a | $^1$H-NMR(CDCl$_3$) δ 1.02(1H, m), 1.25–1.48(8H, m), 1.55–1.66(4H, m), 2.01(1H, m), 2.32 (2H, dt, J=2.1, 7.5Hz), 2.38(3H, s), 2.50(1H, brs), 3.80(1H, m), 5.99(1H, m), 6.07(1H, brd, J=5.7Hz), 6.20(1H, t, J=3.3Hz), 7.18(1H, dd, J=1.8, 3.3Hz), 7.35(1H, d, J=3.9Hz), 7.54(1H, d, J=3.9Hz); IR(CHCl$_3$)3514, 3442, 3149, 3101, 1709, 1657, 1529, 1504, 1375, 1182, 1161, 1053cm$^{-1}$; $[α]_D^{24}$+47.1±0.9°(c=1.003, MeOH)Anal. (C$_{22}$H$_{28}$N$_2$O$_5$S$_2$)Calcd.(%): C, 56.87; H, 6.07; N, 6.03; S, 13.80Found(%): C, 56.59; H, 6.06; N, 5.91; S, 13.52 |
| I-5A-59a | $^1$H-NMR(CDCl$_3$) δ 0.97(1H, m), 1.16–1.68(12H, m), 1.98 (1H, d, J=3.9Hz), 2.31(2H, t, J=7.5Hz), 2.47(1H, m), 3.79(1H, m), 5.86(1H, d, J=4.5Hz), 7.01(1H, dd, J= 5.4, 3.6Hz), 7.04(1H, d, J=3.6Hz), 7.28(1H, dd, J= 3.6, 1.2Hz), 7.31(1H, d, J=3.6Hz), 7.42(1H, dd, J= 5.4, 1.2Hz); IR(CHCl$_3$)3516, 3444, 3425, 2671, 1709, 1645, 1531, 1498, 1421cm$^{-1}$; $[α]_D^{25.0}$+49.1±0.9°(c=1.003, MeOH)Anal.(C$_{21}$H$_{25}$NO$_3$S$_3$·0.1H$_2$O)Calcd.(%): C, 57.66; H, 5.81; N, 3.20; S, 21.99Found(%): C, 57.47; H, 5.81; N, 3.23; S, 22.21 |
| I-5A-59b | $^1$H-NMR(CDCl$_3$) δ 0.96(1H, m), 1.16–1.66(12H, m), 1.98 (1H, d, J=3.6Hz), 2.27(2H, dt, J=7.2, 1.8Hz), 2.49 (1H, m), 3.62(3H, s), 3.77(1H, m), 5.85(1H, d, J=6.9Hz), 7.01(1H, dd, J=5.4, 3.6Hz), 7.04(1H, d, J=4.2Hz), 7.29(1H, d, J=3.6, 1.2Hz), 7.31(1H, d, J=4.2Hz), 7.43(1H, dd, J=5.4, 1.2Hz) |
| I-5A-88a | $^1$H-NMR(CDCl$_3$) δ 0.96(1H, m), 1.16–1.70(12H, m), 1.99 (1H, d, J=3.6Hz), 2.32(2H, t, J=7.5Hz), 2.50(1H, m), 3.82(1H, m), 4.16(2H, s), 5.85(1H, d, J=8.1Hz), 6.79 (1H, d, J=3.6Hz), 6.96(1H, dd, J=5.1, 1.5Hz), 7.05 (1H, m), 7.28(1H, dd, J=5.1, 3.0Hz), 7.35(1H, d, J= 3.6Hz); IR(CHCl$_3$)3516, 3446, 3427, 1709, 1641, 1545, 1506, 1458cm$^{-1}$; $[α]_D^{24.0}$+44.9±0.9°(c=1.003, MeOH) Anal.(C$_{22}$H$_{27}$NO$_3$S$_2$·0.1H$_2$O)Calcd.(%): C, 63.00; H, 6.54; N, 3.34; S, 15.29Found(%): C, 63.06; H, 6.53; N, 3.43; S, 15.01 |

TABLE 19

| Compd. No.. | Physical property |
|---|---|
| I-5A-104a | $^1$H-NMR(CDCl$_3$) δ 0.99(1H, m), 1.18–1.70(12H, m), 1.99 (1H, m), 2.33(2H, t, J=7.5Hz), 2.50(1H, m), 3.82(1H, m), 4.10(2H, s), 5.88(1H, d, J=8.4Hz), 6.70(1H, d, J= 3.6Hz), 6.95(1H, dd, J=5.4, 3.6Hz), 7.04(1H, dd, J= 3.6, 1.2Hz), 7.28(1H, d, J=3.6Hz), 7.36(1H, dd, J=5.4, 1.2Hz); IR(CHCl$_3$)3514, 3446, 2669, 1709, 1643, 1543, 1506, 1458cm$^{-1}$; $[α]_D^{25.0}$+44.5±1.3° (c=0.670, MeOH)Anal. (C$_{22}$H$_{27}$NO$_3$S$_3$·0.2H$_2$O)Calcd.(%): C, 58.30; H, 6.09; N, 3.09; S, 21.22Found(%): C, 58.34; H, 6.09; N, 3.25; S, 21.10 |
| I-5A-143a | $^1$H-NMR(CDCl$_3$) δ 1.01(1H, m), 1.16–1.72(12H, m), 2.00 (1H, m), 2.33(2H, t, J=7.5Hz), 2.57(1H, m), 3.93(1H, m), 4.24(2H, s), 6.03(1H, d, J=7.5Hz), 7.18–7.34(6H, m), 7.42(1H, t, J=7.8Hz), 7.80 (1H, s), 8.17(1H, d, J=7.8Hz); IR(CHCl$_3$)3514, 3438, 1709, 1651, 1516, 1495cm$^{-1}$; $[α]_D^{24.0}$+41.4±0.8°(c=1.000, MeOH)Anal.(C$_{28}$H$_{31}$NO$_3$S· 0.3H$_2$O)Calcd.(%): C, 72.01; H, 6.82; N, 3.00; S, 6.87 Found(%): C, 72.05; H, 6.81; N, 3.02; S, 6.75 |
| I-5A-197a | $^1$H-NMR(CDCl$_3$) δ 0.96(1H, m), 1.18–1.68(12H, m), 1.97 (1H, d, J=3.9Hz), 2.32(2H, t, J=7.5Hz), 2.48(1H, m), 3.22(2H, t, J=8.7Hz), 3.80(1H, m), 4.07(2H, s), 4.57 (2H, t, J=8.7Hz), 5.83(1H, d, J=7.8Hz), 6.79(1H, t, J= 7.5Hz), 6.81(1H, d, J=3.9Hz), 6.97(1H, d, J=7.5Hz), |

TABLE 19-continued

| Compd. No. | Physical property |
|---|---|
| | 7.09(1H, d, J=7.5Hz), 7.33(1H, d, J=3.9Hz); IR (CHCl$_3$)3516, 3446, 3427, 2679, 1709, 1641, 1543, 1506, 1458cm$^{-1}$; [α]$_D^{25.0}$+14.7±0.5° (c=1.009, MeOH)Anal.(C$_{26}$H$_{31}$NO$_4$S·0.6H$_2$O)Calcd.(%): C, 67.24; H, 6.99; N, 3.01; S, 6.90Found(%): C, 67.14; H, 6.85; N, 3.03; S, 6.64 |
| I-5B-1a | $^1$H-NMR(CDCl$_3$) δ 1.08–1.70(7H, m), 2.04(1H, m), 2.10–2.18 (2H, m), 2.53(1H, brs), 3.14(1H, d, J=6.0Hz), 3.81 (1H, m), 5.52–5.67(2H, m), 6.25 (1H, d, J=6.9Hz), 6.33–6.34 (2H, m), 7.14–7.16(2H, m), 7.35(1H, d, J=3.9Hz), 7.54(1H, d, J=3.9Hz); IR(CHCl$_3$)3512, 3440, 1712, 1658, 1531, 1504, 1456, 1383, 1192, 1167, 1057, 1034cm$^{-1}$; [α]$_D^{27}$+61.4±1.0°(c=1.008, MeOH)Anal. (C$_{21}$H$_{24}$N$_2$O$_5$S$_2$·0.3H$_2$O)Calcd.(%): C, 55.56; H, 5.46; N, 6.17; S, 14.13Found(%): C, 55.47; H, 5.42; N, 6.54; S, 14.26 |
| I-5C-1a | mp149–152°C.; $^1$H-NMR(CDCl$_3$) δ 1.07(1H, m), 1.24–1.32(2H, m), 1.41–1.48(2H, m), 1.53–1.69(4H, m), 2.01(1H, m), 2.23–2.30(2H, m), 2.49(1H, brs), 3.87(1H, m), 5.78(1H, d, J=15.6Hz), 6.15(1H, d, J=7.2Hz), 6.33–6.34(2H, m), 7.02(1H, dt, J=15.6and7.2Hz), 7.15–7.17(2H, m), 7.37 and7.56(each1H, eachd, eachJ=4.2Hz); IR(CHCl$_3$) 3523, 3440, 2679, 1695, 1655, 1529, 1504, 1456, 1383, 1192, 1167, 1057, 1034cm$^{-1}$; [α]$_D^{24}$+38.7±0.8°(c=1.001, MeOH)Anal.(C$_{21}$H$_{24}$N$_2$O$_5$S$_2$·0.2H$_2$O)Calcd.(%): C, 55.78; H, 5.44; N, 6.20; S, 14.18Found(%): C, 55.70; H, 5.36; N, 6.20; S, 14.08 |

TABLE 20

| Compd. No. | Physical property |
|---|---|
| I-5C-31a | $^1$H-NMR(CDCl$_3$) δ 0.99(1H, m), 1.22–1.29(2H, m), 1.42–1.49(2H, m), 1.53–1.69(4H, m), 1.99(1H, m), 2.18–2.33(2H, m), 2.49(1H, brs), 3.88(1H, m), 4.14(2H, s), 5.79(1H, d, J=15.6Hz), 5.85(1H, d, J=7.8Hz), 6.78 (1H, d, J=3.6Hz), 7.03(1H, dt, J=6.9and15.6Hz), 7.23–7.33(5H, m), 7.36(1H, d, J=3.6Hz); IR(CHCl$_3$) 3523, 3446, 3427, 2679, 1695, 1649, 1543, 1506, 1456, 1308, 1282cm$^{-1}$; [α]$_D^{24}$+41.2±0.8° (c=1.011, MeOH) Anal.(C$_{24}$H$_{27}$NO$_3$S·0.2H$_2$O)Calcd.(%): C, 69.77; H, 6.68; N, 3.39; S, 7.76Found(%): C, 69.72; H, 6.55; N, 3.40; S, 7.65 |
| I-5C-47a | $^1$H-NMR(CDCl$_3$) δ 1.09(1H, m), 1.25–1.31(2H, m), 1.42–1.47(2H, m), 1.56–1.64(4H, m), 2.00(1H, m), 2.24–2.31(2H, m), 2.49(1H, brs), 3.88(1H, m), 5.78(1H, d, J=15.6Hz), 6.25(1H, d, J=8.1Hz), 7.02(1H, dt, J=15.6and6.8Hz), 7.12(1H, dd, J=3.6and4.8Hz), 7.42 and7.61(each1H, eachd, eachJ=3.9Hz), 7.70(1H, dd, J=1.5and4.8Hz), 7.75(1H, dd, J=1.5and3.6Hz); IR (CHCl$_3$)3523, 3440, 3373, 2681, 1695, 1653, 1529, 1504, 1335, 1402, 1153, 1095, 1020cm$^{-1}$; [α]$_D^{24}$+39.1±0.8° (c=1.000, MeOH)Anal. (C$_{21}$H$_{33}$NO$_5$S$_3$·0.3H$_2$O)Calcd.(%): C, 53.55; H, 5.05; N, 2.97; S, 20.42Found(%): C, 53.58; H, 4.97; N, 3.04; S, 20.17 |
| I-5C-88a | $^1$H-NMR(CDCl$_3$) δ 1.00(1H, m), 1.23–1.30(2H, m), 1.43–1.48(2H, m), 1.53–1.69(4H, m), 2.00(1H, m), 2.19–2.33(2H, m), 2.50(1H, brs), 3.88(1H, m), 4.16(2H, s), 5.79(1H, dt, J=15.6and1.5Hz), 5.90(1H, d, J=8.1Hz), 6.79(1H, d, J=3.6Hz), 6.95–7.08(3H, m), 7.28(1H, dd, J=2.7and4.8Hz), 7.36(1H, d, J=3.6Hz); IR (CHCl$_3$)3523, 3446, 2679, 1695, 1649, 1543, 1506, 1458, 1284cm$^{-1}$; [α]$_D^{24}$+39.9±0.8° (c=1.011, MeOH) |

TABLE 20-continued

| Compd. No. | Physical property |
|---|---|
| | Anal.(C$_{24}$H$_{27}$NO$_3$S·0.2H$_2$O)Calcd.(%): C, 63.04; H, 6.11; N, 3.34; S, 15.30Found(%): C, 63.12; H, 5.96; N, 3.44; S, 15.22 |
| I-5D-1a | mp150–152°C.; $^1$H-NMR(CDCl$_3$) δ 1.32–1.66(6H, m), 1.96(1H, m), 2.12–2.46(5H, m), 2.61(1H, brs), 3.87 (1H, m), 5.28(1H, m), 5.41(1H, dd, J=9.6, 10.5Hz), 6.33(2H, t, J=2.4Hz), 6.68(1H, br d, J=7.2Hz), 7.15 (2H, t, J=2.4Hz), 7.44(1H, d, J=3.9Hz), 7.48(1H, d, J= 3.9Hz); IR(CHCl$_3$)3510, 3390, 3145, 3101, 2673, 1709, 1655, 1531, 1506, 1456, 13811192, 1167, 1057, 1034cm$^{-1}$; [α]$_D^{25}$+9.2±0.5° (c=1.011, MeOH)Anal. (C$_{21}$H$_{24}$N$_2$O$_5$S$_2$)Calcd.(%): C, 56.23; H, 5.39; N, 6.25; S, 14.30Found(%): C, 56.20; H, 5.44; N, 6.23; S, 14.23 |

TABLE 21

| Compd. No. | Physical property |
|---|---|
| I-5E-1a | mp155–159°C.; $^1$H-NMR(CDCl$_3$) δ 1.18–1.82(9H, m), 2.00(1H, m), 2.61(1H, m), 3.50–3.59(2H, m), 3.79(1H, m), 3.99and4.10(each1H, Abq, J=17.1Hz), 5.54–5.70 (2H, m), 6.32–6.34(2H, m), 6.47(1H, d, J=6.3Hz), 7.14–7.17(2H, m), 7.39(1H, d, J=4.2Hz), 7.54(1H, d, J= 4.2Hz); IR(CHCl$_3$)3423, 1764, 1730, 1655, 1531, 1506, 1456, 1383, 1192, 1167, 1057cm$^{-1}$; [α]$_D^{23}$+ 28.9±0.7°(c=1.011, MeOH)Anal.(C$_{20}$H$_{26}$N$_2$O$_6$S$_2$) Calcd.(%): C, 53.08; H, 5.35; N, 6.00; S, 13.70 |
| I-6A-1a | mp109–111°C.; $^1$H-NMR(CDCl$_3$) δ 1.02(1H, m), 1.24–1.56 (14H, m), 1.98(1H, brs), 2.29(2H, t, J=7.2Hz), 2.48(1H, brs), 3.79(1H, m), 6.28(1H, d, J=7.2Hz), 6.33(2H, t, J=2.4Hz), 7.15(1H, t, J=2.4Hz), 7.38 and 7.55(each1H, eachd, eachJ=4.2Hz); IR(KBr)3352, 1709, 1624, 1541, 1512, 1456, 1377, 1192, 1167, 1057, 1036cm$^{-1}$; [α]$_D^{24.5}$+47.7±0.9° (c=1.003, MeOH)Anal. (C$_{22}$H$_{28}$N$_2$O$_5$S$_2$·0.2H$_2$O)Calcd.(%): C, 56.44; H, 6.11; N, 5.98; S, 13.70Found(%): C, 56.50; H, 6.11; N, 6.18; S, 13.51 |
| I-6B-1a | $^1$H-NMR(CDCl$_3$) δ 1.08(1H, m), 1.21–1.31(2H, m), 1.40–1.45(2H, m), 1.58–1.66(2H, m), 2.03–2.19(3H, m), 2.32–2.46(4H, m), 2.52(1H, brs), 3.80(1H, m), 5.33–5.45 (2H, m), 6.24(1H, d, J=7.8Hz), 6.32–6.34(2H, m), 7.15–7.16(2H, m), 7.36(1H, d, J=3.9Hz), 7.55(1H, d, J= 3.9Hz); IR(CHCl$_3$)3514, 3440, 1711, 1657, 1531, 1504, 1456, 1383, 1192, 1167, 1057, 1034cm$^{-1}$; [α]$_D^{24.5}$+ 69.8±1.1°(c=1.006, MeOH)Anal. (C$_{22}$H$_{26}$N$_2$O$_5$S$_2$·0.2H$_2$O)Calcd.(%): C, 56.68; H, 5.71; N, 6.01; S, 13.76Found(%): C, 56.67; H, 5.70; N, 6.14; S, 13.89 |
| I-6B-31a | $^1$H-NMR(CDCl$_3$) δ 1.04(1H, m), 1.17–1.28(2H, m), 1.41–1.46(2H, m), 1.55–1.66(2H, m), 2.00(1H, m), 2.04–2.24(2H, m), 2.31–2.44(4H, m), 2.51(1H, brs), 3.82 (1H, m), 4.13(2H, s), 5.32–5.44(2H, m), 5.96(1H, d, J= 6.6Hz), 6.76(1H, dt, J=3.6and0.9Hz), 7.22–7.35(5H, m), 7.36(1H, d, J=3.6Hz); IR(CHCl$_3$)3514, 3444, 3427, 2671, 1711, 1643, 1545, 1506, 1454, 1309, 1279cm$^{-1}$; [α]$_D^{24}$+67.7±1.1°(c=1.002, MeOH)Anal. (C$_{25}$H$_{29}$NO$_3$S)Calcd.(%): C, 70.89; H, 6.90; N, 3.31; S, 7.57Found(%): C, 70.67; H, 6.95; N, 3.36; S, 7.42 |
| I-6D-1a | $^1$H-NMR(CDCl$_3$) δ 1.26–1.34(2H, m), 1.43–1.48(2H, m), 1.55–1.76(4H, m), 1.96–2.13(4H, m), 2.32(2H, t, J=7.2Hz), 2.59(1H, br s), 3.92(1H, m), 5.28–5.44(2H, m), 6.33 (2H, t, J=2.1Hz), 6.69(1H, br d, J=6.6Hz), 7.15(2H, t, J=2.1Hz), 7.39(1H, d, J=4.2Hz), 7.53(1H, d, J= 4.2Hz); IR(CHCl$_3$)3512, 3368, 1706, 1654, 1532, 1506, 1455, 1382, 1212, 1132, 1106, 1075, 1016cm$^{-1}$; Anal. (C$_{22}$H$_{26}$N$_2$O$_5$S$_2$)Calcd.(%): C, 57.12; H, 5.67; N, 6.06; S, 13.86Found(%): C, 56.91; H, 5.71; N, 6.18; S, 13.75 |

TABLE 22

| Compd. No.. | Physical property |
|---|---|
| I-7A-1a | mp114–117°C.; $^1$H-NMR(CDCl$_3$) δ 1.05(1H, m), 1.18–1.70 (16H, m), 2.00(1H, m), 2.32(2H, t, J=6.9Hz), 2.49 (1H, m), 3.80(1H, m), 6.05(1H, d, J=7.2Hz), 6.32–6.35 (2H, m), 7.15–7.18(2H, m), 7.35(1H, d, J=3.9Hz), 7.57 (1H, d, J=3.9Hz); IR(CHCl$_3$)3442, 1708, 1657, 1529, 1504, 1456, 1383, 1192, 1167, 1057, 1034cm$^{-1}$; [α]$_D^{24}$+ 45.9±0.9°(c=1.004, MeOH)Anal.(C$_{23}$H$_{30}$N$_2$O$_5$S$_2$) Calcd.(%): C, 57.72; H, 6.32; N, 5.85; S, 13.40Found (%): C, 57.56; H, 6.44; N, 5.82; S, 13.11 |
| I-7A-1e | $^1$H-NMR(CDCl$_3$) δ 1.01(1H, m), 1.29–1.67(16H, m), 1.99 (1H, m), 2.30(2H, t, J=7.2Hz), 2.45(1H, m), 3.28(3H, s), 3.84(1H, m), 6.14(1H, d, J=7.8Hz), 6.34(2H, d, J= 4.5Hz), 7.16(2H, d, J=4.5Hz), 7.40(1H, d, J=3.9Hz), 7.58(1H, d, J=3.9Hz); IR(CHCl$_3$)3386, 2954, 2929, 2877, 2858, 1720, 1651, 1531, 1506, 1456, 1425, 1398, 1385, 1342, 1167, 1076, 1067, 1034cm$^{-1}$; [α]$_D^{25}$+ 38.5±0.8°(c=1.01, MeOH)Anal. (C$_{24}$H$_{33}$N$_3$O$_6$S$_3$·0.8MeOH)Calcd.(%): C, 51.24; H, 6.28; N, 7.23; S, 16.55Found(%): C, 51.59; H, 6.17; N, 7.40; S, 16.22 |
| I-7A-1h | mp134–136°C.; $^1$H-NMR(CDCl$_3$) δ 0.97(1H, m), 1.28–1.69 (18H, m), 2.01(1H, m), 2.49(1H, brs), 3.61(2H, t, J= 6.6Hz), 3.81(1H, m), 6.05(1H, d, J=7.8Hz), 6.33–6.35 (2H, m), 7.16–7.17(2H, m), 7.35and7.57(each1H, eachd, eachJ=3.9Hz); IR(Nujol)3357, 3244, 1621, 1554, 1371, 1186, 1169, 1061, 1038cm$^{-1}$; [α]$_D^{24}$+ 47.8±0.9°(c=1.005, MeOH)Anal. (C$_{23}$H$_{32}$N$_2$O$_4$S$_2$·0.2AcOEt)Calcd.(%): C, 59.27; H, 7.02; N, 5.81; S, 13.30Found(%): C, 59.53; H, 7.09; N, 5.92; S, 13.29 |
| I-7A-1i | mp82–84°C.; $^1$H-NMR(CDCl$_3$) δ 0.95(1H, m), 1.26–1.65 (18H, m), 2.01(1H, m), 2.49(1H, brs), 3.32(3H, s), 3.34 (2H, t, J=6.6Hz), 3.80(1H, m), 5.97(1H, d, J=7.5Hz), 6.33–6.34(2H, m), 7.16–7.17(2H, m), 7.33and7.58(each 1H, eachd, eachJ=3.9Hz); IR(CHCl$_3$)3442, 1658, 1529, 1504, 1456, 1385, 1192, 1167, 1113, 1057, 1034cm$^{-1}$; [α]$_D^{25}$+43.9±0.8°(c=1.003, MeOH)Anal. (C$_{24}$H$_{34}$N$_2$O$_4$S$_2$)Calcd.(%): C, 60.22; H, 7.16; N, 5.85; S, 13.40Found(%): C, 60.27; H, 7.14; N, 5.79; S, 13.29 |
| I-7A-31a | $^1$H-NMR(CDCl$_3$) δ 0.92(1H, m), 1.18–1.66(16H, m), 1.96 (1H, m), 2.31(2H, t, J=7.5Hz), 2.48(1H, m), 3.81(1H, m), 4.13(2H, s), 5.83(1H, d, J=8.1Hz), 6.77(1H, d, J= 3.9Hz), 7.21–7.36(6H, m); IR(CHCl$_3$)3516, 3446, 3427, 1709, 1643, 1543, 1506, 1456cm$^{-1}$; [α]$_D^{24.0}$+41.0±0.8° (c=1.006, MeOH)Anal.(C$_{26}$H$_{33}$NO$_3$S·0.2H$_2$O)Calcd.(%): C, 70.46; H, 7.60; N, 3.16; S, 7.23Found(%): C, 70.43; H, 7.66; N, 3.21; S, 7.07 |

TABLE 23

| Compd. No.. | Physical property |
|---|---|
| I-7A-47a | $^1$H-NMR(CDCl$_3$) δ 0.98(1H, m), 1.16–1.70(16H, m), 1.99 (1H, m), 2.31(2H, t, J=7.5Hz), 2.49(1H, m), 3.80(1H, m), 6.05(1H, d, J=7.8Hz), 7.10(1H, dd, J=4.8, 3.6Hz), 7.39(1H, d, J=3.9Hz), 7.64(1H, d, J=3.9Hz), 7.69(1H, dd, J=4.8, 1.2Hz), 7.75(1H, dd, J=3.6, 1.2Hz); IR (CHCl$_3$)3514, 3442, 3375, 2677, 1709, 1655, 1529, 1504, 1402, 1336, 1153, 1095, 1022cm$^{-1}$; [α]$_D^{24.0}$+45.7±0.9° (c=1.010, MeOH)Anal.(C$_{23}$H$_{29}$NO$_5$S$_3$·0.2H$_2$O)Calcd.(%): C, 55.33; H, 5.94; N, 2.80; S, 19.26Found(%): C, 55.42; H, 6.04; N, 2.86; S, 19.03 |
| I-7A-47i | $^1$H-NMR(CDCl$_3$) δ 0.96(1H, m), 1.26–1.35(11H, m), 1.40–1.46 (2H, m), 1.51–1.67(5H, m), 2.01(1H, m), 2.50(1H, brs), 3.32(3H, s), 3.34(2H, t, J=6.9Hz), 3.80(1H, m), 6.03(1H, d, J=7.5Hz), 7.11(1H, dd, J=3.9and4.8Hz), 7.38and7.65(each1H, eachd, eachJ=3.9Hz), 7.70(1H, dd, J=1.5and4.8Hz), 7.76(1H, dd, J=1.5and3.9Hz); IR(CHCl$_3$)3442, 1657, 1529, 1504, 1402, 1336, 1153, 1113, 1095, 1020cm$^{-1}$; [α]$_D^{25}$+43.7±0.8° (c=1.008, MeOH)Anal. (C$_{24}$H$_{33}$NO$_4$S$_3$·0.1H$_2$O)Calcd.(%): C, 57.94; H, 6.73; N, 2.82; S, 19.34Found(%): C, 57.81; H, 6.68; N, 2.90; S, 19.42 |
| I-7A-59a | $^1$H-NMR(CDCl$_3$) δ 0.93(1H, m), 1.16–1.68(16H, m), 1.98 (1H, d, J=3.6Hz), 2.31(2H, t, J=7.2Hz), 2.47(1H, m), 3.78(1H, m), 5.87(1H, d, J=7.5Hz), 7.00(1H, dd, J=5.7, 3.9Hz), 7.04(1H, d, J=3.6Hz), 7.28(1H, dd, J=3.9, 1.2Hz), 7.31(1H, d, J=3.6Hz), 7.42(1H, dd, J=5.7, 1.2Hz); IR(CHCl$_3$)3516, 3444, 3427, 2671, 1709, 1645, 1529, 1498, 1421cm$^{-1}$; [δ]$_D^{25.0}$+41.2±0.8° (c=1.003, MeOH)Anal. (C$_{23}$H$_{29}$NO$_3$S$_3$)Calcd.(%): C, 59.58; H, 6.30; N, 3.02; S, 20.75Found(%): C, 59.70; H, 6.27; N, 3.03; S, 20.56 |
| I-7A-88a | $^1$H-NMR(CDCl$_3$) δ 0.93(1H, m), 1.16–1.68(16H, m), 1.98 (1H, d, J=3.6Hz), 2.31(2H, t, J=7.5Hz), 2.49(1H, m), 3.81(1H, m), 4.15(2H, s), 5.86(1H, d, J=7.5Hz), 6.79 (1H, d, J=3.6Hz), 6.96(1H, dd, J=4.8, 1.2Hz), 7.05(1H, dd, J=3.0, 1.2Hz), 7.28(1H, dd, J=4.8, 3.0Hz), 7.35(1H, d, J=3.6Hz); IR(CHCl$_3$)3516, 3446, 3427, 1709, 1641, 1545, 1506, 1458cm$^{-1}$; [α]$_D^{24.0}$+40.2±0.8° (c=1.007, MeOH) Anal.(C$_{24}$H$_{31}$NO$_3$S$_2$·0.1H$_2$O)Calcd.(%): C, 64.42; H, 7.03; N, 3.13; S, 14.33Found(%): C, 64.52; H, 7.00; N, 3.18; S, 14.04 |
| I-7A-88h | mp92–93°C.; $^1$H-NMR(CDCl$_3$) δ 0.94(1H, m), 1.20–1.34 (11H, m), 1.42–1.47(2H, m), 1.48–1.63(5H, m), 1.98(1H, m), 2.49(1H, brs), 3.61(2H, t, J=6.6Hz), 3.83(1H, m), 4.16(2H, s), 5.86(1H, d, J=8.1Hz), 6.79(1H, d, J= 3.6Hz), 6.97(1H, dd, J=1.2and4.8Hz), 7.06(1H, m), 7.29 (1H, dd, J=3.0and4.8Hz), 7.35(1H, d, J=3.6Hz); IR (Nujol)3315, 3259, 1599, 1549, 1527, 1317cm$^{-1}$; [α]$_D^{24}$+ 45.0±0.9°(c=1.001, MeOH)Anal.(C$_{24}$H$_{33}$NO$_2$S$_2$) Calcd.(%): C, 66.78; H, 7.71; N, 3.24; S, 14.86Found(%): C, 66.85; H, 7.71; N, 3.37; S, 14.57 |

TABLE 24

| Compd. No.. | Physical property |
|---|---|
| I-7A-88i | mp47–48°C.; $^1$H-NMR(CDCl$_3$) δ 0.93(1H, m), 1.23–1.32 (11H, m), 1.41–1.46(2H, m), 1.51–1.63(5H, m), 1.98(1H, m), 2.50(1H, brs), 3.31(3H, s), 3.34(2H, t, J=6.6Hz), 3.81(1H, m), 4.16(2H, s), 5.81(1H, d, J=7.2Hz), 6.79 (1H, d, J=3.9Hz), 6.97(1H, dd, J=0.9and4.8Hz), 7.06 (1H, m), 7.29(1H, dd, J=3.0and4.8Hz), 7.34(1H, d, J= 3.9Hz); IR(CHCl$_3$)3446, 3426, 1643, 1543, 1506, 1460, 1113cm$^{-1}$; [α]$_D^{25.5}$+43.0±0.8° (c=1.008, MeOH)Anal. (C$_{25}$H$_{35}$NO$_2$S$_2$)Calcd.(%): C, 67.37; H, 7.92; N, 3.14; S, 14.39Found(%): C, 67.32; H, 7.91; N, 3.19; S, 14.32 |
| I-7A-104a | $^1$H-NMR(CDCl$_3$) δ 0.95(1H, m), 1.18–1.70(16H, m), 2.00 (1H, m), 2.32(2H, t, J=7.5Hz), 2.50(1H, m), 3.82(1H, m), 4.10(2H, s), 5.87(1H, d, J=7.2Hz), 6.70 (1H, d, J=3.6Hz), 6.95(1H, dd, J=5.4, 3.6Hz), 7.04(1H, dd, J=3.6, 1.2Hz), 7.28(1H, d, J=3.6Hz), 7.36(1H, dd, J= 5.4, 1.2Hz); IR(CHCl$_3$)3516, 3446, 3427, 2671, 1709, 1643, 1543, 1506, 1458cm$^{-1}$; [α]$_D^{25.0}$+39.4±0.8°.(c=1.004, MeOH)Anal.(C$_{24}$H$_{31}$NO$_3$S$_3$)Calcd.(%): C, 60.34; H, 6.54; N, 2.93; S, 20.14Found(%): C, 60.12; H, 6.51; N, 3.05; S, 19.95 |
| I-7A-143a | $^1$H-NMR(CDCl$_3$) δ 0.97(1H, m), 1.16–1.70(16H, m), 2.00 (1H, m), 2.31(2H, t, J=7.5Hz), 2.58(1H, m), 3.93(1H, m), 4.24(2H, s), 6.01(1H, d, J=7.2Hz), 7.18–7.32(6H, m), |

TABLE 24-continued

| Compd. No. | Physical property |
|---|---|
| | 7.42(1H, t, J=7.8Hz), 7.80(1H, s), 8.18(1H, d, J=7.2Hz); IR(CHCl$_3$)3516, 3438, 1709, 1651, 1516, 1495cm$^{-1}$; [α]$_D^{24.0}$+41.9±0.8°(c=1.006, MeOH)Anal.(C$_{30}$H$_{35}$NO$_3$S·0.2H$_2$O)Calcd.(%): C, 73.05; H, 7.23; N, 2.84; S, 6.50 Found(%): C, 73.10; H, 7.13; N, 2.86; S, 6.39 |
| I-7A-197a | $^1$H-NMR(CDCl$_3$) δ 0.93(1H, m), 1.18–1.68(16H, m), 1.97 (1H, d, J=3.9Hz), 2.31(2H, t, J=7.5Hz), 2.48(1H, m), 3.22(2H, t, J=9.0Hz), 3.81(1H, m), 4.07(2H, s), 4.57 (2H, t, J=9.0Hz), 5.82(1H, d, J=7.5Hz), 6.79(1H, t, J=7.2Hz), 6.80(1H, d, J=7.2Hz), 6.96(1H, d, J=7.2Hz), 7.09(1H, d, J=7.2Hz), 7.33(1H, d, J=7.2Hz); IR (CHCl$_3$)3516, 3446, 3427, 2671, 1709, 1641, 1543, 1506, 1458cm$^{-1}$; [α]$_D^{25.0}$+37.9±0.8° (c=1.003, MeOH)Anal.(C$_{28}$H$_{35}$NO$_4$S·0.3H$_2$O)Calcd.(%): C, 69.05; H, 7.39; N, 2.88; S, 6.58Found(%): C, 69.11; H, 7.24; N, 2.99; S, 6.61 |
| I-7A-315a | $^1$H-NMR(CDCl$_3$) δ 1.00(1H, m), 1.23–1.63(16H, m), 2.00 (1H, m), 2.31(2H, t, J=7.2Hz), 2.58(1H, m), 3.94(1H, m), 4.26(2H, s), 6.06(1H, d, J=7.8Hz), 7.00–7.18(5H, m), 7.42(1H, m), 7.82(1H, s), 8.18(1H, d, J=7.2Hz); IR(CHCl$_3$)3516, 3438, 2954, 2927, 2875, 2856, 1709, 1653, 1516, 1492, 1456, 1396, 1298, 1271cm$^{-1}$; [α]$_D^{25.5}$+39.0±0.8° (c=1.04, MeOH)Anal.(C$_{30}$H$_{34}$FNO$_3$S·0.5MeOH)Calcd.(%): C, 69.95; H, 6.93; N, 2.67; F, 3.63; S, 6.12Found(%): C, 70.24; H, 6.80; N, 2.98; F, 3.19; S, 6.08 |

TABLE 25

| Compd. No. | Physical property |
|---|---|
| I-7A-316a | $^1$H-NMR(CDCl$_3$) δ 0.98(1H, m), 1.22–1.63(16H, m), 2.00 (1H, m), 2.31(2H, t, J=7.5Hz), 2.58(1H, m), 3.82(3H, s), 3.92(1H, m), 4.23(2H, s), 6.03(1H, d, J=8.1Hz), 6.85–6.91(2H, m), 7.02–7.23(3H, m), 7.39(1H, m), 7.83 (1H, s), 8.14(1H, d, J=8.4Hz); IR(CHCl$_3$)3518, 3438, 2954, 2929, 1709, 1653, 1601, 1516, 1493, 1464, 1439, 1394, 1246cm$^{-1}$; [α]$_D^{26.0}$+35.2±0.7°(c=1.03, MeOH) Anal.(C$_{31}$H$_{37}$NO$_4$S·0.2H$_2$O)Calcd.(%): C, 71.15; H, 7.20; N, 2.68; S, 6.13Found(%): C, 71.03; H, 7.35; N, 2.86; S, 5.99 |
| I-7B-1a | $^1$H-NMR(CDCl$_3$) δ 0.98–2.49(20H, m), 1.14(3H, d, J=6.9Hz), 3.80(1H, m), 6.05(1H, d, J=5.2Hz), 6.33(2H, d, J=4.2Hz), 7.16(2H, d, J=4.2Hz), 7.35(1H, m), 7.57 (1H, m); IR(CHCl$_3$)3442, 2954, 2929, 2877, 2858, 1705, 1657, 1529, 1504, 1456, 1383, 1167, 1057, 1034cm$^{-1}$; [α]$_D^{24.5}$+41.6±1.6°(c=0.50, CHCl$_3$)Anal. (C$_{24}$H$_{32}$N$_2$O$_5$S$_2$·0.4MeOH)Calcd.(%): C, 57.98; H, 6.70; N, 5.54; S, 12.69Found(%): C, 58.27; H, 6.47; N, 5.50; S, 12.33 |
| I-7D-1a | $^1$H-NMR(CDCl$_3$) δ 0.98(1H, m), 1.22–2.33(17H, m), 2.48 (1H, m), 3.79(1H, m), 4.92(1H, dt, J=6.0and44.1Hz), 6.07(1H, d, J=7.2Hz), 6.33(2H, d, J=4.8Hz), 7.16 (2H, d, J=4.8Hz), 7.36(1H, d, J=3.6Hz), 7.57(1H, d, J=3.6Hz); IR(CHCl$_3$)3440, 2956, 2875, 1732, 1657, 1531, 1504, 1456, 1383, 1167, 1057, 1034cm$^{-1}$; [α]$_D^{25}$+30.2±0.7°(c=1.02, MeOH)Anal. (C$_{23}$H$_{29}$FN$_2$O$_5$S$_2$·0.3MeOH)Calcd.(%): C, 55.28; H, 6.01; N, 5.53; F, 3.75; S, 12.67Found(%): C, 55.58; H, 6.14; N, 5.61; S, 12.05 |
| I-7E-1c | $^1$H-NMR(CDCl$_3$) δ 1.18–1.30(3H, m), 1.40–1.45(2H, m), 1.57–1.82(5H, m), 1.95–2.28(6H, m), 2.54(1H, br s), 3.75(1H, m), 5.26(1H, br), 5.30–5.46(2H, m), 5.89(1H, br), 6.33(2H, t, J=2.4Hz), 6.69(1H, br d, J=6.0Hz), 7.17(2H, t, J=2.4Hz), 7.48(1H, d, J=3.9Hz), 7.57 (1H, d, J=3.9Hz); IR(CHCl$_3$)3527, 3485, 3442, 3411, 3340, 1674, 1531, 1504, 1456, 1383, 1192, 1167, 1057, 1034cm$^{-1}$; [α]$_D^{24}$+79.9±1.2°(c=1.002, MeOH)Anal. |

TABLE 25-continued

| Compd. No. | Physical property |
|---|---|
| | (C$_{23}$H$_{29}$N$_3$O$_4$S$_2$·0.3H$_2$O)Calcd.(%): C, 57.43; H, 6.20; N, 8.74; S, 13.33Found(%): C, 57.55; H, 6.50; N, 8.76; S, 13.28 |
| I-7E-1d | $^1$H-NMR(CDCl$_3$) δ 1.19–1.27(3H, m), 1.40–1.45(2H, m), 1.56–1.82(5H, m), 1.97–2.20(6H, m), 2.56(1H, br s), 2.75 (3H, d, J=4.8Hz), 3.73(1H, m), 5.29–5.42(2H, m), 5.90 (1H, br), 6.33(2H, t, J=2.1Hz), 6.79(1H, br d, J=7.8Hz), 7.16(2H, t, J=2.1Hz), 7.54and7.57(each1H, ABq, J=3.9Hz); [α]$_D^{24}$+76.1±1.2°(c=1.006, MeOH) Anal.(C$_{24}$H$_{31}$N$_3$O$_4$S$_2$·0.3H$_2$O)Calcd.(%): C, 58.23; H, 6.43; N, 8.49; S, 12.95Found(%): C, 58.22; H, 6.64; N, 8.45; S, 12.81 |

TABLE 26

| Compd. No. | Physical property |
|---|---|
| I-7E-1e | $^1$H-NMR(CDCl$_3$) δ 1.16–2.24(13H, m), 2.32(2H, d, J=7.2Hz), 2.57(1H, m), 3.27(3H, s), 3.74(1H, m), 5.25–5.32 (2H, m), 6.14(1H, d, J=7.5Hz), 6.35(2H, d, J=4.8Hz), 7.18(2H, d, J=4.8Hz), 7.46(1H, d, J=3.9Hz), 7.60(1H, d, J=3.9Hz), 9.96(1H, s); IR(CHCl$_3$)2956, 2879, 1716, 1645, 1533, 1506, 1456, 1385, 1342, 1167, 1122, 1057, 1034cm$^{-1}$; [α]$_D^{24}$+90.4±1.3° (c=1.00, CHCl$_3$) Anal.(C$_{24}$H$_{31}$N$_3$O$_6$S$_3$·0.8MeOH)Calcd.(%): C, 51.41; H, 5.95; N, 7.25; S, 16.60Found(%): C, 51.77; H, 5.70; N, 7.53; S, 16.22 |
| I-7E-1f | $^1$H-NMR(CDCl$_3$) δ 1.07–2.19(13H, m), 2.51(1H, m), 2.58 (2H, t, J=7.5Hz), 3.22(3H, s), 3.27(3H, s), 3.84(1H, m), 5.32–5.43(2H, m), 6.26(1H, d, J=7.8Hz), 6.33(2H, d, J=4.5Hz), 7.17(2H, d, J=4.5Hz), 7.39(1H, d, J=4.2Hz), 7.58(1H, d, J=4.2Hz); IR(CHCl$_3$)3394, 2956, 2877, 1699, 1655, 1531, 1504, 1456, 1381, 1354, 1167, 1057, 1034cm$^{-1}$; [α]$_D^{24.5}$+47.4±0.9° (c=1.00, CHCl$_3$) Anal.(C$_{25}$H$_{33}$N$_3$O$_6$S$_3$·0.2H$_2$O)Calcd.(%): C, 52.55; H, 5.89; N, 7.35; S, 16.84Found(%): C, 52.85; H, 5.81; N, 7.26; S, 16.45 |
| I-7E-1g | $^1$H-NMR(CDCl$_3$) δ 1.12–1.86(9H, m), 2.01–2.10(5H, m), 2.55(1H, br s), 2.96–3.04(2H, m), 3.57(1H, m), 5.27–5.40 (2H, m), 6.36(2H, t, J=2.1Hz), 7.17(2H, t, J=2.1Hz), 7.46(1H, d, J=3.9Hz), 7.60(1H, d, J=3.9Hz); IR (CHCl$_3$)3462, 3336, 1657, 1531, 1506, 1456, 1383, 1192, 1167, 1057, 1036cm$^{-1}$; [α]$_D^{25}$+74.0±1.1°(c=1.000, MeOH)Anal.(C$_{23}$H$_{28}$N$_6$O$_3$S$_2$·0.4Et$_2$O)Calcd.(%): C, 55.72; H, 6.08; N, 15.85; S, 12.09Found(%): C, 55.45; H, 6.10; N, 15.85; S, 11.84 |
| I-7E-1h | mp123–125°C.; $^1$H-NMR(CDCl$_3$) δ 1.09(1H, m), 1.16–1.75 (10H, m), 1.99–2.20(5H, m), 2.52(1H, brs), 3.63 (2H, t, J=6.5Hz), 3.81(1H, m), 5.28–5.44(2H, m), 6.24 (1H, d, J=7.2Hz), 6.33–6.34(2H, m), 7.15–7.17(2H, m), 7.37and7.57(each1H, eachd, eachJ=3.9Hz); IR (Nujol)3388, 3255, 1618, 1552, 1373, 1190, 1163, 1057, 1039cm$^{-1}$; [α]$_D^{25}$+80.1±1.2° (c=1.014, MeOH)Anal. (C$_{23}$H$_{30}$N$_2$O$_4$S$_2$)Calcd.(%): C, 59.71; H, 6.54; N, 6.06; S, 13.86Found(%): C, 59.59; H, 6.50; N, 6.08; S, 13.82 |
| I-7E-1i | $^1$H-NMR(CDCl$_3$) δ 1.06(1H, m), 1.19–1.31(2H, m), 1.34–1.44(4H, m), 1.52–1.65(4H, m), 2.01–2.13(5H, m), 2.53(1H, brs), 3.32(3H, s), 3.37(2H, t, J=6.3Hz), 3.82 (1H, m), 5.28–5.44(2H, m), 6.15(1H, d, J=7.5Hz), 6.32–6.34(2H, m), 7.15–7.17(2H, m), 7.35and7.57(each 1H, eachd, eachJ=4.2Hz); IR(CHCl$_3$)3442, 1658, 1529, 1504, 1456, 1382, 1192, 1167, 1115, 1057, 1034cm$^{-1}$; [α]$_D^{24}$+73.8±1.1°(c=1.006, MeOH)Anal. (C$_{24}$H$_{32}$N$_2$O$_4$S$_2$·0.2H$_2$O)Calcd.(%): C, 60.02; H, 6.80; N, 5.83; S, 13.35Found(%): C, 60.09; H, 6.75; N, 5.79; S, 13.19 |

TABLE 27

| Compd. No.. | Physical property |
|---|---|
| I-7E-47i | $^1$H-NMR(CDCl$_3$) δ 1.08(1H, m), 1.21–1.31(2H, m), 1.21–1.31(2H, m), 1.37–1.46(4H, m), 2.01–2.13(5H, m), 2.53(1H, brs), 3.32(3H, s), 3.37(1H, t, J=6.6Hz), 3.82(1H, m), 5.28–5.43(2H, m), 6.19(1H, d, J=7.2Hz), 6.19(1H, d, J=7.2Hz), 7.11(1H, dd, J=3.9and5.1Hz), 7.39and7.63(each1H, eachd, eachJ=3.9Hz), 7.69(1H, dd, J=1.5and5.1Hz), 7.75(1H, dd, J=1.5and3.9Hz); IR(CHCl$_3$)3442, 1657, 1529, 1504, 1402, 1336, 1153, 1115, 1097, 1020cm$^{-1}$; [α]$_D^{24}$+76.3±1.2°(c=1.011, MeOH)Anal.(C$_{24}$H$_{31}$NO$_4$S$_3$·0.5H$_2$O)Calcd.(%): C, 57.34; H, 6.42; N, 2.79; S, 19.14Found(%): C, 57.25; H, 6.25; N, 2.83; S, 19.25 |
| I-7E-88e | $^1$H-NMR(CDCl$_3$) δ 1.11–1.66(9H, m), 1.93–2.34(7H, m), 2.59(1H, m), 3.24(3H, s), 3.70(1H, m), 4.17(2H, s), 5.21–5.31(2H, m), 5.92(1H, d, J=9.6Hz), 6.84(1H, d, J= 3.6Hz), 6.98(1H, dd, J=1.5and4.8Hz), 7.08(1H, dd, J=1.2and1.8Hz), 7.30(1H, m), 7.50(1H, d, J=3.6Hz), 10.78(1H, s); IR(CHCl$_3$)3444, 3425, 2954, 2877, 1714, 1630, 1545, 1510, 1456, 1408, 1342, 1169, 1122cm$^{-1}$; [α]$_D^{24}$+66.0±2.1°(c=0.50, MeOH)Anal.(C$_{25}$H$_{32}$N$_2$O$_4$S$_3$·0.3H$_2$O)Calcd.(%): C, 57.07; H, 6.25; N, 5.32; S, 18.28Found(%): C, 57.38; H, 6.34; N, 5.52; S, 17.92 |
| I-7E-88h | $^1$H-NMR(CDCl$_3$) δ 1.04(1H, m), 1.19–1.75(10H, m), 2.02–2.24(5H, m), 2.53(1H, brs), 3.63(2H, t, J=6.6Hz), 3.83(1H, m), 4.16(2H, s), 5.30–5.44(2H, m), 5.90(1H, d, J=6.9Hz), 6.79(1H, d, J=3.6Hz), 6.96(1H, dd, J=1.5 and4.8Hz), 7.05(1H, m), 7.28(1H, dd, J=1.5and3.0Hz), 7.35(1H, d, J=3.6Hz); IR (CHCl$_3$)3624, 3446, 3429, 1643, 1545, 1506cm$^{-1}$; [α]$_D^{24}$+74.7±1.1°(c=1.009, MeOH)Anal. (C$_{24}$H$_{31}$NO$_2$S$_2$·0.2H$_2$O)Calcd.(%): C, 66.54; H, 7.31; N, 3.23; S, 14.80Found(%): C, 66.55; H, 7.26; N, 3.38; S, 14.57 |
| I-7E-88i | $^1$H-NMR(CDCl$_3$) δ 1.03(1H, m), 1.18–1.29(2H, m), 1.34–1.47(4H, m), 1.53–1.67(4H, m), 2.01–2.14(5H, m), 2.54(1H, brs), 3.32(3H, s), 3.36(2H, t, J=6.6Hz), 3.84(1H, m), 4.16(2H, s), 5.29–5.43(2H, m), 5.90(1H, d, J=7.5Hz), 6.79(1H, dt, J=3.9and0.9Hz), 6.96(1H, dd, J=1.5and5.1Hz), 7.06(1H, m), 7.29(1H, dd, J=3.0and5.1Hz), 7.35(1H, d, J=3.9Hz); IR(CHCl$_3$)3446, 3429, 1643, 1543, 1506, 1458, 1115cm$^{-1}$; [α]$_D^{25}$+68.1±1.1°(c=1.019, MeOH)Anal.(C$_{25}$H$_{33}$NO$_2$S$_2$·0.2H$_2$O)Calcd.(%): C, 67.13; H, 7.53; N, 3.13; S, 14.34Found(%): C, 67.10; H, 7.53; N, 3.21; S, 14.32 |

TABLE 28

| Compd. No.. | Physical property |
|---|---|
| I-7F-1a | $^1$H-NMR(CDCl$_3$) δ 1.09–2.51(16H, m), 1.17(3H, m), 3.80(1H, s), 5.28–5.42(2H, m), 6.24(1H, m), 6.33(2H, d, J=4.5Hz), 7.15(2H, d, J=4.5Hz), 7.39(1H, d, J=4.2Hz), 7.56(1H, d, J=4.2Hz); IR(CHCl$_3$)3442, 2956, 2877, 1705, 1657, 1531, 1504, 1456, 1383, 1167, 1057, 1034cm$^{-1}$; [α]$_D^{24}$+49.0±0.9°(c=1.00, CHCl$_3$)Anal. (C$_{24}$H$_{30}$N$_2$O$_5$S$_2$·0.7H$_2$O)Calcd.(%): C, 57.28; H, 6.29; N, 5.57; S, 12.74Found(%): C, 57.49; H, 6.11; N, 5.66; S, 12.46 |
| I-7G-1a | $^1$H-NMR(CDCl$_3$) δ 1.06–2.18(14H, m), 1.21(6H, s), 2.51(1H, m), 2.75(1H, m), 5.27–5.43(2H, m), 6.17(1H, d, J=6.9Hz), 6.33(2H, dd, J=4.5and2.4Hz), 7.16(2H, dd, J=4.5and2.4Hz), 7.37(1H, d, J=4.2Hz), 7.57(1H, d, J=4.2Hz); IR(CHCl$_3$)3442, 2956, 2877, 1728, 1699, 1657, 1531, 1504, 1475, 1456, 1383, 1167, 1074, 1057, 1034cm$^{-1}$; [α]$_D^{25}$+43.4±0.8°(c=1.00, CHCl$_3$) |
| I-7G-88a | $^1$H-NMR(CDCl$_3$) δ 1.04–2.24(14H, m), 1.20(3H, s), 1.21(3H, s), 2.50(1H, m), 3.85(1H, m), 4.16(2H, s), 5.29–5.43(2H, m), 5.97(1H, d, J=7.5Hz), 6.79(1H, d, J=3.9Hz), 6.96(1H, dd, J=5.1and1.2Hz), 7.05(1H, d, J=1.2Hz), 7.29(1H, m), 7.37(1H, d, J=3.9Hz); IR(CHCl$_3$) 3446, 3427, 2956, 2877, 1728, 1699, 1743, 1545, 1506, 1475, 1458, 1282, 1024cm$^{-1}$; [α]$_D^{26}$+48.6±0.9°(c=1.02, CHCl$_3$)Anal.(C$_{26}$H$_{33}$NO$_3$S$_2$·0.3H$_2$O)Calcd.(%): C, 65.46; H, 7.10; N, 2.94; S, 13.44Found(%): C, 65.66; H, 6.96; N, 3.12; S, 13.05 |
| I-7G-126a | $^1$H-NMR(CDCl$_3$) δ 0.95(1H, d, J=9.9Hz), 1.08(3H, s), 1.17(3H, s), 1.90(3H, s), 1.21(3H, s), 1.53–2.51(12H, m), 3.84(3H, s), 4.12(2H, s), 4.24(1H, m), 5.39–5.43(2H, m), 6.04(1H, d, J=8.7Hz), 6.77(1H, d, J=2.7Hz), 6.86–6.92(2H, m), 7.14–7.23(2H, m), 7.31(1H, d, J=3.6Hz); IR(CHCl$_3$)3450, 3431, 2924, 1728, 1699, 1641, 1601, 1543, 1506, 1471, 1406, 1387, 1367, 1319, 1288, 1126, 1049, 1030cm$^{-1}$; [α]$_D^{25}$+29.7±0.7°(c=1.00, CHCl$_3$) Anal.(C$_{31}$H$_{41}$NO$_4$S·0.3H$_2$O)Calcd.(%): C, 70.37; H, 7.92; N, 2.65; S, 6.06Found(%): C, 70.50; H, 8.03; N, 2.78; S, 5.84 |
| I-7I-1a | $^1$H-NMR(CDCl$_3$) δ 0.98(1H, m), 1.19–1.49(10H, m), 1.54–1.67(2H, m), 2.00(1H, m), 2.16–2.24(2H, m), 2.48(1H, brs), 3.81(1H, m), 5.79(1H, d, J=15.6Hz), 6.12(1H, d, J=7.2Hz), 6.33–6.34(2H, m), 7.03(1H, dt, J=15.6and7.2Hz), 7.15–7.17(2H, m), 7.35and7.56(each 1H, eachd, eachJ=3.9Hz); IR(CHCl$_3$)3523, 3442, 2681, 1695, 1655, 1529, 1504, 1456, 1425, 1383, 1192, 1167, 1057, 1034cm$^{-1}$; [α]$_D^{24.5}$+40.1±0.8°(c=1.003, MeOH)Anal.(C$_{23}$H$_{28}$N$_2$O$_5$S$_2$·0.3H$_2$O)Calcd.(%): C, 57.31; H, 5.98; N, 5.81; S, 13.30Found(%): C, 57.59; H, 5.98; N, 5.86; S, 14.04 |

TABLE 29

| Compd. No.. | Physical property |
|---|---|
| I-7I-31a | mp134–136°C.; $^1$H-NMR(CDCl$_3$) δ 0.94(1H, m), 1.18–1.46(10H, m), 1.54–1.68(2H, m), 1.98(1H, m), 2.16–2.23(2H, m), 2.48(1H, brs), 3.83(1H, m), 4.14(2H, s), 5.79(1H, dt, J=15.6and1.5Hz), 5.83(1H, d, J=6.9Hz), 6.78(1H, d, J=3.3Hz), 7.03(1H, dt, J=6.8and15.6Hz), 7.23–7.33(5H, m), 7.35(1H, d, J=3.3Hz); IR(KBr) 3329, 1695, 1649, 1616, 1549, 1527, 1454, 1319, 1288cm$^{-1}$; [α]$_D^{25}$+35.6±0.8°(c=1.004, MeOH)Anal. (C$_{26}$H$_{31}$NO$_3$S)Calcd.(%): C, 71.36; H, 7.14; N, 3.20; S, 7.33Found(%): C, 71.15; H, 7.14; N, 3.28; S, 7.22 |
| I-7I-47a | $^1$H-NMR(CDCl$_3$) δ 1.00(1H, m), 1.26–1.46(10H, m), 1.55–1.65(2H, m), 2.00(1H, m), 2.17–2.24(2H, m), 2.49(1H, brs), 3.82(1H, m), 5.79(1H, d, J=15.6Hz), 6.16(1H, d, J=7.5Hz), 7.03(1H, dt, J=15.6and7.1Hz), 7.11(1H, dd, J=3.6and4.8Hz), 7.40and7.63(each1H, eachd, eachJ=3.9Hz), 7.70(1H, dd, J=1.2and4.8Hz), 7.75(1H, dd, J=1.2and3.6Hz); IR(CHCl$_3$)3523, 3442, 3375, 2681, 1695, 1653, 1529, 1504, 1402, 1336, 1402, 1153, 1095, 1022cm$^{-1}$; [α]$_D^{24}$+40.3±0.80°(c=1.015, MeOH)Anal.(C$_{23}$H$_{27}$NO$_5$S$_3$·0.2H$_2$O)Calcd.(%): C, 55.55; H, 5.55; N, 2.82; S, 19.35Found(%): C, 55.52; H, 5.46; N, 2.92; S, 19.31 |
| I-7I-88a | $^1$H-NMR(CDCl$_3$) δ 0.95(1H, m), 1.21–1.46(10H, m), 1.55–1.68(2H, m), 1.98(1H, m), 2.16–2.33(2H, m), 2.49(1H, brs), 3.83(1H, m), 4.16(2H, s), 5.79(1H, d, J=15.6Hz), 5.88(1H, d, J=7.5Hz), 6.79(1H, d, J=3.6Hz), 6.95–7.08(3H, m), 7.28(1H, dd, J=3.0and4.8Hz), 7.35(1H, d, J=3.6Hz); IR(CHCl$_3$)3523, 3446, 3427, 2679, 1695, 1647, 1545, 1506, 1458, 1300, 1281cm$^{-1}$; [α]$_D^{24}$+34.7±0.70°(c=1.004, MeOH)Anal.(C$_{24}$H$_{29}$NO$_3$S$_2$) Calcd.(%): C, 64.98; H, 6.59; N, 3.16; S, 14.46Found(%): C, 64.71; H, 6.61; N, 3.24; S, 14.17 |
| I-7I-93a | mp116–120°C.; $^1$H-NMR(CDCl$_3$) δ 0.95(1H, m), 1.21–1.68(12H, m), 1.98(1H, m), 2.17–2.23(2H, m), 2.48(1H, brs), 3.84(1H, m), 4.34(2H, s), 5.80(1H, br d, J=15.6Hz), 5.84(1H, d), 6.85(1H, br d, J=3.3Hz), 6.90(1H, m), 6.95(1H, dd, J=3.6, 5.1Hz), 7.02(1H, dt, J=15.9, 6.9Hz), 7.19(1H, dd, J=1.2, 5.1Hz), 7.35(1H, d, J= |

TABLE 29-continued

| Compd. No. | Physical property |
|---|---|
| | 3.3Hz); IR(Nujol)3032, 1695, 1648, 1542, 1506, 1458, 1223, 1213cm$^{-1}$; $[\alpha]_D^{26.0}$+37.6±0.80°(c=1.015, MeOH) Anal.(C$_{24}$H$_{29}$NO$_3$S$_2$·0.1H$_2$O)Calcd.(%): C, 64.72; H, 6.61; N, 3.14; S, 14.40Found(%): C, 64.64; H, 6.58; N, 3.24; S, 14.50 |

TABLE 30

| Compd. No. | Physical property |
|---|---|
| I-7I-126a | $^1$H-NMR(CDCl$_3$) δ 0.93(1H, m), 1.20–1.48(10H, m), 1.54–1.64 (2H, s), 1.97(1H, d, J=3.6Hz), 2.19(2H, dd, J=13.8, 6.9Hz), 2.47(1H, m), 3.84(3H, s), 4.12(2H, s), 5.80(1H, dt, J=15.6, 1.5Hz), 5.81(1H, d, J=6.9Hz), 6.78(1H, d, J=3.9Hz), 6.86–6.93(2H, m), 7.01(1H, dt, J=15.6, 6.9Hz), 7.16 (1H, d, J=7.2Hz), 7.22(1H, d, J=7.2Hz), 7.31(1H, d, J= 3.9Hz); IR(Nujol)3276, 3079, 3058, 2678, 1691, 1604, 1552, 1456, 1319, 1247cm$^{-1}$; $[\alpha]_D^{27.0}$+34.3±0.70° (c=1.010, MeOH) Anal.(C$_{27}$H$_{33}$NO$_4$S)Calcd.(%): C, 69.35; H, 7.11; N, 3.00; S, 6.86Found(%): C, 69.19; H, 7.10; N, 3.12; S, 6.62 |
| I-7I-143a | $^1$H-NMR(CDCl$_3$) δ 1.00(1H, m), 1.21–1.50(10H, m), 1.59–1.65(2H, m), 2.00(1H, m), 2.17–2.21(2H, m), 2.57(1H, brs), 3.94(1H, m), 4.24(2H, s), 5.79(1H, d, J=15.6Hz), 6.07 (1H, d, J=7.8Hz), 7.03(1H, dt, J=15.6and7.2Hz), 7.18–7.30(6H, m), 7.42(1H, t, J=7.8Hz), 7.81(1H, s), 8.18(1H, d, J= 7.8Hz); IR(CHCl$_3$)3523, 3438, 2683, 1695, 1651, 1516, 1495cm$^{-1}$; $[\alpha]_D^{24}$+41.7±0.80°(c=1.002, MeOH)Anal. (C$_{30}$H$_{33}$NO$_3$S) Calcd.(%): C, 73.62; H, 6.84; N, 2.86; S, 6.55Found(%): C, 73.54; H, 6.77; N, 2.92; S, 6.49 |
| I-7I-270a | $^1$H-NMR(CDCl$_3$) δ 0.99(1H, m), 1.18–1.70(12H, m), 2.01 (1H, brd), 2.17–2.24(2H, m), 2.42(6H, s), 2.48(1H, brs), 3.81(1H, m), 5.79(1H, dt, J=15.6, 1.5Hz), 5.88(2H, s), 6.05(1H, d, J=7.5Hz), 7.03(1H, dt, J=15.6, 6.9Hz), 7.35(1H, d, J= 3.9Hz), 7.50(1H, d, J=3.9Hz); IR(CHCl$_3$)3525, 3442, 2677, 1695, 1655, 1529, 1504, 1375, 1180, 1119cm$^{-1}$; $[\alpha]_D^{25}$+37.2±0.8°(c=1.009, MeOH)Anal. (C$_{25}$H$_{32}$N$_2$O$_5$S$_2$·0.3H$_2$O) Calcd.(%): C, 58.87; H, 6.44; N, 5.49; S, 12.57 Found(%): C, 58.99; H, 6.39; N, 5.51; S, 12.48 |
| I-7I-307a | mp171–173°C.; $^1$H-NMR(CDCl$_3$) δ 0.91(1H, m), 1.17–1.41(10H, m), 1.50–1.59(2H, m), 1.93(1H, m), 2.12–2.19(2H, m), 2.44(1H, m), 3.78(1H, m), 3.97(3H, s), 4.59(2H, s), 5.77 (1H, d, J=15.6Hz), 5.81(1H, d, J=7.2Hz), 6.75(1H, d, J=3.6Hz), 7.01(1H, dt, J=15.6, 7.1Hz), 7.28(1H, d, J=3.6Hz), 7.25–7.36(3H, m), 7.46(1H, m), 7.78–7.82(1H, m), 7.92 (1H, d, J=8.7Hz); IR(Nujol)3365, 3059, 2638, 1689, 1622, 1552, 1527, 1516, 1464, 1263, 1252, 1092cm$^{-1}$; $[\alpha]_D^{25.5}$+31.6±0.7°(c=1.001, MeOH)Anal. (C$_{31}$H$_{35}$NO$_4$S)Calcd.(%): C, 71.92; H, 6.81; N, 2.71; S, 6.19Found(%): C, 71.62; H, 6.90; N, 2.79; S, 6.20 |
| I-7I-327a | mp176–179°C.; $^1$H-NMR(CDCl$_3$) δ 0.98(1H, m), 1.20–1.70 (12H, m), 2.00(1H, d, J=3.6Hz), 2.16–2.24(2H, m), 2.47 (1H, brs), 3.00(2H, t, J=8.4Hz), 3.80(1H, m), 3.98 (2H, t, J=8.4Hz), 5.79(1H, dt, J=1.8, 15.3Hz), 6.01(1H, d, J=7.8Hz), 6.97–7.24(4H, m), 7.33(1H, d, J=4.2Hz), 7.46(1H, d, J= 4.2Hz), 7.58(1H, d, J=8.4Hz); IR(Nujol)3332, 2925, 2854, 1689, 1608, 1554, 1479, 1460, 1365, 1238, 1161cm$^{-1}$; |

TABLE 30-continued

| Compd. No. | Physical property |
|---|---|
| | $[\alpha]_D^{26}$+36.3±0.8°(c=1.012%, MeOH); Anal.(C$_{27}$H$_{32}$N$_2$O$_5$S$_2$) Calcd.(%)C, 61.34; H, 6.10; N, 5.30; S, 12.13Found(%)C, 61.08; H, 6.22; N, 5.24; S, 11.82 |

TABLE 31

| Compd. No. | Physical property |
|---|---|
| I-7I-332a | mp136–139°C.; $^1$H-NMR(CDCl$_3$) δ 0.98(1H, m), 1.20–1.82 (14H, m), 2.01(1H, d, J=3.0Hz), 2.21(2H, q, J= 6.9Hz), 2.48(1H, brs), 2.53(2H, t, J=6.6Hz), 3.53 (2H, t, J=6.3Hz), 3.79–3.87(3H, m), 5.79(1H, dt, J= 1.5, 15.6Hz), 6.01(1H, d, J=7.2Hz), 6.97–7.26(5H, m), 7.31(1H, d, J=3.9Hz), 7.77(1H, dd, J=0.9, 7.8Hz); IR (Nujol)3371, 3325, 2922, 1728, 1693, 1614, 1549, 1342, 1163cm$^{-1}$; $[\alpha]_D^{24}$+35.4±0.8° (c=1.009%, MeOH); Anal. (C$_{28}$H$_{34}$N$_2$O$_5$S$_2$)Calcd.(%)C, 61.97; H, 6.31; N, 5.16; S, 11.82Found(%)C, 61.94; H, 6.47; N, 5.14; S, 11.69 |
| I-7I-343a | $^1$H-NMR(CDCl$_3$) δ 1.07(1H, m), 1.22–1.62(12H, m), 1.98 (1H, m), 2.22(1H, m), 2.54(1H, m), 3.94(1H, m), 5.80 (1H, d, J=15.6Hz), 6.27(1H, d, J=8.1Hz), 7.02(1H, m), 7.45–7.60(5H, m), 7.89(1H, s), 7.99–8.05(3H, m), 8.59(1H, d, J=8.1Hz); IR(KBr)3381, 3292, 3066, 2949, 2927, 2873, 1685, 1655, 1620, 1558, 1477, 1446, 1385, 1319, 1308, 1284, 1244, 1230, 1209cm$^{-1}$; $[\alpha]_D^{26.0}$+32.6±1.5° (c=0.50, DMSO)Anal.(C$_{29}$H$_{31}$NO$_5$S$_2$·0.4H$_2$O) Calcd.(%): C, 63.92; H, 5.88; N, 2.57; S, 11.77Found(%): C, 64.07; H, 5.82; N, 2.75; S, 11.41 |
| I-7I-385a | $^1$H-NMR(CDCl$_3$) δ 1.03(1H, m), 1.20–1.74(12H, m), 2.04 (1H, m), 2.14–2.26(2H, m), 2.57(1H, m), 3.97(1H, m), 5.77(1H, d, J=15.6Hz), 6.27(2H, t, J=2.4Hz), 6.37 (1H, d, J=8.4Hz), 7.02(1H, dt, J=15.6, 6.9Hz), 7.22 (2H, t, J=2.4Hz), 7.57(1H, t, J=7.8Hz), 7.67(1H, d, J= 7.8Hz), 8.37(1H, d, J=7.8Hz), 8.44(1H, s); IR (CHCl$_3$)3452, 3023, 2954, 2877, 1695, 1650, 1516, 1456, 1373, 1282, 1188, 1163, 1057cm$^{-1}$; $[\alpha]_D^{22.0}$+39.4±0.8° (c=1.017, MeOH)Anal.(C$_{27}$H$_{30}$N$_2$O$_5$S$_2$·0.1H$_2$O) Calcd.(%): C, 61.36; H, 5.76; N, 5.30; S, 12.14Found(%): C, 61.26; H, 5.89; N, 5.11; S, 11.95 |
| I-7I-389a | mp140–143°C.; $^1$H-NMR(CDCl$_3$) δ 0.96(1H, m), 1.21–1.46(10H, m), 1.54–1.64(2H, m), 1.99(1H, m), 2.23(3H, s)+2.16–2.23(2H, m), 2.48(1H, m), 3.21(2H, t, J=8.7Hz), 3.81(1H, m), 4.62(2H, t, J=8.7Hz), 5.79(1H, d, J=15.6Hz), 5.88(1H, d, J=7.8Hz), 6.89(1H, s), 6.96 (1H, s), 7.02(1H, dd, J=15.6, 6.9Hz), 7.08(1H, d, J=3.9Hz), 7.35(1H, d, J=3.9Hz); IR(Nujol)3294, 3066, 2675, 1695, 1649, 1604, 1550, 1512, 1327, 1203cm$^{-1}$; $[\alpha]_D^{25}$+29.2±0.7°(c=1.013, MeOH)Anal. (C$_{28}$H$_{33}$NO$_4$S$_2$)Calcd.(%): C, 65.72; H, 650; N, 2.74; S, 12.53Found(%): C, 65.57; H, 6.62; N, 2.62; S, 12.37 |

TABLE 32

| Compd. No. | Physical property |
|---|---|
| I-7I-391a | mp204–207°C.; $^1$H-NMR(CDCl$_3$) δ 1.01(1H, m), 1.25–1.46 (10H, m), 1.54–1.64(2H, m), 2.00(1H, m), 2.17–2.23(2H, m), 2.31(3H, s), 2.48(1H, m), 3.18(2H, t, J=8.7Hz), 3.81 (1H, m), 4.71(2H, t, J=8.7Hz), 5.79(1H, d, J=15.6Hz), 6.20(1H, d, J=7.8Hz), 7.02(1H, dt, J=15.6, 6.9Hz), 7.21 (1H, s), 7.41(1H, d, J=3.9Hz), 7.50(1H, s), 7.70(1H, d, |

TABLE 32-continued

| Compd. No. | Physical property |
|---|---|
| | J=3.9Hz); IR(Nujol)3398, 3197, 3086, 1716, 1689, 1639, 1541, 1313, 1151cm$^{-1}$; [α]$_D^{25}$+37.9±0.8°(c=1.005, MeOH) Anal.(C$_{28}$H$_{33}$NO$_6$S$_2$)Calcd.(%): C, 61.85; H, 6.12; N, 2.58; S, 11.80Found(%): C, 61.61; H, 6.08; N, 2.50; S, 11.69 |
| I-7J-1a | mp116–118°C.; $^1$H-NMR(CDCl$_3$) δ 0.99(1H, m), 1.19–1.82(12H, m), 1.79(3H, d, J=1.2Hz), 2.01(1H, m), 2.17(2H, brq, J=7.8Hz), 2.48(1H, m), 3.82(1H, m), 6.00(1H, d, J=7.8Hz), 6.32–6.35(2H, m), 6.85(1H, m), 7.15–7.17(2H, m), 7.33(1H, d, J=3.9Hz), 7.63(1H, d, J=3.9Hz), 7.57 (1H, d, J=3.9Hz); IR(Nujol)3354, 3141, 3099, 3076, 2669, 2557, 1682, 1641, 1624, 1539, 1390, 1375, 1302, 1190, 1167cm$^{-1}$; [α]$_D^{26}$37.1±0.6°(c=1.002, MeOH)Anal. (C$_{24}$H$_{30}$N$_2$O$_5$S$_2$)Calcd.(%): C, 58.75; H, 6.16; N, 5.71; S, 13.07Found(%): C, 58.55; H, 6.14; N, 5.70; S, 12.89 |
| I-7K-1a | mp168–171°C.; $^1$H-NMR(CDCl$_3$) δ 0.99(1H, m), 1.20–1.82 (12H, m), 2.01–2.20(3H, m), 2.12(3H, d, J=0.9Hz), 2.48 (1H, m), 3.82(1H, m), 4.05(2H, s), 5.65(1H, s), 5.97(1H, d, J=7.5Hz), 6.33–6.35(2H, m), 7.16–7.18(2H, m), 7.33 (1H, d, J=3.9Hz), 7.63(1H, d, J=3.9Hz), 7.58(1H, d, J=3.9Hz); IR(Nujol)3330, 3086, 1693, 1633, 1614, 1544, 1456, 1377, 1250, 1194, 1169, 1057cm$^{-1}$; [α]$_D^{26}$+34.0±1.5° (c=0.509, MeOH)Anal. (C$_{24}$H$_{30}$N$_2$O$_5$S$_2$·0.6CHCl$_3$) Calcd.(%): C, 52.55; H, 5.49; N, 4.98; S, 11.41; Cl, 11.35 Found(%): C, 52.62; H, 5.19; N, 4.93; S, 11.11; Cl, 10.53 |
| I-7M-1a | $^1$H-NMR(CDCl$_3$) δ 1.00–1.70(13H, m), 2.01(1H, m), 2.47 (1H, m), 3.52(2H, t, J=6.6Hz), 3.82(1H, m), 4.04(2H, s), 5.54–5.70(2H, m), 6.13(1H, d, J=7.2Hz), 6.32–6.35(2H, m), 7.15–7.18(2H, m), 7.37(1H, d, J=4.2Hz), 7.57(1H, d, J=4.2Hz); IR(CHCl$_3$)3440, 1778, 1731, 1655, 1531, 1504, 1456, 1383, 1192, 1167, 1128, 1057, 1034cm$^{-1}$; [α]$_D^{24}$+ 40.9±0.8°(c=1.007, MeOH)Anal. (C$_{22}$H$_{28}$N$_2$O$_6$S$_2$·0.4H$_2$O) Calcd.(%): C, 54.17; H, 5.95; N, 5.74; S, 13.15Found(%): C, 54.51; H, 6.00; N, 5.58; S, 12.76 |
| I-7M-1e | $^1$H-NMR(CDCl$_3$) δ 1.02–1.70(13H, m), 2.02(1H, m), 2.48 (1H, m), 3.31(3H, s), 3.50(2H, t, J=6.6Hz), 3.85(1H, m), 3.99(2H, s), 6.05(1H, d, J=8.1Hz), 6.34(2H, m), 7.16 (2H, m), 7.36(1H, d, J=3.9Hz), 7.58(1H, d, J=3.9Hz), 8.88(1H, s); IR(CHCl$_3$)3442, 3352, 2956, 2877, 1730, 1657, 1531, 1504, 1456, 1423, 1402, 1385, 1350, 1167, 1076, 1057, 1034cm$^{-1}$; [α]$_D^{25.5}$+35.6±0.8°(c=1.00, MeOH) Anal.(C$_{23}$H$_{31}$N$_3$O$_7$S$_3$·0.8MeOH)Calcd.(%): C, 48.29; H, 5.74; N, 7.34; S, 16.81Found(%): C, 48.00; H, 5.68; N, 7.74; S, 17.12 |

TABLE 33

| Compd. No. | Physical property |
|---|---|
| I-7M-40a | $^1$H-NMR(CDCl$_3$) δ 1.03(1H, m), 1.22–1.74(12H, m), 2.01 (1H, m), 2.51(1H, brs), 3.54(2H, dt, J=1.5, 6.3Hz), 3.91 (1H, m), 4.05(2H, s), 6.03(1H, d, J=8.1Hz), 7.25–7.64 (7H, m); IR(CHCl$_3$)2954, 1780, 1732, 1643, 1541, 1510, 1491, 1454, 1219, 1213, 1132cm$^{-1}$; [α]$_D^{25}$+50.9±0.9° (c=1.013%, MeOH); Anal.(C$_{24}$H$_{29}$NO$_4$S·0.5H$_2$O)Calcd.(%) C, 66.03; H, 6.93; N, 3.21; S, 7.34Found(%)C, 66.14; H, 6.92; N, 3.26; S, 7.22 |
| I-7M-43a | mp132–134°C.; $^1$H-NMR(CDCl$_3$) δ 1.01(1H, m), 1.20–1.75 (12H, m), 2.01(1H, d, J=3.0Hz), 2.47(1H, brs), 3.53(2H, t, J=6.0Hz), 3.79–3.96(5H, m), 4.05(2H, s), 6.06(1H, d, J=7.8Hz), 6.85(1H, dd, J=1.5, 8.1Hz), 6.96(1H, m), 7.11 |

TABLE 33-continued

| Compd. No. | Physical property |
|---|---|
| | (1H, m), 7.29(1H, d, J=4.2Hz), 7.34(1H, d, J=4.2Hz), 7.83(1H, dd, J=1.5, 8.1Hz); IR(Nujol)3325, 3084, 2924, 1730, 1612, 1562, 1491, 1460, 1369, 1250, 1236, 1165, 1138cm$^{-1}$; [α]$_D^{26}$+53.6±0.9° (c=1.009%, MeOH); Anal. (C$_{22}$H$_{27}$NO$_4$S$_2$)Calcd.(%)C, 60.94; H, 6.28; N, 3.23; S, 14.79Found(%)C, 60.77; H, 6.32; N, 3.38; S, 14.51 |
| I-7M-47a | mp116–118°C.; $^1$H-NMR(CDCl$_3$) δ 1.06(1H, m), 1.19–1.70(12H, m), 2.00(1H, m), 2.49(1H, m), 3.52(2H, t, J=6.3Hz), 3.84(1H, m), 4.05(2H, s), 6.21(1H, d, J=7.8Hz), 7.11(1H, dd, J=3.9, 4.5Hz), 7.42(1H, d, J=3.9Hz), 7.63 (1H, d, J=3.9Hz), 7.70(1H, dd, J=0.9, 4.8Hz), 7.75(1H, dd, J=0.9, 3.9Hz); IR(Nujol)3319, 3097, 2557, 1732, 1618, 1566, 1444, 1432, 1321, 1232, 1151, 1031cm$^{-1}$; [α]$_D^{24}$+ 44.4±0.8°(c=1.009, MeOH)Anal.(C$_{22}$H$_{27}$NO$_6$S$_3$) Calcd.(%): C, 53.10; H, 5.47; N, 2.81; S, 19.33Found(%): C, 52.90; H, 5.37; N, 2.91; S, 19.10 |
| I-7M-59a | mp103–104°C.; $^1$H-NMR(CDCl$_3$) δ 0.99(1H, m), 1.20–1.70(12H, m), 1.99(1H, d, J=3.3Hz), 2.45(1H, m), 3.23(2H, t, J=8.7Hz), 3.48–3.55(2H, m), 3.84(1H, m), 4.04(2H, s), 5.89(1H, d, J=8.1Hz), 7.01(1H, dd, J=3.6, 5.1Hz), 7.04 (1H, d, J=3.9Hz), 7.29(1H, dd, J=1.5, 3.6Hz), 7.33(1H, d, J=3.9Hz), 7.43(1H, dd, J=1.5, 5.1Hz); IR(Nujol) 3332, 2922, 2854, 1930, 1601, 1564, 1458, 1439, 1331, 1230, 1134cm$^{-1}$; [α]$_D^{26}$+40.0±0.8°(c=1.004%, MeOH); Anal.(C$_{22}$H$_{27}$NO$_4$S$_3$)Calcd.(%)C, 56.75; H, 5.84; N, 3.01; S, 20.66Found(%)C, 56.59; H, 5.81; N, 3.04; S, 20.65 |
| I-7M-88a | mp90–91.5°C.; $^1$H-NMR(CDCl$_3$) δ 1.00(1H, m), 1.18–1.70 (12H, m), 1.99(1H, m), 2.46(1H, m), 3.52(2H, dt, J=1.8, 8.7Hz), 387(1H, m), 4.04and4.16(each2H, s), 4.58(1H, brs), 5.91(1H, d, J=8.7Hz), 6.80(1H, d, J=3.6Hz), 6.96 (1H, dd, J=1.2, 5.1Hz), 7.06(1H, m), 7.29(1H, dd, J= 3.0, 4.8Hz), 7.37(1H, d, J=3.9Hz); IR(Nujol)3332, 3095, 3080, 2553, 1735, 1597, 1562, 1537, 1435, 1325, 1304, 1228, 1146cm$^{-1}$; [α]$_D^{24}$+39.8±0.8°(c=1.002, MeOH)Anal. (C$_{23}$H$_{29}$NO$_4$S$_2$)Calcd.(%): C, 61.72; H, 6.53; N, 3.13; S, 14.33Found(%): C, 61.60; H, 6.20; N, 3.24; S, 14.01 |

TABLE 34

| Compd. No. | Physical property |
|---|---|
| I-7M-126a | $^1$H-NMR(CDCl$_3$) δ 0.96(1H, m), 1.23–1.26(2H, m), 1.38–1.46 (6H, m), 1.54–1.63(4H, s), 1.97(1H, d, J=3.6Hz), 2.45(1H, m), 3.48–3.53(2H, m), 3.83(3H, s), 3.85(1H, m), 4.03(2H, s), 4.12(2H, s), 5.88(1H, d, J=7.8Hz), 6.77(1H, d, J=3.6Hz), 6.86–6.90(2H, m), 7.16(1H, dd, J=4.5, 1.8Hz), 7.21(1H, dd, J=7.8, 1.8Hz), 7.33(1H, d, J=3.6Hz); IR(CHCl$_3$)3427, 2875, 1639, 1504, 1460, 1248, 1221cm$^{-1}$; [α]$_D^{27.0}$+36.8±1.5°(c=0.508, MeOH)Anal. (C$_{26}$H$_{33}$NO$_5$S·0.3H$_2$O)Calcd.(%): C, 65.47; H, 7.10; N, 2.94; S, 6.72Found(%): C, 65.30; H, 7.01; N, 3.02; S, 6.54 |
| I-7M-143a | mp123–125°C.; $^1$H-NMR(CDCl$_3$) δ 1.04(1H, m), 1.20–1.75 (12H, m), 2.01(1H, brs), 2.55(1H, brs), 3.53(2H, dt, J= 1.8, 6.0Hz), 3.98(1H, m), 4.02and4.24(2H, s), 6.08(1H, d, J=7.8Hz), 7.17–7.45(7H, m), 7.83(1H, s), 8.16(1H, d, J=7.8Hz); IR(Nujol)3280, 2924, 1722, 1612, 1566, 1454, 1242, 1228, 1137cm$^{-1}$; [α]$_D^{26}$+39.2±0.6°(c=1.012%, MeOH); Anal.(C$_{29}$H$_{33}$NO$_4$S)Calcd.(%)C, 70.85; H, 6.77; N, 2.85; S, 6.52Found(%)C, 70.58; H, 6.70; N, 2.94; S, 6.40 |

TABLE 34-continued

| Compd. No. | Physical property |
|---|---|
| I-7M-197a | $^1$H-NMR(CDCl$_3$) δ 0.98(1H, m), 1.20–1.70(12H, m), 1.98 (1H, d, J=3.3Hz), 2.45(1H, m), 3.23(2H, t, J=8.7Hz), 3.49–3.54(2H, m), 3.86(1H, m), 4.03and4.08(2H, s), 4.58 (2H, t, J=8.7Hz), 5.88(1H, d, J=8.4Hz), 6.20(1H, t, J= 3.6Hz), 6.77–6.82(2H, m), 6.96(1H, d, J=7.2Hz), 7.10 (1H, d, J=7.2Hz), 7.35(1H, d, J=3.6Hz); IR(CHCl$_3$) 2954, 1732, 1641, 1545, 1506, 1477, 1458, 1254, 1225, 1221, 1213, 1207, 1130cm$^{-1}$; $[α]_D^{26}$+37.2±0.8°(c=1.008%, MeOH); Anal.(C$_{27}$H$_{33}$NO$_5$S·0.3H$_2$O)Calcd.(%)C, 66.31; H, 6.93; N, 2.86; S, 6.56Found(%)C, 66.24; H, 6.91; N, 2.92; S, 6.52 |
| I-7M-270a | mp.141–143°C.; $^1$H-NMR(CDCl$_3$) δ 1.02(1H, br), 1.18–1.70 (12H, m), 2.01(1H, brd), 2.42(6H, s), 2.48(1H, brs), 3.53 (2H, dt, J=0.9, 6.6Hz), 3.83(1H, m), 4.06(2H, s), 5.88 (2H, s), 6.11(1H, d, J=7.8Hz), 7.36(1H, d, J=3.9Hz), 7.50(1H, d, J=3.9Hz); IR(Nujol)3327, 3097, 3084, 2555, 1732, 1616, 1556, 1234, 1219, 1176, 1134, 1113cm$^{-1}$; $[α]_D^{26}$+ 40.5±0.8°(c=1.014, MeOH)Anal.(C$_{24}$H$_{32}$N$_2$O$_6$S$_2$) Calcd.(%): C, 56.67; H, 6.37; N, 5.51; S, 12.61Found(%): C, 56.56; H, 6.10; N, 5.48; S, 12.38 |
| I-7M-307a | mp131–132°C.; $^1$H-NMR(CDCl$_3$) δ 0.94(1H, m), 1.20–1.23 (2H, m), 1.34–1.39(6H, m), 1.51–1.63(4H, m), 1.94(1H, m), 2.42(1H, m), 3.45–3.49(2H, m), 3.81(1H, m), 3.98(3H, s), 4.01(2H, s), 4.59(2H, s), 5.85(1H, d, J=7.5Hz), 6.75(1H, d, J=3.3Hz), 7.28–7.36(3H, m,), 7.47(1H, t, J=7.7Hz), 7.79(1H, d, J=3.9Hz), 7.82(1H, d, J=4.8Hz), 7.92(1H, d, J=8.4Hz); IR(Nujol)3340, 3068, 2744, 2546, 1738, 1604, 1560, 1435, 1250, 1236, 1146cm$^{-1}$; $[α]_D^{25.5}$+36.1±0.8° (c=1.000, MeOH)Anal.(C$_{30}$H$_{35}$NO$_5$S)Calcd.(%): C, 69.07; H, 6.76; N, 2.68; S, 6.15Found(%): C, 68.99; H, 6.87; N, 2.74; S, 6.05 |

TABLE 35

| Compd. No. | Physical property |
|---|---|
| I-7M-315a | $^1$H-NMR(CDCl$_3$) δ 1.04(1H, m), 1.26–1.64(12H, m), 2.03 (1H, m), 2.55(1H, m), 3.54(2H, t, J=5.1Hz), 3.99 (1H, m), 4.03(2H, s), 4.26(2H, s), 6.07–6.10(1H, d, J=7.5Hz), 7.00–7.23(5H, m), 7.43(1H, m), 7.85(1H, s), 8.16(1H, d, J= 8.1Hz); IR(CHCl$_3$)3508, 3437, 2954, 2875, 1780, 1732, 1651, 1518, 1477, 1456, 1396, 1363cm$^{-1}$; $[α]_D^{24.0}$+38.1±0.8° (c=1.03, MeOH)Anal.(C$_{29}$H$_{32}$FNO$_4$S·0.6MeOH)Calcd.(%): C, 67.22; H, 6.56; N, 2.65;F, 3.59; S, 6.06Found(%): C, 67.31; H, 6.57; N, 2.92;F, 3.21; S, 6.09 |
| I-7M-316a | $^1$H-NMR(CDCl$_3$) δ 1.04(1H, m), 1.23–1.68(11H, m), 2.01 (1H, m), 2.55(1H, m), 3.54(2H, t, J=6.6Hz), 3.82(3H, s), 3.99(1H, m), 4.02(2H, s), 4.23(2H, s), 6.09(1H, d, J=8.1Hz), 6.83–6.91(2H, m), 7.05–7.23(3H, m), 7.39(1H, m), 7.85(1H, s), 8.12(1H, d, J=8.1Hz); IR(CHCl$_3$)3437, 2954, 2875, 1780, 1732, 1651, 1601, 1516, 1493, 1464, 1394, 1363, 1246cm$^{-1}$; $[α]_D^{26.0}$+35.2±1.5°(c=0.50, MeOH) Anal.(C$_{30}$H$_{35}$NO$_5$S·0.2H$_2$O)Calcd.(%): C, 68.60; H, 6.79; N, 2.67; S, 6.10Found(%): C, 68.56; H, 6.89; N, 2.86; S, 5.93 |
| I-7M-317a | $^1$H-NMR(CDCl$_3$) δ 1.03(1H, m), 1.22–1.65(11H, m), 2.02 (1H, m), 2.57(1H, m), 3.54(2H, d, J=6.0Hz), 4.00(1H, m), 4.03(3H, s), 4.35(2H, s), 6.10(1H, d, J=7.8Hz), 7.08–7.24(4H, m), 7.39–7.44(2H, m), 7.85(1H, s), 8.18(1H, d, J=8.4Hz); IR(CHCl$_3$)3508, 3437, 2954, 2875, 1780, 1732, 1651, 1568, 1518, 1495, 1475, 1444, 1394, 1363cm$^{-1}$; $[α]_D^{26.0}$+34.9±0.8°(c=1.00, MeOH)Anal. (C$_{29}$H$_{32}$ClNO$_4$S)Calcd.(%): C, 66.21; H, 6.13; N, 2.66; Cl, 6.74; S, 6.10Found(%): C, 66.01; H, 6.32; N, 2.89; Cl, 6.03; S, 5.91 |
| I-7M-318a | $^1$H-NMR(CDCl$_3$) δ 1.05(1H, m), 1.22–1.64(12H, m), 2.01 (1H, m), 2.56(1H, m), 3.49–3.52(2H, m), 3.97(2H, s), 3.50 (1H, m), 4.24(2H, s), 6.12(1H, d, J=6.3Hz), 6.81–6.91 (2H, m), 7.11–7.18(3H, m), 7.39(1H, m), 7.84(1H, s), 8.12 (1H, d, J=7.8Hz); IR(CHCl$_3$)3597, 3435, 2954, 2875, 1780, 1730, 1649, 1518, 1496, 1456, 1394, 1363, 1327cm$^{-1}$; $[α]_D^{27.0}$+36.9±0.8° (c=1.01, MeOH)Anal. (C$_{29}$H$_{33}$NO$_5$S·1.2H$_2$O)Calcd.(%): C, 65.81; H, 6.74; N, 2.65; S, 6.06Found(%): C, 65.74; H, 6.59; N, 2.79; S, 5.90 |
| I-7M-327a | mp137–139°C.; $^1$H-NMR(CDCl$_3$) δ 1.01(1H, m), 1.20–1.70(12H, m), 2.00(1H, d, J=3.0Hz), 2.46(1H, brs), 3.01(2H, t, J=8.7Hz), 3.52(2H, t, J=6.3Hz), 3.81(1H, m), 3.98 (2H, t, J=8.4Hz), 4.04(2H, s), 6.11(1H, d, J=7.5Hz), 6.98–7.24(3H, m), 7.35(1H, d, J=3.9Hz), 7.46(1H, d, J= 3.9Hz), 7.57(1H, d, J=8.1Hz); IR(Nujol)3325, 2924, 1730, 1616, 1566, 1460, 1444, 1373, 1236, 1163, 1138cm$^{-1}$; $[α]_D^{26}$+39.2±0.8°(c=1.006%, MeOH); Anal. (C$_{26}$H$_{32}$N$_2$O$_6$S$_2$·0.2H$_2$O)Calcd.(%)C, 58.23; H, 6.09; N, 5.22; S, 11.96Found(%)C, 58.19; H, 6.14; N, 5.22; S, 11.85 |

TABLE 36

| Compd. No. | Physical property |
|---|---|
| I-7M-329a | mp137–139°C.; $^1$H-NMR(d$_6$-DMSO) δ 1.14–1.60(13H, m), 1.91(1H, d, J=3.0Hz), 2.29(1H, brs), 3.05(2H, t, J=8.4Hz), 3.37(2H, t, J=6.3Hz), 3.57(1H, m), 3.91(2H, s), 4.01(2H, t, J=8.4Hz), 6.91(1H, m), 7.27–7.37(2H, m), 7.78(1H, d, J=3.9Hz), 7.93(1H, d, J=3.9Hz), 8.53 (1H, d, J=6.9Hz); IR(Nujol)3325, 2924, 1730, 1618, 1566, 1460, 1444, 1435, 1375, 1234, 1165, 1138, 1070cm$^{-1}$; $[α]_D^{25}$+38.2±0.8°(c=1.015%, MeOH); Anal. (C$_{26}$H$_{31}$FN$_2$O$_6$S$_2$)Calcd.(%)C, 56.71; H, 5.67;F, 3.45; N, 5.09; S, 11.65Found(%)C, 56.61; H, 5.47;F, 3.32; N, 5.12; S, 11.54 |
| I-7M-330a | mp158–160°C.; $^1$H-NMR(d$_6$-DMSO) δ 1.13–1.58(13H, m), 1.91(1H, d, J=3.0Hz), 2.29(1H, brs), 2.97(2H, t, J= 8.4Hz), 3.37(2H, t, J=6.9Hz), 3.57(1H, m), 3.91(2H, s), 3.97(2H, t, J=8.4Hz), 7.10(1H, d, J=8.7Hz), 7.43 (1H, dd, J=4.5, 8.4Hz), 7.72(1H, d, J=3.9Hz), 7.92 (1H, d, J=3.9Hz), 8.52(1H, d, J=6.9Hz); IR(Nujol) 3325, 3095, 2924, 1732, 1618, 1566, 1481, 1460, 1444, 1373, 1236, 1221, 1167, 1140, 1038cm$^{-1}$; $[α]_D^{25}$+ 38.2±0.8°(c=1.009%, MeOH); Anal.(C$_{26}$H$_{31}$FN$_2$O$_6$S$_2$) Calcd.(%)C, 56.71; H, 5.67;F, 3.45; N, 5.09; S, 11.65 Found(%)C, 56.51; H, 5.74;F, 3.30; N, 5.09; S, 11.57 |
| I-7M-331a | mp152–154°C.; $^1$H-NMR(d$_6$-DMSO) δ 1.14–1.60(13H, m), 1.92(1H, d, J=2.7Hz), 2.29(1H, brs), 2.98(2H, t, J= 8.4Hz), 3.37(2H, t, J=6.6Hz), 3.58(1H, m), 3.91(2H, |

TABLE 36-continued

| Compd. No.. | Physical property |
|---|---|
| | s), 3.99(2H, t, J=8.4Hz), 6.88(1H, ddd, J=2.4, 8.1, 9.0Hz), 7.16–7.26(2H, m), 7.82(1H, d, J=4.2Hz), 7.94(1H, d, J=4.2Hz), 8.54(1H, d, J=7.5Hz); IR(Nujol)3317, 3091, 2924, 1734, 1616, 1568, 1491, 1460, 1446, 1435, 1371, 1261, 1234, 1221, 1176, 1163, 1142, 1092, 1036cm$^{-1}$; [α]$_D^{25}$+38.7±0.8°(c=1.012%, MeOH); Anal. (C$_{26}$H$_{31}$FN$_2$O$_6$S$_2$)Calcd.(%)C, 56.71; H, 5.67; F, 3.45; N, 5.09; S, 11.65Found(%)C, 56.49; H, 5.36;F, 3.34; N, 5.10; S, 11.27 |
| I-7M-332a | mp100–103°C.; $^1$H-NMR(CDCl$_3$) δ 1.01(1H, m), 1.20–1.82(14H, m), 2.01(1H, d, J=3.3Hz), 2.47(1H, brs), 2.53(2H, t, J=6.6Hz), 3.53(2H, t, J=6.3Hz), 3.79–3.88 (3H, m), 4.05(2H, s), 6.07(1H, d, J=7.8Hz), 7.03–7.23(4H, m), 7.32(1H, d, J=3.9Hz), 7.78(1H, dd, J=0.9, 8.1Hz); IR(Nujol)3329, 2925, 1730, 1614, 1562, 1458, 1363, 1346, 1234, 1159cm$^{-1}$; [α]$_D^{24}$+37.7±0.8° (c=1.018%, MeOH); Anal.(C$_{27}$H$_{34}$N$_2$O$_6$S$_2$·0.4H$_2$O) Calcd.(%)C, 58.55; H, 6.33; N, 5.06; S, 11.58Found(%) C, 58.84; H, 6.41; N, 5.02; S, 11.30 |

TABLE 37

| Compd. No.. | Physical property |
|---|---|
| I-7M-333a | mp 125–128° C.; $^1$H-NMR(CDCl$_3$) δ 1.01(1H, m), 1.20–1.75(12H, m), 2.01(1H, d, J=3.0Hz), 2.47(1H, m), 3.53(2H, t, J=6.0Hz), 3.79–3.96(5H, m), 4.05(2H, s), 6.06(1H, d, J=7.8Hz), 6.85(1H, dd, J=1.5, 8.1Hz), 6.96(1H, m), 7.11(1H, m), 7.29(1H, d, J=4.2Hz), 7.34 (1H, d, J=4.2Hz), 7.83(1H, dd, J=1.5, 8.1Hz); IR (Nujol) 3325, 3084, 2924, 1730, 1612, 1562, 1491, 1460, 1369, 1250, 1236, 1165, 1138cm$^{-1}$; [α]$_D^{26}$+36.4±0.8° (c=1.008%, MeOH); Anal.(C$_{26}$H$_{32}$N$_2$O$_7$S$_2$·0.3H$_2$O) Calcd.(%) C, 56.36; H, 5.93; N, 5.06; S, 11.57 Found(%) C, 56.36; H, 5.72; N, 5.08; S, 11.53 |
| I-7M-334a | mp 127–129° C.; $^1$H-NMR(CDCl$_3$) δ 1.02(1H, m), 1.20–1.70(12H, m), 2.01(1H, d, J=3.3Hz), 2.48(1H, brs), 3.05(2H, dd, J=5.7, 9.0Hz), 3.53(2H, t, J=6.3Hz), 3.82(1H, m), 4.03–4.07(4H, m), 6.08(1H, d, J=8.1Hz), 7.07–7.33(5H, m), 7.67(1H, m); IR(Nujol) 3315, 2924, 1761, 1728, 1616, 1550, 1467, 1363, 1165cm$^{-1}$; [α]$_D^{24}$+37.1±0.8°(c=1.010%, MeOH); Anal. (C$_{26}$H$_{32}$N$_2$O$_5$S$_3$·0.1Hexane) Calcd.(%) C, 55.72; H, 5.87; N, 4.89; S, 16.78 Found(%) C, 55.86; H, 5.94; N, 4.84; S, 16.61 |
| I-7M-336a | mp 209–212° C.; $^1$H-NMR(d$_6$-DMSO) δ 1.11–1.56(13H, m), 1.91(1H, brs), 2.29(1H, brs), 3.37(2H, t, J=6.3Hz), 3.58(1H, m), 3.91(2H, s), 4.63(4H, s), 7.20–7.35(4H, m), 7.77(1H, d, J=3.9Hz), 7.96(1H, d, J=3.9Hz), 8.51 (1H, d, J=7.5Hz); IR(Nujol) 3332, 2924, 1736, 1616, 1562, 1468, 1354, 1240, 1165, 1140, 1092cm$^{-1}$; Anal. (C$_{26}$H$_{32}$N$_2$O$_6$S$_2$) Calcd.(%) C, 58.62; H, 6.06; N, 5.26; S, 12.04 Found(%) C, 58.38; H, 5.98; N, 5.25; S, 11.82 |
| I-7M-337a | $^1$H-NMR(CDCl$_3$) δ 1.04(1H, m), 1.23–1.32(3H, m), 1.43–1.69(8H, s), 2.02(1H, m), 2.52–2.54(2H, m), 3.53 (2H, t, J=6.3Hz), 4.01(1H, m), 4.03(2H, s), 4.28(2H, s), 6.06(1H, d, J=8.1Hz), 7.01–7.07(2H, m), 7.15–7.31 (4H, m), 7.65(1H, dd, J=7.5, 0.9Hz), 8.17(1H, s); IR (CHCl$_3$) 3323, 2656, 2548, 1728, 1621, 1562, 1456, 1234, 1130cm$^{-1}$; [α]$_D^{27.0}$+26.7±0.7° (c=1.001, MeOH) Anal. |

TABLE 37-continued

| Compd. No.. | Physical property |
|---|---|
| | (C$_{29}$H$_{32}$FNO$_5$·0.5H$_2$O) Calcd.(%): C, 69.31; H, 6.62; N, 2.79; F, 3.58 Found(%): C, 69.19; H, 6.67; N, 2.82; F, 3.28 |
| I-7M-342a | $^1$H-NMR(CDCl$_3$) δ 1.05(1H, m), 1.22–1.63(12H, m), 2.01 (1H, m), 2.55(1H, m), 3.49–3.53(2H, m), 3.99(1H, m), 4.01(2H, s), 6.14(1H, br), 7.18–7.26(5H, m), 7.43–7.54 (2H, m), 7.85(1H, s), 8.32(1H, d, J=7.8Hz); IR(CHCl$_3$) 3438, 2954, 2875, 1780, 1730, 1649, 1583, 1516, 1477, 1456, 1375cm$^{-1}$; [α]$_D^{26.0}$+38.5±0.8°(c=1.03, MeOH) |

TABLE 38

| Compd. No.. | Physical property |
|---|---|
| I-7M-343a | $^1$H-NMR(CDCl$_3$) δ 1.05(1H, m), 1.24–1.63(12H, m), 2.05 (1H, m), 2.54(1H, m), 3.54(2H, t, J=8.1Hz), 3.94(1H, m), 4.03(2H, s), 6.17(1H, d, J=7.5Hz), 7.45–7.63(4H, m), 7.94(1H, s), 8.01–8.11(3H, m), 8.62(1H, d, J=8.4Hz); IR(CHCl$_3$) 3437, 3375, 2954, 2875, 1780, 1730, 1518, 1383, 1315, 1309cm$^{-1}$; [α]$_D^{25.0}$+33.3±0.7°(c=1.04, MeOH) |
| I-7M-385a | $^1$H-NMR(CDCl$_3$) δ 1.07(1H, m), 1.20–1.72(12H, m), 2.04 (1H, m), 2.56(1H, m), 3.52(2H, dt, J=6.3, 1.8Hz), 3.97 (1H, s), 4.03(2H, s), 6.27(2H, t, J=2.4Hz), 6.42(1H, d, J=7.2Hz), 7.21(2H, t, J=2.4Hz), 7.56(1H, t, J=7.8Hz), 7.68(1H, d, J=7.8Hz), 8.38(1H, dd, J=7.8, 1.2Hz), 8.43(1H, s); IR(CHCl$_3$) 3450, 3103, 3022, 2954, 2875, 1732, 1651, 1518, 1456, 1373, 1221, 1188, 1163, 1057cm$^{-1}$; [α]$_D^{22.0}$+39.9±0.8°(c=1.006, MeOH) Anal. (C$_{26}$H$_{30}$N$_2$O$_6$S$_2$·0.1H$_2$O) Calcd.(%): C, 58.65; H, 5.72; N, 5.26; S, 12.04 Found(%): C, 58.40; H, 5.82; N, 5.08; S, 11.88 |
| I-7M-389a | mp 94–96° C.; $^1$H-NMR(CDCl$_3$) δ 0.99(1H, m), 1.21–1.27 (2H, m), 1.38–1.46(6H, m), 1.55–1.68(4H, m), 1.99(1H, m), 2.23(3H, s), 2.46(1H, m), 3.21(2H, t, J=8.7Hz), 3.46–3.57(2H, m), 3.83(1H, m), 4.05(2H, s), 4.62(2H, t, J=8.7Hz), 5.95(1H, d, J=7.8Hz), 6.90(1H, s), 6.96 (1H, s), 7.07(1H, d, J=3.9Hz), 7.37(1H, d, J=3.9Hz); IR(Nujol) 3327, 3074, 2750, 2650, 2613, 2551, 1728, 1604, 1562, 1234, 1223, 1136cm$^{-1}$; [α]$_D^{23}$+35.5±0.7° (c=1.014, MeOH) Anal.(C$_{27}$H$_{33}$NO$_5$S$_2$) Calcd.(%): C, 62.88; H, 6.45; N, 2.72; S, 12.44 Found(%): C, 62.96; H, 6.46; N, 2.68; S, 12.33 |
| I-7M-390a | mp 99–101° C.; $^1$H-NMR(CDCl$_3$) δ 0.99(1H, m), 1.20–1.27(2H, m), 1.37–1.45(6H, m), 1.54–1.63(4H, m), 1.98 (1H, m), 2.39(3H, s), 2.46(1H, m), 3.46–3.56(2H, m), 3.83 (1H, m), 4.04(2H, s), 5.95(1H, d, J=7.8Hz), 6.72(1H, d, J=2.1Hz), 7.09(1H, m), 7.18(1H, d, J=3.9Hz), 7.33 (1H, m), 7.39(1H, d, J=3.9Hz), 7.63(1H, d, J=2.1Hz); IR(CHCl$_3$) 3508, 3444, 3425, 2667, 2567, 1780, 1732, 1645, 1531, 1500, 1421, 1321, 1130cm$^{-1}$; [α]$_D^{24}$+36.1±0.8°(c=1.008, MeOH) Anal. (C$_{27}$H$_{31}$NO$_5$S$_2$·0.2H$_2$O) Calcd.(%): C, 62.69; H, 6.12; N, 2.71; S, 12.40 Found(%): C, 62.54; H, 5.98; N, 2.68; S, 12.55 |

TABLE 39

| Compd. No. | Physical property |
| --- | --- |
| I-7M-391a | $^1$H-NMR(CDCl$_3$) δ 1.06(1H, m), 1.24–1.29(2H, m), 1.38–1.47 (6H, m), 1.55–1.59(4H, m), 2.00(1H, m), 2.32(3H, s), 2.48(1H, m), 3.19(2H, t, J=8.7Hz), 3.52(2H, t, J=6.3Hz), 3.83(1H, m), 4.05(2H, s), 4.72(2H, t, J=8.7Hz), 6.26(1H, d, J=7.8Hz), 7.22(1H, s), 7.43(1H, d, J=3.9Hz), 7.50(1H, s), 7.70(1H, d, J=3.9Hz); IR(CHCl$_3$) 3508, 3440, 3423, 3377, 2567, 2463, 1778, 1732, 1653, 1529, 1504, 1481, 1327, 1151cm$^{-1}$; [α]$_D^{25}$+40.6±0.8°(c=1.004, MeOH) Anal. (C$_{27}$H$_{33}$NO$_7$S$_2$.0.5H$_2$O) Calcd.(%): C, 58.25; H, 6.16; N, 2.52; S, 11.52 Found(%): C, 58.18; H, 6.07; N, 2.45; S, 11.55 |
| I-7M-392a | mp 136–140° C.; $^1$H-NMR(CDCl$_3$+CD$_3$OD) δ 1.09(1H, m), 1.22–1.29(2H, m), 1.33–1.43(5H, m), 1.52–1.58(4H, m), 1.96 (1H, m), 2.48–2.51(2H, m)+2.51(3H, s), 3.42–3.53(2H, m), 3.75(1H, m), 4.01(2H, s), 6.68(1H, d, J=7.2Hz), 6.78(1H, d, J=2.1Hz), 7.48(1H, d, J=3.9Hz), 7.64(1H, s), 7.74(1H, d, J=2.1Hz), 7.76(1H, s), 7.82(1H, d, J=3.9Hz); IR (Nujol) 3280, 3141, 3114, 3084, 2750, 2650, 2548, 1732, 1618, 1566, 1460, 1323, 1223, 1153, 1126cm$^{-1}$; [α]$_D^{25}$+ 40.5±0.8°(c=1.004, MeOH) Anal.(C$_{27}$H$_{31}$NO$_7$S$_2$.0.2H$_2$O) Calcd.(%): C, 59.04; H, 5.76; N, 2.55; S, 11.68 Found(%): C, 59.01; H, 5.77; N, 2.51; S, 11.50 |
| I-7M-393a | mp 104–107° C.; $^1$H-NMR(CDCl$_3$) δ 0.90(3H, t, J=7.4Hz), 0.98(3H, m), 1.21–1.64(16H, m), 1.99(1H, m), 2.46–2.51(3H, m), 3.23(2H, t, J=8.7Hz), 3.49–3.55(2H, m), 3.84(1H, m), 4.05(2H, s), 4.62(2H, t, J=8.7Hz), 5.92(1H, d, J=7.8Hz), 6.93(1H, s), 6.98(1H, s), 7.07(1H, d, J=3.6Hz), 7.36(1H, d, J=3.6Hz); IR(CHCl$_3$) 3444, 3425, 2569, 1780, 1732, 1643, 1531, 1498, 1479, 1464, 1419, 1317, 1132cm$^{-1}$; [α]$_D^{24}$+ 33.3±0.7°(c=1.009, MeOH) Anal.(C$_{30}$H$_{39}$NO$_5$S$_2$.0.2H$_2$O) Calcd.(%): C, 64.19; H, 7.07; N, 2.50; S, 11.42 Found(%): C, 64.09; H, 6.95; N, 2.55; S, 11.36 |
| I-7M-396a | $^1$H-NMR(CDCl$_3$) δ 1.06(1H, m), 1.26–1.69(12H, m), 2.03 (1H, m), 2.56(1H, m), 3.55(2H, t, J=5.1Hz), 4.00(1H, m), 4.04(2H, s), 6.11(1H, d, J=8.1Hz), 6.88(1H, d, J=7.5Hz), 7.07–7.19(3H, m), 7.34–7.42(3H, m), 7.89(1H, s), 8.03(1H, d, J=8.1Hz); IR(KBr) 3383, 3076, 2949, 2929, 2868, 2520, 1736, 1604, 1550, 1487, 1466, 1390, 1298, 1281, 1248, 1213, 1134cm$^{-1}$; [α]$_D^{25.0}$+35.4±3.0°(c=0.26, MeOH) Anal. (C$_{28}$H$_{31}$NO$_5$S.0.5H$_2$O) Calcd.(%): C, 66.91; H, 6.42; N, 2.79; S, 6.38 Found(%): C, 66.98; H, 6.35; N, 2.85; S, 6.29 |
| I-7M-412a | $^1$H-NMR(CDCl$_3$) δ 1.05(1H, m), 1.22–1.70(12H, m), 2.01 (1H, m), 2.01(1H, d, J=3.3Hz), 2.50(1H, brs), 3.53(2H, t, J=6.3Hz), 3.92(1H, m), 4.05(2H, s), 6.11(1H, d, J=7.8Hz), 7.27–7.62 (6H, m), 7.79(1H, d, J=1.8Hz); IR(CHCl$_3$) 3444, 2954, 1780, 1732, 1649, 1547, 1514, 1491, 1219, 1213, 1128cm$^{-1}$; [α]$_D^{24}$+49.9±0.9°(c=1.008%, MeOH); Anal. (C$_{24}$H$_{29}$NO$_4$S.0.3H$_2$O) Calcd.(%) C, 66.58; H, 6.89; N, 3.24; S, 7.41 Found(%) C, 66.73; H, 6.90; N, 3.35 S, 7.29 |

TABLE 40

| Compd. No. | Physical property |
| --- | --- |
| I-7M-424a | $^1$H-NMR(CDCl$_3$) δ 1.00(1H, m), 1.22–1.64(12H, m), 1.98 (1H, m), 2.55(1H, m), 3.48(2H, t, J=6.9Hz), 3.94(1H, m), 3.99(2H, s), 4.15(2H, s), 6.13(1H, d, J=8.1Hz), 6.84(1H, d, J=2.1Hz), 7.20–7.30(5H, m), 7.74(1H, s), 7.79(1H, d, J=2.1Hz); IR(KBr) 3433, 3246, 3024, 2954, 2875, 1730, 1639, 1599, 1518, 1495, 1475, 1454, 1421, 1352cm$^{-1}$; [α]$_D^{26.0}$+34.0±0.7°(c=1.00, MeOH) Anal.(C$_{29}$H$_{33}$NO$_5$S.0.6H$_2$O) Calcd.(%): C, 67.18; H, 6.65; N, 2.70; S, 6.18 Found(%): C, 67.21; H, 6.66; N, 2.71; S, 5.99 |
| I-7M-446a | $^1$H-NMR(CDCl$_3$) δ 1.00(1H, m), 1.22–1.64(12H, m), 1.98(1H, m), 2.55(1H, m), 3.47(2H, t, J=6.3Hz), 3.96 (1H, m), 3.98(2H, s), 4.17(2H, s), 6.16(1H, d, J=8.1Hz), 6.82(1H, d, J=2.4Hz), 6.99–7.22(4H, m), 7.76(1H, s), 7.82(1H, d, J=2.4Hz); IR(CHCl$_3$) 3593, 3433, 3244, 2954, 2875, 1728, 1639, 1599, 1518, 1491, 1456, 1421, 1362cm$^{-1}$; [α]$_D^{22.0}$+31.2±0.7°(c=1.01, MeOH) Anal. (C$_{29}$H$_{32}$FNO$_5$S.0.9H$_2$O) Calcd.(%): C, 64.28; H, 6.29; N, 2.58; F, 3.51; S, 5.92 Found(%): C, 64.39; H, 6.29; N, 2.52; F, 3.40; S, 5.72 |
| I-7M-447a | $^1$H-NMR(CDCl$_3$) δ 1.04(1H, m), 1.22–1.69(12H, m), 2.03 (1H, m), 2.55(1H, m), 3.55(2H, t, J=6.6Hz), 3.96(1H, m), 4.04(2H, s), 6.08(1H, d, J=7.8Hz), 7.16(1H, dd, J= 8.7 and 2.7Hz), 7.25–7.35(5H, m), 7.88(1H, s), 8.03 (1H, dd, J=9.6 and 2.7Hz); IR(CHCl$_3$) 3510, 3438, 2954, 2875, 1780, 1732, 1655, 1591, 1558, 1514, 1477, 1441, 1383cm$^{-1}$; [α]$_D^{24.0}$+38.1±0.8°(c=1.01, MeOH) Anal.(C$_{28}$H$_{30}$FNO$_4$S$_2$.0.9H$_2$O) Calcd.(%): C, 61.83; H, 5.89; N, 2.58; F, 3.49; S, 11.79 Found(%): C, 61.91; H, 5.73; N, 2.65; F, 3.56; S, 11.67 |
| I-7M-448a | $^1$H-NMR(CDCl$_3$) δ 1.05(1H, m), 1.22–1.63(12H, m), 2.00 (1H, m), 2.53(1H, m), 3.54(2H, t, J=6.3Hz), 3.90(1H, m), 4.04 (2H, s), 6.19(1H, d, J=7.8Hz), 7.47–7.83(3H, m), 7.85 (1H, dd, J=7.8 and 2.4Hz), 8.00–8.05(3H, m), 8.38(1H, dd, J=9.3 and 2.4Hz); IR(CHCl$_3$) 3437, 3386, 2954, 2875, 1780, 1730, 1655, 1601, 1518, 1477, 1446, 1396, 1325, 1309cm$^{-1}$; [α]$_D^{24.0}$+31.5±0.7°(c=1.01, MeOH) Anal.(C$_{28}$H$_{30}$FN$_6$S$_2$.0.9H$_2$O) Calcd.(%): C, 58.40; H, 5.57; N, 2.43; F, 3.30; S, 11.14 Found(%): C, 58.43; H, 5.54; N, 2.38; F, 3.16; S, 10.78 |

TABLE 40-continued

| Compd. No.. | Physical property |
|---|---|
| I-7N-1a | $^1$H-NMR(CDCl$_3$) δ 1.10–1.70(7H, m), 2.00–2.32(3H, m), 2.51(1H, m), 3.83(1H, m), 4.07–4.21(4H, m), 5.54–5.70 (2H, m), 6.26(1H, d, J=7.5Hz), 6.32–6.35(2H, m), 7.15–7.18(2H, m), 7.38(1H, d, J=4.2Hz), 7.57(1H, d, J= 4.2Hz); IR(CHCl$_3$) 3440, 1732, 1655, 1531, 1506, 1456, 1383, 1192, 1167, 1057, 1034cm$^{-1}$; [α]$_D^{24}$+67.3±1.1°(c=1.005, MeOH) Anal. (C$_{22}$H$_{26}$N$_2$O$_6$S$_2$.0.3H$_2$O) Calcd.(%): C, 54.60; H, 5.54; N, 5.79; S, 13.25 Found(%): C, 54.58; H, 5.50; N, 5.65; S, 13.15 |

TABLE 41

| No. fo Compd. | Physical property |
|---|---|
| I-7N-1b | $^1$H-NMR(CDCl$_3$) δ 1.16–1.70(7H, m), 2.04(1H, m), 2.12–2.18(2H, m), 2.56(1H, brs), 3.72(3H, s), 3.78(1H, m), 4.05–4.16(4H, m), 5.57–5.76(2H, m), 6.32–6.34(2H, m), 6.39(1H, d, J=6.6Hz), 7.15–7.17(2H, m), 7.40(1H, d, J= 3.9Hz), 7.56(1H, d, J=3.9Hz) |
| I-7P-1a | $^1$H-NMR(CD$_3$OD) δ 1.28–1.64(8H, m), 2.02–2.13(3H, m), 2.47(1H, m), 3.71(1H, m), 3.98(2H, s), 4.25(2H, d, J= 22.2Hz), 5.30(1H, dt, J=8.4 and 22.2Hz), 6.36(2H, m), 7.23(2H, m), 7.70(1H, d, J=3.9Hz), 7.75(1H, d, J=3.9Hz); IR(CHCl$_3$) 3419, 2956, 1635, 1604, 1537, 1508, 1456, 1431, 1381, 1167, 1076, 1057, 1036cm$^{-1}$; [α]$_D^{25}$+45.7±0.8° (c=1.02, MeOH) |
| I-7P-1e | $^1$H-NMR(CDCl$_3$) δ 1.10–1.72(7H, m), 2.06–2.26(3H, m), 2.51(1H, m), 3.29(3H, s), 3.84(1H, m), 4.01–4.31(4H, m), 5.36(1H, dt, J=9.0 and 20.7Hz), 6.15(1H, d, J=6.6Hz), 6.34(2H, m), 7.16(2H, m), 7.38(1H, d, J=4.2Hz), 7.58 (1H, d, J=4.2Hz), 9.26(1H, s); IR(CHCl$_3$) 3442, 3352, 2956, 2829, 1728, 1655, 1531, 1506, 1456, 1452, 1402, 1383, 1348, 1167, 1109, 1057, 1034cm$^{-1}$; [α]$_D^{25}$+51.8±0.9° (c=1.03, MeOH) Anal.(C$_{23}$H$_{28}$FN$_3$O$_7$S$_3$.0.5MeOH) Calcd.(%): C, 47.86; H, 5.13; N, 7.13; F, 3.22; S, 16.31 Found(%): C, 48.09; H, 5.02; N, 7.38; F, 3.12; S, 16.12 |
| I-7R-1a | $^1$H-NMR(CDCl$_3$) δ 1.02(1H, m), 1.23–1.72(12H, m), 2.02 (1H, d, J=3.9Hz), 2.48(1H, brs), 2.63(2H, t, J=7.2Hz), 3.21(2H, s), 3.83(1H, m), 6.17(1H, d, J=7.5Hz), 6.32–6.35 (2H, m), 7.15–7.17(2H, m), 7.37(1H, d, J=3.9Hz), 7.57(1H, d, J=3.9Hz); IR(Nujol) 3348, 2924, 1711, 1641, 1622, 1550, 1541, 1456, 1375, 1290, 1190, 1167, 1057cm$^{-1}$; [α]$_D^{25}$+42.8±0.8°(c=1.005%, MeOH); Anal. (C$_{22}$H$_{28}$N$_2$O$_5$S$_3$) Calcd.(%) C, 53.20; H, 5.68; N, 5.64; S, 19.37 Found(%) C, 53.41; H, 5.58; N, 5.54; S, 19.08 |
| I-7R-88a | $^1$H-NMR(CDCl$_3$) δ 0.99(1H, m), 1.21–1.72(12H, m), 1.98 (1H, d, J=3.9Hz), 2.47(1H, brs), 2.64(2H, t, J=7.2Hz), 3.20(2H, s), 3.87(1H, m), 4.16(2H, s), 5.96(1H, d, J=7.5Hz), 6.79(1H, d, J=3.6Hz), 6.96(1H, d, J=4.8Hz), 7.06 (1H, d, J=2.1Hz), 7.26–7.30(2H, m), 7.37(1H, d, J=3.9Hz); IR(CHCl$_3$) 2877, 1711, 1641, 1545, 1508, 1458, 1298, 1282, 1225, 1205cm$^{-1}$; [α]$_D^{25+42.8±0.8°(c=1.005\%,}$ MeOH); Anal.(C$_{23}$H$_{29}$NO$_3$S$_3$.0.2H$_2$O) Calcd.(%) C, 59.12; H, 6.34; N, 3.00; S, 20.59 Found(%) C, 59.18; H, 6.01; N, 3.04; S, 20.28 |
| I-7R-270a | $^1$H-NMR(CDCl$_3$) δ 1.03(1H, br), 1.18–1.70(12H, m), 2.01 (1H, brd), 2.41(6H, s), 2.46(1H, brs), 2.62(2H, t, J=7.2Hz), 3.21(2H, s), 3.82(1H, m), 5.88(2H, s), 6.23(1H, d, J= 7.2Hz), 7.36(1H, d, J=3.9Hz), 7.49(1H, d, J=3.9Hz); IR(CHCl$_3$) 3508, 3442, 2673, 1709, 1657, 1531, 1504, 1375, 1180, 1119cm$^{-1}$; [α]$_D^{26}$+39.2±0.8°(c=1.010, MeOH) Anal. (C$_{24}$H$_{32}$N$_2$O$_5$S$_3$.0.3H$_2$O) Calcd.(%): C, 54.94; H, 6.15; N, 5.34; S, 18.33 Found(%): C, 54.44; H, 6.04; N, 5.28; S, 18.08 |

TABLE 42

| Compd. No.. | Physical property |
| --- | --- |
| I-7R-307a | $^1$H-NMR(CDCl$_3$) δ 0.93(1H, m), 1.17–1.22(2H, m), 1.34–1.41(6H, m), 1.52–1.58(4H, m), 1.94(1H, m), 2.43(1H, m), 2.59 (2H, t, J=7.2Hz), 3.16(2H, s), 3.79(1H, m), 3.97(3H, s), 4.59(2H, s), 5.90(1H, d, J=7.8Hz), 6.74(1H, d, J=3.9Hz), 7.29(1H, d, J=3.9Hz), 7.29–7.36(2H, m,), 7.46(1H, m), 7.78–7.83(2H, m), 7.92(1H, d, J=8.4Hz); IR(CHCl$_3$) 3446, 3425, 3062, 2877, 2673, 1711, 1639, 1597, 1542, 1512, 1265, 1254cm$^{-1}$; [α]$_D^{25.5}$+35.8±0.8°(c=1.007, MeOH) Anal. (C$_{30}$H$_{35}$NO$_4$S$_2$.0.2H$_2$O) Calcd.(%): C, 66.56; H, 6.59; N, 2.59; S, 11.85 Found(%): C, 66.53; H, 6.70; N, 2.65; S, 11.78 |
| I-8B-1a | $^1$H-NMR(CDCl$_3$) δ 1.06(1H, m), 1.19–1.30(2H, m), 1.34–1.44 (4H, m), 1.54–1.68(4H, m), 2.04–2.12(5H, m), 2.35(2H, t, J= 7.5Hz), 2.51(1H, brs), 3.82(1H, m), 5.29–5.42(2H, m), 6.21 (1H, d, J=6.9Hz), 6.32–6.34(2H, m), 7.15–7.17(2H, m), 7.35 and 7.56(each 1H, each d, each J=3.9Hz); IR(CHCl$_3$) 3512, 3442, 2679, 1707, 1657, 1529, 1504, 1456, 1383, 1192, 1167, 1057, 1034cm$^{-1}$; [α]$_D^{24}$+69.7±1.1°(c=1.004, MeOH) Anal. (C$_{24}$H$_{30}$N$_2$O$_5$S$_2$.0.2H$_2$O) Calcd.(%): C, 58.32; H, 6.20; N, 5.67; S, 12.98 Found(%): C, 58.30; H, 6.07; N, 5.67; S, 12.84 |
| I-8C-1a | $^1$H-NMR(CDCl$_3$) δ 1.01(1H, m), 1.25–1.45(10H, m), 1.53–1.66 (4H, m), 2.00(1H, m), 2.48(1H, m), 3.52(2H, t, J=7.1Hz), 3.80(1H, m), 4.08(2H, s), 6.22(1H, d, J=7.5Hz), 6.33–6.34(2H, m), 7.15–7.17(2H, m), 7.38(1H, d, J=3.9Hz), 7.57(1H, d, J=3.9Hz); IR(CHCl$_3$) 3440, 3145, 2578, 1780, 1730, 1657, 1529, 1383, 1192, 1167, 1057cm$^{-1}$; [α]$_D^{25.0}$+ 45.0±0.8°(c=1.010, MeOH) Anal.(C$_{23}$H$_{30}$N$_2$O$_6$S$_2$.0.4H$_2$O) Calcd.(%): C, 55.05; H, 6.19; N, 5.58; S, 12.78 Found(%): C, 55.09; H, 6.08; N, 5.61; S, 12.74 |
| I-8C-88a | $^1$H-NMR(CDCl$_3$) δ 0.97(1H, m), 1.23–1.47(10H, m), 1.55–1.61 (4H, m), 1.97(1H, m), 2.48(1H, m), 3.52(2H, t, J=6.6Hz), 3.83(1H, m), 4.06(2H, s), 4.16(2H, s), 5.93(1H, d, J= 7.8Hz), 6.79(1H, dt, J=3.9, 0.9Hz), 6.96(1H, dd, J=5.1, 1.2Hz), 7.06(1H, m), 7.29(1H, dd, J=5.1, 3.0Hz), 7.37(1H, d, J= 3.9Hz); IR(CHCl$_3$) 3444, 3427, 3107, 3022, 2954, 2875, 1780, 1732, 1643, 1545, 1506, 1221, 1211, 1128cm$^{-1}$; [α]$_D^{25.0}$+ 39.6±0.8°(c=1.016, MeOH) Anal.(C$_{24}$H$_{31}$NO$_4$S$_2$.0.3H$_2$O) Calcd.(%): C, 61.72; H, 6.82; N, 3.00; S, 13.73 Found(%): C, 61.79; H, 6.69; N, 3.11; S, 13.59 |
| I-9B-1a | $^1$H-NMR(CDCl$_3$) δ 1.06(1H, m), 1.22–1.45(8H, m), 1.59–1.67 (4H, m), 2.03–2.13(5H, m), 2.33(2H, t, J=7.5Hz), 2.52(1H, brs), 3.82(1H, m), 5.26–5.42(2H, m), 6.18(1H, d, J=7.2Hz), 6.33–6.34(2H, m), 7.15–7.17(2H, m), 7.36 and 7.57(each 1H, each d, each J=3.9Hz); IR(CHCl$_3$) 3514, 3442, 2677, 1709, 1657, 1529, 1504, 1456, 1383, 1192, 1167, 1057, 1034cm$^{-1}$; [α]$_D^{24.5}$+72.2±1.1°(c=1.006, MeOH) Anal.(C$_{25}$H$_{32}$N$_2$O$_5$S$_2$) Calcd.(%): C, 59.50; H, 6.39; N, 5.55; S, 12.71 Found(%): C, 59.24; H, 6.48; N, 5.60; S, 12.46 |

TABLE 43

| Compd. No.. | Physical property |
| --- | --- |
| II-4A-55a | $^1$H-NMR(CDCl$_3$) δ 0.90(1H, d, J=10.2Hz), 1.09 and 1.22(3H, s), 1.40–2.40(12H, m), 2.38(3H, s), 4.17(1H, m), 4.56(1H, brs), 5.98(1H, m), 6.19(1H, t, J=3.0Hz), 6.24(1H, d, J=8.7Hz), 7.17(1H, dd, J=1.5, 3.3Hz), 7.31(1H, d, J=3.9Hz), 7.51(1H, d, J=3.9Hz); IR (CHCl$_3$) 3446, 1709, 1657, 1529, 1504, 1375, 1182, 1161, 1144, 1053cm$^{-1}$; [α]$_D^{23}$+28.9±0.7°(c=1.011, MeOH) Anal.(C$_{23}$H$_{30}$N$_2$O$_5$S$_2$.0.4H$_2$O) Calcd.(%): C, 56.86 H, 6.39; N, 5.77; S, 13.20 Found(%): C, 57.24; H, 6.36; N, 5.73; S, 12.72. |
| II-4B-55a | $^1$H-NMR(CDCl$_3$) δ 0.90(1H, d, J=10.5Hz), 1.10(3H, s), 1.23(3H, s), 1.43–2.35(10H, m), 2.38(3H, s), 4.20(1H, m), 4.96(1H, dt, J=11.4 and 49.2Hz), 5.98(1H, m), 6.19–6.21(2H, m), 7.17(1H, m), 7.29(1H, d, J=3.9Hz), 7.51(1H, d, J=3.9Hz); IR(CHCl$_3$) 3446, 2925, 2870, 1730, 1657, 1529, 1504, 1471, 1375, 1159, 1144, 1053, 1022cm$^{-1}$; [α]$_D^{24}$+24.6±0.6°(c=1.04, MeOH) Anal. (C$_{23}$H$_{29}$FN$_2$O$_5$S$_2$.0.6MeOH) Calcd.(%): C, 54.95; H, 6.14; N, 5.43; F, 3.68; S, 12.43 Found(%): C, 54.94; H, 5.97; N, 5.65; F, 3.55; S, 12.24 |
| II-4C-55a | $^1$H-NMR(CDCl$_3$) δ 0.92(1H, d, J=10.5Hz), 1.10 and 1.24(3H, s), 1.56(1H, ddd, J=2.7, 5.7, 12.0Hz), 1.96–2.70 (8H, m), 2.37(3H, s), 4.25(1H, m), 5.88(1H, brd, J= 15.9Hz), 5.99(1H, m), 6.17–6.21(2H, m), 7.03(1H, dt, J=7.2, 15.9Hz), 7.17(1H, dd, J=1.5, 3.3Hz), 7.27(1H, d, J=3.9Hz), 7.47(1H, d, J=3.9Hz); IR(CHCl$_3$) 3446, 1697, 1655, 1529, 1504, 1375, 1182, 1161, 1144, 1053cm$^{-1}$; [α]$_D^{23}$+5.4±0.5°(c=1.002, MeOH) Anal. (C$_{23}$H$_{28}$N$_2$O$_5$S$_2$.0.4H$_2$O) Calcd.(%):C, 57.10; H, 6.00; N, 5.79; S, 13.26 Found(%): C, 57.14; H, 5.89; N, 5.78; S, 13.01. |
| II-4D-55a | $^1$H-NMR(CDCl$_3$) δ 0.97(1H, d, J=10.5Hz), 1.09 and 1.23(3H, s), 1.60(1H, ddd, J=2.7, 5.7, 10.8Hz), 1.96–2.40 (6H, m), 2.39(3H, s), 2.72–3.01(2H, m), 4.25(1H, m), 5.85(1H, brd, J=11.7Hz), 5.98(1H, m), 6.17–6.21 (2H, m), 6.40(1H, dt, J=7.8, 11.7Hz), 7.18(1H, dd, J= |

TABLE 43-continued

| Compd. No.. | Physical property |
|---|---|
| | 1.8, 3.3Hz), 7.32(1H, d, J=4.2Hz), 7.54(1H, d, J=4.2Hz); IR(CHCl$_3$) 3519, 3446, 1697, 1658, 1529, 1504, 1375, 1182, 1161, 1144, 1053cm$^{-1}$; $[\alpha]_D^{23}$+63.6±1.0° (c=1.006, MeOH) Anal.(C$_{23}$H$_{328}$N$_2$O$_5$S$_2$.0.3H$_2$O) Calcd.(%): C, 57.31; H, 5.98; N, 5.81; S, 13.30 Found(%): C, 57.48; H, 5.93; N, 5.75; S, 12.90 |

TABLE 44

| Compd. No.. | Physical property |
|---|---|
| II-4F-55a | $^1$H-NMR(CDCl$_3$) δ 0.94(1H, d, J=10.5Hz), 1.09(3H, s), 1.24(3H, s), 1.59(1H, m), 2.03–2.34(5H, m), 2.39(3H, s), 2.62(1H, m), 2.92(1H, m), 4.26(1H, m), 5.99(1H, m), 6.06(1H, dt, J=8.4 and 21.0Hz), 6.20(1H, m), 7.18 (1H, m), 7.28(1H, m), 7.33(1H, d, J=3.9Hz), 7.53(1H, d, J=3.9Hz); IR(CHCl$_3$) 33446, 2925, 2870, 1711, 1658, 1529, 1504, 1442, 1375, 1161, 1070, 1053, 1018cm$^{-1}$; $[\alpha]_D^{25}$+52.9±0.9°(c=1.02, MeOH) Anal. (C$_{23}$H$_{27}$FN$_2$O$_5$S$_2$.0.8MeOH) Calcd.(%): C, 54.95; H, 5.85; N, 5.38; F, 3.65; S, 12.33 Found(%): C, 54.72; H, 5.61; N, 5.67; F, 3.43; S, 12.16 |
| II-5A-1a | $^1$H-NMR(CDCl$^3$) δ 0.91(1H, d, J=10.5Hz), 1.08(3H, s), 1.22(3H, s), 1.33–2.38(14H, m), 4.18(2H, s), 6.08(1H, d, J=9.0Hz), 6.34(2H, t, J=2.4Hz), 7.16(2H, t, J=2.4Hz), 7.28(1H, d, J=3.9Hz), 7.57(1H, d, J=3.9Hz); IR (CHCl$_3$) 3512, 3446, 1709, 1657, 1504, 1456, 1385, 1192, 1167, 1057, 1034cm$^{-1}$; $[\alpha]_D^{25.0}$+26.2±0.7°(c=1.008, MeOH) Anal.(C$_{23}$H$_{30}$N$_2$O$_5$S$_2$.0.6H$_2$O.0.3AcOEt) Calcd.(%): C, 56.33; H, 6.65; N, 5.45; S, 12.40 Found(%): C, 56.31; H, 6.35; N, 5.64; S, 12.08 |
| II-5A-31a | $^1$H-NMR(CDCl$_3$) δ 0.90(1H, d, J=10.2Hz), 1.08(3H, s), 1.20(3H, s), 1.30–2.38(14H, m), 4.13(2H, s), 4.18(1H, m), 5.93(1H, d, J=10.2Hz), 6.77(1H, d, J=3.6Hz), 7.20–7.38(6H, m); IR(CHCl$_3$) 3512, 3450, 3431, 1709, 1643, 1543, 1506, 1456cm$^{-1}$; $[\alpha]_D^{24.0}$+20.4±0.6° (c=1.011, MeOH) Anal.(C$_{26}$H$_{33}$NO$_3$S.0.6H$_2$O) Calcd.(%): C, 71.04; H, 7.57; N, 3.19; S, 7.29 Found(%): C, 69.33; H, 7.65; N, 3.31; S, 7.11 |
| II-5A-47a | $^1$H-NMR(CDCl$_3$) δ 0.91(1H, d, J=10.8Hz), 1.08(3H, s), 1.21(3H, s), 1.30–2.38(14H, m), 4.19(1H, m), 6.08(1H, d, J=9.3Hz), 7.11(1H, dd, J=5.1, 3.9Hz), 7.32(1H, d, J=3.9Hz), 7.64(1H, d, J=3.9Hz), 7.69(1H, dd, J= 5.1, 1.2Hz), 7.75(1H, dd, J=3.6, 1.2Hz); IR(CHCl$_3$) 3516, 3446, 2679, 1709, 1655, 1529, 1504, 1402, 1336, 1153, 1095, 1074, 1024cm$^{-1}$; $[\alpha]_D^{24.0}$+23.5±0.6° (c=1.004, MeOH) Anal.(C$_{23}$H$_{29}$NO$_5$S$_3$.0.5H$_2$O) Calcd.(%): C, 54.74; H, 5.99; N, 2.78; S, 19.06 Found(%): C, 54.90; H, 5.76; N, 2.85; S, 18.81 |
| II-5A-55a | $^1$H-NMR(CDCl$_3$) δ 0.91(1H, d, J=10.2Hz), 1.09 and 1.22(3H, s), 1.22–2.30(12H, m), 2.33(2H, t, J=7.5Hz), 2.39(3H, s), 4.19(1H, m), 5.99(1H, m), 6.09(1H, d, J= 8.7Hz), 6.20(1H, t, J=3.3Hz), 7.19(1H, dd, J=1.8, 6.3Hz), 7.29(1H, d, J=3.9Hz), 7.55(1H, d, J=3.9Hz); IR (CHCl$_3$) 3446, 1709, 1657, 1529, 1504, 1375, 1205, 1182, 1161, 1053cm$^{-1}$; $[\alpha]_D^{24}$+25.3±0.7°(c=1.002, MeOH) Anal.(C$_{24}$H$_{32}$N$_2$O$_5$S$_2$) Calcd.(%): C, 58.51; H, 6.55; N, 5.69; S, 13.02 Found(%): C, 58.21; H, 6.53; N, 5.69; S, 12.93 |

TABLE 45

| Compd. No.. | Physical property |
|---|---|
| II-5A-55c | $^1$H-NMR(CDCl$_3$) δ 0.89(1H, d, J=10.5Hz), 1.08(3H, s), 1.22(3H, s), 1.36–2.36(14H, m), 2.39(3H, s), 4.16(1H, m), 5.24(1H, brs), 5.50(1H, brs), 5.99(1H, m), 6.20(1H, t, J=3.3Hz), 7.19(1H, dd, J=4.2Hz), 7.32(1H, d, J= 4.2Hz), 7.56(1H, d, J=4.2Hz); IR(CHCl$_3$) 3529, 3446, 3411, 3348, 1678, 1591, 1529, 1504, 1375, 1182, 1161, 1144, 1053cm$^{-1}$; $[\alpha]_D^{26.0}$+23.0±0.6°(c=1.016, MeOH) Anal.(C$_{24}$H$_{33}$N$_3$O$_4$S$_2$.0.4H$_2$O) Calcd.(%): C, |

TABLE 45-continued

| Compd. No.. | Physical property |
|---|---|
| | 57.78; H, 6.83; N, 8.42; S, 12.86 Found(%): C, 57.79; H, 6.81; N, 8.37; S, 12.68 |
| II-5A-55g | $^1$H-NMR(CDCl$_3$) δ 0.89(1H, d, J=10.5Hz), 1.12(3H, s), 1.25(3H, s), 1.33–2.35(12H, m), 2.39(3H, s), 2.95–3.11 (2H, m), 4.19(1H, m), 6.00(1H, m), 6.21(1H, t, J=3.3Hz), 6.45(1H, d, J=8.7Hz), 7.18(1H, dd, J=3.3, 1.5Hz), 7.38(1H, d, J=3.9Hz), 7.54(1H, d, J=3.9Hz); IR (CHCl$_3$) 3149, 2624, 1641, 1533, 1508, 1375, 1205, 1182, 1160cm$^{-1}$; $[\alpha]_D^{25.0}$+17.9±0.6°(c=1.018, MeOH) Anal. (C$_{24}$H$_{32}$N$_6$O$_3$S$_2$.0.4CHCl$_3$) Calcd.(%): C, 51.62; H, 5.79; N, 14.89; S, 11.36 Found(%): C, 51.53; H, 5.99; N, 14.82; S, 11.09 |
| II-5A-59a | $^1$H-NMR(CDCl$_3$) δ 0.90(1H, d, J=10.2Hz), 1.07(3H, s), 1.21(3H, s), 1.28–2.36(14H, m), 4.17(1H, m), 5.91(1H, d, J=8.4Hz), 7.00(1H, dd, J=5.4, 3.6Hz), 7.05(1H, d, J=3.9Hz), 7.25(1H, d, J=3.9Hz), 7.28(1H, dd, J= 3.6, 1.2Hz), 7.42(1H, dd, J=5.4, 1.2Hz); IR(CHCl$_3$) 3516, 3450, 3431, 2671, 1709, 1645, 1529, 1500, 1471, 1421cm$^{-1}$; $[\alpha]_D^{25.0}$+23.3±0.6°(c=1.013, MeOH) Anal. (C$_{23}$H$_{29}$NO$_3$S$_3$.0.2H$_2$O) Calcd.(%): C, 59.12; H, 6.34; N, 3.00; S, 20.58 Found(%): C, 59.12; H, 6.30; N, 3.07; S, 20.84 |
| II-5A-88a | $^1$H-NMR(CDCl$_3$) δ 0.91(1H, d, J=10.2Hz), 1.09(3H, s), 1.21(3H, s), 1.18–2.33(14H, m), 4.15(2H, s), 4.19(1H, m), 5.94(1H, d, J=9.6Hz), 6.79(1H, d, J=3.6Hz), 6.96(1H, dd, J=5.1, 1.2Hz), 7.05(1H, dd, J=1.8, 1.2Hz), 7.28(1H, dd, J=5.1, 1.8Hz), 7.30(1H, d, J=3.6Hz); IR(CHCl$_3$) 3516, 3450, 3431, 1709, 1641, 1545, 1506, 1471cm$^{-1}$; $[\alpha]_D^{24.0}$+19.6±0.6°(c=1.009, MeOH) Anal.(C$_{24}$H$_{31}$NO$_3$S$_2$.0.3H$_2$O) Calcd.(%): C, 63.91; H, 7.06; N, 3.11; S, 14.22 Found(%): C, 63.89; H, 6.89; N, 3.31; S, 14.28 |
| II-5A-104a | $^1$H-NMR(CDCl$_3$) δ 0.92(1H, d, J=10.2Hz), 1.10(3H, s), 1.22(3H, s), 1.28–2.38(14H, m), 4.10(2H, s), 4.20(1H, m), 5.97(1H, d, J=9.6Hz), 6.70(1H, d, J=3.6Hz), 6.95(1H, m), 7.04(1H, dd, J=3.3, 1.2Hz), 7.24(1H, d, J= 3.6Hz), 7.37(1H, dd, J=5.1, 1.2Hz); IR(CHCl$_3$) 3516, 3450, 2669, 1709, 1643, 1543, 1508, 1471cm$^{-1}$; $[\alpha]_D^{25.0}$+ 20.8±0.6°(c=1.015, MeOH) Anal.(C$_{24}$H$_{31}$NO$_3$S$_3$. 0.3H$_2$O) Calcd.(%): C, 59.67; H, 6.59; N, 2.90; S, 19.91 Found(%): C, 59.65; H, 6.49; N, 3.13; S, 20.18 |

TABLE 46

| Compd. No.. | Physical property |
|---|---|
| II-5A-143a | $^1$H-NMR(CDCl$_3$) δ 0.95(1H, d, J=9.9Hz), 1.04(3H, s), 1.23(3H, s), 1.32–2.40(14H, m), 4.24(2H, s), 4.32(1H, m), 6.11(1H, d, J=9.0Hz), 7.16–7.32(6H, m), 7.42(1H, dd, J=8.1, 7.2Hz), 7.76(1H, s), 8.18(1H, d, J=8.1Hz); IR(CHCl$_3$) 3516, 3442, 1709, 1651, 1513, 1495, 1471cm$^{-1}$; $[\alpha]_D^{24.0}$+31.6±0.7°(c=1.000, MeOH) Anal. (C$_{30}$H$_{35}$NO$_3$S.0.3H$_2$O) Calcd.(%): C, 72.78; H, 7.25; N, 2.83; S, 6.48 Found(%): C, 72.79; H, 7.27; N, 2.87; S, 6.44 |
| II-5A-197a | $^1$H-NMR(CDCl$_3$) δ 0.90(1H, d, J=9.9Hz), 1.08(3H, s), 1.20(3H, s), 1.30–2.36(14H, m), 3.22(2H, t, J=9.0Hz), 4.07(2H, s), 4.18(1H, m), 4.57(2H, t, J=9.0Hz), 5.92 (1H, d, J=8.4Hz), 6.78(1H, t, J=7.5Hz), 6.80(1H, d, J= 3.9Hz), 6.95(1H, d, J=7.5Hz), 7.09(1H, d, J=7.5Hz), 7.28(1H, d, J=3.9Hz); IR(CHCl$_3$) 3516, 3450, 3431, 1709, 1641, 1543, 1506, 1458cm$^{-1}$; $[\alpha]_D^{25.0}$+ 41.1±0.8°(c=1.002, MeOH) Anal.(C$_{28}$H$_{35}$NO$_4$S.0.3H$_2$O) Calcd.(%): C, 69.05; H, 7.37; N, 2.88; S, 6.58 Found(%): C, 69.05; H, 7.20; N, 3.06; S, 6.51 |
| II-5B-55a | $^1$H-NMR(CDCl$_3$) δ 0.93(1H, d, J=10.5Hz), 1.08 and 1.23(3H, s), 1.55(1H, m), 1.91–2.42(7H, m), 2.39(3H, s), 3.18(2H, d, J=6.6Hz), 4.20(1H, m), 5.56–5.73(2H, m), 5.99(1H, m), 6.18–6.23(2H, m), 7.19(1H, dd, J=1.5, 3.3Hz), 7.30(1H, d, J=3.9Hz), 7.54(1H, d, J=3.9Hz); IR(CHCl$_3$) 3446, 1711, 1657, 1529, 1504, 1375, 1182, 1161, 1144, 1053cm$^{-1}$; $[\alpha]_D^{25}$+38.8±0.8°(c=1.001, |

TABLE 46-continued

| Compd. No.. | Physical property |
|---|---|
|  | MeOH) Anal.($C_{24}H_{39}N_2O_5S_2.0.3H_2O$) Calcd.(%): C, 58.11; H, 6.22; N, 5.65; S, 12.93 Found(%): C, 58.13; H, 6.09; N, 5.68; S, 12.73. |
| II-5C-1a | $^1$H-NMR(CDCl$_3$) δ 0.95(1H, d, J=10.5Hz), 1.08(3H, s), 1.23(3H, s), 1.42–2.33(10H, m), 4.22(1H, m), 5.78(1H, d, J= 15.9Hz), 6.07(1H, d, J=8.1Hz), 6.33(2H, t, J= 2.4Hz), 7.03(1H, dt, J=15.9, 6.9Hz), 7.16(2H, t, J= 2.4Hz), 7.28(2H, d, J=4.2Hz), 7.57(1H, d, J=4.2Hz); IR(CHCl$_3$) 3523, 3446, 1697, 1655, 1529, 1504, 1456, 1385, 1192, 1167, 1057, 1034cm$^{-1}$; [α]$_D^{25.0}$+29.7±0.7° (c=1.005, MeOH) Anal.($C_{23}H_{28}N_2O_5S_2.0.2H_2O$) Calcd.(%): C, 57.52; H, 5.96; N, 5.83; S, 13.35 Found(%): C, 57.51; H, 5.89; N, 5.88; S, 13.31 |
| II-5C-55a | $^1$H-NMR(CDCl$_3$) δ 0.92(1H, d, J=10.5Hz), 1.09 and 1.23(3H, s), 1.48–2.40(10H, m), 2.39(3H, s), 4.24(1H, m), 5.79(1H, d, J=15.6Hz), 5.99(1H, m), 6.09(1H, d, J=8.7Hz), 6.20(1H, t, J=3.6Hz), 7.03(1H, dt, J=6.9, 15.6Hz), 7.19(1H, dd, J=1.8, 3.3Hz), 7.29(1H, d, J= 4.2Hz), 7.55(1H, d, J=4.2Hz).; IR(CHCl$_3$) 3446, 1697, 1655, 1529, 1504, 1375, 1182, 1161, 1144, 1053cm$^{-1}$; [α]$_D^{26.5}$+27.9±0.7°(c=1.005, MeOH) Anal. ($C_{24}H_{39}N_2O_5S_2.0.3H_2O$) Calcd.(%): C, 58.11; H, 6.22; N, 5.65; S, 12.93 Found(%): C, 58.12; H, 6.22; N, 5.62; S, 12.91. |

TABLE 47

| Compd. No.. | Physical property |
|---|---|
| II-5E-1a | mp 154–155° C.; $^1$H-NMR(CDCl$_3$) δ 0.90(1H, d, J=10.2Hz), 1.10 and 1.23(3H, s), 1.51(1H, ddd, J=2.1, 5.1, 12.9Hz), 1.72–2.40(7H, m), 3.58–3.64(2H, m), 3.98 and 4.07(each 1H, Abq, J=16.8Hz), 4.23(1H, m), 6.27(1H, d, J=8.7Hz), 6.32–6.35(2H, m), 7.15–7.17(2H, m), 7.31(1H, d, J=3.9Hz), 7.55(1H, d, J=3.9Hz); IR(CHCl$_3$) 3444, 1730, 1655, 1529, 1504, 1456, 1385, 1192, 1167, 1057, 1034cm$^{-1}$; [α]$_D^{24}$ −2.2±0.4°(c=1.009, MeOH) Anal.($C_{22}H_{28}N_2O_6S_2$) Calcd.(%): C, 54.98; H, 5.87; N, 5.83; S, 13.34 Found(%): C, 54.97; H, 5.92; N, 5.89; S, 13.12 |
| II-5E-55a | $^1$H-NMR(CDCl$_3$) δ 0.90(1H, d, J=9.9Hz), 1.10 and 1.23 (3H, s), 1.51(1H, ddd, J=2.7, 4.8, 12.6Hz), 1.74–2.40(7H, m), 2.39(3H, s), 3.58–3.64(2H, m), 3.98 and 4.07(each 1H, Abq, J=17.1Hz), 4.23(1H, m), 5.99(1H, m), 6.20(1H, t, J=3.6Hz), 6.29(1H, d, J=8.1Hz), 7.19(1H, dd, J=1.5, 3.3Hz), 7.33(1H, d, J=3.9Hz), 7.53(1H, d, J=3.9Hz); IR (CHCl$_3$) 3444, 1729, 1655, 1529, 1504, 1375, 1182, 1161, 1142, 1053cm$^{-1}$; [α]$_D^{24}$ −2.8±0.4°(c=1.013, MeOH) Anal. ($C_{23}H_{30}N_2O_6S_2.1.2H_2O$) Calcd.(%): C, 53.51; H, 6.33; N, 5.43; S, 12.42 Found(%): C, 53.53; H, 5.93; N, 5.45; S, 12.55 |
| II-5F-31a | $^1$H-NMR(CDCl$_3$) δ 0.90(1H, d, J=10.2Hz), 1.09 and 1.22 (3H, s), 1.47(1H, ddd, J=2.4, 4.8, 12.9Hz), 1.74(1H, m), 1.91–2.38(6H, m), 2.61–2.80(2H, m), 3.49(2H, s), 4.13(2H, s), 4.21(1H, m), 6.07(1H, d, J=8.4Hz), 6.77(1H, dt, J=0.9, 3.6Hz), 7.22–7.35(6H, m); IR(CHCl$_3$) 2924, 1711, 1641, 1543, 1508, 1471, 1454, 1286, 1257, 1227, 1223cm$^{-1}$; [α]$_D^{26}$+30.7±1.4°(c=0.512%, MeOH); Anal.($C_{25}H_{31}NO_3S_2.0.3H_2O$) Calcd.(%) C, 64.85; H, 6.88; N, 3.02; S, 13.85 Found(%) C, 64.73; H, 6.81; N, 3.13; S, 13.81 |
| II-5F-55a | $^1$H-NMR(CDCl$_3$) δ 0.90(1H, d, 10.2Hz), 1.10 and 1.23(3H, s), 1.49(1H, ddd, J=2.7, 5.7, 13.5Hz), 1.64–2.38(7H, m), 2.39(3H, s), 2.60–2.80(2H, m), 3.21(2H, ABq, J=15.0Hz), 4.19(1H, m), 5.98(1H, m), 6.20(1H, t, J=3.0Hz), 6.25(1H, d, J=8.4Hz), 7.18(1H, m), 7.33(1H, d, J=4.2Hz), 7.53 (1H, d, J=4.2Hz); IR(CHCl$_3$) 2925, 1710, 1657, 1529, 1504, 1375, 1227, 1213, 1207, 1182, 1161cm$^{-1}$; [α]$_D^{26}$+29.6±1.4° (c=0.503%, MeOH); Anal.($C_{23}H_{30}N_2O_5S_3.0.4H_2O$) Calcd.(%) |

TABLE 47-continued

| Compd. No.. | Physical property |
|---|---|
|  | C, 53.34; H, 5.99; N, 5.41; S, 18.57 Found(%) C, 53.41; H, 6.01; N, 5.47; S, 18.65 |
| II-5F-88a | $^1$H-NMR(CDCl$_3$) δ 0.91(1H, d, 10.2Hz), 1.10 and 1.22(3H, s), 1.48(1H, m), 1.67–2.38(7H, m), 2.60–2.80(2H, m), 3.21 (2H, br s), 4.18(2H, d, J=0.9Hz), 4.22(1H, m), 6.08(1H, d, J=8.4Hz), 6.79(1H, dt, J=0.9, 3.6Hz), 6.96(1H, dd, J= 1.5, 5.1Hz), 7.05(1H, m), 7.27–7.33(2H, m); IR(CHCl$_3$) 2923, 1710, 1643, 1543, 1508, 1471, 1286, 1221, 1205cm$^{-1}$; [α]$_D^{26}$+30.3±1.4°(c=0.508%, MeOH); Anal. ($C_{23}H_{29}NO_3S_3.0.2H_2O$) Calcd.(%) C, 59.12; H, 6.34; N, 3.00; S, 20.59 Found(%) C, 59.10; H, 6.31; N, 3.09; S, 20.47 |

TABLE 48

| Compd. No.. | Physical property |
|---|---|
| II-6A-55a | $^1$H-NMR(CDCl$_3$) δ 0.88(1H, d, J=10.2Hz), 1.08 and 1.21(3H, s), 1.22–2.36(16H, m), 2.38(3H, s), 4.16(1H, m), 5.98(1H, m), 6.19(1H, t, J=3.3Hz), 6.30(1H, d, J=8.7Hz), 7.17(1H, dd, J=1.8, 3.3Hz), 7.33(1H, d, J=4.2Hz), 7.52(1H, d, J=4.2Hz); IR(CHCl$_3$) 3446, 1709, 1657, 1529, 1504, 1375, 1182, 1161, 1144, 1053cm$^{-1}$; [α]$_D^{25}$+22.7±0.6°(c=1.002, MeOH) Anal. ($C_{25}H_{34}N_2O_5S_2.0.3H_2O$) Calcd.(%): C, 58.64; H, 6.81; N, 5.47; S, 12.52 Found(%): C, 58.73; H, 6.68; N, 5.45; S, 11.93. |
| II-6B-55a | $^1$H-NMR(CDCl$_3$) δ 0.94(1H, d, J=10.5Hz), 1.08 and 1.22(3H, s), 1.55(1H, dd, J=2.4, 5.7, 13.2Hz), 1.84–2.50 (11H, m), 2.39(3H, s), 4.20(1H, m), 5.37–5.52(2H, m), 5.99(1H, m), 6.17–6.21(2H, m), 7.18(1H, dd, J=1.8, 6.3Hz), 7.31(1H, d, J=4.2Hz), 7.54(1H, d, J=4.2Hz); IR(CHCl$_3$) 3446, 1711, 1657, 1529, 1504, 1392, 1375, 1182, 1161, 1144, 1053cm$^{-1}$; [α]$_D^{25}$+44.6±0.8°(c=1.004, MeOH) Anal.($C_{25}H_{32}N_2O_5S_2$) Calcd.(%): C, 59.50; H, 6.39; N, 5.55; S, 12.71 Found(%): C, 59.16; H, 6.27; N; 5.54; S, 12.44 |
| II-7A-31a | $^1$H-NMR(CDCl$_3$) δ 0.91(1H, d, J=9.9Hz), 1.08(3H, s), 1.20(3H, s), 1.22–2.34(18H, m), 4.13(1H, s), 4.19(1H, m), 5.92(1H, m, J= 9.0Hz), 6.77(1H, d, J=3.6Hz), 7.22–7.35(6H, m); IR(CHCl$_3$) 3516, 3450, 3431, 1709, 1641, 1545, 1506, 1404, 1456cm$^{-1}$; [α]$_D^{24.0}$+20.4±0.6° (c=1.000, MeOH) Anal.($C_{28}H_{37}NO_3S.0.2H_2O$) Calcd.(%): C, 71.36; H, 8.00; N, 2.97; S, 6.80 Found(%): C, 71.44; H, 7.99; N, 3.02; S, 6.69 |
| II-7A-47a | $^1$H-NMR(CDCl$_3$) δ 0.91(1H, d, J=10.5Hz), 1.09(3H, s), 1.21(3H, s), 1.22–2.33(18H, m), 4.19(1H, m), 6.06(1H, d, J= 9.0Hz), 7.11(1H, dd, J=5.1, 3.9Hz), 7.33(1H, d, J=3.9Hz), 7.65(1H, d, J=3.9Hz), 7.70(1H, dd, J= 5.1, 1.5Hz), 7.76(1H, d, J=3.6, 1.5Hz); IR(CHCl$_3$) 3516, 3446, 2679, 1709, 1657, 1529, 1504, 1402, 1336, 1153, 1095, 1022cm$^{-1}$; [α]$_D^{24.0}$ 30 25.3±0.7°(c=1.004, MeOH) Anal.($C_{25}H_{33}NO_5S_3.0.3H_2O$) Calcd.(%): C, 56.75; H, 6.40; N, 2.65; S, 18.07 Found(%): C, 56.88; H, 6.43; N, 2.68; S, 17.79 |
| II-7A-55a | $^1$H-NMR(CDCl$_3$) δ 0.90(1H, d, J=10.2Hz), 1.08 and 1.22(3H, s), 1.22–2.32(18H, m), 2.39(3H, s), 4.18(1H, m), 4.65(1H, br s), 5.99(1H, m), 6.12(1H, d, J=9.0Hz), 6.20(1H, t, J=3.6Hz), 7.03(1H, dt, J=6.9, 15.6Hz), 7.19(1H, dd, J=1.8, 3.3Hz), 7.30(1H, d, J=4.2Hz), 7.54(1H, d, J=3.9Hz); IR(CHCl$_3$) 3446, 1708, 1657, 1529, 1504, 1375, 1182, 1161, 1144, 1053cm$^{-1}$; [α]$_D^{25}$+25.1±0.6°(c=1.009, MeOH) Anal. ($C_{26}H_{36}N_2O_5S_2.0.2H_2O$) Calcd.(%): C, 59.56; H, 7.00; N, 5.34; S, 12.23 Found(%): C, 59.59; H, 7.01; N, 5.33; S, 11.85. |

TABLE 49

| Compd. No.. | Physical property |
|---|---|
| II-7A-55e | $^1$H-NMR(CDCl$_3$) δ 0.93(1H, d, J=10.2Hz), 1.10(3H, s), 1.23(3H, s), 1.32–2.34(16H, m), 2.29(2H, d, J=7.5Hz), 2.39(3H, s), 3.28(3H, s), 4.21(1H, m), 6.00(1H, m), 6.17(1H, d, J=9.3Hz), 6.21(1H, m), 7.19(1H, m), 7.36 (1H, d, J=3.9Hz), 7.56(1H, d, J=3.9Hz), 8.76(1H, br); IR(CHCl$_3$) 3386, 2927, 2862, 1718, 1651, 1531, 1506, 1398, 1375, 1344, 1159, 1053, 1020cm$^{-1}$; [α]$_D^{24}$+20.8±0.6°(c=1.00, MeOH) Anal. (C$_{27}$H$_{39}$N$_3$O$_6$S$_3$·0.5MeOH) Calcd.(%): C, 53.81; H, 6.73; N, 6.85; S, 15.67 Found(%): C, 53.91; H, 6.64; N, 7.13; S, 15.29 |
| II-7A-55g | $^1$H-NMR(CDCl$_3$) δ 0.94(1H, d, J=10.5Hz), 1.13(3H, s), 1.25(3H, s), 1.26–2.40(16H, m), 2.38(3H, s), 2.93–3.00 (2H, m), 4.28(1H, m), 6.00(1H, m), 6.21(1H, t, J=3.3Hz), 6.43(1H, d, J=8.7Hz), 7.17(1H, dd, J=3.3, 1.5Hz), 7.42(1H, d, J=3.9Hz), 7.56(1H, d, J=3.9Hz); IR (CHCl$_3$) 3426, 2626, 1639, 1533, 1508, 1375, 1222, 1216, 1205, 1184, 1160cm$^{-1}$; [α]$_D^{24.0}$+22.7±0.6°(c=1.002, MeOH) Anal.(C$_{26}$H$_{36}$N$_6$O$_3$S$_2$·0.6H$_2$O) Calcd.(%): C, 56.21; H, 6.75; N, 15.03; S, 11.43 Found(%): C, 56.32; H, 6.52; N, 14.80; S, 11.13 |
| II-7A-59a | $^1$H-NMR(CDCl$_3$) δ 0.90(1H, d, J=10.2Hz), 1.07(3H, s), 1.20(3H, s), 1.24–2.33(18H, m), 4.17(1H, m), 5.91(1H, d, J= 9.0Hz), 7.00(1H, dd, J=5.4, 3.6Hz), 7.05(1H, d, J=3.6Hz), 7.26(1H, d, J=3.6Hz), 7.28(1H, dd, J= 3.6, 1.2Hz), 7.42(1H, d, J=5.4, 1.2Hz); IR(CHCl$_3$) 3516, 3450, 3431, 2673, 1709, 1645, 1529, 1500, 1471, 1421cm$^{-1}$; [α]$_D^{25.0}$+20.1±0.6°(c=1.010, MeOH) Anal. (C$_{25}$H$_{33}$NO$_3$S$_3$) Calcd.(%): C, 61.06; H, 6.76; N, 2.85; S, 19.56 Found(%): C, 60.86; H, 6.87; N, 2.93; S, 19.29 |
| II-7A-88a | $^1$H-NMR(CDCl$_3$) δ 0.91(1H, d, J=10.2Hz), 1.09(3H, s), 1.21(3H, s), 1.24–2.33(18H, m), 4.15(2H, s), 4.19(1H, m), 5.94(1H, d, J= 9.0Hz), 6.79(1H, d, J=3.6Hz), 6.96 (1H, dd, J=5.1, 1.2Hz), 7.05(1H, m), 7.27(1H, d, J= 4.8, 1.2Hz), 7.30(1H, d, J=3.6Hz); IR(CHCl$_3$) 3518, 3450, 3431, 1709, 1641, 1545, 1506, 1469cm$^{-1}$; [α]$_D^{24.0}$+19.2±0.6°(c=1.012, MeOH) Anal. (C$_{26}$H$_{35}$NO$_3$S$_2$·0.1H$_2$O) Calcd.(%): C, 65.67; H, 7.46; N, 2.95; S, 13.09 Found(%): C, 65.81; H, 7.43; N, 2.94; S, 12.99 |
| II-7A-104a | $^1$H-NMR(CDCl$_3$) δ 0.92(1H, d, J=10.5Hz), 1.10(3H, s), 1.22(3H, s), 1.25–2.34(18H, m), 4.10(2H, s), 4.20(1H, m), 5.95(1H, d, J=8.7Hz), 6.70(1H, d, J=3.3Hz), 6.95(1H, dd, J=5.1, 3.9Hz), 7.04(1H, dd, J=3.9, 1.2Hz), 7.25(1H, d, J=3.3Hz), 7.36(1H, dd, J=5.1, 1.2Hz); IR(CHCl$_3$) 3516, 3450, 3431, 1709, 1643, 1543, 1506, 1471cm$^{-1}$; [α]$_D^{25.0}$+19.8±0.6°(c=1.009, MeOH) Anal.(C$_{26}$H$_{35}$NO$_3$S$_3$·0.1H$_2$O) Calcd.(%): C, 61.53, H, 6.99, N, 2.76; S, 18.95 Found(%): C, 61.42; H, 6.85; N, 2.86; S, 18.89 |

TABLE 50

| Compd. No.. | Physical property |
|---|---|
| II-7A-143a | $^1$H-NMR(CDCl$_3$) δ 0.96(1H, d, J=10.2Hz), 1.10(3H, s), 1.23(3H, s), 1.26–2.38(18H, m), 4.24(2H, s), 4.32(1H, m), 6.11(1H, d, J= 8.7Hz), 7.19–7.28(6H, m), 7.42(1H, dd, J=8.1, 7.2Hz), 7.76(1H, s), 8.19(1H, d, J=8.1Hz); IR(CHCl$_3$) 3516, 3442, 1709, 1651, 1514, 1495, 1469cm$^{-1}$; [α]$_D^{24.0}$+34.1±0.7°(c=1.004, MeOH) Anal. (C$_{32}$H$_{39}$NO$_3$S·0.2H$_2$O) Calcd.(%): C, 73.73; H, 7.62; N, 2.69; S, 6.15 Found(%): C, 73.72; H, 7.68; N, 2.65; S, 5.88 |
| II-7A-197a | $^1$H-NMR(CDCl$_3$) δ 0.91(1H, d, J=9.9Hz), 1.08(3H, s), 1.20(3H, s), 1.24–2.33(18H, m), 3.22(2H, t, J=8.7Hz), 4.05(2H, s), 4.19(1H, m), 4.57(2H, t, J=8.7Hz), 5.92 (1H, d, J=9.3Hz), 6.79(1H, t, J=7.2Hz), 6.80(1H, d, J= 3.9Hz), 6.96(1H, d, J=7.2Hz), 7.09(1H, d, J=7.2Hz), 7.28(1H, d, J=3.9Hz); IR(CHCl$_3$) 3516, 3450, 3431, 2671, 1709, 1639, 1543, 1506, 1458cm$^{-1}$; [α]$_D^{25.0}$+ 17.4±0.6°(c=1.001, MeOH) Anal.(C$_{30}$H$_{39}$NO$_4$S·0.3H$_2$O) Calcd.(%): C, 69.95; H, 7.75; N, 2.72; S, 6.22 Found(%): C, 69.86; H, 7.65; N, 2.80; S, 6.08 |
| II-7A-315a | $^1$H-NMR(CDCl$_3$) δ 0.96(1H, d, J=9.9Hz), 1.11(3H, s), 1.24(3H, s), 1.33–2.36(16H, m), 2.3(2H, t, J=7.2Hz), 4.26(2H, s), 4.33(1H, m), 6.12(1H, d, J=9.3Hz), 7.00–7.23(5H, m), 7.42(1H, m), 7.78(1H, s), 8.20(1H, d, J=7.5Hz); IR(CHCl$_3$) 3516, 3442, 2925, 2858, 1709, 1651, 1585, 1570, 1514, 1492, 1469, 1396cm$^{-1}$; [α]$_D^{25.5}$+33.4±0.7°(c=1.00, MeOH) Anal. (C$_{32}$H$_{38}$FNO$_3$S·0.5MeOH) Calcd.(%): C, 70.75; H, 7.31; N, 2.54; F, 3.44; S, 5.81 Found(%): C, 70.85; H, 7.34; N, 2.80; F, 3.06; S, 5.66 |
| II-7A-316a | $^1$H-NMR(CDCl$_3$) δ 0.96(1H, d, J=10.2Hz), 1.11(3H, s), 1.24(3H, s), 1.32–2.36(16H, m), 2.30(2H, t, J=7.2Hz), 3.82(3H, s), 4.23(2H, s), 4.33(1H, m), 6.12(1H, d, J= 9.0Hz), 6.82–6.91(2H, m), 7.05–7.22(3H, m), 7.39(1H, m), 7.78(1H, s), 8.14(1H, d, J=8.1Hz); IR(CHCl$_3$) 3516, 3442, 2925, 2858, 1709, 1651, 1601, 1514, 1493, 1468, 1439, 1394, 1246cm$^{-1}$; [α]$_D^{26.0}$+31.4±0.7°(c=1.04, MeOH) Anal.(C$_{33}$H$_{41}$NO$_4$S·0.1H$_2$O) Calcd.(%): C, 72.12; H, 7.56; N, 2.55; S, 5.23 Found(%): C, 71.93; H, 7.73; N, 2.77; S, 5.60 |
| II-7B-55a | $^1$H-NMR(CDCl$_3$) δ 0.91(1H, d, J=10.2Hz), 1.08(3H, s), 1.15(3H, s), 1.22(3H, s), 1.29–2.45(17H, m), 2.39(3H, s), 4.19(1H, m), 5.98(1H, d, J=2.4Hz), 6.06 (1H, d, J=9.0Hz), 6.20(1H, dd, J=3.3 and 3.6Hz), 7.19(1H, dd, J=2.4 and 3.3Hz), 7.29(1H, d, J=3.9Hz), 7.55(1H, d, J=3.9Hz); IR(CHCl$_3$) 3448, 2927, 2860, 1739, 1705, 1657, 1529, 1504, 1469, 1375, 1281, 1161, 1144, 1070, 1053, 1022cm$^{-1}$; [α]$_D^{24}$+21.4±0.6°(c=1.02, MeOH) Anal.(C$_{27}$H$_{38}$N$_2$O$_5$S$_2$·0.3H$_2$O) Calcd.(%): C, 60.04; H, 7.20; N, 5.19; S, 11.87 Found(%): C, 60.26; H, 7.22; N, 5.28; S, 11.50 |

TABLE 51

| Compd. No.. | Physical property |
|---|---|
| II-7E-55c | $^1$H-NMR(CDCl$_3$) δ 0.93(1H, d, J=10.5Hz), 1.08(3H, s), 1.21(3H, s), 1.50–2.40(14H, m), 2.39(3H, s), 4.14(1H, m), 5.24(1H, brs), 5.33–5.50(2H, m), 5.99(1H, m), 5.99(1H, brs), 6.20(1H, t, J=3.3Hz), 6.48(1H, d, J=7.2Hz), 7.19 (1H, m), 7.39(1H, d, J=4.2Hz), 7.55(1H, t, J=4.2Hz); IR(CHCl$_3$) 3527, 3485, 3448, 3411, 3348, 1676, 1591, 1529, 1504, 1375, 1182, 1161, 1144, 1053cm$^{-1}$; [α]$_D^{26.0}$+55.5±1.0° (c=1.010, MeOH) Anal.(C$_{26}$H$_{35}$N$_3$O$_4$S$_2$·0.3H$_2$O) Calcd.(%): C, 59.70; H, 6.86; N, 8.03; S, 12.26 Found(%): C, 59.79; H, 6.75; N, 8.05; S, 12.14 |
| II-7E-55e | mp 70–72° C.; $^1$H-NMR(CDCl$_3$) δ 0.96(1H, d, J=10.8Hz), 1.09(3H, s), 1.22(3H, s), 1.60–2.37(14H, m), 2.41(3H, s), 3.25(3H, s), 4.10(1H, m), 5.28–5.47(2H, m), 6.00(1H, m), 6.06(1H, d, J=8.7Hz), 6.22(1H, dd, J=3.3 and 3.6Hz), 7.19(1H, dd, J=1.8 and 3.3Hz), 7.41(1H, d, J=3.9Hz), 7.57(1H, d, J=3.9Hz); IR(CHCl$_3$) 3427, 3386, 2927, 1714, 1647, 1531, 1506, 1454, 1375, 1342, 1161, 1120, 1053, 1020cm$^{-1}$; [α]$_D^{24}$+50.0±0.9°(c=1.00, MeOH) Anal. (C$_{27}$H$_{37}$N$_3$O$_6$S$_3$·0.4H$_2$O) Calcd.(%): C, 53.78; H, 6.32; N, 6.97; S, 15.95 Found(%): C, 53.89; H, 6.28; N, 7.05; S, 15.57 |
| II-7E-55g | $^1$H-NMR(CDCl$_3$) δ 0.76(1H, d, J=10.8Hz), 1.10(3H, s), 1.24(3H, s), 1.44–2.31(12H, m), 2.40(3H, s), 2.92–3.08 (2H, m), 3.98(1H, m), 5.37–5.39(2H, m), 6.01(1H, m), 6.22 (1H, t, J=3.3Hz), 6.30(1H, d, J=8.4Hz), 7.19(1H, dd, J= 3.3, 1.8Hz), 7.41(1H, d, J=3.9Hz), 7.58(1H, d, J=3.9Hz); IR(CHCl$_3$) 3151, 1639, 1533, 1508, 1375, 1184, 1160cm$^{-1}$; [α]$_D^{25.0}$+40.9±0.8°(c=1.010, MeOH) Anal. (C$_{26}$H$_{34}$N$_6$O$_3$S$_2$·1.3H$_2$O) Calcd.(%): C, 55.16; H, 6.52; N, 14.44; S, 10.43 Found(%): C, 55.44; H, 6.42; N, 14.17; S, 10.66 |

TABLE 51-continued

| Compd. No.. | Physical property |
|---|---|
| II-7F-55a | $^1$H-NMR(CDCl$_3$) δ 0.94(1H, d, J=9.9Hz), 1.08(3H, s), 1.16 or 1.18(3H, d, J=4.2Hz), 1.22(3H, s), 1.47–2.52 (13H, m), 2.39(3H, s), 4.20(1H, m), 5.38–5.41(2H, m), 5.99(1H, m), 6.14–6.21(2H, m), 7.19(1H, m), 7.31(1H, m), 7.54(1H, m); IR(CHCl$_3$) 3446, 2925, 2870, 1738, 1705, 1657, 1529, 1504, 1469, 1375, 1182, 1161, 1144, 1070, 1053, 1022cm$^{-1}$; [α]$_D^{24}$+49.8±0.9°(c=1.02, MeOH) Anal. (C$_{27}$H$_{36}$N$_2$O$_5$S$_2$.0.4H$_2$O) Calcd.(%): C, 60.06; H, 6.87; N, 5.19; S, 11.88 Found(%): C, 60.03; H, 6.71; N, 5.31; S, 11.76 |
| II-7I-1a | mp 111–115° C.; $^1$H-NMR(CDCl$_3$) δ 0.91(1H, d, J=10.5Hz), 1.09 and 1.22(3H, s), 1.22–2.40(12H, m), 4.19(1H, m), 5.79(1H, br d, J=15.6Hz), 6.06(1H, d, J=9.3Hz), 6.32–6.35(2H, m), 7.03(1H, dt, J=7.8, 15.6Hz), 7.15–7.17 (2H, m), 7.27(1H, d, J=3.9Hz), 7.57(1H, d, J=3.9Hz); IR(CHCl$_3$) 3446, 1695, 1654, 1529, 1504, 1456, 1385, 1192, 1167, 1057, 1034cm$^{-1}$; [α]$_D^{25}$+20.5±0.6°(c=1.007, MeOH) Anal.(C$_{25}$H$_{32}$N$_2$O$_5$S$_2$) Calcd.(%): C, 59.50; H, 6.39; N, 5.55; S, 12.71 Found(%): C, 59.19; H, 6.39; N, 5.48; S, 12.39 |

TABLE 52

| Compd. No.. | Physical property |
|---|---|
| II-7I-47a | $^1$H-NMR(CDCl$_3$) δ 0.91(1H, d, J=10.8Hz), 1.09 and 1.22(3H, s), 1.22–2.40(12H, m), 4.20(1H, m), 5.79(1H, br d, J=15.6Hz), 5.99(1H, m), 6.08(1H, d, J=9.0Hz), 7.03(1H, dt, J=7.2, 15.6Hz), 7.11(1H, dd, J=3.9, 5.1Hz), 7.33(1H, d, J=3.9Hz), 7.65(1H, d, J=3.9Hz) 7.70 (1H, dd, J=1.2, 6.0Hz), 7.76(1H, dd, J=1.2, 3.9Hz); IR(CHCl$_3$) 3446, 2680, 1695, 1655, 1529, 1504, 1336, 1153, 1022cm$^{-1}$; [α]$_D^{24}$+20.2±0.6°(c=1.000, MeOH) Anal.(C$_{25}$H$_{31}$NO$_5$S$_3$.0.3H$_2$O) Calcd.(%): C, 56.96; H, 6.04; N, 2.66; S, 18.25 Found(%):C, 57.07; H, 6.12; N, 2.72; S, 17.88 |
| II-7I-55a | $^1$H-NMR(CDCl$_3$) δ 0.91(1H, d, J=10.5Hz), 1.09 and 1.22(3H, s), 1.22–2.40(12H, m), 2.39(3H, s), 4.20(1H, m), 5.79(1H, br d, J=15.6Hz), 5.99(1H, m), 6.06(1H, d, J=9.0Hz), 6.20(1H, t, J=3.6Hz), 7.03(1H, dt, J=6.9, 15.6Hz), 7.19(1H, dd, J=1.8, 3.3Hz), 7.29(1H, d, J=3.9Hz), 7.55(1H, d, J=3.9Hz); IR(CHCl$_3$) 3448, 1695, 1655, 1529, 1504, 1375, 1182, 1161, 1144, 1053cm$^{-1}$; [α]$_D^{25}$+19.7±0.6°(c=1.007, MeOH) Anal. (C$_{26}$H$_{34}$N$_2$O$_5$S$_2$.0.2H$_2$O) Calcd.(%): C, 59.79; H, 6.64; N, 5.36; S, 12.28 Found(%): C, 59.83; H, 6.40; N, 5.42; S, 12.10. |
| II-7I-55b | $^1$H-NMR(CDCl$_3$) δ 0.91(1H, d, J=9.9Hz), 1.09 and 1.22 (3H, s), 1.27–1.78(8H, m), 1.99–2.38(6H, m), 2.39(3H, s), 3.72(3H, s), 4.19(1H, m), 5.79(1H, dt, J=15.6, 1.5Hz), 5.98(1H, m), 6.03(1H, d, J=9.0Hz), 6.20(1H, t, J= 3.3Hz), 6.93(1H, dt, J=15.6, 6.9Hz), 7.19(1H, dd, J= 1.8, 3.3Hz), 7.28(1H, d, J=3.9Hz), 7.55(1H, d, J= 3.9Hz). |
| II-7I-59a | mp 143–145° C.; $^1$H-NMR(CDCl$_3$) δ 0.90(1H, d, J=10.2Hz), 1.08 and 1.21(3H, s), 1.24–2.40(14H, m), 4.18(1H, m), 5.79(1H, br d, J=15.6Hz), 5.91(1H, d, J=9.0Hz), 6.98–7.08(3H, m), 7.26(1H, d, J=3.6Hz), 7.29(1H, dd, J=1.2, 3.6Hz), 7.42(1H, dd, J=1.2, 5.4Hz); IR(Nujol) 3419, 3184, 1705, 1670, 1626, 1525, 1500, 1180cm$^{-1}$; [α]$_D^{26}$+12.7±0.6°(c=1.007%, MeOH) Anal.(C$_{25}$H$_{31}$NO$_5$S$_3$) Calcd.(%): C, 61.31; H, 6.38; N, 2.86; S, 19.64 Found(%): C, 61.11; H, 6.41; N, 2.92; S, 19.42 |
| II-7I-88a | $^1$H-NMR(CDCl$_3$) δ 0.91(1H, d, J=10.2Hz), 1.09(3H, s), 1.21(3H, s), 1.26–2.34(14H, m), 4.15(2H, m), 4.20(1H, m), 5.79(1H, d, J=15.6, 1.2Hz), 5.94(1H, d, J=9.3Hz), 6.79(1H, d, J=3.6Hz), 6.97(1H, d, J=4.8, 1.5Hz), 7.05(1H, m), 7.25–7.33(3H, m); IR(CHCl$_3$) 3523, 3450, 3431, 2679, 1695, 1647, 1545, 1506, 1471cm$^{-1}$; [α]$_D^{26.5}$+12.7±0.5°(c=1.002, MeOH) Anal. (C$_{26}$H$_{33}$NO$_3$S$_2$.0.4H$_2$O) Calcd.(%): C, 65.21; H, 6.92; N, |

TABLE 52-continued

| Compd. No.. | Physical property |
|---|---|
| | 3.92; S, 13.39 Found(%): C, 65.16; H, 6.63; N, 3.76; S, 13.48 |

TABLE 54

| Compd. No.. | Physical property |
|---|---|
| II-7I-104a | $^1$H-NMR(CDCl$_3$) δ 0.92(1H, d, J=10.2Hz), 1.10(3H, s), 1.22(3H, s), 1.28–2.36(14H, m), 4.10(2H, s), 4.21(1H, m), 5.79(1H, dt, J=15.9, 1.5Hz), 5.96(1H, d, J=9.0Hz), 6.70(1H, d, J=3.6Hz), 6.95(1H, dd, J=5.1, 3.6Hz), 7.03(1H, dt, J=15.9, 3.6Hz), 7.04(1H, dd, J=3.6, 1.2Hz), 7.25(1H, d, J=3.6Hz), 7.37(1H, dd, J=5.1, 1.2Hz); IR(CHCl$_3$) 3523, 3450, 3431, 2679, 1695, 1649, 1543, 1506cm$^{-1}$; [α]$_D^{25.0}$+11.0±0.7°(c=0.709, MeOH) Anal.(C$_{26}$H$_{33}$NO$_3$S$_3$.0.5H$_2$O) Calcd.(%): C, 60.99; H, 6.68; N, 2.73; S, 19.06 Found(%): C, 60.69; H, 6.45; N, 3.12; S, 19.32 |
| II-7I-126a | $^1$H-NMR(CDCl$_3$) δ 0.90(1H, d, J=10.2Hz), 1.08(3H, s), 1.21(3H, s), 1.27–2.31(14H, m), 3.83(3H, s), 4.12(2H, m), 4.20(1H, m), 5.79(1H, dt, J=15.6, 1.5Hz), 5.92 (1H, d, J=9.3Hz), 6.77(1H, d, J=3.6Hz), 6.86–6.92 (2H, m), 7.02(1H, dt, J=15.6, 6.9Hz), 7.16(1H, d, J= 7.5Hz), 7.22(1H, dd, J=7.5, 1.8Hz), 7.27(1H, d, J= 3.6Hz); IR(CHCl$_3$) 3451, 3433, 2679, 1695, 1647, 1504, 1288, 1248, 1223, 1213cm$^{-1}$; [α]$_D^{27.0}$+14.0±0.5°(c=1.001, MeOH) Anal.(C$_{29}$H$_{37}$NO$_4$S.0.2H$_2$O) Calcd.(%): C, 69.76; H, 7.55; N, 2.81; S, 6.42 Found(%): C, 69.50; H, 7.50; N, 2.88; S, 6.36 |
| II-7I-197a | $^1$H-NMR(CDCl$_3$) δ 0.90(1H, d, J=10.2Hz), 1.08(3H, s), 1.20(3H, s), 1.26–2.36(14H, m), 3.22(2H, t, J=8.7Hz), 4.07(2H, s), 4.19(1H, m), 4.57(2H, t, J=8.7Hz), 5.79 (1H, dt, J=15.6Hz, 1.5Hz), 5.92(1H, d, J=9.0Hz), 6.79(1H, t, J=7.2Hz), 6.80(1H, d, J=3.6Hz), 6.96 (1H, d, J=7.2Hz), 7.01(1H, dt, J=15.6, 6.9Hz), 7.10 (1H, dd, J=7.2, 1.5Hz), 7.29(1H, d, J=3.6Hz); IR (CHCl$_3$) 3525, 3450, 3431, 2679, 1695, 1647, 1543, 1506, 1458cm$^{-1}$; [α]$_D^{25.0}$+13.0±0.5°(c=1.002, MeOH) Anal. (C$_{30}$H$_{37}$NO$_4$S.0.2H$_2$O) Calcd.(%): C, 70.47; H, 7.37; N, 2.74; S, 6.27 Found(%): C, 70.48; H, 7.33; N, 2.74; S, 6.29 |
| II-7I-239a | mp 138–140° C.; $^1$H-NMR(CDCl$_3$) δ 0.87(1H, d, J=10.2Hz), 1.07(3H, s), 1.19(3H, s), 1.26–2.31(12H, m), 4.09 (2H, s), 4.20(1H, m), 5.73(1H, d, J=15.6Hz), 6.08(1H, d, J=9.0Hz), 6.79(1H, d, J=3.6Hz), 6.81–6.86(2H, m), 6.96(1H, dt, J=15.6, 6.9Hz), 7.29(1H, d, J=3.6Hz), 7.45(1H, s); IR(CHCl$_3$) 3342, 3246, 1720, 1701, 1593, 1545, 1520, 1456, 1377, 1203cm$^{-1}$; [α]$_D^{25.0}$+13.8±0.5° (c=1.011, MeOH) Anal.(C$_{30}$H$_{35}$NO$_5$S) Calcd.(%): C, 69.07; H, 6.76; N, 2.68; S, 6.15 Found(%): C, 68.91; H, 6.77; N, 2.75; S, 5.99 |

TABLE 54

| Compd. No.. | Physical property |
|---|---|
| II-7I-270a | $^1$H-NMR(CDCl$_3$) δ 0.91(1H, d, J=10.5Hz), 1.09(3H, s), 1.23(3H, s), 1.26–1.55(6H, m), 1.62–1.82(2H, m), 1.96–2.38 (6H, m), 2.42(6H, s), 4.20(1H, m), 5.79(1H, dt, J= 15.6, 1.5Hz), 5.88(2H, s), 6.06(1H, d, J=9.0Hz), 7.03 (1H, dt, J=15.6, 6.6Hz), 7.27(1H, d, J=3.9Hz), 7.50 (1H, d, J=3.9Hz); IR(CHCl$_3$) 3525, 3448, 2679, 1695, 1655, 1529, 1504, 1375, 1180, 1119cm$^{-1}$; [α]$_D^{25}$+19.4±0.6° (c=1.008, MeOH) Anal.(C$_{27}$H$_{36}$N$_2$O$_5$S$_2$.0.2H$_2$O) Calcd.(%): C, 60.47; H, 6.84; N, 5.22; S, 11.96 Found(%): C, 60.41; H, 6.77; N, 5.25; S, 11.90 |
| II-7I-327a | $^1$H-NMR(CDCl$_3$) δ 0.90(1H, d, J=10.5Hz), 1.07 and 1.21 (3H, s), 1.25–2.38(12H, m), 3.00(2H, t, J=8.4Hz), 3.99 (2H, t, J=8.4Hz), 4.17(1H, m), 5.78(1H, dt, J=1.8, 15.9Hz), 6.02(1H, d, J=8.7Hz), 6.97–7.24(4H, m), 7.27(1H, |

TABLE 54-continued

| Compd. No. | Physical property |
|---|---|
|  | d, J=4.2Hz), 7.47(1H, d, J=4.2Hz), 7.58(1H, d, J=8.1Hz); IR(CHCl$_3$) 2927, 1695, 1653, 1529, 1504, 1479, 1367, 1165cm$^{-1}$; [α]$_D^{26}$+21.3±0.6°(c=1.008%, MeOH); Anal.(C$_{29}$H$_{36}$N$_2$O$_5$S$_2$.0.4H$_2$O) Calcd.(%) C, 61.76; H, 6.58; N, 4.97; S, 11.37 Found(%) C, 61.68; H, 6.43; N, 5.02; S, 11.40 |
| II-7I-332a | $^1$H-NMR(CDCl$_3$) δ 0.91(1H, d, J=10.2Hz), 1.07 and 1.22 (3H, s), 1.30–2.40(16H, m), 2.54(2H, t, J=7.2Hz), 3.84–3.89 (2H, m), 4.19(1H, m), 5.79(1H, br d, J=14.4Hz), 6.01(1H, d, J=8.7Hz), 6.97–7.27(5H, m), 7.78(1H, d, J=8.4Hz); IR(CHCl$_3$) 2929, 1695, 1653, 1529, 1502, 1363, 1211, 1161cm$^{-1}$; [α]$_D^{24}$+19.4±0.6°(c=1.010%, MeOH); Anal.(C$_{30}$H$_{38}$N$_2$O$_5$S$_2$.0.3H$_2$O) Calcd.(%) C, 62.54; H, 6.75; N, 4.86; S, 11.13 Found(%) C, 62.56; H, 6.76; N, 4.87; S, 10.90 |
| II-7I-343a | $^1$H-NMR(CDCl$_3$) δ 0.94(1H, d, J=10.2Hz), 1.11(3H, s), 1.22(3H, s), 1.39–2.39(14H, m), 4.29(1H, m), 5.78(1H, d, J=15.6Hz), 6.15(1H, d, J=9.0Hz), 7.02(1H, m), 7.44–7.64 (4H, m), 7.85(1H, s), 8.02–8.12(3H, m), 8.65(1H, d, J= 6.9Hz); IR(CHCl$_3$) 3523, 3444, 2925, 2862, 1695, 1653, 1516, 1493, 1471, 1446, 1419, 1383, 1315cm$^{-1}$; [α]$_D^{25.0}$+ 34.8±0.7°(c=1.03, MeOH) Anal.(C$_{31}$H$_{35}$NO$_5$S$_2$.0.4H$_2$O) Calcd.(%): C, 64.99; H, 6.30; N, 2.44; S, 11.19 Found(%): C, 64.97; H, 6.26; N, 2.62; S, 10.86 |
| II-7I-389a | mp 119–121° C.; $^1$H-NMR(CDCl$_3$) δ 0.90(1H, d, J=10.5Hz), 1.09(3H, s), 1.21(3H, s), 1.33–1.50(6H, m), 1.63–1.78 (2H, m), 1.98(1H, m), 2.18(3H, m), 2.23(3H, s), 2.12–2.32(5H, m), 3.21(2H, t, J=8.7Hz), 4.18(1H, m), 4.62(2H, t, J=8.7Hz), 5.79(1H, d, J=15.6Hz), 5.95(1H, d, J=9.3Hz), 6.90(1H, s), 6.95(1H, s), 7.02(1H, dd, J= 15.6, 6.9Hz), 7.09(1H, d, J=3.6Hz), 7.30(1H, d, J=3.6Hz); IR(Nujol) 3361, 2671, 1695, 1649, 1604, 1583, 1533, 1504, 1415, 1323, 1203cm$^{-1}$; [α]$_D^{25}$+9.7±0.5°(c=1.012, MeOH) Anal.(C$_{30}$H$_{37}$NO$_4$S$_2$.0.1H$_2$O) Calcd.(%): C, 66.54; H, 6.92; N, 2.59; S, 11.84 Found(%): C, 66.42; H, 6.99; N, 2.52; S, 11.92 |

TABLE 55

| Compd. No. | Physical property |
|---|---|
| II-7I-391a | $^1$H-NMR(CDCl$_3$) δ 0.91(1H, d, J=10.5Hz), 1.09(3H, s), 1.22(3H, s), 1.33–1.52(6H, m), 1.67–1.77(2H, m), 2.00(1H, m), 2.12(1H, m), 2.18–2.25(3H, m), 2.32(3H, s)+2.32(1H, m), 3.19(2H, t, J=8.7Hz), 4.20(1H, m), 4.73(2H, t, J=8.7Hz), 5.79(1H, dt, J=15.6, 1.5Hz), 6.89(1H, d, J=9.0Hz), 7.03(1H, dt, J=15.6, 7.1Hz), 7.21(1H, s), 7.35(1H, d, J= 3.9Hz), 7.51(1H, s), 7.74(1H, d, J=3.9Hz); IR(CHCl$_3$) 3523, 3448, 2681, 1695, 1652, 1527, 1502, 1481, 1329cm$^{-1}$; [α]$_D^{25}$+17.1±0.6°(c=1.016, MeOH) Anal. (C$_{30}$H$_{37}$NO$_6$S$_2$.0.5H$_2$O) Calcd.(%): C, 62.04; H, 6.60; N, 2.41; S, 11.07 Found(%): C, 62.16; H, 6.52; N, 2.37; S, 10.85 |
| II-7J-55a | $^1$H-NMR(CDCl$_3$) δ 0.91(1H, d, J=10.2Hz), 1.08(3H, s), 1.22(3H, s), 1.24–2.34(14H, m), 1.78(3H, d, J=1.2Hz), 2.38 (3H, d, J=1.2Hz), 4.19(1H, s), 5.98(1H, m), 6.04(1H, d, J= 9.0Hz), 6.19(1H, t, J=3.3Hz), 6.85(1H, dt, J=7.2, 1.2Hz), 7.19(1H, dd, J=3.3Hz, 1.2Hz), 7.28(1H, d, J=3.9Hz), 7.55(1H, d, J=3.9Hz); IR(CHCl$_3$) 3525, 3446, 2667, 1685, 1657, 1529, 1504, 1375, 1281, 1182, 1161, 1053cm$^{-1}$; [α]$_D^{24.0}$+ 11.5±0.5°(c=1.000, MeOH) Anal.(C$_{27}$H$_{36}$N$_2$O$_5$S$_2$.0.4H$_2$O) Calcd.(%): C, 60.06; H, 6.87; N, 5.19; S, 11.67 Found(%): C, 60.15; H, 6.56; N, 5.00; S, 11.37 |
| II-7K-55a | $^1$H-NMR(CDCl$_3$) δ 0.92(1H, d, J=10.5Hz), 1.08(3H, s), 1.22(3H, s), 1.24–2.40(14H, m), 2.12(3H, d, J=1.2Hz), 2.39 (3H, d, J=1.2Hz), 4.20(1H, m), 5.64(1H, d, J=1.2Hz), 5.99 (1H, m), 6.04(1H, d, J=9.0Hz), 6.20(1H, t, J=3.3Hz), 7.19 (1H, dd, J=3.3, 1.8Hz), 7.28(1H, d, J=4.2Hz), 7.55(1H, d, J=4.2Hz); IR(CHCl$_3$) 3523, 3446, 2575; 1689, 1655, 1530, 1504, 1375, 1182, 1161, 1053, 1022cm$^{-1}$; [α]$_D^{26.5}$+18.3±0.6° (c=1.009, MeOH) Anal.(C$_{27}$H$_{36}$N$_2$O$_5$S$_2$.0.3H$_2$O) Calcd.(%): C, 60.27; H, 6.86; N, 5.20; S, 11.92 Found(%): C, 60.23; H, 6.66; N, 5.17; S, 11.73 |
| II-7L-55a | $^1$H-NMR(CDCl$_3$) δ 0.90(1H, d, J=10.2Hz), 1.00(3H, s), 1.22(3H, s), 1.26–2.61(14H, m), 2.39(3H, s), 4.18(1H, m), 5.95–6.08(2H, m), 6.16–6.21(2H, m), 7.19(1H, m), 7.32(1H, d, J=4.2Hz), 7.55(1H, d, J=4.2Hz); IR(CHCl$_3$) 3510, 3446, 2927, 2862, 1709, 1658, 1529, 1504, 1441, 1375cm$^{-1}$; [α]$_D^{25.0}$+18.4±0.6°(c=1.00, MeOH) Anal. (C$_{26}$H$_{33}$FN$_2$O$_5$S$_2$.0.5H$_2$O) Calcd.(%): C, 57.23; H, 6.28; N, 5.13; F, 3.48; S, 11.75 Found(%): C, 57.44; H, 6.31; N, 5.10; F, 3.28; S, 11.27 |
| II-7M-1a | $^1$H-NMR(CDCl$_3$) δ 0.92(1H, d, J=10.2Hz), 1.09 and 1.23 (3H, s), 1.35–2.40(12H, m), 3.54(2H, t, J=6.0Hz), 4.04(2H, s), 4.21(1H, m), 6.10(1H, d, J=9.6Hz), 6.32–6.35(2H, m), 7.15–7.18(2H, m), 7.29(1H, d, J=3.9Hz), 7.57(1H, d, J= 3.9Hz); IR(CHCl$_3$) 3446, 3431, 1780, 1732, 1657, 1529, 1504, 1456, 1385, 1192, 1167, 1124, 1057, 1034cm$^{-1}$; [α]D$^{25.5}$+ 22.0±0.6°(c=1.000, MeOH) Anal.(C$_{24}$H$_{32}$N$_2$O$_6$S$_2$.0.3H$_2$O) Calcd.(%): C, 56.08 H, 6.39; N, 5.45; S, 12.48 Found(%):C, 56.19; H, 6.39; N, 5.48; S, 12.33 |

TABLE 56

| Compd. No.. | Physical property |
|---|---|
| II-7M-1e | $^1$H-NMR(CDCl$_3$) δ 0.92(1H, d, J=10.2Hz), 1.10(3H, s), 1.23(3H, s), 1.26–2.34(12H, m), 3.32(3H, s), 3.51(2H, d, J=6.3Hz), 3.99(2H, s), 4.20(1H, m), 6.11(1H, d, J=9.3Hz), 6.34(2H, m), 7.17(2H, m), 7.29(1H, d, J=3.9Hz), 7.58(1H, d, J=3.9Hz), 8.90(1H, m, s); IR(CHCl$_3$) 3448, 3352, 2925, 2870, 1730, 1657, 1529, 1504, 1471, 1456, 1423, 1402, 1387, 1354, 1167, 1151, 1120, 1057, 1034cm$^{-1}$; [α]$_D^{26}$ +18.7±1.1°(c=0.52, MeOH) Anal. (C$_{25}$H$_{35}$N$_3$O$_7$S$_3$.0.7MeOH) Calcd.(%): C, 50.75; H, 6.26; N, 6.91; S, 15.82 Found(%): C, 50.76; H, 5.68; N, 6.94; S, 15.49 |
| II-7M-1k | $^1$H-NMR(CDCl$_3$) δ 0.93(1H, d, J=10.2Hz), 1.11(3H, s), 1.23(3H, s), 1.39–2.33(12H, m), 3.46(2H, t, J=6.6Hz), 3.85(2H, s), 4.22(1H, m), 6.12(1H, d, J=9.0Hz), 6.33(2H, m), 7.15(2H, m), 7.29(1H, m), 7.52–7.66(4H, m), 8.09 (2H, d, J=7.8Hz), 9.03(1H, s); IR(CHCl$_3$) 3446, 3350, 2924, 2870, 1732, 1657, 1529, 1504, 1473, 1450, 1415, 1385, 1167, 1120, 1088, 1057, 1034cm$^{-1}$; [α]$_D^{26}$+14.9±0.6° (c=1.00, MeOH) Anal.(C$_{30}$H$_{37}$N$_3$O$_7$S$_3$.0.6H$_2$O) Calcd.(%): C, 54.71; H, 5.85; N, 6.38; S, 14.61 Found(%): C, 54.81; H, 5.76; N, 6.60; S, 14.29 |
| II-7M-31a | $^1$H-NMR(CDCl$_3$) δ 0.92(1H, d, J=10.2Hz), 1.09 and 1.21 (3H, s), 1.39–2.37(12H, m), 3.52(2H, t, J=6.3Hz), 4.03 and 4.14(2H, s), 4.23(1H, m), 6.00(1H, d, J=8.4Hz), 6.77(1H, d, J=3.6Hz), 7.20–7.37(6H, m); IR(CHCl$_3$) 2923, 1780, 1732, 1641, 1545, 1508, 1471, 1456, 1365, 1248, 1219, 1211, 1207, 1124cm$^{-1}$; [α]$_D^{25}$+14.9±1.1° (c=0.509%, MeOH); Anal.(C$_{27}$H$_{35}$NO$_4$S$_2$.0.3H$_2$O) Calcd.(%) C, 68.27; H, 7.55; N, 2.95; S, 6.75 Found(%) C, 68.25; H, 7.62; N, 3.02; S, 6.76 |
| II-7M-40a | $^1$H-NMR(CDCl$_3$) δ 0.94(1H, d, J=10.2Hz), 1.15 and 1.25 (3H, s), 1.21–2.38(12H, m), 3.54(2H, t, J=6.3Hz), 4.05 (2H, s), 4.28(1H, m), 6.11(1H, d, J=9.0Hz), 7.25–7.64 (7H, m); IR(CHCl$_3$) 2924, 1780, 1732, 1641, 1510, 1491, 1471, 1454, 1219, 1211cm$^{-1}$; [α]$_D^{25}$+15.7±0.6° (c=1.010%, MeOH); Anal.(C$_{26}$H$_{33}$NO$_4$S.0.3H$_2$O) Calcd.(%) C, 67.74; H, 7.35; N, 3.04; S, 6.96 Found(%): C, 67.68; H, 7.26; N, 3.107; S, 6.75 |
| II-7M-43a | mp 95–97° C.; $^1$H-NMR(CDCl$_3$) δ 0.94(1H, d, J=10.2Hz), 1.14 and 1.24(3H, s), 1.24–2.38(12H, m), 3.54(2H, t, J=6.3Hz), 4.05(2H, s), 4.27(1H, m), 6.07(1H, d, J=8.7Hz), 7.04(1H, dd, J=3.9, 4.8Hz), 7.11(1H, d, J=3.9Hz), 7.24 (1H, dd, J=1.2, 3.6Hz), 7.28(1H, dd, J=1.2, 5.1Hz), 7.37 (1H, d, 3.9Hz); IR(Nujol) 3346, 2927, 1759, 1728, 1612, 1525, 1504, 1458, 1377, 1132cm$^{-1}$; [α]$_D^{26}$+18.7±0.6° (c=1.011%, MeOH); Anal.(C$_{24}$H$_{31}$NO$_4$S$_2$.0.8H$_2$O) Calcd.(%) C, 60.55; H, 6.90; N, 2.94; S, 13.47 Found(%) C, 60.35; H, 6.61; N, 3.07; S, 13.43 |

TABLE 57

| Compd. No.. | Physical property |
|---|---|
| II-7M-47a | $^1$H-NMR(CDCl$_3$) δ 0.91(1H, d, J=10.5Hz), 1.10 and 1.22 (3H, s), 1.36–2.40(12H, m), 3.53(2H, t, J=6.0Hz), 4.05 (2H, s), 4.21(1H, m), 6.14(1H, d, J=9.3Hz), 7.12(1H, dd, J=0.9, 4.8Hz), 7.35(1H, d, J=3.9Hz), 7.64(1H, d, J=3.9Hz), 7.70(1H, dd, J=1.2, 5.1Hz), 7.76(1H, dd, J=1.2, 3.9Hz); IR(CHCl$_3$) 3446, 3429, 1780, 1732, 1655, 1529, 1504, 1336, 1153, 1124, 1074, 1024cm$^{-1}$; [α]$_D^{24}$+22.5±0.6° (c=1.013, MeOH) Anal.(C$_{24}$H$_{31}$NO$_6$S$_3$.0.4H$_2$O) Calcd.(%): C, 54.09 H, 6.01; N, 2.63; S, 18.05 Found(%): C, 54.29; H, 5.90; N, 2.81; S, 17.77 |
| II-7M-55a | $^1$H-NMR(CDCl$_3$) δ 0.92(1H, d, J=10.2Hz), 1.09 and 1.23 (3H, s), 1.35–2.40(12H, m), 2.39(3H, s), 3.53(2H, t, J=6.3Hz), 4.04(2H, s), 4.21(1H, m), 5.99(1H, m), 6.12(1H, d, J=9.6Hz), 6.20(1H, t, J=3.3Hz), 7.19(1H, dd, J=1.5, 3.3Hz), 7.32(1H, d, J=3.9Hz), 7.55(1H, d, J=3.9Hz); I IR (CHCl$_3$) 3446, 1780, 1731, 1656, 1529, 1504, 1375, 1182, 1161, 1142, 1053cm$^{-1}$; [α]$_D^{24}$+20.9±0.6°(c=1.005, MeOH) Anal.(C$_{25}$H$_{34}$N$_2$O$_6$S$_2$.0.3H$_2$O) Calcd.(%): C, 56.86 H, 6.60; |

TABLE 57-continued

| Compd. No.. | Physical property |
|---|---|
| | N, 5.30; S, 12.14 Found(%):, 56.88; H, 6.60; N, 5.31; S, 11.76 |
| II-7M-59a | $^1$H-NMR(CDCl$_3$) δ 0.91(1H, d, J=10.2Hz), 1.09 and 1.22 (3H, s), 1.36–2.38(12H, m), 3.53(2H, t, J=6.0Hz), 4.04 (2H, s), 4.21(1H, m), 5.98(1H, d, J=8.7Hz), 7.01(1H, dd, J=3.6, 5.4Hz), 7.05 (1H, d, J=3.9Hz), 7.27(1H, d, J=4.2Hz), 7.29(1H, dd, J=1.2, 3.6Hz), 7.43(1H, dd, J=1.5, 5.4Hz); IR(CHCl$_3$) 3448, 3429, 1780, 1732, 1645, 1529, 1500, 1471, 1458, 1124cm$^{-1}$; [α]$_D^{26}$+17.1±0.9°(c=0.608%, MeOH) Anal.(C$_{24}$H$_{31}$NO$_4$S$_3$.0.3H$_2$O) Calcd.(%): C, 57.75 H, 6.38; N, 2.81; S, 19.27 Found(%): C, 57.86; H, 6.39; N, 2.89; S, 19.18 |
| II-7M-88a | $^1$H-NMR(CDCl$_3$) δ 0.92(1H, d, J=10.2Hz), 1.11 and 1.22 (3H, s), 1.42–2.38(12H, m), 3.53(2H, t, J=6.0Hz), 4.03 and 4.16(2H, s), 4.24(1H, m), 6.01(1H, d, J=9.0Hz), 6.79(1H, d, J=2.7Hz), 6.96(1H, dd, J=1.2, 5.1Hz), 7.05 (1H, m), 7.26–7.33(2H, m); IR(CHCl$_3$) 2924, 1780, 1732, 1641, 1545, 1508, 1471, 1221, 1219, 1211, 1207, 1124cm$^{-1}$; [α]$_D^{25}$+15.5±1.1°(c=0.505%, MeOH); Anal. (C$_{25}$H$_{33}$NO$_4$S$_2$.0.3H$_2$O) Calcd.(%) C, 62.42; H, 7.04; N, 2.91; S, 13.33 Found(%) C, 62.57; H, 7.03; N, 2.98; S, 13.15 |
| II-7M-126a | $^1$H-NMR(CDCl$_3$) δ 0.91(1H, d, J=10.2Hz), 1.09(3H, s), 1.21(3H, s), 1.45–2.33(12H, m), 3.51(2H, t, J=6.3Hz), 3.84(3H, s), 4.02(2H, s), 4.11(2H, s), 4.22(1H, m), 5.99 (1H, d, J=9.0Hz), 6.77(1H, d, J=3.9Hz), 6.86–6.92(2H, m), 7.15(1H, dd, J=7.2, 1.8Hz), 7.22(1H, dd, J=4.8, 1.8Hz), 7.29(1H, d, J=3.9Hz); IR(CHCl$_3$) 3431, 1669, 1506, 1463, 1247, 1128cm$^{-1}$; [α]$_D^{27.0}$+14.4±0.5°(c=1.009, MeOH) Anal.(C$_{28}$H$_{37}$NO$_5$S.0.2H$_2$O) Calcd.(%): C, 66.82; H, 7.49; N, 2.78; S, 6.37 Found(%): C, 66.59; H, 7.41; N, 2.82; S, 6.17 |

TABLE 58

| Compd. No.. | Physical property |
|---|---|
| II-7M-197a | $^1$H-NMR(CDCl$_3$) δ 0.92(1H, d, J=10.2Hz), 1.10 and 1.21(3H, s), 1.39–2.38(12H, m), 3.22(2H, t, J=9.0Hz), 3.52(2H, t, J=6.3Hz), 4.02 and 4,07(2H, s), 4.23(1H, m), 4.58(2H, t, J=9.0Hz), 6.00(1H, d, J=8.4Hz), 6.80–7.12(4H, m), 7.30(1H, d, J=3.6Hz); IR(CHCl$_3$) 2923, 1780, 1732, 1639, 1545, 1506, 1477, 1458, 1441, 1365, 1254, 1205, 1126cm$^{-1}$; [α]$_D^{26}$+13.4±1.1° (c=0.506%, MeOH); Anal.(C$_{29}$H$_{37}$NO$_5$S.0.4H$_2$O) Calcd.(%) C, 67.13; H, 7.34; N, 2.70; S, 6.18 Found(%) C, 67.19; H, 7.21; N, 2.75; S, 6.18 |
| II-7M-239a | mp 179–180° C.; $^1$H-NMR(d$_6$-DMSO) δ 0.78(1H, d, J=9.6Hz), 1.05(3H, s), 1.13(3H, s), 1.20–2.30(12H, m), 3.40(2H, t, J=6.3Hz), 3.84(1H, m), 3.93(2H, s), 4.17(1H, m), 6.73(1H, dd, J=8.7, 2.4Hz), 6.79(1H, d, J=2.4Hz), 6.95(1H, d, J=3.6Hz), 7.34(1H, d, J=8.7Hz), 7.66(1H, d, J=3.6Hz), 7.79(1H, d, J=6.9Hz), 7.82(1H, s); IR(KBr) 3338, 3244, 2602, 1739, 1606, 1557, 1550, 1525, 1458, 1367, 1261, 1211cm$^{-1}$; [α]$_D^{25.0}$+14.0±0.5°(c=1.009, MeOH) Anal.(C$_{29}$H$_{35}$NO$_6$.0.3H$_2$O) Calcd.(%): C, 65.59; H, 6.76; N, 2.36; S, 6.04 Found(%): C, 65.62; H, 6.82; N, 2.81; S, 5.92 |
| II-7M-270a | mp.147–149° C.; $^1$H-NMR(CDCl$_3$) δ 0.92(1H, d, J=10.2Hz), 1.09(3H, s), 1.23(3H, s), 1.34–2.38(12H, m), 2.42 (6H, s), 3.54(2H, t, J=6.3Hz), 4.05(2H, s), 4.21(1H, m), 5.88(1H, d, J=9.0Hz), 6.12(1H, d, J=9.0Hz), 7.28(1H, d, J=3.9Hz), 7.49(1H, d, J=3.9Hz); IR(Nujol) 3267, 3099, 2549, 1726, 1610, 1562, 1230, 1211, 1176, 1126, 1113cm$^{-1}$; [α]$_D^{26}$+19.8±0.6°(c=1.010, MeOH) Anal. (C$_{26}$H$_{36}$N$_2$O$_6$S$_2$) Calcd.(%): C, 58.18; H, 6.76; N, 5.22; S, 11.95 Found(%): C, 58.05; H, 6.74; N, 5.16; S, 11.71 |
| II-7M-307a | $^1$H-NMR(CDCl$_3$) δ 0.90(1H, d, J=10.5Hz), 1.06(3H, s), 1.19(3H, s), 1.38–1.79(8H, m), 1.96(1H, m), 2.06(1H, m), 2.15–2.31(2H, m), 3.49(2H, t, J=6.6Hz), 3.99(3H, |

TABLE 58-continued

| Compd. No.. | Physical property |
|---|---|
| | s), 4.20(1H, m), 4.60(2H, s), 5.95(1H, d, J=9.0Hz), 6.74(1H, brd, J=3.6Hz), 7.22(1H, d, J=3.6Hz), 7.32 (1H, d, J=9.3Hz), 7.34(1H, ddd, J=1.5, 6.9, 8.4Hz), 7.47(1H, ddd, J=1.5, 6.9, 8.4Hz), 7.80(1H, brd, J=8.4Hz), 7.82(1H, d, J=9.3Hz), 7.93(1H, brd, J=8.4Hz); IR(Nujol) 3450, 3060, 1780, 1732, 1639, 1597, 1510, 1471, 1265, 1252, 1217cm$^{-1}$; $[\alpha]_D^{26}$+16.1±0.6°(c=1.005, MeOH) Anal.($C_{32}H_{39}NO_5S$.0.4$H_2O$) Calcd.(%): C, 69.01; H, 7.20; N, 2.51; S, 5.76 Found(%): C, 68.97; H, 7.13; N, 2.56; S, 5.62 |

TABLE 59

| Compd. No.. | Physical property |
|---|---|
| II-7M-327a | $^1$H-NMR(CDCl$_3$) δ 0.91(1H, d, J=10.5Hz), 1.07 and 1.21(3H, s), 1.36–2.35(12H, m), 3.01(2H, t, J=8.4Hz), 3.52(2H, t, J=6.6Hz), 3.99(2H, t, J=8.4Hz), 4.03(2H, s), 4.19(1H, m), 6.09(1H, d, J=8.7Hz), 6.99–7.24(3H, m), 7.29(1H, d, J=3.9Hz), 7.47(1H, d, J=3.9Hz), 7.58 (1H, d, J=8.1Hz); IR(CHCl$_3$) 2924, 1780, 1732, 1655, 1529, 1504, 1479, 1460, 1367, 1240, 1225, 1213, 1205, 1165, 1122, 1105cm$^{-1}$; $[\alpha]_D^{26}$+22.2±0.6°(c=1.009%, MeOH) Anal.($C_{28}H_{36}N_2O_6S_2$.0.5$H_2O$) Calcd.(%) C, 59.03; H, 6.55; S, 4.92; S, 11.26 Found(%) C, 58.93; H, 6.75; N, 5.14; S, 11.27 |
| II-7M-329a | $^1$H-NMR(CDCl$_3$) δ 0.91(1H, d, J=10.5Hz), 1.08 and 1.22(3H, s), 1.36–2.38(12H, m), 3.04(2H, t, J=8.4Hz), 3.53(2H, t, J=6.3Hz), 4.04(2H, s), 4.04(2H, t, J=8.4Hz), 4.20(1H, m), 6.11(1H, d, J=8.7Hz), 6.75(1H, m), 7.20(1H, m), 7.30(1H, d, J=3.9Hz), 7.37(1H, brd, J=7.5Hz), 7.49(1H, d, J=3.9Hz); IR(CHCl$_3$) 2924, 1780, 1732, 1655, 1626, 1529, 1504, 1473, 1460, 1369, 1244, 1223, 1213, 1167cm$^{-1}$; $[\alpha]_D^{26}$+21.4±0.6°(c=1.009%, MeOH); Anal.($C_{28}H_{35}FN_2O_6S_2$.0.4$H_2O$) Calcd.(%) C, 57.40; H, 6.16; F, 3.24; N, 4.78; S, 10.95 Found(%) C, 57.37; H, 5.82; F, 3.06; N, 4.86; S, 10.80 |
| II-7M-330a | $^1$H-NMR(CDCl$_3$) δ 0.91(1H, d, J=10.5Hz), 1.08 and 1.22(3H, s), 1.36–2.39(12H, m), 2.97(2H, t, J=8.4Hz), 3.53(2H, t, J=6.3Hz), 4.02(2H, t, J=8.7Hz), 4.04(2H, s), 4.19(1H, m), 6.10(1H, d, J=8.4Hz), 6.82–6.94(2H, m), 7.44(1H, d, J=3.9Hz), 7.53(1H, dd, J=4.5, 8.7Hz); IR(CHCl$_3$) 2924, 1780, 1732, 1655, 1529, 1504, 1481, 1367, 1225, 1165cm$^{-1}$; $[\alpha]_D^{26}$+21.7±0.6° (c=1.008%, MeOH); Anal.($C_{28}H_{35}FN_2O_6S_2$.0.5$H_2O$) Calcd.(%) C, 57.22; H, 6.17; F, 3.23; N, 4.77; S, 10.91 Found(%) C, 57.26; H, 6.14; F, 3.19; N, 4.85; S, 10.76 |
| II-7M-331a | $^1$H-NMR(CDCl$_3$) δ 0.91(1H, d, J=10.5Hz), 1.08 and 1.22(3H, s), 1.36–2.38(12H, m), 3.04(2H, t, J=8.4Hz), 3.53(2H, t, J=6.3Hz), 4.04(2H, s), 4.04(2H, t, J=8.4Hz), 4.20(1H, m), 6.11(1H, d, J=8.7Hz), 6.75(1H, m), 7.20(1H, m), 7.30(1H, d, J=3.9Hz), 7.37(1H, brd, J=7.5Hz), 7.49(1H, d, J=3.9Hz); IR(CHCl$_3$) 2924, 1780, 1732, 1655, 1606, 1529, 1492, 1369, 1261, 1227, 1205, 1165, 1142, 1095cm$^{-1}$; $[\alpha]_D^{25}$+21.4±0.6°(c=1.009%, MeOH); Anal.($C_{28}H_{35}FN_2O_6S_2$.0.3$H_2O$) Calcd.(%) C, 57.57; H, 6.14; F, 3.25; N, 4.80; S, 10.98 Found(%) C, 57.28; H, 5.85; F, 3.20; N, 4.86; S, 10.97 |

TABLE 60

| Compd. No.. | Physical property |
|---|---|
| II-7M-332a | $^1$H-NMR(CDCl$_3$) δ 0.92(1H, d, J=10.2Hz), 1.08 and 1.23 (3H, s), 1.36–2.40(14H, m), 2.55(2H, t, J=6.6Hz), 3.53 (2H, t, J=6.6Hz), 3.84–3.87(2H, m), 4.05(2H, s), 4.20 (1H, m), 6.05(1H, d, J=9.0Hz), 7.04–7.27(5H, m), 7.78 (1H, dd, J=0.9, 8.1Hz); IR(CHCl$_3$) 2925, 1780, 1732, 1655, 1529, 1504, 1489, 1363, 1236, 1225, 1213, 1207, 1161, 1122cm$^{-1}$; $[\alpha]_D^{24}$+19.5±0.6°(c=1.015%, MeOH); Anal.($C_{29}H_{38}N_2O_6S_2$.0.4$H_2O$) Calcd.(%) C, 59.85; H, 6.72; N, 4.81; S, 11.02 Found(%) C, 59.84; H, 6.75; N, 4.92; S, 11.16 |
| II-7M-333a | $^1$H-NMR(CDCl$_3$) δ 0.91(1H, d, J=10.2Hz), 1.08 and 1.23 (3H, s), 1.36–2.40(12H, m), 3.53(2H, t, J=6.3Hz), 3.87–3.96 (4H, m), 4.05(2H, s), 4.20(1H, m), 6.09(1H, d, J=9.0Hz), 6.85(1H, dd, J=1.5, 8.4Hz), 6.96(1H, m), 7.11(1H, m), 7.26–7.30(2H, m), 7.83(1H, dd, J=1.5, 8.1Hz); IR (CHCl$_3$) 2924, 1780, 1732, 1655, 1529, 1502, 1491, 1367, 1248, 1215, 1207, 1165, 1126cm$^{-1}$; $[\alpha]_D^{26}$+20.5±0.6° (c=1.004%, MeOH); Anal.($C_{28}H_{36}N_2O_7S_2$.0.4$H_2O$) Calcd.(%) C, 57.59; H, 6.35; N, 4.80; S, 10.98 Found(%) C, 57.59; H, 6.24; N, 4.89; S, 10.78 |
| II-7M-334a | $^1$H-NMR(CDCl$_3$) δ 0.91(1H, d, J=10.2Hz), 1.08 and 1.23 (3H, s), 1.36–2.40(12H, m), 3.05(2H, dd, J=5.4, 9.0Hz), 3.54(2H, t, J=6.3Hz), 4.03–4.07(4H, m), 4.21(1H, m), 6.07(1H, d, J=8.7Hz), 7.09–7.27(5H, m), 7.67(1H, m); IR (CHCl$_3$) 2924, 1780, 1732, 1655, 1529, 1504, 1473, 1363, 1161cm$^{-1}$; $[\alpha]_D^{24}$+24.4±0.6°(c=1.013%, MeOH); Anal. ($C_{28}H_{36}N_2O_6S_3$.0.4$H_2O$) Calcd.(%) C, 56.05; H, 6.18; N, 4.67; S, 16.03 Found(%) C, 56.18; H, 6.09; N, 4.69; S, 15.74 |
| II-7M-336a | mp 166–168° C.; $^1$H-NMR(d6-DMSO) δ 0.79(1H, d, J=9.6Hz), 1.03 and 1.22(3H, s), 1.22–1.58(8H, m), 1.91(1H, m), 2.08–2.30(4H, m), 3.39(2H, t, J=6.0Hz), 3.85(1H, m), 3.92(2H, s), 4.63(4H, s), 7.20–7.35(4H, m), 7.77(1H, d, J=3.9Hz), 7.94(1H, d, J=3.9Hz), 8.24(1H, d, J=6.9Hz); IR(Nujol) 3369, 3093, 2924, 1730, 1612, 1541, 1516, 1466, 1377, 1344, 1215, 1165, 1126, 1084cm$^{-1}$; $[\alpha]_D^{25}$+19.0±0.6° (c=1.003%, MeOH); Anal.($C_{28}H_{36}N_2O_6S_2$.0.7$H_2O$) Calcd.(%) C, 58.66; H, 6.57; N, 4.89; S, 11.19 Found(%) C, 58.38; H, 6.40; N, 4.99; S, 11.48 |
| II-7M-343a | $^1$H-NMR(CDCl$_3$) δ 0.94(1H, d, J=10.2Hz), 1.11(3H, s), 1.23(3H, s), 1.44–2.36(12H, m), 3.49(2H, t, J=6.9Hz), 3.99(2H, t, J=6.9Hz), 4.29(1H, m), 6.27(1H, d, J=9.3Hz), 7.44–7.63(4H, m), 7.89(1H, s), 8.01–8.11(3H, m), 8.63 (1H, d, J=7.5Hz); IR(CHCl$_3$) 3442, 2924, 2870, 1780, 1730, 1653, 1518, 1417, 1446, 1383, 1317cm$^{-1}$; $[\alpha]_D^{26.0+}$ 24.3±0.6°(c=1.01, MeOH) Anal.($C_{30}H_{35}NO_6S_2$.1.7$H_2O$) Calcd.(%): C, 60.02; H, 6.45; N, 2.33; S, 10.68 Found(%): C, 60.14; H, 6.18; N, 2.40; S, 10.3 |

TABLE 61

| Compd. No.. | Physical property |
|---|---|
| II-7M-385a | $^1$H-NMR(CDCl$_3$) δ 0.96(1H, d, J=10.2Hz), 1.16(3H, s), 1.23(3H, s), 1.37–2.39(12H, m), 3.52(2H, t, J=6.3Hz), 4.02(2H, s), 4.35(1H, m), 6.26(2H, t, J=2.4Hz), 6.48 (1H, d, J=7.8Hz), 7.21(2H, t, J=2.4Hz), 7.57–7.59 (2H, m), 8.39(1H, m), 8.44(1H, s); IR(CHCl$_3$) 3456, 3103, 3022, 2924, 1732, 1651, 1516, 1371, 1221, 1188, 1163, 1057cm$^{-1}$; $[\alpha]_D^{22.0}$+42.9±0.8°(c=1.008, MeOH) Anal.($C_{28}H_{34}N_2O_6S_2$.0.1$H_2O$) Calcd.(%): C, 60.00; H, 6.15; N, 5.00; S, 11.44 Found(%): C, 59.85; H, 6.29; N, 4.82; S, 11.28 |
| II-7M-389a | mp 112–114° C.; $^1$H-NMR(CDCl$_3$) δ 0.91(1H, d, J=10.5Hz), 1.09(3H, s), 1.21(3H, s), 1.39–1.52(4H, m), 1.59–1.81 (4H, m), 1.98(1H, m), 2.11(1H, m), 2.23(3H, s) + 2.18–2.34(2H, m), 3.21(2H, t, J=8.7Hz), 3.52(2H, t, J=6.5Hz), 4.05(2H, s), 4.20(1H, m), 4.62(2H, t, J=8.7Hz), 6.00(1H, d, J=9.0Hz), 6.90(1H, s), 6.96(1H, s), 7.08(1H, d, J=4.2Hz), 7.32(1H, d, J=4.2Hz); IR (Nujol) 3406, 3338, 2729, 1757, 1738, 1614, 1583, 1533, 1503, 1203, 1124cm$^{-1}$; $[\alpha]_D^{23}$+12.2±0.5°(c=1.013, MeOH) Anal.($C_{29}H_{37}NO_5S_2$.0.2$H_2O$) Calcd.(%): C, 63.64; H, 6.89; N, 2.56; S, 11.72 Found(%): C, 63.68; H, 6.83; N, 2.55; S, 11.54 |

TABLE 61-continued

| Compd. No. | Physical property |
|---|---|
| II-7M-390a | mp 120–122° C.; $^1$H-NMR(CDCl$_3$) δ 0.91(1H, d, J=10.2Hz), 1.08(3H, s), 1.21(3H, s), 1.38–1.52(4H, m), 1.56–1.78 (4H, m), 1.98(1H, m), 2.10(1H, m), 2.17–2.33(2H, m), 2.39(3H, s), 3.52(2H, t, J=6.3Hz), 4.04(2H, s), 4.20(1H, m), 6.00(1H, d, J=9.0Hz), 6.72(1H, d, J=2.1Hz), 7.09(1H, m), 7.18(1H, d, J=3.9Hz), 7.33(1H, m) + 7.34(1H, d, J=3.9Hz), 7.63(1H, d, J=2.1Hz) ; IR (CHCl$_3$) 3508, 3448, 3429, 2667, 2568, 1780, 1732, 1645, 1529, 1500, 1471, 1421, 1323, 1246, 1130,cm$^{-1}$; [α]$_D^{24}$+12.5±0.5°(c=1.008, MeOH) Anal. (C$_{29}$H$_{35}$NO$_5$S$_2$.0.3H$_2$O) Calcd.(%): C, 63.66; H, 6.56; N, 2.56; S, 11.72 Found(%): C, 63.74; H, 6.44; N, 2.54; S, 11.78 |
| II-7M-391a | mp 177–179° C.; $^1$H-NMR(CDCl$_3$) δ 0.91(1H, d, J=10.2Hz), 1.10(3H, s), 1.22(3H, s), 1.40–1.53(4H, m), 1.57–1.71 (3H, m), 1.79(1H, m), 2.00(1H, m), 2.11(1H, m), 2.19–2.35(2H, m)+2.32(3H, s), 3.19(2H, t, J=8.7Hz), 3.53(2H, t, J=6.5Hz), 4.05(2H, s), 4.21(1H, m), 4.73 (2H, t, J=8.7Hz), 6.17(1H, d, J=9.0Hz), 7.21(1H, s), 7.36(1H, d, J=3.9Hz), 7.51(1H, s), 7.74(1H, d, J=3.9Hz); IR(Nujol) 3249, 2754, 2677, 2553, 1736, 1622, 1564, 1331, 1225, 1196, 1155, 1134cm$^{-1}$; [α]$_D^{25}$+17.1±0.6°(c=1.006, MeOH) Anal. (C$_{29}$H$_{37}$NO$_7$S$_2$.0.2H$_2$O) Calcd.(%): C, 60.12; H, 6.51; N, 2.42; S, 11.07 Found(%): C, 60.09; H, 6.47; N, 2.32; S, 11.06 |

TABLE 62

| Compd. No. | Physical property |
|---|---|
| II-7M-392a | mp 155–156° C.; $^1$H-NMR(CDCl$_3$) δ 0.89(1H, d, J=9.9Hz), 1.08(3H, s), 1.20(3H, s), 1.36–1.52(4H, m), 1.55–1.69 (3H, m), 1.78(1H, m), 1.99(1H, m), 2.10(1H, m), 2.17–2.34(2H, m), 2.51(2H, t, J=6.5Hz), 3.51(2H, t, J=6.3Hz), 4.04(2H, s), 4.19(1H, m), 6.17(1H, d, J=8.7Hz), 6.78 (1H, d, J=2.1Hz), 7.36(1H, d, J=3.9Hz), 7.64(1H, m), 7.75(1H, d, J=2.1Hz), 7.77(1H, m), 7.83(1H, d, J=3.9Hz); IR(Nujol) 3323, 1734, 1624, 1536, 1321, 1153, 1126cm$^{-1}$; [α]$_D^{25}$+20.4±0.6°(c=1.006, MeOH) Anal. (C$_{29}$H$_{35}$NO$_7$S$_2$.0.6H$_2$O) Calcd.(%): C, 59.59; H, 6.24; N, 2.40; S, 10.97 Found(%): C, 59.57; H, 6.12; N, 2.37; S, 10.77 |
| II-7M-393a | $^1$H-NMR(CDCl$_3$) δ 0.90(3H, t, J=7.2Hz), 0.91(1H, d, J=9.3Hz), 1.09(3H, s), 1.21(3H, s), 1.25–1.79(12H, m), 1.98(1H, m), 2.10(1H, m), 2.17–2.34(2H, m), 2.47(2H, t, J=7.7Hz), 3.23(2H, t, J=8.7Hz), 3.52(2H, t, J=6.3Hz), 4.04(2H, s), 4.21(1H, m), 4.62(2H, t, J=8.7Hz), 5.99(1H, d, J=9.0Hz), 6.93(1H, s), 6.98(1H, s), 7.07 (1H, d, J=3.9Hz), 7.31(1H, d, J=3.9Hz); IR(CHCl$_3$) 3058, 3448, 3429, 1780, 1732, 1643, 1529, 1500, 1466, 1419, 1248, 1124cm$^{-1}$; [α]$_D^{24}$+12.7±0.5°(c=1.014, MeOH) Anal.(C$_{32}$H$_{43}$NO$_5$S$_2$.0.2H$_2$O) Calcd.(%): C, 65.21; H, 7.42; N, 2.38; S, 10.88 Found(%): C, 65.09; H, 7.37; N, 2.35; S, 11.02 |
| II-7N-55a | $^1$H-NMR(CDCl$_3$) δ 0.92(1H, d, J=10.5Hz), 1.08 and 1.23(3H, s), 1.56(1H, ddd, J=2.7, 6.0, 13.5Hz), 1.90–2.46 (7H, m), 2.39(3H, s), 4.11(2H, d, J=1.2Hz), 4.14–4.19 (3H, m), 5.57–5.76(2H, m), 5.99(1H, m), 6.17–6.21 (2H, m), 7.19(1H, dd, J=1.8, 3.3Hz), 7.34(1H, d, J=3.9Hz), 7.55(1H, d, J=3.9Hz); IR(CHCl$_3$) 3446, 1732, 1657, 1529, 1504, 1375, 1182, 1161, 1142, 1119, 1053cm$^{-1}$; [α]$_D^{24}$+40.4±0.8°(c=1.001, MeOH) Anal. (C$_{25}$H$_{32}$N$_2$O$_6$S$_2$.0.3H$_2$O) Calcd.(%): C, 57.08 H, 6.25; N, 5.32; S, 12.19 Found(%): C, 57.07; H, 6.18; N, 5.39; S, 11.91 |
| II-7O-55a | $^1$H-NMR(CDCl$_3$) δ 0.92(1H, d, J=10.2Hz), 1.09 and 1.23(3H, s), 1.55(1H, ddd, J=2.7, 5.7, 13.5Hz), 1.85–2.40 (7H, m), 2.39(3H, s), 3.93–4.05(4H, m), 4.25(1H, m), 5.58–5.79(2H, m), 6.00(1H, m), 6.11(1H, d, J=9.0Hz), 6.20(1H, t, J=3.3Hz), 7.19(1H, dd, J=1.5, 3.3Hz), 7.32(1H, d, J=4.2Hz), 7.55(1H, d, J=4.2Hz); IR (CHCl$_3$) 3444, 1778, 1732, 1657, 1529, 1504, 1375, 1182, 1161, 1144, 1053cm$^{-1}$; [α]$_D^{24.5}$+15.8±0.6°(c=1.008, MeOH) Anal.(C$_{25}$H$_{32}$N$_2$O$_6$S$_2$.0.4H$_2$O) Calcd.(%): C, 56.88 H, 6.26; N, 5.31; S, 12.15 Found(%): C, 56.91; H, 6.17; N, 5.30; S, 12.14 |

TABLE 63

| Compd. No. | Physical property |
|---|---|
| II-7P-55a | $^1$H-NMR(CDCl$_3$) δ 0.89(1H, d, J=10.2Hz), 1.09(3H, s), 1.23(3H, s), 1.54(1H, m), 1.95–2.35(7H, m), 2.39(3H, s), 4.14–4.31(5H, m), 5.39(1H, dt, J=7.8Hz and 20.7Hz), 5.99(1H, m), 6.20(1H, m), 6.29(1H, d, J=5.4Hz), 7.18 (1H, m), 7.36(1H, d, J=3.9Hz), 7.53(1H, d, J=3.9Hz); IR(CHCl$_3$) 3446, 2925, 1732, 1655, 1531, 1504, 1375, 1161, 1142, 1053, 1022cm$^{-1}$; [α]$_D^{24}$+30.1±0.7°(c=1.01, MeOH) Anal.(C$_{25}$H$_{31}$FN$_2$O$_6$S$_2$.0.7MeOH) Calcd.(%): C, 55.01; H, 6.07; N, 4.99; F, 3.39; S, 11.43 Found(%): C, 55.21; H, 5.92; N, 5.11; F, 3.49; S, 11.16 |
| II-7P-55e | $^1$H-NMR(CDCl$_3$) δ 0.91(1H, d, J=10.2Hz), 1.10(3H, s), 1.25(3H, s), 1.97–2.37(8H, m), 2.39(3H, s), 3.28(3H, s), 3.99–4.28(5H, m), 5.41(1H, dt, J=8.7 and 20.4Hz), 5.99 (1H, m), 6.13(1H, d, J=8.4Hz), 6.20(1H, m), 7.19(1H, m), 7.33(1H, d, J=4.2Hz), 7.55(1H, d, J=4.2Hz); IR (CHCl$_3$) 3448, 3352, 2925, 1728, 1657, 1529, 1504, 1425, 1402, 1375, 1348, 1157, 1053, 1020cm$^{-1}$; [α]$_D^{24}$+32.7±1.5° (c=0.49, MeOH) Anal.(C$_{26}$H$_{34}$FN$_3$O$_7$S$_3$.0.45MeOH) Calcd.(%): C, 50.41; H, 5.73; N, 6.67; F, 3.01; S, 15.26 Found(%): C, 50.80; H, 5.81; N, 6.63; F, 2.85; S, 14.87 |
| II-7P-55j | $^1$H-NMR(CDCl$_3$) δ 0.90(1H, d, J=10.2Hz), 1.09(3H, s), 1.24(3H, s), 1.51–2.37(8H, m), 2.39(3H, s), 3.97(2H, s), 4.17–4.25(3H, m), 5.39(1H, dt, J=9.0 and 20.7Hz), 5.99 (1H, m), 6.20(1H, m), 6.37(1H, d, J=8.1Hz), 6.71(1H, m), 7.19(1H, m), 7.39(1H, d, J=3.9Hz), 7.55(1H, d, J=3.9Hz); IR(CHCl$_3$) 3519, 3402, 2925, 2870, 1745, 1689, 1657, 1574, 1529, 1504, 1471, 1448, 1375, 1161, 1144, 1092, 1053, 1022cm$^{-1}$; [α]$_D^{25}$+40.8±1.6°(c=0.51, MeOH) |
| II-7Q-55a | $^1$H-NMR(CDCl$_3$) δ 0.90(1H, d, J=10.2Hz), 1.11 and 1.23 (3H, s), 1.53(1H, ddd, J=2.1, 5.7, 13.5Hz), 1.70–2.38(7H, m), 2.38(3H, s), 3.52(2H, t, J=6.3Hz), 3.96–4.13(2H, m), 4.23(1H, m), 5.97–6.04(2H, m), 6.14(1H, d, J=9.3Hz), 6.20(1H, t, J=3.6Hz), 6.96(1H, dt, J=4.2, 15.6Hz), 7.18 (1H, m), 7.27(1H, d, J=3.9Hz), 7.54(1H, d, J=3.9Hz); IR(CHCl$_3$) 2925, 1701, 1657, 1529, 1504, 1375, 1215, 1182, 1161, 1142cm$^{-1}$; [α]$_{365}^{26}$ −42.1±0.8°(c=1.001%, MeOH); Anal.(C$_{25}$H$_{32}$N$_2$O$_6$S$_2$.0.4H$_2$O) Calcd.(%) C, 56.88; H, 6.26; N, 5.31; S, 12.15 Found(%) C, 56.95; H, 6.11; N, 5.35; S, 12.11 |
| II-7R-55a | $^1$H-NMR(CDCl$_3$) δ 0.92(1H, d, J=10.2Hz), 1.09 and 1.22 (3H, s), 1.35–2.40(12H, m), 2.39(3H, s), 2.64(2H, t, J=7.2Hz), 3.20(2H, s), 4.20(1H, m), 4.52(1H, brs), 5.99(1H, m), 6.16(1H, d, J=8.7Hz), 6.20(1H, t, J=3.3Hz), 7.19 (1H, dd, J=1.8, 3.3Hz), 7.31(1H, d, J=3.9Hz), 7.55(1H, d, J=3.9Hz); IR(CHCl$_3$) 3446, 2675, 2565, 1711, 1657, 1529, 1504, 1375, 1182, 1161, 1144, 1053cm$^{-1}$; [α]$_D^{24}$+23.5±0.6°(c=1.007, MeOH) Anal.(C$_{25}$H$_{34}$N$_2$O$_5$S$_3$.0.3H$_2$O) Calcd.(%): C, 55.18; H, 6.41; N, 5.15; S, 17.68 Found(%): C, 55.29; H, 6.31; N, 5.12; S, 17.46 |

TABLE 64

| Compd. No. | Physical property |
|---|---|
| II-7R-88a | $^1$H-NMR(CDCl$_3$) δ 0.93(1H, d, J=10.2Hz), 1.10 and 1.22(3H, s), 1.36–2.40(12H, m), 2.65(2H, t, J=6.9Hz), 3.17 and 3.22(each 1H, ABq, J=14.7Hz), 4.16(2H, s), 4.23(1H, m), 4.60(1H, brs), 6.04(1H, d, J=9.3Hz), 6.79(1H, brd, J=3.9Hz), 6.96(1H, dd, J=1.5, 5.1Hz), 7.05(1H, m), 7.28(1H, dd, J=3.0, 4.8Hz), 7.32(1H, d, J=3.6Hz); IR(CHCl$_3$) 3450, 3430, 1711, 1641, 1545, 1508, 1471, 1460, 1294, 1263, 1126cm$^{-1}$; [α]$_D^{24}$+18.0±0.6°(c=1.003, MeOH) Anal. (C$_{25}$H$_{33}$NO$_3$S$_3$.0.3H$_2$O) Calcd.(%): C, 60.40; H, 6.81; N, 2.82; S, 19.35 Found(%): C, 60.42; H, 6.60; N, 2.99; S, 19.47 |
| II-7R-270a | mp.150–152° C.; $^1$H-NMR(CDCl$_3$) δ 0.92(1H, d, J=10.5Hz), 1.09(3H, s), 1.23(3H, s), 1.34–2.38(12H, m), 2.42(6H, s), 2.64(2H, t, J=7.2Hz), 3.20(2H, s), 4.21(1H, m), 5.88(2H, s), 6.15(1H, d, J=9.0Hz), 7.29(1H, d, J=3.9Hz), 7.49(1H, d, J=3.9Hz); IR(Nujol) 3365, 3084, 1709, 1622, 1549, 1367, 1176, 1126cm$^{-1}$; [α]$_D^{27}$+22.7±0.6°(c=1.001, MeOH) Anal. (C$_{26}$H$_{36}$N$_2$O$_5$S$_3$.0.2(C$_6$H$_{14}$O)); Calcd.(%): C, 57.31; H, 6.86; N, 4.91; S, 16.88 Found(%): C, 57.18; H, 6.78; N, 4.89; S, 16.95 |
| II-7S-47a | $^1$H-NMR(CDCl$_3$) δ 0.86(1H, d, J=10.2Hz), 1.08 and 1.20(each 3H, s), 1.38–2.40(10H, m), 3.89–4.20(4H, m), 6.68–6.72(2H, d, m), 7.11(1H, dd, J=3.6, 4.8Hz), 7.44(1H, d, J=4.2Hz), 7.59(1H, d, J=4.2Hz), 7.71(1H, dd, J=3.6, 5.1Hz), 7.74(1H, dd, J=1.2, 3.9Hz); IR(CHCl$_3$) 3346, 3097, 1730, 1649, 1533, 1506, 1402, 1335, 1153, 1024cm$^{-1}$; [α]$_D^{24}$+27.5±0.7°(c=1.003, MeOH) Anal. (C$_{24}$H$_{30}$N$_2$O$_6$S$_3$.0.5H$_2$O) Calcd.(%): C, 52.63; H, 5.70; N, 5.11; S, 17.56 Found(%): C, 52.45; H, 5.39; N, 5.211; S, 17.62 |
| II-7S-55a | mp 99–101° C.; $^1$H-NMR(CDCl$_3$) δ 0.87(1H, d, J=10.2Hz), 1.08 and 1.21(each 3H, s), 1.40–2.40(10H, m), 2.38(3H, s), 3.91–4.20(3H, m), 5.99(1H, m), 6.20(1H, t, J=3.6Hz), 6.53–6.60(2H, d, m), 7.17(1H, dd, J=1.8, 3.3Hz), 7.41(1H, d, J=4.2Hz), 7.53(1H, d, J=4.2Hz); IR(Nujol) 3321, 3089, 1736, 1709, 1660, 1633, 1550, 1377, 1236, 1184, 1159, 1051cm$^{-1}$; [α]$_D^{24}$+28.5±0.7°(c=1.006, MeOH) Anal.(C$_{25}$H$_{33}$N$_3$O$_6$S$_2$) Calcd.(%): C, 56.05; H, 6.21; N, 7.84; S, 11.97 Found(%): C, 55.74; H, 6.17; N, 7.71; S, 11.81 |

TABLE 65

| Compd. No. | Physical property |
|---|---|
| II-7T-55a | $^1$H-NMR(CDCl$_3$) δ 0.86(1H×1/2, d, J=10.5Hz), 0.90(1H×1/2, d, J=10.5Hz), 1.05, 1.08, 1.20 and 1.22(each 3H×1/2, s), 1.40–2.57(10H, m), 2.39(3H, s), 4.18(1H, m), 4.47 and 4.57(each 1H×1/2, ABq, J=17.1Hz), 4.49 and 4.59(each 1H×1/2, ABq, J=17.1Hz), 5.99(1H, m), 6.20(1H, m), 6.36(1H, m), 6.73(1H×1/2, t, J=6.0Hz), 7.18(1H, m), 7.32(1H×1/2, d, J=3.9Hz), 7.38(1H×1/2, d, J=3.9Hz), 7.46(1H×1/2, t, J=6.0Hz), 7.53(1H, d, J=3.9Hz); IR(CHCl$_3$) 3446, 1765, 1732, 1655, 1531, 1504, 1375, 1182, 1161, 1144, 1053, 1022cm$^{-1}$; [α]$_D^{25}$ −4.2±0.4°(c=1.008, MeOH) Anal.(C$_{24}$H$_{31}$N$_3$O$_6$S$_2$) Calcd.(%): C, 55.26; H, 5.99; N, 8.06; S, 12.29 Found(%): C, 55.20; H, 5.88; N, 7.81; S, 11.94 |
| II-7U-31a | $^1$H-NMR(CDCl$_3$) δ 0.91(1H, d, J=10.2Hz), 1.10 and 1.22(3H, s), 1.47(1H, m), 1.64–2.63(12H, m), 4.13(2H, s), 4.20(1H, m), 6.07(1H, d, J=8.4Hz), 6.77(1H, d, J=3.9Hz), 7.22–7.36(6H, m); IR(CHCl$_3$) 2924, 1709, 1643, 1543, 1506, 1471, 1454, 1284, 1223, 1213, 1205cm$^{-1}$; [α]$_D^{26}$+25.1±1.3°(c=0.507%, MeOH); Anal. (C$_{27}$H$_{35}$NO$_3$S$_2$.0.3H$_2$O) Calcd.(%) C, 66.03; H, 7.31; N, 2.83; S, 13.06 Found(%) C, 66.03; H, 7.37; N, 2.96; S, 13.09 |

TABLE 65-continued

| Compd. No. | Physical property |
|---|---|
| II-7U-55a | $^1$H-NMR(CDCl$_3$) δ 0.89(1H, d, J=10.2Hz), 1.10 and 1.22(3H, s), 1.48(1H, ddd, J=2.4, 5.4, 13.2Hz), 1.65–2.60(12H, m), 2.40(3H, s), 4.18(1H, m), 5.99(1H, m), 6.20(1H, t, J=3.3Hz), 6.23(1H, d, J=8.4Hz), 7.19(1H, dd, J=1.8, 3.3Hz), 7.33(1H, d, J=4.2Hz), 7.55(1H, d, J=4.2Hz); IR(CHCl$_3$) 2925, 1741, 1709, 1657, 1529, 1504, 1375, 1221, 1211, 1207, 1182, 1161, 1144cm$^{-1}$; [α]$_D^{25}$+29.1±0.7°(c=1.008%, MeOH); Anal.(C$_{25}$H$_{34}$N$_2$O$_5$S$_3$.0.3H$_2$O) Calcd.(%) C, 55.18; H, 6.41; N, 5.15; S, 17.68 Found(%) C, 55.20; H, 6.25; N, 5.21; S, 17.71 |
| II-7U-88a | $^1$H-NMR(CDCl$_3$) δ 0.91(1H, d, J=10.2Hz), 1.11 and 1.22(3H, s), 1.47(1H, m), 1.64–2.63(12H, m), 4.16(2H, s), 4.21(1H, m), 6.08(1H, d, J=8.7Hz), 6.79(1H, d, J=3.9Hz), 6.96(1H, dd, J=1.2, 5.1Hz), 7.05(1H, m), 7.27–7.34(3H, m); IR(CHCl$_3$) 2924, 1709, 1643, 1543, 1508, 1471, 1284, 1238, 1217cm$^{-1}$; [α]$_D^{25}$+24.9±0.6°(c=1.014%, MeOH); Anal.(C$_{25}$H$_{33}$NO$_3$S$_3$.0.4H$_2$O) Calcd.(%) C, 60.18; H, 6.83; N, 2.81; S, 19.28 Found(%) C, 60.20; H, 6.77; N, 2.94; S, 19.34 |
| II-7V-55a | $^1$H-NMR(CDCl$_3$) δ 0.92(1H, d, J=10.8Hz), 1.09(3H, s), 1.23(3H, s), 1.26–2.34(14H, m), 2.39(3H, s), 4.20(1H, m), 5.99–6.07(2H, m), 6.13–6.29(2H, m), 7.19(1H, m), 7.29(1H, d, J=3.9Hz), 7.55(1H, d, J=3.9Hz); IR(CHCl$_3$) 3512, 3446, 2927, 2862, 2553, 1711, 1658, 1529, 1504, 1431, 1375, 1279cm$^{-1}$; [α]$_D^{26.0}$+16.0±1.1°(c=0.50, MeOH) 元素分(C$_{26}$H$_{33}$FN$_2$O$_5$S$_2$.0.6MeOH) Calcd.(%): C, 57.47; H, 6.42; N, 5.04; F, 3.42; S, 11.5 Found(%): C, 57.77; H, 6.28; N, 4.95; F, 3.33; S, 11.15 |

TABLE 66

| Compd. No. | Physical property |
|---|---|
| II-8C-55a | $^1$H-NMR(d$_6$-DMSO) δ 0.77(1H, d, J=9.6Hz), 1.03(3H, s), 1.12(3H, s), 1.13–1.52(9H, m), 1.89(1H, m), 2.06–2.30(4H, m), 2.32(3H, s), 3.39(2H, m), 3.62(2H, s), 3.84(1H, m), 6.10(1H, m), 6.27(1H, t, J=3.3Hz), 7.25(1H, dd, J=3.3, 1.5Hz), 7.87(1H, d, J=3.9Hz), 7.98(1H, d, J=3.9Hz), 8.45(1H, d, J=7.2Hz); IR(Nujol) 3332, 1623, 1536, 1457, 1375, 1182, 1160cm$^{-1}$; [α]$_D^{24.0}$+15.1±0.6°(c=1.006, DMSO) Anal.(C$_{26}$H$_{36}$N$_2$O$_6$S$_2$.2.0H$_2$O) Calcd.(%): C, 53.52; H, 7.04; N, 4.89; S, 11.10 Found(%): C, 53.38; H, 6.74; N, 4.82; S, 10.88 |
| II-8C-88a | $^1$H-NMR(d$_6$-DMSO) δ 0.77(1H, d, J=9.3Hz), 1.05(3H, s), 1.13(3H, s), 1.14–1.66(8H, m), 1.86–2.28(6H, m), 3.38(2H, m), 3.60(2H, s), 3.85(1H, m), 4.13(2H, s), 6.88(1H, d, J=3.6Hz), 6.99(1H, dd, J=5.1, 0.9Hz), 7.28(1H, m), 7.48(1H, dd, J=5.1, 3.0Hz), 7.67(1H, d, J=3.6Hz), 7.82(1H, d, J=7.2Hz); IR(Nujol) 3413, 1623, 1508, 1459, 1091cm$^{-1}$; [α]$_D^{24.0}$+12.6±1.1°(c=0.500, DMSO) Anal. (C$_{26}$H$_{35}$NO$_4$S$_2$.2.0H$_2$O) Calcd.(%): C, 58.40; H, 7.28; N, 2.66; S, 12.00 Found(%): C, 58.43; H, 7.01; N, 2.73; S, 11.73 |
| VI-6A-1a | $^1$H-NMR(CDCl$_3$) δ 0.86(1H, m), 1.04–1.66(15H, m), 1.95(1H, m), 2.15(1H, brs), 2.33(2H, t, J=7.5Hz), 3.26(1H, m), 3.49(1H, m), 6.33(2H, t, J=2.4Hz), 7.16(2H, t, J=2.4Hz), 7.33 and 7.57(each 1H, each d, each J=4.2Hz); IR(CHCl$_3$) 3514, 3446, 2679, 1709, 1658, 1535, 1509, 1456, 1385, 1274, 1192, 1192, 1167, 1057, 1034cm$^{-1}$; [α]$_D^{26}$+8.7±0.5°(c=1.002, MeOH) Anal. (C$_{23}$H$_{30}$N$_2$O$_5$S$_2$.0.1H$_2$O) Calcd.(%): C, 57.50; H, 6.34; N, 5.83; S, 13.35 Found(%): C, 57.56; H, 6.46; N, 5.91; S, 13.04 |
| VI-6A-47a | $^1$H-NMR(CDCl$_3$) δ 0.87(1H, m), 1.04–1.66(15H, m), 1.95(1H, m), 2.16(1H, brs), 2.33(2H, t, J=7.5Hz), 3.27(1H, m), 3.49(1H, m), 6.24(1H, brt), 7.11(1H, dd, J=3.6 and 4.8Hz), 7.39 and 7.63(each 1H, each d, each J=3.9Hz), 7.70(1H, dd, J=1.2 and 4.8Hz), 7.75(1H, dd, J=1.2 and 3.6Hz); IR(CHCl$_3$) 3514, 3446, 1709, 1657, 1533, 1506, |

TABLE 66-continued

| Compd. No. | Physical property |
|---|---|
| | 1402, 1336, 1153, 1097, 1024cm$^{-1}$; $[\alpha]_D^{26}$+7.4±0.5° (c=1.014, MeOH) Anal.(C$_{23}$H$_{29}$NO$_5$S$_3$·0.4H$_2$O) Calcd.(%): C, 55.93; H, 5.97; N, 2.79; S, 19.13 Found(%): C, 55.08; H, 6.09; N, 2.93; S, 19.03 |
| VI-6A-88a | $^1$H-NMR(CDCl$_3$) δ 0.87(1H, m), 1.04–1.68(15H, m), 1.94 (1H, m), 2.17(1H, brs), 2.33(2H, t, J=7.5Hz), 3.20(1H, m), 3.53(1H, m), 4.15(2H, s), 5.87(1H, brt), 6.78(1H, m), 6.96(1H, dd, J=1.2 and 5.1Hz), 7.05(1H, m), 7.28(1H, dd, J=3.0 and 5.1Hz), 7.34(1H, d, J=3.6Hz); IR(CHCl$_3$) 3516, 3452, 1709, 1645, 1547, 1513, 1462cm$^{-1}$; $[\alpha]_D^{26}$+ 8.4±0.5°(c=1.015, MeOH) Anal.(C$_{24}$H$_{31}$NO$_3$S$_2$·0.2H$_2$O) Calcd.(%): C, 64.17; H, 7.04; N, 3.12; S, 14.28 Found(%): C, 64.16; H, 7.13; N, 3.18; S, 14.09 |

TABLE 67

| Compd. No. | Physical property |
|---|---|
| VII-GA-1a | $^1$H-NMR (CDCl$_3$) δ 0.86 (1H, m), 1.08–1.60 (15H, m), 1.95(1H, m), 2.15 (1H, brs), 2.33 (2H, t, J=7.5 Hz), 3.26 (1H, m), 3.49 (1H, m), 6.15 (1H, brt, J=5.1 Hz), 6.33 (2H, t, J=2.4 Hz), 7.16 (2H, t, J=2.4 Hz), 7.33 and 7.57 (each 1H, each d, each J=3.9 Hz); IR (CHCl$_3$) 3514, 3446, 2677, 1709, 1660, 1533, 1508, 1456, 1385, 1275, 1192, 1167, 1057, 1034 cm$^{-1}$; $[\alpha]_D^{24}$ − 7.6 ± 0.5° (c=1.006 MeOH) Anal. (C$_{23}$H$_{30}$N$_2$O$_5$S$_2$·0.3H$_2$O) Calcd.(%): C, 57.07; H, 6.37; N, 5.79; S, 13.25 Found (%): C, 57.16; H, 6.27; N, 5.81; S, 13.19 |
| VII-6A-47a | $^1$H-NMR (CDCl$_3$) δ 0.87 (1H, m), 1.10–1.63 (15H, m), 1.95 (1H, m), 2.16 (1H, brs), 2.33 (2H, t, J=7.5 Hz), 3.27 (1H, m), 3.49 (1H, m), 6.23 (1H, brt, J=5.6 Hz), 7.11 (1H, dd, J=3.9 and 5.1 Hz), 7.38 and 7.63 (each 1H, each d, each J=3.9 Hz), 7.70 (1H, dd, J=1.5 and 5.1 Hz), 7.75 (1H, dd, J=1.5 and 3.9 Hz); IR (CHCl$_3$) 3514, 3446, 1709, 1657, 1533, 1506, 1402, 1336, 1275, 1153, 1097, 1024 cm$^{-1}$; $[\alpha]_D^{24}$ − 8.1 ± 0.5° (c=1.008, MeOH) Anal. (C$_{23}$H$_{29}$NO$_5$S$_3$·0.3H$_2$O) Calcd.(%): C, 55.13; H, 5.95; N, 2.80; S, 19.20 Found (%): C, 55.15; H, 5.94; N, 3.06; S, 19.14 |
| VII-6A-88a | $^1$H-NMR (CDCl$_3$) δ 0.86 (1H, m), 1.09–1.61 (15H, m), 1.94 (1H, m), 2.17 (1H, brs), 2.32 (2H, t, J=7.5 Hz), 3.21 (1H, m), 3.52 (1H, m), 4.15 (2H, s), 5.89 (1H, brt, J=5.4 Hz), 6.78 (1H, d, J=3.6 Hz), 6.96 (1H, dd, J=1.8 and 5.1 Hz), 7.05 (1H, m), 7.28 (1H, dd, J=3.0 and 5.1 Hz), 7.34 (1H, d, J=3.6 Hz); IR (CHCl$_3$) 3517, 3450, 1709, 1645, 1547, 1514, 1462 cm$^{-1}$; $[\alpha]_D^{24}$ − 9.4 ± 0.5° (c=1.012, MeOH) Anal. (C$_{24}$H$_{31}$NO$_3$S$_2$) Calcd.(%): C, 64.68; H, 7.01; N, 3.14; S, 14.39 Found (%): C, 64.51; H, 6.90; N, 3.17; S, 14.53 |

The structure and physical property of the compound prepared as the example of reference are shown below. A compound with a beginning number "I-" means a compound of the formula:

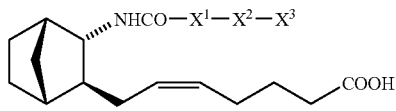

A compound with a beginning number "II-" means a compound of the formula:

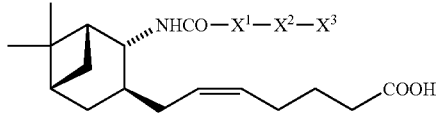

A compound with a beginning number "III-" means a compound of the formula:

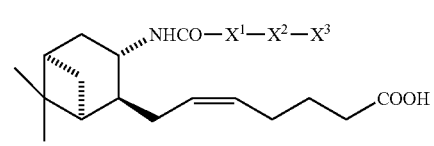

A compound with a beginning number "IV-" means a compound of the formula:

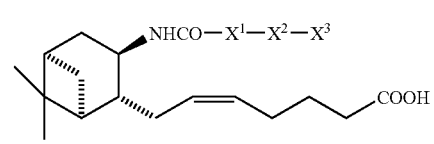

A compound with a beginning number "V-" means a compound of the formula:

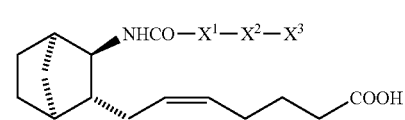

A compound with a beginning number "VI-" means a compound of the formula:

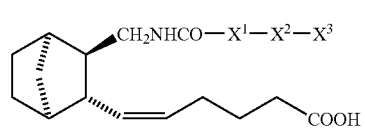

Furthermore, a number following the number (I, II, III, IV, V, and VI) represents a structure of the group of the formula: —X$^1$—X$^2$—X$^3$ and each number is the same meaning as that used in the list of the structure of the formula: —X$^1$—X$^2$—X$^3$.

Compound Number I-1 mp.113–114° C.; $^1$H-NMR(CDCl$_3$) δ: 1.09(1H, m), 1.17–1.32(2H, m), 1.34–1.52(2H, m), 1.56–1.75(4H, m), 2.00–2.18(5H, m), 2.35 (2H, t, J=7.2 Hz), 2.52(1H, m), 3.80(1H, m), 5.31–5.43(2H, m), 6.22(1H, d, J=6.0 Hz), 6.35 and 7.17(each 2H, each t, each J=2.1 Hz), 7.37 and 7.56 (each 1H, each d, each J=3.9 Hz). IR(Nujol): 3369, 3143, 3124, 3068, 2678, 1710, 1626, 1593, 1374, 1200, 1171 cm$^{-1}$. $[\alpha]_D^{26.5}$+75.5±1.2°(c=1.004, MeOH) Anal.

($C_{23}H_{28}N_2O_5S_2$) Calcd.(%): C, 57.96.; H, 5.92; N, 5.88; S, 13.45. Found(%): C, 57.99; H, 5.88; N, 5.66; S, 13.50.

Compound Number I-3

$^1$H-NMR (CDCl$_3$-CD$_3$OD) δ: 1.23(1H, m), 1.28–1.32 (2H, m), 1.44–1.53(2H, m), 1.57–1.74(4H, m), 2.03–2.14 (5H, m), 2.32(2H, t, J=7.2 Hz), 2.56(1H, m), 3.82(1H, m), 5.33–5.47(2H, m), 6.80(1H, m), 7.09–7.12(2H, m), 7.22(1H, t, J=8.1 Hz), 7.63 and 7.86(each 1H, each d, each J=8.1 Hz). IR(CHCl$_3$): 3593 3442, 3111, 1710, 1644, 1519, 1449 cm$^{-1}$. $[α]_D^{25}$+77.6±1.20°(c=1.010, MeOH) Anal. ($C_{25}H_{29}NO_4S.0.2H_2O$) Calcd.(%): C, 67.76; H, 6.69; N, 3.16; S, 7.23. Found(%): C, 67.64; H, 6.77; N, 3.17; S, 7.18.

Compound Number I-4

$^1$H-NMR(CDCl$_3$) δ: 1.06(1H, m), 1.17–1.32(2H, m), 1.40–1.50(2H, m), 1.56–1.80 (4H, m), 2.00–2.22(5H, m), 2.33(2H, t, J=7.2 Hz), 2.53(1H, m), 3.84 (3H, s), 3.85(1H, m), 5.29–5.42(2H, m), 6.18(1H, d, J=6.9 Hz), 6.93, 7.10, 7.44 and 7.59 (each 2H, each d-like). IR(CHCl$_3$): 3516, 3448, 1708, 1650, 1594, 1514, 1494, 1483, 1288, 1248, 1032 cm$^{-1}$. $[α]_D^{26}$+82.8±1.2°(c=1.000, MeOH) Anal. ($C_{28}H_{33}NO_4S.0.2H_2O$) Calcd.(%): C, 69.59; H, 6.97; N, 2.90; S, 6.64. Found(%): C, 69.69; H, 6.93; N, 3.20; S, 6.57.

Compound Number I-5

$^1$H-NMR(CDCl$_3$) δ: 1.06(1H, m), 1.16–1.32(2H, m), 1.36–1.50(2H, m), 1.54–1.80 (4H, m), 2.00–2.22(5H, m), 2.34(2H, t, J=7.2 Hz), 2.53(1H, m), 3.82 (1H, m), 3.83(3H, s), 5.29–5.42(2H, m), 6.14(1H, d, J=7.2 Hz), 6.92 (2H, d-like), 7.20–7.30(2H, m), 7.41–7.51(4H, m). IR(CHCl$_3$): 3509, 3444, 2666, 1708, 1654, 1592, 1570, 1510, 1494, 1468, 1288, 1247, 1082 cm$^{-1}$. $[α]_D^{26}$+58.4±1.4°(c=0.704, MeOH) Anal. ($C_{28}H_{33}NO_4S.0.2H_2O$) Calcd.(%): C, 69.59; H, 6.97; N, 2.90; S, 6.64. Found(%): C, 69.55; H, 6.93; N, 3.03; S, 6.57.

Compound Number I-6

$^1$H-NMR(CDCl$_3$) δ: 1.11(1H, m), 1.20–1.34(2H, m), 1.42–1.52(2H, m), 1.56–1.78(4H, m), 2.00–2.23(5H, m), 2.35(2H, t, J=7.2 Hz), 2.57(1H, m), 3.89 (1H, m), 5.31–5.45 (2H, m), 6.30(1H, d, J=7.2 Hz), 6.37 and 7.12(each 2H, each 2H, each J=2.1 Hz), 7.42 and 7.83(each 2H, each d-like). IR(CHCl$_3$): 3518, 3448, 2662, 1708, 1653, 1609, 1499, 1334 cm$^{-1}$. $[α]_D^{23}$+94.9±1.3°(c=1.005, MeOH) Anal. ($C_{25}H_{30}N_2O_3.0.1H_2O$) Calcd.(%): C, 73.54; H, 7.45; N, 6.86. Found(%): C, 73.43; H, 7.46; N, 7.01.

Compound Number I-7

$^1$H-NMR(CDCl$_3$) δ: 1.12–1.76(9H, m), 1.96–2.24(5H, m), 2.33(2H, t, J=7.2 Hz), 2.53(1H, m), 3.86(1H, m), 5.30–5.47(2H, m), 6.60(1H, d, J=6.9 Hz), 7.05–7.23(5H, m), 7.55(1H, brs), 7.67 and 7.74(each 2H, each d, each J=8.7 Hz). IR(CHCl$_3$): 3516, 3439, 3368, 1708, 1653, 1600, 1519, 1496, 1487, 1401, 1347, 1165 cm$^{-1}$. $[α]_D^{25}$+69.9±1.1° (c=1.019, MeOH) Anal. ($C_{27}H_{34}N_2O_5S.0.1H_2O$) Calcd.(%): C, 64.80; H, 6.89; N, 5.60; S, 6.41. Found(%): C, 64.73; H, 6.56; N, 5.74; S, 6.41.

Compound Number I-8

$^1$H-NMR(CDCl$_3$) δ: 1.19–1.27(3H, m), 1.35–1.43(2H, m), 1.55–1.80(4H, m), 1.90–2.08(3H, m), 2.11–2.21(2H, m), 2.34(2H, t, J=7.2 Hz), 2.53(1H, m), 3.74 (1H, m), 5.29–5.48(2H, m), 6.44(1H, d, J=6.9 Hz), 7.15(1H, d, J=1.5 Hz), 7.46(2H, t, J=7.8 Hz), 7.57(1H, m), 7.60(1H, d, J=1.5 Hz), 7.76–7.78 (2H, m), 7.89(1H, bs). IR(CHCl$_3$): 3440, 3360, 3107, 1708, 1637, 1518, 1448, 1329, 1163 cm$^{-1}$. $[α]_D^{20}$+55.5±1.0°(c=1.003, MeOH) Anal. ($C_{25}H_{30}N_2O_5S_2.0.2H_2O$) Calcd.(%): C, 59.31; H, 6.05; N, 5.53; S, 12.67. Found(%): C, 59.19; H, 6.12; N, 5.66; S, 12.50.

Compound Number I-9 mp.193–194° C.; $^1$H-NMR (d$_6$-DMSO) δ: 1.18–1.59 (9H, m), 1.93 (1H, d, J=2.4 Hz), 1.99–2.07(4H, m), 2.21(2H, t, J=7.2 Hz), 2.36(1H, m), 5.30–5.40(2H, m), 7.25(1H, d, J=1.5 Hz), 7.54–7.63(3H, m), 7.69(1H, d, J=1.5 Hz), 7.99–8.02 (3H, m), 11.6(1H, s), 12.00(1H, brs). IR(Nujol): 3367, 3221, 3186, 3091, 3055, 2654, 1711, 1631, 1566, 1541, 1321 cm$^{-1}$. $[α]_D^{21}$+74.6±1.1°(c=1.006, MeOH) Anal. ($C_{26}H_{30}N_2O_4S$) Calcd.(%): C, 66.93; H, 6.48; N, 6.00; S, 6.87. Found(%): C, 66.76; H, 6.44; N, 5.88; S, 6.76.

Compound Number I-10

$^1$H-NMR(CDCl$_3$) δ: 1.08(1H, m), 1.18–1.34(2H, m), 1.40–1.50(2H, m), 1.56–1.77(4H, m), 2.00–2.20(5H, m), 2.35(2H, t, J=7.2 Hz), 2.55(1H, m), 3.86 (1H, m), 5.31–5.54 (2H, m), 6.26(1H, d, J=7.8 Hz), 6.31 and 7.14(each 2H, each t, each J=2.1 Hz), 7.84 and 7.88(each 2H, each d, each J=8.4 Hz). IR(CHCl$_3$): 3515, 3441, 3144, 2669, 1708, 1662, 1515, 1486, 1455, 1376 cm$^{-1}$. $[α]_D^{22}$+77.4±1.2°(c=1.004, MeOH) Anal. ($C_{25}H_{30}N_2O_5S.0.2H_2O$) Calcd.(%): C, 63.32; H, 6.46; N, 6.91; S, 6.76. Found(%): C, 63.23; H, 6.49; N, 5.88; S, 6.67.

Compound Number I-11

$^1$H-NMR(CDCl$_3$) δ: 1.06(1H, m), 1.18–1.29(2H, m), 1.42–1.46(2H, m), 1.56–1.79 (4H, m), 2.03–2.20(5H, m), 2.34(2H, t, J=7.2 Hz), 2.52(1H, m), 3.82(1H, m), 4.12(2H, s), 5.29–5.43(2H, m), 6.04(1H, d, J=7.5 Hz), 7.09(1H, d, J=1.5 Hz), 7.22–7.34(5H, m), 7.67(1H, d, J=1.5 Hz). IR (CHCl$_3$): 3517, 3446, 2669, 1708, 1647, 1549, 1508, 1454 cm$^{-1}$. $[α]_D^{21.5}$+68.8±1.1°(c=1.016, MeOH) Anal. ($C_{26}H_{31}NO_3S.0.1H_2O$) Calcd.(%): C, 71.07; H, 7.16; N, 3.19; S, 7.30. Found(%): C, 71.05; H, 7.11; N, 3.38; S, 7.33.

Compound Number I-12

$^1$H-NMR(CDCl$_3$) δ: 1.09(1H, m), 1.10–1.30(2H, m), 1.40–1.46(2H, m), 1.56–1.77 (4H, m), 2.00–2.22(5H, m), 2.33(2H, t, J=7.2 Hz), 2.52(1H, m), 3.83(1H, m), 5.28–5.42 (2H, m), 6.26(1H, d, J=6.9 Hz), 7.15 and 7.63(each 2H, each d, each J=8.7 Hz), 7.53(1H, m), 7.78–7.82(2H, m). IR(CHCl$_3$): 3515, 3446, 3371, 3138, 1708, 1648, 1610, 1496, 1163 cm$^{-1}$. $[α]_D^{22.5}$+66.5±1.1°(c=1.004, MeOH) Anal. ($C_{27}H_{34}N_2O_5S.0.4H_2O$) Calcd.(%): C, 64.11; H, 6.93; N, 5.54; S, 6.34. Found(%): C, 64.05; H, 6.63; N, 5.56; S, 6.12.

Compound Number I-13

$^1$H-NMR(CDCl$_3$) δ: 1.19–1.31(3H, m), 1.36–1.44(2H, m), 1.55–1.78(4H, m), 1.85–2.02(2H, m), 2.05(1H, m), 2.13–2.47(4H, m), 2.57(1H, m), 3.71(1H, m), 5.31–5.54(2H, m), 6.53(1H, d, J=6.9 Hz), 7.14–7.32(5H, m), 7.47(1H, br), 8.05 and 8.13 (each 1H, each d, each J=1.5 Hz). IR(CHCl$_3$): 3509, 3360, 3262, 1709, 1649, 1542, 1496, 1349, 1160 cm$^{-1}$. $[α]_D^{23}$+59.1±1.1°(c=1.001, MeOH) Anal. ($C_{25}H_{30}N_2O_5S_2.0.2H_2O$) Calcd.(%): C, 59.31; H, 6.05; N, 5.53; S, 12.67. Found(%): C, 59.17; H, 6.01; N, 5.49; S, 12.37.

Compound Number I-14

$^1$H-NMR(CDCl$_3$) δ: 1.18–1.32(3H, m), 1.38–1.47(2H, m), 1.55–1.78(4H, m), 1.90–2.08(3H, m), 2.15–2.31(2H, m), 2.32–2.49(2H, m), 2.59(1H, m), 3.74 (1H, m), 5.33–5.53 (2H, m), 6.35 and 7.17(each 2H, each t, each J=2.4 Hz), 6.47(1H, d, J=6.3 Hz), 8.21 and 8.22(each 1H, each d, each J=1.5 Hz). IR(CHCl$_3$): 3506, 3412, 3144, 3107, 1727, 1709, 1656, 1540, 1504, 1456, 1382, 1166 cm$^{-1}$. $[α]_D^{23}$+

63.8±1.0°(c=1.005, MeOH) Anal. (C$_{23}$H$_{28}$N$_2$O$_5$S$_2$.0.2H$_2$O) Calcd.(%): C, 57.53; H, 5.96; N, 5.83; S, 13.35. Found(%): C, 57.44; H, 5.96; N, 6.00; S, 13.35.

Compound Number I-15 mp.128–130° C.; $^1$H-NMR(CDCl$_3$) δ: 1.16–1.34(3H, m), 1.40–1.81(6H, m), 2.37 (2H, t, J=7.2 Hz), 2.57(1H, m), 3.89(1H, m), 5.35–5.51(2H, m), 6.37 and 7.20 (each 2H, each d, each J=2.4 Hz), 7.23(1H, d, J=8.7 Hz). IR (Nujol): 3371, 3097, 2662, 1716, 1703, 1671, 1652, 1530, 1367, 1361, 1187, 1162 cm$^{-1}$. [α]$_D^{25}$+47.5±0.9°(c=1.003, MeOH) Anal. (C$_{23}$H$_{28}$N$_2$O$_5$S$_2$) Calcd.(%): C, 57.96; H, 5.92; N, 5.88; S, 13.45. Found(%): C, 58.05; H, 5.91; N, 5.83; S, 13.38.

Compound Number I-16

$^1$H-NMR(CDCl$_3$) δ: 1.09(1H, m), 1.20–1.32(2H, m), 1.42–1.47(2H, m), 1.58–1.75(4H, m), 2.01(3H, d, J=2 Hz), 2.00–2.16(5H, m), 2.35(2H, t, J=7.2 Hz), 2.55(1H, m), 3.86(1H, m), 5.31–5.44(2H, m), 6.14(1H, dd, J=1.5 and 3.0 Hz), 6.29(1H, d, J=7.5 Hz), 6.86(1H, m), 7.04(1H, t, J=3.0 Hz), 7.84 (4H, s). IR(CHCl$_3$): 3517, 3441, 2667, 1708, 1661, 1515, 1485, 1375, 1260, 1178 cm$^{-1}$. [α]$_D^{25}$+73.8±1.1° (c=1.001, MeOH) Anal. (C$_{26}$H$_{32}$N$_2$O$_5$S.0.1H$_2$O) Calcd.(%): C, 64.20; H, 6.67; N, 5.76; S, 6.59. Found(%): C, 64.14; H, 6.65; N, 5.85; S, 6.86.

Compound Number I-17

$^1$H-NMR(CDCl$_3$) δ: 1.20–1.31(3H, m), 1.40–1.47(2H, m), 1.57–1.80(4H, m), 2.00–2.30(5H, m), 2.37(2H, t, J=6.9 Hz), 2.60(1H, m), 3.84(1H, m), 5.32–5.50(2H, m), 6.32(2H, t, J=2.4 Hz), 6.63(1H, d, J=6.6 Hz), 7.16(2H, t, J=2.4 Hz), 7.55(1H, t, J=8.0 Hz), 7.89(1H, m), 8.06(1H, d, J=7.8 Hz), 8.30(1H, t, J=1.7 Hz). IR(CHCl$_3$): 3394, 3145, 1726, 1709, 1659, 1374 cm$^{-1}$. [α]$_D^{25}$+60.3±1.0°(c=1.000, MeOH) Anal. (C$_{25}$H$_{30}$N$_2$O$_5$S.0.2H$_2$O) Calcd.(%): C, 63.32; H, 6.46; N, 5.91; S, 6.76. Found(%): C, 63.39; H, 6.50; N, 6.16; S, 6.80.

Compound Number I-18

$^1$H-NMR(CDCl$_3$) δ: 1.10(1H, m), 1.20–1.32(2H, m), 1.45 (2H, t, J=6.9 Hz), 1.58–1.74(4H, m), 2.04–2.16(5H, m), 2.28(3H, s), 2.35(2H, t, J=6.9 Hz), 2.55 (1H, m), 3.87(1H, m), 5.31–5.44(2H, m), 5.96(1H, m), 6.18(1H, t, J=3.3 Hz), 6.32 (1H, d, J=7.5 Hz), 7.25(1H, dd, J=1.8 and 3.3 Hz), 7.78 and 7.85(each 2H, each d, each J=8.7 Hz). IR(CHCl$_3$): 3514, 3441, 1708, 1661, 1515, 1487, 1368, 1164 cm$^{-1}$. [α]$_D^{25}$+ 74.0±1.1°(c=1.004, MeOH) Anal. (C$_{26}$H$_{32}$N$_2$O$_5$S.0.2H$_2$O) Calcd.(%): C, 63.96; H, 6.69; N, 5.74; S, 6.57. Found(%): C, 63.97; H, 6.69; N, 5.98; S, 6.54.

Compound Number I-19

$^1$H-NMR(CDCl$_3$) δ: 1.07(1H, m), 1.18–1.31(2H, m), 1.41–1.49(2H, m), 1.56–1.76(4H, m), 2.00–2.21(5H, m), 2.34(2H, t, J=7.2 Hz), 2.55(1H, m), 3.86 (1H, m), 5.09(2H, s), 5.29–5.43(2H, m), 6.19(2H, t, J=2.1 Hz), 6.25(1H, d, J=7.5 Hz), 6.67(1H, t, J=2.1 Hz), 7.13 and 7.70(each d, each J=8.4 Hz). IR(CHCl$_3$): 3517, 3446, 3103, 2667, 1708, 1653, 1523, 1497 cm$^{-1}$. [α]$_D^{25}$+57.7±1.0°(c=1.010, MeOH) Anal. (C$_{26}$H$_{32}$N$_2$O$_3$) Calcd.(%): C, 73.63; H, 7.70; N, 6.60. Found(%): C, 73.72; H, 7.77; N, 6.76.

Compound Number I-20

$^1$H-NMR(CDCl$_3$) δ: 1.05(1H, m), 1.15–1.30(2H, m), 1.36–1.45(2H, m), 1.55–1.72 (4H, m), 2.00–2.14(5H, m), 2.32(2H, t, J=7.2 Hz), 2.51(1H, m), 3.82 (1H, m), 5.28–5.42 (2H, m), 6.22(2H, d, J=7.5 Hz), 6.68(1H, d, J=3.6 Hz), 7.22–7.34(2H, m), 7.52–7.55(2H, m), 7.76 and 7.88(each 2H, each d, each J=8.7 Hz), 7.97 (1H, d, J=8.1 Hz). IR(CHCl$_3$): 3510, 3480, 3440, 3145, 3117, 1708, 1661, 1516, 1485, 1445, 1377, 1130 cm$^{-1}$. [α]$_D^{25}$+65.9±1.1° (c=1.010, MeOH) Anal. (C$_{29}$H$_{32}$N$_2$O$_5$S.0.3H$_2$O) Calcd.(%): C, 66.21; H, 6.25; N, 5.33; S, 6.10. Found(%): C, 66.34; H, 6.30; N, 5.63; S, 5.84.

Compound Number I-21

$^1$H-NMR(CDCl$_3$) δ: 1.13(1H, m), 1.20–1.31(2H, m), 1.44 (2H, t, J=6.8 Hz), 1.59–1.72(4H, m), 2.03–2.20(5H, m), 2.32(2H, t, J=7.2 Hz), 2.54(1H, m), 3.83 (1H, m), 4.62(2H, s), 5.31–5.45(2H, m), 6.25–6.26(2H, m), 6.57(1H, d, J=7.2 Hz), 7.25(1H, m), 7.81(4H, s). IR(CHCl$_3$): 3581, 3518, 3440, 3149, 1708, 1660, 1517, 1486, 1371, 1150 cm$^{-1}$. [α]$_D^{27}$+72.2±1.1°(c=1.007, MeOH) Anal. (C$_{26}$H$_{32}$N$_2$O$_6$S) Calcd.(%): C, 62.38; H, 6.44; N, 5.60; S, 6.40. Found(%): C, 62.17; H, 6.52; N, 5.71; S, 6.40.

Compound Number I-22

$^1$H-NMR(d$_6$-DMSO) δ: 1.18–1.33(3H, m), 1.43–1.60(6H, m), 1.92–2.30(5H, m), 2.20(2H, t, J=7.5 Hz), 2.38(1H, m), 3.67(1H, m), 5.30–5.36(2H, m), 6.85 (1H, d, J=4.8 Hz), 7.27(1H, d, J=4.8 Hz), 7.86 and 7.94(each 2H, each d, each J=8.7 Hz), 8.37(1H, d, J=6.9 Hz). IR(KBr): 3360, 3151, 3103, 1707, 1635, 1569, 1530, 1328, 1284, 1140 cm$^{-1}$. [α]$_D^{27}$+67.4±1.1°(c=1.007, DMSO) Anal. (C$_{24}$H$_{29}$N$_3$O$_5$S$_2$.0.3H$_2$O) Calcd.(%): C, 56.62; H, 5.86; N, 8.24; S, 12.60. Found(%): C, 56.74; H, 5.96; N, 8.30; S, 12.31.

Compound Number I-23 mp.231–232° C.; $^1$H-NMR(d$_6$-DMSO) δ: 1.19–1.61(9H, m), 1.95–2.08(5H, m), 2.21(2H, t, J=7.2 Hz), 2.40(1H, m), 3.71(1H, m), 5.34–5.37(2H, m), 7.31 and 7.59(each 1H, each d, each J=3.6 Hz), 7.98 and 8.16(each 2H, each d, each J=8.7 Hz), 8.41(1H, d, J=7.2 Hz). IR(KBr): 3336, 3185, 2541, 1675, 1631, 1548, 1324, 1295, 1163 cm$^{-1}$. [α]$_D^{27}$+ 84.5±1.3°(c=1.000, DMSO) Anal. (C$_{24}$H$_{29}$N$_3$O$_4$S) Calcd. (%):.C, 64.22; H, 6.25; N, 8.99; S, 6.86. Found(%): C, 64.13; H, 6.10; N, 8.92; S, 7.08.

Compound Number I-24

$^1$H-NMR(CDCl$_3$) δ: 1.14(1H, m), 1.22–1.35(2H, m), 1.44–1.53(2H, m), 1.58–1.78 (4H, m), 2.02–2.28(5H, m), 2.36(2H, t, J=7.2 Hz), 2.58(1H, m), 3.87(1H, m), 5.15–5.48 (2H, m), 6.29 and 7.18(each 2H, each t, J=2.4 Hz), 6.38(1H, d, J=7.2 Hz), 7.77(1H, dd, J=1.8 and 8.7 Hz), 7.82(1H, s), 7.91(1H, d, J=8.7 Hz), 8.34(1H, d, J=1.8 Hz). IR(CHCl$_3$): 3512, 3441, 3423, 3144, 2670, 1708, 1530, 1501, 1374, 1164 cm$^{-1}$. [α]$_D^{26}$+96.1±1.4°(c=1.006, MeOH) Anal. (C$_{27}$H$_{30}$N$_2$O$_5$S$_2$.0.2H$_2$O) Calcd.(%): C, 61.16; H, 5.78; N, 5.28; S, 12.09. Found(%): C, 61.17; H, 5.74; N, 5.35; S, 12.12.

Compound Number I-25

$^1$H-NMR(CDCl$_3$) δ: 1.06(1H, m), 1.17–1.31(2H, m), 1.39–1.48(2H, m), 1.56–1.77(4H, m), 1.99–2.20(5H, m), 2.34(2H, t, J=7.2 Hz), 2.53(1H, m), 3.84 (1H, m), 5.29–5.42 (2H, m), 6.20(1H, d, J=7.2 Hz), 7.10–7.17(3H, m), 7.32 (1H, dd, J=1.2 and 3.6 Hz), 7.54(1H, dd, J=1.2 and 5.4 Hz), 7.60–7.64 (2H, m). IR(CHCl$_3$): 3518, 3447, 2669, 1708, 1651, 1596, 1515, 1483 cm$^{-1}$. [α]$_D^{26}$+84.7±1.2°(c=1.003, MeOH) Anal. (C$_{25}$H$_{29}$NO$_3$S$_2$.0.1H$_2$O) Calcd.(%): C, 65.64; H, 6.43; N, 3.06; S, 14.02. Found(%): C, 65.58; H, 6.41; N, 3.10; S, 13.82.

Compound Number I-26

$^1$H-NMR(CDCl$_3$) δ: 1.13(1H, m), 1.20–1.33(2H, m), 1.41–1.50(2H, m), 1.56–1.77(4H, m), 2.00–2.21(5H, m), 2.37(2H, t, J=7.2 Hz), 2.55(1H, m), 3.87(1H, m), 5.31–5.45 (2H, m), 6.48(1H, d, J=7.2 Hz), 7.10(1H, dd, J=3.9 and 5.1 Hz), 7.68(1H, dd, J=1.2 and 5.1 Hz), 7.69(1H, dd, J=1.2 and 3.9 Hz), 7.84–7.88 and 7.95–7.99(each 2H, each m).

IR(CHCl$_3$): 3518, 3441, 3382, 1708, 1659, 1515, 1329, 1158 cm$^{-1}$. [α]$_D^{26}$+75.7±1.2°(c=1.000, MeOH) Anal. (C$_{25}$H$_{29}$NO$_5$S$_2$) Calcd.(%): C, 61.58; H, 5.99; N, 2.87; S, 13.15. Found(%): C, 61.36; H, 6.05; N, 2.91; S, 13.13.

Compound Number I-27 mp.213–215° C.; $^1$H-NMR(d$_6$-DMSO) δ: 1.18–1.61(9H, m), 1.95–2.10 (5H, m), 2.21(2H, t, J=7.5 Hz), 2.40(1H, m), 3.71(1H, m), 5.33–5.38(2H, m), 7.19(1H, m), 7.87(1H, m), 7.96 and 8.10(each 2H, each d, each J=8.2 Hz), 8.21(1H, d, J=8.6 Hz), 8.40(1H, m), 10.92(1H, s), 12.05(1H, brs). IR (Nujol): 3337, 3249, 3205, 3132, 2524, 1678, 1632, 1545, 1433, 1305 cm$^{-1}$. [α]$_D^{23}$+85.2±2.5°(c=0.505, MeOH) Anal. (C$_{27}$H$_{31}$N$_3$O$_4$.0.3H$_2$O) Calcd.(%): C, 69.72; H, 6.80; N, 9.03. Found(%): C, 69.76; H, 6.75; N, 8.76.

Compound Number I-28

$^1$H-NMR(CDCl$_3$) δ: 1.07(1H, m), 1.18–1.32(2H, m), 1.40–1.50(2H, m), 1.56–1.78(4H, m), 2.00–2.21(5H, m), 2.34(2H, t, J=7.2 Hz), 2.54(1H, m), 3.85 (1H, m), 5.29–5.42 (2H, m), 6.17(1H, d, J=6.9 Hz), 7.07(1H, dd, J=1.2 and 5.1 Hz), 7.15(2H, d J=8.7 Hz), 7.43(1H, dd, J=3.0 and 5.1 Hz), 7.51(1H, dd, J=1.2 and 3.0 Hz), 7.62(2H, d, J=8.7 Hz). IR(CHCl$_3$): 3510, 3447, 3110, 2666, 1708, 1651, 1596, 1515, 1482 cm$^{-1}$. [α]$_D^{27}$+85.9±1.3°(c=1.007, MeOH) Anal. (C$_{25}$H$_{29}$NO$_3$S$_2$) Calcd.(%): C, 65.90; H, 6.42; N, 3.07; S, 14.07. Found(%): C, 65.60; H, 6.36; N, 3.36; S, 13.86.

Compound Number I-29 mp.123–125° C.; $^1$H-NMR (CDCl$_3$) δ: 1.12(1H, m), 1.18–1.34(2H, m), 1.42–1.50(2H, m), 1.56–1.78(4H, m), 2.02–2.21(5H, m), 2.35(2H, t, J=7.2 Hz), 2.55(1H, m), 3.88(1H, m), 5.31–5.45(2H, m), 6.42(1H, d, J=6.0 Hz), 7.31 (1H, d, J=5.1 Hz), 7.40(1H, dd, J=3.0 and 5.1 Hz), 7.87 and 7.96(each 2H, each d, each J=8.7 Hz), 8.11(1H, d, J=3.0 Hz). IR(Nujol): 3286, 3108, 2671, 1701, 1641, 1546, 1327, 1156 cm$^{-1}$. [α]$_D^{27}$+75.3±1.2°(c=1.004, MeOH) Anal. (C$_{25}$H$_{29}$NO$_5$S$_2$) Calcd.(%): C, 61.58; H, 5.99; N, 2.87; S, 13.15. Found(%): C, 61.39; H, 5.94; N, 3.02; S, 12.99.

Compound Number I-30

$^1$H-NMR(CDCl$_3$) δ: 1.12(1H, m), 1.23–1.34(2H, m), 1.43–1.52(2H, m), 1.58–1.79(4H, m), 2.02–2.24(5H, m), 2.36(2H, t, J=7.2 Hz), 2.53(1H, m), 3.87 (1H, m), 5.32–5.45 (2H, m), 6.11(1H, d, J=3.6 Hz), 6.28(1H, d, J=7.5 Hz), 6.35 and 7.09(each 2H, each t, each J=2.1 Hz), 7.16(1H, d, J=3.6 Hz). IR (CHCl$_3$): 3512, 3438, 3142, 1741, 1709, 1653, 1623, 1564, 1508 cm$^{-1}$. [α]$_D^{25}$+102.4±1.4°(c=1.006, MeOH) Anal. (C$_{23}$H$_{28}$N$_2$O$_4$.0.2H$_2$O) Calcd.(%): C, 69.05; H, 7.15; N, 7.00. Found(%): C, 69.12; H, 7.10; N, 6.95.

Compound Number I-31

$^1$H-NMR(CDCl$_3$) δ: 1.04(1H, m), 1.08–1.28(2H, m), 1.41–1.46(2H, m), 1.55–1.78(4H, m), 1.99–2.16(5H, m), 2.34(2H, t, J=7.2 Hz), 2.51(1H, m), 3.81(1H, m), 4.13(2H, s), 5.29–5.42(2H, m), 5.96(1H, d, J=8.1 Hz), 6.77(1H, ddd, J=0.9, 0.9 and 3.9 Hz), 7.20–7.35(5H, m), 7.37(1H, d, J=3.9 Hz). IR (CHCl$_3$): 3511, 3445, 2670, 1708, 1642, 1544, 1507, 1455 cm$^{-1}$. [α]$_D^{26}$+67.1±1.1°(c=1.015, MeOH) Anal. (C$_{26}$H$_{31}$NO$_3$S) Calcd.(%): C, 71.36; H, 7.14; N, 3.20; S, 7.33. Found(%): C, 71.19; H, 7.16; N, 3.34; S, 7.26.

Compound Number I-32

$^1$H-NMR(CDCl$_3$) δ: 1.22–1.85(9H, m), 1.95–2.53(7H, m), 2.66(1H, m), 3.84(1H, m), 5.37–5.60(2H, m), 6.79(1H, d, J=6.0 Hz), 7.01–7.17(5H, m), 7.83 (1H, dd J=1.5 and 8.7 Hz), 7.53(1H, d, J=8.7 Hz), 7.89(1H, s), 8.35 (1H, s), 8.83(1H, d, J=1.5 Hz). IR(CHCl$_3$): 3509, 3437, 3364, 3209, 1710, 1634, 1495, 1344, 1158 cm$^{-1}$. [α]$_D^{26}$+36.6±0.8° (c=1.005, MeOH) Anal. (C$_{29}$H$_{32}$N$_2$O$_5$S$_2$.0.2H$_2$O) Calcd. (%): C, 62.61; H, 5.87; N, 5.04; S, 11.53. Found(%): C, 62.53; H, 5.87; N, 5.21; S, 11.42.

Compound Number I-33

$^1$H-NMR(CDCl$_3$) δ: 1.13(1H, m), 1.20–1.37(2H, m), 1.46–1.56(2H, m), 1.60–1.80 (4H, m), 2.02–2.28(5H, m), 2.38(2H, t, J=7.2 Hz), 2.64(1H, m), 3.94 (1H, m), 5.35–5.50 (2H, m), 6.21(1H, d, J=7.2 Hz), 6.28 and 7.21(each 2H, each t, each J=2.4 Hz), 7.81(1H, dd, J=1.8 and 8.7 Hz), 7.91(1H, d, J=8.7 Hz), 7.99(1H, s), 8.97(1H, d, J=1.8 Hz). IR(CHCl$_3$): 3513, 3438, 3144, 3096, 1708, 1656, 1518, 1374 cm$^{-1}$. [α]$_D^{26}$+40.1±0.8°(c=1.010, MeOH) Anal. (C$_{27}$H$_{30}$N$_2$O$_5$S$_2$.0.2H$_2$O) Calcd.(%): C, 61.16; H, 5.78; N, 5.28; S, 12.09. Found(%): C, 61.16; H, 5.76; N, 5.43; S, 12.05.

Compound Number I-34

$^1$H-NMR(CDCl$_3$) δ: 1.18–1.35(3H, m), 1.40–1.48(2H, m), 1.57–1.79(4H, m), 1.99–2.21(5H, m), 2.37(2H, t, J=7.2 Hz), 2.50(1H, m), 3.80(1H, m), 5.32–5.47(2H, m), 6.38(2H, t, J=2.4 Hz), 6.54(1H, d, J=7.5 Hz), 7.12 and 7.13(each 1H, each d, each J=3.6 Hz), 7.20(2H, t, J=2.4 Hz). IR(CHCl$_3$): 3512, 3433, 3144, 2686, 1708, 1669, 1591, 1528, 1475, 1457, 1394 cm$^{-1}$. [α]$_D^{26}$+74.3±1.1°(c=1.007, MeOH) Anal. (C$_{23}$H$_{28}$N$_2$O$_5$S) Calcd.(%): C, 59.98; H, 6.13; N, 6.08; S, 6.96. Found(%): C, 59.71; H, 6.22; N, 6.10; S, 7.02.

Compound Number I-35 mp.102–103° C.; $^1$H-NMR(CDCl$_3$) δ: 1.05(1H, m), 1.18–1.30(2H, m), 1.38–1.48(2H, m), 1.55–1.78(4H, m), 1.99–2.19(5H, m), 2.35(2H, t, J=7.2 Hz), 2.52(1H, m), 3.81(1H, m), 5.20(2H, d, J=0.9 Hz), 5.30–5.42(2H, m), 5.99 (1H, d, J=7.2 Hz), 6.20 and 6.71 (each 2H, each t, each J=2.1 Hz), 6.86(1H, td, J=0.9 and 3.9 Hz), 7.37(1H, d, J=3.9 Hz). IR(Nujol): 3393, 3093, 6064, 2669, 1704, 1616, 1523, 1522 cm$^{-1}$. [α]$_D^{26}$+71.1±1.1°(c=1.005, MeOH) Anal. (C$_{24}$H$_{30}$N$_2$O$_3$S) Calcd.(%): C, 67.58; H, 7.09; N, 6.57; S, 7.52. Found(%): C, 67.45; H, 7.09; N, 6.58; S, 7.67.

Compound Number I-36

$^1$H-NMR(CDCl$_3$) δ: 1.07(1H, m), 1.18–1.31(2H, m), 1.40–1.48(2H, m), 1.56–1.78(4H, m), 2.00–2.20(5H, m), 2.35(2H, t, J=7.2 Hz), 2.53(1H, m), 3.82 (1H, m), 5.31–5.43 (2H, m), 6.02(1H, d, J=7.2 Hz), 7.15 and 7.44 (each 1H, each d, each J=3.9 Hz), 7.20–7.33(5H, m). IR(CHCl$_3$): 3511, 3444, 3426, 3031, 2665, 1708, 1646, 1530, 1499, 1477, 1421, 1318 cm$^{-1}$. [α]$_D^{26}$+74.8±1.1°(c=1.004, MeOH) Anal. (C$_{25}$H$_{29}$NO$_3$S$_2$) Calcd.(%): C, 65.90; H, 6.42; N, 3.07; S, 14.07. Found(%): C, 65.61; H, 6.40; N, 3.19; S, 14.18.

Compound Number I-37

$^1$H-NMR(CDCl$_3$) δ: 1.09(1H, m), 1.17–1.31(2H, m), 1.38–1.47(2H, m), 1.54–1.74(4H, m), 2.00–2.17(5H, m), 2.34(2H, t, J=7.2 Hz), 2.52(1H, m), 3.80 (1H, m), 5.30–5.43 (2H, m), 6.27(1H, d, J=7.2 Hz), 7.41(1H, d, J=4.2 Hz), 7.51–7.64(4H, m), 7.98(2H, m). IR(CHCl$_3$): 3515, 3442, 3366, 1708, 1656, 1530, 1504, 1327, 1156 cm$^{-1}$. [α]$_D^{26}$+73.1±1.1°(c=1.004, MeOH) Anal. (C$_{25}$H$_{29}$NO$_5$S$_2$.0.2H$_2$O) Calcd.(%): C, 61.13; H, 6.03; N, 2.85; S, 13.05. Found(%): C, 60.94; H, 6.02; N, 2.86; S, 3.12.

Compound Number I-38 mp.163–165° C. $^1$H-NMR(CDCl$_3$) δ: 1.24–1.43(3H, m), 1.52–1.87 (8H, m), 2.10(1H, d, J=3.0 Hz), 2.30–2.55(4H, m), 2.71(1H, m), 3.66(1H, m), 5.38 and 5.63(each 1H, each m), 7.13(1H, d, J=1.5 Hz), 7.34(1H, d, J=5.4 Hz), 7.49–7.60 (3H, m), 7.86–7.89(2H, m), 8.49(1H, s), 8.69(1H, d, J=1.5 Hz). IR(KBr): 3367, 3261, 3090, 1726, 1645, 1618, 1589, 1577, 1535, 1513, 1426, 1396, 1289, 1197 cm$^{-1}$. [α]$_D^{23}$+

84.5±1.2°(c=1.006, MeOH) Anal. ($C_{26}H_{30}N_2O_4S$) Calcd. (%): C, 66.93; H, 6.48; N, 6.00; S, 6.87. Found(%): C, 66.97; H, 6.36; N, 6.01; S, 6.89.

Compound Number I-39

$^1$H-NMR(CDCl$_3$) δ: 1.25–1.80(9H, m), 1.87–2.05(3H, m), 2.14–2.29(2H, m), 2.37(2H, t, J=6.9 Hz), 2.57(1H, m), 3.73(1H, m), 5.35 and 5.49(each 1H, each m), 6.71(1H, d, J=6.6 Hz), 6.87(1H, d, J=1.5 Hz), 7.43–7.48(2H, m), 7.56 (1H, m), 7.63(1H s), 7.64((1H, d, J=1.5 Hz), 7.73–7.76(2H, m). IR (CHCl$_3$): 3510, 3379, 3247, 3108, 1709, 1637, 1556, 1516, 1448, 1365, 1319, 1161 cm$^{-1}$. $[α]_D^{23}$+61.1±1.0° (c=1.004, MeOH) Anal. ($C_{25}H_{30}N_2O_5S_2$.0.2H$_2$O) Calcd. (%): C, 59.31; H, 6.05; N, 5.53; S, 12.67. Found(%): C, 59.38; H, 6.11; N, 5.75; S, 12.41.

Compound Number I-40

$^1$H-NMR(CDCl$_3$) δ: 1.11(1H, m), 1.24–1.31(2H, m), 1.44–1.52(2H, m), 1.60–1.79 (4H, m), 2.00–2.21(5H, m), 2.37(2H, t, J=7.2 Hz), 2.56(1H, m), 3.86 (1H, m), 5.32–5.46 (2H, m), 6.11(1H, d, J=7.8 Hz), 7.25 and 7.49(each 1H, each d, each J=4.2 Hz), 7.30–7.43(3H, m), 7.60–7.63(2H, m). IR(CHCl$_3$): 3510, 3445, 3428, 1739, 1708, 1643, 1540, 1510, 1491, 1454 cm$^{-1}$. $[α]_D^{35}$+88.0±1.3°(c=1.012, MeOH) Anal. ($C_{25}H_{29}NO_3S$.0.2H$_2$O) Calcd.(%): C, 70.29; H, 6.94; N, 3.28; S, 7.51. Found(%): C, 70.35; H, 7.01; N, 3.59; S, 7.46.

Compound Number I-41

$^1$H-NMR(CDCl$_3$) δ: 1.13(1H, m), 1.22–1.32(2H, m), 1.46–1.51(2H, m), 1.60–1.76(4H, m), 2.04–2.17(5H, m), 2.36(2H, t, J=7.2 Hz), 2.57(1H, m), 3.86(1H, m), 5.32–5.46 (2H, m), 6.30(1H, d, J=8.4 Hz), 7.48–7.65(5H, m), 7.84–7.88(2H, m). IR(CHCl$_3$): 3511, 3443, 3425, 1708, 1643, 1529, 1506, 1448 cm$^{-1}$. $[α]_D^{25}$+92.4±1.3°(c=1.000, MeOH) Anal. ($C_{26}H_{29}NO_4S_2$.0.2H$_2$O) Calcd.(%): C, 68.61; H, 6.51; N, 3.08; S, 7.04. Found(%): C, 68.55; H, 6.52; N, 3.13; S, 7.03.

Compound Number I-42

$^1$H-NMR(CDCl$_3$) δ: 1.10(1H, m), 1.27–1.31(2H, m), 1.49 (2H, brs), 1.59–1.80 (4H, m), 2.00–2.20(5H, m), 2.36(2H, t, J=7.2 Hz), 2.55(1H, m), 3.85 (1H, m), 5.31–5.45(2H, m), 6.14(1H, d, J=7.2 Hz), 7.13(1H, d, J=3.9 Hz), 7.30 (1H, dd, J=1.2 and 5.1 Hz), 7.36(1H, dd, J=3.0 and 5.1 Hz), 7.45–7.46 (2H, m). IR(CHCl$_3$): 3511, 3445, 3428, 3109, 1708, 1642, 1523, 1499, 1456 cm$^{-1}$. $[α]_D^{25}$+82.9±1.20 (c=1.006, MeOH) Anal. ($C_{23}H_{27}NO_3S_2$.0.1H$_2$O) Calcd.(%): C, 64.04; H, 6.36; N, 3.25; S, 14.86. Found(%): C, 63.99; H, 6.52; N, 3.23; S, 14.85.

Compound Number I-43

$^1$H-NMR(CDCl$_3$) δ: 1.10(1H, m), 1.22–1.31(2H, m), 1.46–1.51(2H, m), 1.60–1.80(4H, m), 2.03–2.22(5H, m), 2.37(2H, t, J=7.2 Hz), 2.55(1H, m), 3.85 (1H, m), 5.32–5.45 (2H, m), 6.07(1H, d, J=7.5 Hz), 7.04(1H, dd, J=3.6 and 5.4 Hz), 7.11(1H, d, J=3.9 Hz), 7.24(1H, dd, J=1.2 and 3.6 Hz), 7.28(1H, dd, J=1.2 and 5.4 Hz), 7.42(1H, d J=3.9 Hz). IR(CHCl$_3$): 3511, 3445, 3428, 3113, 3073, 2667, 1708, 1643, 1521, 1498, 1455 cm$^{-1}$. $[α]_D^{25}$+89.5±1.30°(c=1.005, MeOH) Anal. ($C_{23}H_{27}NO_3S_2$.0.1H$_2$O) Calcd.(%): C, 64.04; H, 6.36; N, 3.25; S, 14.86. Found(%): C, 63.93; H, 6.39; N, 3.46; S, 14.61.

Compound Number I-44 mp.146–147° C.; $^1$H-NMR(CDCl$_3$) δ: 1.10(1H, m), 1.24–1.31(2H, m), 1.46–1.51(2H, m), 1.61–1.82(4H, m), 2.00–2.24(5H, m), 2.37(2H, t, J=7.2 Hz), 2.37(3H, s), 2.56 (1H, m), 3.85(1H, m), 5.31–5.45 (2H, m), 6.06(1H, d, J=6.9 Hz), 7.20 and 7.51(each 2H, each d, each J=9.0 Hz), 7.21 and 7.48(each 1H, each d, each J=3.9 Hz). IR(CHCl$_3$): 3517, 3445, 3428, 1740, 1708, 1642, 1542, 1518, 1498, 1451 cm$^{-1}$. $[α]_D^{26}$+89.3±1.3°(c=1.009, MeOH) Anal. ($C_{26}H_{31}NO_3S$) Calcd.(%): C, 71.36; H, 7.14; N, 3.20; S, 7.33. Found(%): C, 71.51; H, 7.10; N, 3.20; S, 7.33.

Compound Number I-45 mp.110–116° C. $^1$H-NMR(CDCl$_3$) δ: 1.10(1H, m), 1.24–1.31(2H, m), 1.46–1.51(2H, m), 1.61–1..83(4H, m), 2.00–2.25(5H, m), 2.37(2H, t, J=7.2 Hz), 2.56(1H, m), 3.84(3H, s), 3.85(1H, m), 5.31–5.45(2H, m), 6.04(1H, d, J=7.5 Hz), 6.93 and 7.55(each 2H, each d, each J=8.7 Hz), 7.15 and 7.46 (each 2H, each d, each J=4.2 Hz). IR(CHCl$_3$): 3515, 3445, 3428, 1740, 1708, 1640, 1608, 1541, 1499, 1453, 1178 cm$^{-1}$. $[α]_D^{26}$+88.0±1.3°(c=1.010, MeOH) Anal. ($C_{26}H_{31}NO_4S$) Calcd.(%): C, 68.85; H, 6.89; N, 3.09; S, 7.07. Found(%): C, 68.87; H, 6.82; N, 3.11; S, 7.19.

Compound Number I-46 mp.124–125° C.,; $^1$H-NMR(CDCl$_3$) δ: 1.10(1H, m), 1.24–1.32(2H, m), 1.46–1.51(2H, m), 1.61–1.82(4H, m), 2.00–2.24(5H, m), 2.37(2H, t, J=7.2 Hz), 2.56 (1H, m), 3.85(1H, m), 5.32–5.45(2H, m), 6.06(1H, d, J=7.2 Hz), 7.10 (2H, t, J=8.7 Hz), 6.19 and 7.47(each 1H, each d, each J=3.6 Hz), 7.56–5.60 (2H, m). IR(CHCl$_3$): 3516, 3445, 3428, 2672, 1740, 1708, 1643, 1542, 1519, 1498, 1452 cm$^{-1}$. $[α]_D^{26}$+83.3±1.2°(c=1.005, MeOH) Anal. ($C_{25}H_{28}FNO_3S$) Calcd.(%): C, 68.00; H, 6.39; N, 3.17; F, 4.30; S, 7.26. Found(%): C, 67.90; H, 6.34; N, 3.25; F, 4.31; S, 7.20.

Compound Number I-47

$^1$H-NMR(CDCl$_3$) δ: 1.10(1H, m), 1.18–1.32(2H, m), 1.38–1.48(2H, m), 1.56–1.76(4H, m), 2.00–2.18(5H, m), 2.35(2H, t, J=7.2 Hz), 2.53(1H, m), 3.81 (1H, m), 5.31–5.43 (2H, m), 6.32(1H, d, J=7.5 Hz), 7.11(1H, dd, J=3.9 and 5.1 Hz), 7.4 and 7.62(each 1H, each d, each J=3.9 Hz), 7.70(1H, dd, J=1.5 and 5.1 Hz), 7.74(1H, dd, J=1.5 and 3.9 Hz). IR(CHCl$_3$): 3516, 3442, 3378, 1708, 1655, 1530, 1504, 1336, 1153 cm$^{-1}$. $[α]_D^{25}$+74.3±1.1°(c=1.000, MeOH) Anal. ($C_{23}H_{27}NO_5S_3$.0.1H$_2$O) Calcd.(%): C, 55.76; H, 5.53; N, 2.83; S, 19.41. Found(%): C, 55.49; H, 5.64; N, 3.09; S, 19.32.

Compound Number I-48 mp.112–115° C. $^1$H-NMR(CDCl$_3$) δ: 1.13–1.30(3H, m), 1.34–1.45 (2H, m), 1.50–1.82(4H, m), 1.94–2.27(5H, m), 2.34(2H, t, J=7.2 Hz), 2.56 (1H, m), 3.74(1H, m), 5.22(2H, s), 5.31–5.50(2H, m), 6.64(1H, d, J=6.6 Hz), 6.84 (1H, (1, J=3.9 Hz), 6.93 and 7.05(each 1H, each s), 7.47(1H, d, J=3.9 Hz), 7.66(1H, s). IR(Nujol): 3339, 3102, 2464, 1691, 1635, 1622, 1551, 1288 cm$^{-1}$. $[α]_D^{25}$+71.2±1.1°(c=1.005, MeOH) Anal. ($C_{23}H_{29}N_3O_3S$) Calcd.(%): C, 64.61; H, 6.84; N, 9.83; S, 7.50. Found(%): C, 64.54; H, 6.85; N, 9.78; S, 7.42.

Compound Number I-49

$^1$H-NMR(CDCl$_3$) δ: 1.08(1H, m), 1.16–1.30(2H, m), 1.38–1.47(2H, m), 1.54–1.77(4H, m), 1.98–2.20(5H, m), 2.34(2H, t, J=7.2 Hz), 2.52(1H, m), 3.79 (1H, m), 5.30–5.42 (2H, m), 5.47(2H, s), 6.16(1H, d, J=6.9 Hz), 6.30(1H, t, J=2.1 Hz) 6.94 and 7.41(each 1H, each d, each J=3.6 Hz), 7.47 and 7.57 (each 1H, each d, each J=2.1 Hz). IR(CHCl$_3$): 3510, 3444, 3426, 1709, 1646, 1546, 1512 cm$^{-1}$. $[α]_D^{25}$+68.6±1.1°(c=1.011, MeOH) Anal. ($C_{23}H_{29}N_3O_3S$.0.1H$_2$O) Calcd.(%): C, 64.34; H, 6.85; N, 9.79; S, 7.47. Found(%): C, 64.10; H, 6.93; N, 9.90; S, 7.52.

Compound Number I-50 mp.126–128° C.; $^1$H-NMR(CDCl$_3$) δ: 1.12(1H, m), 1.18–1.33(2H, m), 1.40–1.50(2H, m), 1.55–1.78(4H, m), 2.00–2.21(5H, m), 2.54(1H, m), 3.87(1H, m), 5.30–5.44(2H, m), 6.43(1H, d, J=6.6 Hz), 7.48–7.62(3H, m), 7.83–7.95(5H, m). IR(Nujol): 3284, 3058, 2669, 1701, 1641, 1546, 1326, 1294, 1160 cm$^{-1}$. [α]hd $_D^{25}$+77.2±1.2°(c=1.007, MeOH) Anal. (C$_{27}$H$_{31}$NO$_5$S) Calcd.(%): C, 67.34; H, 6.49; N, 2.91; S, 6.66. Found(%): C, 67.20; H, 6.38; N, 2.88; S, 6.58.

Compound Number I-51 mp.103–107° C. $^1$H-NMR(CDCl$_3$) δ: 1.14(1H, m), 1.18–1.33(2H, m), 1.40–1.50(2H, m), 1.54–1.77(4H, m), 2.00–2.20(5H, m), 2.34(2H, t, J=7.2 Hz), 2.54(1H, m), 3.85(3H, s), 3.86(1H, m), 5.30–5.45(2H, m), 6.48(1H, d, J=6.9 Hz), 6.96(2H, m), 7.81–7.91(6H, m). IR(Nujol): 3273, 3067, 2669, 1702, 1639, 1560, 1548, 1323, 1301, 1274, 1156 cm$^{-1}$. [α]$_D^{25}$+75.4±1.2°(c=1.002, MeOH) Anal. (C$_{28}$H$_{33}$NO$_6$S) Calcd.(%): C, 65.73; H, 6.50; N, 2.74; S, 6.27. Found(%): C, 65.50; H, 6.46; N, 2.82; S, 6.25.

Compound Number I-52

$^1$H-NMR(CDCl$_3$) δ: 1.17(1H, m), 1.26–1.34(2H, m), 1.47–1.53(2H, m), 1.60–1.76(4H, m), 2.04–2.21(5H, m), 2.36(2H, t, J=7.2 Hz), 2.60(1H, m), 3.91(1H, m), 5.32–5.47 (2H, m), 6.46(1H, d, J=8.4 Hz), 7.17(1H, dd, J=3.9 and 5.1 Hz), 7.61(1H, dd, J=1.2 and 3.9 Hz), 7.76(1H, dd, J=1.2 and 5.1 Hz), 7.87(4H, s-like). IR(CHCl$_3$): 3518, 3444, 2663, 1708, 1638, 1517, 1494, 1414 cm$^{-1}$. [α]$_D^{25}$+86.6±1.3° (c=1.008, MeOH) Anal. (C$_{26}$H$_{29}$NO$_4$S) Calcd.(%): C, 69.15; H, 6.47; N, 3.10; S, 7.10. Found(%): C, 68.86; H, 6.70; N, 3.15; S, 6.95.

Compound Number I-53 mp.144–145° C.; $^1$H-NMR(CDCl$_3$) δ: 1.20–2.54(16H, m), 2.62(1H, m), 3.69 (3H, s), 5.35–5.56(2H, m), 6.36 and 7.17(each 2H, each t, each J=2.4 Hz), 6.66(1H, d, J=6.3 Hz), 8.05 and 8.07(each 1H, each d, each J=1.5 Hz). IR(Nujol): 3509, 3406, 3146, 3110, 1728, 1708, 1653, 1535, 1375, 1189, 1166 cm$^{-1}$. [α]$_D^{25}$+67.9±1.1°(c=1.007, MeOH) Anal. (C$_{23}$H$_{28}$N$_2$O$_5$S$_2$) Calcd.(%): C, 57.96; H, 5.92; N, 5.88; S, 13.45. Found(%): C, 58.19; H, 5.95; N, 5.75; S, 13.09.

Compound Number I-54

$^1$H-NMR(CDCl$_3$) δ: 1.22–2.57(16H, m), 2.68(1H, m), 3.66(3H, s), 5.37–5.63 (2H, m), 6.20, 6.35, 6.74 and 6.87 (each 2H, each t, each J=2.4 Hz), 6.92 (1H, d, J=5.4 Hz), 8.27(1H, s). IR(CHCl$_3$): 3402, 3143, 3108, 1725, 1710, 1650, 1516, 1375 cm$^{-1}$. [α]$_D^{26}$+70.0±1.1°(c=1.006, MeOH) Anal. (C$_{27}$H$_{31}$N$_3$O$_5$S$_2$.0.3H$_2$O) Calcd.(%): C, 59.28; H, 5.82; N, 7.68; S, 11.72. Found(%): C, 59.28; H, 5.77; N, 5.58; S, 11.68.

Compound Number I-55

$^1$H-NMR(CDCl$_3$) δ: 1.10(1H, m), 1.18–1.31(2H, m), 1.40–1.45(2H, m), 1.57–1.74(4H, m), 2.00–2.10(5H, m), 2.35(2H, t, J=7.2 Hz), 2.38(3H, s), 2.52 (1H, m), 3.80(1H, m), 5.31–5.43(2H, m), 5.99(1H, m), 6.20(1H, t, J=3.3 Hz), 6.30(1H, d, J=6.91 Hz), 7.18(1H, dd, J=1.8 and 3.3 Hz), 7.40 and 7.53(each 1H, each d, each J=3.9 Hz). IR(CHCl$_3$): 3513, 3442, 3149, 3100, 1708, 1657, 1530, 1504, 1375, 1183, 1161 cm$^{-1}$. [α]$_D^{27}$+70.3±1.5°(c=0.730, MeOH) Anal. (C$_{24}$H$_{30}$N$_2$O$_5$S$_2$.0.4H$_2$O) Calcd.(%): C, 57.90; H, 6.24; N, 5.63; S, 12.88. Found(%): C, 58.08; H, 6.28; N, 5.77; S, 12.54.

Compound Number I-56

$^1$H-NMR((d$_6$-DMSO) δ: 1.06–1.59(9H, m), 1.93–2.07 (5H, m), 2.21(2H, t, J=7.2 Hz), 2.35(1H, m), 3.65(1H, m), 5.30–5.41(2H, m), 6.90 and 7.69 (each 1H, each d, each J=4.2 Hz), 7.55–7.64(3H, m), 7.99–8.04(2H, m), 11.73 (1H, s), 12.01(1H, brs). IR (KBr): 3562, 1708, 1616, 1564, 1523, 1454, 1295 cm$^{-1}$. [α]$_D^{27}$+71.2±1.1°(c=1.000, MeOH) Anal. (C$_{26}$H$_{30}$N$_2$O$_4$S.0.2H$_2$O) Calcd.(%): C, 66.42; H, 6.52; N, 5.96; S, 6.82. Found(%): C, 66.43; H, 6.32; N, 6.17; S, 6.75.

Compound Number I-57

$^1$H-NMR(d$_6$-DMSO) δ: 1.05–1.56(9H, m), 1.91–2.05(5H, m), 2.19(2H, t, J=7.2 Hz), 2.29(1H, m), 3.56(1H, m), 5.28–5.38(2H, m), 6.54 and 7.56(each 1H, each d, each J=4.2 Hz), 7.59–7.62(3H, m), 7.76–7.79(2H, m), 8.06(1H, d, J=6.9 Hz), 11.10(1H, s), 11.99(1H, brs). IR(KBr): 3384, 3084, 1707, 1616, 1553, 1523, 1459, 1350, 1322, 1161 cm$^{-1}$. [α]$_D^{27}$+62.4±1.0°(c=1.005, MeOH) Anal. (C$_{25}$H$_{30}$N$_2$O$_5$S$_2$.0.2H$_2$O) Calcd.(%): C, 59.31; H, 6.05; N, 5.53; S, 12.66. Found(%): C, 59.36; H, 5.75; N, 5.55; S, 12.38.

Compound Number I-58

$^1$H-NMR(CDCl$_3$) δ: 1.07(1H, m), 1.17–1.33(2H, m), 1.36–1.50(2H, m), 1.54–1.75(4H, m), 2.00–2.20(5H, m), 2.35(2H, t, J=7.2 Hz), 2.45(3H, s), 2.52 (1H, m), 3.80(1H, m), 5.31–5.43(2H, m), 6.12(1H, d, J=7.5 Hz), 6.32 and 7.18(each 2H, each t, each J=2.4 Hz), 7.22(1H, s). IR(CHCl$_3$): 3316, 3442, 3145, 2668, 1708, 1657, 1545, 1509, 1455, 1375, 1190, 1165, 1057 cm$^{-1}$. [α]$_D^{26}$+75.8±1.2° (c=1.002, MeOH) Anal. (C$_{24}$H$_{30}$N$_2$O$_5$S$_2$.0.1H$_2$O) Calcd. (%): C, 58.54; H, 6.18; N, 5.69; S, 13.02. Found(%): C, 58.35; H, 6.29; N, 5.74; S, 12.92.

Compound Number I-59

$^1$H-NMR(CDCl$_3$) δ: 1.05(1H, m), 1.16–1.30(2H, m), 1.38–1.48(2H, m), 1.53–1.79(4H, m), 1.98–2.17(5H, m), 2.34(2H, t, J=7.2 Hz), 2.50(1H, m), 3.79(1H, m), 5.30–5.42 (2H, m), 6.00(1H, d, J=7.5 Hz), 7.01(1H, dd, J=3.6 and 5.4 Hz), 7.03(1H, d, J=3.9 Hz), 7.29(1H, dd, J=1.2 and 3.6 Hz), 7.33(1H, d, J=3.9) 7.43(1H, dd, J=1.2 and 5.4 Hz). IR(CHCl$_3$): 3517, 3444, 3426, 2670, 1708, 1645, 1530, 1499, 1421, 1318 cm$^{-1}$. [α]$_D^{26}$+70.8±1.1°(c=1.018, MeOH) Anal. (C$_{23}$H$_{27}$NO$_3$S$_3$) Calcd.(%): C, 59.84; H, 5.89; N, 3.03; S, 20.84. Found(%): C, 59.73; H, 5.99; N, 3.15; S, 20.70.

Compound Number I-60

$^1$H-NMR(CDCl$_3$) δ: 1.07(1H, m), 1.17–1.32(2H, m), 1.40–1.50(2H, m), 1.56–1.80(4H, m), 1.99–2.21(5H, m), 2.34(2H, t, J=7.2 Hz), 2.54(1H, m), 3.85 (1H, m), 5.29–5.42 (2H, m), 6.20(1H, d, J=6.9 Hz), 7.23–7.45(7H, m), 7.55 (2H, d, J=8.1 Hz). IR(CHCl$_3$): 3516, 3447, 2667, 1708, 1651, 1596, 1514, 1481 cm$^{-1}$. [α]$_D^{26}$+89.1±1.3°(c=1.006, MeOH) Anal. (C$_{27}$H$_{31}$NO$_3$S.0.2H$_2$O) Calcd.(%): C, 71.56; H, 6.98; N, 3.09; S, 7.07. Found(%): C, 71.39; H, 6.97; N, 3.16; S, 6.94.

Compound Number I-61

$^1$H-NMR(CDCl$_3$) δ: 1.06(1H, m), 1.18–1.31(2H, m), 1.41–1.50(2H, m), 1.55–1.80(4H, m), 1.99–2.20(5H, m), 2.35(2H, t, J=7.2 Hz), 2.52(1H, m), 3.82(1H, m), 5.31–5.43 (2H, m), 5.97(1H, d, J=6.6 Hz), 6.45(1H, d, J=4.2 Hz), 7.11–7.20(3H, m), 7.28(1H, d, J=4.2 Hz), 7.33–7.40(2H, m). IR(CHCl$_3$): 3515, 3445, 3427, 2667, 1740, 1708, 1640, 1506, 1475 cm$^{-1}$. [α]$_D^{27}$+71.3±1.1°(c=1.002, MeOH) Anal. (C$_{25}$H$_{29}$NO$_4$S) Calcd.(%): C, 68.31; H, 6.65; N, 3.19; S, 7.29. Found(%): C, 68.41; H, 6.87; N, 3.22; S, 7.35.

Compound Number I-62

$^1$H-NMR(CDCl$_3$) δ: 1.14(1H, m), 1.20–1.35(2H, m), 1.42–1.54(2H, m), 1.57–1.77(4H, m), 2.00–2.23(5H, m), 2.35(2H, t, J=7.2 Hz), 2.58(1H, m), 3.88(1H, m), 5.32–5.46 (2H, m), 6.31 and 7.19(each 2H, each t, each J=2.4 Hz), 6.33(1H, d, J=6.9 Hz), 7.77(1H, dd, J=1.8 and 8.4 Hz), 7.77(1H, s), 7.87(1H, d, J=8.4 Hz), 8.38(1H, d, J=1.8 Hz). IR(CHCl$_3$): 3514, 3442, 3422, 3144, 2670, 1708, 1654, 1525, 1375, 1193, 1171 cm$^{-1}$. [α]$_D^{26}$+$^{89.8±1.3°}$(c=1.000, MeOH) Anal. (C$_{27}$H$_3$N$_2$O$_5$S$_2$) Calcd.(%): C, 61.58; H, 5.74; N, 5.32; S, 12.17. Found(%): C, 61.42; H, 5.86; N, 5.57; S, 11.98.

Compound Number I-63 mp.180–181° C.; $^1$H-NMR(CDCl$_3$) δ: 1.04(1H, m), 1.22–1.30(2H, m), 1.41–1.46 (2H, m), 1.59–1.82(4H, m), 1.94–2.16(3H, m), 2.25–2.37(2H, m), 2.42 (2H, t, J=6.9 Hz), 2.52(1H, m), 2.52(3H, s), 3.79(1H, m), 5.41–5.59(2H, m), 5.73(1H, d, J=6.6 Hz), 7.48–7.53(2H, m), 7.60(1H, m), 8.07–8.10(2H, m). IR(Nujol): 3372, 3173, 3053, 2544, 1690, 1672, 1632, 1559, 1496, 1362, 1317 cm$^{-1}$. $[α]_D^{28}$+ 77.7±1.2°(c=1.007, MeOH) Anal. (C$_{26}$H$_{31}$N$_3$O$_4$S) Calcd. (%): C, 64.84; H, 6.49; N, 8.72; S, 6.66. Found(%): C, 64.66; H, 6.31; N, 8.73; S, 6.65.

Compound Number I-64

$^1$H-NMR(d$_6$-DMSO) δ: 1.07(1H, m), 1.28–1.58(8H, m), 1.91–2.08(5H, m), 2.20(2H, t, J=7.2 Hz), 2.31(3H, s), 2.32 (1H, s), 3.96(1H, m), 5.28–5.40(2H, m), 7.52–7.62(3H, m), 7.80–7.83(2H, m), 7.94(1H, d, J=6.9 Hz). IR(Nujol): 3316, 3161, 3106, 2677, 1709, 1629, 1531, 1284, 1142 cm$^{-1}$. $[α]_D^{27}$+76.2±1.2°(c=1.002, MeOH) Anal. (C$_{25}$H$_{31}$N$_3$O$_5$S$_2$.0.1H$_2$O) Calcd.(%): C, 57.80; H, 6.05; N, 8.09; S, 12.34. Found(%): C, 57.59; H, 6.15; N, 8.10; S, 12.57.

Compound Number I-65

$^1$H-NMR(CDCl$_3$) δ: 1.28–1.31(2H, m), 1.47(2H, brs), 1.56–1.84(4H, m), 1.94–2.30(5H, m), 2.39(2H, t, J=6.9 Hz), 2.62(1H, s), 2.63(3H, s), 3.77(1H, m), 5.35–5.67(2H, m), 6.42(1H, d, J=6.3 Hz), 7.29–7.43(3H, m), 7.46(1H, s), 7.72(2H, d, J=7.2 Hz). IR(CHCl$_3$): 3517, 3421, 3350, 3150, 2538, 1708, 1651, 1590, 1512, 1474, 1442, 1164 cm$^{-1}$. $[α]_D^{28}$+100.8±1.4°(c=1.002, MeOH) Anal. (C$_{27}$H$_{31}$N$_3$O$_3$S.0.5H$_2$O) Calcd.(%): C, 66.64; H, 6.63; N, 8.63; S, 6.59. Found(%): C, 66.55; H, 6.59; N, 8.68; S, 6.76.

Compound Number I-66

$^1$H-NMR(CDCl$_3$) δ: 1.08(1H, m), 1.19–1.33(2H, m), 1.42–1.50(2H, m), 1.58–1.79(4H, m), 2.01–2.22(5H, m), 2.35(2H, t, J=7.2 Hz), 2.55(1H, m), 3.86(1H, m), 4.37(2H, s), 5.30–5.43(2H, m), 6.19(1H, d, J=7.5 Hz), 6.90(1H, dd, J=3.6 and 5.1 Hz), 6.93(1H, m), 7.17(1H, dd, J=1.2 and 5.1 Hz), 7.33 and 7.65(each 2H, each d, J=8.4 Hz). IR(CHCl$_3$): 3518, 3447, 2665, 1708, 1651, 1596, 1515, 1484 cm$^{-1}$. $[α]_D^{26}$+82.4±1.4°(c=0.900, MeOH) Anal. (C$_{26}$H$_{31}$NO$_3$S$_2$.0.1H$_2$O) Calcd.(%): C, 66.24; H, 6.67; N, 2.97; S, 13.60. Found(%): C, 66.14; H, 6.72; N, 2.96; S, 13.53.

Compound Number I-67

$^1$H-NMR(CDCl$_3$) δ: 1.16(1H, m), 1.21–1.34(2H, m), 1.43–1.52(2H, m), 1.57–1.76(4H, m), 2.04–2.22(5H, m), 2.35(2H, t, J=7.2 Hz), 2.56(1H, m), 3.89 (1H, m), 4.53(2H, s), 5.33–5.48(2H, m), 6.58(1H, d, J=6.9 Hz), 6.83(1H, dd, J=1.2 and 3.9 Hz), 6.93(1H, dd, J=3.9 and 5.1 Hz), 7.28(1H, dd, J=1.2 and 5.1 Hz), 7.65 and 7.81(each 2H, each d, J=8.4 Hz). IR(CHCl$_3$): 3518, 3442, 3373, 2666, 1708, 1658, 1516, 1483, 1323, 1153 m$^{-1}$. $[α]_D^{26}$+69.6±1.1°(c=1.003, MeOH) Anal. (C$_{26}$H$_{31}$NO$_5$S$_2$.0.5H$_2$O) Calcd.(%): C, 61.15; H, 6.32; N, 2.74; S, 12.56. Found(%): C, 66.16; H, 6.25; N, 2.90; S, 12.57.

Compound Number I-68

$^1$H-NMR(CDCl$_3$) δ: 1.13(1H, m), 1.20–1.32(2H, m), 1.38–1.50(2H, m), 1.54–1.77(4H, m), 1.98–2.20(5H, m), 2.35(2H, t, J=7.2 Hz), 2.53(1H, m), 3.80 (1H, m), 5.31–5.46 (2H, m), 6.47(1H, d, J=7.5 Hz), 6.87(1H, dd, J=1.5 and 3.6 Hz), 3.84(1H, dd, J=3.6 and 5.4 Hz), 7.03(1H, dd, J=1.5 and 5.4 Hz), 7.33 and 7.38(each 1H, each d, each J=3.9 Hz), 7.90(1H, br). IR(CHCl$_3$): 3510, 3440, 3358, 3109, 1708, 1647, 1533, 1505, 1364, 1331, 1161 cm$^{-1}$. $[α]_{436}^{29}$+ 151.3±1.9°(c=1.010, MeOH) Anal. (C$_{23}$H$_{28}$N$_2$O$_5$S$_3$.0.1H$_2$O) Calcd.(%): C, 54.12; H, 5.57; N, 5.49; S, 18.84. Found(%): C, 53.84; H, 5.46; N, 5.38; S, 18.62.

Compound Number I-69

$^1$H-NMR(CDCl$_3$) δ: 1.20(1H, m), 1.26–1.38(2H, m), 1.42–1.52(2H, m), 1.57–1.76(4H, m), 2.00–2.24(5H, m), 2.34(2H, t, J=7.2 Hz), 2.53(1H, m), 3.88 (1H, m), 5.31–5.49 (2H, m), 6.63(1H, dd, J=1.2 and 3.9 Hz), 6.69(1H, d, J=7.5 Hz), 6.77(1H, dd, J=3.9 and 5.4 Hz), 6.98(1H, dd, J=1.2 and 5.4 Hz), 7.66 and 7.76(each 2H, each d, each J=8.4 Hz). IR(CHCl$_3$): 3509, 3439, 3363, 3111, 1707, 1651, 1520, 1328, 1167 cm$^{-1}$. $[α]_{436}^{29}$+155.7±2.0°(c=1.003, MeOH) Anal. (C$_{25}$H$_{30}$N$_2$O$_5$S$_3$.0.3H$_2$O) Calcd.(%): C, 59.10; H, 6.07; N, 5.51; S, 12.62. Found(%): C, 59.00; H, 5.95; N, 5.51; S, 12.46.

Compound Number I-70 mp.187–188° C.; $^1$H-NMR(d$_6$-DMSO) δ: 1.16–1.62(9H, m), 1.90–2.14(5H, m), 2.21(2H, t, J=7.2 Hz), 2.38(1H, m), 3.66(1H, m), 5.27–5.41(2H, m), 7.10–7.15 (1H, m), 7.34–7.39(2H, m), 7.42–7.75(2H, m), 7.91 and 7.99(each 1H, each d, each J=3.9 Hz), 8.04(1H, d, J=6.6 Hz), 10.32 (1H, s), 12.02(1H, s). IR(Nujol): 3316, 3075, 2678, 1704, 1635, 1614, 1544, 1323 cm$^{-1}$. $[α]_D^{28}$+83.3±1.2°(c=1.003, MeOH) Anal. (C$_{26}$H$_{30}$N$_2$O$_4$S) Calcd.(%): C, 66.93; H, 6.48; N, 6.00; S, 6.87. Found(%): C, 67.04; H, 6.45; N, 5.98; S, 6.96.

Compound Number I-71 mp.192–194° C.; $^1$H-NMR(d$_6$-DMSO) δ: 1.16–1.62(9H, m), 1.90–2.14(5H, m), 2.21(2H, t, J=7.2 Hz), 2.37(1H, m), 3.65(1H, m), 5.29–5.41(2H, m), 7.18–7.24 (2H, m), 7.33–7.78(2H, m), 7.91 and 7.97(each 1H, each d, each J=3.9 Hz), 8.04(1H, d, J=6.9 Hz), 10.38(1H, s), 12.01(1H, s). IR(Nujol): 3322, 3278, 3150, 3098, 3077, 2678, 1704, 1635, 1615, 1546, 1521, 1508, 1322 cm$^{-1}$. $[α]_D^2$+83.3±1.2° (c=1.000, MeOH) Anal. (C$_{26}$H$_{29}$FN$_2$O$_4$S) Calcd.(%): C, 64.44; H, 6.03; N, 5.78; F, 3.92; S, 6.62. Found(%): C, 64.36; H, 6.00; N, 5.81; F, 3.94; S, 6.46.

Compound Number I-72 mp.192–193° C.; $^1$H-NMR(d$_6$-DMSO) δ: 1.16–1.62(9H, m), 1.92–2.14 (5H, m), 2.21(2H, t, J=7.2 Hz), 2.37(1H, m), 3.66(1H, m), 3.75(3H, s), 5.30–5.41(2H, m), 6.94 and 7.63 (each 2H, each d-like), 7.89 and 7.94(each 1H, each d, each J=3.9 Hz), 8.38(1H, d, J=6.9 Hz), 10.21(1H, s), 12.01(1H, s). IR(Nujol): 3316, 3075, 2678, 1704, 1635, 1614, 1544, 1323 cm$^{-1}$. $[α]_D^{27}$+81.6±1.2°(c=1.000, MeOH) Anal. (C$_{27}$H$_{132}$N$_2$O$_5$S) Calcd.(%): C, 65.30; H, 6.49; N, 5.64; S, 6.46. Found(%): C, 65.19; H, 6.49; N, 5.45; S, 6.31.

Compound Number I-73

$^1$H-NMR(CDCl$_3$) δ: 1.14(1H, m), 1.18–1.32(2H, m), 1.40–1.78(6H, m), 1.94–2.20 (5H, m), 2.35(2H, t, J=7.2 Hz), 2.51(1H, m), 3.80(1H, m), 3.81(6H, s), 3.82(3H, s), 5.30–5.44(2H, m), 6.56(1H, d, J=7.2 Hz), 6.97(2H, s), 7.47 and 7.58(each 1H, each d, each J=3.9 Hz), 8.43(1H, s). IR(CHCl$_3$): 3515, 3438, 3317, 1708, 1650, 1607, 1537, 1508, 1454, 1412, 1131 cm$^{-1}$. $[α]_D^{27}$+75.8±1.2°(c=1.009, MeOH) Anal. (C$_{29}$H$_{36}$N$_2$O$_7$S.0.4H$_2$O) Calcd.(%): C, 61.77; H, 6.58; N, 4.97; S, 5.69. Found(%): C, 61.74; H, 6.64; N, 4.89; S, 5.89.

Compound Number I-74

¹H-NMR(CDCl₃) δ: 1.10(1H, m), 1.20–1.33(2H, m), 1.43–1.52(2H, m), 1.57–1.78(4H, m), 2.00–2.21(5H, m), 2.36(2H, t, J=7.2 Hz), 2.55(1H, m), 3.85(1H, m), 5.32–5.45 (2H, m), 6.09(1H, d, J=6.9 Hz), 6.32 and 7.00(each 2H, each t, each J=2.1 Hz), 6.81 and 7.34(each 1H, each d, each J=3.9 Hz). IR(CHCl₃): 3515, 3445, 3109, 2678, 1740, 1708, 1642, 1507, 1489 cm⁻¹. [α]$_D^{26}$+83.5±1.2°(c=1.007, MeOH) Anal. (C₂₃H₂₈N₂O₃S) Calcd.(%): C, 66.96; H, 6.84; N, 6.79; S, 7.77. Found(%): C, 66.66; H, 6.74; N, 6.74; S, 7.61.

Compound Number I-75

¹H-NMR(CDCl₃) δ: 1.09(1H, m), 1.20–1.32(2H, m), 1.39–1.49(2H, m), 1.57–1.66(4H, m), 2.01–2.22(5H, m), 2.35(2H, t, J=7.2 Hz), 2.56(1H, m), 3.88(1H, m), 3.95(2H, s), 5.30–5.44(2H, m), 6.27(1H, d, J=7.5 Hz), 6.89–6.91(2H, m), 7.32(1H, dd, J=2.4 and 3.9 Hz), 7.19 and 7.66(each d, J=8.4 Hz). IR(CHCl₃): 3516, 3447, 2670, 1708, 1651, 1523, 1496 m⁻¹. [α]$_D^{26}$+71.8±1.1°(c=1.016, MeOH) Anal. (C₂₆H₃NO₃S₂.0.1H₂O) Calcd.(%): C, 66.24; H, 6.67; N, 2.97; S, 13.60. Found(%): C, 66.36; H, 6.67; N, 3.27; S, 13.62.

Compound Number I-76 mp.135–136° C.; ¹H-NMR(CDCl₃) δ: 1.12(1H, m), 1.22–1.33(2H, m), 1.43–1.51(2H, m), 1.59–1.78(4H, m), 2.03–2.22(5H, m), 2.35(2H, t, J=7.2 Hz), 2.56 (1H, m), 3.87(1H, m), 4.44(2H, s), 5.31–5.45(2H, m), 6.30(1H, d, J=7.2 Hz), 7.08(1H, dd, J=3.9 and 5.1 Hz), 7.23(2H, d, J=8.4 Hz), 7.40(1H, dd, J=1.5 and 3.9 Hz), 7.69–7.71(3H, m). IR(CHCl₃): 3516, 3445, 3096, 2665, 1708, 1655, 1523, 1496, 1403, 1327, 1152, 1127 m⁻¹. [α]$_D^{26}$+65.0±1.1° (c=1.000, MeOH) Anal. (C₂₆H₃₁NO₅S₂.0.2H₂O) Calcd.(%): C, 61.81; H, 6.26; N, 2.77; S, 12.69. Found(%): C, 61.76; H, 6.20; N, 2.90; S, 12.57.

Compound Number I-77 mp.215–217° C. ¹H-NMR(d₆-DMSO) δ: 1.16–1.62(9H, m), 1.90–2.14 (5H, m), 2.21(2H, t, J=7.2 Hz), 2.38(1H, m), 3.66(1H, m), 5.29–5.41 (2H, m), 6.91–6.94(2H, m), 7.05 (1H, dd, J=2.4 and 4.2 Hz), 7.93 and 7.96 (each 1H, each d, each J=4.2 Hz), 8.43(1H, d, J=6.6 Hz), 10.67(1H, br), 12.01 (1H, br). IR(Nujol): 3315, 3222, 3097, 3049, 2672, 1705, 1621, 1548, 1504, 1311 cm⁻¹. [α]$_D^{27}$+88.2±1.3°(c=1.009, MeOH) Anal. (C₂₄H₂₈N₂O₄S₂) Calcd.(%): C, 60.99; H, 5.97; N, 5.93; S, 13.57. Found(%): C, 60.94; H, 5.74; N, 5.91; S, 13.61.

Compound Number I-78

¹H-NMR(CDCl₃) δ: 1.09(1H, m), 1.18–1.31(2H, m), 1.40–1.47(2H, m), 1.57–1.73(4H, m), 2.00–2.12(5H, m), 2.31(2H, t, J=7.2 Hz), 2.56(1H, m), 3.79 (1H, m), 4.70(2H, s), 5.30–5.45(2H, m), 6.26–6.30(2H, m), 6.34(1H, d, J=6.9 Hz), 7.22(1H, dd, J=1.8 and 3.3 Hz), 7.41 and 7.62(each 1H, each d, each J=4.2 Hz). IR(CHCl₃): 3589, 3516, 3441, 3355, 3100, 1708, 1656, 1530, 1504, 1377, 1180, 1147 cm⁻¹. [α]$_D^{26.5}$+70.8±1.1°(c=1.009, MeOH) Anal. (C₂₄H₃₀N₂O₆S₂.0.2H₂O) Calcd.(%): C, 56.50; H, 6.01; N, 5.49; S, 12.57. Found(%): C, 56.43; H, 6.02; N, 5.61; S, 12.47.

Compound Number I-79

¹H-NMR(CDCl₃) δ: 1.06(1H, m), 1.16–1.30(2H, m), 1.38–1.50(2H, m), 1.54–1.77(4H, m), 1.98–2.18(5H, m), 2.35(2H, t, J=7.2 Hz), 2.51(1H, m), 3.80(1H, m), 5.30–5.42 (2H, m), 6.03(1H, d, J=7.2 Hz), 7.04–7.06(2H, m), 7.32–7.35(2H, m), 7.37(1H, d, J=3.6 Hz). IR(CHCl₃): 3509, 3444, 3426, 3110, 2667, 1708, 1645, 1530, 1499, 1421 cm⁻¹. [α]$_D^{26.5}$+69.5±1.1°(c=1.001, MeOH) Anal. (C₂₃H₂₇NO₃S₃.0.1H₂O) Calcd.(%): C, 59.61; H, 5.92; N, 3.02; S, 20.76. Found(%): C, 59.66; H, 5.90; N, 3.15; S, 20.52.

Compound Number I-80

¹H-NMR(CDCl₃) δ: 1.10(1H, m), 1.17–1.32(2H, m), 1.38–1.48(2H, m), 1.54–1.77(4H, m), 2.00–2.20(5H, m), 2.35(2H, t, J=7.2 Hz), 2.53(1H, m), 3.81(1H, m), 5.31–5.43 (2H, m), 6.31(1H, d, J=7.2 Hz), 7.37–7.44(3H, m), 7.61(1H, d, J=3.9 Hz), 8.15(1H, dd, J=1.2 and 3.0 Hz). IR(CHCl₃): 3517, 3441, 3371, 3114, 1708, 1655, 1530, 1504, 1331, 1152 cm⁻¹. [α]$_D^{26.5}$+73.9±1.1°(c=1.001, MeOH) Anal. (C₂₃H₂₇NO₅S₃.0.3H₂O) Calcd.(%): C, 55.35; H, 5.57; N, 2.81; S, 19.28 Found(%): C, 55.47; H, 5.50; N, 2.80; S, 19.09.

Compound Number I-81

¹H-NMR(CDCl₃) δ: 1.05(1H, m), 1.16–1.30(2H, m), 1.38–1.48(2H, m), 1.54–1.77 (4H, m), 1.98–2.17(5H, m), 2.34(2H, t, J=7.2 Hz), 2.46(3H, d, J=0.9 Hz), 2.50(1H, m), 3.79(1H, m), 5.29–5.41(2H, m), 5.99(1H, d, J=7.2 Hz), 6.67(1H, m), 6.99, 7.10 and 7.32(each 1H, each d, each J=3.9 Hz). IR(CHCl₃): 3517, 3445, 3426, 2668, 1708, 1644, 1530, 1499, 1420, cm⁻¹. [α]$_D^{26.5}$+66.1±1.1°(c=1.002, MeOH) Anal. (C₂₄H₂₉NO₃S₃.0.1H₂O) Calcd.(%): C, 60.37; H, 6.16; N, 2.93; S, 20.15. Found(%): C, 60.21; H, 6.10; N, 2.90; S, 20.45.

Compound Number I-82

¹H-NMR(CDCl₃) δ: 1.11(1H, m), 1.18–1.32(2H, m), 1.38–1.50(2H, m), 1.54–1.74. (4H, m), 2.00–2.20(5H, m), 2.35(2H, t, J=7.2 Hz), 2.53(4H, d and m, J=0.6 Hz), 3.80 (1H, m), 5.31–5.43(2H, m), 6.34(1H, d, J=6.6 Hz), 6.77 (1H, m), 7.41, 7.55 and 7.58(each 1H, each d, each J=3.9 Hz). IR(CHCl₃): 3511, 3442, 3373, 3096, 1708, 1655, 1530, 1504, 1436, 1335, 1152 cm⁻¹. [α]$_D^{26.5}$+73.0±1.1°(c=1.002, MeOH) Anal. (C₂₄H₂₉NO₅S₃.0.3H₂O) Calcd.(%): C, 56.18; H, 5.81; N, 2.73; S, 18.75. Found(%): C, 56.26; H, 5.74; N, 2.65; S, 18.50.

Compound Number I-83

¹H-NMR(CDCl₃) δ: 1.17(1H, m), 1.24–1.36(2H, m), 1.37–1.82(6H, m), 2.01–2.23 (5H, m), 2.36(2H, t, J=7.2 Hz), 2.51(1H, m), 3.83(1H, m), 5.31–5.45 (2H, m, 7.17(1H, dd, J=3.9 and 5.4 Hz), 7.36(1H, d, J=7.8 Hz), 7.47 (1H, dd, J=1.5 and 3.9 Hz), 7.66(1H, dd, J=1.5 and 5.4 Hz). IR(CHCl₃): 3514, 3404, 3121, 1709, 1657, 1544, 1488, 1425 cm⁻¹. [α]$_D^{25}$+73.2±2.2°(c=0.518, MeOH) Anal. (C₂₂H₂₆N₂O₃S₃.0.2H₂O) Calcd.(%): C, 56.67; H, 5.71; N, 6.01; S, 20.63. Found(%): C, 56.55; H, 5.71; N, 6.03; S, 20.93.

Compound Number I-84

¹H-NMR(CDCl₃) δ: 1.07(1H, m), 1.20–1.32(2H, m), 1.43–1.48(2H, m), 1.57–1.82(4H, m), 2.02(1H, d, J=3.3 Hz), 2.00–2.20(5H, m), 2.35(2H, t, J=7.2 Hz), 2.55(1H, m), 3.86(1H, m), 4.01(2H, s), 5.29–5.43(2H, m), 6.17(1H, d, J=7.2 Hz), 7.15–7.31(7H, m), 7.67(2H, d, J=8.1 Hz). IR(CHCl₃): 3517, 3447, 2669, 1708, 1651, 1523, 1495 cm⁻¹. [α]$_D^{25}$+77.9±1.2°(c=1.016, MeOH) Anal. (C₂₈H₃₃NO₃) Calcd.(%): C, 77.93; H, 7.71; N, 3.25. Found (%): C, 77.65; H, 7.93; N, 3.32.

Compound Number I-85

¹H-NMR(CDCl₃) δ: 1.08(1H, m), 1.21–1.31(2H, m), 1.44–1.49(2H, m), 1.58–1.82(4H, m), 2.00–2.20(5H, m), 2.35(2H, t, J=7.2 Hz), 2.56(1H, m), 3.87(1H, m), 4.19(2H, s), 5.30–5.43(2H, m), 6.19(1H, d, J=7.2 Hz), 6.80(1H, m), 6.93(1H, dd, J=2.6 and 5.1 Hz), 7.16(1H, dd, J=1.5 and 5.1 Hz), 7.30 and 8.69(each 2H, each d, each J=8.1 Hz).

IR(CHCl$_3$): 3510, 3446, 2664, 1708, 1651, 1523, 1496 cm$^{-1}$. [α]$_D^{25}$+73.2±1.1°(c=1.009, MeOH) Anal. (C$_{26}$H$_{31}$NO$_3$S) Calcd.(%): C, 71.36; H, 7.14; N, 3.20; S, 7.33. Found(%): C, 71.48; H, 7.05; N, 3.29; S, 7.13.

Compound Number I-86

$^1$H-NMR(CDCl$_3$) δ: 1.07(1H, m), 1.19–1.31(2H, m), 1.43–1.48(2H, m), 1.58–1.81(4H, m), 2.00–2.17(5H, m), 2.34(2H, t, J=7.2 Hz), 2.55(1H, m), 3.87(1H, m), 3.98(2H, s), 5.30–5.43(2H, m), 6.19(1H, d, J=7.2 Hz), 6.93–7.00(2H, m), 7.09–7.13(2H, m), 7.22 and 7.70(each 2H, each d, each J=8.4 Hz). IR(CHCl$_3$): 3516, 3447, 2664, 1709, 1651, 1612, 1522, 1509, 1496, cm$^{-1}$. [α]$_D^{25}$+71.6±1.1°(c=1.019, MeOH) Anal. (C$_{28}$H$_{32}$FNO$_3$) Calcd.(%): C, 74.81; H, 7.17; N, 3.12; F. 4.23. Found(%): C, 74.66; H, 7.19; N, 3.13; F, 4.10.

Compound Number I-87

$^1$H-NMR(CDCl$_3$) δ: 1.08(1H, m), 1.20–1.31(2H, m), 1.44–1.49(2H, m), 1.58–1.82(4H, m), 2.00–2.22(5H, m), 2.35(2H, t, J=7.2 Hz), 2.56(1H, m), 3.87 (1H, m), 4.02(2H, s), 5.30–5.43(2H, m), 6.18(1H, d, J=7.2 Hz), 6.88(1H, dd, J=1.5 and 4.8 Hz), 6.92(1H, m), 7.25–7.28(3H, m), 7.68(2H, d, J=8.1 Hz). IR(CHCl$_3$): 3516, 3446, 2668, 1709, 1651, 1612, 1523, 1496 cm$^{-1}$. [α]$_D^{25}$+72.7±1.1°(c=1.014, MeOH) Anal. (C$_{26}$H$_{31}$NO$_3$S.0.1H$_2$O) Calcd.(%): C, 71.07; H, 7.16; N, 3.18; S, 7.30. Found(%): C, 70.90; H, 7.08; N, 3.21; S, 7.46.

Compound Number I-88 mp.103–105° C.; $^1$H-NMR(CDCl$_3$) δ: 1.05(1H, m), 1.19–1.29(2H, m), 1.42–1.47(2H, m), 1.58–1.81(4H, m), 2.00–2.15(5H, m), 2.35(2H, t, J=7.2 Hz), 2.52(1H, m), 3.82(1H, m), 4.16(2H, s), 5.30–5.43(2H, m), 5.97(1H, d, J=7.5 Hz), 6.79(1H, dt, J=0.9 and 3.9 Hz), 6.96(1H, dd, J=1.5 and 4.8 Hz), 7.05 (1H, m), 7.28(1H, dd, J=3.0 and 4.8 Hz), 7.37(1H, d, J=3.9 Hz). IR(CHCl$_3$): 3516, 3445, 3427, 2670, 1708, 1642, 1544, 1507 cm$^{-1}$. [α]$_D^{25}$+67.3±1.1° (c=1.002, MeOH) Anal. (C$_{24}$H$_{29}$NO$_3$S$_2$.0.3H$_2$O) Calcd.(%): C, 64.20; H, 6.64; N, 3.12; S, 14.28. Found(%): C, 64.29; H, 6.49; N, 3.10; S, 14.11.

Compound Number I-89

$^1$H-NMR(CDCl$_3$) δ: 1.07(1H, m), 1.20–1.29(2H, m), 1.40–1.49(2H, m), 1.56–1.89(4H, m), 2.00–2.25(6H, m), 2.32–2.38(2H, m), 2.51(1H, m), 3.80 (1H, m), 5.04(2H, s), 5.27–5.41(2H, m), 5.90(1H, d, J=6.6 Hz), 6.38(1H, m), 6.63(1H, t, J=2.4 Hz), 7.14–7.17(2H, m), 7.29–7.35(4H, m). IR(CHCl$_3$): 3510, 3448, 2663, 1736, 1709, 1636, 1555, 1497 cm$^{-1}$. [α]$_D^{25}$+60.8±1.0°(c=1.003, MeOH) Anal. (C$_{26}$H$_{32}$N$_2$O$_3$.0.3H$_2$O) Calcd.(%): C, 73.62; H, 7.70; N, 6.60. Found(%): C, 73.68; H, 7.62; N, 6.73.

Compound Number I-90

$^1$H-NMR(CDCl$_3$) δ: 1.06(1H, m), 1.20–1.29(2H, m), 1.40–1.48(2H, m), 1.56–1.87(4H, m), 2.00–2.24(5H, m), 2.32–2.38(2H, m), 2.50(1H, m), 3.80 (1H, m), 5.19(2H, s), 5.27–5.41(2H, m), 5.90(1H, d, J=7.5 Hz), 6.37(1H, dd, J=2.1 and 3.0 Hz), 6.67(1H, t, J=2.4 Hz), 6.95–6.98(2H, m), 7.27(1H, dd, J=1.8 and 4.5 Hz), 7.31(1H, dd, J=1.8 and 2.1 Hz). IR(CHCl$_3$): 3513, 3448, 2661, 1709, 1637, 1555, 1497 cm$^{-1}$. [α]$_D^{25}$+59.4±1.0°(c=1.011, MeOH) Anal. (C$_{24}$H$_{30}$N$_2$O$_3$S.0.2H$_2$O) Calcd.(%): C, 67.01; H, 7.12; N, 6.51; S, 7.45. Found(%): C, 67.07; H, 7.03; N, 6.62; S, 7.55.

Compound Number I-91

$^1$H-NMR(CDCl$_3$) δ: 1.06(1H, m), 1.23–1.26(2H, m), 1.39–1.48(2H, m), 1.57–1.82(4H, m), 2.00–2.16(5H, m), 2.34(2H, t, J=7.2 Hz), 2.50(1H, m), 3.82(1H, m), 5.03(2H, s), 5.27–5.42(2H, m), 5.98(1H, brs), 6.40(1H, m), 6.91(1H, dd, J=1.2 and 4.8 Hz), 7.08(1H, brs), 7.28–7.31(2H, m). IR(CHCl$_3$): 3516, 3448, 3108, 2663, 1736, 1709, 1636, 1555, 1497 cm$^{-1}$. [α]$_D^{25}$+59.8±1.0°(C=1.008, MeOH) Anal. (C$_{24}$H$_{30}$N$_2$O$_3$S.0.2H$_2$O) Calcd.(%): C, 67.01; H, 7.12; N, 6.51; S, 7.45. Found(%): C, 67.26; H, 7.06; N, 6.61; S, 7.55.

Compound Number I-92

$^1$H-NMR(CDCl$_3$) δ: 1.08(1H, m), 1.18–1.28(2H, m), 1.38–1.43(2H, m), 1.54–1.78(4H, m), 1.96–2.23(5H, m), 2.36(2H, dt, J=1.8 and 6.9 Hz), 2.52 (1H, m) 3.77(1H, m), 5.30–5.45(2H, m), 6.07(1H, d, J=6.9 Hz), 6.58(1H, dd, J=1.5 and 3.3 Hz), 7.14(1H, dd, J=2.1 and 3.3 Hz), 7.51–7.57(2H, m), 7.65 (1H, m), 7.77(1H, t, J=2.1 Hz), 7.88–7.92(2H, m). IR(CHCl$_3$): 3510, 3444, 3144, 1732, 1708, 1651, 1570, 1509, 1382, 1176 cm$^{-1}$. [α]$_D^{24}$+55.9±0.9°(c=1.013, MeOH) Anal. (C$_{25}$H$_{30}$N$_2$O$_5$S.0.3H$_2$O) Calcd.(%): C, 63.08; H, 6.48; N, 5.88; S, 6.74. Found(%): C, 63.24; H, 6.27; N, 6.03; S, 6.74.

Compound Number I-93

$^1$H-NMR(CDCl$_3$) δ: 1.06(1H, m), 1.18–1.29(2H, m), 1.39–1.47(2H, m), 1.56–1.78 (4H, m), 1.98–2.18(5H, m), 2.35(2H, t, J=7.2 Hz), 2.52(1H, m), 3.81(1H, m), 4.33(2H, s), 5.29–5.42(2H, m), 6.03(1H, d, J=7.5 Hz), 6.84(1H, d, J=3.9 Hz), 6.90(1H, m), 6.95(1H, dd, J=3.6 and 5.1 Hz), 7.19(1H, dd, J=1.2 and 5.1 Hz), 7.38(1H, d, J=3.9 Hz). IR(CHCl$_3$): 3510, 3554, 3427, 1708, 1643, 1544, 1507 m$^{-1}$. [α]$_D^{27}$+70.1±1°(c=1.010, MeOH) Anal. (C$_{24}$H$_{29}$NO$_{29}$NO$_3$S$_2$.0.1H$_2$O) Calcd.(%): C, 64.72; H, 6.61; N, 3.14; S, 14.40. Found(%): C, 64.83; H, 6.60; N, 3.31; S, 14.46.

Compound Number I-94

$^1$H-NMR(CDCl$_3$) δ: 1.09(1H, m), 1.20–1.27(2H, m), 1.40–1.44(2H, m), 1.56–1.78(4H, m), 2.00–2.19(5H, m), 2.36(2H, d, J=7.2 Hz), 2.51(1H, m), 3.78 (1H, m), 5.30–5.44 (2H, m), 6.13(1H, d, J=6.9 Hz), 6.59(1H, dd, J=1.5 and 3.3 Hz), 7.10(1H, dd, J=3.6 and 5.1 Hz), 7.16(1H, dd, J=2.1 and 3.3 Hz), 7.69–7.76(3H, m). IR(CHCl$_3$): 3510, 3444, 3143, 1708, 1651, 1571, 1508, 1387, 1179 cm$^{-1}$. [α]$_D^{24}$+56.0±1.0°(c=1.005, MeOH) Anal. (C$_{23}$H$_{28}$N$_2$O$_5$S$_2$.0.2H$_2$O) Calcd.(%): C, 57.53; H, 5.96; N, 5.83; S, 13.35. Found(%): C, 57.54; H, 6.07; N, 5.93; S, 12.91.

Compound Number I-95

$^1$H-NMR(CDCl$_3$) δ: 1.16(1H, m), 1.26–1.37(2H, m), 1.40–1.81(6H, m), 2.04–2.25(5H, m), 2.36(2H, t, J=7.2 Hz), 2.53(1H, m), 3.87(1H, m), 5.32–5.46 (2H, m), 6.37(2H, t, J=2.1 Hz), 7.31(1H, d, J=7.5 Hz), 7.33(2H, t, J=2.1 Hz), 7.82(1H, m). IR(CHCl$_3$): 3512, 3408, 3127, 1708, 1658, 1540, 1525, 1493, 1341 m$^{-1}$. [α]$_D^{25}$+88.2±1.3°(c=1.003, MeOH) Anal. (C$_{22}$H$_{27}$N$_3$O$_3$S.0.1H$_2$O) Calcd.(%): C, 63.62; H, 6.60; N, 10.12; S, 7.72. Found(%): C, 63.72; H, 6.45; N, 9.99; S, 7.75.

Compound Number I-96

$^1$H-NMR(CDCl$_3$) δ: 1.07(1H, m), 1.18–1.30(2H, m), 1.39–1.48(2H, m), 1.57–1.78(4H, m), 2.01–2.22(5H, m), 2.35(2H, t, J=7.2 Hz), 2.52(1H, m), 3.80(1H, m), 5.30–5.43 (2H, m), 6.11(1H, m), 6.98(1H, dd, J=3.6 and 5.4 Hz), 7.24(1H, dd, J=1.2 and 3.6 Hz), 7.38(1H, dd, J=1.2 and 5.4 Hz), 7.43 (1H, d, J=1.5 Hz), 7.85(1H, d, J=1.5 Hz). IR(CHCl$_3$): 3510, 3445, 3108, 1708, 1650, 1535, 1498 m$^{-1}$. [α]$_D^{25}$+70.7±1.1°(c=1.004, MeOH) Anal. (C$_{23}$H$_{27}$NO$_3$S$_3$.0.3H$_2$O) Calcd.(%): C, 59.15; H, 5.96; N, 3.00; S, 20.60. Found(%): C, 59.06; H, 5.66; N, 3.07; S, 20.87.

Compound Number I-97

¹H-NMR(CDCl₃) δ: 1.20–2.52(16H, m), 2.61(1H, m), 3.72(1H, m), 5.34–5.55 (2H, m), 6.66(1H, d, J=6.3 Hz), 71.2(1H, m), 7.71(1H, m), 7.75(1H, m), 8.29(1H, m), 8.37 (1H, brs). IR(CHCl₃): 3512, 3405, 3096, 1726, 1710, 1653, 1542, 1505, 1402, 1329, 1152 m⁻¹. [α]$_D^{25}$+65.4±1.1° (c=1.005, MeOH) Anal. (C₂₃H₂₇NO₅S₃.0.2H₂O) Calcd.(%): C, 55.55; H, 5.55; N, 2.82; S, 19.35. Found(%): C, 55.47; H, 5.54; N, 3.09; S, 19.21.

Compound Number I-98 mp.103–104° C.; ¹H-NMR(CDCl₃) δ: 1.09(1H, m), 1.23–1.31(2H, m), 1.45–1.50(2H, m), 1.60–1.80(4H, m), 2.00–2.23(5H, m), 2.37(2H, t, J=7.2 Hz), 2.55 (1H, m), 3.85(1H, m), 5.31–5.45(2H, m), 6.05(1H, d, J=7.5 Hz), 6.98 and 7.04(each 1H, each d, each J=16.2 Hz), 6.97(1H, d, J=3.9 Hz), 7.25–7.33 (3H, m), 7.41(1H, d, J=3.9 Hz). IR(CHCl₃): 3511, 3445, 3428, 2665, 1708, 1641, 1538, 1519, 1499 cm⁻¹. [α]$_D^{24}$+77.8±1.2°(c=1.007, MeOH) Anal. (C₂₅H₂₉NO₃S₂.0.25AcOEt) Calcd.(%): C, 65.38; H, 6.54; N, 2.93; S, 13.43. Found(%): C, 65.64; H, 6.62; N, 2.95; S, 13.26.

Compound Number I-99

¹H-NMR(CDCl₃) δ: 1.05(1H, m), 1.20–1.30(2H, m), 1.41–1.46(2H, m), 1.59–1.80(4H, m), 2.00–2.20(5H, m), 2.35(2H, t, J=7.2 Hz), 2.52(1H, m), 3.80(1H, m), 5.30–5.43 (2H, m), 5.94(1H, d, J=6.9 Hz), 6.57(2H, s), 6.94(1H, d, J=3.9 Hz), 7.03(1H, dd, J=1.5 and 4.5 Hz), 7.29(1H, s), 7.30(1H, m), 7.34 (1H, d, J=3.91 Hz). IR(CHCl₃): 3511, 3445, 3427, 2670, 1708, 1642, 1536, 1518, 1500 cm⁻¹. [α]$_D^{24}$+62.8±1.0°(c=1.003, MeOH) Anal. (C₂₅H₂₉NO₃S₂.0.2AcOEt) Calcd.(%): C, 65.48; H, 6.52; N, 2.96; S, 13.55. Found(%): C, 65.36; H, 6.47; N, 2.13; S, 13.58.

Compound Number I-100

¹H-NMR(CDCl₃) δ: 1.06(1H, m), 1.17–1.32(2H, m), 1.38–1.50(2H, m), 1.56–1.80 (4H, m), 1.98–2.20(5H, m), 2.35(2H, t, J=7.2 Hz), 2.44(3H, d, J=0.9 Hz), 2.52(1H, m), 3.80(1H, m), 5.30–5.43(2H, m), 5.99(1H, d, J=7.5 Hz), 5.99(1H, t, J=7.5. Hz), 6.70(1H, m), 7.03(1H, d, J=3.9 Hz), 7.10(1H, d, J=1.5 Hz), 7.36(1H, d, J=3.9 Hz). IR(CHCl₃): 3510, 3445, 3426, 2671, 1708, 1644, 1530, 1499, 1420, 1318 cm⁻¹. [α]$_D^{25}$+69.1±1.1°(c=1.018, MeOH) Anal. (C₂₄H₂₉NO₃S₃) Calcd.(%): C, 60.60; H, 6.14; N, 2.94; S, 20.22. Found(%): C, 60.49; H, 6.26; N, 2.98; S, 20.25.

Compound Number I-101

¹H-NMR(CDCl₃) δ: 1.10(1H, m), 1.18–1.32(2H, m), 1.38–1.50(2H, m), 1.54–1.77 (4H, m), 2.00–2.20(5H, m), 2.36(2H, t, J=7.2 Hz), 2.47(3H, d, J=0.9 Hz), 2.53(1H, m), 3.81(1H, m), 5.31–5.44(2H, m), 6.30(1H, d, J=7.2 Hz), 7.03(1H, m), 7.42 and 7.59(each 1H, each d, each J=3.9 Hz), 7.90(1H, d, J=1.5 Hz). IR(CHCl₃): 3517, 3441, 3370, 3115, 2671, 1708, 1655, 1530, 1504, 1442, 1328, 1156, 1142 cm⁻¹. [α]$_D^{24}$+71.6±1.1°(c=1.018, MeOH) Anal. (C₂₄H₂₉NO₅S₃.0.2H₂O) Calcd.(%): C, 56.38; H, 5.80; N, 2.74; S, 18.81. Found(%): C, 56.28; H, 5.74; N, 2.79; S, 18.92.

Compound Number I-102

¹H-NMR(CDCl₃) δ: 1.09(1H, m), 1.21–1.28(2H, m), 1.42–1.47(2H, m), 1.57–1.74(4H, m), 2.00–2.18(5H, m), 2.35(2H, t, J=7.2 Hz), 2.53(1H, m), 3.82 (1H, m), 5.30–5.43 (2H, m), 6.15(1H, d, J=7.5 Hz), 6.51 and 6.68(each 1H, each d, J=11.7 Hz), 6.98(1H, dd, J=3.6 and 5.1 Hz), 7.06(1H, dd, J=0.9 and 3.9 Hz), 7.13(1H, dt, J=0.9 and 3.6 Hz), 7.25(1H, dd, J=0.9 and 5.1 Hz), 7.41(1H, d, J=3.9 Hz). IR(CHCl₃): 3510, 3445, 3427, 2665, 1708, 1643, 1535, 1501 cm⁻¹. [α]$_D^{24}$+68.6±1.1°(c=1.006, MeOH) Anal. (C₂₅H₂₉NO₃S₂.0.2H₂O) Calcd.(%): C, 65.45; H, 6.45; N, 3.05; S, 13.98. Found(%): C, 65.44; H, 6.37; N, 3.28; S, 13.82.

Compound Number I-103 mp.107–108° C.; ¹H-NMR(CDCl₃) δ: 1.09(1H, m), 1.26–1.32(2H, m), 1.45–1.50 (2H, m), 1.60–1.81(4H, m), 2.01–2.23(5H, m), 2.37(2H, t, J=7.2 Hz), 2.55 (1H, m, 3.84(1H, m), 5.31–5.45(2H, m), 6.03(1H, d, J=7.5 Hz), 6.97 and 7.14(each 1H, each d, J=15.9 Hz), 6.97(1H, d, J=3.9 Hz), 7.01(1H, dd, J=3.6 and 5.4 Hz), 7.08(1H, d, J=3.6 Hz), 7.23(1H, d, J=5.4 Hz), 7.40(1H, d, J=3.9 Hz). IR(CHCl₃): 3517, 3445, 3428, 2670, 1708, 1641, 1536, 1518, 1500 cm⁻¹. [α]$_D^{24}$+85.0±1.2°(c=1.009, MeOH) Anal. (C₂₅H₂₉NO₃S₂.0.15AcOEt) Calcd.(%): C, 65.58; H, 6.49; N, 2.99; S, 13.68. Found(%): C, 65.88; H, 6.74; N, 2.98; S, 13.35.

Compound Number I-104

¹H-NMR(CDCl₃) δ: 1.07(1H, m), 1.19–1.30(2H, m), 1.42–1.50(2H, m), 1.57–1.79(4H, m), 2.01–2.24(5H, m), 2.36(2H, t, J=7.2 Hz), 2.53(1H, m), 3.82 (1H, m), 4.10(sH, s), 5.31–5.44(2H, m), 6.03(1H, d, J=7.2 Hz), 6.70(1H, d, J=3.6 Hz), 6.95(1H, dd, J=3.6 and 5.4 Hz), 7.03(1H, dd, J=1.5 and 3.6 Hz), 7.30(1H, d, J=3.6 Hz), 7.36(1H, dd, J=1.5 and 5.4 Hz). IR(CHCl₃): 3518, 3445, 3427, 1708, 1644, 1542, 1507 cm⁻¹. [α]$_D^{24.5}$+65.0±1.0°(c=1.008, MeOH) Anal. (C₂₄H₂₉NO₃S₃.0.4H₂O) Calcd.(%): C, 59.69; H, 6.22; N, 2.90; S, 19.92. Found(%): C, 59.40; H, 5.98; N, 2.95; S, 20.06.

Compound Number I-105

¹H-NMR(CDCl₃) δ: 1.11(1H, m), 1.21–1.31(2H, m), 1.42–1.49(2H, m), 1.58–1.76(4H, m), 2.01–2.21(5H, m), 2.36(2H, t, J=7.2 Hz), 2.53(1H, m), 3.81 (1H, m), 4.60(sH, s), 5.32–5.45(2H, m), 6.18(1H, d, J=7.2 Hz), 6.91(1H, d, J=3.9 Hz), 7.12(1H, dd, J=3.9 and 5.1 Hz), 7.40(1H, d, J=3.9 Hz), 7.52 (1H, dd, J=1.2 and 3.9 Hz), 7.72(1H, dd, J=1.2 and 5.1 Hz). IR(CHCl₃): 3517, 3444, 3425, 3097, 1708, 1648, 1524, 1508, 1402, 1328, 1147 cm⁻¹. [α]$_D^{24.5}$+61.5±1.0° (c=1.008, MeOH) Anal. (C₂₄H₂₉NO₅S₂.0.4H₂O) Calcd.(%): C, 55.98; H, 5.83; N, 2.72; S, 18.68. Found(%): C, 55.77; H, 5.71; N, 2.84; S, 18.73.

Compound Number I-106

¹H-NMR(CDCl₃) δ: 1.07(1H, m), 1.19–1.31(2H, m), 1.41–1.49(2H, m), 1.57–1.78(4H, m), 2.00–2.21(5H, m), 2.36(2H, t, J=7.2 Hz), 2.53(1H, m), 3.81 (1H, m), 4.23(sH, s), 5.31–5.44(2H, m), 6.00(1H, d, J=7.2 Hz), 6.82(1H, m), 6.88(1H, dd, J=3.6 and 5.1 Hz), 6.92(1H, d, J=3.6 Hz), 7.21(1H, dd, J=1.2 and 5.1 Hz), 7.33(1H, d, J=3.6 Hz). IR(CHCl₃): 3514, 3444, 3427, 2665, 1709, 1645, 1529, 1498, 1421, 1317 cm⁻¹. [α]$_D^{24}$+67.1±1.1°(c=1.006, MeOH) Anal. (C₂₄H₂₉NO₃S₃.0.1H₂O) Calcd.(%): C, 60.37; H, 6.16; N, 2.90; S, 20.15. Found(%): C, 60.46; H, 6.14; N, 2.96; S, 20.02.

Compound Number I-107

¹H-NMR(CDCl₃) δ: 1.09–1.32(3H, m), 1.38–1.48(2H, m), 1.53–1.79(4H, m), 1.96–2.20(5H, m), 2.34(2H, t, J=7.2 Hz), 2.54(4H, d and m, J=0.6 Hz), 3.79 (1H, m), 5.30–5.45 (2H, m), 6.48 and 6.51(total 1H, each d, J=7.8 and 7.5 Hz), 7.12 (1H, dd, J=3.9 and 5.1 Hz), 7.42 and 7.43(total 1H, each d, each J=3.9 Hz), 7.52 and 7.53(total 1H, each d, each J=3.9 Hz), 7.58(1H, m), 7.69 (1H, dd, J=1.2 and 5.1 Hz). IR(CHCl₃): 3509, 3443, 3425, 3092, 2666, 1708, 1650, 1532, 1503, 1403, 1322 cm⁻¹. [α]$_D^{23}$+70.4±1.1°(c=1.007, MeOH) Anal. (C$_{23}$H$_{27}$NO$_4$S$_3$.0.4H$_2$O) Calcd.(%): C, 56.97; H, 5.78; N, 2.89; S, 19.84. Found(%): C, 57.03; H, 5.67; N, 3.19; S, 19.73.

Compound Number I-108

$^1$H-NMR(CDCl$_3$) δ: 1.09–1.32(3H, m), 1.39–1.50(2H, m), 1.54–1.77(4H, m), 1.97–2.20(5H, m), 2.35(2H, t, J=7.2 Hz), 2.52 and 2.53(total 3H, each s), 2.54(1H, m), 3.79(1H, m), 5.31–5.45(2H, m), 6.43 and 6.47(total 1H, each d, J=7.5 and 6.6 Hz), 6.76(1H, m), 7.39(1H, t-like), 7.40(1H, dd, J=2.1 and 3.6 Hz), 7.52(1H, dd, J=2.1 and 4.2 Hz). IR(CHCl$_3$): 3510, 3443, 3425, 3092, 1708, 1650, 1531, 1503, 1437, 1237 cm$^{-1}$. [α]$_D^{23}$68.6±1.1°(c=1.011, MeOH) Anal. (C$_{24}$H$_{29}$NO$_4$S$_3$.0.2H$_2$O) Calcd.(%): C, 58.20; H, 5.98; N, 2.83; S, 19.42. Found(%): C, 58.18; H, 5.67; N, 2.90; S, 19.11.

Compound Number I-109

$^1$H-NMR(CDCl$_3$) δ: 1.13(1H, m), 1.21–1.34(2H, m), 1.45–1.52(2H, m), 1.59–1.78(4H, m), 2.03–2.23(5H, m), 2.37(2H, t, J=7.2 Hz), 2.58(1H, m), 3.86(1H, m), 5.32–5.46 (2H, m), 6.28(1H, d, J=6.6 Hz), 7.20(1H, dd, J=3.9 and 5.1 Hz), 7.59(1H, d, J=3.9 Hz), 7.75(1H, dd, J=1.2 and 5.1 Hz), 7.81(1H, d, J=3.9 Hz), 7.92(1H, dd, J=1.2 and 3.9 Hz). IR(CHCl$_3$): 3518, 3442, 3425, 3109, 1709, 1651, 1622, 1529, 1508, 1442, 1414, 1356, 1286, 1267 cm$^{-1}$. [α]$_D^{23}$+89.2±1.3°(c=1.002, MeOH) Anal. (C$_{24}$H$_{27}$NO$_4$S$_2$.0.2H$_2$O) Calcd.(%): C, 62.50; H, 5.99; N, 3.04; S, 13.90. Found(%): C, 62.63; H, 6.07; N, 2.97; S, 13.60.

Compound Number I-110

$^1$H-NMR(CDCl$_3$) δ: 1.12(1H, m), 1.22–1.33(2H, m), 1.44–1.52(2H, m), 1.59–1.79 (4H, m), 2.03–2.24(5H, m), 2.37(2H, t, J=7.2 Hz), 2.57(1H, m), 3.87(1H, m), 4.14(3H, s), 5.32–5.47(2H, m), 6.14(1H, d, J=7.5 Hz), 7.08(1H, dd, J=3.9 and 5.4 Hz), 7.27(1H, dd, J=1.2 and 3.9 Hz), 7.39(1H, dd, J=1.2 and 5.4 Hz), 7.41(1H, d, J=3.9 Hz), 7.49(1H, d, J=3.9 Hz). IR(CHCl$_3$): 3516, 3444, 3425, 2665, 1709, 1649, 1529, 1498, 1049 cm$^{-1}$. [α]$_D^{24}$+73.3±1.1°(c=1.003, MeOH) Anal. (C$_{25}$H$_{30}$N$_2$O$_4$S$_2$.0.6H$_2$O) Calcd.(%): C, 60.36; H, 6.32; N, 5.63; S, 12.89. Found(%): C, 60.30; H, 6.14; N, 5.84; S, 12.95.

Compound Number I-111

$^1$H-NMR(CDCl$_3$) δ: 1.08(1H, m), 1.19–1.30(2H, m), 1.40–1.50(2H, m), 1.55–1.82(4H, m), 1.98–2.21(5H, m), 2.36(2H, t, J=7.2 Hz), 2.53(1H, m), 3.83(1H, m), 5.30–5.44 (2H, m), 5.96(1H, d, J=7.5 Hz), 6.43(1H, br), 6.52 (1H, d, J=3.9 Hz), 6.90(1H, m), 7.08–7.11(2H, m), 7.26–7.32(3H, m). IR(CHCl$_3$): 3514, 3444, 3419, 1739, 1709, 1633, 1601, 1500, 1456 cm$^{-1}$. [α]$_D^{22}$+86.6±1.3°(c=1.005, MeOH) Anal. (C$_{25}$H$_{30}$N$_2$O$_3$S.0.1H$_2$O) Calcd.(%): C, 68.18; H, 6.91; N, 6.36; S, 7.28. Found(%): C, 68.11; H, 6.95; N, 6.43; S, 7.31.

Compound Number I-112

$^1$H-NMR(CDCl$_3$) δ: 1.05(1H, m), 1.18–1.30(2H, m), 1.39–1.48(2H, m), 1.54–1.83(4H, m), 1.98–2.21(5H, m), 2.35(2H, t, J=7.2 Hz), 2.51(1H, m), 3.38 (3H, s), 3.80(1H, m), 5.29–5.42(2H, m), 5.82(1H, d, J=6.0 Hz), 6.15(1H, d, J=4.2 Hz), 7.11–7.39(6H, m). IR(CHCl$_3$): 3514, 3446, 3425, 1741, 1709, 1628, 1597, 1477, 1415 cm$^{-1}$. [α]$_D^{22}$+83.2±1.2°(c=1.001, MeOH) Anal. (C$_{26}$H$_{32}$N$_2$O$_3$S) Calcd. (%): C, 69.00; H, 7.13; N, 6.19; S, 7.08. Found(%): C, 68.74; H, 7.08; N, 6.15; S, 7.01.

Compound Number I-113

$^1$H-NMR(CDCl$_3$) δ: 1.07(1H, m), 1.18–1.31(2H, m), 1.40–1.49(2H, m), 1.55–1.75(4H, m), 1.99–2.16(5H, m), 2.31(3H, s), 2.35(2H, t, J=7.2 Hz), 2.52 (1H, m), 3.82(1H, m), 5.31–5.43(2H, m), 6.06(1H, d, J=7.5 Hz), 7.03–7.20 (5H, m), 7.44(1H, d, J=3.9 Hz). IR(CHCl$_3$): 3516, 3444, 3425, 2671, 1709, 1647, 1529, 1498, 1421, 1317 cm$^{-1}$. [α]$_D^{23}$+70.2±1.1°(c=1.001, MeOH) Anal. (C$_{26}$H$_{31}$NO$_3$S$_2$) Calcd.(%): C, 66.49; H, 6.65; N, 2.98; S, 13.65. Found(%): C, 66.34; H, 6.74; N, 2.94; S, 13.78.

Compound Number I-114 mp.114–116° C.; $^1$H-NMR(CDCl$_3$) δ: 1.09(1H, m), 1.18–1.32(2H, m), 1.37–1.47 (2H, m), 1.55–1.75(4H, m), 2.00–2.18(5H, m), 2.35(2H, t, J=7.2 Hz), 2.42 (3H, s), 2.52(1H, m), 3.80(1H, m), 5.30–5.43(2H, m), 6.23(1H, d, J=7.5 Hz), 7.41(3H, m), 7.59(1H, d, J=3.9 Hz), 7.78(2H, m). IR(CHCl$_3$): 3514, 3442, 3371, 2669, 1707, 1655, 1529, 1504, 1329, 1151 cm$^{-1}$. [α]$_D^{23}$+72.4±1.1°(c=1.004, MeOH) Anal. (C$_{26}$H$_{31}$NO$_5$S$_2$) Calcd.(%): C, 62.25; H, 6.23; N, 2.79; S, 12.78. Found(%): C, 61.83; H, 6.39; N, 2.73; S, 12.78.

Compound Number I-115

$^1$H-NMR(CDCl$_3$) δ: 1.07(1H, m), 1.18–1.31(2H, m), 1.40–1.50(2H, m), 1.56–1.78(4H, m), 1.99–2.20(5H, m), 2.35(2H, t, J=7.2 Hz), 2.53(1H, m), 3.77(3H, s), 3.82(1H, m), 5.31–5.43(2H, m), 6.06(1H, d, J=7.2 Hz), 6.74–6.89(3H, m), 7.16–7.23(2H, m), 7.45(1H, d, J=3.9 Hz). IR(CHCl$_3$): 3516, 3444, 3425, 2669, 1709, 1647, 1591, 1529, 1498, 1477, 1423 cm$^{-1}$. [α]$_D^{23}$+68.7±1.1°(c=1.014, MeOH) Anal. (C$_{26}$H$_{31}$NO$_4$S$_2$) Calcd.(%): C, 64.30; H, 6.43; N, 2.88; S, 13.20. Found(%): C, 64.04; H, 6.56; N, 2.87; S, 13.43.

Compound Number I-116 mp.67–70° C.; $^1$H-NMR(CDCl$_3$) δ: 1.09(1H, m), 1.17–1.32(2H, m), 1.39–1.47 (2H, m), 1.55–1.75(4H, m), 2.00–2.20(5H, m), 2.35(2H, t, J=7.2 Hz), 2.52 (1H, m), 3.80(1H, m), 3.86(3H, m), 5.30–5.43(2H, m), 6.26(1H, d, J=7.2 Hz), 7.12 (1H, m), 7.40–7.47(2H, m), 7.55(1H, m), 7.59(1H, d, J=3.9 Hz). IR (CHCl$_3$): 3514, 3442, 3373, 1707, 1655, 1599, 1529, 1504, 1481, 1327, 1151 cm$^{-1}$. [α]$_D^{23}$+70.0±1.1°(c=1.008, MeOH) Anal. (C$_{26}$H$_{31}$NO$_6$S$_2$.0.7H$_2$O) Calcd.(%): C, 58.89; H, 6.16; N, 2.64; S, 12.09. Found(%): C, 58.87; H, 6.15; N, 2.74; S, 12.10.

Compound Number I-117

$^1$H-NMR(CDCl$_3$) δ: 1.10–1.32(3H, m), 1.37–1.46(2H, m), 1.55–1.73(4H, m), 1.94–2.18(5H, m), 2.34(2H, t, J=7.2 Hz), 2.55(1H, m), 3.78(1H, m), 5.29–5.45(2H, m), 6.56(1H, d, J=6.6 Hz), 7.09(1H, m), 7.37(1H, t, J=8.1 Hz), 7.45 (1H, d, J=3.9 Hz), 7.47–7.53(2H, m), 7.55(1H, d, J=3.9 Hz). IR(KBr): 3365, 3095, 1707, 1628, 1543, 1448, 1306, 1147 cm$^{-1}$. [α]$_D^{23}$+70.8±1.1°(c=1.003, MeOH) Anal. (C$_{25}$H$_{29}$NO$_6$S$_2$.0.3H$_2$O) Calcd.(%): C, 58.99; H, 5.86; N, 2.75; S, 12.60. Found(%): C, 58.85; H, 5.85; N, 2.67; S, 12.77.

Compound Number I-118 mp.133–134° C.; $^1$H-NMR(CDCl$_3$) δ: 1.08(1H, m), 1.18–1.32(2H, m), 1.40–1.49 (2H, m), 1.55–1.78(4H, m), 1.96–2.24(5H, m), 2.34(2H, t, J=7.2 Hz), 2.52(1H, m), 3.81(1H, m), 5.31–5.46(2H, m), 6.14(1H, d, J=6.6 Hz), 6.71 (2H, m), 6.86(1H, m), 7.14(2H, m), 7.42(1H, d, J=3.9 Hz). IR(Nujol): 3336, 3091, 2656, 1703, 1603, 1581, 1545 cm$^{-1}$. [α]$_D^{23}$+73.2±1.1°(c=1.007, MeOH) Anal. (C$_{25}$H$_{29}$NO$_4$S$_2$) Calcd.(%): C, 63.67; H, 6.20; N, 2.97; S, 13.60. Found(%): C, 63.78; H, 6.17; N, 3.10; S, 13.73.

Compound Number I-119

$^1$H-NMR(CDCl$_3$) δ: 1.05(1H, m), 1.17–1.30(2H, m), 1.38–1.48(2H, m), 1.54–1.80 (4H, m), 1.98–2.20(5H, m), 2.34(2H, t, J=7.2 Hz), 2.51(1H, m), 3.79 (3H, s), 3.81(1H, m), 4.10(2H, s), 5.29–5.42(2H, m), 5.97(1H, d, J=7.5 Hz), 6.77–6.84(4H, m), 7.23(2H, m), 7.37(1H, d, J=3.9 Hz). IR (CHCl$_3$): 3514, 3446, 3427, 1741, 1709, 1641, 1543, 1506, 1456 cm$^{-1}$. [α]$_D$$^{22}$+64.3±1.0°(c=1.005, MeOH) Anal. (C$_{27}$H$_{33}$NO$_4$S.0.1H$_2$O) Calcd.(%): C, 69.08; H, 7.13; N, 2.98; S, 6.83. Found(%): C, 69.03; H, 7.25; N, 3.06; S, 7.00.

Compound Number I-120

$^1$H-NMR(CDCl$_3$) δ: 1.07(1H, m), 1.16–1.28(2H, m), 1.36–1.46(2H, m), 1.52–1.78 (4H, m), 1.96–2.17(5H, m), 2.32(2H, t, J=7.2 Hz), 2.50(1H, m), 3.80(1H, m), 4.02(2H, s), 5.28–5.42(2H, m), 6.16(1H, d, J=7.5 Hz), 6.72–6.77(4H, m), 1H, m), 7.36(1H, d, J=3.9 Hz). IR(CHCl$_3$): 3595, 3423, 3207, 1707, 1635, 1599, 1545, 1508, 1456 cm$^{-1}$. [α]$_D$$^{23}$+66.8±1.1°(c=1.009, MeOH) Anal. (C$_{26}$H$_{31}$NO$_4$S.0.4H$_2$O) Calcd.(%): C, 67.77; H, 6.96; N, 3.04; S, 6.96. Found(%): C, 67.83; H, 6.92; N, 3.18; S, 7.14.

Compound Number I-121

$^1$H-NMR(CDCl$_3$) δ: 1.06(1H, m), 1.8–1.31(2H, m), 1.40–1.48(2H, m), 1.55–1.82(4H, m), 1.98–2.22(5H, m), 2.29(3H, s), 2.35(2H, t, J=7.2 Hz), 2.52 (1H, m), 3.80(1H, m), 4.14(2H, s), 5.29–5.43(2H, m), 5.97(1H, d, J=7.5 Hz), 6.78 (1H, m), 6.94–7.00(2H, m), 7.10(1H, m), 7.33(1H, m), 7.36(1H, d, J=3.9 Hz). IR(CHCl$_3$): 3514, 3446, 3427, 2669, 1763, 1745, 1709, 1643, 1545, 1506, 1371 cm$^{-1}$. [α]$_D$$^{23}$+61.3±1.0°(c=1.019, MeOH) Anal. (C$_{28}$H$_{33}$NO$_5$S.0.1H$_2$O) Calcd.(%): C, 67.61; H, 6.73; N, 2.82; S, 6.45. Found(%): C, 67.52; H, 6.77; N, 2.99; S, 6.48.

Compound Number I-122

$^1$H-NMR(CDCl$_3$) δ: 1.06(1H, m), 1.18–1.30(2H, m), 1.40–1.48(2H, m), 1.56–1.76(4H, m), 1.99–2.17(5H, m), 2.35(2H, t, J=7.2 Hz), 2.52(1H, m), 3.81(1H, m), 4.25(2H, s), 5.30–5.43(2H, m), 6.00(1H, d, J=7.5 Hz), 6.81(1H, d, J=3.9 Hz), 7.20–7.36(6H, m). IR(CHCl$_3$): 3516, 3446, 3427, 2667, 1709, 1643, 1543, 1506 cm$^1$. [α]$_D$$^{22}$+65.0±1.0° (c=1.008, MeOH) Anal. (C$_{26}$H$_{31}$NO$_3$S$_2$.0.1H$_2$O) Calcd.(%): C, 66.24; H, 6.67; N, 2.97; S, 13.60. Found(%): C, 66.14; H, 6.63; N, 3.05; S, 13.49.

Compound Number I-123

$^1$H-NMR(CDCl$_3$) δ: 1.08(1H, m), 1.20–1.32(2H, m), 1.40–1.50 (2H, m), 1.56–1.80 (4H, m), 2.00–2.20(5H, m), 2.36(2H, t, J=7.2 Hz), 2.54 (1H, m), 3.84 (1H, m), 5.20(2H, s), 5.31–5.44(2H, m), 6.06(1H, d, J=7.5 Hz), 6.94–7.05 (4H, m), 7.27–7.33(2H, m), 7.42(1H, d, J=3.9 Hz). IR(CHCl$_3$): 3516, 3444, 3427, 2669, 1709, 1645, 1599, 1545, 1508, 1497 cm$^{-1}$. [α]$_D$$^{24}$+65.4±1.1°(c=1.003, MeOH) Anal. (C$_{26}$H$_{31}$NO$_4$S.0.2H$_2$O) Calcd.(%): C, 68.30; H, 6.92; N, 3.06; S, 7.01. Found(%): C, 68.32; H, 6.83; N, 3.08; S, 6.99.

Compound Number I-124

$^1$H-NMR(CDCl$_3$) δ: 1.06(1H, m), 1.18–1.32(2H, m), 1.40–1.50(2H, m), 1.55–1.80(4H, m), 2.00–2.20(5H, m), 2.35(2H, t, J=7.2 Hz), 2.52(1H, m), 3.81(1H, m), 4.51(2H, d, J=0.9 Hz), 5.30–5.43(2H, m), 6.01(1H, d, J=7.5 Hz), 6.65–6.97(3H, m), 6.96(1H, d, J=3.9 Hz), 7.16–7.21(1H, m), 7.41(1H, d, J=3.9 Hz). IR(CHCl$_3$): 3516, 3444, 3427, 1709, 1643, 1603, 1545, 1504, 1309, 1260 cm$^{-1}$. [α]$_D$$^{22}$+65.7±1.0°(c=1.014, MeOH) Anal. (C$_{26}$H$_{32}$N$_2$O$_3$S.0.2H$_2$O) Calcd.(%): C, 68.45; H, 7.16; N, 6.14; S, 7.03. Found(%): C, 68.43; H, 7.18; N, 6.27; S, 6.94.

Compound Number I-125

$^1$H-NMR(CDCl$_3$) δ: 1.05(1H, m), 1.18–1.27(2H, m), 1.40–1.45(2H, m), 1.56–1.77(4H, m), 2.00–2.13(5H, m), 2.28(3H, s), 2.34(2H, t, J=7.5 Hz), 2.51(1H, m), 3.80(1H, m), 4.12(2H, s), 5.29–5.41(2H, m), 5.98(1H, d, J=7.2 Hz), 6.69(1H, d, J=3.6 Hz), 7.18(4H, s), 7.36(1H, d, J=3.6 Hz). IR (CHCl$_3$): 3518, 3446, 3426, 1741, 1709, 1641, 1543, 1506, 1458 cm$^{-1}$. [α]$_D$$^{22.5}$+66.8±1.1°(c=1.003, MeOH) Anal. (C$_{27}$H$_{33}$NO$_3$S.H$_2$O) Calcd.(%): C, 69.05; H, 7.51; N, 2.98; S, 6.83. Found(%): C, 69.07; H, 7.11; N, 3.23; S, 7.04.

Compound Number I-126

$^1$H-NMR(CDCl$_3$) δ: 1.04(1H, m), 1.17–1.28(2H, m), 1.41–1.46(2H, m), 1.55–1.77(4H, m), 2.00–2.20(5H, m), 2.34(2H, t, J=7.2 Hz), 2.51(1H, m), 3.80(1H, m), 4.12(2H, s), 5.29–5.41(2H, m), 5.91(1H, d, J=7.2 Hz), 6.77(1H, d, J=3.3 Hz), 6.86–6.90(2H, m), 7.15(1H, dd, J=1.8 and 7.5 Hz), 7.20–7.26 (1H, m), 7.34(1H, d, J=3.6 Hz). IR(CHCl$_3$): 3519, 3446, 3427, 2669, 1741, 1709, 1641, 1543, 1504, 1458, 1248 cm$^{-1}$. [α]$_D$$^{22.5}$+64.2±1.0°(c=1.005, MeOH) Anal. (C$_{27}$H$_{33}$NO$_4$S.0.1H$_2$O) Calcd.(%): C, 69.08; H, 7.13; N, 2.98; S, 6.83. Found(%): C, 68.97; H, 6.90; N, 3.09; S, 6.77.

Compound Number I-127

$^1$H-NMR(CDCl$_3$) δ: 1.04(1H, m), 1.18 (3H, t, J=7.7 Hz), 1.15–1.29 (2H, m), 1.41–1.46 (2H, m), 1.56–1.80 (4H, m), 2.00–2.15 (5H, m), 2.35 (2H, t, J=7.2 Hz), 2.51 (1H, s), 2.64 (2H, q, J=7.7 Hz), 3.80 (1H, m), 4.16 (2H, s), 5.29–5.41 (2H, m), 5.91 (1H, d, J=7.5 Hz), 6.69 (1H, d, J=3.6 Hz), 7.16–7.25 (4H, m), 7.35 (1H, d, J=3.6 Hz). IR (CHCl$_3$): 3516, 3447, 3427, 2669, 1709, 1641, 1543, 1506, 1456 cm$^{-1}$. [α]$_D$$^{21}$+65.8±1.1°(c=1.011, MeOH). Anal. (C$_{28}$H$_{35}$NO$_3$S.0.2H$_2$O) Calcd.(%): C, 71.67; H, 7.60; N, 2.98; S, 6.83. Found(%): C, 71.83; H, 7.49; N, 3.12; S, 6.89.

Compound Number I-128

$^1$H-NMR(CDCl$_3$) δ: 1.04 (1H, m), 1.18–1.29 (2H, m), 1.41–1.46 (2H, m), 1.56–1.80 (4H, m), 2.00–2.20 (5H, m), 2.24 and 2.31 (each 3H, each s), 2.35 (2H, t, J=7.4 Hz), 2.51 (1H, s), 3.80 (1H, m), 4.19 (2H, s), 5.29–5.41 (2H, m), 5.91 (1H, d, J=7.2 Hz), 6.70 (1H, d, J=3.6 Hz), 6.99 (1H, d, J=7.5 Hz), 7.00 (1H, s), 7.07 (1H, d, J=7.5 Hz), 7.35 (1H, d, J=3.6 Hz). IR (CHCl$_3$): 3514, 3446, 3426, 1741, 1709, 1641, 1543, 1506, 1456 cm$^{-1}$. [α]$_D$$^{21}$+65.2±1.0°(c=1.014, MeOH) Anal. (C$_{28}$H$_{35}$NO$_3$S.0.2H$_2$O) Calcd.(%): C, 71.67; H, 7.60; N, 2.98; S, 6.83. Found(%): C, 71.53; H, 7.49; N, 3.31; S, 6.90.

Compound Number I-129

$^1$H-NMR(CDCl$_3$) δ: 1.05(1H, m), 1.18–1.29(2H, m), 1.42–1.47(2H, m), 1.56–1.78(4H, m), 2.00–2.20(5H, m), 2.35(2H, t, J=7.5 Hz), 2.43(3H, s), 2.52 (1H, s),3.81(1H, m), 4.24(2H, s), 5.30–5.42(2H, m), 5.97(1H, d, J=7.5 Hz), 6.57(1H, m), 6.67(1H, d, J=3.3 Hz), 6.83(1H, d, J=3.9 Hz), 7.37 (1H, d, J=3.9 Hz). IR(CHCl$_3$): 3514, 3446, 3427, 1709, 1643, 1545, 1506, 1456 cm$^{-1}$. [α]$_D$$^{22}$+67.1±1.1°(c=1.002, MeOH) Anal. (C$_{25}$H$_{31}$NO$_3$S$_2$) Calcd.(%): C, 65.61; H, 6.83; N, 3.06; S, 14.01. Found(%): C, 65.42; H, 6.76; N, 3.20; S, 13.73.

Compound Number I-130

$^1$H-NMR(CDCl$_3$) δ: 1.04(1H, m), 1.18–1.28(2H, m), 1.41–1.45(2H, m), 1.55–1.78 (4H, m), 1.99–2.16(5H, m), 2.34(2H, t, J=7.2 Hz), 2.38(3H, s), 2.51 (1H, m), 3.80(1H, m), 4.09(2H, s), 5.29–5.41(2H, m), 5.96(1H, d, J=6.9 Hz), 6.76(1H, d, J=3.6 Hz), 7.12(4H, s), 7.37(1H, d, J=3.6 Hz). IR (CHCl$_3$): 3510, 3446, 3427, 1741, 1709, 1641, 1543, 1508, 1458 cm$^{-1}$. [α]$_D$$^{22}$+67.0±1.1°(c=1.014, MeOH) Anal. (C$_{27}$H$_{33}$NO$_3$S) Calcd.(%): C, 71.81; H, 7.36; N, 3.10; S, 7.10. Found(%): C, 71.53; H, 7.24; N, 3.21; S, 7.36.

Compound Number I-131

$^1$H-NMR(CDCl$_3$) δ: 1.04(1H, m), 1.18–1.28(2H, m), 1.41–1.46(2H, m), 1.56–1.78(4H, m), 1.99–2.19(5H, m), 2.33(3H, s), 2.34(2H, t, J=7.5 Hz), 2.51 (1H, m), 3.81(1H, m), 4.09(2H, s), 5.29–5.42(2H, m), 5.96(1H, d, J=7.2 Hz), 6.77 (1H, d, J=3.6 Hz), 7.02–7.07(3H, m), 7.21(1H, m), 7.37(1H, d, J=3.6 Hz). IR (CHCl$_3$): 3516, 3446, 3427, 1741, 1709, 1641, 1543, 1506, 1458 cm$^{-1}$. $[\alpha]_D^{23}$+66.1±1.1° (c=1.006, MeOH) Anal. (C$_{27}$H$_{33}$NO$_3$S.0.2H$_2$O) Calcd.(%): C, 71.24; H, 7.40; N, 3.08; S, 7.04. Found(%): C, 71.26; H, 7.20; N, 3.19; S, 7.12.

Compound Number I-132

$^1$H-NMR(CDCl$_3$) δ: 1.06(1H, m), 1.19–1.30(2H, m), 1.41–1.49(2H, m), 1.57–1.78(4H, m), 2.00–2.21(5H, m), 2.30(3H, s), 2.35(2H, t, J=7.2 Hz), 2.52(1H, m), 3.81(1H, m), 4.25(2H, s), 5.30–5.43(2H, m), 6.01(1H, d, J=6.9 Hz), 6.82(1H, d, J=3.9 Hz), 7.02(1H, m), 7.10–7.19(3H, m), 7.31(1H, d, J=3.9 Hz). IR(CHCl$_3$): 3516, 3446, 3427, 2671, 1739, 1709, 1643, 1543, 1506, 1475, 1456 cm$^{-1}$. $[\alpha]_D^{23}$+63.2±1.0°(c=1.007, MeOH). (C$_{27}$H$_{33}$NO$_3$S$_2$.0.2H$_2$O) Calcd.(%): C, 66,55; H, 6.91; N, 2.87; S, 13.16. Found(%): C, 66.44; H, 6.87; N, 2.99; S, 13.11.

Compound Number I-133

$^1$H-NMR(CDCl$_3$) δ: 1.07(1H, m), 1.20–1.30(2H, m), 1.45–1.51(2H, m), 1.56–1.82(4H, m), 2.00–2.20(5H, m), 2.35(2H, t, J=7.2 Hz), 2.52(1H, m), 3.82 (1H, m), 4.16(2H, s), 5.30–5.43(2H, m), 5.98(1H, d, J=7.2 Hz), 6.13 (1H, dd, J=3.3 and 0.9 Hz), 6.32(1H, dd, J=3.3 and 1.8 Hz), 6.84(1H, d, J=3.6 Hz), 7.35(1H, dd, J=1.8 and 0.9 Hz), 7.37(1H, d, J=3.6 Hz). IR (CHCl$_3$): 3512, 3446, 3427, 2669, 1709, 1.643, 1545, 1506 cm$^{-1}$. $[\alpha]_D^{22}$+69.6±1.1°(c=1.015, MeOH) Anal. (C$_{24}$H$_{29}$NO$_4$S.0.2H$_2$O) Calcd.(%): C, 66.86; H, 6.87; N, 3.25; S, 7.44. Found(%): C, 66.75; H, 6.63; N, 3.32; S, 7.50.

Compound Number I-134

$^1$H-NMR(CDCl$_3$) δ: 1.07(1H, m), 1.19–1.29(2H, m), 1.45–1.60(2H, m), 1.61–1.80(4H, m), 2.00–2.21(5H, m), 2.36(2H, t, J=7.2 Hz), 2.52(1H, m), 3.81(1H, m), 3.96(2H, s), 5.29–5.42(2H, m), 5.96(1H, d, J=6.9 Hz), 6.30 (1H, m), 6.80(1H, m), 7.32(1H, m), 7.35–7.39(2H, m). IR(CHCl$_3$): 3516, 3446, 3427, 2663, 1709, 1643, 1545, 1506 cm$^{-1}$. $[\alpha]_D^{21}$+70.2±1.1°(c=1.007, MeOH). (C$_{24}$H$_{29}$NO$_4$S) Calcd.(%): C, 67.42; H, 6.84; N, 3.28; S, 7.50. Found(%): C, 67.13; H, 6.57; N, 3.40; S, 7.40.

Compound Number I-135

$^1$H-NMR(CDCl$_3$) δ: 1.06(1H, m), 1.20–1.29(2H, m), 1.42–1.47(2H, m), 1.58–1.82(4H, m), 2.00–2.15(5H, m), 2.35(2H, t, J=7.2 Hz), 2.52(1H, m), 3.81 (1H, m), 4.41(2H, s), 5.29–5.41(2H, m), 5.96(1H, d, J=7.2 Hz), 6.91 (1H, d, J=3.6 Hz), 7.11(1H, s), 7.25–7.35(3H, m), 7.39(1H, d, J=3.6 Hz), 7.76 (1H, d, J=7.8 Hz). IR(CHCl$_3$): 3510, 3444, 3427, 2667, 1709, 1643, 1543, 1508 cm$^{-1}$. $[\alpha]_D^{24}$+66.5±1.1° (c=1.012, MeOH) Anal. (C$_{28}$H$_{31}$NO$_3$S$_2$.0.5H$_2$O)Calcd.(%): C, 66.90; H, 6.42; N, 2.79; S, 12.76. Found(%): C, 66.99; H, 6.12; N, 2.81; S, 12.48.

Compound Number I-136

$^1$H-NMR(CDCl$_3$) δ: 1.07(1H, m), 1.20–1.42(2H, m), 1.44–1.49(2H, m), 1.55–1.80(4H, m), 2.00–2.20(5H, m), 2.35(2H, t, J=7.2 Hz), 2.52(1H, m), 3.81 (1H, m), 4.30(2H, s), 5.29–5.41(2H, m), 5.98(1H, d, J=7.8 Hz), 6.51 (1H, d, J=0.6 Hz), 6.92(1H, d, J=3.9 Hz), 7.17–7.25(2H, m), 7.38–7.51 (3H, m). IR (CHCl$_3$): 3514, 3444, 3427, 2669, 1709, 1643, 1545, 1508, 1454 cm$^{-1}$. $[\alpha]_D^{23}$+63.8±1.0° (c=1.004, MeOH). Anal. (C$_{28}$H$_{31}$NO$_4$S.0.3H$_2$O) Calcd.(%): C, 69.62; H, 6.59; N, 2.90; S, 6.64. Found(%): C, 69.51; H, 6.52; N, 2.92; S, 6.63.

Compound Number I-137

$^1$H-NMR(CDCl$_3$) δ: 1.05(1H, m), 1.18–1.29(2H, m), 1.40–1.48(2H, m), 1.55–1.78(4H, m), 1.98–2.18(5H, m), 2.34(2H, t, J=7.2 Hz), 2.51(1H, m), 3.81(1H, m), 4.17(2H, s), 5.29–5.42(2H, m), 5.98(1H, d, J=7.5 Hz), 6.81 (1H, d, J=3.6 Hz), 7.29–7.46(6H, m), 7.52–7.60(41H, m). IR(CHCl$_3$): 3510, 3446, 3427, 1741, 1709, 1643, 1543, 1506, 1489 cm$^{-1}$. $[\alpha]_D^{23}$+59.4±1.0°(c=1.007, MeOH). (C$_{32}$H$_{35}$NO$_3$S.0.2H$_2$O) Calcd.(%): C, 74.30; H, 6.90; N, 2.71; S, 6.20. Found(%): C, 74.24; H, 6.78; N, 2.97; S, 6.16.

Compound Number I-138

$^1$H-NMR(CDCl$_3$) δ: 1.04(1H, m), 1.17–1.29(2H, m), 1.39–1.47(2H, m), 1.54–1.76(4H, m), 1.97–2.38(5H, m), 2.33(2H, t, J=7.5 Hz), 2.51(1H, m), 3.80 (1H, m), 4.19(2H, s), 5.28–5.41(2H, m), 5.98(1H, d, J=7.5 Hz), 6.79 (1H, d, J=3.6 Hz), 7.21(1H, d, J=7.8 Hz), 7.31–7.49(7H, m), 7.56 (2H, m). IR (CHCl$_3$): 3512, 3446, 3427, 2669, 1741, 1709, 1643, 1543, 1506, 1479, 1456 cm$^{-1}$. $[\alpha]_D^{24}$+59.2±1.0° (c=1.006 MeOH) Anal. (C$_{32}$H$_{35}$NO$_3$S.0.2H$_2$) Calcd.(%): C, 74.30; H, 6.90; N, 2.71; S, 6.20. Found(%): C, 74.26; H, 6.92; N, 3.00; S, 6.20.

Compound Number I-139

$^1$H-NMR(CDCl$_3$) δ: 1.05(1H, m), 1.17–1.32(2H, m), 1.43–1.48(2H, m), 1.58–1.80(4H, m), 2.02–2.24(5H, m), 2.34(2H, t, J=7.2 Hz), 2.58(1H, s), 3.91(1H, m),4.11(2H, s), 5.30–5.44(2H, m), 6.11(1H, d, J=7.2 Hz), 7.18–7.30(6H, m), 7.75(1H, d, J=8.4 Hz), 7.86(1H, s), 8.16(1H, s). IR(CHCl$_3$): 3516, 3430, 2665, 1711, 1709, 1651, 1513, 1494, 1454, 1435 cm$^{-1}$. $[\alpha]_D^{24}$+45.6±0.9°(c=1.004, MeOH) Anal. (CO$_{30}$H$_{33}$NO$_3$S.0.1H$_2$O) Calcd.(%): C, 73.62; H, 6.84; N, 2.86; S, 6.55. Found(%): C, 73.57; H, 6.71; N, 3.07; S, 6.30.

Compound Number I-140

$^1$H-NMR(CDCl$_3$) δ: 1.09(1H, m), 1.20–1.32(2H, m), 1.46–1.51(2H, m), 1.58–1.78(4H, m), 2.02–2.24(5H, m), 2.35(2H, t, J=7.41 Hz), 2.60(1H, s), 3.92(1H, m),4.10(2H, s), 5.32–5.46(2H, m), 6.14(1H, d, J=7.2 Hz), 7.19–7.32(6H, m), 7.64(1H, s), 7.81(1H, s), 8.20(1H, d, J=8.4 Hz). IR(CHCl$_3$): 3516, 3438, 2669, 1709, 1651, 1516, 1494, 1406 cm$^{-1}$. $[\alpha]_D^{24}$+53.0±0.9° (c=1.002, MeOH) Anal. (C$_{30}$H$_{33}$NO$_3$S) Calcd.(%): C, 73.89; H, 6.82; N, 2.87; S, 6.58. Found(%): C, 73.57; H, 7.05; N, 3.08; S, 6.63.

Compound Number I-141 mp.54–56° C.; $^1$-NMR(CDCl$_3$) δ: 0.97(1H, m), 1.10–1.43 (4H, m), 1.53–1.72 (4H, m), 1.97–2.15(5H, m), 2.31(2H, t, J=7.4 Hz), 2.45(1H, s), 3.83(1H, m), 4.39 and 4.52(each 1H, each d, J=16.5 Hz), 5.25–5.40(2H, m), 5.98 (1H, d, J=7.5 Hz), 7.00–7.31(7H, m), 7.57(1H, s), 7.73(1H, d, J=7.5 Hz). IR (CHCl$_3$): 3514, 3433, 2671, 1709, 1655, 1512, 1454 cm$^{-1}$. $[\alpha]_D^{25}$+76.7±1.2°(c=1.005, MeOH) Anal. (C$_{30}$H$_{33}$NO$_3$S.0.1H$_2$O) Calcd.(%): C, 73.62; H, 6.84; N, 2.86; S, 6.55. Found(%): C, 73.45; H, 6.91; N, 3.21; S, 6.34.

Compound Number I-142 mp.118–119° C.; $^1$H-NMR(CDCl$_3$) δ: 1.07(1H, m), 1.20–1.27(2H, m), 1.42–1.46(2H, m), 1.55–1.73(4H, m), 1.99–2.12(5H, m), 2.33(2H, t, J=7.5 Hz), 2.52(1H, s), 3.82 (1H, m), 3.93(2H, s), 5.29–5.42(2H, m), 6.10 (1H, d, J=7.2 Hz), 7.05(1H, d, J=0.9 Hz), 7.16–7.32(6H, m). IR(CHCl$_3$): 3516, 3444, 3429, 2669, 1739, 1709, 1665, 1549, 1508, 1454 cm$^{-1}$. $[\alpha]_D^{24}$+72.7±0.1°(c=1.001, MeOH) Anal. (C$_{26}$H$_{31}$NO$_3$S) Calcd.(%): C, 71.36; H, 7.14; N, 3.20; S, 7.33. Found(%): C, 71.31; H, 7.27; N, 3.36; S, 7.31.

Compound Number I-143

$^1$H-NMR(CDCl$_3$) δ: 1.09(1H, m), 1.19–1.32(2H, m), 1.46–1.51(2H, m), 1.58–1.78(4H, m), 2.02–2.24(5H, m), 2.35(2H, t, J=7.2 Hz), 2.60(1H, s), 3.92(1H, m),4.24($^2$H, s), 5.32–5.47(2H, m), 6.14(1H, d, J=7.5 Hz), 7.18–7.30(6H, m), 7.43(1H, t, J=7.8 Hz), 7.83(1H, s), 8.17(1H, d, J=7.8 Hz). IR(CHCl$_3$): 3516, 3438, 2671, 1709, 1651, 1518, 1495, 1454 cm$^{-1}$. $[\alpha]_D^{25}$+62.8±1.0°(c=1.011, MeOH) Anal.

($C_{30}H_{33}NO_3S\cdot 0.1H_2O$) Calcd.(%): C, 73.62; H, 6.84; N, 2.86; S, 6.55. Found(%): C, 73.52; H, 6.87; N, 3.13; S, 6.47.

Compound Number I-144

$^1$H-NMR(CDCl$_3$) δ: 1.05(1H, m), 1.23–1.29(2H, m), 1.41–1.49(2H, m), 1.58–1.77(4H, m), 2.00–2.21(5H, m), 2.35(2H, t, J=7.2 Hz), 2.52(1H, m), 3.81 (1H, m), 4.05(2H, s), 5.12(2H, s), 5.29–5.42(2H, m), 5.94(1H, d, J=7.8 Hz), 6.76(1H, d, J=3.9 Hz), 6.90–6.98(31H, m), 7.32–7.45 (6H, m). IR (CHCl$_3$): 3516, 3446, 3427, 1741, 1709, 1643, 1543, 1510, 1456, 1273 cm$^{-1}$. $[α]_D^{23}$+53.7±0.9°(c=1.006, MeOH) Anal. ($C_{33}H_{36}FNO_4S\cdot 0.2H_2O$) Calcd.(%): C, 70.11; H, 6.49; N, 2.48; S, 5.67; F, 3.36. Found(%): C, 70.00; H, 6.44; N, 2.50; S, 5.75; F, 3.32.

Compound Number I-145 mp.136–137° C.; $^1$H-NMR(CDCl$_3$) δ: 1.06(1H, m), 1.23–1.29(2H, m), 1.41–1.49(2H, m), 1.58–1.77(4H, m), 2.00–2.21(5H, m), 2.35(2H, t, J=7.2 Hz), 2.52(1H, m), 3.78(1H, m), 4.05(2H, s), 5.29–5.42(2H, m), 5.93 (1H, d, J=10.8 Hz), 6.77(1H, d, J=3.6 Hz), 6.88–6.98(3H, m), 7.36 (1H, d, J=3.6 Hz). IR (Nujol): 3377, 3101, 2752, 1703, 1618, 1601, 1550, 1518 cm$^{-1}$. $[α]_D^{23}$+64.2±1.0°(c=1.009, MeOH) Anal. ($C_{26}H_{30}FNO_4S$) Calcd.(%): C, 66.23; H, 6.41; N, 2.97; S, 6.80; F, 4.03. Found(%): C, 66.15; H, 6.38; N, 2.94; S, 6.76; F, 3.94.

Compound Number I-146

$^1$H-NMR(CDCl$_3$) δ: 1.06(1H, m), 1.20–1.29(2H, m), 1.41–1.46(2H, m), 1.61–1.81(4H, m), 2.00–2.16(5H, m), 2.35(2H, t, J=7.2 Hz), 2.51(1H, m), 3.79 (1H, m), 4.03(2H, s), 5.08(2H, s), 5.29–5.40(2H, m), 5.63(1H, brs), 5.93 (1H, d, J=7.5 Hz), 6.70(1H, dd, J=2.1 and 8.4 Hz), 6.77 (1H, d, J=3.9 Hz), 6.83 (1H, d, J=5.7 Hz). 6.86(1H, d, J=8.4 Hz), 7.36–7.41(6H, m). IR(CHCl$_3$): 3539, 3446, 3425, 1741, 1709, 1641, 1543, 1508, 1475, 1273 cm$^{-1}$. $[α]_D^{23}$+ 53.8±0.9°(c=1.003, MeOH) Anal. ($C_{33}H_{37}NO_5S\cdot 0.5H_2O$) Calcd.(%): C, 69.69; H, 6.73; N, 2.46; S, 5.64. Found(%): C, 69.68; H, 6.85; N, 2.68; S, 5.76.

Compound Number I-147 mp.150–151° C.; $^1$H-NMR(CDCl$_3$) δ: 1.06(1H, m), 1.20–1.29(2H, m), 1.41–1.46(2H, m), 1.58–1.79(4H, m), 2.00–2.16(5H, m), 2.35(2H, t, J=7.2 Hz), 2.51(1H, m), 3.79(1H, m), 3.86(3H, s), 4.06(2H, s), 5.29–5.41 (2H, m), 5.56 (1H, brs), 5.93(1H, d, J=8.4 Hz), 6.72–6.77(3H, m), 6.87 (1H, d, J=8.1 Hz), 7.37(1H, d, J=3.6 Hz). IR(Nujol): 3452, 3361, 3130, 1.743, 1707, 1620, 1599, 1550, 1522, 1286 cm$^{-1}$. $[α]_D^{23}$+62.6±1.0°(c=1.002, MeOH) Anal. ($C_{27}H_{33}NO_5S$) Calcd.(%): C, 67.05; H, 6.88; N, 2.90; S, 6.63. Found(%): C, 67.20; H, 7.04; N, 2.98; S, 6.58.

Compound Number I-148

$^1$H-NMR(CDCl$_3$) δ: 1.07(1H, m), 1.19–1.31(2H, m), 1.41–1.50(2H, m), 1.56–1.81 (4H, m), 1.99–2.21(5H, m), 2.35(2H, t, J=7.2 Hz), 2.53(1H, m), 2.95–3.00 (2H, m), 3.10–3.15(2H, m),3.83(1H, m), 5.31–5.44(2H, m), 6.02 (1H, d, J=7.2 Hz), 6.70(1H, d, J=3.9 Hz), 7.15–7.32(5H, m), 7.33(1H, d, J=3.9 Hz). IR(CHCl$_3$): 3510, 3446, 3429, 2671, 1741, 1709, 1641, 1543, 1506, 1456 cm$^{-1}$. $[α]_D^{23}$+ 68.4±1.1°(c=1.004, MeOH) Anal. ($C_{27}H_{33}NO_3S\cdot 0.1H_2O$) Calcd.(%): C, 71.52; H, 7.38; N, 3.09; S, 7.07. Found(%): C, 71.35; H, 7.37; N, 3.19; S, 7.19.

Compound Number I-149

$^1$H-NMR(CDCl$_3$) δ: 1.07(1H, m), 1.19–1.32(2H, m), 1.41–1.50(2H, m), 1.56–1.81 (4H, m), 1.99–2.23(5H, m), 2.36(2H, t, J=7.2 Hz), 2.43(3H, s), 2.53 (1H, m), 3.05–3.19 (4H, m), 3.83(1H, m), 5.31–5.44(2H, m), 6.00(1H, d, J=6.9 Hz), 6.23–6.56(2H, m), 6.75 and 7.34(each 1H, each d, each J=3.6 Hz). IR (CHCl$_3$): 3510, 3446, 3429, 2669, 1709, 1641, 1543, 1506, 1458 cm$^{-1}$. $[α]_D^{23}$+64.6±1.0°(c=1.014, MeOH) Anal. ($C_{26}H_{33}NO_3S_2\cdot 0.1H_2O$) Calcd.(%): C, 65.96; H, 7.07; N, 2.96; S, 13.54. Found(%): C, 65.87; H, 7.03; N, 3.02; S, 13.50.

Compound Number I-150

$^1$H-NMR(CDCl$_3$) δ: 1.07(1H, m), 1.19–1.31(2H, m), 1.41–1.50(2H, m), 1.56–1.80(4H, m), 1.99–2.20(5H, m), 2.35(2H, t, J=7.5 Hz), 2.53(1H, m), 3.18(3H, s), 3.83(1H, m), 5.31–5.44(2H, m), 6.05(1H, d, J=7.2 Hz), 6.74 (1H, d, J=3.6 Hz), 6.79(1H, m), 6.91(1H, dd, J=3.6 and 5.4 Hz), 7.13(1H, dd, J=1.2 and 5.4 Hz), 7.34(1H, d, J=3.6 Hz). IR(CHCl$_3$): 3516, 34446, 3429, 2669, 1709, 1641, 1543, 1506 cm$^{-1}$. $[α]_D^{24}$30 66.1±1.0°(c=1.019, MeOH) Anal. ($C_{25}H_{31}NO_3S_2$) Calcd.(%): C, 65.61; H, 6.83; N, 3.06; S, 14.01. Found(%): C, 65.47; H, 6.89; N, 3.12; S, 13.82.

Compound Number I-151

$^1$H-NMR(CDCl$_3$) δ: 1.09(1H, m), 1.20–1.32(2H, m), 1.42–1.51(2H, m), 1.57–1.81(4H, m), 2.00–2.22(5H, m), 2.33(2H, t, J=7.5 Hz), 2.56(1H, m), 2.99–3.05(2H, m), 3.11–3.17(2H, m), 3.88(1H, m), 5.30–5.44(2H, m), 6.22 (1H, d, J=7.2 Hz), 6.74(1H, m), 6.89(1H, dd, J=3.3 and 5.1 Hz), 7.11(1H, dd, J=1.2 and 5.1 Hz), 7.23 and 7.67(each 2H, each d, each J=8.1 Hz). IR (CHCl$_3$): 3516, 3448, 2665, 1709, 1651, 1523, 1496 cm$^{-1}$. $[α]_D^{24}$+71.8±1.1°(c=1.009, MeOH) Anal. ($C_{27}H_{33}NO_3S$) Calcd.(%): C, 71.81; H, 7.37; N, 3.10; S, 7.10. Found(%): C, 71.68; H, 7.40; N, 3.18; S, 6.96.

Compound Number I-152

$^1$H-NMR(CDCl$_3$) δ: 1.07(1H, m), 1.19–1.31(2H, m), 1.42–1.50(2H, m), 1.56–1.81(4H, m), 2.00–2.21(5H, m), 2.36(2H, t, J=7.2 Hz), 2.53(1H, m), 2.92–2.97(2H, m), 3.07–3.12(2H, m), 5.31–5.44(2H, m), 5.99 (1H, d, J=7.2 Hz), 6.68(1H, d, J=3.6 Hz), 6.92–7.00(2H, m), 7.08–7.15(2H, m), 7.32(1H, d, J=3.6 Hz). IR(CHCl$_3$): 3516, 3446, 3429, 1741, 1709, 1641, 1543, 1510, 1458 cm$^{-1}$. $[α]_D^{23}$+64.1±1.0°(c=1.012, MeOH) Anal. ($C_{27}H_{32}FNO_3S$) Calcd.(%): C, 69.06; H, 6.87; N, 2.98; S, 6.83; F, 4.05. Found(%): C, 68.92; H, 6.90; N, 3.03; S, 6.81; F, 4.02.

Compound Number I-153

$^1$H-NMR(CDCl$_3$) δ: 1.05(1H, m), 1.19–1.29(2H, m), 1.41–1.46(2H, m), 1.56–1.78(4H, m), 2.00–2.19(5H, m), 2.29(6H, s), 2.34(2H, t, J=7.5 Hz), 2.51(1H, m), 3.81(1H, m), 4.05(2H, s), 5.29–5.42(2H, m), 5.96(1H, d, J=7.5 Hz), 6.77(1H, td, J=0.9 and 3.6 Hz), 6.85(2H, s), 6.88(1H, s), 7.37 (1H, d, J=3.6 Hz). IR(CHCl$_3$): 3516, 3446, 3427, 1739, 1709, 1641, 1606, 1543, 1506, 1458 cm$^{-1}$. $[α]_D^{23}$+ 64.6±1.0°(c=1.004, MeOH) Anal. ($C_{28}H_{35}NO_3S\cdot 0.1H_2O$) Calcd.(%): C, 71.94; H, 7.59; N, 3.00; S, 6.86. Found(%): C, 71.87; H, 7.52; N, 3.31; S, 6.94.

Compound Number I-154

$^1$H-NMR(CDCl$_3$) δ: 1.05(1H, m), 1.18–1.29(2H, m), 1.41–1.46(2H, m), 1.56–1.78 (4H, m), 2.00–2.19(5H, m), 2.34(2H, t, J=7.5 Hz), 2.51(1H, m), 3.81(1H, m), 4.10(2H, s), 5.29–5.42(2H, m), 5.98(1H, d, J=7.2 Hz), 6.75 (1H, td, J=0.9 and 3.9 Hz), 6.97–7.03(2H, m), 7.17–7.22(2H, m), 7.36(1H, d, J=3.9 Hz). IR(CHCl$_3$): 3512, 3446, 3427, 1741, 1709, 1643, 1543, 1508 cm$^{-1}$. $[α]_D^{24}$+66.1±1.1°(c=1.008, MeOH) Anal. ($C_{26}H_{30}FNO_3S$) Calcd.(%): C, 68.54; H, 6.64; N, 3.07; S, 7.04; F, 4.17. Found(%): C, 68.41; H, 6.70; N, 3.19; S, 6.90; F,3.98.

Compound Number I-155

$^1$H-NMR(CDCl$_3$) δ: 1.05(1H, m), 1.19–1.29(2H, m), 1.42–1.46(2H, m), 1.58–1.78(4H, m), 2.00–2.17(5H, m), 2.35(2H, t, J=7.5 Hz), 2.52(1H, m), 3.81 (1H, m), 4.19(2H, s), 5.29–5.42(2H, m), 5.97(1H, d, J=7.8 Hz), 6.75 (1H, td, J=0.9 and 3.6 Hz), 7.34–7.37(3H, m), 7.56–7.59(2H, m). IR (CHCl$_3$): 3512, 3444, 3427, 1741, 1709, 1643, 1543, 1506, 1325, 1167, 1130, 1066 cm$^{-1}$. $[\alpha]_D^{24}$+60.3±1.0°(c=1.001, MeOH) Anal. (C$_{27}$H$_{30}$F$_3$NO$_3$S) Calcd.(%): C, 64.14; H, 5.98; N, 2.77; S, 6.34; F, 11.27. Found(%): C, 64.16; H, 6.04; N, 3.02; S, 6.19; F, 11.17.

Compound Number I-156 mp.66–70° C.; $^1$H-NMR(CDCl$_3$) δ: 1.11(1H, m), 1.22–1.30(2H, m), 1.43–1.50(2H, m), 1.60–1.78(4H, m), 2.03–2.22(5H, m), 2.36(2H, t, J=7.5 Hz), 2.54(1H, m), 3.87(1H, m), 4.08(2H, s), 5.31–5.45(2H, m), 6.21 (1H, d, J=7.2 Hz), 7.18–7.32(6H, m), 7.60(1H, d, J=0.9 Hz), 7.70 (1H, d, J=0.6 Hz), 7,74 (1H, d, J=8.1 Hz). IR(KBr): 3338, 1707, 1616, 1556, 1537 cm$^{-1}$. $[\alpha]_D^{23}$+97.2±1.4°(c=1.016, MeOH) Anal. (C$_{30}$H$_{33}$NO$_3$S.0.3H$_2$O) Calcd.(%): C, 73.08; H, 6.87; N, 2.84; S, 6.50. Found(%): C, 73.19; H, 7.11; N, 2.98; S, 6.32.

Compound Number I-157

$^1$H-NMR(CDCl$_3$) δ: 1.03(1H, m), 1.17–1.29(2H, m), 1.38–1.47(2H, m), 1.55–1.76(4H, m), 1.97–2.18(5H, m), 2.33(2H, t, J=7.5 Hz), 2.50(1H, m), 3.80 (1H, m), 4.29(2H, s), 5.28–5.40(2H, m), 5.94(1H, d, J=7.5 Hz), 6.81 (1H, d, J=3.9 Hz), 7.32–7.39(2H, m), 7.42–7.50(2H, m), 7.69(1H, s), 7.77–7.83 (3H, m). IR(CHCl$_3$): 3516, 3446, 3427, 2665, 1739, 1709, 1643, 1543, 1506, 1458 cm$^{-1}$. $[\alpha]_D^{23}$+62.8±1.0°(c=1.005, MeOH) Anal. (C$_{30}$H$_{12}$NO$_3$S.0.2H$_2$O) Calcd.(%): C, 73.35; H, 6.85; N, 2.85; S, 6.53. Found(%): C, 73.36; H, 6.84; N, 3.19; S, 6.55.

Compound Number I-158

$^1$H-NMR(CDCl$_3$) δ: 1.07(1H, m), 1.20–1.32(2H, m), 1.42–1.50(2H, m), 1.57–1.84 (4H, m), 2.00–2.23(5H, m), 2.36(2H, t, J=7.5 Hz), 2.53(1H, m), 2.95–3.00(2H, m), 3.06–3.12(2H, m), 3.82(1H, m),3.83(3H, s), 5.30–5.43 (2H, m), 5.95(1H, d, J=6.9 Hz), 6.73(1H, d, J=3.6 Hz), 6.84–6.89 (2H, m), 7.09 (1H, dd, J=1.5 and 7.5 Hz), 7.20(1H, dt, J=1.5 and 7.5 Hz), 7.34(1H, d, J=3.6 Hz). IR(Nujol): 3367, 3221, 3186, 3091, 3055, 2654, 1711, 1631, 1566, 1541, 1321 cm$^{-1}$. $[\alpha]_D^{25}$+61.3±1.020 (c=1.003, MeOH) Anal. (C$_{28}$H$_{35}$NO$_4$S) Calcd.(%): C, 69.82; H, 7.32; N, 2.91; S, 6.66. Found(%): C, 69.93; H, 7.48; N, 3.09; S, 6.54.

Compound Number I-159

$^1$H-NMR(CDCl$_3$) δ: 1.07(1H, m), 1.18–1.30(2H, m), 1.40–1.50(2H, m), 1.54–1.78(4H, m), 1.98–2.21(5H, m), 2.33(2H, t, J=7.2 Hz), 2.53(1H, m), 2.94–3.03 (2H, m), 3.06–3.15(2H, m), 3.83(1H, m), 5.29–5.43(2H, m), 6.12 (1H, d, J=7.5 Hz), 6.72(1H, d, J=3.6 Hz), 6.77–6.83(2H, m), 7.04–7.08(2H, m), 7.36(1H, d, J=3.6 Hz). IR(CHCl$_3$): 3599, 3444, 3425, 3195, 1709, 1635, 1543, 1508, 1456 cm$^{-1}$. $[\alpha]_D^{25}$+64.8±1.0°(c=1.006, MeOH) Anal. (C$_{27}$H$_{33}$NO$_4$S.0.2H$_2$O) Calcd.(%): C, 68.82; H, 7.14; N, 2.97; S, 6.80. Found(%): C, 68.81; H, 7.10; N, 3.03; S, 6.88.

Compound Number I-160 mp.139–141° C.; $^1$H-NMR(CDCl$_3$) δ: 1.12(1H, m), 1.25–1.31(2H, m), 1.45–1.51(2H, m), 1.60–1.78(4H, m), 2.02–2.22(5H, m), 2.35(2H, t, J=7.5 Hz), 2.57 (1H, m), 3.87(1H, m), 4.09(2H, s), 5.31–5.45(2H, m), 6.22 (1H, d, J=7.2 Hz), 7.19–7.33(6H, m), 7.63(1H, m), 7.71(1H, m), J=8.7 Hz), 7,73(1H, s). IR (KBr): 3338, 1705, 1616, 1560, 1537 cm$^{-1}$. $[\alpha]_D^{25}$+92.1±1.3°(c=1.006, MeOH) Anal. (C$_{30}$H$_{33}$NO$_3$S) Calcd.(%): C, 73.89; H, 6.82; N, 2.87; S, 6.58. Found(%): C, 73.69; H, 6.75; N, 2.91; S, 6.58.

Compound Number I-161

$^1$H-NMR(CDCl$_3$) δ: 1.12(1H, m), 1.25–1.31(2H, m), 1.47–1.51(2H, m), 1.60–1.76(4H, m), 2.03–2.20(5H, m), 2.36(2H, t, J=7.2 Hz), 2.57(1H, m), 3.87 (1H, m), 4.08(2H, s), 5.31–5.45(2H, m), 6.22(1H, d, J=7.5 Hz), 6.90 (1H, dd, J=1.2 and 4.8 Hz), 6.93(1H, m), 7.25–7.29(2H, m), 7.61 and 7.71 (each 1H, each s), 7.75(1H, d, J=8.4 Hz). IR(CHCl$_3$): 3512, 3444, 3423, 2671, 1709, 1649, 1531, 1502 cm$^{-1}$. $[\alpha]_D^{25}$+96.1±1.4°(c=1.005, MeOH) Anal. (C$_{28}$H$_{31}$NO$_3$S$_2$) Calcd.(%): C, 68.12; H, 6.33; N, 2.84; S, 12.99. Found(%): C, 67.89; H, 6.32; N, 2.88; S, 12.88.

Compound Number I-162

$^1$H-NMR(CDCl$_3$) δ: 1.12(1H, m), 1.24–1.31(2H, m), 1.45–1.51(2H, m), 1.60–1.78(4H, m), 2.03–2.22(5H, m), 2.36(2H, t, J=7.2 Hz), 2.57(1H, m), 3.87(1H, m), 4.25(2H, s), 5.31–5.45(2H, m), 6.25(1H, d, J=7.2 Hz), 6.81 (1H, m), 6.93(1H, dd, J=3.3 and 5.4 Hz), 7.15(1H, dd, J=1.5 and 5.4 Hz), 7.31 (1H, dd, J=1.5 and 8.1 Hz), 7.65 and 7.71(each 1H, each s), 7.76(1H, d, J=8.1 Hz). IR(CHCl$_3$): 3516, 3444, 3423, 1741, 1709, 1649, 1531, 1502 cm$^{-1}$. $[\alpha]_D^{25}$+98.5±1.4°(c=1.007, MeOH) Anal. (C$_{28}$H$_{31}$NO$_3$S$_2$.0.1H$_2$O) Calcd.(%): C, 67.87; H, 6.35; N, 2.83; S, 12.94. Found(%): C, 67.83; H, 6.29; N, 3.00; S, 12.99.

Compound Number I-163 mp.114–115° C.; $^1$NMR(CDCl$_3$) δ: 1.09(1H, m), 1.20–1.30(2H, m), 1.40–1.49 (2H, m), 1.55–1.77(4H, m), 1.99–2.19(5H, m), 2.34(2H, t, J=7.2 Hz), 2.53(1H, m, 3.83 (1H, m), 4.12(2H, s), 5.30–5.43(2H, m), 6.14 (1H, d, J=7.5 Hz), 6.81 and 6.93(each 1H, each m), 7.14–7.17(2H, m), 7.37(1H, d, J=1.8 Hz). IR (CHCl$_3$): 3516, 3444, 3428, 2671, 1709, 1645, 1550, 1508, 1435 cm$^{-1}$. $[\alpha]_D^{25}$+71.6±1.1° (c=1.002, MeOH) Anal. (C$_{24}$H$_{29}$NO$_3$S$_2$.0.1H$_2$O) Calcd.(%): C, 64.72; H, 6.61; N, 3.14; S, 14.40. Found(%): C, 64.50; H, 6.54; N, 3.24; S, 14.45.

Compound Number I-164

$^1$H-NMR(CDCl$_3$) δ: 1.08(1H, m), 1.20–1.31(2H, m), 1.41–1.49(2H, m), 1.56–1.77(4H, m), 1.99–2.19(5H, m), 2.34(2H, t, J=7.211 Hz), 2.53(1H, m), 3.83(1H, m, 3.94(2H, s), 5.30–5.43(2H, m), 6.08(1H, d, J=6.9 Hz), 6.91 and 6.95 (each 1H, each m), 7.08(1H, d, J=1.5 Hz), 7.27(1H, m), 7.34(1H, d, J=1.5 Hz). IR(CHCl$_3$): 3512. 3444, 3429, 1739, 1709, 1644, 1550, 1508 cm$^{-1}$. $[\alpha]_D^{25}$+69.7±1.1°(c=1.000, MeOH) Anal. (C$_{24}$H$_{29}$NO$_3$S$_2$.0.2H$_2$O) Calcd.(%): C, 64.45; H, 6.63; N, 3.13; S, 14.34. Found(%): C, 64.37; H, 6.49; N, 3.16; S, 14.41.

Compound Number I-165

$^1$H-NMR(CDCl$_3$) δ: 1.08(1H, m), 1.19–1.31(2H, m), 1.41–1.51(2H, m), 1.55–1.74(4H, m), 1.99–2.16(5H, m), 2.34(2H, t, J=7.2 Hz), 2.53(1H, m), 3.73(2H, s), 3.83(1H, m), 5.30–5.42(2H, m), 6.15(1H, d, J=6.6 Hz), 6.25, 7.10 and 7.24(each 1H, each s), 7.35–7.38(2H, m). IR(CHCl$_3$): 3510, 3444, 3429, 2669, 1709, 1645, 1550, 1508 cm$^{-1}$. $[\alpha]_D^{25}$+71.635 1.1°(c=1.008, MeOH) Anal. (C$_{24}$H$_{29}$NO$_4$S.0.2H$_2$O) Calcd.(%): C, 66.85; H, 6.78; N, 3.25; S, 7.44. Found(%): C, 66.94; H, 6.81; N, 3.26; S, 7.38.

Compound Number I-166

$^1$H-NMR(CDCl$_3$) δ: 1.02(1H, m), 1.15–1.27(2H, m), 1.36–1.45(2H, m), 1.53–1.76(4H, m), 1.96–2.14(5H, m), 2.32(2H, t, J=7.2 Hz), 2.49(1H, m), 3.78 (1H, m), 4.58(2H, s), 5.27–5.39(2H, m), 5.92(1H, d, J=7.2 Hz), 6.73 and 7.32(each 1H, each d, each J=3.9 Hz), 7.37–7.51(4H, m), 7.80(1H, d, J=7.5 Hz), 7.87(each 1H, each m). IR(CHCl$_3$): 3516, 3446, 3427, 2669, 1739, 1709, 1641, 1543, 1508, 1458 cm$^{-1}$. $[\alpha]_D^{25.5}$+62.8±1.0°(c=1.012, Compound Number I-167 mp.129–130° C.; ¹H-NMR(CDCl₃) δ: 1.04(1H, m), 1.16–1.28(2H, m), 1.38–1.46(2H, m), 1.54–1.73(4H, m), 1.97–2.15(5H, m), 2.31(2H, t, J=7.2 Hz), 2.51(1H, m), 3.81(1H, m), 4.37(2H, s), 5.28–5.41(2H, m), 6.04 (1H, d, J=7.5 Hz), 6.97(1H, s), 7.30–7.50(5H, m), 7.77(1H, d, J=8.1 Hz), 7.86 and 7.94(each 1H, each m). IR(CHCl₃): 3514, 3444, 3427, 1739, 1709, 1645, 1549, 1508 cm⁻¹. $[\alpha]_D^{24}$+59.4±1.0°(c=1.011, MeOH) Anal. ($C_{30}H_{33}NO_3S$) Calcd. (%): C, 73.89; H, 6.82; N, 2.87; S, 6.58. Found(%): C, 73.85; H, 6.90; N, 2.85; S, 6.81.

Compound Number I-168

¹H-NMR(CDCl₃) δ: 1.10(1H, m), 1.21–1.33(2H, m), 1.47–1.52(2H, m), 1.59–1.80 (4H, m), 2.04–2.27(5H, m), 2.36(2H, t, J=7.5 Hz), 2.61(1H, m), 3.93(1H, m), 4.42(2H, s), 5.33–5.47(2H, m), 6.13(1H, d, J=7.5 Hz), 6.88 (1H, m), 6.92(1H, m), 7.15(1H, dd, J=1.2 and 5.1 Hz), 7.28(1H, d, J=7.5 Hz), 7.43 (1H, d, J=8.1 Hz), 7.84(1H, s), 8.20(1H, d, J=8.1 Hz). IR(CHCl₃): 3512, 3438, 1709, 1651, 1518, 1495 cm⁻¹. $[\alpha]_D^{25}$+61.6±1.0°(c=1.003, MeOH) Anal. ($C_{28}H_{31}NO_3S_2$) Calcd.(%): C, 68.12; H, 6.33; N, 2.84; S, 12.99. Found(%): C, 67.83; H, 6.28; N, 2.96; S, 12.76.

Compound Number I-169

¹H-NMR(CDCl₃) δ: 1.10(1H, m), 1.22–1.32(2H, m), 1.46–1.51(2H, m), 1.58–1.76(4H, m), 2.02–2.24(5H, m), 2.35(2H, t, J=7.2 Hz), 2.60(1H, m), 3.92 (1H, m), 4.23(2H, s), 5.32–5.47(2H, m), 6.18(1H, d, J=8.1 Hz), 6.92 (1H, dd, J=1.2 and 4.8 Hz), 7.01(1H, m), 7.20–7.25(2H, m), 7.41(1H, t, J=8.1 Hz), 7.84(1H, m), 8.18(1H, d, J=7.5 Hz). IR(CHCl₃): 3510, 3438, 2667, 1709, 1651, 1518, 1495 cm⁻¹. $[\alpha]_D^{25}$+61.3±1.0°(c=1.006, MeOH) Anal. ($C_{28}H_{31}NO_3S_2$) Calcd. (%): C, 68.12; H, 6.33; N, 2.84; S, 12.99. Found(%): C, 67.94; H, 6.30; N, 2.97; S, 12.87.

Compound Number I-170

¹H-NMR(CDCl₃) δ: 1.10(1H, m), 1.21–1.33(2H, m), 1.47–1.52(2H, m), 1.59–1.79(4H, m), 2.03–2.27(5H, m), 2.36(2H, t, J=7.5 Hz), 2.61(1H, m), 3.93 (1H, m), 4.03(2H, s), 5.33–5.48(2H, m), 6.15(1H, d, J=7.2 Hz), 7.23 (1H, d, J=7.2 Hz), 7.29(1H, m), 7.35(1H, t, J=1.5 Hz), 7.42(1H, t, J=7.8 Hz), 7.85(1H, m), 8.18(1H, (c, J=7.8 Hz). IR (CHCl₃): 3518, 3438, 2663, 1739, 1709, 1651, 1518, 1496 cm⁻¹. $[\alpha]_D^{25}$+60.3±1.0®(c=1.002, MeOH) Anal. ($C_{28}H_{31}NO_4S.0.1H_2O$) Calcd.(%): C, 70.15; H, 6.56; N, 2.92; S, 6.69. Found(%): C, 70.03; H, 6.49; N, 2.92; S, 6.69.

Compound Number I-171

¹H-NMR(CDCl₃) δ: 1.05(1H, m), 1.18–1.28(2H, m), 1.41–1.46(2H, m), 1.56–1.79(4H, m), 2.00–2.15(5H, m), 2.34(2H, t, J=7.2 Hz), 2.45(3H, s), 2.50(1H, m), 3.80(1H, m), 4.25(2H, s), 5.29–5.42(2H, m), 5,95(1H, d, J=7.5 Hz), 6.78(1H, d, J=3.6 Hz), 7.11–7.27(4H, m), 7.36(1H, d, J=3.6 Hz). IR(CHCl₃): 3512, 3446, 3427, 2669, 1739, 1709, 1643, 1543, 1506 cm⁻¹. $[\alpha]_D^{23.5}$+$^{62.8±1.0}$°(c=1.005, MeOH) Anal. ($C_{27}H_{33}NO_3S_2$) Calcd.(%): C, 67.05; H, 6.88; N, 2.90; S, 13.26. Found(%): C, 66.94; H, 7.05; N, 3.00; S, 13.14.

Compound Number I-172

¹H-NMR(CDCl₃) δ: 1.07(1H, m), 1.19–1.29(2H, m), 1.41–1.46(2H, m), 1.57–1.78(4H, m), 2.01–2.19(5H, m), 2.34(2H, t, J=7.5 Hz), 2.51(1H, m), 2.90(3H, s), 3.80(1H, m), 4.68(2H, s), 5.29–5.43(2H, m), 6.02(1H, d, J=7.5 Hz), 6.84(1H, td, J=0.9 and 3.9 Hz), 7.37(1H,d, J=3.9 Hz), 7.42–7.51 (2H, m), 7.62(1H, dt, J=1.5 and 7.5 Hz), 8.08(1H, dd, J=1,5 and 7.5 Hz). IR(CHCl₃): 3518, 3444, 3427, 1709, 1643, 1543, 1508, 1311, 1153 cm⁻¹. $[\alpha]_D^{23.5}$+59.3±1.0° (c=1.007, MeOH) Anal. ($C_{27}H_{33}NO_5S_2.0.2H_2O$) Calcd.(%): C, 62.45; H, 6.48; N, 2.70; S, 12.35. Found(%): C, 62.47; H, 6.60; N, 2.73; S, 12.36.

Compound Number I-173

¹H-NMR(CDCl₃) δ: 1.13(1H, m), 1.23–1.36(2H, m), 1.43–1.80(6H, m), 2.03–2.24(5H, m), 2.36(2H, t, J=7.2 Hz), 2.60(1H, m), 3.91(1H, m), 3.93 (2H, s), 5.31–5.46(2H, m), 6.31(1H, d, J=7.2 Hz), 7.32–7.42(2H, m), 7.57 (1H, d, J=6.9 Hz), 7.73–7.82(3H, m), 7.94(1H, s). IR(CHCl₃): 3516, 3446, 2665, 1709, 1649, 1616, 1514, 1481, 1468 cm⁻¹. $[\alpha]_D^{24}$+100.7±1.4°(c=1.008, MeOH) Anal. ($C_{28}H_{31}NO_3.0.2H_2O$) Calcd.(%): C, 77.64; H, 7.31; N, 3.23. Found(%): C, 77.64; H, 7.57; N, 3.29.

Compound Number I-174

¹H-NMR(CDCl₃) δ: 1.06(1H, m), 1.19–1.28(2H, m), 1.40–1.47(2H, m), 1.57–1.78(4H, m), 1.99–2.18(5H, m), 2.35(2H, t, J=7.4 Hz), 2.51(1H, s), 3.21(2H, t, J=8.7 Hz), 3.81(1H, m), 4.01(2H, s), 4.58(2H, t, J=8.7 Hz), 5.29–5.42 (2H, m), 6.02(1H, d, J=7.5 Hz), 6.80(1H, d, J=3.9 Hz), 7.06(1H, d, J=1.8 Hz), 7.18(1H, d, J=1.8 Hz), 7.36(1H, d, J=3.9 Hz). IR (CHCl₃): 3512, 3446, 3427, 2669, 1709, 1641, 1543, 1506, 1477, 1460, 1173 cm⁻¹. $[\alpha]_D^{25}$+53.8±0.9° (c=1.007, MeOH) Anal. ($C_{28}H_{32}BrNO_4S.0.1H_2O$) Calcd. (%): C, 60.02; H, 5.79; Br, 14.26; N, 2.50; S, 5.72. Found (%): C, 59.87; H, 5.68; Br, 14.13; N, 2.59; S, 5.71.

Compound Number I-175

¹H-NMR(CDCl₃) δ: 1.12(1H, m), 1.23–1.31(2H, m), 1.44–1.51(2H, m), 1.60–1.78(4H, m), 2.03–2.28(5H, m), 2.36(2H, t, J=7.4 Hz), 2.56(1H, s), 3.87(1H, m),4.21(2H, s), 5.31–5.45(2H, m), 6.21(1H, d, J=7.2 Hz), 7.18–7.37(7H, m), 7.70(1H, d, J=7.2 Hz), 7.80(1H, s). IR(CHCl₃): 3514, 3444, 3423, 2667, 1709, 1649, 1537, 1502, 1454 cm⁻¹. $[\alpha]_D^{25}$+78.2±1.2°(c=1.002, MeOH) Anal. ($C_{30}H_{33}BrNO_3S.0.1H_2O$) Calcd.(%): C, 73.62; H, 6.84; N, 2.86; S, 6.55. Found(%): C, 73.49; H, 6.88; N, 2.89; S, 6.57.

Compound Number I-176

¹H-NMR(CDCl₃) δ: 1.12(1H, m), 1.23–1.32(2H, m), 1.44–1.51(2H, m), 1.61–1.78(4H, m), 2.03–2.28(5H, m), 2.36(2H, t, J=7.4 Hz), 2.57(1H, s), 3.88 (1H, m),4.21(2H, s), 5.31–5.45(2H, m), 6.22(1H, d, J=7.2 Hz), 6.94 (1H, dd, J=1.5 and 4.8 Hz), 7.04(1H, m), 7.21–7.25(2H, m), 7.35(1H, dd, J=7.2 and 7.8 Hz), 7.71(1H, d, J=7.2 Hz), 7.80(1H, s). IR(CHCl₃): 3512, 3444, 3423, 2669, 1709, 1647, 1539, 1504 cm⁻¹. $[\alpha]_D^{25}$+77.1±1.2°(c=1.002, MeOH) Anal. ($C_{28}H_{31}NO_3S_2.0.2H_2O$) Calcd.(%): C, 67.63; H, 6.36; N, 2.82; S, 12.90. Found(%): C, 67.57; H, 6.34; N, 2.97; S, 12.98.

Compound Number I-177

¹H-NMR(CDCl₃) δ: 1.12(1H, m), 1.25–1.32(2H, m), 1.44–1.51(2H, m), 1.60–1.78(4H, m), 2.03–2.28(5H, m), 2.31(3H, s), 2.36(2H, t, J=7.2 Hz), 2.56 (1H, s),3.87(1H, m),4.17(2H, s), 5.31–5.45(2H, m), 6.22(1H, d, J=7.2 Hz), 7.09 and 7.15(each 2H, each d, J=8.1 Hz), 7.19(1H, d, J=7.2 Hz), 7.34(1H, dd, J=7.2 and 7.8 Hz), 7.69(1H, d, J=7.8 Hz), 7.79(1H, s). IR (CHCl₃): 3510, 3444, 3423, 2669, 1709, 1647, 1537, 1504 cm⁻¹. $[\alpha]_D^{25}$+75.9±1.2°(c=1.004, MeOH) Anal. ($C_{31}H_{35}NO_3S$) Calcd.(%): C, 74.22; H, 7.03; N, 2.79; S, 6.39. Found(%): C, 73.93; H, 7.13; N, 2.91; S, 6.38.

Compound Number I-178

¹H-NMR(CDCl₃) δ: 1.13(1H, m), 1.24–1.31(2H, m), 1.44–1.51(2H, m), 1.60–1.77(4H, m), 2.03–2.22(5H, m), 2.36(2H, t, J=7.2 Hz), 2.56(1H, s), 3.88(1H, m),4.39(2H, s), 5.31–5.45(2H, m), 6.26(1H, d, J=7.2 Hz), 6.90–6.94(2H, m), 7.15(1H, dd, J=1.5 and 5.1 Hz), 7.27(1H, d, J=7.5 Hz), 7.36 (1H, t, J=7.5 Hz), 7.71(1H, d, J=7.5 Hz), 7.80(1H, s). IR(CHCl$_3$): 3510, 3444, 3423, 2667, 1709, 1649, 1537, 1504 cm$^{-1}$. [α]$_D^{25}$+76.6±1.2°(c=1.00$^3$, MeOH) Anal. (C$_{23}$H$_{31}$NO$_3$S$_2$) Calcd.(%): C, 68.12; H, 6.33; N, 2.84; S, 12.99. Found(%): C, 67.83; H, 6.45; N, 3.04; S, 13.03.

Compound Number I-179

$^1$H-NMR(CDCl$_3$) δ: 1.04(1H, m), 1.18–1.28(2H, m), 1.39–1.47(2H, m), 1.56–1.78(4H, m), 1.98–2.18(5H, m), 2.34(2H, t, J=7.2 Hz), 2.50(1H, m), 3.8(1H, m), 4.08(2H, s), 5.29–5.41(2H, m), 5.95(1H, d, J=7.2 Hz), 6.53 (1H, d, J=3.6 Hz), 7.23–7.41(10H, m). IR(CHCl$_3$): 3518, 3446, 3427, 1741, 1709, 1641, 1543, 1506, 1479, 1456 cm$^{-1}$. [α]$_D^{24.5}$+ 57.6±1.0°(c=1.007, MeOH) Anal. (C$_{32}$H$_{35}$NO$_3$S.0.2H$_2$O) Calcd.(%): C, 74.30; H, 6.90; N, 2.71; S, 6.20. Found(%): C, 74.24; H, 6.89; N, 2.88; S, 6.47.

Compound Number I-180

$^1$H-NMR(CDCl$_3$) δ: 1.17(1H, m), 1.24–1.35(2H, m), 1.48–1.55(2H, m), 1.61–1.79(4H, m), 2.06–2.26(5H, m), 2.37(2H, t, J=7.2 Hz), 2.61(1H, m), 3.90 (1H, m), 5.33–5.48 (2H, m), 6.44(1H, d, J=7.2 Hz), 7.31(1H, m), 7.47–7.65 (5H, m), 7.90(1H, s). IR(CHCl$_3$): 3516, 3440, 1714, 1655, 1604, 1514, 1473, 1446 cm$^{-1}$. [α]$_D^{25}$+92.1±1.3°(c=1.001, MeOH) Anal. (C$_{28}$H$_{29}$NO$_4$.0.3H$_2$O) Calcd.(%): C, 74.91; H, 6.65; N, 3.12. Found(%): C, 74.81; H, 6.51; N, 3.29.

Compound Number I-181

$^1$H-NMR(CDCl$_3$) δ: 1.04(1H, m), 1.18–1.28(2H, m), 1.41–1.46(2H, m), 1.55–1.77(4H, m), 1.99–2.16(5H, m), 2.34(2H, t, J=7.4 Hz), 2.51(1H, s), 3.79(3H, s), 3.80(1H, m), 4.08(2H, s), 5.29–5.42(2H, m), 5.97(1H, d, J=7.2 Hz), 6.75(1H, d, J=3.9 Hz), 6.85 and 7.15(each 2H, each d, J=8.4 Hz), 7.37(1H, d, J=3.9 Hz). IR(CHCl$_3$): 3518, 3446, 3427, 1741, 1709, 1641, 1612, 1543, 1510, 1458 cm$^{-1}$. [α]$_D^{25}$+ 63.6±1.0°(c=1.000, MeOH) Anal. (C$_{27}$H$_{33}$NO$_4$S.0.2H$_2$O) Calcd.(%): C, 68.88; H, 7.14; N, 2.97; S, 6.80. Found(%): C, 68.92; H, 7.02; N, 3.12; S, 6.96.

Compound Number I-182

$^1$H-NMR(CDCl$_3$) δ: 1.04(1H, m), 1.18–1.27(2H, m), 1.40–1.45(2H, m), 1.59–1.78(4H, m), 1.99–2.14(5H, m), 2.34(2H, t, J=7.4 Hz), 2.51(1H, s), 3.80 (1H, m), 4.37(2H, s), 5.29–5.41(2H, m), 5.97(1H, d, J=7.2 Hz), 6.82 (1H, d, J=3.6 Hz), 7.20(1H, s), 7.34–7.37(3H, m), 7.69(1H, m), 7.86(1H, m). IR (CHCl$_3$): 3512, 3444 3427, 2669, 1709, 1643, 1543, 1508, 1458, 1431 cm$^{-1}$. [α]$_D^{25}$+60.7±1.0°(c=1.008, MeOH) Anal. (C$_{28}$H$_{31}$NO$_3$S$_2$.0.3H$_2$O) Calcd.(%): C, 67.39; H, 6.38; N, 2.81; S, 12.85. Found(%): C, 67.44; H, 6.30; N, 3.15; S, 12.81.

Compound Number I-183

$^1$H-NMR(CDCl$_3$) δ: 1.04(1H, m), 1.18–1.26(2H, m), 1.39–44(2H, m), 1.54–1.75(4H, m), 1.99–2.15(5H, m), 2.32 (2H, t, J=7.4 Hz), 2.50(1H, s), 3.80 (1H, m), 4.12(2H, s), 5.28–5.42(2H, m), 6.05(1H, d, J=7.5 Hz), 6.78 (1H, d, J=3.9 Hz), 6.82–6.87(2H, m), 7.07–7.14(2H, m), 7.35(1H, d, J=3.9 Hz). IR (CHCl$_3$): 3508, 3444, 3197, 1707, 1635, 1543, 1508, 1456 cm$^{-1}$. [α]$_D^{25}$+64.7±1.0°((c=1.004, MeOH) Anal. (C$_{26}$H$_{31}$NO$_4$S.0.2H$_2$O) Calcd.(%): C, 68.30; H, 6.92; N, 3.06; S, 7.01. Found(%): C, 68.21; H, 6.96; N, 3.09; S, 6.93.

Compound Number I-184

$^1$H-NMR(CDCl$_3$) δ: 1.15(1H, m), 1.26–1.35(2H, m), 1.47–1.56(2H, m), 1.62–1.82(4H, m), 2.05–2.26(5H, m), 2.37(2H, t, J=7.2 Hz), 2.61(1H, m), 3.92(1H, m), 3.93(2H, s), 5.32–5.47(2H, m), 6.34(1H, d, J=6.9 Hz), 7.31–7.43 (2H, m), 7.53–7.59(2H, m), 7.67(1H, m), 7.5(1H, d, J=6.9 Hz), 8.17 (1H, s). IR(CHCl$_3$): 3514, 3444, 2667, 1709, 1651, 1572, 1516, 1481, 1452 cm$^{-1}$. [α]$_D^{24}$+81.2±1.2°(c=1.002, MeOH) Anal. (C$_{28}$H$_{31}$NO$_3$.0.2H$_2$O) Calcd.(%): C, 77.64; H, 7.31; N, 3.23. Found(%): C, 77.59; H, 7.15; N, 3.44.

Compound Number I-185

$^1$H-NMR(CDCl$_3$) δ: 1.06(1H, m), 1.21–1.28(2H, m), 1.41–1.46(2H, m), 1.58–1.78(4H, m), 2.00–2.16(5H, m), 2.35(2H, t, J=7.2 Hz), 2.51(1H, m), 3.79 (1H, m), 4.16(2H, s), 5.31–5.40(2H, m), 5.93(1H, d, J=7.8 Hz), 6.80 (1H, d, J=3.6 Hz), 7.03–7.12(2H, m), 7.20–7.28(2H, m), 7.35(1H, d, J=3.6 Hz). IR (CHCl$_3$): 3518, 3444, 3427, 1741, 1709, 1643, 1543, 1506, 1456 cm$^{-1}$. [α]$_D^{24}$+56.2±0.9°(c=1.03, CHCl$_3$) Anal. (C$_{26}$H$_{30}$FNO$_3$S.0.4H$_2$O) Calcd.(%): C, 67.48; H, 6.71; N, 3.03; S, 6.93; F, 4.11. Found(%): C, 67.49; H, 6.72; N, 3.09; S, 6.93; F, 4.11.

Compound Number I-186

$^1$H-NMR(CDCl$_3$) δ: 1.04(1H, m), 1.19–1.29(2H, m), 1.41–1.46(2H, m), 1.58–1.82(4H, m), 2.00–2.16(5H, m), 2.34(2H, t, J=7.4 Hz), 2.51(1H, s), 3.80(1H, m), 4.17(2H, s), 5.08(2H, s), 5.28–5.41(2H, m), 5.90(1H, d, J=7.5 Hz), 6.76(1H, d, J=3.9 Hz), 6.90–6.95(2H, m), 7.18–7.25(2H, m), 7.31–7.38 (6H, m). IR(CHCl$_3$): 3516, 3446, 3427, 1741, 1709, 1641, 1601, 1543, 1502, 1454 cm$^{-1}$. [α]$_D^{24}$+ 53.9±0.9°(c=1.005, MeOH) Anal. (C$_{33}$H$_{37}$NO$_4$S) Calcd. (%): C, 72.90; H, 6.86; N, 2.58; S, 5.90. Found(%): C, 72.64; H, 6.92; N, 2.52; S, 5.74.

Compound Number I-187

$^1$H-NMR(CDCl$_3$) δ: 1.04(1H, m), 1.18–1.28(2H, m), 1.41–1.46(2H, m), 1.57–1.78(4H, m), 1.99–2.15(5H, m), 2.34(2H, t, J=7.4 Hz), 2.51(1H, s), 3.80 (1H, m), 4.16(2H, s), 4.54–4.57(2H, m), 5.24–5.41(4H, m), 5.94(1H, d, J=7.5 Hz), 6.04(1H, m), 6.79(1H, d, J=3.9 Hz), 6.85–6.93(2H, m), 7.15–7.24 (2H, m), 7.34(1H, d, J=3.9 Hz). IR(CHCl$_3$): 3516, 3446, 3427, 1739, 1709, 1641, 1543, 1506, 1477 cm$^{-1}$. [α]$_D^{24}$+59.0±1.0°(c=1.007, MeOH) Anal. (C$_{29}$H$_{35}$NO$_4$S.0.2H$_2$O) Calcd.(%): C, 70.05; H, 7.18; N, 2.82; S, 6.45. Found(%): C, 69.97; H, 7.16; N, 2.80; S, 6.52.

Compound Number I-188 mp.84–85° C.; $^1$-NMR(CDCl$_3$) δ: 1.04(1H, m), 1.18–1.29 (2H, m), 1.41–1.46 (2H, m), 1.56–1.81(4H, m), 2.00–2.17 (5H, m), 2.35(2H, t, J=7.2 Hz), 2.51 (1H, s), 3.80(1H, m), 4.07(2H, s), 5.05(2H, s), 5.29–5.42(2H, m), 5.93 (1H, d, J=7.5 Hz), 6.75(1H, d, J=3.9 Hz), 6.92 and 7.15(each 2H, each d, J=8.7 Hz), 7.31–7.44(6H, m). IR(CHCl$_3$): 3521, 3446, 3427, 1741, 1709, 1643, 1612, 1543, 1510, 1456 cm$^{-1}$. [α]$_D^{24}$+56.1±1.0°(c=1.002, MeOH) Anal. (C$_{33}$H$_{37}$NO$_4$S) Calcd.(%): C, 72.90; H, 6.86; N, 2.58; S, 5.90. Found(%): C, 72.78; H, 6.88; N, 2.74; S, 5.84.

Compound Number I-189

$^1$H-NMR(CDCl$_3$) δ: 1.04(1H, m), 1.19–1.29(2H, m), 1.41–1.46(2H, m), 1.56–1.79(4H, m), 2.00–2.15(5H, m), 2.35(2H, t, J=7.2 Hz), 2.51(1H, s), 3.80 (1H, m), 4.07(2H, s), 4.51–4.53(2H, m), 5.26–5.44(4H, m), 5.94(1H, d, J=7.5 Hz), 6.05(1H, m), 6.76(1H, d, J=3.9 Hz), 6.87 and 7.14(each 2H, each d, J=8.7 Hz), 7.36(1H, d, J=3.9 Hz). IR(CHCl$_3$): 3512, 3446, 3427, 1741, 1709, 1643, 1612, 1543, 1508, 1458 cm$^{-1}$. [α]$_D^{24}$+61.6±1.0°(c=1.004, MeOH) Anal. (C$_{29}$H$_{35}$NO$_4$S.0.4H$_2$O) Calcd.(%): C, 69.54; H, 7.20; N, 2.78; S, 6.40. Found(%): C, 69.47; H, 7.22; N, 2.84; S, 6.51.

Compound Number I-190

$^1$H-NMR(CDCl$_3$) δ: 1.05(1H, m), 1.18–1.32(2H, m), 1.39–1.48(2H, m), 1.54–1.80(4H, m), 1.98–2.20(5H, m), 2.34(2H, t, J=7.2 Hz), 2.51(1H, m), 3.81(1H, m), 4.04(2H, s), 5.29–5.42(2H, m), 5.93(1H, d, J=7.5 Hz), 6.68–6.78(2H, m), 7.36(1H, d, J=3.6 Hz). IR(CHCl$_3$): 3517, 3446, 3427, 1741, 1709, 1643, 1543, 1504, 1489, 1444, 1250, 1041 cm$^{-1}$. [α]$_D^{24}$+59.4±1.0°(c=1.0111, MeOH) Anal. (C$_{27}$H$_{31}$NO$_5$S) Calcd.(%): C, 67.34; H, 6.49; N, 2.91; S, 6.66. Found(%): C, 67.27; H, 6.45; N, 3.04; S, 6.63.

Compound Number I-191
$^1$H-NMR(CDCl$_3$) δ: 1.06(1H, m), 1.18–1.32(2H, m), 1.39–1.48(2H, m), 1.54–1.80(4H, m), 1.98–2.20(5H, m), 2.34(2H, t, J=7.5 Hz), 2.51(1H, m), 3.81 (1H, m), 4.12(2H, s), 5.30–5.42(2H, m), 6.04(1H, d, J=7.2 Hz), 6.77 (1H, d, J=3.6 Hz), 6.89–7.04(3H, m), 7.28(1H, m), 7.38(1H, d, J=3.6 Hz). IR(CHCl$_3$): 3518, 3446, 3427, 1739, 1709, 1643, 1545, 1506 cm$^{-1}$. [α]$_D^{25}$+62.6±1.0°(c=1.009, MeOH) Anal. (C$_{26}$H$_{30}$FNO$_3$S) Calcd.(%): C, 68.54; H, 6.64; N, 3.07; S, 7.04; F, 4.17. Found(%): C, 68.25; H, 6.37; N, 3.19; S, 7.12; F, 4.12.

Compound Number I-192
$^1$H-NMR(CDCl$_3$), : 1.06(1H, m), 1.18–1.32(2H, m), 1.40–1.48(2H, m), 1.54–1.80(4H, m), 1.98–2.20(5H, m), 2.35(2H, t, J=7.5 Hz), 2.52(1H, m), 3.81(1H, m), 4.19(2H, s), 5.30–5.42(2H, m), 5.99(1H, d, J=7.2 Hz), 6.78 and 7.37(each 1H, each d, each J=3.6 Hz), 7.40–7.54(4H, m). IR(CHCl$_3$): 3516, 3446, 3427, 1740, 1709, 1643, 1545, 1506, 1450, 1330, 1167, 1130, 1074 cm$^{-1}$. [α]$_D^{25}$+55.4±0.9° (c=1.029, MeOH) Anal. (C$_{27}$H$_{30}$F$_3$NO$_3$S) Calcd.(%): C, 64.14; H, 5.98; N, 2.77; S, 6.34; F, 11.27. Found(%): C, 63.95; H, 5.99; N, 2.90; S, 6.36; F, 10.98.

Compound Number I-193
$^1$H-NMR(CDCl$_3$) δ: 1.05(1H, m), 1.24–1.28(2H, m), 1.42–1.46(2H, m), 1.58–1.79(4H, m), 2.01–2.21(5H, m), 2.35(2H, t, J=7.2 Hz), 2.51(1H, m), 3.80 (1H, m), 4.26(2H, s), 5.33–5.38(2H, m), 5.94(1H, (c, J=7.2 Hz), 6.79 (1H, d, J=3.9 Hz), 7.21–7.28(3H, m), 7.35–7.40(2H, m). IR(CHCl$_3$): 3518, 3446, 3427, 1743, 1709, 1643, 1506 cm$^{-1}$. [α]$_D^{25}$+55.5±0.9°(c=1.06, CHCl$_3$) Anal. (C$_{26}$H$_{30}$ClNO$_3$S.0.3H$_2$O) Calcd.(%): C, 65.41; H, 6.46; N, 2.93; S, 6.72; Cl, 7.43. Found(%): C, 65.41; H, 6.40; N, 3.08; S, 6.75; Cl, 7.31.

Compound Number I-194
$^1$H-NMR(CDCl$_3$) δ: 1.04(1H, m), 1.18–1.28(2H, m), 1.39–1.46(2H, m), 1.56–1.78 (4H, m), 1.98–2.16(5H, m), 2.30(6H, s), 2.34(2H, t, J=7.2 Hz), 2.50 (1H, m), 3.80(1H, m), 4.16(2H, s), 5.28–5.41(2H, m), 5.93(1H, d, J=6.9 Hz), 6.78(1H, d, J=3.9 Hz), 7.03–7.14(3H, m), 7.77(1H, d, J=3.9 Hz). IR (CHCl$_3$): 3516, 3446, 3427, 2669, 1709, 1641, 1543, 1506, 1456 cm$^{-1}$. [α]$_D^{24}$+66.6±1.0°(c=1.009, MeOH) Anal. (C$_{28}$H$_{35}$NO$_3$S.0.2H$_2$O) Calcd.(%): C, 71.67; H, 7.60; N, 2.98; S, 6.83. Found(%): C, 71.71; H, 7.54; N, 3.15; S, 6.81.

Compound Number I-195
$^1$H-NMR(CDCl$_3$) δ: 1.05(1H, m), 1.22–1.28(2H, m), 1.42–1.47(2H, m), 1.59–1.78(4H, m), 2.01–2.17(5H, m), 2.35(2H, t, J=7.2 Hz), 2.50(1H, m), 3.82(1H, m), 4.32(2H, s), 5.35–5.37(2H, m), 5.94(1H, d, J=6.9 Hz), 6.76 (1H, d, J=3.9 Hz), 7.33–7.39(3H, m), 7.50 (1H, m), 7.69(1H, d, J=3.9 Hz). IR (CHCl$_3$): 3316, 3446, 3427, 1743, 1709, 1643, 1543, 1506, 1456, 1163, 1126 cm$^{-1}$. [α]$_D^{25}$+54.5±1.0° (c=1.00, CHCl$_3$) Anal. (C$_{27}$H$_{30}$F$_3$NO$_3$S.0.2H$_2$O) Calcd.(%): C, 63.93; H, 6.02; N, 2.75; S, 6.30. Found(%): C, 63.92; H, 5.85; N, 2.94; S, 6.38.

Compound Number I-196
$^1$H-NMR(CDCl$_3$) δ: 1.05(1H, m), 1.22–1.28(2H, m), 1.42–1.46.(2H, m), 1.58–1.80 (4H, m), 2.01–2.21(5H, m), 2.35(2H, t, J=7.2 Hz), 2.52(1H, m), 3.81 (1H, m), 3.88(3H, s), 4.06(2H, s), 5.33–5.38(2H, m), 5.94(1H, d, J=10.2 Hz), 6.70(1H, d, J=3.6 Hz), 6.87–6.97(3H, m), 7.36(1, d, J=3.6 Hz). IR (CHCl$_3$): 3517, 3446, 3427, 2673, 1741, 1709, 1643, 1543, 1516, 1274 1030 cm$^{-1}$. [α]$_D^{25}$+54.2±0.9°(c=1.00, CHCl$_3$) Anal. (C$_{27}$H$_{32}$FNO$_4$S.0.3H$_2$O) Calcd.(%): C, 66.04; H, 6.69; N, 2.85; S, 6.53; F, 3.87. Found(%): C, 66.16; H, 6.61; N, 2.82; S, 6.34; F, 3.66.

Compound Number I-197
$^1$H-NMR(CDCl$_3$) δ: 1.05(1H, m), 1.18–1.27(2H, m), 1.41–1.45(2H, m), 1.56–1.77(4H, m), 1.98–2.13(5H, m), 2.34(2H, t, J=7.5 Hz), 2.50(1H, s), 3.21 (2H, t, J=8.7 Hz), 3.80(1H, m), 4.07(2H, s), 4.57(2H, t, J=8.7 Hz), 5.29–5.41 (2H, m), 6.00(1H, d, J=7.5 Hz), 6.79(1H, d, J=3.6 Hz), 6.79(1H, dd, J=7.2 and 7.5 Hz), 6.95(1H, d, J=7.5 Hz), 7.09(1H, d, J=7.2 Hz), 7.36(1H, d, J=3.6 Hz). IR(CHCl$_3$): 3514, 3446, 3427, 2669,.1739, 1709, 1641, 1543, 1506, 1477, 1456, 1441 cm$^{-1}$. [α]$_D^{25}$+61.1±1.0°(c=1.004, MeOH) Anal. (C$_{28}$H$_{33}$NO$_4$S.0.2H$_2$O) Calcd.(%): C, 69.60; H, 6.97; N, 2.90; S, 6.63. Found(%): C, 69.68; H, 6.89; N, 3.19; S, 6.65.

Compound Number I-198
$^1$H-NMR(CDCl$_3$) δ: 1.04(1H, m), 1.18–1.27(2H, m), 1.40–1.46(2H, m), 1.56–1.76(4H, m), 1.98–2.13(5H, m), 2.33(2H, t, J=7.5 Hz), 2.50(1H, s), 3.21(2H, t, J=8.7 Hz), 3.80(1H, m), 4.24(2H, s), 5.28–5.40(2H, m), 5.97(1H, d, J=7.2 Hz), 6.79(1H, d, J=3.6 Hz), 7.22(1H, dd, J=1.2 and 8.1 Hz), 7.29 (1H, d, J=5.4 Hz), 7.38(1H, d,J=3.6 Hz), 7.44(1H, d, J=5.4 Hz), 7.68(1H, d, J=5.4 Hz), 7.81(1H, d, J=8.1 Hz). IR(CHCl$_3$): 3516, 3446, 3427, 1741, 1709, 1643, 1543, 1506, 1547 cm$^{-1}$. [α]$_D^{25}$+62.0±1.0°(c=1.000, MeOH) Anal. (C$_{28}$H$_{31}$NO$_3$S$_2$.0.2H$_2$O) Calcd.(%): C, 67.63; H, 6.36; N, 2.82; S, 12.90. Found(%): C, 67.55; H, 6.28; N, 2.97; S, 12.90.

Compound Number I-199
$^1$H-NMR(CDCl$_3$) δ: 1.04(1H, m), 1.17–1.27(2H, m), 1.40–1.45(2H, m), 1.54–1.77(4H, m), 1.98–2.15(5H, m), 2.34(2H, t, J=7.2 Hz), 2.51(1H, s), 3.80 (1H, m),4.25(2H, s), 5.28–5.41(2H, m), 5.97(1H, d, J=7.2 Hz), 6.79(1H, d, J=3.9 Hz), 7.24(1H, dd, J=1.5 and 8.1 Hz), 7.30(1H, d, J=5.4 Hz), 7.38(1H, d, J=3.6 Hz), 7.41(1H, d, J=5.4 Hz), 7.73(1H, m), 7.76(1H, d, J=8.1 Hz). IR(CHCl$_3$): 3516, 3447, 3427, 1741, 1709, 1643, 1543, 1506, 1458 cm$^{-1}$. [α]$_D^{25}$+62.1±1.0° (c=1.008, MeOH). Anal. (C$_{28}$H$_{31}$NO$_3$S$_2$.0.3H$_2$O) Calcd.(%): C, 67.39; H, 6.38; N, 2.81; S, 12.85. Found(%): C, 67.42; H, 6.29; N, 2.99; S, 12.94.

Compound Number I-200
$^1$H-NMR(CDCl$_3$) δ: 1.03(1H, m), 1.16–1.22(2H, m), 1.39–1.44(2H, m), 1.53–1.76 (4H, m), 1.97–2.14(5H, m), 2.33(2H, t, J=7.5 Hz), 2.49(1H, s), 3.79 (1H, m),4.39(2H, s), 5.28–5.40(2H, m), 5.98(1H, d, J=7.5 Hz), 6.86(1H, d, J=3.9 Hz), 7.21(1H, d, J=6.9 Hz), 7.35 (1H, dd, J=6.9 and 8.1 Hz), 7.36(1H, d, J=5.4 Hz), 7.36(1H, d, J=3.9 Hz), 7.42(1H, d, J=5.4 Hz), 7.74(1H, d, J=8.1 H). IR(CHCl$_3$): 3516, 3446, 3427, 1739, 1709, 1643, 1543, 1506, 1458 cm$^{-1}$. [α]$_D^{25}$+58.4±1.0°(c=1.003, MeOH) Anal. (C$_{28}$H$_{31}$NO$_3$S$_2$.0.2H$_2$O) Calcd.(%): C, 67.63; H, 6.36; N, 2.82; S, 12.90. Found(%): C, 67.62; H, 6.27; N, 3.09; S, 12.92.

Compound Number I-201
$^1$H-NMR(CDCl$_3$+CD$_3$OD) δ: 1.08(1H, m), 1.22–1.28(2H, m), 1.41–1.46(2H, m), 1.55–1.71(4H, m), 2.01–2.10(5H, m), 2.29(2H, t, J=7.4 Hz), 2.51(1H, s), 3.77 (1H, m), 4.29(2H, s), 5.34–5.40(2H, m), 6.80(1H, d, J=3.9 Hz), 6.93(1H, dd, J=1.8 and 8.7 Hz), 7.10(1H, d, J=1.8 Hz), 7.22(1H, s), 7.36(1H, d, J=3.9 Hz), 7.65(1H, d, J=8.7 Hz). IR(CHCl$_3$): 3508, 3423, 3236, 1709, 1633, 1601, 1545, 1510, 1441 cm$^{-1}$. $[\alpha]_D^{25}$+57.5±1.0°(c=1.006, MeOH) Anal. (C$_{28}$H$_{31}$NO$_4$S$_2$.0.2H$_2$O) Calcd.(%): C, 64.84; H, 6.21; N, 2.70; S, 12.36. Found(%): C, 67.57; H, 6.20; N, 2.93; S, 12.38.

Compound Number I-202

$^1$H-NMR(CDCl$_3$) δ: 1.05(1H, m), 1.24–1.28(2H, m), 1.41–1.48(2H, m), 1.58–1.79(4H, m), 2.02–2.22(5H, m), 2.33(2H, t, J=7.5 Hz), 2.51(1H, m), 3.78 (1H, m), 4.25(2H, s), 4.70(2H, s), 5.31–5.42(2H, m), 6.00(1H, d, J=7.2 Hz), 6.74(1H, d, J=3.6 Hz), 7.24–7.42(5H, m). IR(CHCl$_3$): 3518, 3444, 3427, 1709, 1643, 1543, 1506, 1456 cm$^{-1}$. $[\alpha]_D^{26}$+51.9±0.9°(c=1.04, CHCl$_3$) Anal. (C$_{27}$H$_{33}$FNO$_4$S.0.7H$_2$O) Calcd.(%): C, 67.53; H, 7.22; N, 2.92; S, 6.02. Found(%): C, 67.92; H, 7.13; N, 2.88; S, 6.11.

Compound Number I-203

$^1$H-NMR(CDCl$_3$) δ: 1.02(1H, m), 1.22–1.28(2H, m), 1.40–1.42(2H, m), 1.57–1.72(4H, m), 1.82–1.85(4H, m), 2.01–2.13(5H, m), 2.27(2H, t, J=7.5 Hz), 2.49(1H, m), 2.71–2.73(4H, m), 3.67(1H, d, J=13.2 Hz), 3.76 (1H,m), 3.83(1H, d, J=13.2 Hz), 4.26(1H, d, J=16.5 Hz), 4.34(1H, d, J=16.5 Hz), 5.33–5.45(2H, m), 6.04(1H, d, J=7.2 Hz), 6.70(1H, d, J=3.6 Hz), 7.16–7.33 (4H, m), 7.43((1H, d, J=3.6 Hz). IR(CHCl$_3$): 3518, 3446, 3424, 2472, 1707, 1643, 1545, 1506, 1456 cm$^{-1}$. $[\alpha]_D^{26}$+41.9.±0.8°(c=1.03, CHCl$_3$) Anal. (C$_{31}$H$_{40}$N$_2$O$_3$S.0.6H$_2$O) Calcd.(%): C, 70.05; H, 7.81; N, 5.27; S, 6.03. Found(%): C, 70.01; H, 7.81; N, 5.18; S, 5.86.

Compound Number I-204

$^1$H-NMR(CDCl$_3$) δ: 1.06(1H, m), 1.22–1.29(2H, m), 1.41–1.46(2H, m), 1.58–1.72(4H, m), 2.03–2.17(5H, m), 2.31(2H, t, J=7.2 Hz), 2.51(1H, m), 2.60 (6H, s), 3.79(1H, m), 3.94(1H, d, J=13.2 Hz), 3.99(1H, d, J=13.2 Hz), 4.39 (2H,s), 5.30–5.44(2H, m), 6.01(1H, d, J=7.2 Hz), 6.72(1H, d, J=3.9 Hz), 7.26–7.40(4H, m), 7.56(1H, d, J=7.2 Hz). IR(CHCl$_3$): 3519, 3444, 3425, 2455, 1753, 1712, 1643, 1545, 1508, 1458 cm$^{-1}$. $[\alpha]_D^{26}$+41.2±0.8°(c=1.02, CHCl$_3$) Anal. (C$_{29}$H$_{38}$N$_2$O$_3$S.1.7H$_2$0.2CHCl$_3$) Calcd.(%): C, 63.86; H, 7.63; N, 5.10; S, 5.84; Cl, 3.87. Found(%): C, 63.88; H, 7.51; N, 4.94; S, 5.63; Cl, 4.22.

Compound Number I-205

$^1$H-NMR(CDCl$_3$) δ: 1.14(1H, m), 1.24–1.36(2H, m), 1.45–1.54(2H, m), 1.60–1.79(4H, m), 2.03–2.26(5H, m), 2.36(2H, t, J=7.5 Hz), 2.58(1H, m), 3.19–3.26(4H, m), 3.89(1H, m), 5.32–5.45(2H, m), 6.33(1H, d, J=6.3 Hz), 7.24(1H, d, J=7.2 Hz), 7.34 and 7.46(each 1H, each m), 7.61(1H, dd, J=1.5 and 8.4 Hz), 7.68(1H, d, J=1.5 Hz), 7.98–8.04(2H, m). IR(CHCl$_3$): 3518, 3444, 2667, 1709, 1649, 1597, 1514, 1483, 1450, 1294 cm$^{-1}$. $[\alpha]_D^{25}$+78.7±1.2°(c=1.003, MeOH) Anal. (C$_{30}$H$_{33}$NO$_4$) Calcd.(%): C, 75.54; H, 7.10; N, 2.94. Found(%): C, 75.62; H, 7.05; N, 2.94.

Compound Number I-206

$^1$H-NMR(CDCl$_{33}$) δ: 1.10(1H, m), 1.22–1.36(2H, m), 1.40–1.52(2H, m), 1.56–1.81(4H, m), 2.00–2.24(5H, m), 2.35(2H, t, J=7.2 Hz), 2.50(1H, m), 3.84 (1H, m), 3.99(2H, s), 5.30–5.43(2H, m), 6.05(1H, d, J=3.3 Hz), 6.29(1H, d, J=7.8 Hz), 6.99–7.05(3H, m), 7.17–7.22(2H, m). IR(CHCl$_3$): 3512, 3435, 1739, 1709, 1653, 1606, 1549, 1510 cm$^{-1}$. $[\alpha]_D^{26}$+71.0±1.1°(c=1.005, MeOH) Anal. (C$_{26}$H$_{30}$FNO$_4$O) Calcd.(%): C, 71.05; H, 6.88; N, 3.19; F, 4.32. Found(%): C, 70.78; H, 6.97; N, 3.30; F, 4.27.

Compound Number I-207

$^1$H-NMR(CDCl$_3$) δ: 1.10(1H, m), 1.22–1.34(2H, m), 1.40–1.50(2H, m), 1.56–1.81(4H, m), 2.00–2.24(5H, m), 2.35(2H, t, J=7.2 Hz), 2.50(1H, m), 3.84 (1H, m), 4.02(2H, s), 5.30–5.43(2H, m), 6.07(1H, d, J=3.3 Hz), 6.30(1H, d, J=7.5 Hz), 7.02(1H, d, J=3.3 Hz), 7.22–7.36(5H, m). IR(CHCl$_3$): 3516, 3435, 2669, 1709, 1651, 1606, 1547, 1498 cm$^{-1}$. $[\alpha]_D^{24}$+76.5±1.2°(c=1.005, MeOH) Anal. (C$_{26}$H$_{31}$FNO$_4$.0.1H$_2$O) Calcd.(%): C, 73.77; H, 7.43; N, 3.31. Found(%): C, 73.63; H, 7.27; N, 3.42.

Compound Number I-208

$^1$H-NMR(CDCl$_3$) δ: 1.04(1H, m), 1.16–1.26(2H, m), 1.39–1.44(2H, m), 1.55–1.76(4H, m), 1.98–2.18(5H, m), 2.33(2H, t, J=7.2 Hz), 2.50(1H, s), 3.79 (1H, m), 4.42(2H, s), 5.28–5.40(2H, m), 5.98(1H, d, J=6.9 Hz), 6.78(1H, d, J=2.1 Hz), 6.84(1H, d, J=3.6 Hz), 7.12–7.21(2H, m), 7.36(1H, d, J=3.6 Hz), 7.50(1H, dd, J=1.5 and 7.5 Hz), 7.63(1H, d, J=2.1 Hz). IR(CHCl$_3$): 3516, 3446, 3427, 2665, 1741, 1709, 1643, 1523, 1506, 1458, 1427 cm$^{-1}$. $[\alpha]_D^{25}$+63.4±1.0°(c=1.006, MeOH) Anal. (C$_{28}$H$_{31}$NO$_4$S.0.2H$_2$O) Calcd.(%): C, 69.89; H, 6.58; N, 2.91; S, 6.66. Found(%): C, 69.68; H, 6.48; N, 3.10; S, 6.62.

Compound Number I-209

$^1$H-NMR(CDCl$_3$) δ: 1.07(1H, m), 1.22–1.29(2H, m), 1.42–1.47(2H, m), 1.59–1.82(4H, m), 2.01–2.20(5H, m), 2.35(2H, t, J=7.2 Hz), 2.52(1H, m), 2.94 (3H,s), 3.81(1H, m), 4.19(2H, s), 4.44(2H, s), 5.31–5.38(2H, m), 5.35 (1H,d, J=7.2 Hz), 6.63–6.72(4H, m), 7.16–7.25(6H, m), 7.36(1H, d, J=3.6 Hz). IR (CHCl$_3$): 3514, 3444, 3427, 1741, 1709, 1643, 1599, 1543, 1506, 1456 cm$^{-1}$. $[\alpha]_D^{26}$+50.8±0.9°(c=1.04, CHCl$_3$) Anal. (C$_{34}$H$_{40}$N$_2$O$_3$S.0.7H$_2$O) Calcd.(%): C, 71.72; H, 7.33; N, 4.92; S, 5.63. Found(%): C, 71.81; H, 7.29; N, 4.81; S, 5.54.

Compound Number I-210

$^1$H-NMR (CHCl$_3$) δ: 1.14–1.68(11H, m), 1.91–2.16(9H, m), 2.21(2H, t, J=7.2 Hz), 2.57(1H, m), 2.98(1H, m), 3.71(1H, m), 3.89(2H, s), 4.28(1H, d, J=16.5 Hz), 4.30(1H, d, J=16.5 Hz), 5.28–5.50(3H, m), 6.56(1H, m), 6.75(1H, m), 7.20–7.33 (2H, m), 7.49–7.55(2H, m). IR(CHCl$_3$): 3518, 3425, 1753, 1711, 1641, 1545, 1508, 1456 cm$^{-1}$. $[\alpha]_D^{26}$+35.6±0.7°(c=1.03, CHCl$_3$)

Compound Number I-211

$^1$H-NMR(CDCl$_3$) δ: 1.04(1H, m), 1.17–1.28(2H, m), 1.39–1.46(2H, m), 1.54–1.78(4H, m), 1.98–2.19(5H, m), 2.33(2H, t, J=7.2 Hz), 2.51(1H, m), 3.80(1H, m), 4.29(2H, s), 5.28–5.40(2H, m), 5.95(1H, d, J=7.2 Hz), 6.82(1H, d, J=3.6 Hz), 7.23(1H, dd, J=1.5 and 8.1 Hz), 7.30–7.47(4H, m), 7.55(1H, d, J=8.1 Hz), 7.89(1H, d, J=7.8 Hz), 7.93(1H, dd, J=1.5 and 7.8 Hz). IR (CHCl$_3$): 3510, 3446, 3427, 2671, 1739, 1709, 1641, 1545, 1506, 1458, 1427 cm$^{-1}$. $[\alpha]_D^{24}$+60.2±1.0°(c=1.006, MeOH) Anal. (C$_{32}$H$_{33}$NO$_4$S.0.2H$_2$O) Calcd.(%): C, 72.34; H, 6.34; N, 2.64; S, 6.04. Found(%): C, 72.28; H, 6.25; N, 2.72; S, 5.93.

Compound Number I-212

$^1$H-NMR(CDCl$_3$) δ: 1.05(1H, m), 1.18–1.30(2H, m), 1.38–1.47(2H, m), 1.54–1.80(4H, m), 1.98–2.20(5H, m), 2.34(2H, t, J=7.5 Hz), 2.51(1H, m), 3.78 (3H, s), 3.80(1H, m), 3.86(3H, s), 4.15(2H, s), 5.29–5.42(2H, m), 5.93(1H, d, J=7.5 Hz), 6.78–6.85(3H, m), 7.01(1H, t, J=8.1 Hz), 7.36 (1H, d, J=3.9 Hz). IR(CHCl$_3$): 3516, 3446, 3425, 2667, 1739, 1709, 1641, 1543, 1506, 1481, 1273, 1076 cm$^{-1}$. $[\alpha]_D^{25}$+60.8±1.0°(c=1.002, MeOH) Anal. (C$_{28}$H$_{35}$NO$_5$S.0.1H$_2$O) Calcd.(%): C, 67.33; H, 7.10; N, 2.80; S, 6.42. Found(%): C, 67.21; H, 7.08; N, 2.92; S, 6.45.

Compound Number I-213

$^1$H-NMR(CDCl$_3$) δ: 1.08(1H, m), 1.19–1.30(2H, m), 1.42–1.47(2H, m), 1.58–1.78(4H, m), 2.01–2.16(5H, m), 2.38(2H, t, J=7.2 Hz), 2.39(3H, s), 2.53 (1H, s),3.82(1H, m), 4.15(2H, s), 5.31–5.44(2H, m), 5.87(1H, s), 6.05(1H, d, J=7.2 Hz), 6.86(1H, d, J=3.9 Hz), 7.38(1H, d, J=3.9 Hz). IR(CHCl$_3$): 3516, 3444, 3427, 2669, 1709, 1643, 1608, 1545, 1508, 1456 cm$^{-1}$. $[\alpha]_D^{25}$+64.3±1.0°(c=1.012, MeOH) Anal. (C$_{24}$H$_{30}$N$_2$O$_4$S.0.2H$_2$O) Calcd.(%): C, 64.61; H, 6.87; N, 6.28; S, 7.19. Found(%): C, 64.70; H, 6.84; N, 6.34; S, 7.27.

Compound Number I-214

$^1$H-NMR(CDCl$_3$) δ: 1.06(1H, m), 1.19–1.28(2H, m), 1.41–1.46(2H, m), 1.58–1.79(4H, m), 2.00–2.15(5H, m), 2.33–2.37(5H, m), 2.51(1H, s), 3.81–3.82 (4H,m), 4.08(2H, s), 5.29–5.42(2H, m), 5.93(1H, d, J=6.9 Hz), 6.70(1H, s), 6.72(1H, d, J=7.8 Hz), 6.77(1H, d, J=3.6 Hz), 7.04(1H, d, J=7.8 Hz), 7.34 (1H, d, J=3.6 Hz). IR(CHCl$_3$): 3516, 3446, 3427, 2669, 1741, 1709, 1641, 1614, 1583, 1506, 1458 cm$^{-1}$. $[\alpha]_D^{25}$+58.9±1.0°(c=1.012, MeOH) Anal. (C$_{28}$H$_{35}$N$_4$S.0.2H$_2$O) Calcd.(%): C, 69.31; H, 7.35; N, 2.89; S, 6.61. Found(%): C, 69.21; H, 7.35; N, 3.03; S, 6.65.

Compound Number I-215 mp.128–129° C.; $^1$H-NMR(CDCl$_3$) δ: 1.05 (1H, m), 1.19–1.28 (2H, m), 1.41–1.46 (2H, m), 1.56–1.79(4H, m), 2.00–2.15(5H, m), 2.34(2H, t, J=7.2 Hz), 2.51(1H, s), 3.80 (1H, m), 3.84(3H, s), 4.33(2H, s), 5.29–5.42 (2H, m), 5.94(1H, d, J=6.9 Hz), 6.83(1H, d, J=3.6 Hz), 7.01(1H, dd, J=2.7 and 9.0 Hz), 7.11(1H, d, J=2.7 Hz), 7.21(1H, s), 7.36(1H, d, J=3.6 Hz), 7.72 (1H, d, J=9.0 Hz). IR(CHCl$_3$): 3516, 3446, 3427, 1739, 1709, 1643, 1601, 1543, 1506, 1458, 1427 cm$^{-1}$. $[\alpha]_D^{25}$+55.7±1.0°(c=1.008, MeOH) Anal. (C$_{29}$H$_{33}$NO$_4$S$_2$) Calcd.(%): C, 66.51; H, 6.35; N, 2.67; S, 12.25. Found(%): C, 66.41; H, 6.30; N, 2.96; S, 12.15.

Compound Number I-216

$^1$H-NMR(CDCl$_3$) δ: 1.04(1H, m), 1.16–1.29(2H, m), 1.39–1.46(2H, m), 1.55–1.79 (4H, m), 1.98–2.19(5H, m), 2.34(2H, t, J=7.2 Hz), 2.51(1H, m), 3.80 (1H, m), 3.87 and 4.20(each 2H, each s), 5.28–5.40(2H, m), 5.93(1H, d, J=8.1 Hz), 6.81(1H, d, J=3.9 Hz), 7.24–7.39(5H, m), 7.53(1H, d, J=7.2 Hz), 7.71–7.77(2H, m). IR(CHCl$_3$): 3516, 3446, 3427, 1739, 1709, 1643, 1543, 1506, 1456 cm$^{-1}$. $[\alpha]_D^{25}$+56.7±1.0°(c=1.000, MeOH) Anal. (C$_{33}$H$_{35}$NO$_3$S.0.1H$_2$O) Calcd.(%): C, 75.14; H, 6.73; N, 2.66; S, 6.08. Found(%): C, 75.14; H, 6.80; N, 2.74; S, 5.83.

Compound Number I-217

$^1$H-NMR(CDCl$_3$) δ: 1.07(1H, m), 1.19–1.32(2H, m), 1.40–1.48(2H, m), 1.56–1.78 (4H, m), 2.00–2.21(5H, m), 2.34(2H, t, J=7.5 Hz), 2.54(1H, m), 3.13–3.24 (4H, m), 3.85(1H, m), 4.13(2H, s), 5.28–5.42(2H, m), 6.17(1H, d, J=7.2 Hz), 7.06–7.17(4H, m), 7.22(1H, d, J=7.8 Hz), 7.44 (1H, dd, J=1.8 and 7.8 Hz), 7.53(1H, d, J=1.8 Hz). IR(CHCl$_3$): 3518, 3446, 1739, 1709, 1651, 1570, 1518, 1491, 1456 cm$^{-1}$. $[\alpha]_D^{25}$+73.3±1.1°(c=1.000, MeOH) Anal. (C$_{30}$H$_{35}$NO$_3$.0.2H$_2$O) Calcd.(%): C, 78.13; H, 7.44; N, 3.04. Found(%): C, 78.25; H, 7.76; N, 3.29.

Compound Number I-218

$^1$H-NMR(CDCl$_3$) δ: 1.05(1H, m), 1.18–1.30(2H, m), 1.39–1.48(2H, m), 1.54–1.81(4H, m), 1.98–2.20(5H, m), 2.34(2H, t, J=7.2 Hz), 3.80(1H, m), 3.82, 3.85 and 3.87(each 3H, each s), 4.07(2H, s), 5.29–5.42 (2H, m), 5.94(1H, d, J=7.5 Hz), 6.62(1H, d, J=8.7 Hz), 6.76(1H, d, J=3.6 Hz), 6.85(1H, d, J=8.7 Hz), 7.35(1H, d, J=3.6 Hz). IR(CHCl$_3$): 3514, 3446, 3427, 1739, 1709, 1641, 1603, 1543, 1495, 1468, 1277, 1259, 1097 cm$^{-1}$. $[\alpha]_D^{26}$+54.8±1.0°(c=1.013, MeOH) Anal. (C$_{29}$H$_{37}$NO$_6$S.0.2H$_2$O) Calcd.(%): C, 65.56; H, 7.10; N, 2.64; S, 6.04. Found(%): C, 65.54; H, 6.96; N, 2.74; S, 5.98.

Compound Number I-219

$^1$H-NMR(CDCl$_3$) δ: 1.05(1H, m), 1.18–1.30(2H, m), 1.39–1.48(2H, m), 1.54–1.81(4H, m), 1.98–2.20(5H, m), 2.34(2H, t, J=7.2 Hz), 2.51(1H, m), 3.80 (1H, m), 3.82, 3.85 and 3.87(each 3H, each s), 4.07(2H, s), 5.29–5.42 (2H, m), 5.94(1H, d, J=7.5 Hz), 6.62(1H, d, J=8.7 Hz), 6.76(1H, d, J=3.6 Hz), 6.85(1H, d, J=8.7 Hz), 7.35(1H, d, J=3.6 Hz). IR(CHCl$_3$): 3514, 3446, 3427, 1739, 1709, 1641, 1603, 1543, 1495, 1468, 1277, 1259, 1097 cm$^{-1}$. $[\alpha]_D^{26}$+54.8±1.0°(c=1.013, MeOH) Anal. (C$_{29}$H$_{37}$NO$_6$S.0.2H$_2$O) Calcd.(%): C, 65.56; H, 7.10; N, 2.64; S, 6.04. Found(%): C, 65.54; H, 6.96; N, 2.74; S, 5.98.

Compound Number I-220 mp.131–133° C.; $^1$H-NMR(CDCl$_3$) δ: 1.06(1H, m), 1.18–1.31(2H, m), 1.40–1.48 (2H, m), 1.56–1.82(4H, m), 2.00–2.21(5H, m), 2.35(2H, t, J=7.5 Hz), 2.52 (1H, m), 3.82(1H, m), 3.83(3H, s), 3.84(6H, s), 4.07(2H, s), 5.30–5.42 (2H, m), 5.95(1H, d, J=7.5 Hz), 6.45(2H, s), 6.79(1H, d, J=3.6 Hz), 7.36(1H, d, J=3.6 Hz). IR(CHCl$_3$): 3516, 3446, 3427, 1739, 1709, 1643, 1593, 1543, 1506, 1462, 1421, 1331, 1240, 1130 cm$^{-1}$. $[\alpha]_D^{24}$+57.5±1.0° (c=1.007, MeOH) Anal. (C$_{29}$H$_{37}$NO$_6$S) Calcd.(%): C, 66.01; H, 7.07; N, 2.65; S, 6.08. Found(%): C, 65.84; H, 6.93; N, 2.71; S, 6.06.

Compound Number I-221

$^1$H-NMR(CDCl$_3$) δ: 1.05(1H, m), 1.17–1.30(2H, m), 1.39–1.48(2H, m), 1.54–1.80(4H, m), 1.98–2.20(5H, m), 2.34(2H, t, J=7.5 Hz), 2.51(1H, m), 3.81 (1H, m), 4.08(2H, s), 5.29–5.42(2H, m), 5.95(2H, s), 5.98(1H, d, J=7.5 Hz), 6.68–6.80(4H, m), 7.35(1H, d, J=3.9 Hz). IR(CHCl$_3$): 3516, 3446, 3427, 1741, 1709, 1641, 1543, 1504, 1460, 1252, 1063 cm$^{-1}$. $[\alpha]_D^{24}$+62.7±1.0°(c=1.006, MeOH) Anal. (C$_{27}$H$_{31}$NO$_5$S) Calcd.(%): C, 67.34; H, 6.49; N, 2.91; S, 6.66. Found(%): C, 67.12; H, 6.37; N, 2.98; S, 6.55.

Compound Number I-222

$^1$H-NMR(CDCl$_3$) δ: 1.08(1H, m), 1.24–1.28(2H, m), 1.41–1.45(2H, m), 1.56–1.78(4H, m), 1.97–2.20(5H, m), 2.14(3H, s), 2.33(2H, t, J=7.2 Hz), 2.51 (1H, m), 3.77(1H, m), 4.06(2H, s), 5.28–5.42(2H, m), 6.16(1H, d, J=7.2 Hz), 6.74 (1H, d, J=3.6 Hz), 6.96(1H, d, J=7.5 Hz), 7.24(1H, t, J=8.7 Hz), 7.35–7.38 (3H, m), 7.74(1H, br s). IR(KBr): 3309, 1707, 1672, 1614, 1547, 1523, 1489, 1441, 1371, 1319 cm$^{-1}$. $[\alpha]_D^{26}$+57.7±1.0°(c=1.012, MeOH) Anal. (C$_{28}$H$_{34}$N$_2$O$_4$S.0.4H$_2$O) Calcd.(%): C, 67.01; H, 6.99; N, 5.58; S, 6.39. Found(%): C, 66.98; H, 6.72, N, 5.47; S, 6.27.

Compound Number I-223

$^1$H-NMR(CDCl$_3$) δ: 1.05(1H, m), 1.22–1.28(2H, m), 1.42–1.46(2H, m), 1.55–1.75(4H, m), 2.02–2.22(5H, m), 2.34(2H, t, J=7.5 Hz), 2.51(1H, m), 2.99 (3H, s), 3.81(1H, m), 4.11(2H, s), 5.29–5.45(2H, m), 6.04(1H, d, J=7.2 Hz), 6.78 (1H, d, J=3.6 Hz), 7.04–7.06(2H, m), 7.16(1H, m), 7.25(1H, br s), 7.29(1H, t, J=7.8 Hz), 7.36 (1H, d, J=3.6 Hz). IR (CHCl$_3$): 3512, 3444, 3427, 3371, 1709, 1639, 1608, 1545, 1508, 1475, 1458, 1389, 1335, 1151 cm$^{-1}$. $[\alpha]_D^{24}$+55.0±1.0°(c=1.003, MeOH) Anal. (C$_{27}$H$_{34}$N$_2$O$_5$S$_2$.0.2H$_2$O) Calcd.(%): C, 60.69; H, 6.49; N, 5.24; S, 12.00. Found(%): C, 60.70; H, 6.44; N, 5.15; S, 11.56.

Compound Number I-224

$^1$H-NMR(CDCl$_3$) δ: 1.07(1H, m), 1.22–1.28(2H, m), 1.42–1.53(2H, m), 1.57–1.74(4H, m), 2.00–2.24(5H, m), 2.35(2H, t, J=7.2 Hz), 2.52(1H, m), 3.81 (1H, m), 4.33(2H, s), 5.29–5.42(2H, m), 5.98(1H, d, J=7.8 Hz), 6.86, 6.88 and 7.14 (each 1H, each d, each J=3.6 Hz), 7.22–7.37(4H, m), 7.53–7.56(2H, m).

Compound Number I-225

$^1$H-NMR (CDCl$_3$) δ: 1.05(1H, m), 1.17–1.30(2H, m), 1.39–1.48(2H, m), 1.54–1.81(4H, m), 1.98–2.20(5H, m), 2.35(2H, t, J=7.5 Hz), 2.51(1H, m), 3.81 (1H, m), 4.08(2H, s), 4.23–4.30(4H, m), 5.29–5.42(2H, m), 5.95(1H, d, J=7.2 Hz), 6.71–6.80(4H, m), 7.34(1H, d, J=3.6 Hz). IR(CHCl$_3$): 3514, 3446, 3427, 1739, 1709, 1641, 1603, 1543, 1506, 1475, 1456, 1284, 1090 cm$^{-1}$. [α]$_D^{24.5}$+58.9±1.0°(c=1.013, MeOH) Anal. (C$_{28}$H$_{33}$NO$_5$S) Calcd.(%): C, 67.85; H, 6.71; N, 2.83; S, 6.47. Found(%): C, 68.01; H, 6.72; N, 2.97; S, 6.50.

Compound Number I-226

$^1$H-NMR(CDCl$_3$) δ: 1.05(1H, m), 1.18–1.30(2H, m), 1.38–1.47(2H, m), 1.54–1.81 (4H, m), 1.98–2.20(5H, m), 2.31(3H, s), 2.34(2H, t, J=7.5 Hz), 2.51(1H, m), 3.70(3H, s), 3.80(1H, m), 4.16(2H, s), 5.29–5.42(2H, m), 5.95 (1H, d, J=7.2 Hz), 6.78(1H, d, J=3.6 Hz), 6.96–7.11(3H, m), 7.37 (1H, d, J=3.6 Hz). IR(CHCl$_3$): 3514, 3446, 3427, 2669, 1709, 1641, 1543, 1506, 1473, 1458, 1259, 1011 cm$^{-1}$. [α]$_D^{24}$+62.7±1.0°(c=1.009, MeOH) Anal. (C$_{28}$H$_{35}$NO$_4$S) Calcd.(%): C, 69.82; H, 7.32; N, 2.91; S, 6.66. Found(%): C, 69.55; H, 7.27; N, 3.09; S, 6.55.

Compound Number I-227

$^1$H-NMR(CDCl$_3$) δ: 1.07(1H, m), 1.24–1.28(2H, m), 1.41–1.46(2H, m), 1.56–1.79(4H, m), 2.00–2.17(5H, m), 2.16(3H, s), 2.33(2H, t, J=7.5 Hz), 2.51 (1H, m), 3.79(1H, m), 4.08(2H, s), 5.28–5.42(2H, m), 6.05(1H, d, J=7.5 Hz), 6.75 (1H, d, J=3.6 Hz), 7.16(2H, d, J=8.1 Hz), 7.37(1H, d, J=3.6 Hz), 7.43 (2H, d, J=8.1 Hz), 7.53(1H, br s). IR(CHCl$_3$): 3512, 3437, 1707, 1639, 1543, 1516, 1410 cm$^{-1}$. [α]$_D^{24.5}$+60.7±1.0°(c=1.012, MeOH) Anal. (C$_{28}$H$_{34}$N$_2$O$_4$S.0.5H$_2$O) Calcd.(%): C, 67.77; H, 7.00; N, 5.56; S, 6.37. Found(%): C, 66.84; H, 6.91; N, 5.56; S, 6.26.

Compound Number I-228

$^1$H-NMR(CDCl$_3$) δ: 1.06(1H, m), 1.22–1.29(2H, m), 1.41–1.46(2H, m), 1.58–1.76 (4H, m), 2.01–2.17(5H, m), 2.34(2H, t, J=7.5 Hz), 2.51(1H, m), 2.99 (3H, s), 3.80(1H, m), 4.11(2H, s), 5.29–5.43(2H, m), 6.01(1H, d, J=7.5 Hz), 6.78(1H, d, J=3.6 Hz), 6.86(1H, br s), 7.17–7.23(4H, m), 7.36(1H, d, J=3.6 Hz). IR(CHCl$_3$): 3510, 3444, 3427, 3371, 1709, 1639, 1543, 1510, 1456, 1389, 1338, 1155 cm$^{-1}$. [α]$_D^{24.5}$+56.5±1.0°(c=0.953, MeOH) Anal. (C$_{27}$H$_{34}$N$_2$O$_5$S$_2$.0.1H$_2$O) Calcd.(%): C, 60.90; H, 6.47; N, 5.26; S, 12.04. Found(%): C, 61.06; H, 6.45; N, 5.29; S, 11.52.

Compound Number I-229 mp.103–105° C.; $^1$H-NMR(CDCl$_3$) δ: 1.02 (1H, m), 1.15–1.27 (2H, m), 1.37–1.45(2H, m), 1.53–1.77(4H, m), 1.96–2.18(5H, m), 2.33 (2H, t, J=7.5 Hz), 2.49(1H, m), 3.79(1H, m), 4.40(2H, s), 5.27–5.39 (2H, m), 5.94(1H, d, J=7.8 Hz), 6.89(1H, d, J=3.9 Hz), 7.32–7.37(2H, m), 7.43–7.48 (3H, m), 7.84(1H, m), 8.08(1H, d, J=6.9 Hz), 8.15(1H, m). IR(CHCl$_3$): 3514, 3444, 3427, 2667, 1739, 1709, 1643, 1543, 1506, 1458, 1444 cm$^{-1}$. [α]$_D^{24.5}$+58.9±1.0°(c=1.006, MeOH) Anal. (C$_{32}$H$_{33}$NO$_3$S$_2$) Calcd. (%): C, 70.68; H, 6.12; N, 2.58; S, 11.79. Found(%): C, 70.52; H, 6.11; N, 2.67; S, 11.72.

Compound Number I-230 mp.86–87° C.; $^1$H-NMR(CDCl$_3$) δ: 1.02(1H, m), 1.16–1.28(2H, m), 1.37–1.45 (2H, m), 1.54–1.77(4H, m), 1.97–2.17(5H, m), 2.32(2H, t, J=7.5 Hz), 2.49 (1H, m), 3.78(1H, m), 3.79 and 4.26(each 2H, each s), 5.27–5.39(2H, m), 5.93 (1H, d, J=7.2 Hz), 6.78(1H, d, J=3.9 Hz), 7.18(1H, d, J=7.2 Hz), 7.29 (1H, m), 7.34–7.40(3H, m), 7.52(1H, d, J=7.2 Hz), 7.72(1H, d, J=7.5 Hz), 7.78(1H, d, J=7.2 Hz). IR(CHCl$_3$): 3514, 3446, 3427, 2669, 1709, 1641, 1543, 1506, 1456 cm$^{-1}$. [α]$_D^{24.5}$+59.2±1.0°(c=1.006, MeOH) Anal. (C$_{33}$H$_{35}$NO$_3$S) Calcd.(%): C, 75.40; H, 6.71; N, 2.66; S, 6.10. Found(%): C, 75.33; H, 6.73; N, 2.75; S, 6.06.

Compound Number I-231

$^1$H-NMR (CHCl$_3$) δ: 1.04(1H, m), 1.16–1.30(2H, m), 1.38–1.46(2H, m), 1.54–1.81(4H, m), 1.98–2.16(5H, m), 2.21 and 2.50(each 3H, each s), 2.34 (2H, t, J=7.2 Hz), 2.51(1H, m), 3.66(3H, s), 3.80(1H, m), 4.13(2H, s), 5.29–5.42 (2H, m), 5.93(1H, d, J=6.9 Hz), 6.78(1H, d, J=3.6 Hz), 6.89 and 6.96 (each 1H, each d, each J=7.5 Hz), 7.36(1H, d, J=3.6 Hz). IR(CHCl$_3$): 3516, 3446, 3425, 2669, 1709, 1641, 1545, 1506, 1458, 1263, 1084, 1009 cm$^{-1}$. [α]D$^{24}$+61.8±1.0°(c=1.006, MeOH) Anal. (C$_{29}$H$_{37}$NO$_4$S.0.2H$_2$O) Calcd.(%): C, 69.76; H, 7.55; N, 2.81; S, 6.42. Found(%): C, 69.80; H, 7.59; N, 2.97; S, 6.34.

Compound Number I-232

$^1$H-NMR(CDCl$_3$) δ: 1.02(1H, m), 1.16–1.27(2H, m), 1.37–1.45(2H, m), 1.53–1.77(4H, m), 1.96–2.15(5H, m), 2.33(2H, t, J=7.5 Hz), 2.50(1H, m), 3.79 (1H, m), 4.50(2H, s), 5.27–5.40(2H, m), 5.94(1H, d, J=7.5 Hz), 6.88(1H, d, J=3.9 Hz), 7.29–7.38(4H, m), 7.47(1H, m), 7.58(1H, d, J=8.4 Hz), 7.86(1H, m), 7.95(1H, d, J=7.8 Hz). IR(CHCl$_3$): 3512, 3444, 3427, 2669, 1739, 1708, 1641, 1543, 1506, 1475, 1452, 1423 cm$^{-1}$. [α]$_D^{24}$+58.5±1.0°(c=1.006, MeOH) Anal. (C$_{32}$H$_{33}$NO$_4$S.0.2H$_2$O) Calcd.(%): C, 72.34; H, 6.34; N, 2.64; S, 6.04. Found(%): C, 72.36; H, 6.16; N, 2.72; S, 5.94.

Compound Number I-233 mp.125–126° C.; $^1$H-NMR(CDCl$_3$) δ: 1.05(1H, m), 1.18–1.28(2H, m), 1.41–1.45 (2H, m), 1.57–1.78(4H, m), 2.00–2.20 (5H, m), 2.33(2H, t, J=7.4 Hz), 2.51 (1H, s), 3.80(1H, m),4.05 (2H, s), 5.28–5.42 (2H, m), 5.98(1H, d, J=6.6 Hz), 6.76 (1H, d, J=3.6 Hz), 6.80 and 7.09(each 2H, each d, J=8.4 Hz), 7.37(1H, d, J=3.6 Hz). IR(KBr): 3354, 3132, 2688, 1703, 1616, 1599, 1549, 1514, 1458, 1250 cm$^{-1}$. [α]$_D^{25}$+67.7±1.1°(c=1.001, MeOH) Anal. (C$_{26}$H$_{31}$NO$_4$S) Calcd.(%): C, 68.85; H, 6.89; N, 3.09; S, 7.07. Found(%): C, 69.12; H, 6.95; N, 3.10; S, 7.12.

Compound Number II-1

$^1$H-NMR(CDCl$_3$) δ: 0.93(1H, d, J=10.2 Hz), 1.08 and 1.21(each 3H, each s), 1.50–2.41(14H, m), 4.20(1H, m), 5.35–5.47(2H, m), 6.16(1H, d, J=8.7 Hz), 6.33 and 7.16 (each 2H, each t, each J=2.4 Hz), 7.30 and 7.56 (each 1H, each d, each J=3.9 Hz). IR(CHCl$_3$): 3515, 3446, 3144, 3100, 1708, 1658, 1529, 1504, 1456, 1385, 1167 cm$^{-1}$. [α]$_D^{26.5}$+54.1±0.9°(c=1.004, MeOH) Anal. (C$_{25}$H$_{32}$N$_2$O$_5$S$_2$.0.2H$_2$O) Calcd.(%): C, 59.08; H, 6.43; N, 5.51; S, 12.62. Found(%): C, 59.12; H, 6.36; N, 5.57; S, 12.59.

Compound Number II-6

$^1$H-NMR(CDCl$_3$) δ: 0.98(1H, d, J=10.2 Hz), 1.14 and 1.24(each 3H, each s), 1.54–2.48(14H, m), 4.30(1H, m), 5.35–5.52(2H, m), 6.26 (1H, d, J=8.7 Hz), 6.38 and 7.13 (each 2H, each t, J=2.1 Hz), 7.44 and 7.79 (each 2H, each d, each J=8.4 Hz). IR(CHCl$_3$): 3453, 2662, 1739, 1708, 1652, 1609, 1500, 1333 cm$^{-1}$. [α]$_D^{22}$+65.2±1.1°(c=1.006, MeOH) Anal. (C$_{27}$H$_{34}$N$_2$O$_3$.0.3H$_2$O) Calcd.(%): C, 73.71; H, 7.93; N, 6.37. Found(%): C, 73.85; H, 7.88; N, 6.37.

Compound Number II-7

¹H-NMR(CDCl₃) δ: 0.95(1H, d, J=10.2 Hz), 1.10 and 1.22 (each 3H, each s), 1.52–2.42(14H, m), 4.25(1H, m), 5.34–5.51(2H, m), 6.35(1H, d, J=8.7 Hz), 7.07–7.15(3H, m), 7.21–7.26(2H, m), 7.73 and 7.77(each 2H, each d, each J=8.7 Hz). IR(CHCl₃): 3518, 3446, 3365, 3249, 2673, 1709, 1655, 1516, 1348, 1167 cm⁻¹. $[\alpha]_D^{21.5}$+56.1±0.9°(c=1.000, MeOH) Anal. (C₂₉H₃₆N₂O₅S.0.6H₂O) Calcd.(%): C, 65.05; H, 7.00; N, 5.23; S, 5.99. Found(%): C, 65.07; H, 6.94; N, 5.37; S, 6.03.

Compound Number II-8

¹H-NMR(CDCl₃) δ: 0.89(1H, d, J=10.2 Hz), 1.05 and 1.19(each 3H, each s), 1.50–2.44(14H, m), 4.15(1H, m), 5.31–5.50(2H, m), 6.31 (1H, d, J=8.1 Hz), 7.00(1H, d, J=1.8 Hz), 7.42–7.47(2H, m), 7.54 (1H, d, J=1.8 Hz), 7.56(1H, m), 7.76–7.79(2H, m), 8.29(1H, s). IR (CHCl₃): 3509, 3446, 3360, 3108, 1708, 1639, 1515, 1448, 1330, 1164 cm⁻¹. $[\alpha]_D^{20}$+39.0±0.8°(c=1.006, MeOH) Anal. (C₂₇H₃₄N₂O₅S₂.0.2H₂O) Calcd.(%): C, 60.09; H, 6.54; N, 5.19; S, 11.88. Found(%): C, 60.07; H, 6.48; N, 5.31; S, 11.92.

Compound Number II-9

¹H-NMR(CDCl₃) δ: 0.73(1H, d, J=10.2 Hz), 1.06 and 1.16(each 3H, each s), 1.43–2.36(14H, m), 4.07(1H, m), 5.28–5.49(2H, m), 6.37 (1H, d, J=8.7 Hz), 7.28 and 7.33 (each 1H, each d, each J=1.8 Hz), 7.38–7.43 (2H, m), 7.50(1H, m), 7.96–7.99(2H, m). IR(CHCl₃): 3440, 3254, 3096, 3062, 1708, 1643, 1560, 1530, 1298 cm⁻¹. $[\alpha]_D^{20}$+49.0±0.9°(c=1.008, MeOH) Anal. (C₂₈H₃₄N₂O₄S.0.4H₂O) Calcd.(%): C, 67.01; H, 6.99; N, 5.58; S, 6.39. Found(%): C, 66.96; H, 7.04; N, 5.67; S, 6.32.

Compound Number II-10

¹H-NMR(CDCl₃) δ: 0.96(1H, d, J=10.5 Hz), 1.09 and 1.22(each 3H, each s), 1.52–2.44(14H, m), 4.26(1H, m), 5.33–5.49(2H, m), 6.26(1H, d, J=8.4 Hz), 6.31 and 7.15 (each 2H, each t, each J=2.1 Hz), 7.81 and 7.89 (each 2H, each d, each J=8.4 Hz). IR(CHCl₃): 3514, 3446, 3144, 1708, 1663, 1514, 1377, 1173 cm⁻¹. $[\alpha]_D^{22}$+64.1±0.9°(c=1.000, MeOH) Anal. (C₂₇H₃₄N₂O₅S.0.2H₂O) Calcd.(%): C, 64.57; H, 6.90; N, 5.58; S, 6.38. Found(%): C, 64.50; H, 6.97; N, 5.71; S, 6.28.

Compound Number II-11

¹H-NMR(CDCl₃) δ: 0.94(1H, d, J=10.2 Hz), 1.08 and 1.21(each 3H, each s), 1.50–2.43(14H, m), 4.12(2H, s), 4.22(1H, m), 5.33–5.49(2H, m), 6.06(1H, d, J=8.7 Hz), 7.04(1H, d, J=1.2 Hz), 7.22–7.34(2H, m), 7.63 (1H, d, J=1.2 Hz). IR(CHCl₃): 3517, 3451, 3087, 3065, 2670, 1708, 1708, 1647, 1549, 1508 cm⁻¹. $[\alpha]_D^{21.5}$+41.9±0.8°(c=1.015, MeOH) Anal. (C₂₈H₃₅NO₃S) Calcd.(%): C, 72.22; H, 7.58; N, 3.01; S, 6.89. Found(%): C, 72.07; H, 7.57; N, 3.21; S, 6.77.

Compound Number II-12

¹H-NMR(CDCl₃) δ: 0.94(1H, d, J=10.5 Hz), 1.09 and 1.21(each 3H, each s), 1.50–2.44 (14H, m), 4.24(1H, m), 5.32–5.48(2H, m), 6.24(1H, d, J=8.7 Hz), 7.17 and 7.60 (each 2H, each d, each J=8.7 Hz), 7.41–7.46 (2H, m), 7.54(1H, m), 7.80–7.84(2H, m). IR(CHCl₃): 3510, 3451, 3371, 3139, 1709, 1647, 1609, 1496, 1163 cm⁻¹. $[\alpha]_D^{22.5}$+47.1±0.9°(c=1.006, MeOH) Anal. (C₂₉H₃₆N₂O₅S.0.4H₂O) Calcd.(%): C, 65.49; H, 6.97; N, 5.27; S, 6.03. Found(%): C, 65.51; H, 6.87; N, 5.39; S, 5.89.

Compound Number II-14

¹H-NMR(CHCl₃) δ: 0.92(1H, d, J=10.2 Hz), 1.09 and 1.21(each 3H, each s), 1.53–2.47(14H, m), 4.17(1H, m), 5.35–5.55(2H, m), 6.35 and 7.17 (each 2H, each t, each J=2.1 Hz), 6.38(1H, d, J=8.7 Hz), 8.09 and 8.17 (each 1H, each d, each J=1.5 Hz). IR(CHCl₃): 3510, 3409, 3144, 3107, 1727, 1709, 1657, 1538, 1503, 1456, 1387, 1166 cm⁻¹. $[\alpha]_D^{25}$+46.1±0.9°(c=1.005, MeOH) Anal. (C₂₅H₃₂N₂O₅S₂.0.2H₂O) Calcd.(%): C, 59.08; H, 6.43; N, 5.51; S, 12.62. Found(%): C, 59.10; H, 6.45; N, 5.69; S, 12.58.

Compound Number II-15 mp.119–121° C. ¹H-NMR(CDCl₃) δ: 0.97(1H, d, J=10.2 Hz), 1.11 and 1.24(each 3H, each s), 1.53–2.49(14H, m), 4.29(1H, m), 5.39–5.57 (2H, m), 6.37 and 7.22(each 2H, each t, each J=2.1 Hz), 7.13 (1H, d, J=8.4 Hz), 7.50 and 7.93(each 1H, each d, each J=3.9 Hz). IR(Nujol): 3365, 3145, 3100, 1739, 1621, 1548, 1405, 1367, 1187 cm⁻¹. $[\alpha]_D^{26.5}$+45.5±0.8°(c=1.012, MeOH) Anal. (C₂₅H₃₂N₂O₅S₂) Calcd.(%): C, 59.74; H, 6.02; N, 5.57; S, 12.76. Found(%): C, 59.56; H, 6.33; N, 5.64; S, 12.76.

Compound Number II-17

¹H-NMR(CDCl₃) δ: 0.96 (1H, d, J=10.5 Hz), 1.11 and 1.23(each 3H, each s), 1.54–2.49(14H, m), 4.25(1H, m), 5.35–5.56(2H, m), 6.33 (2H, t, J=2.4 Hz), 6.56(1H, d, J=7.8 Hz), 7.17(2H, t, J=2.4 Hz), 7.58(1H, t, J=7.8 Hz), 7.93(1H, m), 8.04(1H, d, J=7.8 Hz), 8.24(1H, m). IR (CHCl₃): 3513, 3389, 3144, 2669, 1726, 1709, 1659, 1515, 1470, 1455, 1375 cm⁻¹. $[\alpha]_D^{25}$+54.0±0.9°(c=1.008, MeOH) Anal. (C₂₇H₃₄N₂O₅S.0.2H₂O) Calcd.(%): C, 64.46; H, 6.90; N, 5.53; S, 6.38. Found(%): C, 64.45; H, 6.89; N, 5.75; S, 6.42.

Compound Number II-18

¹H-NMR(CDCl₃) δ: 0.96(1H, d, J=10.2 Hz), 1.10 and 1.23(each 3H, each s), 1.52–2.42(14H, m), 2.29(3H, t), 4.26(1H, m), 5.35–5.49(2H, m), 5.96(1H, brs), 6.19(1H, t, J=3.2 Hz), 6.26(1H, d, J=8.1 Hz), 7.25 (1H, m), 7.81(4H, s). IR(CHCl₃): 3511, 3446, 3152, 1708, 1662, 1514, 1485, 1368, 1164 cm⁻¹. $[\alpha]_D^{27}$+59.4±1.0°(c=1.006, MeOH) Anal. (C₂₈H₃₆N₂O₅S) Calcd.(%): C, 65.60; H, 7.08; N, 5.46; S, 6.25. Found(%): C, 65.41; H, 7.00; N, 5.67; S, 6.24.

Compound Number II-19

¹H-NMR(CDCl₃) δ: 0.97(1H, d, J=10.5 Hz), 1.03 and 1.22(each 3H, each s), 1.452–2.46 (14H, m), 4.26(1H, m), 5.33–5.50(2H, m), 6.20 (2H, t, J=2.1 Hz), 6.22(1H, d, J=8.1 Hz), 6.68(2H, t, J=2.1 Hz), 7.15 and 7.67 (each 2H, each d, each J=8.1 Hz). IR(CHCl₃): 3511, 3452, 3103, 2666, 1709, 1652, 1523, 1496 cm⁻¹. $[\alpha]_D^{23}$+57.7±1.0°(c=1.010, MeOH) Anal. (C₂₈H₃₆N₂O₃.0.1H₂O) Calcd.(%): C, 74.67; H, 8.10; N, 6.22. Found(%): C, 74.69; H, 8.21; N, 6.38.

Compound Number II-20

¹H-NMR(CDCl₃) δ: 0.94(1H, d, J=10.2 Hz), 1.06 and 1.20(each 3H, each s), 1.49–2.40(14H, m), 4.21(1H, m), 5.31–5.45(2H, m), 6.19(1H, d, J=8.4 Hz), 6.88(1H, d, J=3.6 Hz), 7.22–7.35(2H, m), 7.52–7.55(2H, m), 7.74 and 7.91 (each 2H, each d, each J=8.4 Hz), 7.98(1H, d, J=8.4 Hz). IR(CHCl₃): 3481, 3440, 3145, 3116, 2661, 1709, 1660, 1516, 1485, 1446, 1377, 1261, 1178, 1130 cm⁻¹. $[\alpha]_D^{26}$+56.6±1.0°(c=1.000, MeOH) Anal. (C₃₁H₃₆N₂O₅S.0.1H₂O) Calcd.(%): C, 67.64; H, 6.63; N, 5.09; S, 5.82. Found(%): C, 67.68; H, 6.72; N, 5.35; S, 5.73.

Compound Number II-21

¹H-NMR(CDCl₃) δ: 0.95(1H, d, J=10.2 Hz), 1.09 and 1.22 (each 3H, each s), 1.52–2.45(14H, m), 4.24(1H, m), 4.63(2H, s), 5.34–5.50(2H, m), 6.25–6.27(2H, m), 6.40(1H, d, J=8.4 Hz), 7.25(1H, dd, J=1.8 and 3.0 Hz), 7.80 and 7.85(each 2H, each d, each J=8.7 Hz). IR(CHCl₃): 3581, 3518, 3445, 3149, 2666, 1709, 1661, 1515, 1472, 1371, 1182, 1150 cm$^{-1}$. $[\alpha]_D^{27}$+58.1±1.0°(c=1.007, MeOH) Anal. (C$_{28}$H$_{36}$N$_2$O$_6$S) Calcd.(%): C, 63.61; H, 6.86; N, 5.30; S, 6.07. Found(%): C, 63.50; H, 6.84; N, 5.44; S, 5.89.

Compound Number II-31 mp.98–100° C. $^1$H-NMR(CDCl$_3$) δ: 0.94(1H, d, J=10.2 Hz), 1.08 and 1.21(each 3H, each s), 1.50–2.43(14H, m), 4.13(2H, s), 4.20 (1H, m), 5.33–5.49(2H, m), 5.97(1H, d, J=8.4 Hz), 6.77(1H, m), 7.21–7.35(6H, m). IR(KBr): 3407, 2674, 1703, 1630, 1511 cm$^{-1}$. $[\alpha]_D^{24}$+46.8±0.9°(c=1.006, MeOH) Anal. (C$_{28}$H$_{35}$NO$_3$S) Calcd.(%): C, 72.22; H, 7.58; N, 3.01; S, 6.89. Found(%): C, 72.04; H, 7.36; N, 3.27; S, 6.91.

Compound Number II-37

$^1$H-NMR(CDCl$_3$) δ: 0.93(1H, d, J=10.5 Hz), 1.08 and 1.21(each 3H, each s), 1.50–2.41(14H, m), 4.20(1H, m), 5.39–5.47(2H, m), 6.19(1H, d, J=8.4 Hz), 7.35(1H, d, J=3.9 Hz), 7.51–7.64(4H, m), 7.98(2H, m). IR(CHCl$_3$): 3516, 3446, 2667, 1709, 1657, 1529, 1504, 1327, 1157 cm$^{-1}$. $[\alpha]_D^{20}$+55.6°±1.0°(c=1.004, MeOH) Anal. (C$_{27}$H$_3$NO$_5$S.0.2H$_2$O) Calcd.(%) C, 62.45; H, 6.48; N, 2.70; S, 12.35. Found(%): C, 62.46; H, 6.40; N, 2.75; S, 12.19.

Compound Number II-47

$^1$H-NMR(CDCl$_3$) δ: 0.93(1H, d, J=10.2 Hz), 1.08 and 1.21(each 3H, each s), 1.50–2.41(14H, m), 4.21(1H, m), 5.34–5.48(2H, m), 6.21(1H, d, J=8.4 Hz), 7.36 and 7.63 (each 1H, each d, each J=3.9 Hz), 7.70(1H, dd, J=1.5 and 5.1 Hz), 7.75(1H, dd, J=1.5 and 3.9 Hz). IR(CHCl$_3$): 3516, 3446, 3097, 1708, 1656, 1529, 1504, 1337, 1153 cm$^{-1}$. $[\alpha]_D^{25}$+54.1±0.9°(c=1.000, MeOH) Anal. (C$_{25}$H$_{31}$NO$_5$S$_3$) Calcd.(%): C, 57.56; H, 5.99; N, 2.68; S, 18.44. Found(%): C, 57.33; H, 5.95; N, 2.68; S, 18.38.

Compound Number II-55

$^1$H-NMR(CDCl$_3$) δ: 0.93(1H, d, J=10.5 Hz), 1.08 and 1.22(each 3H, each s), 1.50–2.41(14H, m), 2.39(3H, d, J=0.6 Hz), 4.21(1H, m), 5.35–5.48(2H, m), 5.99(1H, m), 6.15(1H, d, J=8.7 Hz), 6.20(1H, t, J=3.3 Hz), 7.18(1H, dd, J=1.8 and 3.3 Hz), 7.31 and 7.54(each 1H, each d, each J=3.9 Hz). IR(CHCl$_3$): 3511, 3446, 3150, 3101, 1708, 1658, 1529, 1504, 1375, 1183, 1160 cm$^{-1}$. $[\alpha]_D^{23}$+50.3±0.9°(c=1.007, MeOH) Anal. (C$_{26}$H$_{34}$N$_2$O$_5$S$_2$.0.2H$_2$O) Calcd.(%): C, 59.79; H, 6.64; N, 5.36; S, 12.28. Found(%): C, 59.72; H, 6.61; N, 5.51; S, 12.37.

Compound Number II-59

$^1$H-NMR(CDCl$_3$) δ: 0.93(1H, d, J=10.2 Hz), 1.07 and 1.21(each 3H, each s), 1.49–2.41(14H, m), 4.19(1H, m), 5.33–5.47(2H, m), 5.99(1H, d, J=8.7 Hz), 7.01(1H, dd, J=3.6 and 5.4 Hz), 7.04 and 7.28(each 1H, each d, each J=3.6 Hz), 7.29(1H, dd, J=1.2 and 3.6 Hz), 7.43(1H, dd, J=1.2 and 5.4 Hz). IR(CHCl$_3$): 3518, 3449, 3430, 2672, 1708, 1646, 1530, 1500, 1421 cm$^{-1}$. $[\alpha]_D^{25.5}$+45.9±0.9° (c=1.010, MeOH) Anal. (C$_{25}$H$_{31}$NO$_3$S$_3$) Calcd.(%): C, 61.32; H, 6.38; N, 2.86; S, 19.64. Found(%): C, 61.17; H, 6.42; N, 3.00; S, 19.80.

Compound Number II-60

$^1$H-NMR (CHCl$_3$) δ: 0.96 (1H,d,J=10.2 Hz),1.10 and 1.22 (each 3H, each s), 1.51–1.79 (3H, m), 1.83–2.44 (11H, m), 4.26 (1H, m), 5.33–5.49 (2H, m), 6.21 (1H, d, J=8.7 Hz), 7.25 (2H, d, J=9.0 Hz), 7.34–7.47 (5H,m), 7.60 (2H, d, J=9.0 Hz) IR (CHCl$_3$): 3453, 3062, 3029, 3014, 2925, 2870, 1739, 1708, 1651, 1595, 1583, 1557, 1515, 1481 cm$^{-1}$. $[\alpha]_D^{22}$+61.0°(c=1.01,CH$_3$OH) Anal. (C$_{29}$H$_{35}$NO$_3$S.0.1H$_2$O) Calcd. (%): C, 72.65; H, 7.48; N, 2.92; S, 6.69. Found (%): C, 72.50; H, 7.45; N, 3.19; S, 6.69.

Compound Number II-81

$^1$H-NMR(CDCl$_3$) δ: 0.93(1H, d, J=10.2 Hz), 1.07 and 1.21(each 3H, each s), 1.49–2.41(14H, m), 2.46(3H, d, J=1.2 Hz), 4.18(1H, m), 5.33–5.47(2H, m), 5.99(1H, d, J=8.4 Hz), 6.66(1H, m), 6.99(1H, d, J=3.9 Hz), 7.10(1H, d, J=3.3 Hz), 7.26(1H, d, J=3.9 Hz). IR(CHCl$_3$): 3509, 3449, 2671, 1708, 1645, 1530, 1500, 1420 cm$^{-1}$. $[\alpha]_D^{25.5}$+43.5±0.8°(c=1.002, MeOH) Anal. (C$_{26}$H$_{33}$NO$_3$S$_3$) Calcd.(%): C, 61.99; H, 6.60; N, 2.78; S, 19.10. Found(%): C, 61.77; H, 6.68; N, 2.83; S, 18.91.

Compound Number II-82 mp.118–120° C. $^1$H-NMR(CDCl$_3$) δ: 0.94(1H, d, J=10.2 Hz), 1.09 and 1.22(each 3H, each s), 1.51–2.42(14H, m), 2.53(3H, d, J=0.9 Hz), 4.20 (1H, m), 5.35–5.48(2H, m), 6.17(1H, d, J=8.7 Hz), 6.77(1H, m), 7.34 (1H, d, J=3.9 Hz), 7.57(1H, d, J=3.6 Hz), 7.60(1H, d, J=3.9 Hz). IR (Nujol): 3399, 3082, 1733, 1613, 1543, 1328, 1318, 1151 cm$^{-1}$. $[\alpha]_D^{25.5}$+54.0±0.9°(c=1.012, MeOH) Anal. (C$_{26}$H$_{33}$NO$_5$S$_3$) Calcd.(%): C, 58.29; H, 6.21; N, 2.61; S, 17.95. Found(%): C, 58.08; H, 6.18; N, 2.73; S, 17.66.

Compound Number II-88 mp.91–92° C. $^1$H-NMR(CDCl$_3$) δ: 0.95(1H, d, J=10.5 Hz), 1.09 and 1.22(each 3H, each s),1.51–2.44(14H, m), 4.16(2H, s), 4.20 (1H, m), 5.34–5.49(2H, m), 5.99(1H, d, J=8.7 Hz), 6.79(1H, d, J=3.9 Hz), 6.96 (1H, dd, J=1.2 and 4.8 Hz), 7.05(1H, m), 7.28(1H, dd, J=3.0 and 4.8 Hz), 7.32(1H, d, J=3.9 Hz). IR(Nujol): 3408, 2677, 1703, 1626, 1541, 1514, 1246 cm$^{-1}$. $[\alpha]_D^{26}$+43.8±0.8°(c=1.005, MeOH) Anal. (C$_{26}$H$_{33}$NO$_3$S$_2$) Calcd.(%): C, 66.21; H, 7.05; N, 2.97; S, 13.60. Found(%): C, 66.00; H, 7.81; N, 3.11; S, 13.69.

Compound Number II-92 mp.165–166° C. $^1$H-NMR(CDCl$_3$) δ: 0.93(1H, d, J=10.2 Hz), 1.08 and 1.20(each 3H, each s), 1.50–2.45(14H, m), 4.17(1H, m), 5.33–5.51(2H, m), 6.04(1H, d, J=8.4 Hz), 6.51(1H, dd, J=1.5 and 3.3 Hz), 7.15(1H, dd, J=2.4 and 3.3 Hz), 7.52–7.57(2H, m), 7.65(1H, m), 7.74(1H, dd, J=1.8 and 2.1 Hz), 7.89–7.93(1H, m). IR(CHCl$_3$): 3510, 3449, 3144, 1733, 1708, 1650, 1570, 1507, 1384, 1185, 1176 cm$^{-1}$. $[\alpha]_D^{24}$+33.8±0.7°(c=1.011, MeOH) Anal. (C$_{27}$H$_{34}$N$_2$O$_5$S) Calcd.(%): C, 65.04; H, 6.87; N, 5.62; S, 6.43. Found(%): C, 64.95; H, 6.68; N, 5.69; S, 6.40.

Compound Number II-93

$^1$H-NMR(CDCl$_3$) δ: 0.93(1H, d, J=10.2 Hz), 1.08 and 1.21(each 3H, each s), 150–2.46(14H, m), 4.19(1H, m), 5.33–5.50(2H, m), 6.03(1H, d, J=8.7 Hz), 6.52(1H, dd, J=1.5 and 3.3 Hz), 7.11(1H, dd, J=3.9 and 4.8 Hz), 7.17(1H, dd, J=2.1 and 3.3 Hz), 7.70–7.72(2H, m), 7.74(1H, dd, J=1.2 and 3.9 Hz). IR(CHCl$_3$): 3510, 3448, 3143, 2666, 1733, 1708, 1650, 1572, 1507, 1387, 1179 cm$^{-1}$. $[\alpha]_D^{24}$+39.1°±0.8° (c=1.003, MeOH) Anal. (C$_{25}$H$_{32}$N$_2$O$_5$S$_2$) Calcd. (%): C, 59.50; H, 6.39; N, 5.55; S, 12.71. Found(%): C, 59.49; H, 6.46; N, 5.47; S, 12.70.

Compound Number II-94 mp.132–133° C. 300 MHz $^1$H-NMR(CDCl$_3$) δ: 0.93(1H, d, J=10.2 Hz), 1.08 and 1.21(each 3H, each s), 1.54–2.44 (14H, m), 4.19(1H, m), 5.33–5.50 (2H, m), 6.03(1H, d, J=8.7 Hz), 6.52(1H, dd, J=1.5 and 3.3 Hz), 7.11(1H, dd, J=3.9 and 4.8 Hz), 7.17(1H, dd, J=2.1 and 3.3 Hz), 7.70–7.72(2H, m), 7.74(1H, dd, J=1.5 and 3.9 Hz). IR(CHCl$_3$): 3510, 3448, 3143, 3099, 1733, 1708, 1650, 1572, 1507, 1473, 1387, 1179 cm$^{-1}$. $[\alpha]_D^{24}$+39.1°±0.8° (c=1.003, MeOH) Anal. (C$_{25}$H$_{32}$N$_2$O$_5$S$_2$) Calcd.(%): C, 59.50; H, 6.39; N, 5.55; S, 12.71. Found(%): C, 59.49; H, 6.46; N, 5.47; S, 12.70.

Compound Number II-98
mp.138–139° C. $^1$H-NMR(CDCl$_3$) δ: 0.97(1H, d, J=10.2 Hz), 1.13 and 1.24(each 3H, each s), 1.50–2.47(14H, m), 4.24(1H, m), 5.36–5.52 (2H, m), 6.06(1H, d, J=8.4 Hz), 6.98(1H, d, J=3.9 Hz), 6.99 and 7.05 (each 1H, each d, each J=16.2 Hz), 7.28–7.34(3H, m), 7.37 (1H, d, J=3.9 Hz). IR(CHCl$_3$): 3518, 3449, 3431, 2665, 1708, 1642, 1538, 1519, 1500 cm$^{-1}$. [α]$_D^{24}$+49.1±0.9°(c=1.014, MeOH) Anal. (C$_{27}$H$_{33}$NO$_3$S$_2$) Calcd.(%): C, 67.05; H, 6.88; N, 2.90; S, 13.26. Found(%): C, 67.94; H, 6.86; N, 2.99; S, 13.23.

Compound Number II-99
$^1$H-NMR(CDCl$_3$) δ: 0.94(1H, d, J=9.9 Hz), 1.07 and 1.22 (each 3H, each s), 1.50–2.44(14H, m), 4.20(1H, m), 5.30–5.51(2H, m), 5.97(1H, d, J=9.0 Hz), 6.58(2H, s), 6.95(1H, d, J=3.9 Hz), 7.02(1H, dd, J=1.5 and 4.8 Hz), 7.25–7.31(2H, m), 7.31(1H, d, J=3.9 Hz). IR(CHCl$_3$): 3517, 3449, 3430, 2664, 1708, 1642, 1536, 1519, 1501 cm$^{-1}$. [α]$_D^{24}$+38.6±0.8°(c=1.006, MeOH) Anal. (C$_{27}$H$_{33}$NO$_3$S$_2$.0.2H$_2$O) Calcd.(%): C, 66.55; H, 6.91; N, 2.87; S, 13.16. Found(%): C, 66.52; H, 6.81; N, 3.11; S, 12.93.

Compound Number II-100
$^1$H-NMR(CDCl$_3$) δ: 0.94(1H, d, J=10.2 Hz), 1.09 and 1.22(each 3H, each s), 1.50–2.39(14H, m), 2.44(3H, d, J=0.9 Hz), 4.20(1H, m), 5.34–5.49(2H, m), 5.98(1H, d, J=8.7 Hz), 6.70(1H, m), 7.06(1H, d, J=3.9 Hz), 7.10(1H, d, J=1.8 Hz), 7.30(1H, d, J=3.9 Hz). IR(CHCl$_3$): 3518, 3450, 3430, 3110, 2669, 1740, 1708, 1645, 1530, 1499, 1420 cm$^{-1}$. [α]$_D^{24}$+46.0±0.9°(c=0.968, MeOH) Anal. (C$_{26}$H$_{33}$NO$_3$S$_3$) Calcd. (%): C, 61.99; H, 6.60; N, 2.78; S, 19.10. Found(%): C, 61.99; H, 6.61; N, 2.87; S, 19.18.

Compound Number II-101
$^1$H-NMR(CDCl$_3$) δ: 0.94(1H, d, J=10.5 Hz), 1.09 and 1.22(each 3H, each s), 1.51–2.42(14H, m), 2.47(3H, d, J=0.9 Hz), 4.21(1H, m), 5.35–5.49(2H, m), 6.18(1H, d, J=8.7 Hz), 7.04(1H, m), 7.36 and 7.60(each 1H, each d, each J=3.9 Hz), 7.91(1H, d, J=1.5 Hz). IR(CHCl$_3$): 3510, 3447, 3115, 2670, 1708, 1656, 1529, 1504, 1443, 1329, 1156, 1143 cm$^{-1}$. [α]$_D^{24}$+53.8±0.9°(c=1.008, MeOH) Anal. (C$_{26}$H$_{33}$NO$_5$S$_3$) Calcd.(%): C, 58.29; H, 6.21; N, 2.61; S, 17.96. Found(%): C, 58.07; H, 6.05; N, 2.69; S, 17.94.

Compound Number II-102
$^1$H-NMR(CDCl$_3$) δ: 0.94(1H, d, J=10.2 Hz), 1.09 and 1.22(each 3H, each s), 1.50–2.45(14H, m), 4.22(1H, m), 5.35–5.49(2H, m), 6.04(1H, d, J=8.7 Hz), 6.52 and 6.69 (each 1H, each d, each J=12.0 Hz), 6.99 (1H, dd, J=3.6 and 5.1 Hz), 7.07(1H, d, J=3.9 Hz), 7.13(1H, d, J=3.9 Hz), 7.27(1H, dd, J=0.9 and 5.1 Hz) 7.36 (1H, d, J=3.9 Hz). IR (CHCl$_3$): 3510, 3449, 3430, 2664, 1708, 1643, 1536, 1501 cm$^{-1}$. [α]$_D^{24}$+40.3±0.8°(c=1.011, MeOH) Anal. (C$_{27}$H$_{33}$NO$_3$S$_2$.0.3H$_2$O) Calcd.(%): C, 66.31; H, 6.92; N, 2.86; S, 13.11. Found(%): C, 66.29; H, 6.81; N, 3.07; S, 13.13.

Compound Number II-103
mp.117–118° C. $^1$H-NMR(CDCl$_3$) δ: 0.97(1H, d, J=10.2 Hz), 1.13 and 1.24(each 3H, each s), 1.50–2.47(14H, m), 4.24(1H, m), 5.36–5.52(2H, m), 6.06(1H, d, J=8.7 Hz), 6.97 and 7.15(each 1H, each d, each J=15.9 Hz), 6.98(1H, d, J=3.9 Hz), 7.01(1H, dd, J=3.3 and 4.8 Hz), 7.09 (1H, d, J=3.3 Hz), 7.23(1H, d, J=4.8 Hz), 7.36(1H, d, J=3.9 Hz). IR(CHCl$_3$): 3517, 3450, 2670, 1738, 1708, 1641, 1537, 1518, 1500 cm$^{-1}$. [α]$_D^{24}$+55.7±1.0°(c=1.001, MeOH) Anal. (C$_{27}$H$_{33}$NO$_3$S$_2$) Calcd.(%): C, 67.05; H, 6.88; N, 2.90; S, 13.26. Found(%): C, 66.91; H, 6.83; N, 2.97; S, 13.13.

Compound Number II-107
$^1$H-NMR(CDCl$_3$) δ: 0.93(1H, d, J=10.2 Hz), 1.09 and 1.22(each 3H, each s), 1.51–2.44(14H, m), 4.20(1H, m), 5.34–5.50(2H, m), 6.22 and 6.23(total 1H, each d, J=8.1 and 8.7 Hz), 7.12(1H, dd, J=3.9 and 5.1 Hz), 7.44(2H, m), 7.60(1H, m), 7.69(1H, m). IR(CHCl$_3$): 3509, 3447, 3092, 1708, 1653, 1530, 1503 cm$^{-1}$. [α]$_D^{23}$+49.3±0.9°(c=1.002, MeOH) Anal. (C$_{25}$H$_{31}$NO$_4$S$_3$.0.4H$_2$O) Calcd.(%): C, 58.54; H, 6.25; N, 2.73; S, 18.75. Found(%): C, 58.62; H, 6.16; N, 2.88; S, 18.72.

Compound Number II-108
$^1$H-NMR(CDCl$_3$) δ: 0.94(1H, d, J=10.2 Hz), 1.09 and 1.10(total 3H, each s), 1.22 and 1.23(total 3H, each s), 1.51–2.44(14H, m), 2.52 and 2.53(total 3H, each d, J=0.6 Hz), 4.20(1H, m), 5.35–5.50(2H, m), 6.23 and 6.24(total 1H, each d, J=8.7 and 8.4 Hz), 6.77(1H, m), 7.39–7.46 (3H, m). IR (CHCl$_3$): 3510, 3447, 3429, 3093, 2665, 1708, 1652, 1530, 1502, 1437 cm$^{-1}$. [α]$_D^{23}$+47.4±0.9°(c=1.008, MeOH) Anal. (C$_{26}$H$_{33}$NO$_4$S$_3$.0.3H$_2$O) Calcd.(%): C, 59.47; H, 6.45; N, 2.67; S, 18.32. Found(%): C, 59.59; H, 6.16; N, 2.76; S, 18.11.

Compound Number II-112
$^1$H-NMR(CDCl$_3$) δ: 0.94(1H, d, J=10.2 Hz), 1.09 and 1.21(each 3H, each s), 1.51–2.43(14H, m), 3.38(3H, s), 4.18(1H, m), 5.33–5.50(2H, m), 5.83(1H, d, J=8.7 Hz), 6.16(1H, d, J=3.9 Hz), 7.14(1H, m), 7.21–7.27 (4H, m), 7.33–7.39(2H, m). IR(CHCl$_3$): 3514, 3450, 2661, 1739, 1709, 1628, 1597, 1495, 1479, 1415, 1132 cm$^{-1}$. [α]$_D^{23.5}$+50.8°±0.9° (c=1.005, MeOH) Anal. (C$_{28}$H$_{36}$N$_2$O$_3$S.0.2H$_2$O) Calcd.(%): C, 69.45; H, 7.58; N, 5.78; S, 6.62. Found(%): C, 69.45; H, 7.39; N, 5.99; S, 6.65.

Compound Number II-113
$^1$H-NMR(CDCl$_3$) δ: 0.95(1H, d, J=10.5 Hz), 1.09 and 1.22(each 3H, each s), 1.50–2.44(14H, m), 2.31(3H, s), 4.22(1H, m), 5.35–5.49(2H, m), 6.01(1H, d, J=8.7 Hz), 7.03–7.21(4H, m), 7.38(1H, d, J=3.9 Hz). IR(CHCl$_3$): 3516, 3448, 3429, 1739, 1709, 1647, 1529, 1500, 1473, 1421 cm$^{-1}$. [α]$_D^{20}$+46.2°±1.0°(c=1.003, MeOH) Anal. (C$_{28}$H$_{35}$NO$_3$S$_2$.0.2H$_2$O) Calcd.(%): C, 67.08; H, 7.12; N, 2.79; S, 12.79. Found(%): C, 67.12; H, 7.04; N, 2.94; S, 12.88.

Compound Number II-114
mp.112–115° C. $^1$H-NMR(CDCl$_3$) δ: 0.93(1H, d, J=10.2 Hz), 1.08 and 1.21(each 3H, each s), 1.50–2.39(14H, m), 2.42(3H, s), 4.20(1H, m), 5.34–5.47(2H, m), 6.17(1H, d, J=8.7 Hz), 7.34(1H, d, J=3.9 Hz), 7.41 (2H, m), 7.59(1H, d, J=3.9 Hz), 7.78(2H, m). IR(CHCl$_3$): 3516, 3446, 1739, 1707, 1655, 1529, 1504, 1331, 1151 cm$^{-1}$. [α]$_D^{20}$+53.0°±0.9°(c=1.002, MeOH) Anal. (C$_{28}$H$_{35}$NO$_5$S$_2$.0.2H$_2$O) Calcd.(%): C, 63.06; H, 6.69; N, 2.63; S, 12.02. Found(%): C, 63.07; H, 6.62; N, 2.73; S, 12.04.

Compound Number II-115
$^1$H-NMR(CDCl$_3$) δ: 0.95(1H, d, J=10.2 Hz), 1.09 and 1.22(each 3H, each s), 1.50–2.44(14H, m), 3.77(3H, s), 4.22(1H, m), 5.35–5.49(2H, m), 6.04(1H, d, J=8.7 Hz), 6.74–6.89(3H, m), 7.17–7.23(2H, m), 7.40 (1H, d, J=3.9 Hz). IR(CHCl$_3$): 3514, 3448, 3431, 1739, 1707, 1649, 1529, 1500, 1477 cm$^{-1}$. [α]$_D^{20}$+45.8°±0.9°(c=1.011, MeOH) Anal. (C$_{28}$H$_{35}$NO$_4$S$_2$.0.3H$_2$O) Calcd.(%): C, 64.78; H, 6.91; N, 2.70; S, 12.35. Found(%): C, 64.62; H, 6.83; N, 2.85; S, 12.65.

Compound Number II-116
$^1$H-NMR(CDCl$_3$) δ: 0.93(1H, d, J=10.5 Hz), 1.08 and 1.21(each 3H, each s), 1.50–2.41(14H, m), 3.86(3H, s), 4.20(1H, m), 5.34–5.47 (2H, m), 6.17(1H, d, J=8.7 Hz), 7.12(1H, m), 7.35(1H, d, J=3.9 Hz), 7.40–7.48(2H, m), 7.56(1H, m), 7.60(1H, d, J=3.9 Hz). IR(CHCl$_3$): 3514, 3446, 2667, 1707, 1657, 1599, 1529, 1504, 1481, 1329, 1252, 1151 cm$^{-1}$. [α]$_D^{20}$+52.6°±0.9°(c=1.011, MeOH) Anal. (C$_{28}$H$_{35}$NO$_6$S$_2$.0.2H$_2$O) Calcd.(%): C, 61.22; H, 6.50; N, 2.55; S, 11.67. Found(%): C, 61.10; H, 6.36; N, 2.65; S, 11.73.

Compound Number II-117

$^1$H-NMR(CDCl$_3$) δ: 0.92(1H, d, J=10.5 Hz), 1.07 and 1.20(each 3H, each s), 1.52–2.43(14H, m), 4.18(1H, m), 5.33–5.50(2H, m), 6.42(1H, d, J=8.4 Hz), 7.07(1H, m), 7.33–7.39(2H, m), 7.46–7.51(2H, m), 7.56 (1H, d, J=3.9 Hz). IR(CHCl$_3$): 3587, 3442, 3280, 1707, 1643, 1531, 1329, 1308, 1149 cm$^{-1}$. [α]$_D^{20}$+53.2°±0.9°(c=1.010, MeOH) Anal. (C$_{27}$H$_{33}$NO$_6$S$_2$.0.4H$_2$O) Calcd.(%): C, 60.18; H, 6.32; N, 2.60; S, 11.90. Found(%): C, 60.19; H, 6.06; N, 2.63; S, 11.99.

Compound Number II-118

$^1$H-NMR(CDCl$_3$) δ: 0.91(1H, d, J=10.2 Hz), 1.08 and 1.21(each 3H, each s), 1.50–2.45(14H, m), 4.20(1H, m), 5.33–5.50(2H, m), 6.17(1H, d, J=8.7 Hz), 6.72(2H, m), 6.79(1H, m), 7.11(2H, m), 7.38(1H, d, J=3.9 Hz). IR(CHCl$_3$): 3342, 2669, 1707, 1622, 1583, 1535 cm$^{-1}$. [α]$_D^{23}$+45.6°±0.9°(c=1.007, MeOH) Anal. (C$_{27}$H$_{33}$NO$_4$S$_2$.0.2H$_2$O) Calcd.(%): C, 64.44; H, 6.69; N, 2.78; S, 12.74. Found(%): C, 64.33; H, 6.59; N, 2.83; S, 13.07.

Compound Number II-119

$^1$H-NMR(CDCl$_3$) δ: 0.94(1H, d, J=10.5 Hz), 1.08 and 1.21(each 3H, each s), 1.50–2.43(14H, m), 3.79(3H, s), 4.10(2H, s), 4.20(1H, m), 5.33–5.49(2H, m), 5.98(1H, d, J=8.7 Hz), 6.76–6.85(4H, m), 7.24(1H, m), 7.32(1H, d, J=3.9 Hz). IR(CHCl$_3$): 3516, 3450, 3431, 2669, 1738, 1709, 1641, 1600, 1437, 1261 cm$^{-1}$. [α]$_D^{23.5}$+42.8°±0.8°(c=1.005, MeOH.) Anal. (C$_{29}$H$_{37}$NO$_4$S) Calcd.(%): C, 70.27; H, 7.52; N, 2.83; S, 6.47. Found(%): C, 70.05; H, 7.55; N, 2.84; S, 6.45.

Compound Number II-125

$^1$H-NMR(CDCl$_3$) δ: 0.93(1H, d, J=9.9 Hz), 1.08 and 1.21(each 3H, each s), 1.50–2.42(14H, m), 2.28(3H, s), 4.12(2H, s), 4.20(1H, m), 5.33–5.48 (2H, m), 5.98(1H, d, J=9.0 Hz), 6.71(1H, d, J=3.6 Hz), 7.17 (4H, s), 7.30(1H, d, J=3.6 Hz). IR(CHCl$_3$): 3518, 3450, 3430, 1739, 1709, 1641, 1543, 1506, 1471, 1458 cm$^{-1}$. [α]$_D^{22.5}$+42.9°±0.8°(c=1.000, MeOH) Anal. (C$_{29}$H$_{37}$NO$_3$S) Calcd.(%): C, 72.61; H, 7.77; N, 2.92; S, 6.68. Found(%): C, 72.43; H, 7.78; N, 3.09; S, 6.62.

Compound Number II-126

$^1$H-NMR(CDCl$_3$) δ: 0.93(1H, d, J=10.5 Hz), 1.08 and 1.21(each 3H, each s), 1.50–2.42(14H, m), 3.84(3H, s), 4.12(2H, s), 4.19(1H, m), 5.33–5.48 (2H, m), 5.98(1H, d, J=9.0 Hz), 6.77(1H, dt, J=0.9 and 3.9 Hz), 6.88(1H, d, J=8.1 Hz), 9.90(1H, m), 7.15(1H, m), 7.23(1H, m), 7.28(1H, d, J=3.9 Hz). IR(CHCl$_3$): 3509, 3450, 3431, 2664, 1739, 1708, 1639, 1544, 1506, 1464 cm$^{-1}$. [α]$_D^{24}$+40.4°±0.8°(c=1.003, MeOH) Anal. (C$_{29}$H$_{37}$NO$_4$S.0.1H$_2$O) Calcd.(%): C, 70.02; H, 7.53; N, 2.81; S, 6.45. Found(%): C, 69.92; H, 7.53; N, 2.96; S, 6.46.

Compound Number II-127

$^1$H-NMR(CDCl$_3$) δ: 0.94(1H, d, J=10.5 Hz), 1.08 and 1.21(each 3H, each s), 1.18(3H, t, J=7.8 Hz), 1.50–2.42(14H, m), 2.64(2H, q, J=7.8 Hz), 4.15(2H, s), 4.19(1H, m), 5.33–5.48(2H, m), 5.96(1H, d, J=9.3 Hz), 6.68 (1H, d, J=3.6 Hz), 7.16–7.25(4H, m), 7.29(1H, d, J=3.6 Hz). IR (CHCl$_3$): 3516, 3450, 3431, 2667, 1739, 1709, 1641, 1543, 1506, 1471, 1456 cm$^{-1}$. [α]$_D^{21}$+41.9°±0.8°(c=1.013, MeOH) Anal. (C$_{30}$H$_{39}$NO$_3$S.0.1H$_2$O) Calcd.(%): C, 72.72; H, 7.97; N, 2.83; S, 6.47. Found(%): C, 72.55; H, 7.88; N, 3.19; S, 6.62.

Compound Number II-129

$^1$H-NMR(CDCl$_3$) δ: 0.94(1H, d, J=9.9 Hz), 1.09 and 1.22(each 3H, each s),1.50–2.42(14H, m), 2.43(3H, s), 4.20 (1H, m), 4.24(2H, s), 5.34–5.49 (2H, m), 5.99(1H, d, J=8.7 Hz), 6.58(1H, m), 6.67(1H, d, J=3.3 Hz), 6.83(1H, d, J=3.9 Hz), 7.32(1H, d, J=3.9 Hz). IR (CHCl$_3$): 3516, 3450, 3431, 2667, 1709, 1643, 1545, 1508, 1471, 1458 cm$^{-1}$. [α]$_D^{22}$+42.8±0.8°(c=1.006, MeOH) Anal. (C$_{27}$H$_{35}$NO$_3$S$_2$) Calcd. (%): C, 66.77; H, 7.26; N, 2.88; S, 13.20. Found(%): C, 66.60; H, 7.23; N, 2.93; S, 13.19.

Compound Number II-132

$^1$H-NMR(CDCl$_3$) δ: 0.94(1H, d, J=10.5 Hz), 1.09 and 1.22(each 3H, each s), 1.50–2.44(14H, m), 2.31(3H, s), 4.21(1H, m), 4.25(2H, s), 5.34–5.49 (2H, m), 6.01(1H, d, J=8.7 Hz), 6.83(1H, d, J=3.9 Hz), 7.03 (1H, m), 7.11–7.20 (3H, m), 7.27(1H, d, J=3.9 Hz). IR(CHCl$_3$): 3516, 3450, 3431, 2665, 1739, 1709, 1643, 1543, 1508, 1473 cm$^1$. [α]$_D^{22}$+42.6±1.0°(c=0.861, MeOH) Anal. (C$_{29}$H$_{37}$NO$_3$S$_2$.H$_2$O) Calcd.(%): C, 67.59; H, 7.31; N, 2.72; S, 12.44. Found(%): C, 67.49; H, 7.27; N, 2.82; S, 12.35.

Compound Number II-133

$^1$H-NMR(CDCl$_3$) δ: 0.95(1H, d, J=10.5 Hz), 1.09 and 1.21(each 3H, each s), 1.50–2.44(14H, m), 4.15(2H, s), 4.20(1H, m), 5.33–5.49(2H, m), 6.0(1H, d, J=9.3 Hz), 6.13(1H, dd, J=0.6 and 3.0 Hz), 6.32(1H, dd, J=1.8 and 3.0 Hz), 6.84 and 7.22(each 1H, each d, each J=3.6 Hz), 7.47(1H, m, J=0.6 and 1.8 Hz). IR(CHCl$_3$): 3518, 3450, 3431, 2669, 1739, 1709, 1643, 1545, 1506 cm$^{-1}$. [α]$_D^{23}$+45.8±0.9°(c=1.003, MeOH) Anal. (C$_{26}$H$_{33}$NO$_4$S.0.6H$_2$O) Calcd.(%): C, 66.95; H, 7.39; N, 3.00; S, 6.87. Found(%): C, 67.04; H, 7.17; N, 3.11; S, 7.03.

Compound Number II-134

$^1$H-NMR(CDCl$_3$) δ: 0.95(1H, d, J=10.5 Hz), 1.10 and 1.22(each 3H, each s), 1.52–2.45(14H, m), 3.96(2H, s), 4.20(1H, m), 5.33–5.49(2H, m), 6.00(1H, d, J=8.7 Hz), 6.30(1H, dd, J=0.9 and 1.8 Hz), 6.81(1H, d, J=3.6 Hz), 7.31–7.33(2H, m), 7.38(1H, t, J=1.8 Hz). IR(CHCl$_3$): 3516, 3450, 3431, 2663, 1739, 1709, 1643, 1545, 1506 cm$^{-1}$. [α]$_D^{21}$+46.5±0.9°(c=1.002, MeOH) Anal. (C$_{26}$H$_{33}$NO$_4$S.0.1H$_2$O) Calcd.(%): C, 68.27; H, 7.32; N, 3.06; S, 7.01. Found(%): C, 68.08; H, 7.14; N, 3.21; S, 7.19.

Compound Number II-135

$^1$H-NMR(CDCl$_3$) δ: 0.94(1H, d, J=10.2 Hz), 1.09 and 1.21(each 3H, each s), 1.50–2.42(14H, m), 4.20(1H, m), 4.41(2H, s), 5.33–5.49(2H, m), 6.01(1H, d, J=8.7 Hz), 6.91(1H, d, J=3.6 Hz), 7.11(1H, s), 7.27–7.35(3H, m), 7.68–7.77(2H, m). IR(CHCl$_3$): 3512, 3446, 3431, 1709, 1645, 1543, 1508 cm$^{-1}$. [α]$_D^{24}$+44.9±0.9°(c=1.002, MeOH) Anal. (C$_{30}$H$_{35}$NO$_3$S$_2$.0.3H$_2$O) Calcd.(%): C, 68.35; H, 6.81; N, 2.66; S, 12.17. Found(%): C, 68.17; H, 6.52; N, 2.68; S, 12.04.

Compound Number II-136

$^1$H-NMR(CDCl$_3$) δ: 0.94(1H, d, J=10.5 Hz), 1.09 and 1.21(each 3H, each s), 1.50–2.41(14H, m), 4.19(1H, m), 4.29(2H, s), 5.33–5.48(2H, m), 6.02(1H, d, J=8.4 Hz), 6.51(1H, m), 6.91(1H, d, J=3.6 Hz), 7.16–7.25 (2H, m), 7.34(1H, d, J=3.6 Hz), 7.42(1H, d, J=8.4 Hz), 7.50(1H, m). IR(CHCl$_3$): 3516, 3450, 3431, 1739, 1709, 1643, 1545, 1508, 1454 cm$^{-1}$. [α]$_D^{23}$+42.3±0.8°(c=1.001, MeOH) Anal.

($C_{30}H_{35}NO_4S \cdot 0.3H_2O$) Calcd.(%): C, 70.50; H, 7.02; N, 2.74; S, 6.27. Found(%): C, 70.36; H, 6.94; N, 2.70; S, 6.17.

Compound Number II-138

$^1$H-NMR(CDCl$_3$) δ: 0.94(1H, d, J=10.2 Hz), 1.08 and 1.20(each 3H, each s), 1.49–2.42(14H, m), 4.20(1H, m), 4.19(2H, s), 5.33–5.48(2H, m), 5.99(1H, d, J=9.0 Hz), 6.80(1H, d, J=3.6 Hz), 7.22 (1H, d, J=7.5 Hz), 7.31–7.50 (7H, m), 7.57(2H, m). IR(CHCl$_3$): 3518, 3450, 3431, 2671, 1739, 1709, 1643, 1543, 1506, 1471, 1456 cm$^{-1}$. $[α]_D^{24}$+ 38.7±0.8°(c=1.014, MeOH) Anal. ($C_{34}H_{39}NO_3S \cdot 0.2H_2O$) Calcd.(%): C, 74.88; H, 7.28; N, 2.57; S, 5.88. Found(%): C, 74.92; H, 7.30; N, 2.75; S, 5.99.

Compound Number II-139

$^1$H-NMR(CDCl$_3$) δ: 0.97(1H, d, J=10.2 Hz), 1.06 and 1.22(each 3H, each s),1.52–2.48(14H, m), 4.11(2H, s), 4.31 (1H, m), 5.34–5.51(2H, m), 6.15(1H, d, J=9.0 Hz), 7.19–7.30(6H, m), 7.76(1H, d, J=8.1 Hz), 7.83(1H, s), 8.15(1H, s) IR(CHCl$_3$): 3516, 3442, 2667, 1739, 1709, 1651, 1514, 1495, 1471, 1454, 1435 cm$^{-1}$. $[α]_D^{24}$+ 42.8±0.8°(c=1.011, MeOH) Anal. ($C_{32}H_{37}NO_3S$) Calcd. (%): C, 74.53; H, 7.23; N, 2.72; S, 6.22. Found(%): C, 74.25; H, 7.20; N, 2.97; S, 6.05.

Compound Number II-140

$^1$H-NMR(CDCl$_3$) δ: 0.98(1H, d, J=10.2 Hz), 1.10 and 1.23(each 3H, each s),1.52–2.49(14H, m), 4.10(2H, s), 4.32 (1H, m), 5.35–5.53(2H, m), 6.17(1H, d, J=8.7 Hz), 7.19–7.32(6H, m), 7.64(1H, d, J=0.9 Hz), 7.76(1H, s), 8.21(1H, d, J=8.4 Hz). IR(CHCl$_3$): 3518, 3442, 2671, 1739, 1707, 1651, 1514, 1493, 1469, 1454, 1404 cm$^{-1}$. $[α]_D^{24}$+ 47.1±0.9°(c=1.001, MeOH) Anal. ($C_{32}H_{37}NO_3S \cdot 0.2H_2O$) Calcd.(%): C, 74.01; H, 7.26; N, 2.70; S, 6.17. Found(%): C, 73.89; H, 7.44; N, 2.93; S, 6.04.

Compound Number II-141 mp.134–135° C. 300 MHz $^1$H-NMR(CDCl$_3$) δ: 0.93(1H, d, J=10.5 Hz), 0.98 and 1.15(each 3H, each s),1.48–2.43 (14H, m), 4.20(1H, m), 4.40 and 4.54(each 1H, each d, J=16.5 Hz), 5.33–5.50(2H, m), 6.04(1H, d, J=8.4 Hz), 6.99–7.30(6H, m), 7.55(1H, s), 7.73(1H, d, J=8.4 Hz). IR(CHCl$_3$): 3518, 3437, 2669, 1741, 1709, 1653, 1510, 1471, 1454 cm$^{-1}$. $[α]_D^{25}$+54.2±0.9°(c=1.003, MeOH) Anal. ($C_{32}H_{37}NO_3S \cdot 0.1H_2O$) Calcd.(%): C, 74.27; H, 7.25; N, 2.71; S, 6.20. Found(%): C, 74.11; H, 7.16; N, 3.15; S, 6.25.

Compound Number II-142

$^1$H-NMR(CDCl$_3$) δ: 0.94(1H, d, J=10.5 Hz), 1.08 and 1.21(each 3H, each s),1.49–2.43(14H, m), 3.94(2H, s), 4.22 (1H, m), 5.33–5.49(2H, m), 6.03(1H, d, J=8.7 Hz), 7.04(1H, s), 7.17–7.33(6H, m). IR(CHCl$_3$): 3516, 3448, 3433, 2669, 1739, 1709, 1645, 1549, 1508, 1471, 1454 cm$^{-1}$. $[α]_D^{25}$+ 40.5±0.8°(c=1.003, MeOH) Anal. ($C_{28}H_{35}NO_3S \cdot 0.1H_2O$) Calcd.(%): C, 71.95; H, 7.59; N, 3.00; S, 6.86. Found(%): C, 71.82; H, 7.49; N, 3.37; S, 6.83.

Compound Number II-143

$^1$H-NMR(CDCl$_3$) δ: 0.98(1H, d, J=10.5 Hz), 1.10 and 1.23(each 3H, each s),1.53–2.50(14H, m), 4.24(2H, s), 4.33 (1H, m), 5.35–5.54(2H, m), 6.18(1H, d, J=8.4 Hz), 7.19–7.30(6H, m), 7.42(1H, t, J=7.8 Hz), 7.78(1H, s), 8.18 (1H, d, J=7.8 Hz). IR(CHCl$_3$): 3514, 3442, 2671, 1709, 1651, 1516, 1495, 1471, 1454, cm$^{-1}$. $[α]_D^{25}$+53.6±0.9° (c=1.003, MeOH), Anal. ($C_{32}H_{37}NO_3S \cdot 0.1H_2O$) Calcd.(%): C, 74.27; H, 7.25; N, 2.71; S, 6.20. Found(%): C, 74.18; H, 7.24; N, 2.90; S, 6.14.

Compound Number II-147 mp.117–118° C. 300 MHz $^1$H-NMR(CDCl$_3$) δ: 0.94(1H, d, J=9.9 Hz), 1.09 and 1.21(each 3H, each s), 1.55–2.42 (14H, m), 3.87(3H, s), 4.06 (2H, s), 4.18(1H, m), 5.35–5.49 (2H, m), 5,56(1H, brs), 5.89(1H, d, J=8.7 Hz), 6.72–6.77 (3H, m), 6.87(1H, d, J=8.1 Hz), 7.31(1H, d, J=3.6 Hz). IR(Nujol): 3373, 3184, 2667, 1705, 1622, 1599, 1547, 1520, 1286 cm$^{-1}$. $[α]_D^{23}$+42.0±0.8°(c=1.008, MeOH) Anal. ($C_{29}H_{37}NO_3S$) Calcd.(%): C, 68.07; H, 7.29; N, 2.74; S, 6.27. Found(%): C, 67.84; H, 7.43; N, 2.71; S, 6.18.

Compound Number II-148

$^1$H-NMR(CDCl$_3$) δ: 0.95(1H, d, J=9.9 Hz), 1.10 and 1.23(each 3H, each s), 1.53–2.45(14H, m), 3.87(3H, s), 2.96–3.01(2H, m), 3.10–3.16(2H, m), 4.22(1H, m), 5.34–5.50(2H, m), 6.01(1H, d, J=8.4 Hz), 6.71(1H, d, J=3.9 Hz), 7.16–7.32(6H, m). IR(CHCl$_3$): 3518, 3450, 3431, 2671, 1739, 1709, 1641, 1545, 1508 cm$^{-1}$. $[α]_D^{22}$+44.3±0.8° (c=1.006, MeOH) Anal. ($C_{29}H_{37}NO_3S \cdot 0.1H_2O$) Calcd.(%): C, 72.34; H, 7.79; N, 2.91; S, 6.66. Found(%): C, 72.24; H, 7.68; N, 3.11; S, 6.73.

Compound Number II-149

$^1$H-NMR(CDCl$_3$) δ: 0.95(1H, d, J=10.2 Hz), 1.10 and 1.23(each 3H, each s), 1.52–2.45(14H, m), 2.43(3H, d, J=0.9 Hz), 3.07–3.18(4H, m), 4.21(1H, m), 5.35–5.50(2H, m), 6.02(1H, d, J=8.4 Hz), 6.53–6.57(2H, m), 6.76 and 7.30 (each 1H, each d, each J=3.9 Hz). IR(CHCl$_3$): 3516, 3450, 3431, 2667, 1709, 1641, 1543, 1508 cm$^{-1}$. $[α]_D^{22}$+ 43.1±0.8°(c=1.005, MeOH) Anal. ($C_{28}H_{37}NO_3S_2 \cdot 0.3H_2O$) Calcd.(%): C, 66.58; H, 7.50; N, 2.77; S, 12.70. Found(%): C, 66.47; H, 7.46; N, 2.99; S, 12.62.

Compound Number II-150

$^1$H-NMR(CDCl$_3$) δ: 0.95(1H, d, J=10.2 Hz), 1.10 and 1.23(each 3H, each s), 1.52–2.45(14H, m), 3.19(4H, s), 4.21(1H, m), 5.34–5.50(2H, m), 6.01(1H, d, J=8.4 Hz), 6.75(1H, d, J=3.9 Hz), 6.79(1H, m), 6.91 (1H, dd, J=3.6 and 5.1 Hz), 7.13(1H, dd, J=0.9 and 5.1 Hz), 7.29(1H, d, J=3.9 Hz). IR(CHCl$_3$): 3514, 3450, 3433, 2667,n 1739, 1709, 1641, 1545, 1508 cm$^{-1}$. $[α]_D^{24}$+33.5±0.8°(c=1.009, MeOH) Anal. ($C_{27}H_{35}NO_3S_2$) Calcd.(%): C, 66.77; H, 7.26; N, 2.88; S, 13.20. Found(%): C, 66.48; H, 7.31; N, 2.97; S, 13.22.

Compound Number II-151

$^1$H-NMR(CDCl$_3$) δ: 0.97(1H, d, J=9.9 Hz), 1.12 and 1.23(each 3H, each s), 1.53–2.47(14H, m), 3.00–3.06(2H, m), 3.12–3.17(2H, m), 4.27 (1H, m), 5.34–5.51(2H, m), 6.24(1H, d, J=9.0 Hz), 6.75(1H, m), 6.90(1H, dd, J=3.6 and 5.4 Hz), 7.12(1H, dd, J=1.2 and 5.4 Hz), 7.25 and 7.64(each 2H, each d-like). IR(CHCl$_3$): 3516, 3452, 2665, 1738, 1709, 1649, 1523, 1495 cm$^{-1}$. $[α]_D^{24}$+54.5±0.9°(c=1.016, MeOH) Anal. ($C_{29}H_{37}NO_3S$) Calcd.(%): C, 72.61; H, 7.77; N, 2.92; S, 6.68. Found(%): C, 72.51; H, 7.69; N, 2.98; S, 6.62.

Compound Number II-152

$^1$H-NMR(CDCl$_3$) δ: 0.95(1H, d, J=10.2 Hz), 1.10 and 1.23(each 3H, each s), 1.51–2.45(14H, m), 2.92–2.97(2H, m), 3.08–3.13(2H, m), 4.22 (1H, m), 5.34–5.50(2H, m), 6.00(1H, d, J=8.7 Hz), 6.69(1H, d, J=3.6 Hz), 6.92–7.00 (2H, m), 7.09–7.15(2H, m), 7.28(1H, d, J=3.6 Hz). IR(CHCl$_3$): 3516, 3450, 3431, 1741, 1709, 1641, 1543, 1510, 1471 cm$^{-1}$. $[α]_D^{23}$+42.6±0.8°(c=1.014, MeOH) Anal. ($C_{29}H_{36}FNO_3S$) Calcd.(%): C, 69.99; H, 7.29; N, 2.81; S, 6.44; F, 3.82. Found(%): C, 69.87; H, 7.29; N, 2.88; S, 6.50; F, 3.85.

Compound Number II-156 mp.93–95° C. $^1$H-NMR(CDCl$_3$) δ: 0.96(1H, d, J=10.2 Hz), 1.13 and 1.23(each 3H, each s), 1.52–2.47(14H, m), 4.08(2H, s), 4.27(1H, m), 5.34–5.51(2H, m), 6.21(1H, d, J=8.7 Hz), 7.18–7.32(6H, m), 7.61 and 7.66(each 1H, each s), 7.74(1H, d, J=8.4 Hz). IR(KBr): 3367, 1705, 1618, 1556, 1533, 1508 cm$^{-1}$. $[\alpha]_D^{23}$+60.4±0.8°(c=1.012, MeOH) Anal. ($C_{32}H_{37}NO_3S$) Calcd.(%): C, 74.53; H, 7.23; N, 2.72; S, 6.22. Found(%): C, 74.31; H, 7.37; N, 2.99; S, 6.10.

Compound Number II-157

$^1$H-NMR(CDCl$_3$) δ: 0.92(1H, d, J=10.2 Hz), 1.06 and 1.19(each 3H, each s), 1.47–2.42(14H, m), 4.20(1H, m), 4.28(2H, s), 5.32–5.47(2H, m), 5.98(1H, d, J=8.7 Hz), 6.80(1H, d, J=3.3 Hz), 7.32–7.36(2H, m), 7.41–7.50(2H, m), 7.68(1H, s), 7.77–7.83(3H, m). IR(CHCl$_3$): 3518, 3450, 3431, 1739, 1709, 1641, 1545, 1508, 1471 cm$^{-1}$. $[\alpha]_D^{23}$+42.7±0.8°(c=1.003, MeOH) Anal. ($C_{32}H_{37}NO_3S.0.2H_2O$) Calcd.(%): C, 74.01; H, 7.26; N, 2.70; S, 6.17. Found(%): C, 73.94; H, 7.30; N, 2.89; S, 6.15.

Compound Number II-158

$^1$H-NMR(CDCl$_3$) δ: 0.95(1H, d, J=10.5 Hz), 1.11 and 1.22(each 3H, each s), 1.51–2.45(14H, m), 2.94–3.00(2H, m), 3.06–3.12(2H, m), 3.83 (3H, s), 4.22(1H, m), 5.34–5.50(2H, m), 6.00(1H, d, J=8.7 Hz), 6.73 (1H, d, J=3.6 Hz), 6.84–6.89(2H, m), 7.09(1H, dd, J=1.5 and 7.8 Hz), 7.20 (1H, dt, J=1.5 and 7.8 Hz), 7.30(1H, d, J=3.6 Hz). IR(CHCl$_3$): 3518, 3450, 3431, 1741, 1709, 1639, 1545, 1506, 1496, 1466 cm$^{-1}$. $[\alpha]_D^{25}$+41.3±0.8°(c=1.007, MeOH) Anal. ($C_{30}H_{39}FNO_4S$) Calcd.(%): C, 70.69; H, 7.71; N, 2.75; S, 6.29. Found(%): C, 70.42; H, 7.64; N, 2.78; S, 6.37.

Compound Number II-159

$^1$H-NMR(CDCl$_3$) δ: 0.94(1H, d, J=10.2 Hz), 1.10 and 1.22(each 3H, each s), 1.53–2.48(14H, m), 2.96–3.04(2H, m), 3.07–3.16(2H, m), 4.22 (1H, m), 5.34–5.52(2H, m), 6.04(1H, d, J=8.7 Hz), 6.74(1H, d, J=3.6 Hz), 6.77–6.85 (2H, m), 7.05–7.11 (2H, m), 7.31(1H, d, J=3.6 Hz). IR(CHCl$_3$): 359, 3510, 3429, 3190, 1709, 1636, 1545, 1508, 1456 cm$^{-1}$. $[\alpha]_D^{25}$+42.7±0.8°(c=1.009, MeOH) Anal. ($C_{29}H_{37}NO_4S.0.3H_2O$) Calcd.(%): C, 69.51; H, 7.56; N, 2.80; S, 6.40. Found(%): C, 69.25; H, 7.43; N, 2.89; S, 6.43.

Compound Number II-160 mp.125–126° C. 300 MHz $^1$H-NMR(CDCl$_3$) δ: 0.96(1H, d, J=10.2 Hz), 1.13 and 1.23(each 3H, each s), 1.52–2.47 (14H, m), 4.10(2H, s), 4.27 (1H, m), 5.34–5.51(2H, m), 6.20(1H, d, J=9.0 Hz), 7.19–7.33(6H, m), 7.62 and 7.69 (each 1H, each s), 7.73(1H, d, J=8.4 Hz). IR(KBr): 3415, 3199, 1736, 1703, 1633, 1523 cm$^{-1}$. $[\alpha]_D^{25}$+53.3±0.8° (c=1.002, MeOH) Anal. ($C_{32}H_{37}NO_3S.0.1H_2O$) Calcd.(%): C, 74.27; H, 7.25; N, 2.71; S, 6.23. Found(%): C, 74.19; H, 7.16; N, 2.81; S, 6.23.

Compound Number II-161 mp.98–101° C. $^1$H-NMR(CDCl$_3$) δ: 0.97(1H, d, J=10.5 Hz), 1.14 and 1.24(each 3H, each s), 1.53–2.47(14H, m), 4.08(2H, s), 4.27 (1H, m), 5.35–5.51(2H, m), 6.21(1H, d, J=8.7 Hz), 6.90(1H, dd, J=1.2 and 5.1 Hz), 6.93(1H, m), 7.24–7.29(2H, m), 7.63(1H, s), 7.75(1H, d, J=8.1 Hz). IR(KBr): 3394, 3097, 1707, 1643, 1533, 1500 cm$^{-1}$. $[\alpha]_D^{25}$+58.7±1.0°(c=1.006, MeOH) Anal. ($C_{30}H_{35}NO_3S_2.0.3H_2O$) Calcd.(%): C, 68.35; H, 6.81; N, 2.66; S, 12.17. Found(%): C, 68.27; H, 6.76; N, 2.94; S, 12.17.

Compound Number II-162 mp.106–109° C. $^1$H-NMR(CDCl$_3$) δ: 0.97(1H, d, J=10.2 Hz), 1.14 and 1.24(each 3H, each s), 1.53–2.47(14H, m), 4.26(2H, m), 4.27(1H, m), 5.35–5.51(2H, m), 6.22(1H, d, J=8.7 Hz), 6.82(1H, m), 6.93(1H, dd, J=3.6 and 5.1 Hz), 7.16(1H, dd, J=1.2 and 5.1 Hz), 7.32(1H, dd, J=8.1 and 1.8 Hz), 7.68(2H, m), 7.76(1H, d, J=8.1 Hz). IR(KBr): 3396, 3070, 1707, 1645, 1535, 1500 cm$^{-1}$. $[\alpha]_D^{25}$+59.9±1.0° (c=1.005, MeOH) Anal. ($C_{30}H_{35}NO_3S_2.0.2H_2O$) Calcd.(%): C, 68.59; H, 6.79; N, 2.67; S, 12.21. Found(%): C, 68.57; H, 6.62; N, 2.76; S, 12.17.

Compound Number II-163

$^1$H-NMR(CDCl$_3$) δ: 0.94(1H, d, J=10.2 Hz), 1.09 and 1.22(each 3H, each s), 1.49–2.44(14H, m), 4.12(2H, s), 4.23(1H, m), 5.34–5.49(2H, m), 6.09(1H, d, J=8.7 Hz), 6.82 and 6.93(each 1H, each m), 7.13–7.17 (2H, m), 7.34(1H, d, J=1.5 Hz). IR(CHCl$_{13}$): 3512, 3448, 3431, 1739, 1709, 1645, 1550, 1508, 1471, 1456 cm$^{-1}$. $[\alpha]_D^{25}$+43.3±0.8° (c=1.007, MeOH) Anal. ($C_{26}H_{33}NO_3S_2.0.1H_2O$) Calcd.(%): C, 65.95; H, 7.07; N, 2.96; S, 13.54. Found(%): C, 66.12; H, 7.06; N, 3.04; S, 13.66.

Compound Number II-164

$^1$H-NMR(CDCl$_3$) δ: 0.94(1H, d, J=10.5 Hz), 1.09 and 1.22 (each 3H, each s), 1.49–2.44(14H, m), 3.95(2H, s), 4.22(1H, m), 5.34–5.49 (2H, m), 6.06(1H, d, J=8.7 Hz), 6.92 and 6.96(each 1H, each m), 7.07(1H, d, J=1.5 Hz), 7.28(1H, m), 7.30(1H, d, J=1.5 Hz). IR(CHCl$_3$): 3510, 3431, 1739, 1709, 1645, 1550, 1508, 1471 cm$^{-1}$. $[\alpha]_D^{25}$+41.1±0.8° (c=1.009, MeOH) Anal. ($C_{26}H_{33}NO_3S_2.0.2H_2O$) Calcd.(%): C, 65.70; H, 7.08; N, 2.95; S, 13.49. Found(%): C, 65.57; H, 6.97; N, 3.08; S, 13.63.

Compound Number II-165

$^1$H-NMR(CDCl$_3$) δ: 0.95(1H, d, J=10.2 Hz), 1.10 and 1.22(each 3H, each s), 1.50–2.44(14H, m), 3.74(2H, s), 4.23(1H, m), 5.34–5.50(2H, m), 6.07(1H, d, J=8.0 Hz), 6.23(1H, s), 7.08(1H, d, J=1.5 Hz), 7.24(1H, s), 7.31(1H, d, J=1.5 Hz), 7.36(1H, m). IR(CHCl$_3$): 3510, 3448, 3431, 2663, 1709, 1645, 1550, 1508, 1471 cm$^{-1}$. $[\alpha]_D^{25}$+44.2±0.8°(c=1.001, MeOH) Anal. ($C_{26}H_{33}NO_4S.0.2H_2O$) Calcd.(%): C, 68.00; H, 7.33; N, 3.05; S, 6.98. Found(%): C, 68.00; H, 7.30; N, 3.15; S, 7.12.

Compound Number II-166

$^1$H-NMR(CDCl$_3$) δ: 0.92(1H, d, J=10.2 Hz), 1.05 and 1.19(each 3H, each s), 1.48–2.40(14H, m), 4.17(1H, m), 4.58(2H, s), 5.31–5.46(2H, m), 5.96(1H, d, J=8.7 Hz), 6.72 and 7.26(each 1H, each d, each J=3.9 Hz), 7.37–7.51(4H, m), 7.79(1H, d, J=8.1 Hz), 7.87 and 7.97 (each 1H, each m). IR(CHCl$_3$): 3516, 3450, 3431, 2667, 1739, 1709, 1641, 1543, 1508, 1471 cm$^{-1}$. $[\alpha]_D^{25.5}$+41.9±0.8°(c=1.011, MeOH) Anal. ($C_{32}H_{37}NO_3S.0.2H_2O$) Calcd.(%): C, 74.01; H, 7.26; N, 2.70; S, 6.17. Found(%): C, 74.10; H, 7.13; N, 2.99; S, 6.15.

Compound Number II-167

$^1$H-NMR(CDCl$_3$) δ: 0.93(1H, d, J=10.2 Hz), 1.05 and 1.20(each 3H, each s), 1.48–2.42(14H, m), 4.20(1H, m), 4.39(2H, m), 5.31–5.46(2H, m), 6.00(1H, d, J=9.0 Hz), 6.96(1H, s), 7.30–7.33(2H, m), 7.40–7.50 (3H, m), 7.78(1H, d, J=8.1 Hz), 7.87 and 7.95(each 1H, each m). IR(CHCl$_3$): 3518, 3448, 3431, 2665, 1738, 1709, 1645, 1549, 1508, 1471 cm$^{-1}$. $[\alpha]_D^{24}$+37.9±0.8°(c=1.004, MeOH) Anal. ($C_{32}H_{37}NO_3S.0.1H_2O$) Calcd.(%): C, 74.27; H, 7.25; N, 2.71; S, 6.20. Found(%): C, 74.13; H, 7.18; N, 2.87; S, 6.26.

Compound Number II-169

$^1$H-NMR(CDCl$_3$) δ: 0.98(1H, d, J=10.5 Hz), 1.10 and 1.23(each 3H, each s),1.53–2.50(14H, m), 4.23(2H, s), 4.33 (1H, m), 5.35–5.54(2H, m), 6.18(1H, d, J=8.7 Hz), 6.92(1H, dd, J=1.2 and 4.8 Hz), 7.01(1H, m), 7.22(1H, d, J=7.8 Hz), 7.24(1H, dd, J=3.0 and 4.8 Hz), 7.42(1H, d, J=7.8 and 8.1 Hz), 7.79(1H, d, J=8.1 Hz), 8.18(1H, d, J=8.1 Hz). IR(CHCl$_3$): 3516, 3442, 2667, 1709, 1651, 1516, 1495, 1471 cm$^{-1}$. $[\alpha]_D^{26}$+50.9±0.9°(c=1.009, MeOH), Anal. ($C_{30}H_{35}NO_3S_2.0.2H_2O$)

Calcd.(%): C, 68.59; H, 6.79; N, 2.67; S, 12.21. Found(%): C, 68.51; H, 6.69; N, 2.73; S, 12.39.

Compound Number II-170

$^1$H-NMR(CDCl$_3$) δ: 0.99(1H, d, J=10.2 Hz), 1.11 and 1.24(each 3H, each s), 1.53–2.50(14H, m), 4.03(2H, s), 4.34(1H, m), 5.36–5.54 (2H, m), 6.20(1H, d, J=8.4 Hz), 7.24(1H, d, J=8.4 Hz), 7.24(1H, d, J=7.2 Hz), 7.30(1H, m), 7.35(1H, t, J=1.8 Hz), 7.42(1H, dd, J=7.2 and 8.1 Hz), 7.81(1H, s), 8.19(1H, d, J=7.2 Hz). IR(CHCl$_3$): 3518, 3442, 1739, 1709, 1651, 1516, 1496, 1471 cm$^{-1}$. $[α]_D^{25}$+54.3±1.0°(c=1.002, MeOH) Anal. (C$_{30}$H$_{35}$NO$_4$S.0.1H$_2$O) Calcd.(%): C, 71.00; H, 6.99; N, 2.76; S, 6.32. Found(%): C, 70.95; H, 6.82; N, 2.74; S, 6.35.

Compound Number II-173

$^1$H-NMR(CDCl$_3$) δ: 0.99(1H, d, J=10.5 Hz), 1.16 and 1.24(each 3H, each s), 1.53–2.48(14H, m), 3.93(2H, s), 4.32(1H, m), 5.34–5.52(2H, m), 6.35(1H, d, J=8.7 Hz), 7.31–7.42(2H, m), 7.56(1H, d, J=6.9 Hz), 7.71(1H, dd, J=1.5 and 8.1 Hz), 7.78–7.83(2H, m), 7.92(1H, s). IR (CHCl$_3$): 3516, 3452, 3026, 2667, 1738, 1709, 1649, 1641, 1514, 1481, 1469, 1454 cm$^{-1}$. $[α]_D^{24}$+67.5±1.1°(c=1.005, MeOH) Anal. (C$_{30}$H$_{35}$NO$_3$.0.1H$_2$O) Calcd.(%): C, 78.43; H, 7.72; N, 3.05. Found(%): C, 78.36; H, 7.99; N, 3.24.

Compound Number II-174

$^1$H-NMR(CDCl$_3$) δ: 0.93(1H, d, J=10.2 Hz), 1.09 and 1.21(each 3H, each s),1.50–2.42(14H, m), 3.21(2H, t, J=8.7 Hz), 4.02(2H, s), 4.20 (1H, m), 4.59(2H, t, J=8.7 Hz), 5.34–5.49(2H, m), 6.01(1H, d, J=8.7 Hz), 6.80 (1H, d, J=3.6 Hz), 7.06(1H, d, J=1.8 Hz), 7.19(1H, m), 7.30 (1H, d, J=3.6 Hz). IR(CHCl$_3$): 3512, 3450, 3431, 2667, 1739, 1709, 1641, 1543, 1508, 1460 cm$^{-1}$. $[α]_D^{25}$+35.7±0.8°(c=1.002, MeOH), Anal. (C$_{30}$H$_{36}$BrNO$_4$S) Calcd.(%): C, 61.43; H, 6.19; Br, 13.62; N, 2.39; S, 5.47. Found(%): C, 61.26; H, 6.11; Br, 13.54; N, 2.46; S, 5.47.

Compound Number II-175

$^1$H-NMR(CDCl$_3$) δ: 0.96(1H, d, J=10.2 Hz), 1.14 and 1.23(each 3H, each s),1.52–2.46(14H, m), 4.21((2H, s), 4.28(1H, m), 5.34–5.51(2H, m), 6.23(1H, d, J=9.0 Hz), 6.94(1H, dd, J=1.2 and 4.8 Hz), 7.05(1H, m), 7.21–7.26(2H, m), 7.35(1H, dd, J=7.5 and 8.1 Hz), 7.71(1H, d, J=7.5 Hz), 7.75(1H, s). IR(CHCl$_3$): 3510, 3448, 3427, 2665, 1709, 1649, 1539, 1504, 1469, 1454 cm$^{-1}$. $[α]_D^{25}$+47.4±0.9° (c=1.005, MeOH), Anal. (C$_{32}$H$_{37}$NO$_3$S.0.1H$_2$O) Calcd.(%): C, 74.27; H, 7.25; N, 2.71; S, 6.20. Found(%): C, 74.15; H, 7.14; N, 2.89; S, 6.26.

Compound Number II-176

$^1$H-NMR(CDCl$_3$) δ: 0.97(1H, d, J=10.2 Hz), 1.14 and 1.24(each 3H, each s), 1.53–2.47(14H, m), 4.22((2H, s), 4.27(1H, m), 5.35–5.51(2H, m), 6.22(1H, d, J=8.7 Hz), 6.94(1H, dd, J=1.2 and 4.8 Hz), 7.05(1H, m), 7.21–7.26(2H, m), 7.35(1H, dd, J=7.5 and 8.1 Hz), 7.71(1H, d, J=7.5 Hz), 7.75(1H, s). IR(CHCl$_3$): 3512, 3448, 3427, 2665, 1709, 1649, 1539, 1504, 1469 cm$^{-1}$. $[α]_D^{25}$+46.1±0.9°(c=1.011, MeOH), Anal. (C$_{30}$H$_{35}$NO$_3$S$_2$) Calcd.(%): C, 69.06; H, 6.76; N, 2.68; S, 12.29. Found(%): C, 68.77; H, 6.84; N, 2.78; S, 12.30.

Compound Number II-177

$^1$H-NMR(CDCl$_3$) δ: 0.96(1H, d, J=10.2 Hz), 1.14 and 1.24(each 3H, each s),1.53–2.46(14H, m), 2.31(3H, s), 4.17((2H, s), 4.28(1H, m), 5.34–5.51 (2H, m), 6.22(1H, d, J=9.0 Hz), 7.09 and 7.15(each 2H, each d, J=7.8 Hz), 7.19(1H, d, J=7.2 Hz), 7.34(1H, dd, J=7.2 and 7.8 Hz), 7.70 (1H, d, J=7.8 Hz), 7.75(1H, s). IR(CHCl$_3$): 3510, 3448, 3427, 2669, 1709, 1649, 1537, 1504, 1469 cm$^{-1}$. $[α]_D^{25}$+45.6±0.9° (c=1.005, MeOH), Anal. (C$_{33}$H$_{39}$NO$_3$S.0.1H$_2$O) Calcd.(%): C, 74.57; H, 7.43; N, 2.64; S, 6.03. Found(%): C, 74.46; H, 7.48; N, 2.78; S, 6.15.

Compound Number II-178

$^1$H-NMR(CDCl$_3$) δ: 0.97(1H, d, J=10.2 Hz), 1.14 and 1.24(each 3H, each s),1.53–2.47(14H, m), 2.31(3H, s), 4.28 (1H, m), 4.40((2H, s), 5.35–5.51 (2H, m), 6.23(1H, d, J=8.7 Hz), 6.92–6.94(2H, m), 7.16(1H, dd, J=1.5 and 5.1 Hz), 7.28(1H, d, J=7.5 Hz), 7.36(1H, t, J=7.5 Hz), 7.72 (1H, d, J=7.5 Hz), 7.75(1H, s). IR(CHCl$_3$): 3508, 3448, 3427, 2663, 1709, 1649, 1539, 1504, 1469 cm$^{-1}$. $[α]_D^{25}$+46.2±0.9° (c=1.005, MeOH), Anal. (C$_{30}$H$_{35}$NO$_3$S$_2$) Calcd.(%): C, 69.06; H, 6.76; N, 2.68; S, 12.29. Found(%): C, 68.84; H, 6.86; N, 2.79; S, 12.28.

Compound Number II-179

$^1$H-NMR(CDCl$_3$) δ: 0.94(1H, d, J=10.5 Hz), 1.08 and 1.21(each 3H, each s), 1.51–2.42(14H, m), 4.09(2H, s), 4.18(1H, m), 5.33–5.48(2H, m), 5.96(1H, d, J=9.3 Hz), 6.54(1H, d, J=3.6 Hz), 7.24–7.42(10H, m). IR(CHCl$_3$): 3510, 3450, 3431, 1739, 1709, 1641, 1543, 1506, 1479, 1458 cm$^{-1}$. $[α]_D^{24.5}$+39.4±0.8°(c=1.007, MeOH) Anal. (C$_{34}$H$_{39}$NO$_3$S.0.1H$_2$O) Calcd.(%): C, 75.13; H, 7.27; N, 2.58; S, 5.90. Found(%): C, 75.05; H, 7.32; N, 2.69; S, 6.17.

Compound Number II-180

$^1$H-NMR(CDCl$_3$) δ: 1.00(1H, d, J=10.2 Hz), 1.15 and 1.26(each 3H, each s), 1.55–2.49(14H, m), 4.30(1H, m), 5.37–5.53(2H, m), 6.38(1H, d, J=8.1 Hz), 7.32(1H, m), 7.49–7.58(3H, m), 7.64–7.67(2H, m), 7.92 (1H, s). IR(CHCl$_3$): 3514, 3446, 1714, 1655, 1618, 1514, 1469, 1446 cm$^{-1}$. $[α]_D^{25}$+66.7±1.1°(c=1.005, MeOH) Anal. (C$_{30}$H$_{33}$NO$_4$.0.2H$_2$O) Calcd.(%): C, 75.83; H, 7.08; N, 2.95. Found(%): C, 75.69; H, 7.05; N, 3.08.

Compound Number II-181 mp.103–104° C. 300 MHz $^1$H-NMR(CDCl$_3$) δ: 0.93(1H, d, J=10.2 Hz), 1.08 and 1.21(each 3H, each s),1.49–2.42 (14H, m), 3.79(3H, s), 4.07 ((2H, s), 4.20(1H, m), 5.33–5.48 (2H, m), 5.98(1H, d, J=8.7 Hz), 6.75 (1H, d, J=3.6 Hz), 6.85 and 7.15(each 2H, each d, J=8.4 Hz), 7.31 (1H, d, J=3.6 Hz). IR(CHCl$_3$): 3519, 3450, 3431, 1741, 1709, 1641, 1612, 1543, 1510, 1464 cm$^{-1}$. $[α]_D^{25}$+43.8±0.8°(c=1.009, MeOH) Anal. (C$_{29}$H$_{37}$NO$_4$S) Calcd.(%): C, 70.27; H, 7.52; N, 2.83; S, 6.47. Found(%): C, 70.33; H, 7.55; N, 3.05; S, 6.46.

Compound Number II-182

$^1$H-NMR(CDCl$_3$) δ: 0.93(1H, d, J=10.5 Hz), 1.07 and 1.21(each 3H, each s),1.49–2.42(14H, m), 4.20(1H, m), 4.37(2H, s), 5.33–5.48(2H, m), 5.99(1H, d, J=8.4 Hz), 6.82(1H, d, J=3.6 Hz), 7.21(1H, m), 7.30 (1H, d, J=3.6 Hz), 7.34–7.37(2H, m), 7.69(1H, m), 7.86(1H, m). IR (CHCl$_3$): 3512, 3450, 3431, 2671, 1739, 1709, 1643, 1543, 1508, 1471, 1460 cm$^{-1}$. $[α]_D^{25}$+40.2±0.8°(c=1.005, MeOH), Anal. (C$_{30}$H$_{35}$NO$_3$S$_2$.0.4H$_2$O) Calcd.(%): C, 68.12; H, 6.82; N, 2.64; S, 12.12. Found(%): C, 68.05; H, 6.70; N, 2.87; S, 12.00.

Compound Number II-183

$^1$H-NMR(CDCl$_3$) δ: 0.93(1H, d, J=10.2 Hz), 1.08 and 1.21(each 3H, each s), 1.50–2.47(14H, m), 4.13(2H, s), 4.20(1H, m), 5.33–5.50(2H, m), 6.01(1H, d, J=9.0 Hz), 6.80(1H, m), 6.82(1H, m), 6.86(1H, m), 7.12 (1H, m), 7.15(1H, m), 7.31(1H, d, J=3.9 Hz). IR(CHCl$_3$): 3597, 3510, 3448, 3427, 3190, 1709, 1633, 1545, 1514, 1508, 1456 cm$^{-1}$. $[α]_D^{24}$+41.8°±0.8°(c=1.004, MeOH) Anal. (C$_{28}$H$_{35}$NO$_4$S.0.3H$_2$O) Calcd.(%): C, 69.11; H, 7.37; N, 2.88; S, 6.59. Found(%): C, 68.94; H, 7.42; N, 2.96; S, 6.73.

Compound Number II-184

¹H-NMR(CDCl₃) δ: 1.00(1H, d, J=10.5 Hz), 1.17 and 1.25(each 3H, each s), 1.55–2.50(14H, m), 3.93 (2H, s), 4.32(1H, m), 5.35–5.49(2H, m), 6.37(1H, d, J=8.7 Hz), 7.31–7.43(2H, m), 7.54–7.63(3H, m), 7.84 (1H, d, J=7.2 Hz), 8.16(1H, s). IR (CDCl₃): 3514, 3450, 2667, 1709, 1651, 1572, 1514, 1481, 1452 cm⁻¹. $[\alpha]_D^{24}$+58.3±1.0°(c=1.003, MeOH) Anal. (C₃₀H₃₅NO₃.0.1H₂O) Calcd.(%): C, 78.43; H, 7.72; N, 3.05. Found(%): C, 78.26; H, 7.73; N, 3.28.

Compound Number II-185

¹H-NMR(CDCl₃) δ: 0.94(1H, d, J=10.2 Hz), 1.09 and 1.21(each 3H, each s), 1.52–2.42(14H, m), 4.16(2H, s), 4.19(1H, m), 5.33–5.47(2H, m), 5.99(1H, d, J=9.3 Hz), 6.78(1H, d, J=3.6 Hz), 7.00–7.12(2H, m), 7.20–7.27 (2H, m), 7.30(1H, d, J=3.6 Hz). IR(CHCl₃): 3510, 3450, 3431, 1741, 1709, 1643, 1543, 1508, 1456 cm⁻¹. $[\alpha]_D^{24}$+38.0±0.8°(c=1.03, CHCl₃) Anal. (C₂₈H₃₄FNO₃S.0.5H₂O) Calcd.(%): C, 68.26; H, 7.16; N, 2.86; S, 6.51; F, 3.86. Found(%): C, 68.24; H, 7.08; N, 2.93; S, 6.50; F, 3.80.

Compound Number II-188 mp.53–55° C. 300 MHz ¹H-NMR(CDCl₃) δ: 0.94(1H, d, J=10.2 Hz), 1.08 and 1.21(each 3H, each s),1.51–2.42(14H, m), 4.07(2H, s), 4.19 (1H, m), 5.05(2H, s), 5.33–5.48(2H, m), 5.98(1H, d, J=9.0 Hz), 6.76 (1H, d, J=3.6 Hz), 6.92 and 7.15(each 2H, each d, J=8.7 Hz), 7.31(1H, d, J=3.6 Hz), 7.32.–7.43 (5H, m) IR(CHCl₃): 3518, 3450, 3431, 1741, 1709, 1641, 1612, 1545, 1510, 1469, 1456 cm⁻¹. $[\alpha]_D^{24}$+36.0±0.8°(c=1.005, MeOH), Anal. (C₃₅H₄₁NO₄S.0.4H₂O) Calcd.(%): C, 72.61; H, 7.28; N, 2.42; S, 5.54. Found(%): C, 72.58; H, 7.33; N, 2.65; S, 5.53.

Compound Number II-189

300 MHz ¹H-NMR(CDCl₃) δ: 0.94(1H, d, J=10.5 Hz), 1.08 and 1.21 (each 3H, each s),1.51–2.42(14H, m), 4.07 (2H, s), 4.19(1H, m), 4.51–4.53 (2H, m), 5.26–5.46(4H, m), 5.98(1H, d, J=8.7 Hz), 6.05(1H, m), 6.76 (1H, d, J=3.6 Hz), 6.87 and 7.14(each 2H, each d, J=8.7 Hz), 7.31 (1H, d, J=3.6 Hz). IR(CHCl₃): 3511, 3450, 3431, 1741, 1709, 1641, 1612, 1543, 1508, 1471, 1458 cm⁻¹. $[\alpha]_D^{24}$+39.7±0.8°(c=1.008, MeOH), Anal. (C₃₁H₃₉NO₄S.0.2H₂O) Calcd.(%): C, 70.88; H, 7.56; N, 2.67; S, 6.10. Found(%): C, 70.86; H, 7.60; N, 2.68; S, 6.17.

Compound Number II-190

¹H-NMR(CDCl₃) δ: 0.94(1H, d, J=10.2 Hz), 1.09 and 1.21(each 3H, each s),1.50–2.43(14H, m), 4.04(2H, s), 4.20 (1H, m), 5.33–5.49(2H, m), 5.94(2H, s), 5.98(1H, d, J=8.7 Hz), 6.68–6.78(4H, m), 7.31(1H, d, J=3.9 Hz). IR(CHCl₃): 3518, 3450, 3431, 1739, 1709, 1641, 1543, 1504, 1489, 1444, 1250, 1041 cm⁻¹. $[\alpha]_D^{24}$+42.2±0.8°(c=1.010, MeOH), Anal. (C₂₉H₃₅NO₅S) Calcd.(%): C, 68.34; H, 6.92; N, 2.75; S, 6.29. Found(%): C, 68.19; H, 6.88; N, 2.86; S, 6.20.

Compound Number II-191 mp.76–80° C. ¹H-NMR(CDCl₃) δ: 0.94(1H, d, J=9.9 Hz), 1.09 and 1.21(each 3H, each s),1.51–2.43(14H, m), 4.13 (2H, s), 4.20(1H, m), 5.34–5.49(2H, m), 6.00(1H, d, J=8.4 Hz), 6.78(1H, d, J=3.9 Hz), 6.90–7.04 (3H, m), 7.27(1H, m), 7.32(1H, d, J=3.9 Hz). IR(Nujol): 3408, 1703, 1631, 1514, 1250 cm⁻¹. $[\alpha]_D^{25}$+51.0±0.9°(c=1.001, MeOH), Anal. (C₂₈H₃₄FNO₃S) Calcd.(%): C, 69.54; H, 7.09; N, 2.90; S, 6.63; F, 3.93. Found(%): C, 69.77; H, 7.23; N, 2.95; S, 6.55; F, 3.93.

Compound Number II-192

¹H-NMR(CDCl₃) δ: 0.94(1H, d, J=10.2 Hz), 1.09 and 1.22(each 3H, each s),1.51–2.44(14H, m), 4.19(2H, s), 4.20 (1H, m), 5.34–5.49(2H, m), 6.00(1H, d, J=8.4 Hz), 6.78 and 7.32(each 1H, each d, each J=3.6 Hz), 7.40–7.54(4H, m). IR(CHCl₃): 3516, 3450, 3431, 1739, 1709, 1643, 1543, 1508, 1331, 1167, 1130 cm⁻¹. $[\alpha]_D^{25}$+39.5±0.8°(c=1.012, MeOH), Anal. (C₂₉H₃₄F₃NO₃S) Calcd.(%): C, 65.27; H, 6.42; N, 2.62; S, 6.01; F, 10.68. Found(%): C, 65.05; H, 6.46; N, 2.74; S, 6.02; F, 10.63.

Compound Number II-193

¹H-NMR(CDCl₃) δ: 0.94(1H, d, J=10.2 Hz), 1.09 and 1.21(each 3H, each s), 1.51–2.26(14H, m), 4.19(1H, m), 4.26(2H, s), 5.33–5.49(2H, m), 6.00(1H, d, J=8.4 Hz), 6.79(1H, d, J=3.9 Hz), 7.20–7.25(3H, m), 7.30(1H, d, J=3.9 Hz), 7.37–7.40(1H, m). IR(CHCl₃): 3516, 3450, 3431, 1709, 1643, 1543, 1508, 1471 cm⁻¹. $[\alpha]_D^{25}$+38.5±0.8° (c=1.00, CHCl₃) Anal. (C₂₈H₃₄FNO₃S.0.5H₂O) Calcd.(%): C, 66.06; H, 6.93; N, 2.75; S, 6.30; Cl, 6.96. Found(%): C, 66.21; H, 6.87; N, 2.97; S, 6.24; Cl, 6.75.

Compound Number II-194

¹H-NMR(CDCl₃) δ: 0.93(1H, d, J=10.5 Hz), 1.07 and 1.20(each 3H, each s), 1.49–2.42(14H, m), 2.30(6H, s), 4.15(2H, s), 4.19(1H, m), 5.33–5.48 (2H, m), 5.97(1H, d, J=8.7 Hz), 6.56(1H, d, J=3.9 Hz), 7.03–7.13 (3H, m), 7.26(1H, d, J=3.9 Hz). IR(CHCl₃): 3518, 3450, 3431, 2671, 1739, 1709, 1641, 1543, 1506, 1471 cm⁻¹. $[\alpha]_D^{24}$+43.7±0.8°(c=1.004, MeOH) Anal. (C₃₀H₃₉FNO₃S.0.1H₂O) Calcd.(%): C, 72.72; H, 7.97; N, 2.83; S, 6.47. Found(%): C, 72.68; H, 7.95; N, 2.96; S, 6.48.

Compound Number II-195

¹H-NMR(CDCl₃) δ: 0.94(1H, d, J=9.9 Hz), 1.09 and 1.21(each 3H, each s), 1.53–2.50(14H, m), 4.19(1H, m), 4.32(2H, s), 5.34–5.47(2H, m), 6.00(1H, d, J=8.7 Hz), 6.76(1H, d, J=3.6 Hz), 7.28–7.39(3H, m), 7.50 (1H, m), 7.66(1H, d, J=3.6 Hz). IR(CHCl₃): 3516, 3450, 3431, 2669, 1741, 1709, 1643, 1543, 1508, 1456, 1315, 1163, 1126, 1059, 1038 cm⁻¹. $[\alpha]_D^{25}$+36.4±0.7°(c=1.03, CHCl₃) Anal. (C₂₉H₃₄F₃NO₃S) Calcd.(%): C, 65.27; H, 6.42; N, 2.62; S, 6.01. Found(%): C, 65.34; H, 6.30; N, 2.82; S, 6.00.

Compound Number II-197

¹H-NMR(CDCl₃) δ: 0.93(1H, d, J=10.5 Hz), 1.08 and 1.20(each 3H, each s),1.49–2.42(14H, m), 3.22(2H, t, J=8.7 Hz), 4.07(2H, s), 4.20 (1H, m), 4.57(2H, t, J=8.7 Hz), 5.33–5.48(2H, m), 5.99(1H, d, J=9.0 Hz), 6.79 (1H, t, J=7.5 Hz), 6.80(1H, d, J=3.6 Hz), 6.95(1H, d, J=7.5 Hz), 7.09(1H, d, J=7.5 Hz), 7.30(1H, d, J=3.6 Hz). IR(CDCl₃): 3514, 3450, 3431, 2667, 1739, 1709, 1641, 1545, 1506, 1458 cm⁻¹. $[\alpha]_D^{25}$+42.0±0.8°(c=1.004, MeOH), Anal. (C₃₀H₃₇NO₄S.0.1H₂O) Calcd.(%): C, 70.72; H, 7.36; N, 2.75; S, 6.29. Found(%): C, 70.59; H, 7.39; N, 2.95; S, 6.31.

Compound Number II-198

¹H-NMR(CDCl₃) δ: 0.92 (1H, d, J=10.5 Hz), 1.07 and 1.19 (each 3H, each s),1.47–2.41(14H, m), 4.20(1H, m), 4.24(2H, s), 5.32–5.47(2H, m), 6.00(1H, d, J=8.7 Hz), 6.78(1H, d, J=3.9 Hz), 7.21(1H, dd, J=1.8 and 8.4 Hz), 7.26(1H, d, J=5.7 Hz), 7.33(1H, d, J=3.9 Hz), 7.43(1H, d, J=5.7 Hz), 7.67(1H, d, J=1.8 Hz), 7.81(1H, d, J=8.4 Hz). IR(CHCl₃): 3516, 3450, 3431, 1739, 1709, 1641, 1545, 1458 cm⁻¹. $[\alpha]_D^{25}$+40.9±0.8°(c=1.002, MeOH), Anal. (C₃₀H₃₅NO₃S₂.0.3H₂O) Calcd.(%): C, 68.36; H, 6.81; N, 2.66; S, 12.17. Found(%): C, 68.30; H, 6.68; N, 2.94; S, 12.25.

Compound Number II-199

¹H-NMR(CDCl₃) δ: 0.93(1H, d, J=10.5 Hz), 1.07 and 1.20(each 3H, each s),1.49–2.42(14H, m), 4.20(1H, m), 4.27(2H, s), 5.32–5.48(2H, m), 5.99(1H, d, J=8.7 Hz), 6.80(1H, d, J=3.6 Hz), 7.24(1H, dd, J=1.5 and 8.1 Hz), 7.31(1H, dd, J=0.6 and 5.4 Hz), 7.33(1H, d, J=3.6 Hz), 7.40 (1H, d, J=5.4 Hz), 7.73(1H, m), 7.77(1H, d, J=8.1 Hz). IR (CHCl$_3$): 3516, 3450, 3431, 1741, 1709, 1641, 1543, 1508, 1469 cm$^{-1}$. $[\alpha]_D^{25}$+41.5±0.8°(c=1.002, MeOH), Anal. (C$_{30}$H$_{35}$NO$_3$S$_2$.0.3H$_2$O) Calcd.(%): C, 68.36; H, 6.81; N, 2.66; S, 12.17. Found(%): C, 68.37; H, 6.73; N, 2.86; S, 12.21.

Compound Number II-200

$^1$H-NMR(CDCl$_3$) δ: 0.93(1H, d, J=10.2 Hz), 1.06 and 1.19(each 3H, each s),1.48–2.41(14H, m), 4.19(1H, m), 4.39(2H, s), 5.32–5.47(2H, m), 5.99(1H, d, J=8.7 Hz), 6.86(1H, d, J=3.6 Hz), 7.21(1H, d, J=7.2 Hz), 7.30(1H, d, J=3.6 Hz), 7.35(1H, t, J=7.2 Hz), 7.36(1H, d, J=5.4 Hz), 7.42(1H, d, J=5.4 Hz), 7.74(1H, d, J=7.2 Hlz). IR(CHCl$_3$): 3516, 3450, 3431, 1739, 1709, 1641, 1543, 1508, 1471, 1460 cm$^{-1}$. $[\alpha]_D^{25}$+42.0±0.8°(c=1.001, MeOH), Anal. (C$_{30}$H$_{35}$NO$_3$S$_2$.0.3H$_2$O) Calcd.(%): C, 68.36; H, 6.81; N, 2.66; S, 12.17. Found(%): C, 68.63; H, 6.78; N, 2.84; S, 12.26.

Compound Number II-201

$^1$H-NMR(CDCl$_3$) δ: 0.92(1H, d, J=10.2 Hz), 1.07 and 1.20(each 3H, each s),1.52–2.47(14H, m), 4.20(1H, m), 4.23(2H, s), 5.32–5.51(2H, m), 6.08(1H, d, J=8.7 Hz), 6.75(1H, d, J=3.6 Hz), 6.95(1H, dd, J=2.4 and 9.0 Hz), 7.10(1H, d, J=2.4 Hz), 7.19(1H, s), 7.27(1H, d, J=3.6 Hz), 7.66(1H, d, J=9.0 Hz). IR(CHCl$_3$): 3427, 3249, 1707, 1633, 1601, 1545, 1510, 1442 cm$^{-1}$. $[\alpha]_D^{25}$+40.1±0.8°(c=1.007, MeOH), Anal. (C$_{30}$H$_{35}$NO$_4$S$_2$.0.3H$_2$O) Calcd.(%): C, 66.34; H, 6.61; N, 2.58; S, 11.81. Found(%): C, 66.21; H, 6.70; N, 2.70; S, 11.75.

Compound Number II-202

$^1$H-NMR(CDCl) δ: 0.93(1H, d, J=10.2 Hz), 1.08 and 1.21(each 3H, each s), 1.53–2.45(14H, m), 4.17(1H, m), 4.24(2H, m), 4.69(2H, m), 5.35–5.47(2H, m), 6.02(1H, d, J=9.3 Hz), 6.72(1H, d, J=3.9 Hz), 7.23–7.31(4H, m), 7.40 (1H, m). IR(CHCl$_3$): 3516, 3450, 3431, 1709, 1641, 1527, 1508, 1456 cm$^{-1}$. $[\alpha]_D^{26}$+32.7±0.7°(c=1.00, CHCl$_3$)

Compound Number II-203

$^1$H-NMR(CDCl$_3$) δ: 0.92(1H, d, J=10.2 Hz), 1.08 and 1.21(each 31H, each s), 1.54–2.48(18H, m), 3.20 (4H, m), 4.11–4.22(3H, m), 4.43(2H, m), 5.33–5.55(2H, m), 5.99(1H, d, J=8.4 Hz), 6.67(1H, d, J=4.2 Hz), 7.30–7.43 (4H, m), 7.64(1H, d, J=4.2 Hz). IR(CHCl$_3$): 3514, 3448, 3420, 2555, 2459, 1711, 1643, 1543, 1508, 1456 cm$^{-1}$. $[\alpha]_D^{26}$+20.4±0.6°(c=1.05, CHCl$_3$) Anal. (C$_{33}$H$_{44}$N$_2$O$_3$S.1.1H$_2$O) Calcd.(%): C, 69.71; H, 8.19; N, 4.93; S, 5.64. Found(%): C, 69.69; H, 8.08; N, 4.92; S, 5.54.

Compound Number II-204

$^1$H-NMR(CDCl$_3$) δ: 0.93(1H, d, J=10.5 Hz), 1.07 and 1.21(each 3H, each s), 1.53–2.46(14H, m), 2.49(6H,s), 3.79 (1H, d, J=10.8 Hz), 3.84 (1H, d, J=10.8 Hz), 4.19(1H, m), 4.35(1H, d, J=20.1 Hz), 4.37(1H, d, J=20.1 Hz), 5.36–5.54 (2H, m), 5.94(1H, d, J=9.0 Hz), 6.71(1H, d, J=3.6 Hz), 7.25–7.43(5H, m). IR(CHCl$_3$): 3516, 3448, 3429, 2553, 2459, 1711, 1643, 1545, 1506, 1471 cm$^{-1}$. $[\alpha]_D^{26}$+20.9±0.6°(c=1.03, CHCl$_3$) Anal. (C$_{31}$H$_{42}$N$_2$O$_3$S.3.1H$_2$O) Calcd.(%): C, 64.35; H, 8.40; N, 4.84; S, 5.54. Found(%): C, 64.36; H, 7.87; N, 4.63; S, 5.17.

Compound Number II-205

$^1$H-NMR(CDCl$_3$) δ: 0.98(1H, d, J=10.5 Hz), 1.13 and 1.24(each 3H, each s), 1.53–2.47(14H, m), 3.20–3.27(4H, m), 4.28(1H, m), 5.35–5.51 (2H, m), 6.32(1H, d, J=8.4 Hz), 7.24(1H, d, J=7.5 Hz), 7.34 and 7.46 (each 1H, each m), 7.55(1H, dd, J=1.8 and 8.4 Hz), 7.67(1H, d, J=1.8 Hz), 8.00–8.04(2H, m). IR(CHCl$_3$): 3518, 3448, 1709, 1649, 1597, 1514, 1294 cm$^{-1}$. $[\alpha]_D^{25}$+58.8±1.0°(c=1.001, MeOH) Anal. (C$_{32}$H$_{37}$NO$_4$.0.2H$_2$O) Calcd.(%): C, 76.37; H, 7.49; N, 2.78. Found(%): C, 76.33; H, 7.50; N, 2.88.

Compound Number II-206

$^1$H-NMR(CDCl$_3$) δ: 0.95(1H, d, J=10.2 Hz), 1.07 and 1.22(each 3H, each s), 1.51–2.43(14H, m), 3.97(2H, s), 4.21(1H, m), 5.34–5.49(2H, m), 6.07(1H, d, J=3.3 Hz), 6.38(1H, d, J=9.3 Hz), 6.98–7.04(3H, m), 7.13–7.22(2H, m). IR (CHCl$_3$): 3518, 3438, 1739, 1709, 1651, 1606, 1549, 1508 cm$^{-1}$. $[\alpha]_D^{26}$+57.2±1.0°(c=1.016, MeOH) Anal. (C$_{28}$H$_{34}$FNO$_4$.0.1H$_2$O) Calcd.(%): C, 71.65; H, 7.34; N, 2.98; F, 4.05. Found(%): C, 71.57; H, 7.44; N, 3.14; F, 4.01.

Compound Number II-207

$^1$H-NMR(CDCl$_3$) δ: 0.96(1H, d, J=10.5 Hz), 1.07 and 1.21(each 3H, each s), 1.52–2.43(14H, m), 4.00(2H, s), 4.21(1H, m), 5.34–5.49(2H, m), 6.09(1H, d, J=3.3 Hz), 6.40(1H, d, J=9.6 Hz), 7.01(1H, d, J=3.3 Hz), 7.22–7.36(5H, m). IR (CHCl$_3$): 3516, 3439, 2667, 1738, 1709, 1651, 1606, 1547, 1498 cm$^{-1}$. $[\alpha]_D^{24}$+62.2±1.0°(c=1.007, MeOH) Anal. (C$_{28}$H$_{35}$NO$_4$.0.2H$_2$O) Calcd.(%): C, 74.21; H, 7.87; N, 3.09. Found(%): C, 74.14; H, 7.81; N, 3.25.

Compound Number II-208

$^1$H-NMR(CDCl$_3$) δ: 0.92(1H, d, J=10.2 Hz), 1.07 and 1.20(each 3H, each s),1.48–2.42(14H, m), 4.19(1H, m), 4.42(2H, s), 5.32–5.47(2H, m), 5.98(1H, d, J=8.7 Hz), 6.78(1H, d, J=2.1 Hz), 6.84(1H, d, J=3.9 Hz), 7.13(1H, dd, J=1.5 and 7.5 Hz), 7.19(1H, t, J=7.5 Hz), 7.30(1H, d, J=3.9 Hz), 7.50(1H, dd, J=1.5 and 7.5 Hz), 7.63(1H, d, 2.1 Hz). IR(CHCl$_3$): 3516, 3450, 3431, 1741, 1709, 1641, 1543, 1508, 1471, 1458, 1427 cm$^{-1}$. $[\alpha]_D^{25}$+43.5±0.8°(c=1.010, MeOH), Anal. (C$_{30}$H$_{35}$NO$_4$S.0.2H$_2$O) Calcd.(%): C, 70.75; H, 7.01; N, 2.75; S, 6.30. Found(%): C, 70.80; H, 7.02; N, 2.96; S, 6.26.

Compound Number II-209

$^1$H-NMR(CDCl$_3$) δ: 0.94(1H, d, J=10.2 Hz), 1.09 and 1.22(each 3H, each s), 1.55–2.41(14H, m), 2.95(3H, s), 4.18–4.21(3H, m), 4.45(2H, s), 5.39–5.43(2H, m), 6.00(1H, d, J=8.7 Hz), 6.63–6.71(4H, m), 7.16–7.26(6H, m), 7.32(1H, m). IR(CHCl$_3$): 3516, 3450, 3431, 1739, 1709, 1643, 1599, 1543, 1505, 1454 cm$^{-1}$. $[\alpha]_D^{26}$+32.2±0.7°(c=1.00, CHCl$_3$) Anal. (C$_{36}$H$_{44}$N$_2$O$_3$S.0.6H$_2$O) Calcd.(%): C, 72.59; H, 7.65; N, 4.70; S, 5.38. Found(%): C, 72.68; H, 7.47; N, 4.74; S, 5.29.

Compound Number II-211

$^1$H-NMR(CDCl$_3$) δ: 0.93(1H, d, J=9.9 Hz), 1.07 and 1.20(each 3H, each s), 1.49–2.41(14H, m), 4.19(1H, m), 4.30(2H, s), 5.32–5.48(2H, m), 5.99(1H, d, J=9.0 Hz), 6.82(1H, d, J=3.6 Hz), 7.24(1H, dd, J=1.5 and 8.1 Hz), 7.30–7.36(2H, m), 7.4–7.47(2H, m), 7.55(1H, d, J=8.1 Hz), 7.87–7.94(2H, m). IR(CHCl$_3$): 3510, 3450, 3431, 2669, 1739, 1709, 1641, 1545, 1506, 1458, 1429 cm$^{-1}$. $[\alpha]_D^{24}$+39.4±0.8°(c=1.002, MeOH) Anal. (C$_{34}$H$_{37}$NO$_4$S.0.1H$_2$O) Calcd.(%): C, 73.25; H, 6.73; N, 2.51; S, 5.75. Found(%): C, 73.13; H, 6.53; N, 2.69; S, 5.79.

Compound Number II-212

$^1$H-NMR(CDCl$_3$) δ: 0.93(1H, d, J=10.2 Hz), 1.08 and 1.21(each 3H, each s), 1.50–2.43(14H, m), 3.79 and 3.86 (each 3H, each s), 4.14(2H, s), 4.19(1H, m), 5.33–5.48(2H, m), 5.96(1H, d, J=8.4 Hz), 6.78–6.85 (3H, m), 7.00(1H, t, J=8.1 Hz), 7.30(1H, d, J=3.6 Hz). IR(CHCl$_3$): 3516, 3450, 3431, 2667, 1739, 1709, 1641, 1543, 1506, 1481, 1273, 1076 cm$^{-1}$. $[\alpha]_D^{26}$+39.6±0.8°(c=1.007, MeOH) Anal.

($C_{30}H_{39}NO_5S\cdot0.1H_2O$) Calcd.(%): C, 68.31; H, 7.49; N, 2.66; S, 6.08. Found(%): C, 68.17; H, 7.50; N, 2.76; S, 6.13.

Compound Number II-213

$^1$H-NMR(CDCl$_3$) δ: 0.94(1H, d, J=10.2 Hz), 1.09 and 1.22 (each 3H, each s),1.51–2.45(14H, m), 2.39(3H, s), 4.15(2H, s), 4.21(1H, m), 5.34–5.50 (2H, m), 5.87(1H, s), 6.04(1H, d, J=8.7 Hz), 6.86(1H, d, J=3.6 Hz), 7.32(1H, d, J=3.6 Hz). IR(CHCl$_3$): 3514, 3450, 3431, 1709, 1645, 1608, 1545, 1508, 1471, 1456 cm$^{-1}$. $[\alpha]_D^{25}$+47.0±0.9°(c=1.017, MeOH), Anal. ($C_{26}H_{34}N_2O_4S\cdot0.3H_2O$) Calcd.(%): C, 65.60; H, 7.33; N, 5.88; S, 6.74. Found(%): C, 65.49; H, 7.31; N, 6.00; S, 6.86.

Compound Number II-214

$^1$H-NMR(CDCl$_3$) δ: 0.93(1H, d, J=10.2 Hz), 1.08 and 1.21(each 3H, each s),1.50–2.42(14H, m), 2.33(3H, s), 3.82 (3H, s), 4.07(2H, s), 4.18 (1H, m), 5.33–5.48(2H, m), 5.96(1H, d, J=8.7 Hz), 6.69(1H, s), 6.74 (1H, d, J=7.8 Hz), 6.76(1H, d, J=3.6 Hz), 7.03(1H, d, J=7.8 Hz), 7.28 (1H, d, J=3.6 Hz). IR(CHCl$_3$): 3516, 3450, 3431, 1741, 1709, 1639, 1614, 1543, 1506, 1464 cm$^{-1}$. $[\alpha]_D^{24}$+43.3±0.8°(c=1.012, MeOH), Anal. ($C_{30}H_{39}NO_4S\cdot0.1H_2O$) Calcd.(%): C, 70.45; H, 7.73; N, 2.74; S, 6.27. Found(%): C, 70.35; H, 7.78; N, 2.96; S, 6.20.

Compound Number II-215

$^1$H-NMR(CDCl$_3$) δ: 0.93(1H, d, J=10.2 Hz), 1.07 and 1.21(each 3H, each s),1.49–2.43(14H, m), 3.84(3H, s), 4.20 (1H, m), 4.32(2H, s), 5.33–5.48(2H, m), 5.99(1H, d, J=8.4 Hz), 6.83(1H, d, J=3.6 Hz), 7.01 (1:H, dd, J=2.4 and 8.7 Hz), 7.12(1H, d,J=2.4 Hz), 7.21(1H, s), 7.31 (1H, d, J=3.6 Hz), 7.71(1H, d, J=8.7 Hz). IR(CDCl$_3$): 3516, 3450, 3431, 1739, 1709, 1643, 1601, 1543, 1508, 1458, 1427 cm$^{-1}$. $[\alpha]_D^{25}$+38.5±0.8°(c=1.004, MeOH), Anal. ($C_{31}H_{37}NO_4S_2\cdot0.1H_2O$) Calcd.(%): C, 67.26; H, 6.72; N, 2.53; S, 11.58. Found(%): C, 67.24; H, 6.73; N, 2.77; S, 11.51.

Compound Number II-216

$^1$H-NMR(CDCl$_3$) δ: 0.94(1H, d, J=10.5 Hz), 1.07 and 1.20(each 3H, each s), 1.50–2.42(14H, m), 3.87(2H, s), 4.18(1H, m), 4.20(2H, s), 5.32–5.48 (2H, m), 5.98(1H, d, J=7.2 Hz), 6.81(1H, d, J=3.6 Hz), 7.23–7.41 (5H, m), 7.53(1H, d, J=7.5 Hz), 7.71–7.77(2H, m). IR(CHCl$_3$): 3514, 3450, 3431, 1739, 1709, 1641, 1545, 1506, 1469, 1456 cm$^{-1}$. $[\alpha]_D^{25}$+38.5±0.8°(c=1.007, MeOH) Anal. ($C_{35}H_{39}NO_3S\cdot0.2H_2O$) Calcd.(%): C, 75.42; H, 7.13; N, 2.51; S, 5.75. Found(%): C, 75.36; H, 7.18; N, 2.79; S, 5.50.

Compound Number II-217

$^1$H-NMR(CDCl$_3$) δ: 0.96(1H, d, J=10.2 Hz), 1.10 and 1.21(each 3H, each s), 1.52–2.44(14H, m), 3.14–3.24(4H, m), 4.13(2H, s), 4.24(1H, m), 5.32–5.49(2H, m), 6.19(1H, d, J=9.0 Hz), 7.06–7.18(4H, m), 7.22 (1H, d, J=8.1 H), 7.39 (1H, dd, J=1.8 and 8.1 Hz), 7.51(1H, d, J=1.8 Hz). IR(CHCl$_3$): 3516, 3452, 1738, 1709, 1649, 1570, 1518, 1491, 1471 cm$^{-1}$. $[\alpha]_D^{25}$+54.4±0.9°(c=1.002, MeOH) Anal. ($C_{32}H_{39}NO_4\cdot0.1H_2O$) Calcd.(%): C, 78.85; H, 8.11.; N, 2.87. Found(%): C, 78.74; H, 8.14; N, 3.17.

Compound Number II-218

$^1$H-NMR(CDCl$_3$) δ: 0.94(1H, d, J=10.2 Hz), 1.08 and 1.21(each 3H, each s), 1.50–2.43(14H, m), 3.83, 3.85 and 3.86(each 3H, each s), 4.07 (2H, s), 4.19(1H, m), 5.33–5.49 (2H, m), 5.97(1H, d, J=9.0 Hz), 6.62 (1H, d, J=8.7 Hz), 6.76(1H, td, J=0.9 and 3.6 Hz), 6.87(1H, d, J=8.7 Hz), 7.30 (1H, d, (1, J=3.6 Hz). IR(CHCl$_3$): 3516, 3450, 3431, 1739, 1709, 1641, 1603, 1543, 1495, 1469, 1277, 1259, 1097 cm$^{-1}$. $[\alpha]_D^{26}$+38.4±0.8°(c=1.013, MeOH) Anal. ($C_{31}H_{41}NO_6S\cdot0.2H_2O$) Calcd.(%): C, 66.57; H, 7.46; N, 2.50; S, 5.73. Found(%): C, 66.54; H, 7.42; N, 2.61; S, 5.71.

Compound Number II-219

$^1$H-NMR(CDCl$_3$) δ: 0.94(1H, d, J=10.2 Hz), 1.08 and 1.21(each 3H, each s), 1.50–2.42(14H, m), 2.18 and 2.29 (each 3H, each s), 4.14(2H, s), 4.19(1H, m), 5.33–5.49(2H, m), 5.96(1H, d, J=8.4 Hz), 6.67(1H, td, J=0.9 and 3.6 Hz), 7.02–7.12(3H, m), 7.29(1H, t, J=3.6 Hz). IR (CDCl$_3$): 3516, 3450, 3431, 1741, 1709, 1641, 1543, 1506, 1471 cm$^{-1}$. $[\alpha]_D^{26}$+42.8±0.8°(c=1.007, MeOH) Anal. ($C_{30}H_{39}NO_3S$) Calcd.(%): C, 72.98; H, 7.96; N, 2.84; S, 6.50. Found(%): C, 72.67; H, 7.98; N, 2.94; S, 6.38.

Compound Number II-220

$^1$H-NMR(CDCl$_3$) δ: 0.95(1H, d, J=10.2 Hz), 1.09 and 1.22(each 3H, each s), 1.51–2.44(14H, m), 3.83(3H, s), 3.84(6H, s), 4.07(2H, s), 4.20 (1H, m), 5.34–5.49(2H, m), 6.00(1H, d, J=8.7 Hz), 6.45(2H, s), 6.79 and 7.31 (each 1H, each d, each J=3.6 Hz). IR(CHCl$_3$): 3516, 3450, 3431, 1741, 1709, 1641, 1593, 1543, 1506, 1464, 1421, 1331, 1240, 1130 cm$^{-1}$. $[\alpha]_D^{24}$+38.3±0.8°(c=1.004, MeOH) Anal. ($C_{31}H_{41}NO_6S\cdot0.2H_2O$) Calcd.(%): C, 66.57; H, 7.46; N, 2.50; S, 5.73. Found(%): C, 66.48; H, 7.37; N, 2.59; S, 5.63.

Compound Number II-221

$^1$H-NMR(CDCl$_3$) δ: 0.94(1H, d, J=10.2 Hz), 1.08 and 1.21(each 3H, each s), 1.50–2.43(14H, m), 4.08(2H, s), 4.20(1H, m), 5.33–5.49(2H, m), 5.95(2H, s), 5.99(1H, d, J=8.7 Hz), 6.68–6.82(4H, m), 7.30(1H, d, J=3.6 Hz). IR(CHCl$_3$): 3512, 3450, 3431, 1739, 1709, 1641, 1545, 1506, 1460, 1252, 1063 cm$^{-1}$. $[\alpha]_D^{24}$+41.8±0.8°(c=1.007, MeOH) Anal. ($C_{29}H_{35}NO_5S$) Calcd.(%): C, 68.34; H, 6.92; N, 2.75; S, 6.29. Found(%): C, 68.04; H, 6.90; N, 2.79; S, 6.29.

Compound Number II-222

$^1$H-NMR(CDCl$_3$) δ: 0.92(1H, d, J=10.5 Hz), 1.09 and 1.21(each 3H, each s), 1.51–2.45(14H, m), 2.14(3H, s), 4.08(2H, s), 4.18(1H, m), 5.32–5.50 (2H, m), 6.08(1H, d, J=8.4 Hz), 6.76(1H, d, J=3.6 Hz), 6.97 (1H, d, J=7.8 Hz), 7.24(1H, t, J=8.4 Hz), 7.30(1H, d, J=3.6 Hz), 7.38–7.40 (2H, m), 7.74(1H, br s). IR(CHCl$_3$): 3514, 3435, 3311, 1705, 1639, 1612, 1534, 1508, 1439 cm$^{-1}$. $[\alpha]_D^{25}$+40.1±0.8° (c=1.008, MeOH) Anal. ($C_{30}H_{38}N_2O_4S\cdot0.4H_2O$) Calcd.(%): C, 68.00; H, 7.38; N, 5.29; S, 6.05. Found(%): C, 68.11; H, 7.17; N, 5.22; S, 5.93.

Compound Number II-223

$^1$H-NMR(CDCl$_3$) δ: 0.94(1H, d, J=10.5 Hz), 1.09 and 1.22(each 3H, each s), 1.53–2.50(14H, m), 2.99(3H, s), 4.13(2H, s), 4.21(1H, m), 5.34–5.52 (2H, m), 6.02(1H, d, J=9.3 Hz), 6.80(1H, d, J=3.9 Hz), 7.04–7.07(2H, m), 7.16 (1H, m), 7.25–7.32(3H, m). IR(CHCl$_3$): 3510, 3440, 3431, 3371, 1709, 1639, 1608, 1543, 1508, 1471, 1386, 1335, 1151 cm$^{-1}$. $[\alpha]_D^{24}$+38.3±0.8°(c=1.006, MeOH) Anal. ($C_{29}H_{38}N_2O_5S_2\cdot0.2H_2O$) Calcd.(%): C, 61.94; H, 6.88; N, 4.98; S, 11.40. Found(%): C, 61.99; H, 6.92; N, 4.95; S, 10.97.

Compound Number II-224

$^1$H-NMR(CDCl$_3$) δ: 0.94(1H, d, J=10.2 Hz), 1.09 and 1.21(each 3H, each s), 1.50–2.44(14H, m), 4.21(1H, m), 4.32(2H, s), 5.34–5.50(2H, m), 6.01(1H, d, J=9.0 Hz), 6.86, 6.88 and 7.14(each 1H, each d, each J=3.6 Hz), 7.23–7.37 (4H, m), 7.53–7.56(2H, m).

Compound Number II-225

$^1$H-NMR(CDCl$_3$) δ: 0.94 (1H, d, J=10.2 Hz), 1.08 and 1.21(each 311, each s), 1.50–2.43(14H, m), 4.08(2H, s), 4.17–4.30(5H, m), 5.33–5.49 (2H, m), 5.98(1H, d, J=8.4 Hz), 6.71–6.80(4H, m), 7.28(1H, d, J=3.6 Hz). IR(CHCl$_3$): 3516, 3450, 3431, 1739, 1709, 1639, 1602, 1543, 1506, 1475, 1456, 1284, 1090 cm$^{-1}$. [α]$_D$$^{24.5}$+40.2±0.8°(c=1.011, MeOH) Anal. (C$_{30}$H$_{37}$NO$_5$S.0.2H$_2$O) Calcd.(%): C, 68.34; H, 7.15; N, 2.66; S, 6.08. Found(%): C, 68.35; H, 7.03; N, 2.71; S, 6.17.

Compound Number II-226

$^1$H-NMR(CDCl$_3$) δ: 0.94(1H, d, J=10.2 Hz), 1.08 and 1.21(each 3H, each s), 1.50–2.43(14H, m), 2.31 and 3.70 (each 3H, each s), 4.15(2H, s), 4.19(1H, m), 5.33–5.49(2H, m), 5.98(1H, d, J=8.7 Hz), 6.77(1H, d, J=3.9 Hz), 6.96–7.11 (3H, m), 7.31(1H, d, J=3.9 Hz). IR(CHCl$_3$): 3516, 3450, 3431, 2669, 1738, 1709, 1641, 1545, 1506, 1471, 1259, 1011 cm$^{-1}$. [α]$_D$$^{24}$+41.2±0.8°(c=1.003, MeOH) Anal. (C$_{30}$H$_{39}$NO$_4$S) Calcd.(%): C, 70.69; H, 7.71; N, 2.75; S, 6.29. Found(%): C, 70.41; H, 7.76; N, 2.97; S, 6.04.

Compound Number II-227

$^1$H-NMR(CDCl$_3$) δ: 0.93(1H, d, J=10.2 Hz), 1.08 and 1.21(each 3H, each s), 1.51–2.42(14H, m), 2.16(3H, s), 4.09(2H, s), 4.18(1H, m), 5.32–5.50 (2H, m), 6.01(1H, d, J=8.7 Hz), 6.77(1H, d, J=3.6 Hz), 7.17 (2H, d, J=8.1 Hz), 7.32(1H, d, J=3.6 Hz), 7.43(1H, br s), 7.44(2H, d, J=8.1 Hz). IR(CHCl$_3$): 3514, 3435, 3311, 1705, 1639, 1541, 1513, 1410 cm$^{-1}$. [α]$_D$$^{24.5}$+40.8±0.8°(c=1.000, MeOH) Anal. (C$_{30}$H$_{38}$N$_2$O$_4$S.0.4H$_2$O) Calcd.(%): C, 68.00; H, 7.38; N, 5.29; S, 6.05. Found(%): C, 68.06; H, 7.38; N, 5.28; S, 5.92.

Compound Number II-228

$^1$H-NMR(CDCl$_3$) δ: 0.94(1H, d, J=9.9 Hz), 1.09 and 1.21(each 3H, each s), 1.51–2.42(14H, m), 2.99(3H, s), 4.11(2H, s), 4.20(1H, m), 5.33–5.49(2H, m), 6.01(1H, d, J=9.3 Hz), 6.78(1H, d, J=3.6 Hz), 6.86 (1H, br s), 7.17–7.25 (4H, m), 7.31(1H, d, J=3.6 Hz). IR(CHCl$_3$): 3510, 3448, 3431, 3371, 1707, 1639, 1543, 1510, 1471, 1456, 1387, 1330, 1155 cm$^{-1}$. [α]$_D$$^{24.5}$+37.6±0.8°(c=1.006, MeOH) Anal. (C$_{29}$H$_{38}$N$_2$O$_5$S$_2$.0.3H$_2$O) Calcd.(%): C, 61.74; H, 6.90; N, 4.97; S, 11.37. Found(%): C, 61.84; H, 6.93; N, 5.03; S, 11.14.

Compound Number II-229 mp.149–150° C. $^1$H-NMR(CDCl$_3$) δ: 0.92(1H, d, J=10.5 Hz), 1.05 and 1.19(each 3H, each s), 1.47–2.40(14H, m), 4.18(1H, m), 4.40 (2H, s), 5.31–5.46(2H, m), 5.98(1H, d, J=8.4 Hz), 6.88(1H, d, J=3.9 Hz), 7.30–7.35(2H, m), 7.42–7.48(3H, m), 7.58(1H, m), 8.08(1H, d, J=6.6 Hz), 8.14(1H, m). IR(CHCl$_3$): 3514, 3450, 3431, 2667, 1738, 1707, 1643, 1543, 1508, 1471, 1458, 1444 cm$^{-1}$. [α]$_D$$^{24.5}$+39.7±0.8°(c=1.008, MeOH) Anal. (C$_{34}$H$_{37}$NO$_3$S$_2$) Calcd.(%): C, 71.42; H, 6.52; N, 2.45; S, 11.22. Found(%): C, 71.21; H, 6.53; N, 2.51; S, 10.97.

Compound Number II-230

$^1$H-NMR(CDCl$_3$) δ: 0.92(1H, d, J=10.5 Hz), 1.06 and 1.19(each 3H, each s), 1.48–2.40(14H, m), 3.79(2H, s), 4.18(1H, m), 4.26(2H, s), 5.21–5.47(2H, m), 5.96(1H, d, J=8.4 Hz), 6.78(1H, d, J=3.6 Hz), 7.18 (1H, d, J=7.2 Hz), 7.27–7.40(4H, m), 7.53(1H, d, J=7.2 Hz), 7.72(1H, d, J=7.8 Hz), 7.78(1H, d, J=6.9 Hz). IR(CHCl$_3$): 3510, 3450, 3431, 2669, 1739, 1709, 1641, 1543, 1506, 1471, 1456 cm$^{-1}$. [α]$_D$$^{24}$+36.6±0.8°(c=1.006, MeOH) Anal. (C$_{35}$H$_{39}$NO$_3$S.0.2H$_2$O) Calcd.(%): C, 75.42; H, 7.13; N, 2.51; S, 5.75. Found(%): C, 75.46; H, 7.15; N, 2.73; S, 5.55.

Compound Number II-231

$^1$H-NMR(CDCl$_3$) δ: 0.93(1H, d, J=9.9 Hz), 1.08 and 1.21(each 3H, each s), 1.50–2.43(14H, m), 2.20, 2.45 and 3.67(each 3H, each s), 4.13 (2H, s), 4.19(1H, m), 5.33–5.49 (2H, m), 5.97(1H, d, J=8.4 Hz), 6.77 (1H, td, J=0.9 and 3.9 Hz), 6.89 and 6.95(each 1H, each d, each J=7.8 Hz), 7.31(1H, d, J=3.6 Hz). IR(CHCl$_3$): 3516, 3450, 3431, 1738, 1709, 1641, 1545, 1506, 1458, 1263, 1084, 1009 cm$^{-1}$. [α]$_D$$^{24}$+39.8±0.8°(c=1.006, MeOH) Anal. (C$_{31}$H$_{41}$NO$_4$S) Calcd.(%): C, 71.09; H, 7.89; N, 2.67; S, 6.12. Found(%): C, 70.80; H, 8.02; N, 2.92; S, 6.06.

Compound Number II-232

$^1$H-NMR(CDCl$_3$) δ: 0.93(1H, d, J=10.2 Hz), 1.06 and 1.19(each 3H, each s), 1.49–2.41(14H, m), 4.18(1H, m), 4.50(2H, s), 5.32–5.47(2H, m), 5.98(1H, d, J=9.0 Hz), 6.89(1H, d, J=3.9 Hz), 7.29–7.38(4H, m), 7.47 (1H, m), 7.59(1H, d, J=8.4 Hz), 7.86(1H, m), 7.95(1H, d, J=7.8 Hz). IR(CHCl$_3$): 3510, 3450, 3431, 2669, 1739, 1709, 1641, 1545, 1508, 1471, 1450, 1423 cm$^{-1}$. [α]$_D$$^{24}$+40.3±0.8° (c=1.007, MeOH) Anal. (C$_{34}$H$_{37}$NO$_4$S.0.2H$_2$O) Calcd.(%): C, 73.01; H, 6.74; N, 2.50; S, 5.73. Found(%): C, 72.91; 11, 6.58; N, 2.59; S, 5.75.

Compound Number II-233

$^1$H-NMR(CDCl$_3$) δ: 0.92(1H, d, J=10.2 Hz), 1.08 and 1.20(each 3H, each s),1.50–2.43(14H, m), 4.04(2H, s), 4.20 (1H, m), 5.32–5.49(2H, m), 6.03(1H, d, J=9.0 Hz), 6.75(1H, d, J=3.6 Hz), 6.80 and 7.06(each 2H, each d, J=8.7 Hz), 7.32(1H, d, J=3.6 Hz). IR(CHCl$_3$): 3446, 3510, 3182, 2673, 1709, 1635, 1614, 1545, 1512, 1471, 1458 cm$^{-1}$. [α]$_D$$^{25}$+43.8±0.8°(c=1.000, MeOH), Anal. (C$_{28}$H$_{35}$NO$_4$S) Calcd.(%): C, 69.82; H, 7.32; N, 2.91; S, 6.66. Found(%): C, 69.57; H, 7.43; N, 3.00; S, 6.61.

Compound Number II-295 mp.156–157° C. $^1$H-NMR(CDCl$_3$) δ: 1.00(1H, d, J=10.2 Hz), 1.17 and 1.25 (each 3H, each s), 1.57–2.51(14H, m), 4.31(1H, m), 5.34–5.54(2H, m), 6.37(1H, d, J=9.3 Hz), 7.33–7.47(3H, m), 7.61(1H, m), 7.64(1H, m), 7.70–7.73 (2H, m), 7.87(1H, d, J=8.4 Hz), 8.15(1H, d, J=1.2 Hz). IR (CHCl$_3$); 3518, 3452, 1741, 1709, 1649, 1510 cm$^{-1}$. [α]$_D$$^{23}$+67.2±2.1°(c=0.503, MeOH) Anal. (C$_{31}$H$_{35}$NO$_3$S.0.1H$_2$O) Calcd.(%): C, 73.95; H, 7.05; N, 2.78; S, 6.37. Found(%): C, 73.94; H, 7.08; N, 3.04; S, 6.53.

Compound Number II-296 mp.126–127° C. $^1$H-NMR(CDCl$_3$) δ: 0.93(1H, d, J=10.2 Hz), 1.08 and 1.20(each 3H, each s), 1.50–2.46(14H, m), 4.17(1H, m), 5.33–5.51(2H, m), 6.04(1H, d, J=8.4 Hz), 6.51(1H, dd, J=1.5 and 3.3 Hz), 7.13(1H, dd, J=2.7 and 3.3 Hz), 7.22(1H, dd, J=7.8 and 9.0 Hz), 7.73(1H, dd, J=1.5 and 2.1 Hz), 7.91–7.96(2H, m). IR(CHCl$_3$): 3513, 3449, 3144, 1733, 1709, 1651, 1592, 1507, 1496, 1385, 1181 cm$^{-1}$. [α]$_D$$^{24}$+36.2±0.8°(c=1.005, MeOH) Anal. (C$_{27}$H$_{33}$FN$_2$O$_5$S) Calcd.(%): C, 62.77; H, 6.44; N, 5.42; F, 3.68; S, 6.21. Found(%): C, 62.71; H, 6.49; N, 5.39; F, 3.69; S, 6.21.

Compound Number II-297 mp.145–146° C. $^1$H-NMR(CDCl$_3$) δ: 0.93(1H, d, J=10.2 Hz), 1.08 and 1.20(each 3H, each s), 1.50–2.45(14H, m), 3.86(3H, s), 4.17(1H, m), 5.33–5.51 (2H, m), 6.04(1H, d, J=8.4 Hz), 6.48(1H, dd, J=1.5 and 3.3 Hz), 6.98 and 7.85 (each 2H, each d, each J=9.0 Hz), 7.12(1H, dd, J=2.7 and 3.3 Hz), 7.71(1H, dd, J=1.8 and 2.1 Hz). IR(CHCl$_3$): 3513, 3449, 3413, 3143, 1733, 1709, 1649, 1596, 1576, 1499, 1379, 1266, 1189, 1167 cm$^{-1}$. [α]$_D$$^{24}$+34.5±0.7°(c=1.005, MeOH) Anal. (C$_{28}$H$_{36}$N$_2$O$_6$S) Calcd.(%): C, 63.61; H, 6.86; N, 5.30; S, 6.07. Found(%): C, 63.54; H, 6.93; N, 5.18; S, 6.08.

Compound Number II-298

$^1$H-NMR(CDCl$_3$) δ: 0.97(1H, d, J=10.5 Hz), 1.12 and 1.23(each 3H, each s), 1.50–2.50(14H, m), 4.23(1H, m), 5.39–5.51(2H, m), 6.09(1H, d, J=9.6 Hz), 6.35(1H, dd, J=2.4 and 3.9 Hz), 6.48(1H, dd, J=2.4 and 3.9 Hz), 7.02(1H, dd, J=3.6 and 4.8 Hz), 7.18(1H, dd, J=0.6 and 4.8 Hz), 7.41(1H, dd, J=0.6 and 3.6 Hz), 10.92(1H, brs). IR(CHCl$_3$): 3506, 3447, 3220, 3164, 1704, 1617, 1537, 1508 cm$^{-1}$. $[\alpha]_D^{24}$+50.7±0.9°(c=1.009, MeOH) Anal. (C$_{25}$H$_{32}$N$_2$O$_3$S.0.2H$_2$O) Calcd.(%): C, 67.59; H, 7.35; N, 6.31; S, 7.22. Found(%): C, 67.60; H, 7.23; N, 6.39; S, 7.34.

Compound Number II-299
$^1$H-NMR(CDCl$_3$) δ: 0.93(1H, d, J=10.2 Hz), 1.08 and 1.21(each 3H, each s), 1.50–2.44(14H, m), 2.27(3H, s), 4.05(2H, s), 4.20(1H, m), 5.33–5.49(2H, m), 6.01(1H, d, J=8.7 Hz), 6.71(1H, d, J=3.9 Hz), 7.09 (1H, dd, J=1.2 and 7.8 Hz), 7.17–7.32(3H, m), 7.28(1H, d, J=3.9 Hz). IR(CHCl$_3$): 3516, 3450, 3431, 2669, 1747, 1709, 1641, 1543, 1506, 1456, 1369 cm$^{-1}$. $[\alpha]_D^{24}$+40.2°±0.8°(c=1.006, MeOH) Anal. (C$_{30}$H$_{37}$NO$_5$S.0.2H$_2$O) Calcd.(%): C, 68.34; H, 7.15; N, 2.66; S, 6.08. Found(%): H, 6.94; N, 2.83; S, 6.31.

Compound Number II-300
$^1$H-NMR(CDCl$_3$) δ: 0.93(1H, d, J=9.9 Hz), 1.08 and 1.21(each 3H, each s), 1.50–2.41(14H, m), 2.60(3H, s), 4.20(1H, m), 5.34–5.48(2H, m), 6.18(1H, d, J=8.7 Hz), 7.28(1H, d-like), 7.36(1H, d, J=3.9 Hz), 7.40 (1H, t-like), 7.51(1H, dt, J=1.2 and 7.2 Hz), 7.61(1H, d, J=3.9 Hz), 8.15(1H, dd, J=1.2 and 8.1 Hz). IR(CHCl$_3$): 3512, 3446, 1739, 1709, 1655, 1529, 1504, 1325, 1157 cm$^{-1}$. $[\alpha]_D^{24}$+51.1±0.9°(c=1.010, MeOH) Anal. (C$_{28}$H$_{35}$NO$_5$S$_2$) Calcd.(%): C, 63.49; H, 6.66; N, 2.64; S, 12.11. Found(%): C, 63.23; H, 6.53; N, 2.70; S, 12.17.

Compound Number II-301
$^1$H-NMR(CDCl$_3$) δ: 0.93(1H, d, J=10.2 Hz), 1.07 and 1.21(each 3H, each s), 1.50–2.40(14H, m), 2.42(3H, s), 4.20(1H, m), 5.34–5.47(2H, m), 6.17(1H, d, J=8.7 Hz), 7.32(1H, d-like), 7.34 and 7.57(each 1H, each d, each J=4.2 Hz), 7.86(2H, d-like). IR(CDCl$_3$): 3512, 3446, 1741, 1707, 1655, 1529, 1504, 1331, 1153 cm$^{-1}$. $[\alpha]_D^{24}$+54.9±0.9° (c=1.008, MeOH) Anal. (C$_{28}$H$_{35}$NO$_5$S$_2$) Calcd.(%): C, 63.49; H, 6.66; N, 2.64; S, 12.11. Found(%): C, 63.16; H, 6.54; N, 2.70; S, 12.16.

Compound Number II-302
$^1$H-NMR(CDCl$_3$) δ: 0.96(1H, d, J=10.2 Hz), 1.14 and 1.25(each 3H, each s),1.53–2.47(14H, m), 4.25(1H, m), 5.37–5.52(2H, m), 6.23(1H, d, J=8.7 Hz), 7.16–7.22(2H, m), 7.36(1H, m), 7.46(1H, s), 7.45–7.49(1H, m). IR(CHCl$_3$): 3516, 3446, 3429, 1734, 1703, 1652, 1606, 1521, 1496, 1457, 1419 cm$^{-1}$. $[\alpha]_D^{25}$+72.8°±1.1°(c=1.005, MeOH), Anal. (C$_{28}$H$_{31}$NO$_4$S.0.3H$_2$O) Calcd.(%): C, 69.63; H, 6.59; N, 2.90; S, 6.63. Found(%): C, 69.51; H, 6.72; N, 3.30; S, 6.56.

Compound Number III-1
$^1$H-NMR(CDCl$_3$) δ: 0.88(1H, d, J=10.2 Hz), 1.07 and 1.23(each 3H, each s), 1.56–2.51(13H, m), 2.67(1H, m), 4.41(1H, m), 5.29–5.41(2H, m), 6.07(1H, d, J=8.1 Hz), 6.34 and 7.16(each 2H, each t, each J=2.1 Hz), 7.35 and 7.52 (each 1H, each d, each J=3.9 Hz). IR (CHCl$_3$): 3511, 3431, 3144, 3101, 2668, 1708, 1656, 1530, 1505, 1455, 1384, 1167 cm$^{-1}$. $[\alpha]_D^{24}$+34.2±0.7°(c=1.007, MeOH) Anal. (C$_{25}$H$_{32}$N$_2$O$_5$S$_2$.0.5H$_2$O) Calcd.(%): C, 58.46; H, 6.48; N, 5.45; S, 12.48. Found(%): C, 58.77; H, 6.40; N, 5.65; S, 12.72.

Compound Number III-47
$^1$H-NMR(CDCl$_3$) δ: 0.94(1H, d, J=9.9 Hz), 1.07 and 1.23(each 3H, each s), 1.56–2.48(13H, m), 2.68(1H, m), 4.42(1H, m), 5.29–5.42(2H, m), 6.16(1H, d, J=8.4 Hz), 7.16(1H, dd, J=3.9 and 5.1 Hz), 7.42 and 7.63(each 1H, each d, each J=3.9 Hz), 7.70(1H, dd, J=1.5 and 5.1 Hz), 7.76(1H, dd, J=1.5 and 3.9 Hz). IR (CHCl$_3$): 3516, 3431, 3365, 3097, 1708, 1654, 1530, 1505, 1402, 1336, 1153 cm$^{-1}$. $[\alpha]_D^{24}$+34.5±0.7°(c=1.010, MeOH) Anal. (C$_{25}$H$_{31}$NO$_5$S$_3$.0.1H$_2$O) Calcd.(%): C, 57.36; H, 6.01; N, 2.68; S, 18.38. Found(%): C, 57.16; H, 5.88; N, 2.76; S, 18.36.

Compound Number III-55
$^1$H-NMR (CDCl$_3$) δ: 0.88(1H, d, J=9.9 Hz), 1.07 and 1.23(each 3H, each s), 1.58–2.34(12H, m), 2.39(3H, s), 2.44(1H, m), 2.68(1H, m), 4.41(1H, m), 5.29–5.42(2H, m), 5.99(1H, m), 6.08(1H, d, J=8.4 Hz), 6.20(1H, t, J=3.3 Hz), 7.19(1H, m), 7.38 and 7.55(each 1H, each d, each J=3.9 Hz). IR(CHCl$_3$): 3510, 3431, 3150, 3100, 1708, 1656, 1530, 1505, 1375, 1161 cm$^{-1}$. $[\alpha]_D^{24}$+30.9±0.7°(c=1.000, MeOH) Anal. (C$_{26}$H$_{34}$N$_2$O$_5$S$_2$.0.3H$_2$O) Calcd.(%): C, 59.58; H, 6.65; N, 5.35; 12.24. Found(%): C, 59.57; H, 6.48; N, 5.51; S, 12.22.

Compound Number III-80
$^1$H-NMR(CDCl$_3$) δ: 0.90(1H, d, J=9.9 Hz), 1.06 and 1.23(each 3H, each s), 1.58–2.48(13H, m), 2.67(1H, m), 4.41(1H, m), 5.29–5.42(2H, m), 6.27(1H, d, J=8.1 Hz), 7.38–7.44(3H, m), 6.34(1H, d, J=3.9 Hz), 8.14(1H, dd, J=1.5 and 3.0 Hz). IR(CHCl$_3$): 3517, 3431, 3361, 3114, 1708, 1654, 1530, 1504, 1332, 1151 cm$^{-1}$. $[\alpha]_D^{24}$+33.7±0.7°(c=1.003, MeOH) Anal. (C$_{25}$H$_{31}$NO$_5$S$_3$.0.2H$_2$O) Calcd.(%): C, 57.16; H, 6.02; N, 2.67; S, 18.31. Found(%): C, 57.09; H, 5.88; N, 2.76; S, 18.15.

Compound Number IV-1
$^1$H-NMR(CDCl$_3$) δ: 0.84 and 1.22(each 3H, each s), 1.43(1H, d, J=10.5 Hz), 1.53–2.50(14H, m), 4.09(1H, m), 5.30–5.41(2H, m), 6.17 (1H, d, J=8.7 Hz) 6.33 and 7.16 (each 2H, each t-like), 7.40 and 7.57 (each 1H, each d, each J=3.9 Hz). IR(CHCl$_3$): 3514, 3432, 3144, 3102, 1708, 1657, 1531, 1506, 1456, 1384, 1167 cm$^{-1}$. $[\alpha]_D^{23}$−45.4±0.9° (c=1.010, MeOH) Anal. (C$_{25}$H$_{30}$N$_2$O$_5$S$_2$.0.3H$_2$O) Calcd.(%): C, 59.10; H, 6.07; N, 5.51; S, 12.62. Found(%): C, 59.12; H, 5.83; N, 5.53; S, 12.41.

Compound Number IV-47
$^1$H-NMR(CDCl$_3$) δ: 0.85 and 1.22(each 3H, each s), 1.44(1H, d, J=10.2 Hz), 1.54–2.51(14H, m), 4.10(1H, m), 5.31–5.41(2H, m), 6.21 (1H, d, J=8.4 Hz), 7.11(1H, dd, J=3.9 and 4.8 Hz), 7.44 and 7.63 (each 1H, each d, each J=3.9 Hz), 7.70(1H, dd, J=1.2 and 4.8 Hz), 7.75 (1H, dd, J=1.2 and 3.9 Hz). IR(CHCl$_3$): 3517, 3423, 3366, 3097, 2665, 1708, 1655, 1530, 1505, 1335, 1153 cm$^{-1}$. $[\alpha]_D^{23}$−46.4±0.9°(c=1.010, MeOH) Anal. (C$_{25}$H$_{31}$NO$_5$S$_3$.0.3H$_2$O) Calcd.(%): C, 56.97; H, 6.04; N, 2.66; S, 18.25. Found(%): C, 57.10; H, 5.96; N, 2.70; S, 18.02.

Compound Number V-88
mp.105–106° C.; $^1$H-NMR(CDCl$_3$) δ: 1.06(1H, m), 1.19–1.29(2H, m), 1.42–1.47(2H, m), 1.58–1.78(4H, m), 2.00–2.19(5H, m), 2.35(2H, t, J=7.2 Hz), 2.52(1H, m), 3.82(1H, m), 4.16(2H, s), 5.30–5.42(2H, m), 5.99(1H, d, J=7.5 Hz), 6.79(1H, dt, J=0.9 and 3.9 Hz), 6.96(1H, dd, J=1.5 and 4.8 Hz), 7.05(1H, m), 7.28(1H, dd, J=3.0 and 4.8 Hz), 7.37(1H. d, J=3.9 Hz). IR(KBr): 3367, 2667, 1700, 1612, 1543, 1520, 1317, 1244 cm$^{-1}$. $[\alpha]_D^{24}$+70.2±1.1° (c=1.006, MeOH) Anal. (C$_{24}$H$_{29}$NO$_3$S$_2$) Calcd.(%): C, 64.98; H, 6.59; N, 3.16; S, 14.46. Found(%): C, 64.92; H, 6.52; N, 3.32; S, 14.48.

Compound Number VI-1

$^1$H-NMR(CDCl$_3$) δ: 1.24–2.13(13H, m), 2.22(1H, m), 2.32(2H, t, J=7.2 Hz), 3.41(1H, m), 3.44(1H, m), 5.18–5.36 (2H, m), 6.19(1H, m), 6.33 and 7.15(each 2H, each t, each J=2.4 Hz), 7.28 and 7.55(each 2H, each t, each J=3.9 Hz). IR(CHCl$_3$): 3512, 3439, 3144, 3100, 1708, 1658, 1535, 1508, 1446, 1167 cm$^{-1}$. [α]$_D^{26}$+69.5±1.1°(c=1.012, MeOH) Anal. (C$_{23}$H$_{28}$N$_2$O$_5$S.0.5H$_2$O) Calcd.(%): C, 56.89; H, 6.02; N, 5.77; S, 13.21. Found(%): C, 56.91; H, 5.96; N, 5.91; S, 13.37.

Compound Number VI-31

$^1$H-NMR(CDCl$_3$) δ: 1.18–2.10(13H, m), 2.11(1H, m), 2.21–2.35(2H, m), 3.35(1H, m), 3.46(1H, m), 4.12(2H, s), 5.17–5.34(2H, m), 5.88(1H, m), 6.74(1H, d, J=3.9 Hz), 7.21–7.38(6H, m). IR(CHCl$_3$): 3511, 3432, 3065, 1708, 1642, 1547, 1515, 1455 cm$^{-1}$. [α]$_D^{23}$30 69.1±1.1°(c=1.009, MeOH) Anal. (C$_{26}$H$_{31}$NO$_3$S.0.1H$_2$O) Calcd.(%): C, 71.07; H, 7.16; N, 3.19; S, 7.30. Found(%): C, 70.91; H, 7.18; N, 3.19; S, 7.34.

Compound Number VI-40

$^1$H-NMR(CDCl$_3$) δ: 1.18–2.15(14H, m), 2.24–2.34(2H, m), 3.36(1H, m), 3.58(1H, m), 5.19–5.40(2H, m), 6.07(1H, m), 7.28–7.42(3H, m), 7.51(1H, d, J=0.6 Hz), 7.56–7.59(2H, m), 7.72(1H, d, J=0.6 Hz). IR (CHCl$_3$): 3514, 3446, 1709, 1649, 1550, 1520, 1491 cm$^{-1}$. [α]$_D^{22}$+79.4±1.2°(c=1.004, MeOH) Anal. (C$_{25}$H$_{29}$NO$_3$S.0.2H$_2$O) Calcd.(%): C, 70.29; H, 6.94; N, 3.28; S, 7.51. Found(%): C, 70.26; H, 6.68; N, 3.48; S, 7.44.

Compound Number VI-47

$^1$H-NMR(CDCl$_3$) δ: 1.14–2.16(13H, m), 2.23(1H, m), 2.30–2.37(2H, m), 3.41(1H, m), 3.45(1H, m), 5.18–5.36(2H, m), 6.19(1H, m), 7.11 (1H, dd, J=3.9 and 5.1 Hz), 7.32 and 7.62(each 1H, each d, each J=3.9 Hz), 7.39(1H, dd, J=1.5 and 5.1 Hz), 7.75(1H, dd, J=1.5 and 3.9 Hz). IR(CHCl$_3$): 3512, 3440, 3096, 1708, 1657, 1534, 1507, 1402, 1336, 1153 cm$^{-1}$. [α]$_D^{25}$+69.2±1.1°(c=1.006, MeOH) Anal. (C$_{23}$H$_{27}$NO$_5$S$_3$.0.1H$_2$O) Calcd.(%): C, 55.57; H, 5.51; N, 2.83; S, 19.42. Found(%): C, 55.55; H, 5.32; N, 2.85; S, 19.21.

Compound Number VI-55

$^1$H-NMR(CDCl$_3$) δ: 1.18–2.18(13H, m), 2.23(1H, m), 2.31–2.35 (2H, m), 2.38(3H, s), 3.43(2H, m), 5.18–5.36(2H, m), 5.98(1H, m), 6.14(1H, m), 6.19(1H, t, J=3.3 Hz), 7.17(1H, m), 7.29 and 7.53(each 1H, each d, each J=3.9 Hz). IR(CHCl$_3$): 3512 3440, 3150, 3101, 1708, 1658, 1535, 1508, 1375, 1161 cm$^{-1}$. [α]$_D^{24}$+30.9±0.7°(c=1.000, MeOH) Anal. (C$_{26}$H$_{34}$N$_2$O$_5$S$_2$.0.3H$_2$O) Calcd.(%): C, 59.58; H, 6.65; N, 5.35; S, 12.24. Found(%): C, 59.57; H, 6.48; N, 5.51; S, 12.22.

Compound Number VI-80

$^1$H-NMR(CDCl$_3$) δ: 1.16–2.14(13H, m), 2.23(1H, m), 2.28–2.36(2H, m), 3.54–3.46(2H, m), 5.17–5.37(2H, m), 6.14(1H, m), 7.32(1H, d, J=3.9 Hz), 7.38–7.44(2H, m), 7.61(1H, d, J=3.9 Hz), 8.15(1H, dd, J=1.2 and 3.0 Hz). IR(CHCl$_3$): 3508, 3431, 3114, 1708, 1656, 1534, 1508, 1331, 1152, 1102 cm$^{-1}$. [α]$_D^{24}$+66.5±1.1°(c=1.003, MeOH) Anal. (C$_{23}$H$_{27}$NO$_5$S$_3$.0.3H$_2$O) Calcd.(%): C, 55.35; H, 5.57; N, 2.81; S, 19.28. Found(%): C, 55.29; H, 5.54; N, 2.85; S, 19.01.

Compound Number VI-104

$^1$H-NMR(CDCl$_3$) δ: 1.18–2.14(13H, m), 2.25(1H, m), 2.31–2.39(2H, m), 3.32(2H, m), 3.56(1H, m), 4.09(2H, d, J=0.3 Hz), 5.18–5.38(2H, m), 5.89(1H, m), 6.68(1H, d, J=3.6 Hz), 6.94(1H, dd, J=3.6 and 5.1 Hz), 7.02(1H, dd, J=1.5 and 3.6 Hz), 7.23(1H, d, J=3.6 Hz), 7.35(1H, dd, J=1.5 and 5.1 Hz). IR(CHCl$_3$): 3514, 3433, 1709, 1645, 1545, 1516, 1458 cm$^{-1}$. [α]$_D^{23}$+61.8±1.0°(c=1.008, MeOH) Anal. (C$_{24}$H$_{29}$NO$_3$S$_3$.0.2H$_2$O) Calcd.(%): C, 60.14; H, 6.18; N, 2.92; S, 20.07. Found(%): C, 60.08; H, 6.11; N, 2.90; S, 20.05.

Compound Number VI-122

$^1$H-NMR(CDCl$_3$) δ: 1.06–2.15(13H, m), 2.27(1H, m), 2.28–2.38(2H, m), 3.31(1H, m), 3.54(1H, m), 4.24(2H, d, J=0.6 Hz), 5.17–5.36(2H, m), 5.87(1H, m), 6.78(1H, d, J=3.6 Hz), 7.21–7.42(6H, m). IR(CHCl$_3$): 3514, 3433, 3062, 2669, 1709, 1643, 1545, 1514 cm$^{-1}$. [α]$_D^{22}$+64.3±1.0° (c=1.000, MeOH) Anal. (C$_{26}$H$_{31}$NO$_3$S$_2$.0.5H$_2$O) Calcd.(%): C, 65.24; H, 6.74; N, 2.93; S, 13.40. Found(%): C, 65.23; H, 6.55; N, 3.00; S, 13.46.

Compound Number VI-123

$^1$H-NMR(CDCl$_3$) δ: 1.06–2.15(13H, m), 2.23(1H, m), 2.28–2.38(2H, m), 3.35(1H, m), 3.54(1H, m), 5.20(2H, s), 5.19–5.37(2H, m), 5.95(1H, m), 6.94–7.04(4H, m), 7.27–7.35(3H, m). IR(CHCl$_3$): 3514, 3433, 1709, 1647, 1599, 1547, 1518, 1495 cm$^{-1}$. [α]$_D^{24}$+67.8±1.1°(c=1.008, MeOH) Anal. (C$_{26}$H$_{31}$NO$_4$S.0.2H$_2$O) Calcd.(%): C, 68.30; H, 6.92; N, 3.06; S, 7.01. Found(%): C, 68.31; H, 6.84; N, 3.16; S, 7.11.

Compound Number VI-124

$^1$H-NMR(CDCl$_3$) δ: 1.06–2.14(13H, m), 2.24(1H, m), 2.30–2.37(2H, m), 3.31(1H, m), 3.53(1H, m), 4.50(2H, d, J=0.9 Hz), 5.15–5.36(2H, m), 5.89(1H, m), 6.65–6.79(3H, m), 6.95(1H, d, J=3.9 Hz), 7.15–7.21 (2H, m), 7.33(1H, d, J=3.9 Hz). IR(CHCl$_3$): 3512, 3440, 1707, 1643, 1603, 1547, 1506 cm$^{-1}$. [α]$_D^{22}$+67.3±1.1°(c=1.009, MeOH) Anal. (C$_{26}$H$_{32}$N$_2$O$_3$S.0.3H$_2$) Calcd.(%): C, 68.18; H, 7.17; N, 6.20; S, 7.00. Found(%): C, 68.04; H, 7.09; N, 6.25; S, 7.02.

Compound Number VI-133

$^1$H-NMR(CDCl$_3$) δ: 1.18–1.81(7H, m), 1.85–1.94(2H, m), 2.01–2.13 (2H, m), 2.22–2.33(3H, m), 3.41(1H, m), 3.33(1H, m), 3.49(2H, s), 3.54 (1H, m), 4.15(2H, s), 5.17–5.37(2H, m), 5.90(1H, m), 6.12(1H, dd, J=0.9 and 3.0 Hz), 6.31(1H, dd, J=1.8 and 3.0 Hz), 6.81 and 7.30 (each 1H, each d, each J=3.6 Hz), 7.34(1H, dd, J=0.9 and 1.8 Hz). IR(CHCl$_3$): 3516, 3433, 1709, 1643, 1547, 1516 cm$^{-1}$. [α]$_D^{23}$+71.3±1.1°(c=1.004, MeOH) Anal. (C$_{24}$H$_{29}$NO$_4$S.0.3H$_2$O) Calcd.(%): C, 66.58; H, 6.89; N, 3.24; S, 7.41. Found(%): C, 66.55; H, 6.63; N, 3.37; S, 7.51.

Compound Number VI-303

$^1$H-NMR(CDCl$_3$) δ: 1.18–2.14(13H, m), 2.26(1H, m), 2.31–2.36(2H, m), 3.30(1H, m), 3.64(1H, m), 3.82(3H, s), 5.19–5.39(2H, m), 6.06(1H, m), 6.89–7.0(6H, m), 7.66(2H, d, J=8.1 Hz). IR(CHCl$_3$): 3514, 3446, 1709, 1649, 1550, 1520, 1491 cm$^{-1}$. [α]$_D^{22}$+76.3±1.2°(c=1.009, MeOH) Anal. (C$_{28}$H$_{33}$NO$_5$.0.2H$_2$O) Calcd(%): C, 71.99; H, 7.21; N, 3.00. Found(%): C, 72.05; H, 7.35; N, 2.93.

The compounds prepared in Examples above were tested for determining the in vivo and in vitro activities according to the method as shown in Experimental examples below.

Experiment 1 Binding Activity to PGD$_2$ Receptor (1) Preparation of Human Platelet Membrane Fraction Blood was collected using a plastic syringe containing 3.8% sodium citrate from the vein of healthy volunteers (adult male and female), then put into a plastic test tube and mixed by slow-reversion. The sample was then centrifuged at 1800 rpm, for 10 min at room temperature, and the supernatant containing PRP (platelet-rich plasma) was collected. The PRP was re-centrifuged at 2300 rpm, for 22 min at room temperature to obtain platelets. The platelets were homogenized using a homogenizer (Ultra-Turrax) followed by centrifugation 3 times at 20,000 rpm, 10 min at 4° C. to obtain a platelet membrane fraction. After protein determination, the membrane fraction was adjusted to 2 mg/ml and preserved in a refrigerator at −80° C. until using for the binding test.

(2) Binding to $PGD_2$ Receptor

To a binding-reaction solution (50 mM Tris/HCl, pH 7.4, 5 mM $MgCl_2$) (0.2 ml) were added the human platelet membrane fraction (0.1 mg) and 5 nM [$^3$H]$PGD_2$ (115 Ci/mmol), and the mixture was reacted at 4° C. for 90 min. After the reaction, the mixture was filtered through a glass fiber filter paper and washed several times with cooled physiological saline, then the radioactivity retained on the filter paper was measured. The specific-binding ratio was calculated by subtracting the non-specific binding ratio which is the radioactivity similarly measured in the presence of 10 µM $PGD_2$ from the total binding. The inhibitory activity of each compound was expressed as the concentration required for 50% inhibition ($IC_{50}$), which was determined by depicting a substitution curve by plotting the binding ratio (%) in the presence of each compound, where the binding ratio in the absence of a test compound is 100%.

Experiment 2 Binding Activity to $TXA_2$ Receptor (1) Preparation of Human Platelet Membrane Fraction The human platelet membrane fraction was prepared in accordance with Experiment 1 (1).

(2) Binding to $TXA_2$ Receptor

To a binding-reaction solution (50 mM Tris/HCl, pH 7.4, 10 mM $MgCl_2$) (0.2 ml) were added the human platelet membrane fraction (0.05 mg) and 2 nM Sodium [$^3$H](+)-(5Z)-7-[3-endo-[(phenylsulfonyl)amino]bicyclo[2.2.1]hept-2-exo-yl]heptenoate (Japanese Patent Publication (Kokoku) No.79060/1993, hereinafter referred to as (+)-S-145 sodium salt) (26.4 Ci/mmol), and the mixture was reacted at room temperature for 90 min. After the reaction, the resultant mixture was filtered through a glass fiber filter paper and washed several times with cooled physiological saline, then the radioactivity retained on the filter paper was measured. The specific-binding ratio was calculated by subtracting the non-specific binding ratio (the radio activity similarly determined in the presence of 10 µM (+)-S-145 sodium salt) from the total binding. The inhibitory activity of each compound was expressed as the concentration required for 50% inhibition ($IC_{50}$), which was determined by depicting a substitution curve by plotting the binding ratio (%) in the presence of each compound, where the binding ratio in the absence of a test compound is 100%.

Experiment 3 Evaluation of Antagonistic Activity Against $PGD_2$ Receptor

Receptor Using Human Platelet

Peripheral blood was collected from a healthy volunteer using a syringe in which ⅕ volume of a citric acid/dextrose solution was previously added. The sample was subjected to centrifugation at 1200 rpm for 10 min to obtain the supernatant (PRP: platelet rich plasma). The resultant PRP was washed 3 times with a washing buffer and the number of platelets was counted with a micro cell counter. A suspension adjusted to contain the platelets at a final concentration of $5 \times 10^8$/ml was warmed at 37° C., then subjected to the pre-treatment with 3-isobutyl-1-methylxanthine (0.5 mM) for 5 min. To the suspension was added a test compound diluted at various concentration, and 10 minutes later, 0.1 µM $PGD_2$ was added to induce the reaction 2 minutes later, hydrochloric acid was added to terminate the reaction. The platelet was destroyed with an ultrasonic homogenizer. After centrifugation, the cAMP in the supernatant was determined by radioimmunoassay. $PGD_2$ receptor antagonism of a drug was evaluated as follows: the inhibition rate regarding cAMP increased by the addition of $PGD_2$ was determined at each concentration, and the concentration of the drug required for 50% inhibition ($IC_{50}$) was calculated.

The results of Experiment 1–3 are shown below. The results of Experiment of compounds of Example are shown in Table 68 and Table 69 and the results of Experiment of compounds of Example of reference are shown in Table 70 and Table 71.

TABLE 68

| Compd. No.. | Binding activity to $PGD_2$ receptor in human platelet membrane fraction $IC_{50}$(µM) | Binding activity to $TXA_2$ receptor in human platelet membrane fraction $IC_{50}$(µM) | Inhibitory activity for the increase of cAMP caused by $PGD_2$ in human platelet $IC_{50}$(µM) |
|---|---|---|---|
| I-5A-59a | | 0.011 | 0.079 |
| I-7A-1a | 0.0076 | 0.0046 | 0.035 |
| I-7A-31a | | 0.063 | 0.057 |
| I-7A-47a | 0.073 | 0.003 | 0.018 |
| I-7A-59a | | 0.0098 | 0.012 |
| I-7A-88a | | 0.034 | 0.036 |
| I-7A-104a | | 0.024 | 0.082 |
| I-7A-143a | | 0.084 | 0.036 |
| I-7I-1a | | 0.0026 | 0.064 |
| I-7I-31a | | 0.065 | 0.092 |
| I-7I-47a | | 0.0012 | 0.085 |
| I-7I-88a | | 0.033 | 0.025 |
| I-7I-126a | | 0.061 | 0.021 |
| I-7I-270a | | 0.0009 | 0.026 |
| I-7I-307a | | 0.051 | 0.097 |
| I-7M-1e | | 0.044 | 0.039 |
| I-7M-59a | | 0.040 | 0.024 |
| I-7M-143a | | 0.021 | 0.026 |
| I-7M-270a | | 0.0014 | 0.012 |
| I-7M-307a | | 0.100 | 0.024 |
| I-7M-315a | | 0.039 | 0.028 |
| I-7M-316a | | 0.062 | 0.11 |
| I-7M-317a | | 0.074 | 0.018 |
| I-7M-318a | | 0.068 | 0.028 |
| I-7M-333a | | 0.013 | 0.094 |
| I-7M-337a | | 0.037 | 0.019 |
| I-7M-343a | | 0.029 | 0.033 |
| I-7M-393a | | 0.019 | 0.11 |
| I-7M-424a | | 0.0076 | 0.02 |
| I-7M-446a | | 0.0063 | 0.027 |
| I-7P-1a | | 0.034 | 0.036 |
| I-7R-1a | | 0.01 | 0.018 |
| I-7R-270a | | 0.012 | 0.027 |

TABLE 69

| Compd. No.. | Binding activity to $PGD_2$ receptor in human platelet membrane fraction $IC_{50}$(µM) | Binding activity to $TXA_2$ receptor in human platelet membrane fraction $IC_{50}$(µM) | Inhibitory activity for the increase of cAMP caused by $PGD_2$ in human platelet $IC_{50}$(µM) |
|---|---|---|---|
| II-5A-1a | 0.027 | 0.0012 | 0.066 |
| II-5A-31a | | 0.013 | 0.045 |
| II-5A-55a | 0.0053 | 0.0006 | 0.017 |
| II-5A-88a | | 0.022 | 0.019 |
| II-5A-104a | | 0.013 | 0.047 |
| II-5A-143a | | 0.047 | 0.024 |
| II-5B-55a | 0.0042 | 0.0012 | 0.011 |
| II-5F-55a | | 0.0019 | 0.061 |

TABLE 69-continued

| Compd. No.. | Binding activity to PGD$_2$ receptor in human platelet membrane fraction IC$_{50}$(μM) | Binding activity to TXA$_2$ receptor in human platelet membrane fraction IC$_{50}$(μM) | Inhibitory activity for the increase of cAMP caused by PGD$_2$ in human platelet IC$_{50}$(μM) |
|---|---|---|---|
| II-6A-55a | 0.047 | 0.026 | 0.1 |
| II-7A-31a |  | 0.082 | 0.027 |
| II-7A-47a |  | 0.0038 | 0.059 |
| II-7A-55a | 0.0062 | 0.0042 | 0.057 |
| II-7A-55e |  | 0.019 | 0.19 |
| II-7A-59a |  | 0.040 | 0.042 |
| II-7A-143a |  | 0.037 | 0.019 |
| II-7I-55a | 0.0018 | 0.0023 | 0.063 |
| II-7I-59a |  | 0.015 | 0.015 |
| II-7I-126a |  | 0.102 | 0.013 |
| II-7I-239a |  | 0.046 | 0.042 |
| II-7I-270a |  | 0.0006 | 0.032 |
| II-7I-343a |  | 0.0041 | 0.079 |
| II-7M-1a |  | 0.0012 | 0.054 |
| II-7M-1e |  | 0.011 | 0.12 |
| II-7M-1k |  | 0.020 | 0.02 |
| II-7M-31a |  | 0.047 | 0.033 |
| II-7M-47a | 0.024 | 0.0018 | 0.073 |
| II-7M-55a | 0.0013 | 0.0022 | 0.013 |
| II-7M-59a |  | 0.027 | 0.021 |
| II-7M-88a |  | 0.122 | 0.014 |
| II-7M-126a |  | 0.119 | 0.026 |
| II-7M-197a |  | 0.012 | 0.019 |
| II-7M-239a |  | 0.055 | 0.028 |
| II-7M-270a |  | 0.0006 | 0.034 |
| II-7M-307a |  | 0.077 | 0.021 |
| II-7M-332a |  | 0.0017 | 0.067 |
| II-7M-343a |  | 0.0045 | 0.075 |
| II-7N-55a | 0.0065 | 0.0025 | 0.02 |
| II-7P-55a |  | 0.0084 | 0.047 |
| II-7R-55a |  | 0.0036 | 0.013 |
| II-7R-270a |  | 0.015 | 0.023 |
| II-7U-55a |  | 0.021 | 0.077 |

TABLE 70

| Compd. No.. | Binding activity to PGD$_2$ receptor in human platelet membrane fraction IC$_{50}$(μM) | Binding activity to TXA$_2$ receptor in human platelet membrane fraction IC$_{50}$(μM) | Inhibitory activity for the increase of cAMP caused by PGD$_2$ in human platelet IC$_{50}$(μM) |
|---|---|---|---|
| I-1 | 0.0043 | 0.003 | 0.0013 |
| I-10 | 0.0016 | 0.092 | 0.0018 |
| I-31 | 0.0082 | 0.130 | 0.0057 |
| I-47 | 0.0041 | 0.0062 | 0.007 |
| I-59 | 0.00041 | 0.016 | 0.0046 |
| I-66 | 0.0046 | 0.034 | 0.044 |
| I-79 | 0.00042 | 0.015 | 0.024 |
| I-80 | 0.0066 | 0.0052 | 0.039 |
| I-82 | 0.032 | 0.0018 | 0.053 |
| I-88 | 0.0076 | 0.078 | 0.0047 |
| I-93 | 0.0070 | 0.072 | 0.0084 |
| I-94 | 0.001 | 0.083 | 0.01 |
| I-104 | 0.0001 | 0.039 | 0.0016 |
| I-106 | 0.013 | 0.013 | 0.0093 |
| I-117 | 0.0091 | 0.0038 | 0.047 |
| I-128 | 0.020 | 0.048 | 0.01 |
| I-129 | 0.011 | 0.052 | 0.022 |
| I-131 | 0.044 | 0.019 | 0.041 |
| I-132 | 0.032 | 0.012 | 0.043 |
| I-136 | 0.023 | 0.016 | 0.015 |
| I-143 | 0.0027 | 0.028 | 0.0019 |
| I-146 | 0.044 | 0.019 | 0.073 |
| I-160 | 0.028 | 0.02 | 0.085 |
| I-168 | 0.00046 | 0.034 | 0.029 |
| I-169 | 0.00061 | 0.032 | 0.026 |
| I-170 | 0.00092 | 0.027 | 0.017 |
| I-182 | 0.061 | 0.028 | 0.011. |

TABLE 71

| Compd. No.. | Binding activity to PGD$_2$ receptor in human platelet membrane fraction IC$_{50}$(μM) | Binding activity to TXA$_2$ receptor in human platelet membrane fraction IC$_{50}$(μM) | Inhibitory activity for the increase of cAMP caused by PGD$_2$ in human platelet IC$_{50}$(μM) |
|---|---|---|---|
| II-1 | 0.002 | 0.012 | 0.011 |
| II-18 | 0.0079 | 0.030 | 0.0003 |
| II-37 | 0.026 | 0.0043 | 0.035 |
| II-47 | 0.00096 | 0.0036 | 0.004 |
| II-55 | 0.0015 | 0.0044 | 0.0039 |
| II-59 | 0.0001 | 0.014 | 0.024 |
| II-101 | 0.072 | 0.0040 | 0.045 |
| II-117 | 0.022 | 0.0026 | 0.024 |
| II-126 | 0.0046 | 0.045 | 0.004 |
| II-138 | 0.032 | 0.072 | 0.025 |

Experiment 4 Change of Plasma Concentration of Drug in Rat

Compound (0.5 to 2 mg/kg) was administered intravenously to Jcl-SD male rats. The concentration of the unchanged compound was measured at 2, 5, 15, 30, 60, 120, and 240 min after the administration by the use of HPLC (determination limit; 0.05 μg/ml) and LC/MS/MS (determination limit; 0.001 μg/ml) and the half life of the disappearance was calculated.

TABLE 72

| Compd. No.. | half life of the disappearance (min) |
|---|---|
| Reference Compd.I-1 | 9.4 |
| I-7M-1a | 26.3 |
| Reference Compd.I-143 | 4.7 |
| I-7M-143a | 38.4 |
| Reference Compd.II-59 | 11.0 |
| II-7I-59a | 67.0 |
| II-7M-59a | 92.6 |

A half-life of the disappearance of a compound of the present invention was observed to be about 3 to 8 times as long as that of the compound of reference and the metabolic stability was confirmed.

Experiments for comparing the present compound having a dual antagonistic activity against PGD$_2$/TXA$_2$ receptors (e.g., II-7I-55a, II-7M-55a) with a PGD$_2$ receptor antagonist (e.g., B-1, B-2) and a TXA$_2$ antagonist (e.g., A) are shown below.

Comparative Experiment 1

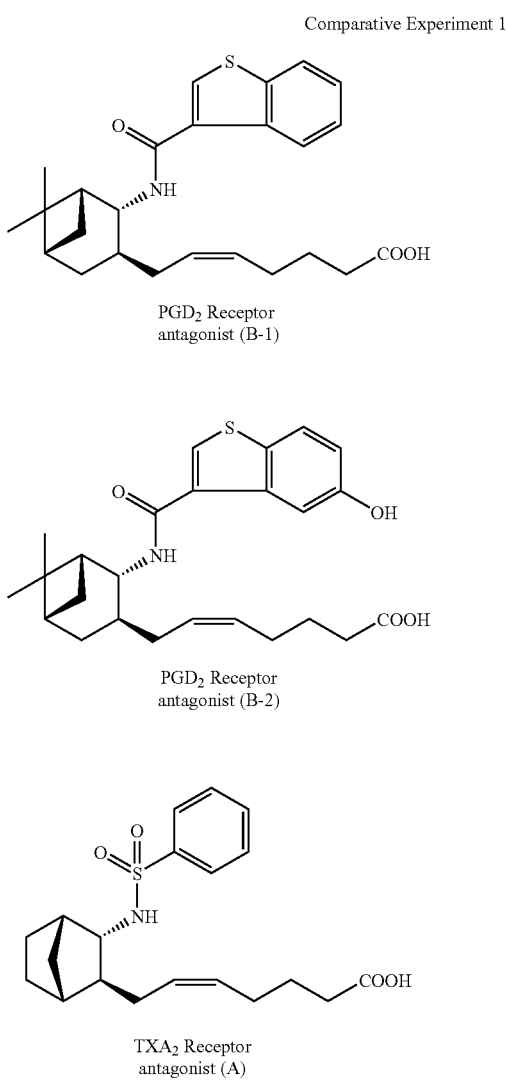

PGD$_2$ Receptor antagonist (B-1)

PGD$_2$ Receptor antagonist (B-2)

TXA$_2$ Receptor antagonist (A)

The experiments were carried out in accordance with the above Experiment 1–3 for the purpose of comparing the compound having a dual antagonistic activity against PGD$_2$/TXA$_2$ receptor with a PGD$_2$ receptor antagonist and a TXA$_2$ receptor antagonist.

TABLE 73

| Compd. | Experiment 1 Antagonistic activity against PGD$_2$ receptor IC$_{50}$ (μM) | Experiment 2 Antagonistic activity against TXA$_2$ receptor IC$_{50}$ (μM) | Experiment 3 Antagonistic activity against PGD$_2$ receptor IC$_{50}$ (μM) |
|---|---|---|---|
| Compound (II-7I-55a) | 0.0018 | 0.0023 | 0.063 |
| Compound (II-7M-55a) | 0.0013 | 0.0022 | 0.013 |
| TXA$_2$ receptor antagonist (A) | >10 | 0.0038 | >10 |
| PGD$_2$ receptor antagonist (B-1) | 0.022 | 0.37 | 0.030 |

Comparative Experiment 2

Antigen-Induced Bronchial Hyperresponsiveness

Male Hartley guinea pigs were actively sensitized to ovalbumin (OVA) by inhalation of aerosolized solution of 1% ovalbumin twice at a week interval. One week after the second sensitization, the animals were treated with antihistamine, diphenhydramine (10 mg/kg, i.p.), and then challenged with 1% OVA aerosol for 5 min. Twenty four hours later, acetylcholine at doses at 3.13, 6.25, 12.5, 25, 50 and 100 micro g/kg was sequentially injected into the animals which were anesthetized with pentobarbital (30 mg/kg, i.p.). The bronchoconstriction induced by each dose of acetylcholine was monitored by the modified method of Konzett-Rössler technique, and made a dose-response curve of acetylcholine. Using the dose-response curve, the dose required for 200% increase in bronchoconstriction from baseline (PD$_{200}$) was calculated in each animal and used as an indication of bronchial responsiveness. Compounds were orally administered 1 hour before antigen challenge. **: P<0.01 vs Vehicle(Dunnett's test), ##: P<0.01 vs Vehicle (Student's t test).

TABLE 74

|  | Log PD$_{200}$ |
|---|---|
| Vehicle | 1.033 ± 0.053 |
| Compound (II-7I-55a)10 mg/kg | 1.442 ± 0.055** |
| Compound (II-7M-55a)10 mg/kg | 1.485 ± 0.119** |
| Negative control | 1.517 ± 0.067## |

TABLE 75

|  | Log PD$_{200}$ |
|---|---|
| Vehicle | 1.125 ± 0.023 |
| Compound (B-2)10 mg/kg | 1.237 ± 0.052 |
| Negative control | 1.465 ± 0.074## |

TABLE 76

|  | Log PD$_{200}$ |
|---|---|
| Vehicle | 1.11 ± 0.06 |
| Compound (A)1 mg/kg | 1.29 ± 0.04 |
| Compound (A)10 mg/kg | 1.61 ± 0.09** |
| Negative control | 1.69 ± 0.06## |

As shown in Table 74 to Table 76, a PGD$_2$ receptor antagonist (B-2) did not inhibit the induction of bronchial hyperresponsiveness, but TXA$_2$ receptor antagonist (A) and PGD$_2$/TXA$_2$ dual receptor antagonist, (e.g., II-71-55a, II-7M-55a) suppressed it, indicating that TXA$_2$ receptor antagonism is necessary for improvement of bronchial hyperresponsiveness.

Comparative Experiment 3

Antigen-Induced Increase in the Eosinophil Number in Bronchoalveolar Lavage Fluid.

Bronchoalveolar lavage was performed with 10 mL of saline, after the animals were sensitized and challenged with antigen. The number of total cells in the recovered fluid was stained with Türk and counted using hemocytometer. *: P<0.05, **:P<0.01 vs Vehicle(Dunnett's test), ##: P<0.01 vs Vehicle(Student's t test). ( ): inhibition %.

TABLE 77

| | Total cells (× $10^6$ cells/animal) |
|---|---|
| Vehicle | 23.36 ± 2.33 |
| Compound (II-7I-55a) 10 mg/kg | 12.26 ± 1.54**(80%) |
| Compound (II-7M-55a) 10 mg/kg | 18.29 ± 1.46 (36%) |
| Negative control | 9.43 ± 0.78## |

TABLE 78

| | Total cells (× $10^6$ cells/animal) |
|---|---|
| Vehicle | 17.12 ± 2.20 |
| Compound (B-2) 10 mg/kg | 9.72 ± 2.32* (53%) |
| Negative control | 3.20 ± 0.52## |

TABLE 79

| | Total cells (× $10^6$ cells/animal) |
|---|---|
| Vehicle | 13.89 ± 2.42 |
| Compound (A) 10 mg/kg | 15.20 ± 2.20 (−12%) |
| Negative control | 2.98 ± 0.28## |

As shown in Table 77 to Table 79, $PGD_2$ receptor antagonist (B-2) and $PGD_2/TXA_2$ dual receptor antagonist (II-71-55a, II-7M55a) significantly suppressed the eosinophil infiltration. But a $TXA_2$ receptor antagonist (A) did not show any inhibitory actions. These results indicate that $PGD_2$ receptor antagonism is necessary for suppression of inflammatory cell infiltration.

Comparative Experiment 4

Acceleration of Vascular Permeability of Conjunctiva Induced by $PGD_2$ and U-46619

Using male Hartley guinea pigs, $PGD_2$- and $TxA_2$ receptor-mediated increase in conjunctival vascular permeability was produced by instillation of each 10 μl solution of either 0.1% $PGD_2$ or U-46619 ($TXA_2$ receptor agonist) to the both eyes without anesthetization. Immediately after that, Evans blue dye (20 mg/kg) was intravenously injected. 30 min after the challenge, guinea pigs were sacrificed by bleeding under anesthesia with Pentobarbital (30 mg/kg, i.p.) and the tissue of conjunctiva was removed. The dye leaked into the tissue was extracted in formamide 3 ml at 60° C. for more than 24 h, and then centrifuged. The absorbance of the supernatant was measured at 620 nm. The amount of dye was calculated from the calibration curve of Evans blue dye. Each compound was suspended in 0.5% methyl-cellulose and administrated orally at 1 h before the challenge. The antagonistic activity was evaluated by the inhibition ratio against the dye leaked into conjunctiva caused by PGD2 or U-46619 at each dose and then a 50% effective dose of inhibition ($ED_{50}$ value) of each compound was calculated.

TABLE 80

| Compound | $ED_{50}$ (mg/kg) | |
|---|---|---|
| | $PGD_2$ | $TXA_2$ (U-46619) |
| II-7I-55a | 0.33 | 0.030 |
| II-7M-55a | 0.043 | 0.083 |
| $PGD_2$ receptor antagonist (B-2) | 0.099 | >10 |
| $TXA_2$ receptor antagonist (A) | >30 | 0.017 |

As shown in Table 80, a $PGD_2$ receptor antagonist (B-2) inhibited the increase in vascular permeability in conjunctiva by the stimulation with $PGD_2$ but did not inhibit that caused by U-46619, viceversa, a TXA2 receptor antagonist (A) suppressed only U-46619-induced response. $PGD_2/TXA_2$ dual receptor antagonist (e.g., II-7I-55a, II-7M-55a) showed both responses. Thus, the inhibition of both receptor-mediated responses was ascertained in vivo.

Formulation Example

It is to be noted that the following Formulation Examples 1 to 8 are mere illustration, but not intended to limit the scope of the invention. The term "Active ingredient" means a compound of the present invention, the prodrug thereof, their pharmaceutically acceptable salt, or their hydrate.

Formulation Example 1

Hard gelatin capsules are prepared using the following ingredients:

| | Dose (mg/capsule) |
|---|---|
| Active ingredient | 250 |
| Starch, dried | 200 |
| Magnesium stearate | 10 |
| Total | 460 mg |

Formulation Example 2

Tablet are prepared using the following ingredients:

| | Dose (mg/tablet) |
|---|---|
| Active ingredient | 250 |
| Cellulose, microcrystals | 400 |
| Silicon dioxide, fumed | 10 |
| Stearic acid | 5 |
| Total | 665 mg |

The ingredients are blended and compressed to form tablets each weighing 665 mg.

Formulation Example 3

An aerosol solution is prepared containing the following components:

|  | Weight |
| --- | --- |
| Active ingredient | 0.25 |
| Ethanol | 25.75 |
| Propellant 22 (chlorodifluoromethane) | 74.00 |
| Total | 100.00 |

The active ingredient is mixed with ethanol and the admixture added to a portion of the propellant 22, cooled to −30° C. and transferred to a filling device. The required amount is then fed to a stainless steel container and diluted with the reminder of the propellant. The valve units are then fitted to the container.

Formulation Example 4

Tablets, each containing 60 mg of active ingredient, are made as follows.

| Active ingredient | 60 mg |
| --- | --- |
| Starch | 45 mg |
| Microcrystals cellulose | 35 mg |
| Polyvinylpyrrolidone (as 10% solution in water) | 4 mg |
| Sodium carboxymethyl starch | 4.5 mg |
| Magnesium stearate | 0.5 mg |
| Talc | 1 mg |
| Total | 150 mg |

The active ingredient, starch, and cellulose are passed through a No. 45 mesh U.S. sieve, and the mixed thoroughly. The aqueous solution containing polyvinylpyrrolidone is mixed with the resultant powder, and the admixture then is passed through a No. 14 mesh U.S. sieve. The granules so produced are dried at 50° C. and passed through a No. 18 mesh U.S. sieve. The sodium carboxymethyl starch, magnesium stearate, and talc, previously passed through No. 60 mesh U.S. sieve, are then added to the granules which, after mixing, are compressed on a tablet machine to yield tablets each weighing 150 mg.

Formulation Example 5

Capsules, each containing 80 mg of active ingredient, are made as follows:

| Active ingredient | 80 mg |
| --- | --- |
| Starch | 59 mg |
| Microcrystals cellulose | 59 mg |
| Magnesium stearate | 2 mg |
| Total | 200 mg |

The active ingredient, cellulose, starch, and magnesium stearate are blended, passed through a No. 45 mesh U.S. sieve, and filled into hard gelatin capsules in 200 mg quantities.

Formulation Example 6

Suppositories, each containing 225 mg of active ingredient, are made as follows:

| Active ingredient | 225 mg |
| --- | --- |
| Saturated fatty acid glycerides | 2000 mg |
| Total | 2225 mg |

The active ingredient; is passed through a No. 60 mesh U.S. sieve and suspended in the saturated fatty acid glycerides previously melted using the minimum heat necessary. The mixture is then poured into a suppository mold of nominal 2 g capacity and allowed to cool.

Formulation Example 7

Suspensions, each containing 50 mg of active ingredient per 5 ml dose, are made as follows:

| Active ingredient | 50 mg |
| --- | --- |
| Sodium carboxymethyl cellulose | 50 mg |
| Syrup | 1.25 ml |
| Benzoic acid solution | 0.10 ml |
| Flavor | q.v. |
| Color | q.v. |
| Purified water to total | 5 ml |

The active ingredient is passed through a No. 45 U.S. sieve, and mixed with the sodium carboxymethyl cellulose and syrup to form a smooth paste. The benzoic acid solution, flavor and color are diluted with a portion of the water and added, with stirring. Sufficient water is then added to produce the required volume.

Formulation Example 8

An intravenous formulation may be prepared as follows:

| Active ingredient | 100 mg |
| --- | --- |
| Isotonic saline | 1000 ml |

The solution of the above ingredients is generally administered intravenously to a subject at a rate of 1 ml per minute.

INDUSTRIAL APPLICABILITY

The pharmacological effect of the compound of the present invention is compared with that of $TXA_2$ receptor antagonist and $PGD_2$ receptor antagonist in the following table.

TABLE 81

|  | $TXA_2$ receptor antagonist | $PGD_2$ receptor antagonist | Compound (I) |
| --- | --- | --- | --- |
| Bronchial asthma |  |  |  |
| Eosinophilic infiltration | x | ◉ | ◉ |
| Advance of respiratory anaphylaxis | ◉ | x | ◉ |
| Respiratory contraction | ◉ | x | ◉ |

In bronchial asthma, a TXA$_2$ receptor antagonist itself can inhibit advance of respiratory anaphylaxis and respiratory contraction, but has no effect for eosinophilic infiltration. A PGD$_2$ receptor antagonist itself can inhibit eosinophilic infiltration, but has no effect for advance of respiratory anaphylaxis and respiratory contraction. On the other hand, a compound having a dual antagonistic activity against PGD$_2$/TXA$_2$ receptors like the compound (I) is efficient for all of eosinophilic infiltration, advance of respiratory anaphylaxis and respiratory contraction.

A TXA$_2$ receptor antagonist has no effect for eosinophilic infiltration but was ascertained to increase the inhibitory effect for eosinophilic infiltration caused by a PGD$_2$ receptor antagonist. That is, a TXA$_2$ receptor antagonist and a PGD$_2$ receptor antagonist were ascertained to show a synergistic effect. Then, a compound having a dual antagonistic activity against PGD$_2$/TXA$_2$ receptors like the compound (I) is very efficient.

The compound having a dual antagonistic activity against PGD$_2$/TXA$_2$ receptors is useful for treating systemic mastocytosis and disorder of systemic mast cell activation as well as tracheal contraction, asthma, allergic rhinitis, allergic conjunctivitis, urticaria, itching, atopic dermatitis, alimentary allergy, ischemic reperfusion injury, cerebrovascular disorder, and inflammation, and effective for treating or improving condition of diseases such as arteriosclerosis, myocardial infarction, acute myocardial ischemia angina, cardiovascular shock or preventing unexpected death and the like, especially asthma or nasal blockage.

With a dual antagonistic activity against both a TXA$_2$ receptor and a PGD$_2$ receptor, the present compound can overcome some problems such as that due to the metabolic rate difference of each compound, which occur upon simultaneous administration of both a TXA$_2$ receptor antagonist and a PGD$_2$ receptor antagonist.

The invention claimed is:

1. A compound of the formula (I):

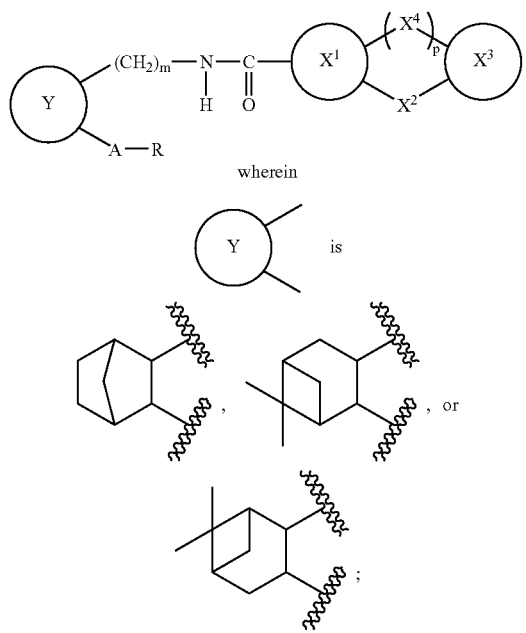

wherein

A is alkylene optionally intervened with a heteroatom, optionally having an oxo group, optionally substituted with halogen and/or optionally having an unsaturated bond;

R is —C(=O)—R$^1$, —CH$_2$—R$^1$, or tetrazolyl;

R$^1$ is hydroxy, alkyloxy, or optionally substituted amino;

m is 0 or 1;

provided that combinations wherein m is 1, A is —CH=CH—CH$_2$—CH$_2$—CH$_2$— and R is —C(=O)—R$^1$ (R$^1$ is hydroxy or alkyloxy) or wherein A is —CH$_2$—CH=CH—CH$_2$—CH$_2$—CH$_2$— and R is —C(=O)—R$^1$ wherein R$^1$ is hydroxy or alkyloxy are excluded, p is 0 or 1, provided that when p=0,

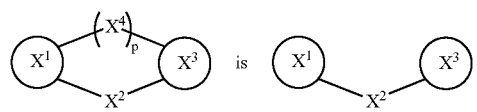

X$^1$ and X$^3$ are each independently optionally substituted aryl, optionally substituted heteroaryl or optionally substituted non-aromatic heterocyclyl;

X$^2$ is a bond, —CH$_2$—, —CH$_2$—CH$_2$—, —C(=O)—, —O—, —S—, —SO—, —SO$_2$—, —NH—, —N(CH$_3$)—, —C(=N—O—CH$_3$)—, —N=N—, —CH=CH—, —(C=O)—NH—, —NH—(C=O)—, —CH$_2$—NH—, —NH—CH$_2$—, —CH$_2$—O—, —O—CH$_2$—, —CH$_2$—S, —S—CH$_2$—, —CH$_2$—SO$_2$—, —SO$_2$—CH$_2$—, —SO$_2$—NH—, —NH—SO$_2$—, —C(=CH$_2$)—, —SO$_2$N(Me)—, —CH$_2$NHSO$_2$—, —CH$_2$NH—(C=O)—, —NH—C(=O)—NH or —NH—C(=O)—N(Me)—;

X$^4$ is —CH$_2$—, —CH$_2$—CH$_2$—, —C(=O)—, —SO—, —SO$_2$—, —(C=O)—NH—, —NH—(C=O)—, —CH$_2$—NH—, —NH—CH$_2$—, —CH$_2$—O—, —O—CH$_2$—, —CH$_2$—S—, —S—CH$_2$—, —CH$_2$—SO$_2$—, —SO$_2$—CH$_2$—, —SO$_2$—NH— or —NH—SO$_2$—, provided that a combination wherein

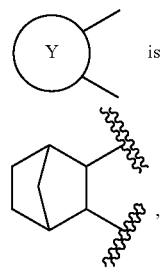

A is —CH=CH—CH$_2$—CH$_2$—CH$_2$—, R is —COOH, m is 1, p is 0, X$^1$ and X$^3$ are phenyl, and X$^2$ is —N=N—, is excluded and provided that when

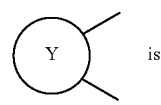

-continued

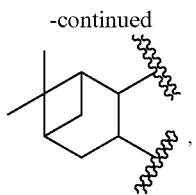

X¹ and X³ are phenyl, X² is —CH=CH—, —O—, or —S—, m is 0, and p is 0, a compound wherein A is —CH=CH—CH₂—CH₂—CH₂—C(CH₃)₂— and R is COOH, A is —CH₂—CH=CH—CH₂—CH₂—C(CH₃)₂— and R is COOH, A is —CH₂—C(=O)—CH₂—CH₂—CH₂—CH₂— and R is COOH, A is —CH₂—CH₂—CH₂—CH₂—CH₂— and R is —COOH, A is —CH₂—CH₂—CH₂—CH₂—CH₂—CH₂— and R is —COOH, A is —CH₂—CH=CH—CH₂—CH₂—CH₂— and R is —CH₂OH, or A is —CH=CH—CH₂—CH₂—CH₂— and R is —CH₂OH, is excluded, a pharmaceutically acceptable salt or a solvate thereof.

2. A compound as described in claim 1 wherein A is alkylene optionally intervened with a heteroatom, optionally having an oxo group, optionally substituted with halogen and/or optionally having an unsaturated bond;

R is —C(=O)—R¹, —CH₂—R¹, or tetrazolyl;

R¹ is hydroxy, alkyloxy, or optionally substituted amino; provided that compounds wherein A is —CH=CH—CH₂—CH₂—CH₂— and R is —C(=O)—R¹ (R¹ is hydroxy or alkyloxy), or A is —CH₂—CH=CH—CH₂—CH₂—CH₂— and R is —C(=O)—R¹ wherein R¹ is hydroxy or alkyloxy are excluded, a pharmaceutically acceptable salt or a solvate thereof.

3. A compound as described in claim 1, wherein A is alkylene intervened with a heteroatom, optionally having an oxo group, optionally substituted with halogen and/or optionally having an unsaturated bond, a pharmaceutically acceptable salt, or a solvate thereof.

4. A compound as described in claim 1, wherein A is C1 to C4 or C7 to C9 alkylene optionally intervened with a heteroatom, optionally having an oxo group, optionally substituted with halogen and/or optionally having an unsaturated bond, a pharmaceutically acceptable salt, or a solvate thereof.

5. A compound as described in claim 1, wherein A is —CH₂—CH₂—CH₂—, —CH₂—CH₂—CH(F)—, —CH₂CH=CH—, —CH₂—O—CH₂—, —CH₂CH=C(F)—, —CH₂—CH₂—CH₂—CH₂—, —CH₂CH=CH—CH₂—, —CH₂—CH₂—CH=CH—, —CH=CH—CH₂—CH₂—, —CH₂—CH₂—O—CH₂—, —CH₂—CH₂—S—CH₂—, —CH₂—CO—NH—CH₂—, —CH₂—CH₂—CH₂—CH₂—CH₂—, CH₂CH=CH—CH₂—CH₂—, —CH₂—CH₂—CH₂—CH=CH—, —CH₂—CH₂—CH₂—O—CH₂—, —CH₂—CH₂—CH₂—S—CH₂—, —CH₂—CH₂—CO—NH—CH₂—, —CH₂—CH₂—CH₂—CH₂—CH₂—CH₂—, —CH₂—CH₂—CH₂—CH₂—CH₂—CH₂—CH(Me)—, —CH₂—CH₂—CH₂—CH₂—CH₂—C(Me)₂—, —CH₂—CH₂—CH₂—CH₂—CH₂—CH(F)—, —CH₂—CH=CH—CH₂—CH₂—CH(Me)—, —CH₂—CH=CH—CH₂—CH₂—C(Me)₂—, —CH₂—CH=CH—CH₂— CH₂—CH(F)—, —CH₂—CH₂—CH₂—CH₂—CH=CH—, —CH₂—CH₂—CH₂—CH₂—CH=C(Me)—, —CH₂—CH₂—CH₂—CH₂—C(Me)=CH—, —CH₂—CH₂—CH₂—CH₂—CH₂—CH=C(F)—, —CH₂—CH₂—CH₂—CH₂—CH₂—O—CH₂—, —CH₂—CH=CH—CH₂—O—CH₂—, —CH₂—CH=CH—CH₂—S—CH₂—, —CH₂—CH=C(F)—CH₂—O—CH₂—, —CH₂—CH₂—O—CH₂—CH=CH—, —CH₂—CH₂—CH₂—CH₂—S—CH₂—, —CH₂—CH₂—CH₂—CO—NH—CH₂—, —CH₂—CH₂—CH=N—O—CH₂—, —CH₂—CH₂—S—CH₂—CH₂—CH₂—, —CH₂—CH₂—CH₂—CH₂—CH₂—CH₂—CH₂—, —CH₂—CH=CH—CH₂—CH₂—CH₂—CH₂—, —CH₂—CH₂—CH₂—CH₂—O—CH₂—, —CH₂—CH₂—CH₂—CH₂—CH₂—CH₂—, or —CH₂—CH=CH—CH₂—CH₂—CH₂—CH₂—, a pharmaceutically acceptable salt, or a solvate thereof.

6. A compound as described in claim 5, wherein A is —CH₂—CH₂—CH₂—CH₂—, —CH₂—CH₂—CH₂—CH₂—CH=CH—, —CH₂—CH₂—CH₂—CH₂—O—CH₂—, —CH₂—CH=CH—CH₂—O—CH₂—, —CH₂—CH=CH—CH₂—S—CH₂—, or —CH₂—CH₂—CH₂—CH₂—S—CH₂—, a pharmaceutically acceptable salt, or a solvate thereof.

7. A compound as described in claim 6, wherein A is —CH₂—CH₂—CH₂—CH₂—O—CH₂—, a pharmaceutically acceptable salt, or a solvate thereof.

8. A compound as described in claim 1, wherein X¹ and X³ are each independently optionally substituted aryl or optionally substituted heteroaryl, a pharmaceutically acceptable salt, or a solvate thereof.

9. A compound as described in claim 8, wherein at least one of X¹ and X³ is optionally substituted heteroaryl, a pharmaceutically acceptable salt, or a solvate thereof.

10. A compound as described in claim 9, wherein X¹ and X³ are each independently optionally substituted heteroaryl, a pharmaceutically acceptable salt, or a solvate thereof.

11. A compound as described in claim 9, wherein at least one of X¹ and X³ is optionally substituted thienyl or optionally substituted benzothienyl, a pharmaceutically acceptable salt, or a solvate thereof.

12. A compound as described in claim 1, wherein X² is a bond, —CH₂—, —S—, —SO₂—, —CH₂—O—, —O—CH₂—, —CH₂—S—, —S—CH₂—, or —NH—C(=O)—NH—, a pharmaceutically acceptable salt, or a solvate thereof.

13. A compound as described in claim 1, wherein m is 0 and p is 0, a pharmaceutically acceptable salt, or a solvate thereof.

14. A compound as described in claim 1, wherein R is —C(=O)—R¹ and R¹ is hydroxy, alkyloxy, or optionally substituted amino, a pharmaceutically acceptable salt, or a solvate thereof.

15. A pharmaceutical composition containing a compound, a pharmaceutically acceptable salt, or a solvate thereof as described in claim 1, together with a pharmaceutically acceptable carrier, excipient, solvent or base.

16. A pharmaceutical composition having a dual antagonistic activity against PGD₂/TXA₂ receptors as described in claim 15.

17. A pharmaceutical composition as described in claim 15, which is used for the treatment of asthma.

18. A pharmaceutical composition as described in claim 15, which is used for the treatment of nasal blockage.

19. A pharmaceutical composition as described in claim 15, which is used for the treatment of allergic conjunctivitis.

20. A pharmaceutical composition as described in claim 15, which is used for the treatment of allergic rhinitis.

21. A method for preparing a pharmaceutical composition for treating asthma, nasal blockage, allergic conjunctivitis or allergic rhinitis, which comprises mixing a compound according to claim 1 together with a pharmaceutically acceptable carrier, excipient, solvent or base.

22. A method for treating nasal blockage, allergic conjunctivitis or allergic rhinitis, which comprises administrating a compound as described in claim 1 to a patient in need thereof.

23. A compound as described in claim 1, wherein A is —$CH_2$—$CH_2$—CH(F)—, —$CH_2$—O—$CH_2$—, —$CH_2$CH═C(F)—, —$CH_2$—$CH_2$—S—$CH_2$—, —$CH_2$—$CH_2$—$CH_2$—$CH_2$—CH(Me)—, —$CH_2$—CH═CH—$CH_2$—$CH_2$—CH(Me)—, —$CH_2$—CH═CH—$CH_2$—$CH_2$—C(Me)$_2$—, $CH_2$—$CH_2$—$CH_2$—$CH_2$—CH═C(Me)—, —$CH_2$—$CH_2$—$CH_2$—$CH_2$—C(Me)═CH—, —$CH_2$—$CH_2$—$CH_2$—$CH_2$—CH═C(F)—, —$CH_2$—$CH_2$—$CH_2$—$CH_2$—O—$CH_2$—, —$CH_2$—CH═CH—$CH_2$—O—$CH_2$—, —$CH_2$—CH═CH—$CH_2$—S—$CH_2$—, —$CH_2$—CH═C(F)—$CH_2$—O—$CH_2$—, —$CH_2$—$CH_2$—O—$CH_2$—CH═CH—, —$CH_2$—$CH_2$—$CH_2$—CO—NH—$CH_2$—, —$CH_2$—$CH_2$—CH═N—O—$CH_2$—, —$CH_2$—$CH_2$—$CH_2$—$CH_2$—O—$CH_2$—, or —$CH_2$—CH═CH—$CH_2$—$CH_2$—$CH_2$—$CH_2$—$CH_2$—, or pharmaceutically acceptable salt, or a solvate thereof.

24. A compound as described in claim 1, wherein p is 1, a pharmaceutically acceptable salt, or a solvate thereof.

* * * * *